US009080143B2

(12) United States Patent
Faaberg et al.

(10) Patent No.: US 9,080,143 B2
(45) Date of Patent: *Jul. 14, 2015

(54) PRRS VIRUSES, INFECTIOUS CLONES, MUTANTS THEREOF, AND METHOD OF USE

(75) Inventors: Kay S. Faaberg, Ames, IA (US); Jun Han, Hershey, PA (US); Gongping Liu, St. Paul, MN (US); Yue Wang, St. Paul, MN (US)

(73) Assignee: University of Minnesota, Minneapolis, MN (US)

( * ) Notice: Subject to any disclaimer, the term of this patent is extended or adjusted under 35 U.S.C. 154(b) by 618 days.

This patent is subject to a terminal disclaimer.

(21) Appl. No.: 13/276,671

(22) Filed: Oct. 19, 2011

(65) Prior Publication Data

US 2012/0149096 A1  Jun. 14, 2012

Related U.S. Application Data

(63) Continuation of application No. 11/922,798, filed as application No. PCT/US2006/024355 on Jun. 23, 2006, now Pat. No. 8,110,390.

(60) Provisional application No. 60/694,021, filed on Jun. 24, 2005.

(51) Int. Cl.
| | |
|---|---|
| C12N 7/00 | (2006.01) |
| C12N 15/40 | (2006.01) |
| C12N 15/85 | (2006.01) |
| C07K 14/08 | (2006.01) |
| C07K 14/005 | (2006.01) |

(52) U.S. Cl.
CPC ............ C12N 7/00 (2013.01); C07K 14/005 (2013.01); C12N 2770/10021 (2013.01); C12N 2770/10022 (2013.01); C12N 2770/10043 (2013.01)

(58) Field of Classification Search
CPC ............ C07K 14/005; C12N 2770/10021; C12N 2770/10022; C12N 7/00
See application file for complete search history.

(56) References Cited

U.S. PATENT DOCUMENTS

| | | | |
|---|---|---|---|
| 3,137,631 A | 6/1964 | Soloway | |
| 3,959,457 A | 5/1976 | Speaker et al. | |
| 4,015,100 A | 3/1977 | Gnanamuthu et al. | |
| 4,122,167 A | 10/1978 | Buynak et al. | |
| 4,205,060 A | 5/1980 | Monsimer et al. | |
| 4,224,412 A | 9/1980 | Dorofeev et al. | |
| 4,452,747 A | 6/1984 | Gersonde et al. | |
| 4,468,346 A | 8/1984 | Paul et al. | |
| 4,554,159 A | 11/1985 | Roizman et al. | |
| 4,606,940 A | 8/1986 | Frank et al. | |
| 4,636,485 A | 1/1987 | van der Smissen | |
| 4,683,195 A | 7/1987 | Mullis et al. | |
| 4,744,933 A | 5/1988 | Rha et al. | |
| 4,753,884 A | 6/1988 | Kit et al. | |
| 4,810,493 A | 3/1989 | Patrick et al. | |
| 4,908,305 A | 3/1990 | Snyder | |
| 4,921,706 A | 5/1990 | Roberts et al. | |
| 4,927,637 A | 5/1990 | Morano et al. | |
| 4,944,948 A | 7/1990 | Uster et al. | |
| 5,008,050 A | 4/1991 | Cullis et al. | |
| 5,009,956 A | 4/1991 | Baumann | |
| 5,132,117 A | 7/1992 | Speaker et al. | |
| 5,143,825 A | 9/1992 | Chacko et al. | |
| 5,206,163 A | 4/1993 | Renard et al. | |
| 5,213,759 A | 5/1993 | Castberg et al. | |
| 5,223,409 A | 6/1993 | Ladner et al. | |
| 5,374,530 A | 12/1994 | Nuzzolo et al. | |
| 5,419,907 A | 5/1995 | Paul et al. | |
| 5,476,778 A | 12/1995 | Chladek et al. | |
| 5,498,551 A | 3/1996 | de Jaeger et al. | |
| 5,510,258 A | 4/1996 | Sanderson et al. | |
| 5,580,859 A | 12/1996 | Felgner et al. | |
| 5,587,164 A | 12/1996 | Sanderson et al. | |
| 5,597,721 A | 1/1997 | Brun et al. | |
| 5,620,691 A | 4/1997 | Wensvoort et al. | |
| 5,663,286 A | 9/1997 | Ahmed et al. | |
| 5,674,500 A | 10/1997 | Peeters et al. | |
| 5,677,429 A | 10/1997 | Benfield | |
| 5,683,865 A | 11/1997 | Collins et al. | |
| 5,690,940 A | 11/1997 | Joo | |
| 5,695,766 A | 12/1997 | Paul et al. | |
| 5,698,203 A | 12/1997 | Visser et al. | |
| 5,789,388 A | 8/1998 | Visser et al. | |
| 5,840,563 A | 11/1998 | Chladek et al. | |

(Continued)

FOREIGN PATENT DOCUMENTS

| | | |
|---|---|---|
| CA | 2103460 A1 | 12/1992 |
| CA | 2290906 C | 12/1992 |

(Continued)

OTHER PUBLICATIONS

Genbank locus DQ176019, Jun. 1, 2006.*
Genbank locus DQ176020, Jun. 1, 2006.*
Johnson et al (Veterinary Immunology and Immunopathology 102: 233-247, 2004).*
Genbank EF484031.1 (Feb. 26, 2008).*
Genbank EF488739.1 (Feb. 26, 2008).*
Han et al, Virus Research 122:175-182, 2006.*
Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.
Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

(Continued)

Primary Examiner — Mary E Mosher
(74) Attorney, Agent, or Firm — Davis, Brown, Koehn, Shors & Roberts, P.C.; Sean D. Solberg

(57) ABSTRACT

The present invention provides isolated infectious polynucleotides, such as infectious clones, having a nucleotide sequence with identity to PRRS viruses such as VR-2332, Lelystad, or others, and optionally further including a deletion in a region of ORF1 that encodes the nsp2 polypeptide.

16 Claims, 86 Drawing Sheets

(56) References Cited

U.S. PATENT DOCUMENTS

| | | |
|---|---|---|
| 5,846,805 A | 12/1998 | Collins et al. |
| 5,858,729 A | 1/1999 | Van Woensel et al. |
| 5,866,401 A | 2/1999 | Hesse |
| 5,888,513 A | 3/1999 | Plana Duran et al. |
| 5,910,310 A | 6/1999 | Heinen et al. |
| 5,925,359 A | 7/1999 | Van Woensel et al. |
| 5,968,525 A | 10/1999 | Fitzgerald et al. |
| 5,976,537 A | 11/1999 | Mengeling et al. |
| 5,977,429 A | 11/1999 | Phillips et al. |
| 5,989,563 A | 11/1999 | Chladek et al. |
| 5,998,601 A | 12/1999 | Murtaugh et al. |
| 6,001,370 A | 12/1999 | Burch et al. |
| 6,015,663 A | 1/2000 | Wesley et al. |
| 6,033,844 A | 3/2000 | Visser et al. |
| 6,042,830 A | 3/2000 | Chladek et al. |
| 6,080,570 A | 6/2000 | Chladek et al. |
| 6,110,467 A | 8/2000 | Paul et al. |
| 6,110,468 A | 8/2000 | Collins et al. |
| 6,194,389 B1 | 2/2001 | Johnston et al. |
| 6,197,310 B1 | 3/2001 | Wensvoort et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,380,376 B1 | 4/2002 | Paul et al. |
| 6,391,314 B1 | 5/2002 | Allan et al. |
| 6,455,245 B1 | 9/2002 | Wensvoort et al. |
| 6,495,138 B1 | 12/2002 | van Nieuwstadt et al. |
| 6,498,008 B2 | 12/2002 | Collins et al. |
| 6,500,662 B1 | 12/2002 | Calvert et al. |
| 6,592,873 B1 | 7/2003 | Paul et al. |
| 6,641,819 B2 | 11/2003 | Mengeling et al. |
| 6,660,513 B2 | 12/2003 | Mengeling et al. |
| 6,773,908 B1 | 8/2004 | Paul et al. |
| 6,806,086 B2 | 10/2004 | Wensvoort et al. |
| 6,841,364 B2 | 1/2005 | Yuan et al. |
| 6,855,315 B2 | 2/2005 | Collins et al. |
| 6,982,160 B2 | 1/2006 | Collins et al. |
| 7,018,638 B2 | 3/2006 | Chu et al. |
| 7,041,443 B2 | 5/2006 | Faaberg et al. |
| 7,081,342 B2 | 7/2006 | Mengeling et al. |
| 7,109,025 B1 | 9/2006 | Eloit et al. |
| 7,122,347 B2 | 10/2006 | Verheije et al. |
| 7,132,106 B2 | 11/2006 | Calvert et al. |
| 7,169,394 B2 | 1/2007 | Chu et al. |
| 7,211,379 B2 | 5/2007 | Ellis et al. |
| 7,232,680 B2 | 6/2007 | Calvert et al. |
| 7,264,804 B2 | 9/2007 | Collins et al. |
| 7,273,617 B2 | 9/2007 | Yuan et al. |
| 7,312,030 B2 | 12/2007 | van Rijn et al. |
| 7,335,361 B2 | 2/2008 | Liao et al. |
| 7,335,473 B2 | 2/2008 | Wensvoort et al. |
| 7,368,117 B2 | 5/2008 | Fetzer et al. |
| 7,611,717 B2 | 11/2009 | Murtaugh et al. |
| 7,618,797 B2 | 11/2009 | Calvert et al. |
| 7,632,636 B2 | 12/2009 | Roof et al. |
| 7,691,389 B2 * | 4/2010 | Calvert et al. ............... 424/204.1 |
| 7,722,878 B2 | 5/2010 | Vaughn et al. |
| 7,897,343 B2 | 3/2011 | Wensvoort et al. |
| 8,110,390 B2 * | 2/2012 | Faaberg et al. ............ 435/235.1 |
| 2002/0012670 A1 | 1/2002 | Elbers et al. |
| 2002/0098573 A1 | 7/2002 | Meulenberg et al. |
| 2002/0172690 A1 | 11/2002 | Calvert et al. |
| 2003/0049274 A1 | 3/2003 | Meulenberg et al. |
| 2003/0118608 A1 | 6/2003 | Wensvoort et al. |
| 2003/0157689 A1 | 8/2003 | Calvert et al. |
| 2003/0219732 A1 | 11/2003 | van Rijn et al. |
| 2004/0009190 A1 | 1/2004 | Elbers et al. |
| 2004/0132014 A1 | 7/2004 | Wensvoort et al. |
| 2004/0197872 A1 | 10/2004 | Meulenberg et al. |
| 2004/0213805 A1 | 10/2004 | Verheije |
| 2004/0224327 A1 | 11/2004 | Meulenberg et al. |
| 2004/0253270 A1 | 12/2004 | Meng et al. |
| 2006/0063151 A1 | 3/2006 | Roof et al. |
| 2006/0205033 A1 | 9/2006 | Meulenberg et al. |
| 2006/0240041 A1 | 10/2006 | Meulenberg et al. |
| 2006/0286123 A1 | 12/2006 | Fetzer et al. |
| 2007/0003570 A1 | 1/2007 | Murtaugh et al. |
| 2007/0042000 A1 | 2/2007 | Mengeling et al. |
| 2008/0268426 A1 | 10/2008 | Murtaugh et al. |
| 2009/0148474 A1 | 6/2009 | Roof et al. |
| 2010/0003278 A1 | 1/2010 | Roof et al. |
| 2010/0028860 A1 | 2/2010 | Roof et al. |
| 2010/0035276 A1 | 2/2010 | Murtaugh et al. |
| 2010/0129398 A1 | 5/2010 | Klinge et al. |
| 2010/0267929 A1 | 10/2010 | Faaberg et al. |
| 2011/0104201 A1 | 5/2011 | Mengeling et al. |
| 2011/0117129 A1 | 5/2011 | Roof et al. |
| 2011/0195088 A1 | 8/2011 | Roof et al. |

FOREIGN PATENT DOCUMENTS

| | | |
|---|---|---|
| CA | 2102036 C | 5/1994 |
| CA | 2410694 A1 | 12/1999 |
| DE | 145705 A1 | 1/1981 |
| EP | 0208672 B1 | 1/1987 |
| EP | 0440219 A1 | 8/1991 |
| EP | 0529584 A2 | 3/1993 |
| EP | 0587780 B1 | 3/1994 |
| EP | 0595436 B1 | 5/1994 |
| EP | 0610250 B1 | 8/1994 |
| EP | 0676467 B1 | 10/1995 |
| EP | 0732340 B1 | 9/1996 |
| EP | 0835929 A1 | 4/1998 |
| EP | 0835930 B1 | 4/1998 |
| EP | 0839912 A1 | 5/1998 |
| EP | 1018557 B1 | 7/2000 |
| FR | 2602791 A1 | 2/1988 |
| GB | 2282811 A | 4/1995 |
| GB | 2289279 A | 11/1995 |
| JP | 62198626 A | 9/1987 |
| JP | 7501049 A | 2/1995 |
| JP | 7138186 A | 5/1995 |
| JP | 7289250 A | 11/1995 |
| JP | 9500544 A | 1/1997 |
| JP | 9503926 A | 4/1997 |
| JP | 11509087 B2 | 8/1999 |
| JP | 2002504317 A | 2/2002 |
| WO | WO8803410 A1 | 5/1988 |
| WO | WO8908701 A1 | 9/1989 |
| WO | WO9221375 A1 | 12/1992 |
| WO | WO9302556 A1 | 2/1993 |
| WO | WO9303760 A1 | 3/1993 |
| WO | WO9306211 A1 | 4/1993 |
| WO | WO9307898 A1 | 4/1993 |
| WO | WO9314196 A1 | 7/1993 |
| WO | WO9418311 A1 | 8/1994 |
| WO | WO9528227 A1 | 10/1995 |
| WO | WO9531550 A1 | 11/1995 |
| WO | WO9604010 A1 | 2/1996 |
| WO | WO9606619 A1 | 3/1996 |
| WO | WO9636356 A1 | 11/1996 |
| WO | WO9640932 A1 | 12/1996 |
| WO | WO9700696 A1 | 1/1997 |
| WO | WO9731651 A1 | 9/1997 |
| WO | WO9731652 A1 | 9/1997 |
| WO | WO9807898 A1 | 2/1998 |
| WO | WO9818933 A1 | 5/1998 |
| WO | 9835023 A1 | 8/1998 |
| WO | WO9850426 A1 | 11/1998 |
| WO | WO9855625 A1 | 12/1998 |
| WO | WO9855626 A2 | 12/1998 |
| WO | WO9939582 A1 | 8/1999 |
| WO | WO0053787 A1 | 9/2000 |
| WO | WO0065032 A1 | 11/2000 |
| WO | 0159077 A1 | 8/2001 |
| WO | WO0159077 A1 | 8/2001 |
| WO | WO0190363 A1 | 11/2001 |
| WO | WO02095040 A1 | 11/2002 |
| WO | WO03062407 A1 | 7/2003 |
| WO | WO2006002193 A2 | 1/2006 |
| WO | WO2006034319 A2 | 3/2006 |
| WO | WO2006074986 A2 | 7/2006 |
| WO | 2007064742 A2 | 6/2007 |

(56) References Cited

FOREIGN PATENT DOCUMENTS

| WO | 2008109237 A2 | 9/2008 |
|---|---|---|
| WO | WO2008121958 A1 | 10/2008 |
| WO | WO2010025109 A1 | 3/2010 |
| WO | WO2011128415 A1 | 10/2011 |

OTHER PUBLICATIONS

Buchner et al., "A method for increasing the yield of properly folded recombinant fusion proteins: single-chain immunotoxins from renaturation of bacterial inclusion bodies," Anal. Biochem., 1992, 205(2):263-270.

Buck, K. W., "Comparison of the Replication of Positive-Stranded RNA Viruses of Plants and Animals". Advances in Virus Research, vol. 47, 1996, pp. 159-251.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

Burroughs, et al., "Relationship of San Miguel Sea Lion Virus to Other Members of the Calicivirus Group". Intervirology, vol. 10, 1978, pp. 51-59.

Cabasso et al., "Propagation of Infectious Canine Hepatitis Virus in Tissue Culture". Proceedings of the Society for Experimental Biology and Medicine, vol. 85, 1954, pp. 239-245.

Caeiro et al., "In vitro DNA replication by cytoplasmic extracts from cells infected with African swine fever virus". Virology, vol. 179, No. 1, Nov. 1990, pp. 87-94.

Callebaut et al., "Antigenic Differentiation between Transmissible Gastroenteritis Virus of Swine and a Related Porcine Respiratory Coronavirus". Journal of General Virology, vol. 69, 1988, pp. 1725-1730.

Carrascosa et al., "Relationship of San Miguel Sea Lion Virus to Other Members of the Calicivirus Group". Journal of Virological Methods, vol. 3, No. 6, Jan. 1982, pp. 303-310.

Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.

Cavanagh et al., "Recommendations of the Coronavirus Study Group for the Nomenclature of the Structural Proteins, mRNAs, and Genes of Corona viruses," Virol.,1990;176:306-307.

Cavanagh, D., "Nidovirales: a new order comprising Coronaviridae and Arteriviridae". Archives of Virology, vol. 142, No. 3, 1997, pp. 629-633.

Chang et al., "A cis-Acting Function for the Coronavirus Leader in Defective Interfering RNA Replication". Journal of Virology, vol. 68, No. 12, Dec. 1994, pp. 8223-8231.

Chang et al., "Evolution of Porcine Reproductive and Respiratory Syndrome Virus during Sequential Passages in Pigs," J. Virol., May 2002; 76(10):4750-4763.

Chao et al., "Monoclonal Antibodies to Metacyclic Stage Antigens of *Trypanosoma cruzi*" The American Journal of Tropical Medicine and Hygiene, vol. 34, No. 4, Jul. 1985, pp. 694-701.

Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.

Chasey et al., "Replication of Atypical Ovine Rotavirus in Small Intestine and Cell Culture". Journal of General Virology, vol. 67, No. 3, Mar. 1986, pp. 567-576.

Chen et al., "Determination of the 5' end of the lactate dehydrogenase-elevating virus genome by two independent approaches," J. Gen. Virol., 1994;75:925-930.

Choi et al., "Identification of 5' and 3' cis-Acting Elements of the Porcine Reproductive and Respiratory Syndrome Virus: Acquisition of Novel 5' Au-Rich Sequences Restored Replication of a 5'-Proximal 7-Nucleotide Deletion Mutant," J. Virol., Jan. 2006;80(2):723-736.

Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.

Christianson et al., "Experimental reproduction of swine infertility and respiratory syndrome in pregnant sows". American Journal of Veterinary Research, vol. 53, No. 4, Apr. 1992, pp. 485-488.

Christianson et al., "Pathogenesis of Porcine Reproductive and Respiratory Syndrome Virus Infection in Mid-gestation Sows and Fetuses", Can J. Vet Res., 1993, 57:262-268.

Christianson et al., "Porcine reproductive and respiratory syndrome: A review"., Journal of Swine Health and Production, vol. 2, No. 2, Mar. and Apr. 1994, pp. 10-28.

Christianson et al., "Swine Infertility and Respiratory Syndrome". Pig Veterinary Journal, vol. 27, No. 9, Apr. 1991, pp. 9-12.

Christopher-Hennings et al., "Identification of Porcine Reproductive and Respiratory Syndrome Virus in Semen and Tissues from Vasectomized and Nonvasectomized Boars", Veterinary Pathology, vol. 35, No. 4, (1998) pp. 260-267.

Christopher-Hennings et al., "Persistence of porcine reproductive and respiratory syndrome virus in serum and semen of adult boars," J. Vet. Diag. Invest., 1995, 7:456-464.

Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.

Clark et al., "Trypsin enhancement of rotavirus infectivity: mechanism of enhancement". Journal of Virology, vol. 39, No. 3, Sep. 1981, pp. 816-822.

Clark, "Refolding of recombinant proteins," Curr. Opin. Biotechnol., 1998, 9(2):157-163.

Coligan et al. (eds.), Current Protocols in Immunology, Ch. 2, John Wiley & Sons (1996).

Coligan et al. (eds.), Current Protocols in Immunology, Ch. 8 (Part 1 of 3), John Wiley & Sons (1996).

Coligan et al. (eds.), Current Protocols in Immunology, Ch. 8 (Part 2 of 3) John Wiley & Sons (1996).

Coligan et al. (eds.), Current Protocols in Immunology, Ch. 8 (Part 3 of 3) John Wiley & Sons (1996).

Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.

Collins et al., "Isolation of swine infertility and respiratory syndrome virus (isolate ATCC VR-2332) in North America and experimental reproduction of the disease in gnotobiotic pigs," J. Vet. Diagn. Invest., 1992, 4:117-126.

Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.

Collins et al., "Respiratory Disease in a Swine Herd Experiencing a Reproductive Failure Syndrome". Minnesota Swine Conference for Veterinarians, Sep. 16-18, 1990, pp. 206-207.

Collins et al., "Swine Diagnostic Pathology". Allen D. Leman Swine Conference, College of Veterinary Medicine, University of Minnesota, Sep. 18-22, 1998, pp. 1-4.

Collins et al., "Swine Infertility and Respiratory Syndrome (Mystery Swine Disease)". Minnesota Swine Conference for Veterinarians, St. Paul, MN, Sep. 15-17, 1991, pp. 200-205.

Collins, J.E., "Newly Recognized Respiratory Syndromes in North American Swine Herds". American Association of Swine Practitioners Newsletter, vol. 3, No. 7, Sep.-Oct. 1991, pp. 7, 10-11.

Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.

Conzelmann et al. "Molecular Characterization of Porcine Reproductive and Respiratory Syndrome Virus, a Member of the Arterivirus Group". Virology. 193:329-339, 1993.

(56) References Cited

OTHER PUBLICATIONS

Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.

Dacso, et al., "Sporadic occurrence of zoonotic swine influenza virus infections". Journal of Clinical Microbiology, vol. 20, No. 4, Oct. 1984, pp. 833-835.

Database WPIL Week 8702, Derwent Publications Ltd., London, GB; AN 87-009295 [2] & EP, A,208672 (Regional Wallonne-Chiron Corp, Wallonne Regional) Jan. 14, 1987.

Database WPIL Week 8741, Derwent Publications Ltd., London, GB; AN 87-286929 [41] & EP, A,62, 198626 (ZA Bieseibutsu Kagaku Ken) Sep. 2, 1987.

Database WPIL Week 8821, Derwent Publications Ltd., London, GB; AN 88-147502 [21] & WO,A,8 803 410 (Inst Pasteur) May 19, 1988.

Setzer et al., "Size Heterogeneity in the 3' End of Dihydrofolate Reductase Messenger RNAs in Mouse Cells". Cell, vol. 22, Nov. 1980, pp. 361-370.

Shaw et al., "Experimental rotavirus infection in three-week-old pigs". American Journal of Veterinary Research, vol. 50, No. 11, Nov. 1989, pp. 1961-1965.

Shen et al., "Determination of the complete nucleotide sequence of a vaccine strain of porcine reproductive and respiratory syndrome virus and identification of the Nsp2 gene with a unique insertion," Arch. Virol.,2000;145:871-883.

Shibata, Darryl K. et al., "Detection of Human Papilloma Virus in Paraffin-Embedded Tissue Using the Polymerase Chain Reaction", J. Exp. Med. 167:225-230, Jan. 1988.

Shieh et al., "The 5'-End Sequence of the Murine Coronavirus Genome: Implications of Multiple Fusion Sites in Leader-Primed Transcription". Virology, vol. 156, 1987, pp. 321-330.

Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.

Shope et al., "The Susceptibility of Swine to the Virus of Human Influenza". Annual Meeting of the Society of American Bacteriologists in New York, 1936, pp. 791-801.

Shortridge et al., "Geographical Distribution of Swine (HSw1N1) and Hong Kong (H3N2) Influenza Virus Variants in in Pigs in Southeast Asia". Intervirology, vol. 11, No. 1, 1979, pp. 9-15.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Immunofluorescence in the Diagnosis of Bovine Fetal Leptospirosis", The Cornell Veterinarian, vol. 57 (1967) pp. 517-526.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs Is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sep. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses," J Gen. Virol., 1998;79:961-979.

Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.

Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stevenson et al., "Idiotypic DNA Vaccines Against B-cell Lymphoma", Immunology Reviews, vol. 145 (1995) pp. 211-228.

Stim, T.B., "Arbovirus Plaquing in Two Simian Kidney Cell Lines". Journal of General Virology, vol. 5, No. 3, Oct. 1969, pp. 329-338.

Suarez et al., "Direct Detection of the porcine reproductive and respiratory syndrome (PRRS) virus by reverse polymerase chain reaction (RT-PCR)" Arch. Vir. 135:89-99, 1994.

Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.

Sumiyoshi et al., "Infectious Japanese Encephalitis Virus RNA Can Be Synthesized from in Vitro-Ligated cDNA Templates". Journal of Virology, vol. 66, No. 9, Sep. 1992, pp. 5425-5431.

Tahara et al., "Coronavirus Translational Regulation: Leader Affects mRNA Efficiency". Virology, vol. 202, No. 1, Aug. 1994, pp. 621-630.

Tao et al., "Host Range Restriction of Parainfluenza Virus Growth Occurs at the Level of Virus Genome Replication". Virology, vol. 220, 1996, pp. 69-77.

Tauraso et al., "Simian Hemorrhagic Fever: III. Characterization of a Viral Agent". The American Journal of Tropical Medicine and Hygiene, vol. 17, No. 3, May 1968, pp. 422-431.

Terpstra et al., "Experimental Reproduction of Porcine Epidemic Abortion and Respiratory Syndrome (Mystery Swine Disease) by Infection with Lelystad Virus: Koch's Postulates Fulfilled", The Veterinary Quarterly, vol. 13, (1991) pp. 131-136.

Thacker, B., "Clinical Manifestations of PRRS Virus". 2003 PRRS Compendium: Second Edition, National Pork Board, Des Moines, IA, 2003, pp. 7-15.

Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.

Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.

Theil et al., "Partial characterization of a bovine group A rotavirus with a short genome electropherotype". Journal of Clinical Microbiology, vol. 26, No. 6, Jun. 1988, p. 1094-1099.

Thompson et al., "The CLUST AL _ X windows interface: flexible strategies for multiple sequence alignment aided by quality analysis tools," Nucleic Acids Res., 1997 ;25(24):4876-4882.

(56) References Cited

OTHER PUBLICATIONS

Thomson et al., "Ontario. Proliferative and necrotizing pneumonia (PNP) of swine: the Ontario situation". Canadian Veterinary Journal, vol. 32, May 1991, p. 313.
Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tobita et al., "Plaque Assay and Primary Isolation of influenza a Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Truong et al., "A highly pathogenic porcine reproductive and respiratory syndrome virus generated from an infectious cDNA clone retains the in vivo virulence and translnissibility properties of the parental virus," Virol., 2004;325:308-319.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Gao et al., "Genomic characterization of two Chinese isolates of Porcine respiratory and reproductive syndrome virus". Archives of Virology, vol. 149, 2004, pp. 1341-1351.
Hennen, J., "Statistical methods for longitudinal research on bipolar disorders". Bipolar Disorders, vol. 5, 2003, pp. 156-168.
Matanin et al., "Purification of the major envelop protein GP5 of porcine reproductive and respiratory syndrome virus (PRRSV) from native virions". Journal of Virological Methods, vol. 147, 2008, pp. 127-135.
Paul et al., "Porcine Reproductive and Respiratory Syndrome: An Overview". Journal of Clinical Veterinary Medicine, vol. 11, No. 12, Nov. 1993, pp. 1-16.
Pesch et al., "New insights into the genetic diversity of European porcine reproductive and respiratory syndrome virus (PRRSV)". Veterinary Microbiology, vol. 107, 2005, pp. 31-48.
UniProt: Accession No. C9E449. "SubName: Full=M protein; SubName: Full= Membrane protein". Nov. 3, 2009.
UniProt: Accession No. DOVEE4. "SubName: Full=Unglycosylated membrane protein". Dec. 15, 2009.
UniProt: Accession No. Q6TLB4. "SubName: Full= Membrane protein M". Jul. 5, 2004.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 991-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
vanNieuwstadt et al., "Proteins Enclosed by Open Reading Frames 3 and 4 of the Genome of Lelystad Virus (Artenriviridae) Are Structural Proteins of the Virion", Journal of Virology, vol. 70, No. 7, (1996) pp. 4767-4772.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins," Gene, 1991;100:189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Vogel et al., "Nucleic Acid Vaccines" Clinical Microbiology Reviews, vol. 8, No. 3 (1995) pp. 406-410.
Von Busse, F.W., Epidemiologic Studies on Porcine Reproductive and Respiratory Syndrome (PRRS). Tierarztliche Umschau, Dec. 1991, pp. 708-717 (Abstract in English p. 711).

(56) References Cited

OTHER PUBLICATIONS

Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ *Escherichia coli* vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "'Blue ear' disease in pigs". Veterinary Record, vol. 128, No. 24, Jun. 1991, p. 574.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research at Lelystad," Vet. Microbiol.,1992;33:185-193.
Wensvoort et al., "Mystery swine disease in the Netherlands: the isolation of Lelystad virus," Vet Q., 1991, 13 (3):121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wensvoort, Gert et al., "Antigenic comparison of Lelystad virus and swine infertility and respiratory syndrome (SIRS) virus", J Vet Diagn Invest 4:134-138 (1992).
Wesley et al., "Differentiation of a porcine reproductive and respiratory syndrome virus vaccine strain from North American field strains by restriction fragment length polymorphism analysis of ORF 5," J Vet. Diagn. Invest., 1998;10: 140-144.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Experimental challenge of pregnant gilts with swine influenza virus after vaccination". Research Communications in Chemical Pathology and Pharmacology, vol. 15, No. 4, Dec. 1976, pp. 787-795.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.
Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.
Mukamoto et al., "Immunogenicity in Aujeszky's disease virus structural glycoprotein gVI (gp50) in swine". Veterinary Microbiology, vol. 29, No. 2, Oct. 1991, pp. 109-121.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Comparison of the structural protein coding sequences of the VR-2332 and Lelystad virus strains of the PRRS virus," Arch. Virol., 1995;140: 1451-1460.
Murtaugh et al., "Genetic Variation in the PRRS Virus," Coronaviruses and Arteriviruses, New York, NY, 1998;787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Inflammatory cytokines and antigen presenting cell activation," Vet. Immunol. Immunopathol., 2002;87:109-121.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, M. "The Evolution of the Swine Veterinary Profession", presented on Swine conference, Sep. 11-14, 1993, The St. Paul Radisson Hotel, St. Paul, Minnesota.
Murtaugh, M.P., "Polymerase Chain Reaction (PCR) Applications in Swine Medicine and Diagnostics", Department of Veterinary PathoBiology.
Murtaugh, Michael P. et al., "Interrelatedness of PRRS virus isolates in North America", Allen D. Leman Swine Conference, vol. 24, 1997, College of Veterinary Medicine, University of Minnesota, pp. 146-149.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
Needleman et al., "A General Method Applicable to the Search for Similarities in the Amino Acid Sequence of Two Proteins," J. Mol. Biol., 1970;48:443-453.
Nelsen et al., "Porcine reproductive and respiratory syndrome virus comparison: divergent evolution of two continents," J. Virol., 1999, 73:270-280.

(56) References Cited

OTHER PUBLICATIONS

Nelson et al., "Differentiation of U.S. and European Isolates of Porcine Reproductive and Respiratory Syndrome Virus by Monoclonal Antibodies", Journal of Clinical Microbiology, vol. 34, (1993), pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus," J. Virol., Mar. 2003;77(6):3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.
Nodelijk et al., "A quantitative assessment of the effectiveness of PRRSV vaccination in pigs under experimental conditions". Vaccine, vol. 19, 2000, pp. 3636-3644.
Notice of Opposition by Akzo Nobel against European Patent No. 0 587 780, Nov. 28, 1995, EP.
Notice of Opposition by Cyanamid Iberica against European Patent No. 0 587 780, Nov. 28, 1995, EP.
Nuttall, P.A., "Growth Characteristics of Two Strains of Bovine Virus Diarrhoea Virus". Archives of Virology, vol. 66, 1980, pp. 365-369.
Office Action in CA 2,650,236 dated Feb. 9, 2011.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes," J. Virol., 200, Apr. 1; 75(7):3277-3290.
Oleksiewicz, M.B. et al., "Procine B-cells recognize epitopes that are conserved between the structural proteins of American and European-type procine reproductive and respiratory syndrome virus", Journal of General Biology, 2002, vol. 83, p. 1407-1418.
Oleksiewicz, M.B. et al., "Semen from boars infected with porcine reproductive and respiratory syndrome virus (PRRSV) contains antibodies against structural as well as nonstructural viral proteins," Veterinary Microbiology, 81:109-125 (2001).
Oleksiewicz, M.B. et al., "Sensitive detection and typing of porcine reproductive and respiratory syndrome virus by RT-PCR amplification of whole viral genes", Veterinary Microbiology 64(1998) 7-22.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain," J. Virol., May 2002; 76(9):4241-4250. Erratum in J. Virol, Jul. 2002:76(13):6863.
Pan et al., "Replication of African swine fever virus in cell cultures". American Journal of Veterinary Research, vol. 41, No. 9, Sep. 1980, pp. 1357-1367.
Pardoll et al., "Exposing the Immunology of Naked DNA Vaccines", Immunity—Cambridge, MA, vol. 3, No. 2 (1995) pp. 165-169.
Park et al., "Pathogenesis of plaque variants of porcine reproductive and respiratory syndrome virus in pregnant sows," Am. J. Vet. Res., Mar. 1996;57(3):320-323.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Paton et al., "'Blue ear' disesase of pigs," Vet. Rec., 1991, 128:617.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Pattnaik et al., "Comparison of liquid-phase and Mab-blocking ELISA for assessment of the reactivity of monoclonal antibodies to foot-and-mouth disease virus," J. Immunol. Methods, 1994;172:265-267.
Pattnaik et al., "Infectious Defective Interfering Particles of VSV from Transcripts of a cDNA Clone," Cell, Jun. 12, 1992;69:1011-1020.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.
Pejsak et al., "Clinical signs and economic losses caused by porcine reproductive and respiratory syndrome virus in a large breeding farm". Veterinary Microbiology, vol. 44, 1997, pp. 317-322.
de Antonio et al., "Quantitative Detection of Porcine Interferon-Gamma in Response to Mitogen, Superantigen and Recall Viral Antigen" Veterinary Immunology and Immunopathology, vol. 61, (1998) 265-277.
De Mazancourt et al., "Antibody response to the rubella virus structural proteins in infants with the congenital rubella syndrome". Journal of Medical Virology, vol. 19, No. 2, Jun. 1986, pp. 111-122.
De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.
De Vries et al., "The Genome Organization of the Nidovirales: Similarities and Differences between Arteri-, Toro-, and Coronaviruses". Seminars in Virology, vol. 8, 1997, pp. 33-47.
De Vries, et al., "All subgenomic mRNAs of equine arteritis virus contain a common leader sequence". Nucleic Acids Research, vol. 18, No. 11, 1990, pp. 3241-3247.
Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.
Dea et al., "Antigenic variant of swine influenza virus causing proliferative and necrotizing pneumonia in pigs". Journal of Veterinary Diagnostic Investigation, vol. 4, No. 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Ultrastructural Characteristics and Morphogenesis of Porcine Reproductive and Respiratory Syndrome Virus propagated in the highly Permissive Marc-145 Cell Clone", Corona- and reated

(56) References Cited

OTHER PUBLICATIONS viruses, 1994, Proceedings of the Sixth International Symposium on corona- and related viruses, Aug. 27, 1994-Sep. 1, 1994, pp. 95-98.
Dea et al., "Virus Isolations from Farms in Quebec Experiencing Severe Outbreaks of Respiratory and Reproductive Problems". Proceedings of the Mystery Swine Disease Committee Meeting, Denver, Co, Oct. 6, 1990, pp. 67-72.
Del Val et al., "Glycosylated components of African swine fever virus particles". Virology, vol. 152, No. 1, Jul. 1986, pp. 39-49.
den Boon et al., "Equine Arteritis virus is not a togavirus but belongs to the Coronaviruslike superfamily," J. Virol, 1991, 65(6)2910-2920.
den Boon et al., "Processing and Evolution of the N-Terminal Region of the Arterivirus Replicase ORF1a Protein: Identification of Two Papainlike Cysteine Proteases," J. Virol., Jul. 1995;69(7):4500-4505.
Deng et al., "An improved procedure for utilizing terminal transferase to add homopolymers to the 3' termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Diamond, "Real-space refinement of the structure of hen egg-white lysozyme," J. Mol. Biol., 1974, 82:371-391.
Dianzani et al., "Is Human Immunodeficiency Virus RNA Load Composed of Neutralized Immune Complexes". The Journal of Infectious Diseases, vol. 185, 2002, pp. 1051-1054.
Dildrop et al., "Immunoglobulin V region variants in hybridoma cells. II. Recombination between V genes". The EMBO Journal, vol. 1, No. 5, 1982, pp. 635-640.
Donnelly et al., "Protective Efficacy of Intramuscular Immunization with Naked DNA", Annuals New York Academy of Sciences DNA Vaccines: A New Era in Vaccinology, vol. 772 (1995), pp. 40-46.
Dreher, T.W., "Functions of the 3'-Untranslated Regions of Positive Strand RNA Viral Genomes". Annual Review of Phytopathology, vol. 37, 1999, pp. 151-174.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9 to 10, 1995, Copenhagen, Denmark, 2 pages.
Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.
Easterday, B.C., (Part Two of Two—pp. 286-315), "Swine Influenza". Diseases of Swine, Sixth Edition, Iowa State University Press, 1986, pp. 244-315.. This NPL is too large for EFS submission. Therefore filing in two parts.
Easterday, B.C., "Swine Influenza". Diseases of Swine, Sixth Edition, Iowa State University Press, 1986, pp. 244-315. (Part One of Two—pp. 244-285). This NPL is too large for EFS submission. Therefore filing in two parts.
Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.

Ehresmann et al., "RNA synthesized in calicivirus-infected cells is atypical of picornaviruses". Journal of Virology, vol. 22, No. 2, May 1977, pp. 572-576.
Ellis, R.W., "New Technologies for Making Vaccines". Vaccines, Chapter 29, Plotkin et al Eds., WB Saunders Company, Philadelphia, PA, 1988, pp. 568-575.
Enjuanes et al., "Isolation and Properties of the DNA of African Swine Fever (ASF) Virus". Journal of General Virology, vol. 32, No. 3, Sep. 1976, pp. 479-492.
*Enzo Biochem Inc.* v. *Gen-Probe Incorporated et al.*, No. 01-01230; Decided Jul. 15, 2002.
Estes et al., "Simian rotavirus SA11 replication in cell cultures". Journal of Virology, vol. 31, No. 3, Sep. 1979, pp. 810-815.
Fang et al., "Heterogeneity in Nsp2 of European-like porcine reproductive and respiratory syndrome viruses isolated in the United States," Virus Res., 2004;100:229-235.
Fenner et al., "Immunization against Viral Diseases", Veterinary Virology, Ch. 14, 1992, pp. 265-271.
Fenner et al., "Viral Genetics and Evolution", Veterinary Virology, Ch. 5, 1992, pp. 89-95.
Ferrari et al., "Isolation of Cytopathic Strains of Rotavirus from Pigs". Microbiologica, vol. 9, No. 3, Jul. 1986, pp. 287-294.
Flint et al., "Virus Cultivation, Detection, and Genetics". Virology, Molecular Biology, Pathogenesis, and Control, Ch. 2, 2000, pp. 40-42.
Foss et al., "Adjuvant Danger Signals Increase the Immune Response to Porcine Reproductive and Respiratory Syndrome Virus". Viral Immunology, vol. 15, No. 4, 2002, pp. 557-566.
Frolov et al., "Alphavirus-based expression vectors: Strategies and applications". Proceedings of the National Academy of Sciences, vol. 93, Oct. 1996, pp. 11371-11377.
Fu et al., "Detection and survival of group A rotavirus in a piggery". Veterinary Record, vol. 125, 1989, pp. 576-578.
Fukuhara et al., "Evidence for endocytosis-independent infection by human rotavirus". Archives of Virology, vol. 97, Nos. 1-2, 1987, pp. 93-99.
Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.
Gao et al., "Genomic characterization of two Chinese isolates of Porcine respiratory and reproductive syndrome virus," Arch. Virol., 2004;149: 1341-1351.
Garwes, D.J., "Transmissible gastroenteritis". Veterinary Record, vol. 122, 1988, pp. 462-463.
Geisbert et al., "Use of Immunoelectron Microscopy to Show Ebola Virus During the 1989 United States Epizootic". Journal of Clinical Pathology, vol. 43, No. 10, Oct. 1990, pp. 813-816.
Girard et al., "Experimentally induced porcine proliferative and necrotising pneumonia with an influenza A virus". The Veterinary Record, vol. 130, Mar. 1992, pp. 206-207.
Godeny et al., "Map location of lactate dehydrogenase-elevating virus (LDV) capsid protein (Vpl) gene", Virology, vol. 177, No. 2, Aug. 1990, pp. 768-771.
Godeny et al., "Simian hemorrhagic fever virus: another ember of the Coronavirus-like superfamily," Proceedings of the 9th International Congress of Virology, Aug. 8-13, 1993, Glasgow, Scotland, p. 22, Abstract No. W4-8.
Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.
Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.
Goldstein, et al., "Evaluation of Three Cell Culture Systems as Substrates for Influenza Virus Assay". Applied Microbiology, vol. 19, No. 4, Apr. 1970, pp. 580-582.
Gong et al., "Characterization of RNA synthesis during a one-step growth curve and of the replication mechanism of bovine viral diarrhoea virus". Journal of General Virology, vol. 77, 1996, pp. 2729-2736.
Gorbalenya et al., "Nidovirales: Evolving the largest RNA virus genome," Virus Res., 2006;117:17-37. Epub Feb. 28, 2006.

(56) References Cited

OTHER PUBLICATIONS

Gorcyca et al., RespPRRS: A new tool for the prevention and control of PRRS in pigs. Proceedings of the American Association of Swine Practitioners, Omaha, Nebraska, Mar. 1995, pp. 1-22.

Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.

Goyal, S., "Porcine Reproductive and Respiratory Syndrome", Journal of Veterinary Diagnostic Investigation, vol. 5, No. 4, 1993, pp. 656-664.

Graham et al., "Characteristics of a Human Cell Line Transformed by DNA from Human Adenovirus Type 5", Journal of General Virology, vol. 36, (1977) pp. 59-72.

Gravell et al., "Differences among isolates of simian hemorrhagic fever (SHF) virus". Proceedings of the Society for Experimental Biology and Medicine, vol. 181, No. 1, 1986, pp. 112-119.

Graves, J.H., "Swine Vesicular Disease". Diseases of Swine, Fifth Edition, Chapter 23, The Iowa State University Press, Ames, Iowa, 1958, pp. 288-293.

Grebennikova et al., "Genomic characterization of virulent, attenuated, and revertant passages of a North American porcine reproductive and respiratory syndrome virus strain". Virology, vol. 321, 2004, pp. 383-390.

Greiner et al., "Quantitative relationship of systemic virus concentration on growth and immune response in pigs". Journal of Animal Science, vol. 78, 2000, pp. 2690-2695.

Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.

Groot Bramel-Verheije et al., "Expression of a Foreign Epitope by Porcine Reproductive and Respiratory Syndrome Virus," Virol., 2000;278:380-389.

Grouse, L.D., "Swine Flue Sequelae"., Journal of the American Medical Association, vol. 243, No. 24, 1980, p. 2489.

Grunert et al., "Sensitivity of Influenza A/New Jersey/8/76 (HswlNI) Virus to Amantadine-HCI". Journal of Infectious Diseases, vol. 136, No. 2, 1977, pp. 297-300.

Guan et al., "Requirement of a 5?—Proximal Linear Sequence on Minus Strands for Plus-Strand Synthesis of a Satellite RNA Associated with Turnip Crinkle Virus". Virology, vol. 268, No. 2, Mar. 2000, pp. 355-363.

Guarino, Helena et al., "Detection of procine reproductive and respiratory syndrome virus by reverse transcription-polymerase chain reaction using different regions of the viral genome", J. Vet Diagn Invest 11:27-33 (1999).

Gubler et al., "A simple and very efficient method for generating cDNA libraries". Gene, vol. 25, 1983, pp. 263-269.

Gustafson, D.P., "Pseudorabies". Diseases of Swine, Fifth Edition, Ch. 14, The Iowa State University Press, Ames, Iowa, 1981, pp. 209-223.

Halbur et al., "Comparative Pathogenicity of Nine US Porcine Reproductive and Respiratory Syndrome Virus (PRRSV) Isolates in a Five-Week-Old Cesarean-Derived, Colostrum-Deprived Pig Model", Journal of Veterinary Diagnositic Investigation, vol. 8, No. 1, (1996) pp. 11-20.

Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.

Halbur et al., "Immunohistochemical Identification of Porcine Reproductive and Respiratory Syndrome Virus (pRRSV) Antigen in the Heart and Lymphoid System of Three-week-old Colostrum-deprived Pigs," Vet. Pathol., 1995;32:200-204.

Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.

Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.

Hamajima et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., Aug. 1998;88(2):205-210.

Han et al., "Complete genome analysis of RFLP 184 isolates of porcine reproductive and respiratory syndrome virus," Vir. Res., 2006;122: 175-182.

Han et al., "Identification of Nonessential Regions of the nsp2 Replicase Protein of Porcine reproductive and Respiratory Syndrome Virus Strain VR-2332 for Replication in Cell Culture", (Journal of Virology 81:9878-9890, 2007).

Hao et al., "Polymorphic genetic characterization of the ORF7 gene of porcine reproductive and respiratory syndrome virus (PRRSV) in China". Virology Journal, vol. 8:73, pp. 1-9, (2011).

Harlow et al., Antibodies: A Laboratory Manual, Cold Spring Harbor Labora~ory Press, Cold Spring Harbor, NY; title page, publisher's page, and table of contents only, 9 pages (1988).

Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.

Heath, et al., "The Behaviour of Some Influenza Viruses in Tissue Cultures of Kidney Cells of Various Species". Archie. f. Virusforschung Bd. VIII, HS, 1958, pp. 577-591.

Hedger et al., "Swine Vesicular Disease Virus". Virus Infections of Porcines, Elsevier Science Publishers, B.V., 1989, pp. 241-250.

Hill, "Overview and history of mystery swine disease (swine infertility and respiratory syndrome)," Proceedings of the Mystery Swine Disease Committee Meeting, Oct. 6, 1990, Denver, CO, Livestock Conservation Institute, Madison, WI, p. 29-30.

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241.

Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.

Howard et al., Veterinary Immunology and Immunopathology, vol. 102, Issues 1-2 and 4, cover page, title page, and table of contents: 7 pgs.

Hsu et al., "Use of Avidin-Biotin-Peroxidase Complex (ABC) in Immunoperoxidase Techniques: A Comparison between ABC and

(56) References Cited

OTHER PUBLICATIONS

Unlabeled Antibody (PAP) Procedures", Journal of Histochemistry and Cytochemistry, vol. 29, (1981) pp. 577-580.
Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.
Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.
Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.
Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.
Hyllseth, B., "Structural Proteins of Equine Arteritis Virus". Archiv Für die gesamte Virusforschung, vol. 30, 1973, pp. 177-188.
Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.
Imagawa et al., "Isolation of Foal Rotavirus in MA-104 Cells". Bulleting of Equine Research Institute, vol. 18, 1981, pp. 119-128.
Imoto et al., "Vertebrate Lysozymes", the Enzymes 1972, Chapter 21, 7:665-868, Academic Press NY.
International Preliminary Examination Report for PCT/NL02/00314 mailed Aug. 26, 2003.
International Search Report and Written Opinion for PCT/EP2006/050098 mailed on Oct. 2, 2007.
International Search Report and Written Opinion for PCT/US2005/021973 mailed on Jan. 4, 2006.
International Search Report and Written Opinion for PCT/US2005/33760 mailed on Apr. 5, 2006.
International Search Report and Written Opinion for PCT/US2008/58898 mailed on Jun. 26, 2008.
International Search Report and Written Opinion for PCT/US2009/054775 mailed Nov. 23, 2009.
International Search Report for PCT/NL1992/00096 mailed on Sep. 15, 1992.
International Search Report for PCT/NL1997/00593 mailed on Mar. 6, 1998.
International Search Report for PCT/NL2000/00152 mailed on Jul. 6, 2000.
International Search Report for PCT/NL2001/00382 mailed on Sep. 12, 2001.
International Search Report for PCT/NL2002/00314 mailed on Aug. 14, 2002.
International Search Report for PCT/US1992/06873 mailed on Nov. 25, 1992.
International Search Report for PCT/US1995/09927 mailed Oct. 19, 1995.
International Search Report for PCT/US1996/06800 mailed on Sep. 5, 1996.
International Search Report for PCT/US2000/10852 mailed on Aug. 3, 2000.
International Search Report for PCT/US92/07826 mailed on Feb. 25, 1993.
Ivanov et al., "Major genetic marker of nidoviruses encodes a replicative endoribonuclease," PNAS, Aug. 24, 2004;101 (34):12694-12699.
Izeta et al., "Replication and Packaging of Transmissible Gastroenteritis Coronavirus-Derived Synthetic Minigenomes". Journal of Virology, vol. 73, No. 2, Feb. 1999, pp. 1535-1545.
Jackwood et al., "Replication of Infectious Bursal Disease Virus in Continuous Cell Lines". Avian Diseases, vol. 31, No. 2, Apr.-Jun. 1987, pp. 370-375.

Johnson et al., "Feline panleucopaenia virus. IV. Methods for obtaining reproducible in vitro results". Research in Veterinary Science, vol. 8, No. 2, Apr. 1967, pp. 256-264.
Johnson et al., "Pathogenic and humoral immune responses to porcine reproductive and respiratory syndrome virus (PRRSV) are related to viral load in acute infection," Vet. Immunol. Immunopathol., 2004, 102:233-247.
Johnson et al., "Replication of Flock House Virus RNAs from Primary Transcripts Made in Cells by RNA Polymerase II," J. Virol., Apr. 1997; 71 (4): 3323-3327.
Johnston et al., "Genetic to genomic vaccination". Vaccine, vol. 15, No. 8, 1997, pp. 808-809.
Joo et al., "Encephalomyocarditis Virus As a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kapur et al., "Genetic variation in porcine reproductive and respiratory syndrome virus isolates in the midwestern United States," J. Gen. Virol., 1996;77:1271-1276.
Kasza et al., "Establishment, viral susceptibility and biological characteristics of a swine kidney cell line SK-6". Research in Veterinary Science, vol. 13, No. 1, Jan. 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reproductive and respiratory syndrome virus (PRRSV) are encloded by the carboxyterminal portion of viral open reading frame 3", Veterinary microbiology, vol. 44, 1995, pp. 65-76.
Keffaber, K, "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Characterization of encephalomyocarditis virus isolated from aborted swine fetuses" Am J Vet Res., 1991, 52(10):1649-1652.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation of MA-104 cell line," Arch. Virol., 1993;133:477-483.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Sympo-

(56) References Cited

OTHER PUBLICATIONS sium, PRRS and PRRSV-Related Diseases: Prevention and Control Strategies, Chicago, IL, Nov. 30-Dec. 1, 2007.

Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.

Penzes et al., "Characterization of a Replicating and Packaged Defective RNA of Avian Coronavirus Infectious Bronchitis Virus". vol. 203, No. 2, Sep. 1994, pp. 286-293.

Percy et al., "Expression of a Foreign Protein by Influenza A Virus". Journal of Virology, vol. 68, No. 7, Jul. 1994, pp. 4486-4492.

Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.

Plagemann and Moennig, "Lactate Dehydrogenase-elevating virus, equine arteritis virus, and simian hemorrhagic fever virus: a new group of positive-strnad RNA viruses," Adv. Vir. Res., 1992 41:99-192.

Plagemann et al., "The primary neutralization epitope of porcine respiratory and reproductive syndrome virus strain VR-2332 is located in the middle of the GP5 ectodomain," Arch. Virol. ,2002;147:2327-2347.

Plagemann P.G., "Complexity of the Single Linear Neutralization Epitope of the Mouse Arterivirus Lactate Dehydrogenase-Elevating Virus," Virology, 2001;290:11-20.

Plagemann, "Lactate Dehydrogenase-elevating virus and related viruses," Fields Virology, 1996, 3rd ed. Fields et al. (eds.), Philadelphia, Lippincott-Raven, p. 1105-1120.

Plotkin, Stanley A. MD et al., "New Technologies for Making Vaccines", Vaccines, 1988, 568-575.

Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.

Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.

Polson et al., "Financial Implications of Mystery Swine Disease (MSD)". 1993, pp. 8-28.

Polson, DD, "Answers to Your Questions on PRRS". NOBL Laboratories, 1993, 18 Pages.

Polson, DD, "RespPRRS a PRRS Vaccine Review", NOBL Laboratories, 1993, 22 pages.

Porcine reproductive and respiratory syndrome virus antibody test kit, 1997, IDEXX Laboratories, 4 pages.

Poser, C.M., "Swine Influenza Vaccination: Truth and Consequences". Archives of Neurology, vol. 42, No. 11, 1985, pp. 1090-1092.

Potgieter et al., "Isolation of Swine Influenza Virus in Oklahoma". Journal of the American Veterinary Medical Association, vol. 171, No. 8, 1977, pp. 758-760.

Potts et al., "Peroxidase-labeled primary antibody method for detection of pestivirus contamination in cell cultures". Journal of Virological Methods, vol. 26, No. 1, Oct. 1989, pp. 119-124.

Prager et al., "Widespread distribution of lysozyme g in egg white of birds," J. Biol. Chem., 1974, 249(22):7295-7297.

Quaife, T. "Mystery Agent Isolated! Isolation of the etiological agent behind mystery swine disease is a major breakthrough". Swine Practitioner, Mystery Disease: Part 8, Nov. 1991, pp. 4-7.

Reed et al., "A Simple Method of Estimating Fifty Per Cent Endpoints"., The American Journal of Hygiene, vol. 27, No. 3, May 1938, pp. 493-497.

Reed et al., "Persistent Respiratory Virus Infection in Tracheal Organ Cultures". British Journal of Experimental Pathology, vol. 50, 1969, pp. 378-388.

Response to Opposition to European Patent No. 0 587 780, Aug. 30, 1996.

Rice et al., "Production of Infectious RNA Transcripts from Sindbis Virus cDNA Clones: Mapping of Lethal Mutations, Rescue of a Temperature-Sensitive Marker, and in Vitro Mutagenesis to Generate Defined Mutants". Journal of Virology, vol. 61, No. 12, Dec. 1987, pp. 3809-3819.

Roberts and Bazer, "The functions of uterine secretions," J. Reprod. Fert., 1988, 82:875-892.

Roberts et al., "Abortion in Swine". Veterinary Ostetrics and Genital Diseases, Edwards Brothers, Inc., Ann Arbor, 1986, pp. 180-192.

Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.

Ropp et al., "Characterization of Emerging European-Like Porcine Reproductive and Respiratory Syndrome Virus Isolates in the United States," J. Virol., Apr. 2004; 78(7):3684-3703.

Rossow et al., "Experimental porcine reproductive and respiratory syndrome virus infection in one-, four-, and 10-week-old pigs". Journal of Veterinary Diagnostic Investigation, vol. 6, 1993, pp. 3-12.

Rossow et al., "Pathogenesis of Porcine Reproductive and Respiratory Syndrome Virus Infection in Gnotobiotic Pigs", Veterinary Pathology, vol. 32, No. 4, (1995) pp. 361-373.

Rossow K.D., "Porcine Reproductive and Respiratory Syndrome," Vet. Pathol., 1998;35:1-20.

Rost et al., "Topology prediction for helical transmembrane proteins at 86% accuracY,"Protein Sci., 1996;5:1704-1718.

Rost et al.,"The PredictProtein server," Nucleic Acids Res., 2004;32(Web Server issue):W321-326.

Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.

Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.

Rottier et al., "Predicted Membrane Topology of the Coronavirus Protein E1". Biochemistry, vol. 25, 1986, pp. 1335-1339.

Rovira et al., "Experimental Inoculation of Conventional Pigs with Porcine Reproductive and Respiratory Syndrome virus and Porcine Circovirus 2", J. Virol, Apr. 2002, vol. 76, No. 7, pp. 3232-3239.

Rowland et al., "The localization of porcine reproductive and respiratory syndrome virus nucleocapsid protein to the nucleolus of infected cells and identification of a potential nucleolar localization signal sequence," Virus Res., 1999;64:1-12.

Sagripanti et al., "The Cap Structure of Simian Hemorrhagic Fever Virion RNA". Virology, vol. 151, 1986, pp. 143-150.

Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.

Saif, L.J., "Coronavirus Immunogens". Veterinary Microbiology, vol. 37, No. 3-4, Nov. 1993, pp. 285-297.

Sambrook et al., Molecular Cloning: A Laboratory Manual, Books 1-3, Cold Spring Harbor Laboratory Press, Cold Spring Harbor, NY, 1989; title page, publisher's page and table of contents only (30) pgs.

Sarnow, P. "Role of 3'-End Sequences in Infectivity of Poliovirus Transcripts Made in Vitro". Journal of Virology, vol. 63, No. 1, Jan. 1989, pp. 467-470.

Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.

Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.

Scott, F.W., "Immunization against feline coronaviruses". Advances in Experimental Medicine and Biology, vol. 218, 1987, pp. 569-576.

Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

(56) References Cited

OTHER PUBLICATIONS

Seal et al., "Isolation of caliciviruses from skunks that are antigenically and genotypically related to San Miguel sea lion virus Original Research". Virus Research, vol. 37, No. 1, Jun. 1995, pp. 1-12.
Seneca, H., "Influenza: epidemiology, etiology, immunization and management". Journal of American Geriatrics Society, vol. 28, No. 6, Jun. 1980, pp. 241-250.
Sethna et al., "Coronavirus subgenomic minus-strand RNAs and the potential for mRNA replicons". Proceedings of the National Academy of Sciences, vol. 86, Jul. 1989, pp. 5626-5630.
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.
"Frontiers closing to mystery disease pigs". Animal Pharm., No. 228, May 24, 1991, p. 2.
"Revision of the taxonomy of the Coronavirus, Torovirus, and Arterivirus genera". Archives of Virology, vol. 135, 1994, pp. 227-239.
Abdallah et al., "Non-Viral Gene Transfer: Applications in Developmental Biology and Gene Therapy", Biology of the Cell, vol. 85, No. 1 (1995), pp. 1-7.
Abstracts of Papers Presented at the 71st Annual Meeting of the Conference of Research Workers in Animal Disease, No.'s 1-6, Nov. 5-6, 1990, 2 pages.
Aksenova et al., "Cultivation of the rabies virus in the continuous kidney cell line 4647 from the green marmoset". Vopr. Virusol., vol. 30, No. 2, 1985, pp. 180-182. (See AXENOVA for English Abstract).
Albina et al., "Immune responses in pigs infected with porcine reproductive and respiratory syndrome virus (PRRSV)". Veterinary Immunology and Immunopathology, vol. 61, 1998, pp. 49-66.
Albina, "Porcine reproductive and respiratory syndrome: Ten years of experience (1986-1996) with this undesirable virus infections," Veterinary Research (Paris), 1997, 28(4): 305-352.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allende et al., "Mutations in the genome of porcine reproductive and respiratory syndrome virus responsible for the attenuation phenotype," Arch. Virol., 2000, 145(6):1149-1161.
Allende et al., "North American and European porcine reproductive and respiratory syndrome viruses differ in non-sructural protein coding regions," J. Gen. Virol., 1999;80:307-315.
Altschul et al., "Basic Local Alignment Search Tool". Journal of Molecular Biology, vol. 215, 1990, pp. 403-410.
Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.
Ashworth et al., "Antibody-dependent cell-mediated cytotoxicity (ADCC) in Aujeszky's disease". Archives of Virology, vol. 59, No. 4, 1979, pp. 307-318.
Ausubel et al. (eds.), "Purification of proteins by precipitation," Short Protocols in Molecular Biology, 1992, Ch. 10, Section VI, Green Publishing Associates and John Wiley & Sons.
Ausubel, et al., "Current Protocols in Molecular Biology" vol. 1, (1994), Table of Contents.
Axenova, T.A. "Propagation of Rabies Vaccine Virus in Continuous Green Monkey Kidney Cells 4647". Vopr. Virusol., vol. 30, No. 2, 1985, p. 182. (English Abstract of AKSENOVA Reference.)
Backstrom et al., "Respiratory Diseases of Swine". Veterinary Clinics of North America: Large Animal Practice, vol. 4, No. 2, Nov. 1982, pp. 259-276.
Bairoch et al., "The PROSITE database, its status in 1997," Nucleic Acids Res., 1997;25(1):217-221.
Baldo et al., "Comparison of different blocking agents and nitrocelluloses in the solid phase detection of proteins by labelled antisera and protein A," J. Biochem. Biophys. Meth., 1986, 12:271-279.

Bardfoed, Annette M. et al., DNA vaccination of pigs with open reading fram 107 of PRRS virus, Vaccine, vol. 22, 3628-3641, Apr. 10, 2004.
Barfoed et al., "DNA vaccination of pigs with open reading frame 1-7 of PRRS virus". Vaccine, vol. 22, 2004, pp. 3628-3641.
Baric et al., "Interactions between Coronavirus Nucleocapsid Protein and Viral RNAs: Implications for Viral Transcription". Journal of Virology, vol. 62, No. 11, Nov. 1988, pp. 4280-4287.
Baric et al., "Subgenomic Negative-Strand RNA Function during Mouse Hepatitis Virus Infection". Journal of Virology, vol. 74, No. 9, May 2000, pp. 4039-4046.
Bautista et al., "Comparison of porcine alveolar macrophages and CL 2621 for the detection of porcine reproductive and respiratory syndrome (PRRS) virus and anti-PRRS antibody," J. Vet. Diagn. Invest., 1993;5:163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, AJ, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Bendtsen et al., "Improved Prediction of Signal Peptides: SignalP 3.0," J. Mol. Biol., 2004;340:783-795.
Benfield et al, Characterization of swine infertility and respiratory syndrome (SIRS) virus (isolate ATCC VR-2332), J. Vet. Diagn. Invest. 4:127-133, 1992.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.
Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.
Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.
Bierk et al., "Diagnostic investigation of chronic porcine reproductive and respiratory syndrome virus in a breeding herd of pigs," Vet. Rec., 2001, 148:687-690.
Bilodeau et al., "Porcine Reproductive and Respiratory Syndrome' in Quebec". The Veterinary Record, Aug. 3, 1991, p. 102.
Blackburn et al., "Use of human influenza vaccine to protect against blue-eared pig disease". Veterinary Record, vol. 129, No. 1, Jul. 1991, p. 19.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Bouillant et al., "Viral Susceptibility of a Cell Line Derived from the Pig Oviduct". Canadian Journal of Comparative Medicine, vol. 39, 1975, pp. 450-456.
Boursnell et al., "Sequence of the membrane protein gene from avian coronavirus IBV". Virus Research, vol. 1, 1984, pp. 303-313.
Boursnell et all., "Completion of the Sequence of the Genome of the Coronavirus Avian Infectious Bronchitis Virus". Journal of General Virology, vol. 68, 1987, pp. 57-77.
Bowie et al., "Deciphering the Message of Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, No. 2, Feb. 1994, pp. 415-426.
Bramel-Verheije et al., "Expression of a Foreign Epitope by Porcine Reproductive and Respiratory Syndrome Virus". Virology, vol. 278, 2000, pp. 380-389.

(56) References Cited

OTHER PUBLICATIONS

Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.
Brenner et al., "A Negative Staining Method for High Resolution Electron Microscopy of Viruses". Biochimica Et Biophysica Acta, vol. 34, 1959, pp. 103-110.
Brinton-Darnell et al., "Structure and chemical-physical characteristics of lactate dehydrogenase-elevating virus and its RNA". Journal of Virology, vol. 16, No. 2, Aug. 1975, pp. 420-433.
Brinton-Darnell, M. "Lactate Dehydrogenase-Elevating, Equine Arteritis and Lelystad Viruses". Encyclopedia of Virology, vol. 2, 1999, pp. 763-771.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp, Barbara G. et al., "Sequence and Expression of the Glycoprotein gH Gene of pseudorabies Virus", Virology 182:732-741, 1991.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
Kouvelos et al., "Comparison of Bovine, Simian and Human Rotavirus Structural Glycoproteins". Journal of General Virology, vol. 65, Jul. 1984, pp. 1211-1214.
Kreutz, L.C., "Cellular membrane factors are the major determinants of porcine reproductive and respiratory syndrome virus tropism". Virus Research, vol. 53, 1998, pp. 121-128.
Krogh et al., "Predicting Transmembrane Protein Topology with a Hidden Markov Model: Application to Complete Genomes," J. Mol. Biol., 2001;305:567-580.
Kundin, W.D., "Hong Kong A-2 Influenza Virus Infection among Swine during a Human Epidemic in Taiwan". Nature, vol. 228, Nov. 1970, p. 857.
Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.
Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.
Kutsuzawa et al., "Isolation of Human Rotavirus Subgroups 1 and 2 in Cell Culture". Journal of Clinical Microbiology, vol. 16, No. 4, Oct. 1982, pp. 727-730.
Kwang et al., "Antibody and Cellular Immune Responses of Swine Following Immunisation with Plasmid DNA including the PRRS Virus ORF's 4,5,6 and 7", Short Communication. Research in Veterinary Science (1999) vol. 67, pp. 199-201.
Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Laemmli, "Cleavage of structural proteins during the assembly of the head of bacteriophage T4," Nature, 1974, 227:680-684.
Lai et al., "Coronavirus: how a large RNA viral genome is replicated and transcribed". Infectious Agents and Disease, vol. 3, Nos. 2-3, 1994, pp. 98-105.
Lai et al., "Coronavirus: organization, replication and expression of genome". Annual Review of Microbiology, vol. 33, 1990, pp. 303-333.
Lai et al., "Infectious RNA transcribed from stably cloned full-length cDNA of dengue type 4 virus". Proceedings of the National Academy of Sciences, vol. 88, Jun. 1991, pp. 5139-5143.
Lai M.M.C., "Transcription, Replication, Recombination, and Engineering of Coronavirus Genes," Advances in Experimental Medicine and Biology Corona- and Related Viruses, New York, NY, 1995;463-472.
Larochelle et al., "Detection of porcine reproductive and respiratory syndrome virus in paraffin-embedded tissues: comparision of immunohistochemistry and in situ hybridization", Journal of Virological Methods. 1997; 63: 227-235.
Larochelle et al., "Evaluation of the presence of procine reproductive and respiratory syndrome virus in packaged pig meat using virus isolation and plymerase chain reaction (PCR) method", Veterinary Microbiology. 1997; 58: 1-8.
Larochelle, R. et al., "Differentiation of North American and European porcine reproductive and respiratory syndrome virus genotypes by in situ hybridization", Journal of Virological Methods 68 (1997) 161-168.
Lawson et al., "Porcine reproductive and respiratory syndrome virus infection of gnotobiotic pigs: sites of virus replication and co-localization with MAC-387 staining at 21 dats post-infection," Virus Res., 1997, 51:105-113.
Lazar et al., "Transforming Growth Factor a: Mutation of Aspartic Acid 47 and Leucine 48 Results in Different Biological Activities". Molecular and Cellular Biology, vol. 8, No. 3, Mar. 1988, pp. 1247-1252.
Lee et al., "A DNA-launched reverse genetics system for porcine reproductive and respiratory syndrome virus reveals that homodimerization of the nucleocapsid protein is essential for virus infectivity," Virol., 2005;331:47-62.
Lee et al., "Mutations within the nuclear localization signal of the porcine reproductive and respiratory syndrome virus nucleocapsid protein attenuate virus replication," Virol., 2006; 346:238-250.
Leitner et al., "DNA and RNA-based vaccines: principles, progress and prospects". Vaccine, vol. 18, 2000, pp. 765-777.
Levy et al., "Freeze-drying is an effective method for preserving infectious type C retroviruses". Journal of Virological Methods, vol. 5, Nos. 3-4, Nov. 1982, pp. 165-171.
Liljestrom et al., "A New Generation of Animal Cell Expression Vectors Based on the Semliki Forest Virus Replicon". Nature Biotechnology, vol. 9, 1991, pp. 1356-1361.
Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.
Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.
Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.
Liu et al., "A Specific Host Cellular Protein Binding Element Near the 3? End of Mouse Hepatitis Virus Genomic RNA". Virology, vol. 232, No. 1, May 1997, pp. 74-85.
Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.
Loula, T., "Mystery Pig Disease", Agri-Practice, vol. 12, No. 1, Jan.-Feb. 1991, pp. 29-34.
Lowrie et al., "DNA Vaccines Methods and Protocols", Humana Press, Totowa, NJ (2000). Xix p. 529: ill.; 24 cm.
Luytjes et al., "Replication of Synthetic Defective Interfering RNAs Derived from Coronavirus Mouse Hepatitis Virus-A59". Virology, vol. 216, No. 1, Feb. 1996, pp. 174-183.

(56) References Cited

OTHER PUBLICATIONS

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.
Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.
Madin, S.H. "Vesicular Exanthema Virus". Virus Infections of Porcines, Elsevier Science Publishers B.V., 1989, pp. 267-271.
Magar et al., "Antigenic Comparison of Canadian and US Isolates of Porcine Reproductive and Respiratory Syndrome Virus Using Monoclonal Antibodies to the Nucleocapsid Protein," Can J Vet. Res., 1995;59:232-234.
Magar et al., "Isolation and Experimental Oral Transmission in Pigs of a Porcine Reproductive and Respiratory Syndrome Virus Isolate", Corona- and reated viruses, 1994, Proceedings of the Sixth International Symposium on corona- and related viruses, Aug. 27, 1994-Sep. 1, 1994, pp. 139-144.
Makabe et al., "Hemagglutination with Ovine Rotavirus". Archives of Virology, vol. 90, 1986, pp. 153-158.
Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.
Makino et al., "Primary Structure and Translation of a Defective Interfering RNA of Murine Coronavirus". Virology, vol. 166, 1988, pp. 550-560.
Malet et al., "from RNA to quasispecies: a DNA polymerase with proofreading activity is highly recommended for accurate assessment of viral diversity," J Virol. Methods, 2003;109:161-170.
Mardassi et al., "Identification of major differences in the nucleosapsid protein genes of a Quebec strain and European strains of porcine reproductive and respiratory syndrome virus," J Gen Virol., 1994;75:681-685.
Mardassi et al., "Molecular analysis fo the Ofs 3 to 7 of procine reproductive and respiratory syndrome virus, Quebec reference strain", 1995 Arch Virol 140: 1405-1418.
International Search Report and Written Opinion issued in PCT/US2006/024355, mailed May 10, 2007, 20 pages.
Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.
Wootton et al., "Full-length sequence of a Canadian porcine reproductive and respiratory syndrome virus (PRRSV) isolate," Arch. Virol.,2000;145:2297-2323.
Wootton et al., "Homo-Oligomerization of the Porcine Reproductive and Respiratory Syndrome Virus Nucleocapsid Protein and the Role of Disulfide Linkages," J Virol., Apr. 2003;77(8):4546-4557.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.
Wu et al., "A 10-kDa Structural Protein of Porcine Reproductive and Respiratory Syndrome Virus Encoded by ORF2b," Virology, 2001;287:183-191.
Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yang et al., "Developing Particle-Mediated Gene Transfer Technology for Research into Gene Therapy of Cancer", Molecular Medicine Today, vol. 2, No. Ref. (1996) pp. 476-481.
Yoon et al., "A modified serum neutralization test for the detection of antibody to porcine reproductive and respiratory syndrome virus in swine sera", J. Vet. Dign. Invest., 1994, 6:;289-292.
Yoon et al., "An Indirect Fluorescent Antibody Test for the Detection of Antibody to Swine Infertility and Respoiratory Syndrome Virus in Swine Area" Journal of Veterinary Diagnostic Investigation, vol. 4 (1992) pp. 144-147.
Yoon et al., "Characterization of the humoral immune response to porcine reproductive and respiratory syndrome (PRRS) virus infection," J. Vet. Diagn. Invest., 1995, 7:305-312.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Genetic and Antigenic Stability of PRRS Virus in Pigs. Field and experimental prospectives," The Nidoviruses (Coronaviruses and Arteriviruses), New York, NY, 2001, 25-30.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Characterization of heteroclite subgenomic RNAs associated with PRRSV infection," Virus Res., 2004;105:75-87.
Yuan et al., "Complete genome comparison of porcine reproductive and respiratory syndrome virus parental and attenuated strains," Virus Res., 2001;74:99-110.
Yuan et al., "Erratum to 'Complete genome comparison of porcine reproductive and respiratory syndrome virus parental and attenuated strains' [Virus Research 74 (2001) 99-110]". Virus Research, vol. 79, 2001, p. 187.
Yuan et al., "Heteroclite Subgenomic RNAs are Produced in Porcine Reproductive and Respiratory Syndrome Virus Infection," Virology, 2000;275: 158-169.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., "Recombination between North American strains of porcine reproductive and respiratory syndrome virus," Virus Res., 1999;61:87-98.
Yuan et al., American Society for Virology, 16th Annual Meeting, Bozeman, Montana, Jul. 19-23, 1997, Abstract P29-5, p. 229.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Ziebuhr et al., "Virus-encoded proteinases and proteolytic processing in the Nidovirales," J. Gen. Virol., 2000;81:853-879.
Zimmerman et al., "General overview of PRRSV: A perspective from the United States". Veterinary Microbiology, vol. 55, Nos. 1-4, Apr. 1997, pp. 187-196.
Wesley et al. "Differentiation of vaccine (strain RespPRRS) and field strains of porcine reproductive and respiratory syndrome virus by restriction enzyme analysis." Proceedings of the American Association on Swine Practitioners, Nashville, TN, USA, 1996, pp. 141-143.
Cano et al., "Impact of a modified-live porcine reproductive and respiratory syndrome virus vaccine intervention on a population of pigs infected with a heterologous isolate". Vaccine, vol. 25, 2007, pp. 4382-4391.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, 1991, pp. 5227-5232.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
Masters et al., "Functions of the coronavirus nucleocapsid protein". Coronaviruses and Their Diseases, Plenum Press, New York, 1990, pp. 235-238.

\* cited by examiner

Fig. 1A-1

```
ATGACGTATAGGTGTTGGCTCTATGCCTTGGCATTTGTATTGTCAGGAGCTGTGACCATT
GGCACAGCCCAAAACTTGCTGCACAGAAACACCCTTCTGTGATAGCCTCCTTCAGGGGAGCTTAGGGTTTGTCCCTAGCA
CCTTGCTTCCGGAGTTGCACTGCTTTACGGTCTCTCCACCCCTTTAACCATGTCTGGGATACTTGATCGGTGCACGTGTA
CCCCCAATGCCAGGGTGTTTATGGCGGAGGGCCAAGTCTACTGCACACGATGCCTCAGTGCACGGTCTCTCCTTCCCCTG
AACCTCCAGGTTTCTGAGCTCGGGGTGCTAGGCCTATTCTACAGGCCCGAAGAGCCACTCCGGTGGACGTTGCCACGTGC
ATTCCCCACTGTTGAGTGCTCCCCCGCCGGGGCCTGCTGGCTTTCTGCAATCTTTCCAATCGCACGAATGACCAGTGGAA
ACCTGAACTTCCAACAAAGAATGGTACGGGTCGCAGCTGAGCTTTACAGAGCCGGCCAGCTCACCCCTGCAGTCTTGAAG
GCTCTACAAGTTTATGAACGGGGTTGCCGCTGGTACCCCATTGTTGGACCTGTCCCTGGAGTGGCCGTTTTCGCCAATTC
CCTACATGTGAGTGATAAACCCTTCCCGGGAGCAACTCACGTGTTGACCAACCTGCCGCTCCCGCAGAGACCCAAGCCTG
AAGACTTTTGCCCCTTTGAGTGTGCTATGGCTACTGTCTATGACATTGGTCATGACGCCGTCATGTATGTGGCCGAAAGG
AAAGTCTCCTGGGCCCCTCGTGGCGGGGATGAAGTGAAATTTGAAGCTGTCCCCGGGGAGTTGAAGTTGATTGCGAACCG
GCTCCGCACCTCCTTCCCGCCCCACCACACAGTGGACATGTCTAAGTTCGCCTTCACAGCCCCTGGGTGTGGTGTTTCTA
TGCGGGTCGAACGCCAACACGGCTGCCTTCCCGCTGACACTGTCCCTGAAGGCAACTGCTGGTGGAGCTTGTTTGACTTG
CTTCCACTGGAAGTTCAGAACAAAGAAATTCGCCATGCTAACCAATTTGGCTACCAGACCAAGCATGGTGTCTCTGGCAA
GTACCTGCAGCGGAGGCTGCAAGTTAATGGTCTCCGAGCAGTAACTGACCTAAACGGACCTATCGTCGTACAGTACTTCT
CCGTTAAGGAGAGTTGGATCCGCCATTTGAAACTGGCGGGAGAACCCAGCTACTCTGGGTTTGAGGACCTCCTCAGAATA
AGGGTTGAGCCTAACACGTCGCCATTGGCTGACAAGGAAGAAAAAATTTTCCGGTTTGGCAGTCACAAGTGGTACGGCGC
TGGAAAGAGAGCAAGAAAAGCACGCTCTTGTGCGACTGCTACAGTCGCTGGCCGCGCTTTGTCCGTTCGTGAAACCCGGC
AGGCCAAGGAGCACGAGGTTGCCGGCGCCAACAAGGCTGAGCACCTCAAACACTACTCCCCGCCTGCCGAAGGGAATTGT
GGTTGGCACTGCATTTCCGCCATCGCCAACCGGATGGTGAATTCCAAATTTGAAACCACCCTTCCCGAAAGAGTGAGACC
TCCAGATGACTGGGCTACTGACGAGGATCTTGTGAATGCCATCCAAATCCTCAGACTCCCTGCGGCCTTAGACAGGAACG
GTGCTTGTACTAGCGCCAAGTACGTACTTAAGCTGGAAGGTGAGCATTGGACTGTCACTGTGACCCCTGGGATGTCCCCT
TCTTTGCTCCCTCTTGAATGTGTTCAGGGCTGTTGTGGGCACAAGGGCGGTCTTGGTTCCCCAGATGCAGTCGAGGTCTC
CGGATTTGACCCTGCCTGCCTTGACCGGCTGGCTGAGGTGATGCACCTGCCTAGCAGTGCTATCCCAGCCGCTCTGGCCG
AAATGTCTGGCGATTCCGATCGTTCGGCTTCTCCGGTCACCACCGTGTGGACTGTTTCGCAGTTCTTTGCCCGTCACAGC
GGAGGGAATCACCCTGACCAAGTGCGCTTAGGGAAAATTATCAGCCTTTGTCAGGTGATTGAGGACTGCTGCTGTTCCCA
GAACAAAACCAACCGGGTCACCCCGGAGGAGGTCGCAGCAAAGATTGACCTGTACCTCCGTGGTGCAACAAATCTTGAAG
AATGCTTGGCCAGGCTTGAGAAAGCGCGCCCGCCACGCGTAATCGACACCTCCTTTGATTGGGATGTTGTGCTCCCTGGG
GTTGAGGCGGCAACCCAGACGATCAAGCTGCCCCAGGTCAACCAGTGTCGTGCTCTGGTCCCTGTTGTGACTCAAAAGTC
CTTGGACAACAACTCGGTCCCCCTGACCGCCTTTTCACTGGCTAACTACTACTACCGTGCGCAAGGTGACGAAGTTCGTC
ACCGTGAAAGACTAACCGCCGTGCTCTCCAAGTTGGAAAAGGTTGTTCGAGAAGAATATGGGCTCATGCCAACCGAGCCT
GGTCCACGGCCCACACTGCCACGCGGGCTCGACGAACTCAAAGACCAGATGGAGGAGGACTTGCTGAAACTGGCTAACGC
CCAGACGACTTCGGACATGATGGCCTGGGCAGTCGAGCAGGTTGACCTAAAAACTTGGGTCAAGAACTACCCGCGGTGGA
CACCACCACCCCTCCGCCAAAAGTTCAGCCTCGAAAAACGAAGCCTGTCAAGAGCTTGCCGGAGAGAAAGCCTGTCCCC
GCCCCGCGCAGGAAGGTTGGGTCCGATTGTGGCAGCCCGGTTTCATTAGGCGGCGATGTCCCTAACAGTTGGGAAGATTT
GGCTGTTAGTAGCCCCTTTGATCTCCCGACCCCACCTGAGCCGGCCAACCACCTTCAAGTGAGCTGGTGATTGTGTCCTCAC
CGCAATGCATCTTCAGGCCGGCGACACCCTTGAGTGAGCCGGCTCCAATTCCCGCACCTCGCCGGAACTGTGTCTCGACCG
GTGACACCCTTGAGTGAGCCGATCCCTGTGCCCGCACCGCGGCGTAAGTTTCAGCAGGTGAAAAGATTGAGTTCGCGGC
GGCAATCCCACCGTACCAGGACGAGCCCCTGGATTTGTCTGCTTCCTCACAGACTGAATATGAGGCCTCTCCCCCAGCAC
CGCCGCAGAGCGGGGCGGTTCTGGGAGTAGAGGGGCATGAAGCTGAGGAAACCCTGAGTGAAATCTCGGACATGTCGGGT
AACATTAAACCTGCGTCCGTGTCATCAAGCAGCTCCTTGTCCAGCGTGAGAATCACACGCCCAAAATACTCAGCTCAAGC
CATCATCGACTCGGGCGGGCCCTGCAGTGGGCATCTCCAAGAGGTAAAGGAAACATGCCTTAGTGTCATGCGCGAGGCAT
GTGATGCGACTAAGCTTGATGACCCTGCTACGCAGGAATGGCTTTCTCGCATGTGGGATCGGGTGGACATGCTGACTTGG
CGCAACACGTCTGTTTACCAGGCGATTTGCACCTTAGATGGCAGGTTAAAGTTCCTCCCAAAAATTGATACTCGAGACACC
GCCGCCCTATCCGTGTGAGTTTGTGATGATGCCTCACACGGCCTGCACCTTCCGTAGGTGCGGAGAGCGACCTTACCATTG
GCTCAGTTGCTACTGAAGATGTTCCACGCATCCTCGAGAAAATAGAAATGTCGGCGAGATGGCCAACCAGGGACCCTTG
GCCTTCTCCGAGGATAAACCGGTAGATGACCAACTTGTCAACGACCCCGGATATCGTCGCGGAGGCCTGACGAGAGCAC
ATCAGCTCCGTCCGCCAGGCACAGGTGGCGCCGGCTCTTTTACCGATTTGCCGCCTTCAGATGGCGCGGATGCGGACGGGG
GGGGGCCGTTTCGGACGGTAAAAAGAAAAGCTGAAAGGCTCTTTGACCAACTGAGCCGTCAGGTTTTTGACCTCGTCTCC
CATCTCCCTGTTTTCTTCTCACGCCTTTTCTACCCTGGCGGTGGTTATTCTCCGGGTGATTGGGGTTTTGCAGCTTTTAC
TCTATTGTGCCTCTTTTTATGTTACAGTTACCCAGCCTTTGGTATTGCTCCCCTCTTGGGTGTGTTTTCTGGGTCTTCTC
GGCGCGTTCGAATGGGGGTTTTTGGCTGCTGGTTGGCTTTTGCTGTTGGTCTGTTCAAGCCTGTCTCCGACCCAGTCGGC
GCTGTTGTGAGTTTGACTCCCAGAGTGTAGAAACATCCTTCATTCTTTTGAGCTTCTCAAACCTTGGGACCCTGTTCG
CAGCCTTGTTGTGGGCCCCGTCGGTCTCGGTCTTGCCATTCTTGGCAGGTTACTGGGCGGGGCACGCTGCATCTGGCACT
TTTTGCTTAGGCTTGGCATTGTTGCAGACTGTATCTTGGCTGGAGCTTACGTGCTTTCTCAAGGTAGGTGTAAAAAGTGC
```

*Fig. 1A-2*

```
TGGGGATCTTGTATAAGAACTGCTCCCAATGAGGTCGCTTTTAACGTGTTTCCTTTCACACGTGCGACCAGGTCGTCACT
TATCGACCTGTGCGATCGGTTTTGTGCGCCAAAAGGAATGGACCCCATTTTTCTCGCCACTGGGTGGCGCGGGTGCTGGG
CCGGCCGAAGCCCCATTGAGCAACCCTCTGAAAAACCCATCGCGTTTGCCCAGTTGGATGAAAAGAAGATTACGGCTAGG
ACTGTGGTCGCCCAGCCTTATGACCCCAACCAAGCCGTAAAGTGCTTGCGGGTATTGCAGGCGGGTGGGGCGATGGTGGC
TAAGGCGGTCCCAAAAGTGGTCAAGGTTTCCGCTGTTCCATTCCGAGCCCCCTTCTTTCCCACTGGAGTGAAAGTTGACC
CTGATTGCAGGGTCGTGGTTGACCCTGACACTTTCACTGCAGCTCTCCGGTCTGGCTACTCCACCACAAACCTCGTCCTT
GGTGTGGGGGACTTTGCCCAGCTGAATGGATTAAAAATCAGGCAAATTTCCAAGCCTTCAGGGGGAGGCCCACATCTCAT
GGCTGCCCTGCATGTTGCCTGCTCGATGGCTCTGCACATGCTTGCTGGGATTTATGTGACTGCGGTGGGTTCTTGCGGCA
CCGGCACCAACGACCCGTGGTGCGCTAACCCGTTTGCCGTCCCTGGCTACGGACCTGGCTCTCTCTGCACGTCCAGATTG
TGCATTTCCCAACACGGCCTTACCCTGCCCTTGACAGCACTTGTGGCGGGATTCGGTATTCAAGAAATTGCCTTGGTCGT
TTTGATTTTTGTTTCCATCGGAGGCATGGCTCATAGGTTGAGCTGTAAGGCTGACATGCTGTGTGTCTTGCTTGCAATTG
CCAGCTATGTTTGGGTACCTCTTACCTGGTTGCTTTGTGTGTTTCCTTGCTGGTTGCGCTGTTTTTCTTTGCACCCCCTC
ACCATCCTATGGTTGGTGTTTTCTTGATTTCTGTGAATATGCCTTCAGGAATCTTGGCCATGGTGTTGTTGGTTTCTCT
TTGGCTTCTTGGTCGTTATACTAATGTTGCTGGCCTTGTCACCCCCTACGACATTCATCATTACACCAGTGGCCCCCGCG
GTGTTGCCGCCTTGGCTACCGCACCAGATGGGACCTACTTGGCCGCTGTCCGCCGCGCTGCGTTGACTGGCCGCACCATG
CTGTTTACCCCGTCCCAGCTTGGGTCTCTTCTTGAGGGTGCTTTCAGAACTCGAAAGCCCTCACTGAACACCGTCAATGT
GATCGGGTCCTCCATGGGCTCTGGCGGGGTGTTTACCATCGACGGGAAAGTCAAGTGCGTAACTGCCGCACATGTCCTTA
CGGGCAATTCAGCTCGGGTTTCCGGGGTCGGCTTCAATCAAATGCTTGACTTTGACGTAAAGGGAGATTTCGCTATAGCT
GATTGCCCGAATTGGCAAGGGGCTGCCCCCAAGACCCAATTCTGCACGGATGGATGGACTGGCCGTGCCTATTGGCTAAC
ATCCTCTGGCGTCGAACCCGGCGTCATTGGAAAAGGATTCGCCTTCTGCTTCACCGCATGTGGCGATTCCGGGTCCCCAG
TGATCACCGAGGCCGGTGAGCTTGTCGGCGTTCACACGGGATCGAATAAACAAGGGGGGGGCATTGTTACGCGCCCTCA
GGCCAGTTTTGTAATGTGGCACCCATCAAGCTAAGCGAATTAAGTGAATTCTTTGCTGGGCCTAAGGTCCCGCTCGGTGA
TGTGAAGGTCGGCAGCCACATAATTAAAGACATAAGCGAGGTGCCTTCAGATCTTTGTGCCTTGCTTGCTGCCAAACCTG
AACTGGAAGGAGGCCTCTCCACCGTCCAACTTCTTTGTGTGTTTTTCTCCTGTGGAGAATGATGGGACATGCCTGGACG
CCCTTGGTTGCTGTGAGTTTCTTTATTTTGAATGAGGTTCTCCCAGCCGTCCTGGTCCGGAGTGTTTTCTCCTTTGGAAT
GTTTGTGCTATCCTGGCTCACGCCATGGTCTGCGCAAGTTCTGATGATCAGGCTTCTGACAGCAGCTCTTAACAGGAACA
GATGGTCACTTGCCTTTTTCAGCCTCGGTGCAGTGACCGGTTTTGTCGCAGATCTTGCGGCCACTCAGGGGCATCCGTTG
CAGGCAGTGATGAATTTGAGCACCTATGCATTCCTGCCTCGGATGATGGTTGTGACCTCACCAGTCCCAGTGATCACGTG
TGGTGTCGTGCACCTACTTGCCATCATTTTGTACTTGTTTAAGTACCGTGGCCTGCACCATATCCTTGTTGGCGATGGAG
TGTTCTCTGCGGCTTTCTTCTTGAGATACTTTGCCGAGGGAAAGTTGAGGGAAGGGGTGTCGCAATCCTGCGGAATGAAT
CATGAGTCTCTGACTGGTGCCCTCGCTATGAGACTCAATGACGAGGACTTGGATTTCCTTATGAAATGGACTGATTTTAA
GTGCTTTGTTTCTGCGTCCAACATGAGGAATGCAGCGGGTCAATTTATCGAGGCTGCCTATGCTAAAGCACTTAGAGTAG
AACTGGCCCAGTTGGTGCAGGTTTGATAAAGTTCGAGGTACTTTGCCCAAACTTGAAGCTTTTGCTGATACCGTGGCACCT
CAACTCTCGCCCGGTGACATTGTTGTCGCTCTCGGCCACACGCCTGTTGGCAGTATCTTCGACCTAAAGGTTGGTAGCAC
CAAGCATACCCTCCAAGCCATTGAGACCAGACTCCTTGCTGGGTCCAAAATGACCGTGGCGCGCGTCGTCGACCCGACCC
CCACGCCCCCACCCGCACCCGTGCCCATCCCCCTCCCACCGAAAGTTCTGGAGAATGGCCCCAACGCTTGGGGGGATGAG
GACCGTTTGAATAAGAAGAAGAGGCCAGGATGGAAGCCCTCGGCATCTATGTTATGGCGGGAAAAAATACCAGAAATT
TTGGGACAAGAATTCCGGTGATGTGTTTTATGAGGAGGTCCATAATAACACAGATGAGTGGGAGTGTCTCAGAGTTGGCG
ACCCTGCCGACTTTGACCCTGAGAAGGGAACTCTGTGTGGACATGTCACCATTGAAAACAAGGCTTACCATGTTTACACC
TCCCCATCTGGTAAGAAGTTCTTGGTCCCCGTCAACCCAGAGAATGGAAGAGTCCAATGGGAAGCTGCAAAGCTTTCCGT
GGAGCAGGCCCTAGGTATGATGAATGTCGACGGCGAACTGACTGCCAAAGAACTGGAGAAACTGAAAAGAATAATTGACA
AACTCCAGGGCCTGACTAAGGAGCAGTGTTAAACTGCTAGCCGCCACGGACTTGACCCGCTGTGGTCGCGGCGGCTTGG
TTGTTACTGAAACAGCGGTAAAAATAGTCAAATTTCACAACCGGACCTTCACCCTGGGACCTGTGAATTTAAAAGTGGCC
AGTGAGGTTGAGCTAAAAGACGCGGTTGAGCACAACCAACACCCGGTTGCGAGACCGATCGATGGTGGAGTTGTGCTCCT
GCGTTCCGCGGTTCCTTCGCTTATAGACGTCTTGATCTCCGGTGCTGATGCATCTCCCAAGTTACTTGCCCATCACGGGC
CGGGAAACACTGGGATCGATGGCACGCTCTGGGATTTTGAGTCCGAAGCCACTAAAGAGGAAGTCGCACTCAGTGCGCAA
ATAATACAGGCTTGTGACATTAGGCGCGGCGACGCTCCTGAAATTGGTCTCCCTTACAAGCTGTACCCTGTTAGGGGTAA
CCCTGAGCGGGTGAAAGGAGTTCTGCAGAATACAAGGTTTGGAGACATACCTTACAAAACCCCAGTGACACTGGAAGCC
CAGTGCACGCGGCTGCCTGCCTTACGCCCAACGCCACTCCGGTGACTGATGGGCGCTCCGTCTTGGCCACGACCATGCCC
CCCGGGTTTGAGTTATATGTACCGACCATACCAGCGTCTGTCCTTGATTACCTTGACTCTAGGCCTGACTGCCCTAAACA
GCTGACAGAGCACGGCTGCGAAGATGCCGCACTGAAAGACCTCTCTAAATATGACTTGTCCACCCAAGGCTTTGTTTTAC
CTGGAGTTCTTCGCCTTGTGCGGAAATACCTGTTTGCCCGTGTAGGTAAGTGCCCACCCGTTCATCGGCCTTCTACTTAC
CCTGCTAAGAATTCTATGGCTGGAATAAATGGGAACAGGTTCCCAACCAAGGACATTCAGAGCGTCCCTGAAATCGACGT
TCTGTGCGCACAGGCTGTGCGAGAAAACTGGCAAACTGTCACCCCTTGTACTCTTAAGAAACAGTATTGCGGGAAGAAGA
AGACTAGGACCATACTCGGCACCAATAACTTCATCGCACTAGCCCACCGAGCAGTGTTGAGTGGTGTTACCCAGGGCTTC
ATGAAAAAGGCGTTTAACTCGCCCATCGCCCTCGGAAAGAACAAGTTTAAGGAGCTACAGACTCCGGTCCTGGGCAGGTG
CCTTGAAGCTGATCTCGCATCCTGCGATCGATCCACGCCTGCAATTGTCCGCTGGTTTGCCGCCAACCTTCTTTATGAAC
TTGCCTGTGCTGAAGAGCATCTACCGTCGTACGTGCTGAACTGCTGCCACGACTTACTGGTCACGCAGTCCGGCGCAGTG
```

Fig. 1A-3

```
ACTAAGAGAGGTGGCCTGTCGTCTGGCGACCCGATCACCTCTGTGTCTAACACCATTTATAGTTTGGTGATCTATGCACA
GCATATGGTGCTTAGTTACTTCAAAAGTGGTCACCCCCATGGCCTTCTGTTCTTACAAGACCAGCTAAAGTTTGAGGACA
TGCTCAAGGTTCAACCCCTGATCGTCTATTCGGACGACCTCGTGCTGTATGCCGAGTCTCCCACCATGCCAAACTATCAC
TGGTGGGTTGAACATCTGAATTTGATGCTGGGGTTTCAGACGGACCCAAAGAAGACAGCAATAACAGACTCGCCATCATT
TCTAGGCTGTAGAATAATAAATGGGCGCCAGCTAGTCCCCAACCGTGACAGGATCCTCGCGGCCCTCGCCTATCACATGA
AGGCGAGTAATGTTTCTGAATACTATGCCTCAGCGGCTGCAATACTCATGGACAGCTGTGCTTGTTTGGAGTATGATCCT
GAATGGTTTGAAGAACTTGTAGTTGGAATAGCGCAGTGCGCCCGCAAGGACGGCTACAGCTTTCCCGGCACGCCGTTCTT
CATGTCCATGTGGGAAAAACTCAGGTCCAATTATGAGGGGAAGAAGTCGAGAGTGTGCGGGTACTGCGGGGCCCCGGCCC
CGTACGCTACTGCCTGTGGCCTCGACGTCTGCATTTACCACACCCACTTCCACCAGCATTGTCCAGTCACAATCTGGTGT
GGCCATCCAGCGGGTTCTGGTTCTTGTAGTGAGTGCAAATCCCCTGTAGGGAAAGGCACAAGCCCTTTAGACGAGGTGCT
GGAACAAGTCCCGTATAAGCCCCCACGGACCGTTATCATGCATGTGGAGCAGGGTCTCACCCCCCTTGATCCAGGTAGAT
ACCAAACTCGCCGCGGATTAGTCTCTGTCAGGCGTGGAATTAGGGGAAATGAAGTTGGACTACCAGACGGTGATTATGCT
AGCACCGCCTTGCTCCCTACCTGCAAAGAGATCAACATGGTCGCTGTCGCTTCCAATGTATTGCGCAGCAGGTTCATCAT
CGGCCCACCCGGTGCTGGGAAAACATACTGGCTCCTTCAACAGGTCCAGGATGGTGATGTTATTTACACACCAACTCACC
AGACCATGCTTGACATGATTAGGGCTTTGGGGACGTGCCGGTTCAACGTCCCGGCAGGCACAACGCTGCAATTCCCCGTC
CCCTCCCGCACCGGTCCGTGGGTTCGCATCCTAGCCGGCGGTTGGTGTCCTGGCAAGAATTCCTTCCTAGATGAAGCAGC
GTATTGCAATCACCTTGATGTTTGAGGCTTCTTAGTAAAACTACCCTCACCTGTCTAGGAGACTTCAAGCAACTCCACC
CAGTGGGTTTTGATTCTCATTGCTATGTTTTTGACATCATGCCTCAAACTCAACTGAAGACCATCTGGAGGTTTGGACAG
AATATCTGTGATGCCATTCAGCCAGATTACAGGGACAAACTCATGTCCATGGTCAACACAACCCGTGTGACCTACGTGGA
AAAACCTGTCAGGTATGGGCAGGTCCTCACCCCCTACCACAGCGACCGAGAGGACGACGCCATCACTATTGACTCCAGTC
AAGGCGCCACATTCGATGTGGTTACATTGCATTTGCCCACTAAAGATTCACTCAACAGGCAAAGAGCCCTTGTTGCTATC
ACCAGGGCAAGACACGCTATCTTTGTGTATGACCCACACAGGCAGCTGCAGGCTTGTTTGATCTTCCTGCAAAAGGCAC
GCCCGTCAACCTCGCAGTGCACTGCGACGGGCAGCTGATCGTCTGGATAGAAATAACAAAGAATGCACGGTTGCTCAGG
CTCTAGGCAACGGGGATAAATTTAGGGCCACAGACAAGCGTGTTGTAGATTCTCTCCGCGCCATTTGTGCTGATCTAGAA
GGGTCGAGCTCTCCGCTCCCCAAGGTCGCACACAACTTGGGATTTTATTTCTCACCTGATTTAACACAGTTTGCTAAACT
CCCAGTAGAACTTGCACCTCACTGGCCCGTGGTGTCAACCCAGAACAATGAAAAGTGGCCGGATCGGCTGGTTGCCAGCC
TTCGCCCTATCCATAAATACAGCCGCGCGTGCATCGGTGCCGGCTATATGGTGGGCCCTTCGGTGTTTCTAGGCACTCCT
GGGGTCGTGTCATACTATCTCACAAAATTTGTTAAGGGCGGGCTCAAGTGCTTCCGGAGACGGTTTTCAGCACCGGCCG
AATTGAGGTAGACTGCCGGGAATATCTTGATGATCGGGAGCGAGAAGTTGCTGCGTCCCTCCCACACGCTTTCATTGGCG
ACGTCAAAGGCACTACCGTTGGAGGATGTCATCATGTCACCTCCAGATACCTCCCGCGCGTCCTTCCCAAGGAATCAGTT
GCGGTAGTCGGGGTTTCAAGCCCCGGAAAAGCCGCGAAAGCATTGTGCACACTGACAGATGTGTACCTCCCAGATCTTGA
AGCCTATCTCCACCCGGAGACCCAGTCCAAGTGCTGGAAAATGATGTTGGACTTCAAAGAAGTTCGACTAATGGTCTGGA
AAGACAAAACAGCCTATTTCCAACTTGAAGGTCGCTATTTCACCTGGTATCAGCTTGCCAGCTATGCCTCGTACATCCGT
GTTCCCGTCAACTCTACGGTGTACTTGGACCCCTGCATGGGCCCCGCCCTTTGCAACAGGAGAGTCGTCGGGTCCACCCA
CTGGGGGGCTGACCTCGCGGTCACCCCTTATGATTACGGCGCTAAAATTATCCTGTCTAGCGCGTACCATGGTGAAATGC
CCCCCGGATACAAAATTCTGGCGTGCGCGGAGTTCTCGTTGGATGACCCAGTTAAGTACAAACATACCTGGGGGTTTGAA
TCGGATACAGCGTATCTGTATGAGTTCACCGGAAACGGTGGGAGGATTACAATGATGCGTTTCGTGCGCGCCA
GGAAGGGAAAATTTATAAGGCCACTGCCACCAGCTTGAAGTTTTATTTTCCCCGGGCCCTGTCATTGAACCAACTTTAG
GCCTGAATTGAAATGAAATGGGGTCCATGCAAAGCCTTTTTGACAAAATTGGCCAACTTTTTGTGGATGCTTTCACGGAG
TTCTTGGTGTCCATTGTTGATATCATTATATTTTTGGCCATTTTGTTTGGCTTCACCATCGCCGGTTGGCTGGTGGTCTT
TTGCATCAGATTGGTTTGCTCCGCGATACTCCGTACGCGCCCTGCCATTCACTCTGAGCAATTACAGAAGATCTTATGAG
GCCTTTCTTTCCCAGTGCCAAGTGGACATTCCCACCTGGGGAACTAAACATCCTTTGGGGATGCTTTGGCACCATAAGGT
GTCAACCCTGATTGATGAAATGGTGTCGCGTCGAATGTACCGCATCATGGAAAAAGCAGGGCAGGCTGCCTGGAAACAGG
TGGTGAGCGAGGCTACGCTGTCTCGCATTAGTAGTTTGGATGTGGTGGCTCATTTTCAGCATCTAGCCGCCATTGAAGCC
GAGACCTGTAAATATTTGGCCTCCCGGCTGCCCATGCTACACAACCTGCGCATGACAGGGTCAAATGTAACCATAGTGTA
TAATAGCACTTTGAATCAGGTGTTTGCTATTTTTCCAACCCCTGGTTCCCGGCCAAAGCTTCATGATTTTCAGCAATGGT
TAATAGCTGTACATTCCTCCATATTTTCCTCTGTTGCAGCTTCTTGTACTCTTTTTGTTGTGCTGTGGTTGCGGGTTCCA
ATACTACGTACTGTTTTGGTTTCCGCTGGTTAGGGGCAATTTTCTTTCGAACTCACAGTGAATTACACGGTGTGTCCA
CCTTGCCTCACCCGGCAAGCAGCCACAGAGATCTACGAACCCGGTAGGTCTCTTTGGTGCAGGATAGGGTATGACCGATG
TGGGGAGGACGATCATGACGAGCTAGGGTTTATGATACCGCCTGGCCTCTCCAGCGAAGGCCACTTGACTGGTGTTTACG
CCTGGTTGGCGTTCTTGTCCTTCAGCTACACGGCCGATTCCATCCCGAGATATTCGGGATAGGGAATGTGAGTCGAGTT
TATGTTGACATCAAACATCAACTCATCTGCGCCGAACATGACGGGCAGAACACCACCTTGCCTCGTCATGACAACATTTC
AGCCGTGTTTCAGACCTATTACCAACATCAAGTCGACGGCGGCAATTGGTTTCACCTAGAATGGCTTCGTCCCTTCTTTT
CCTCGTGGTTGGTTTTAAATGTCTCTTGGTTTCTCAGGCGTTCGCCTGCAAACCATGTTTCAGTTCGAGTCTTGCAGATA
TTAAGACCAACACCACCGCAGCGGCAAGCTTTGCTGTCCTCCAAGACATCAGTTGCCTTAGGCATCGCGACTCGGCCTCT
GAGGCGATTCGCAAAATCCCTCAGTGCCGTACGGCGATAGGGACACCCGTGTATGTTACCATCACAGCCAATGTGACAGA
TGAGAATTATTTACATTCTTCTGATCTCCTCATGCTTTCTTCTTGCCTTTTCTATGCTTCTGAGATGAGTGAAAAGGGAT
TTAAGGTGGTATTTGGCAATGTGTCAGGCATCGTGGCTGTGTGTGTCAATTTTACCAGCTACGTCCAACATGTCAAGGAG
```

Fig. 1A-4

```
TTTACCCAACGCTCCCTGGTGGTCGACCATGTGCGGTTGCTCCATTTCATGACACCTGAGACCATGAGGTGGGCAACTGT
TTTAGCCTGTCTTTTTGCCATTCTGTTGGCAATTTGAATGTTTAAGTATGTTGGAGAAATGCTTGACCGCGGGCTGTTGC
TCGCGATTGCTTTCTTTGTGGTGTATCGTGCCGTTCTGTTTTGCTGTGCTCGCCAACGCCAGCAACGACAGCAGCTCCCA
TCTACAGCTGATTTACAACTTGACGCTATGTGAGCTGAATGGCACAGATTGGCTAGCTAACAAATTTGATTGGGCAGTGG
AGAGTTTTGTCATCTTTCCCGTTTTGACTCACATTGTCTCCTATGGTGCCCTCACTACCAGCCATTTCCTTGACACAGTC
GCTTTAGTCACTGTGTCTACCGCCGGGTTTGTTCACGGGCGGTATGTCCTAAGTAGCATCTACGCGGTCTGTGCCCTGGC
TGCGTTGACTTGCTTCGTCATTAGGTTTGCAAAGAATTGCATGTCCTGGCGCTACGCGTGTACCAGATATACCAACTTTC
TTCTGGACACTAAGGGCAGACTCTATCGTTGGCGGTCGCCTGTCATCATAGAGAAAAGGGGCAAAGTTGAGGTCGAAGGT
CATCTGATCGACCTCAAAAGAGTTGTGCTTGATGGCTCCGTGGCAACCCCTATAACCAGAGTTTCAGCGGAACAATGGGG
TCGTCCTTAGATGACTTCTGTCACGATAGCACGGCTCCACAAAAGGTGCTTTTGGCGTTTTCTATTACCTACACGCCAGT
GATGATATATGCCCTAAAGGTGAGTCGCGGCCGACTGCTAGGGCTTCTGCACCTTTTGATCTTCCTGAATTGTGCTTTCA
CCTTCGGGTACATGACTTTCGCGCACTTTCAGAGTACAAATAAGGTCGCGCTCACTATGGGAGCAGTAGTTGCACTCCTT
TGGGGGGTGTACTCAGCCATAGAAACCTGGAAATTCATCACCTCCAGATGCCGTTTGTGCTTGCTAGGCCGCAAGTACAT
TCTGGCCCCTGCCCACCACGTTGAAAGTGCCGCAGGCTTTCATCCGATTGCGGCAAATGATAACCACGCATTTGTCGTCC
GGCGTCCCGGCTCCACTACGGTCAACGGCACATTGGTGCCCGGGTTAAAAAGCCTCGTGTTGGGTGGCAGAAAAGCTGTT
AAACAGGGAGTGGTAAACCTTGTCAAATATGCCAAATAACAACGGCAAGCAGCAGAAGAGAAAGAACGGGGATGGCCAGC
CAGTCAATCAGCTGTGCCAGATGCTGGGTAAGATCATCGCTCAGCAAAACCAGTCCAGAGGCAAGGGACCGGGAAAGAAA
AATAAGAAGAAAAACCCGGAGAAGCCCCATTTTCCTCTAGCGACTGAAGATGATGTCAGACATCACTTTACCCCTAGTGA
GCGGCAATTGTGTCTGTCGTCAATCCAGACCGCCTTTAATCAAGCGCTGGGACTTGCACCCTGTCAGATTCAGGGAGGA
TAAGTTACACTGTGGAGTTTAGTTTGCCTACGCATCATACTGTGCGCCTGATCCGCGTCACAGCATCACCCTCAGCATGA
TGGGCTGGCATTCTTGAGGCATCTCAGTGTTTGAATTGGAAGAATGTGTGGTGAATGGCACTGATTGACATTGTGCCTCT
AAGTCACCTATTCAATTAGGGCGACCGTGTGGGGGTGAGATTTAATTGGCGAGAACCATGCGGCCGAAATTAAAAAAAA
```

Fig. 1B-1

```
>VR-V5.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCTCCGCCA
AAAGTTCAGCCTCGAAAAACGAAGCCTGTCAAGAGCTTGCCGGAGAGAAAGCCTGTCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGAGAGCGACCTTACCATTGGCTCAGTTGCTACTGAAGAT
GTTCCACGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA
```

*Fig. 1B-2*

```
CAGGTGGCGCCGGCTCTTTTACCGATTTGCCGCCTTCAGATGGCGCGGATGCGGACGGGGGGGGGCCGTTTCGGACGGTA
AAAAGAAAAGCTGAAAGGCTCTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGGTCGTGGTT
GACCCTGACACTTTCACTGCAGCTCTCCGGTCTGGCTACTCCACCACAAACCTCGTCCTTGGTGTGGGGGACTTTGCCCA
GCTGAATGGATTAAAAATCAGGCAAATTTCCAAGCCTTCAGGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGATGAGGACCGTTTGAATAAGAAGAA
GAGGCGCAGGATGGAAGCCCTCGGCATCTATGTTATGGGCGGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGGAAACAAGGCTTACCATGTTTACACCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

Fig. 1B-3

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

Fig. 1B-4

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAGATATTAAGACCAACACCACCGCA
GCGGCAAGCTTTGCTGTCCTCCAAGACATCAGTTGCCTTAGCGCATCGCGACTCGGCCTCTGAGGCGATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAÀGGGGGATGGCCAGCCAGTCAATCAGCTGTGCCAG
ATGCTGGGTAAGATCATCACTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

*Fig. 1B-5*

```
ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAAA
AAAAAAAAAAAAAAAAAA
```

*Fig. 1C-1*

```
>VR-V5G7475A.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCGCAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCAGCACCGCCGCAGAGCGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGAGAGCGACCTTACCATTGGCTCAGTTGCTACTGAAGAT
GTTCCACGGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA
```

*Fig. 1C-2*

```
CAGGTGGCGCCGGCTCTTTTACCGATTTGCCGCCTTCAGATGGCGCGGATGCGGACGGGGGGGGGCCGTTTCGGACGGTA
AAAAGAAAAGCTGAAAGGCTCTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGGTCGTGGTT
GACCCTGACACTTTCACTGCAGCTCTCCGGTCTGGCTACTCCACCACAAACCTCGTCCTTGGTGTGGGGGACTTTGCCCA
GCTGAATGGATTAAAAATCAGGCAAATTTCCAAGCCTTCAGGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGGATGAGGACCGTTTGAATAAGAAGAA
GAGGCGCAGGATGGAAGCCCTCGGCATCTATGTTATGGGCGGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGAAAACAAGGCTTACCATGTTTACACCCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

*Fig. 1C-3*

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

*Fig. 1C-4*

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAAATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGGGACAGATGAGAATTATCTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTCTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGGATGGCCAGCCAGTCAATCAGCTGTGCCAG
ATGCTGGGTAAGATCATCACTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

*Fig. 1C-5*

ATCTCAGTGTTTGAATTGGAAGAATGTGTGGTGAATGGCACTGATTGACATTGTGCCTCTAAGTCACCTATTCAATTAGG
GCGACCGTGTGGGGGTGAGATTTAATTGGCGAGAACCATGCGGCCGAAATTAAAAAAAAAAAAAAAAAAAAAAAAAAAAA
AAAAAAAAAAAAAAAAACCC

Fig. 1D-1

>VR-V6.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTGTGAGT
TTGTGATGATGCCTCACACGCCTGCACCTTCCGTAGGTGCGGAGAGCGACCTTACCATTGGCTCAGTTGCTACTGAAGAT
GTTCCACGCATCCTCGAGAAAATAGAAAATGTCGGCGAGATGGCCAACCAGGGACCCTTGGCCTTCTCCGAGGATAAACC
GGTAGATGACCAACTTGTCAACGACCCCCGGATATCGTCGCGGAGGCCTGACGAGAGCACATCAGCTCCGTCCGCAGGCA

Fig. 1D-2

```
CAGGTGGCGCCGGCTCTTTTACCGATTTGCCGCCTTCAGATGGCGCGGATGCGGACGGGGGGGGGCCGTTTCGGACGGTA
AAAAGAAAAGCTGAAAGGCTCTTTTGACCAACTGAGCCGTCAGGTTTTTGACCTCGTCTCCCATCTCCCTGTTTTCTTCTC
ACGCCTTTTCTACCCTGGCGGTGGTTATTCTCCGGGTGATTGGGGTTTTGCAGCTTTTACTCTATTGTGCCTCTTTTTAT
GTTACAGTTACCCAGCCTTTGGTATTGCTCCCCTCTTGGGTGTGTTTTCTGGGTCTTCTCGGCGCGTTCGAATGGGGGTT
TTTGGCTGCTGGTTGGCTTTTGCTGTTGGTCTGTTCAAGCCTGTGTCCGACCCAGTCGGCGCTGCTTGTGAGTTTGACTC
GCCAGAGTGTAGAAACATCCTTCATTCTTTTGAGCTTCTCAAACCTTGGGACCCTGTTCGCAGCCTTGTTGTGGGCCCCG
TCGGTCTCGGTCTTGCCATTCTTGGCAGGTTACTGGGCGGGGCACGCTGCATCTGGCACTTTTTGCTTAGGCTTGGCATT
GTTGCAGACTGTATCTTGGCTGGAGCTTACGTGCTTTCTCAAGGTAGGTGTAAAAAGTGCTGGGGATCTTGTATAAGAAC
TGCTCCCAATGAGGTCGCTTTTAACGTGTTTCCTTTCACACGTGCGACCAGGTCGTCACTTATCGACCTGTGCGATCGGT
TTTGTGCGCCAAAAGGAATGGACCCCATTTTTCTCGCCACTGGGTGGCGCGGGTGCTGGGCCGGCCGAAGCCCCATTGAG
CAACCCTCTGAAAAACCCATCGCGTTTGCCCAGTTGGATGAAAAGAAGATTACGGCTAGGACTGTGGTCGCCCAGCCTTA
TGACCCCAACCAAGCCGTAAAGTGCTTGCGGGTATTGCAGGCGGGTGGGGCGATGGTGGCTAAGGCGGTCCCAAAAGTGG
TCAAGGTTTCCGCTGTTCCATTCCGAGCCCCCTTCTTTCCCACTGGAGTGAAAGTTGACCCTGATTGCAGGGTCGTGGTT
GACCCTGACACTTTCACTGCAGCTCTCCGGTCTGGCTACTCCACCACAAACCTCGTCCTTGGTGTGGGGACTTTGCCCA
GCTGAATGGATTAAAAATCAGGCAAATTTCCAAGCCTTCAGGGGGAGGCCCACATCTCATGGCTGCCCTGCATGTTGCCT
GCTCGATGGCTCTGCACATGCTTGCTGGGATTTATGTGACTGCGGTGGGTTCTTGCGGCACCGGCACCAACGACCCGTGG
TGCGCTAACCCGTTTGCCGTCCCTGGCTACGGACCTGGCTCTCTCTGCACGTCCAGATTGTGCATTTCCCAACACGGCCT
TACCCTGCCCTTGACAGCACTTGTGGCGGGATTCGGTATTCAAGAAATTGCCTTGGTCGTTTTGATTTTTGTTTCCATCG
GAGGCATGGCTCATAGGTTGAGCTGTAAGGCTGACATGCTGTGTGTCTTGCTTGCAATTGCCAGCTATGTTTGGGTACCT
CTTACCTGGTTGCTTTGTGTGTTTCCTTGCTGGTTGCGCTGTTTTTCTTTGCACCCCCTCACCATCCTATGGTTGGTGTT
TTTCTTGATTTCTGTGAATATGCCTTCAGGAATCTTGGCCATGGTGTTGTTGGTTTCTCTTTGGCTTCTTGGTCGTTATA
CTAATGTTGCTGGCCTTGTCACCCCCTACGACATTCATCATTACACCAGTGGCCCCCGCGGTGTTGCCGCCTTGGCTACC
GCACCAGATGGGACCTACTTGGCCGCTGTCCGCCGCGCTGCGTTGACTGGCCGCACCATGCTGTTTACCCCGTCCCAGCT
TGGGTCTCTTCTTGAGGGTGCTTTCAGAACTCGAAAGCCCTCACTGAACACCGTCAATGTGATCGGGTCCTCCATGGGCT
CTGGCGGGGTGTTTACCATCGACGGGAAAGTCAAGTGCGTAACTGCCGCACATGTCCTTACGGGCAATTCAGCTCGGGTT
TCCGGGGTCGGCTTCAATCAAATGCTTGACTTTGACGTAAAGGGAGATTTCGCTATAGCTGATTGCCCGAATTGGCAAGG
GGCTGCCCCCAAGACCCAATTCTGCACGGATGGATGGACTGGCCGTGCCTATTGGCTAACATCCTCTGGCGTCGAACCCG
GCGTCATTGGAAAAGGATTCGCCTTCTGCTTCACCGCATGTGGCGATTCCGGGTCCCCAGTGATCACCGAGGCCGGTGAG
CTTGTCGGCGTTCACACGGGATCGAATAAACAAGGGGGGGGCATTGTTACGCGCCCCTCAGGCCAGTTTTGTAATGTGGC
ACCCATCAAGCTAAGCGAATTAAGTGAATTCTTTGCTGGGCCTAAGGTCCCGCTCGGTGATGTGAAGGTCGGCAGCCACA
TAATTAAAGACATAAGCGAGGTGCCTTCAGATCTTTGTGCCTTGCTTGCTGCCAAACCTGAACTGGAAGGAGGCCTCTCC
ACCGTCCAACTTCTTTGTGTGTTTTTTCTCCTGTGGAGAATGATGGGACATGCCTGGACGCCCTTGGTTGCTGTGAGTTT
CTTTATTTTGAATGAGGTTCTCCCAGCCGTCCTGGTCCGGAGTGTTTTCTCCTTTGGAATGTTTGTGCTATCCTGGCTCA
CGCCATGGTCTGCGCAAGTTCTGATGATCAGGCTTCTGACAGCAGCTCTTAACAGGAACAGATGGTCACTTGCCTTTTTC
AGCCTCGGTGCAGTGACCGGTTTTGTCGCAGATCTTGCGGCCACTCAGGGGCATCCGTTGCAGGCAGTGATGAATTTGAG
CACCTATGCATTCCTGCCTCGGATGATGGTTGTGACCTCACCAGTCCCAGTGATCACGTGTGGTGTCGTGCACCTACTTG
CCATCATTTTGTACTTGTTTAAGTACCGTGGCCTGCACCATATCCTTGTTGGCGATGGAGTGTTCTCTGCGGCTTTCTTC
TTGAGATACTTTGCCGAGGGAAAGTTGAGGGAAGGGGTGTCGCAATCCTGCGGAATGAATCATGAGTCTCTGACTGGTGC
CCTCGCTATGAGACTCAATGACGAGGACTTGGATTTCCTTATGAAATGGACTGATTTTAAGTGCTTTGTTTCTGCGTCCA
ACATGAGGAATGCAGCGGGTCAATTTATCGAGGCTGCCTATGCTAAAGCACTTAGAGTAGAACTGGCCCAGTTGGTGCAG
GTTGATAAAGTTCGAGGTACTTTGGCCAAACTTGAAGCTTTTGCTGATACCGTGGCACCTCAACTCTCGCCCGGTGACAT
TGTTGTCGCTCTCGGCCACACGCCTGTTGGCAGTATCTTCGACCTAAAGGTTGGTAGCACCAAGCATACCCTCCAAGCCA
TTGAGACCAGAGTCCTTGCTGGGTCCAAAATGACCGTGGCGCGCGTCGTCGACCCGACCCCCACGCCCCCACCCGCACCC
GTGCCCATCCCCCTCCCACCGAAAGTTCTGGAGAATGGCCCCAACGCTTGGGGGGATGAGGACCGTTTGAATAAGAAGAA
GAGGCGCAGGATGGAAGCCCTCGGCATCTATGTTATGGGCGGGAAAAAATACCAGAAATTTTGGGACAAGAATTCCGGTG
ATGTGTTTTATGAGGAGGTCCATAATAACACAGATGAGTGGGAGTGTCTCAGAGTTGGCGACCCTGCCGACTTTGACCCT
GAGAAGGGAACTCTGTGTGGACATGTCACCATTGGAAACAAGGCTTACCATGTTTACACCTCCCCATCTGGTAAGAAGTT
CTTGGTCCCCGTCAACCCAGAGAATGGAAGAGTCCAATGGGAAGCTGCAAAGCTTTCCGTGGAGCAGGCCCTAGGTATGA
```

Fig. 1D-3

```
TGAATGTCGACGGCGAACTGACTGCCAAAGAACTGGAGAAACTGAAAAGAATAATTGACAAACTCCAGGGCCTGACTAAG
GAGCAGTGTTTAAACTGCTAGCCGCCAGCGACTTGACCCGCTGTGGTCGCGGCGGCTTGGTTGTTACTGAAACAGCGGTA
AAAATAGTCAAATTTCACAACCGGACCTTCACCCTGGGACCTGTGAATTTAAAAGTGGCCAGTGAGGTTGAGCTAAAAGA
CGCGGTTGAGCACAACCAACACCCGGTTGCGAGACCGATCGATGGTGGAGTTGTGCTCCTGCGTTCCGCGGTTCCTTCGC
TTATAGACGTCTTGATCTCCGGTGCTGATGCATCTCCCAAGTTACTTGCCCATCACGGGCCGGGAAACACTGGGATCGAT
GGCACGCTCTGGGATTTTGAGTCCGAAGCCACTAAAGAGGAAGTCGCACTCAGTGCGCAAATAATACAGGCTTGTGACAT
TAGGCGCGGCGACGCTCCTGAAATTGGTCTCCCTTACAAGCTGTACCCTGTTAGGGGTAACCCTGAGCGGGTGAAAGGAG
TTCTGCAGAATACAAGGTTTGGAGACATACCTTACAAAACCCCAGTGACACTGGAAGCCCAGTGCACGCGGCTGCCTGC
CTTACGCCCAACGCCACTCCGGTGACTGATGGGCGCTCCGTCTTGGCCACGACCATGCCCCCGGGTTTGAGTTATATGT
ACCGACCATACCAGCGTCTGTCCTTGATTACCTTGACTCTAGGCCTGACTGCCCTAAACAGCTGACAGAGCACGGCTGCG
AAGATGCCGCACTGAAAGACCTCTCTAAATATGACTTGTCCACCCAAGGCTTTGTTTTACCTGGAGTTCTTCGCCTTGTG
CGGAAATACCTGTTTGCCCATGTAGGTAAGTGCCCACCCGTTCATCGGCCTTCTACTTACCCTGCTAAGAATTCTATGGC
TGGAATAAATGGGAACAGGTTCCCAACCAAGGACATTCAGAGCGTCCCTGAAATCGACGTTCTGTGCGCACAGGCTGTGC
GAGAAAACTGGCAAACTGTCACCCCTTGTACTCTTAAGAACAGTATTGCGGGAAGAAGAAGACTAGGACCATACTCGGC
ACCAATAACTTCATCGCACTAGCCCACCGAGCAGTGTTGAGTGGTGTTACCCAGGGCTTCATGAAAAAGGCGTTTAACTC
GCCCATCGCCCTCGGAAAGAACAAGTTTAAGGAGCTACAGACTCCGGTCCTGGGCAGGTGCCTTGAAGCTGATCTCGCAT
CCTGCGATCGATCCACGCCTGCAATTGTCCGCTGGTTTGCCGCCAACCTTCTTTATGAACTTGCCTGTGCTGAAGAGCAT
CTACCGTCGTACGTGCTGAACTGCTGCCACGACTTACTGGTCACGCAGTCCGGCGCAGTGACTAAGAGAGGTGGCCTGTC
GTCTGGCGACCCGATCACCTCTGTGTCTAACACCATTTATAGTTTGGTGATCTATGCACAGCATATGGTGCTTAGTTACT
TCAAAAGTGGTCACCCCCATGGCCTTCTGTTCTTACAAGACCAGCTAAAGTTTGAGGACATGCTCAAGGTTCAACCCCTG
ATCGTCTATTCGGACGACCTCGTGCTGTATGCCGAGTCTCCCACCATGCCAAACTATCACTGGTGGGTTGAACATCTGAA
TTTGATGCTGGGGTTTCAGACGGACCCAAAGAAGACAGCAATAACAGACTCGCCATCATTTCTAGGCTGTAGAATAATAA
ATGGGCGCCAGCTAGTCCCCAACCGTGACAGGATCCTCGCGGCCCTCGCCTATCACATGAAGGCGAGTAATGTTTCTGAA
TACTATGCCTCAGCGGCTGCAATACTCATGGACAGCTGTGCTTGTTTGGAGTATGATCCTGAATGGTTTGAAGAACTTGT
AGTTGGAATAGCGCAGTGCGCCCGCAAGGACGGCTACAGCTTTCCCGGCACGCCGTTCTTCATGTCCATGTGGGAAAAAC
TCAGGTCCAATTATGAGGGGAAGAAGTCGAGAGTGTGCGGGTACTGCGGGGCCCCGGCCCCGTACGCTACTGCCTGTGGC
CTCGACGTCTGCATTTACCACACCCACTTCCACCAGCATTGTCCAGTCACAATCTGGTGTGGCCATCCAGCGGGTTCTGG
TTCTTGTAGTGAGTGCAAATCCCCTGTAGGGAAAGGCACAAGCCCTTTAGACGAGGTGCTGGAACAAGTCCCGTATAAGC
CCCCACGGACCGTTATCATGCATGTGGAGCAGGGTCTCACCCCCCTTGATCCAGGTAGATACCAAACTCGCCGCGGATTA
GTCTCTGTCAGGCGTGGAATTAGGGGAAATGAAGTTGGACTACCAGACGGTGATTATGCTAGCACCGCCTTGCTCCCTAC
CTGCAAAGAGATCAACATGGTCGCTGTCGCTTCCAATGTATTGCGCAGCAGGTTCATCATCGGCCCACCCGGTGCTGGGA
AAACATACTGGCTCCTTCAACAGGTCCAGGATGGTGATGTTATTTACACACCAACTCACCAGACCATGCTTGACATGATT
AGGGCTTTGGGGACGTGCCGGTTCAACGTCCCGGCAGGCACAACGCTGCAATTCCCCGTCCCTCCCGCACCGGTCCGTG
GGTTCGCATCCTAGCCGGCGGTTGGTGTCCTGGCAAGAATTCCTTCCTAGATGAAGCAGCGTATTGCAATCACCTTGATG
TTTTGAGGCTTCTTAGTAAAACTACCCTCACCTGTCTAGGAGACTTCAAGCAACTCCACCCAGTGGGTTTTGATTCTCAT
TGCTATGTTTTTGACATCATGCCTCAAACTCAACTGAAGACCATCTGGAGGTTTGGACAGAATATCTGTGATGCCATTCA
GCCAGATTACAGGGACAAACTCATGTCCATGGTCAACACAACCCGTGTGACCTACGTGGAAAAACCTGTCAGGTATGGGC
AGGTCCTCACCCCCTACCACAGGGACCGAGAGGACGACGCCATCACTATTGACTCCAGTCAAGGCGCCACATTCGATGTG
GTTACATTGCATTTGCCCACTAAAGATTCACTCAACAGGCAAAGAGCCCTTGTTGCTATCACCAGGGCAAGACACGCTAT
CTTTGTGTATGACCCACACAGGCAGCTGCAGGGCTTGTTTGATCTTCCTGCAAAAGGCACGCCCGTCAACCTCGCAGTGC
ACTGCGACGGGCAGCTGATCGTGCTGGATAGAAATAACAAAGAATGCACGGTTGCTCAGGCTCTAGGCAACGGGGATAAA
TTTAGGGCCACAGACAAGCGTGTTGTAGATTCTCTCCGCGCCATTTGTGCTGATCTAGAAGGGTCGAGCTCTCCGCTCCC
CAAGGTCGCACACAACTTGGGATTTTATTTCTCACCTGATTTAACACAGTTTGCTAAACTCCCAGTAGAACTTGCACCTC
ACTGGCCCGTGGTGTCAACCCAGAACAATGAAAAGTGGCCGGATCGGCTGGTTGCCAGCCTTCGCCCTATCCATAAATAC
AGCCGCGCGTGCATCGGTGCCGGCTATATGGTGGGCCCTTCGGTGTTTCTAGGCACTCCTGGGGTCGTGTCATACTATCT
CACAAAATTTGTTAAGGGCGGGGCTCAAGTGCTTCCGGAGACGGTTTTCAGCACCGGCCGAATTGAGGTAGACTGCCGGG
AATATCTTGATGATCGGGAGCGAGAAGTTGCTGCGTCCCTCCCACACGCTTTCATTGGCGACGTCAAAGGCACTACCGTT
GGAGGATGTCATCATGTCACCTCCAGATACCTCCCGCGCGTCCTTCCCAAGGAATCAGTTGCGGTAGTCGGGGTTTCAAG
```

*Fig. 1D-4*

```
CCCCGGAAAAGCCGCGAAAGCATTGTGCACACTGACAGATGTGTACCTCCCAGATCTTGAAGCCTATCTCCACCCGGAGA
CCCAGTCCAAGTGCTGGAAAATGATGTTGGACTTCAAAGAAGTTCGACTAATGGTCTGGAAAGACAAAACAGCCTATTTC
CAACTTGAAGGTCGCTATTTCACCTGGTATCAGCTTGCCAGCTATGCCTCGTACATCCGTGTTCCCGTCAACTCTACGGT
GTACTTGGACCCCTGCATGGGCCCCGCCCTTTGCAACAGGAGAGTCGTCGGGTCCACCCACTGGGGGCTGACCTCGCGG
TCACCCCTTATGATTACGGCGCTAAAATTATCCTGTCTAGCGCGTACCATGGTGAAATGCCCCCCGGATACAAAATTCTG
GCGTGCGCGGAGTTCTCGTTGGATGACCCAGTTAAGTACAAACATACCTGGGGGTTTGAATCGGATACAGCGTATCTGTA
TGAGTTCACCGGAAACGGTGAGGACTGGGAGGATTACAATGATGCGTTTCGTGCGCGCCAGGAAGGGAAAATTTATAAGG
CCACTGCCACCAGCTTGAAGTTTTATTTTCCCCCGGGCCCTGTCATTGAACCAACTTTAGGCCTGAATTGAAATGAAATG
GGGTCCATGCAAAGCCTTTTTGACAAAATTGGCCAACTTTTTGTGGATGCTTTCACGGAGTTCTTGGTGTCCATTGTTGA
TATCATTATATTTTTGGCCATTTTGTTTGGCTTCACCATCGCCGGTTGGCTGGTGGTCTTTTGCATCAGATTGGTTTGCT
CCGCGATACTCCGTACGCGCCCTGCCATTCACTCTGAGCAATTACAGAAGATCTTATGAGGCCTTTCTTTCCCAGTGCCA
AGTGGACATTCCCACCTGGGGAACTAAACATCCTTTGGGGATGCTTTGGCACCATAAGGTGTCAACCCTGATTGATGAAA
TGGTGTCGCGTCGAATGTACCGCATCATGGAAAAAGCAGGGCAGGCTGCCTGGAAACAGGTGGTGAGCGAGGCTACGCTG
TCTCGCATTAGTAGTTTGGATGTGGTGGCTCATTTTCAGCATCTAGCCGCCATTGAAGCCGAGACCTGTAAATATTTGGC
CTCCCGGCTGCCCATGCTACACAACCTGCGCATGACAGGGTCAAATGTAACCATAGTGTATAATAGCACTTTGAATCAGG
TGTTTGCTATTTTTCCAACCCCTGGTTCCCGGCCAAAGCTTCATGATTTTCAGCAATGGTTAATAGCTGTACATTCCTCC
ATATTTTCCTCTGTTGCAGCTTCTTGTACTCTTTTTGTTGTGCTGTGGTTGCGGGTTCCAATACTACGTACTGTTTTTGG
TTTCCGCTGGTTAGGGGCAATTTTTCTTTCGAACTCACAGTGAATTACACGGTGTGTCCACCTTGCCTCACCCGGCAAGC
AGCCACAGAGATCTACGAACCCGGTAGGTCTCTTTGGTGCAGGATAGGGTATGACCGATGTGGGGAGGACGATCATGACG
AGCTAGGGTTTATGATACCGCCTGGCCTCTCCAGCGAAGGCCACTTGACTGGTGTTTACGCCTGGTTGGCGTTCTTGTCC
TTCAGCTACACGGCCCAGTTCCATCCCGAGATATTCGGGATAGGGAATGTGAGTCGAGTTTATGTTGACATCAAACATCA
ACTCATCTGCGCCGAACATGACGGGCAGAACACCACCTTGCCTCGTCATGACAACATTTCAGCCGTGTTTCAGACCTATT
ACCAACATCAAGTCGACGGCGGCAATTGGTTTCACCTAGAATGGCTTCGTCCCTTCTTTTCCTCGTGGTTGGTTTTAAAT
GTCTCTTGGTTTCTCAGGCGTTCGCCTGCAAACCATGTTTCAGTTCGAGTCTTGCAGATATTAAGACCAACACCACCGCA
GCGGCAAGCTTTGCTGTCCTCCAAGACATCAGTTGCCTTAGGCATCGCGACTCGGCCTCTGAGGCGATTCGCAAAATCCC
TCAGTGCCGTACGGCGATAGGGACACCCGTGTATGTTACCATCACAGCCAATGTGACAGATGAGAATTATTTACATTCTT
CTGATCTCCTCATGCTTTCTTCTTGCCTTTTCTATGCTTCTGAGATGAGTGAAAAGGGATTTAAGGTGGTATTTGGCAAT
GTGTCAGGCATCGTGGCTGTGTGTGTCAATTTTACCAGCTACGTCCAACATGTCAAGGAGTTTACCCAACGCTCCCTGGT
GGTCGACCATGTGCGGTTGCTCCATTTCATGACACCTGAGACCATGAGGTGGGCAACTGTTTTAGCCTGTCTTTTTGCCA
TTCTGTTGGCAATTTGAATGTTTAAGTATGTTGGAGAAATGCTTGACCGCGGGCTGTTGCTCGCGATTGCTTTCTTTGTG
GTGTATCGTGCCGTTCTGTTTTGCTGTGCTCGCCAACGCCAGCAACGACAGCAGCTCCCATCTACAGCTGATTTACAACT
TGACGCTATGTGAGCTGAATGGCACAGATTGGCTAGCTAACAAATTTGATTGGGCAGTGGAGAGTTTTGTCATCTTTCCC
GTTTTGACTCACATTGTCTCCTATGGTGCCCTCACTACCAGCCATTTCCTTGACACAGTCGCTTTAGTCACTGTGTCTAC
CGCCGGGTTTGTTCACGGGCGGTATGTCCTAAGTAGCATCTACGCGGTCTGTGCCCTGGCTGCGTTGACTTGCTTCGTCA
TTAGGTTTGCAAAGAATTGCATGTCCTGGCGCTACGCGTGTACCAGATATACCAACTTTCTTCTGGACACTAAGGGCAGA
CTCTATCGTTGGCGGTCGCCTGTCATCATAGAGAAAAGGGGCAAAGTTGAGGTCGAAGGTCATCTGATCGACCTCAAAAG
AGTTGTGCTTGATGGCTCCGTGGCAACCCCTATAACCAGAGTTTCAGCGGAACAATGGGTCGTCCTTAGATGACTTCTG
TCACGATAGCACGGCTCCACAAAAGGTGCTTTTGGCGTTTTCTATTACCTACACGCCAGTGATGATATATGCCCTAAAGG
TGAGTCGCGGCCGACTGCTAGGGCTTCTGCACCTTTTGATCTTCCTGAATTGTGCTTTCACCTTCGGGTACATGACTTTC
GCGCACTTTCAGAGTACAAATAAGGTCGCGCTCACTATGGGAGCAGTAGTTGCACTCCTTTGGGGGGTGTACTCAGCCAT
AGAAACCTGGAAATTCATCACCTCCAGATGCCGTTTGTGCTTGCTAGGCCGCAAGTACATTCTGGCCCCTGCCCACCACG
TTGAAAGTGCCGCAGGCTTTCATCCGATTGCGGCAAATGATAACCACGCATTTGTCGTCCGGCGTCCCGGCTCCACTACG
GTCAACGGCACATTGGTGCCCGGGTTAAAAAGCCTCGTGTTGGGTGGCAGAAAAGCTGTTAAACAGGGAGTGGTAAACCT
TGTCAAATATGCCAAATAACAACGGCAAGCAGCAGAAGAGAAAGAAGGGGGATGGCCAGCCAGTCAATCAGCTGTGCCAG
ATGCTGGGTAAGATCATCGCTCAGCAAAACCAGTCCAGAGGCAAGGGACCGGGAAAGAAAAATAAGAAGAAAAACCCGGA
GAAGCCCCATTTTCCTCTAGCGACTGAAGATGATGTCAGACATCACTTTACCCCTAGTGAGCGGCAATTGTGTCTGTCGT
CAATCCAGACCGCCTTTAATCAAGGCGCTGGGACTTGCACCCTGTCAGATTCAGGGAGGATAAGTTACACTGTGGAGTTT
AGTTTGCCTACGCATCATACTGTGCGCCTGATCCGCGTCACAGCATCACCCTCAGCATGATGGGCTGGCATTCTTGAGGC
```

*Fig. 1D-5*

ATCTCAGTGTTTGAATTGGAAGAATGTGTGGTGAATGGCACTGATTGACATTGTGCCTCTAAGTCACCTATTCAATTAGG
GCGACCGTGTGGGGTGAGATTTAATTGGCGAGAACCATGCGGCCGAAATTAAAAAAAAAAAAAAAAAAAAAAAAAAAAAA
AAAAAAAAAAAAAAAA

Fig. 1E-1

```
>MN184A_DQ176019.seq
ATGACGTATAGGTGTTGGCTCTATGCCACGACATTTGTATTGTCAGGAGCTGTGACCACTGGCACAGCCCAAAGCTTGCT
GCACAGAAACACCCTTCTGTGACGGCCTCCTTCAGGGGAGTTTAGGGGTTTATCCCTAGCACCTTGTTTCTGGAGTTGCA
CTGCTTTACGGTCTCTCCACCCCTTTAACCATGTCTGGGATTCTTGATCGGTGCACGTGCACCCCCAATGCCAGGGTGTT
TATGGCAGAGGGCCAAGTCTACTGCACACGATGTCTCAGTGCACGGTCCCTCCTTCCCCTGAATCTCCAAGTCCCTGAGC
TCGGAGTGTTGGGCTTGTTTTATAGGCCCGAAGAGCCGCTCCGGTGGACGTTGCCACGCGCATTCCCCACTGTTGAGTGC
TCCCCTGCTGGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTATAGTCCTAAAGAATCTACAAGTCTATGAAC
GGGGTTGCCGATGGTACCCCATCGTTGGACCTGTCCCTGGAGTTGCCGTTTTCGCCAACTCCCTACATGTGAGTGATAGA
CCTTTCCCAGGGGSTACTCACGTGCTAACCAACCTGCCGCTCCCGCAGAGACCTAAGCCTGAAGATTTTTGCCCCTTTGA
GTGTGCTATGGCTGMCGTCTATGAYATTGGTCATGACGCCGTTATGTTCGTGGCCGAAGGGAGAGTCTCCTGGGCTCCGC
GTGGTGGGGGAAAAGGAAAATTTGAAACTGTTCCCGAGGAGTTGAGGTTGATTGCAGAGCAACTTTATACCTCCTTCCCG
CCCCACCACGTGGTGGACATGTCGAAATTCACCTTTACGGCCCCTGAGTGTGGTGCTTCCATGCGAGTCGAACGCCATTA
TGGCTGCCTCCCCGCCGGCACTGTCCCTGACGGCAATTGCTGGTGGAGTTTGTTTAGCTCGCTCCCATTGGAAATCCAGT
ACAAAGAAATTCGCCACGCCACCCAATTTGGCTATCAAACTAAGCATGGCGTTGCTGGCAAGTACCTACAGCGGAGGCTG
CAAGTTAATGGTCTCCGAGCAGTGGTTGACTCGAATGGACCTATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGCTCCGCCTACTCGTGAAACCCAGCAAGCCAAGAAACACGAGGC
TGCTAGTGCCAACAAGGCTGAGCTTCTTGAACGCTACTCCCCGCCTGCTGAAGGGAATTGCGGCTGGCACTGTATTTCCG
CCATCGCCAATCGGATGGTAAATTCTAAGTTTGAGACTGCCCTTCCCGAAAGAGTGAGATCCCCAGAAGACTGGGCTACT
GATGAGGATCTTGTGAATACTATCCARATCCTCAGGCTCCCYGCGGCCTTAGACAGGAACGGCGCCTGTGCAAGCGCCAA
GTACATCCTTAAGCTGGAAGGTGAGCACTGGACTGTTTCAGTGATTCCCGGAATGYCCCCTTCCTTGCTCCCCCTTGAAT
GCGTTCAGGGTTGCTGTGAGCATAAGGGTAATCTTGGTTCTCCGAACGCGGTCGGGGTTTTTGGATTCGACCCTGCCAGC
CTTGACCGACTTGCTGGGGTGATGCACCTGCCCAGCAGTGCCATCCCAGCCGCTCTGGCCGAGTTGTCTGGCGACCTTGA
TCGTCCAACTTCCCCGGCCGCCACTGTGTGGACTGTCTCGCAGTTTTATGCTCGTCATAGTGGAGGRGAGCATCCTGATC
AAAAGTGTTTAAAAAAAATTATCAGTCTCTGTGAGGTGATCGAGAGTTGTTGCTGTTCTCRGAACAAAACTAACCGGGTC
ACCCCGGAAGAGGTCACAGCAAAGATTGATCTGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTTGGGRCGGCTGCTCAAG
CAGCAAAACTGCCCCTCACCAACCAGCGTCACGCTCTAGCCACTGTTGTGACYCAAAGGTCTTTGCCGAAATTTCAACCT
CGAAAAGCGGAGTCTGTCAAGAGCCTACCAGAGAGCAGGCCACTCCCTGCCCCGCGCAAAAAGATTAGGTCCAGGTGTGG
TAGTCCGATTTCATTGGGCGGCAATCTCCCTGACAGCCAGGAAGACTTGGCCGGTGGTTCCTTTGATTTCCCAACCCTAC
CTGAGTTGGTGGTAAGCTCGAGTGAGTCTGTGCCTGTCCCTGCACCGCGCAGGGTTGTGTCCCGATTAGTGTCGTCTCCG
ATAGTGTCGACCCCTGTGCCCGCACCACGACGTGGGCTTCGGCAGGTGGAGGGAATGAATTTGGCGGCAGTGACTCTAGC
GTGCCAGGACGAGCCCCTCGATTTGTCTGCGTCCTCGCAGACTGAATATGAGGCGTCCCCCTTGGCATTGCCGCTGAGTG
AGGATGTCCTGGCGGTGGAGAGACGAGAAGTTGAAGAAGTCCTGAGCGGAATATCGGGCATGTCAGATGACATCAGGTTG
GCGCCCGTGTCATCAAGTAGCTCCCTGTCAAGCATAGAGATCACACGTCCAAAGTACTCAGCTCAAGCCATCATTAACTC
AGGTGGGCCCTGTTGTGGGCACCTCCAGGAGGTGAAAGAGAAATACCTTAATGTGATGCGTGAGGCATGTGATGCGACCA
AGCTTGATGACCCTGCCACGCAAGAATGGCTTTCCCGTATGTGGGATAGGGTAGACATGCTAACCTGGCGCAACACGTCC
ATTTTTCAGGCGCCTTTCACCTTGGCTGACAAGTTTAAGTCCCTCCCGAAGATGATACTCGAAACACCGCCGCCCTACCC
TTGTGGGTTTGTGATGATGCCCCGCACGCCTGCACCTTCTGTAGGTGCGGAGAGCGACCTCACCGTTGGCTCAGTTGCTA
CTGAAGATGTCCCGCGCATTCTCGGGAAGGTACAAGGTGTTGGCGAAACGACCGACCAGGGACCCTTGGCACTCTTCGCA
GATGAATTGGCAGATGACCAACCTGCTAGAGAACCCCGGACACAAACCCCTCCTGCAAGCGCAGGTGGCGCCGGCTTAGT
TTTGGATTCTGGAGGGTCGCCGGAGCTCACTGACCTGCCGCTTCCARACGGTACAGACGCGGGCGGAGGGGGACCGTTAC
ACACGGTCAAGAAGAAAGCTGAGAGGTGCTTTGACCAGCTGAGCCGTCGGGTTTTTGACATTGTCTCCCATCTCCCTGTC
TTCTTCTCACGCCTTTTCAAGCCTGACAGTCACTACTCTTCGGGTGACTGGAGTTTTGCAGCTTTTACTTTATTGTGCCT
CTTTCTATGTTACAGTTACCCGGCCTTTGGTGTTGCTCCCCTATTGGGTGTATTTTCTGGGTCTTCTCGGCGCGTTCGCA
TGGGGGTTTTTGGCTGCTGGTTGGCTTTTCGCTGTTGGTTTGTTCAAGCCTGCACCCGACCCAGTCGGTGCTGCTTGTGAG
```

Fig. 1E-2

```
TTTGATTCGCCAGAGTGTAGAGACATCCTTCATTCTTTTGAGCTCCTGCAACCTTGGGATCCTGTTCGCAGCCTTGTGGT
GGGACCCGTCGGTCTCGGTCTTGCCATTATTGGCAGGTTACTGGGCGGGGCACGCTACGTCTGGCTGCTTTTGCTTAGGC
TTGGCATCGTTTCAGACTGTATCTTGGCTGGAGCTTACGTGCTTTCGCAAGGTAGGTGTAAAAAGTGTTGGGGATCTTGT
ATAAGAACTGCCCCCAGTGAGGTCGCCTTCAATGTGTTTCCCTTCACACGTGCAACCAGATCGTCACTTGTCGACCTGTG
CGACCGGTTTTGTGCGCCCAAGGGCATGGACCCCATCTTCCTCGCCACTGGATGGCGCGGATGCTGGTCCGGCCAGAGCC
CCGTTGAGCAACCCACTGAGAAACCCATTGCATTCGCCCAGTTGGATGAGAAGAAAATCACGGCAAGGACTGTGGTTGCC
CAACCTTATGACCCCAACCAAGCTGTGAAGTGCTTACGAGTCTTGCAGGCGGGTGGGGCGATGGTGGCTGAGGCGATTCC
AAAAGTGGTTAAGGTCTCTGCTGTCCCATTTCGAGCCCCCTTCTTCCCCACCGGAGTGAAAGTTGATCCTGAATGCAGGG
TCGTGGTTGACCCAGACACCTTCACAACTGCTCTCCGGTCCGGCTACTCCACCACAAACCTCATTCTTGGTGTGGGGGAT
TTTGCCCAGCTGAATGGGTTGAAAATCAGACAAATTTCCAAGCCTTCAGGAGGAGGCCCATACCTCATGGCGGCCTTACA
TGTCGCTTGCTCGATGGCCTTGCACATGCTCGTTGGGATTTATGTTACCGCGGTGGGTTCTTGTGGTTCTGGCACTAACG
ATCCGTGGTGCACTAACCCGTTTGCCGTCCCTGTCTACGGGCCTGGCTCTCTTTGCACGTCCAGGTTGTGCATCTCCCAG
CATGGCCTTACTCTGCCTTTAACAGCGCTTGTGGCGGGGTTTGGTATTCAGGAAGTTGCTTTGGTTGTTTTAATCTTTGC
TTCCATCGGGGGTATGGCTCACAGGTTGAGTTGCAAGGCCGATGTGCTGTGCATTCTGCTTGCAATTGCCAGCTATGTTT
GGGTACCCTTCACCTGGTTGCTTTGTGTGTTTCCTTGCTGGTTGCGCTGGTTTTCTTTGCATCCCCTCACCATTCTATGG
TTGGTGTTTTTTTTGATTTCTGTGAACATGCCCTCAGGAATCTTGGCTTTAGTGTTGTTGATCTCTCTCTGGCTCCTTGG
TCGCTATACCAATGTCGCTGGCCTTGTCACCCCTTATGACATTCACCATTACACCAACGGCCCCCGCGGCGTTGCCGCCT
TGGCCACTGCCCCGGATGGGACCTATTTGGCTGCTGTCCGCCGCGCTGCGTTGACTGGCCGTACCATGCTGTTTACCCCG
TCTCAACTTGGGTCACTCCTTGAGGGCGCCTTTAGAACCCAAAAGCCTTCACTGAATACCGTCAATGTGGTTGGGTCCTC
CATGGGCTCCGGCGGGGTGTTCACCATTGACGGGAAAATTAAATGCGTGACCGCCGCACATATCCTCACGGGTAACTCTG
CTAGGGTCTCTGGGGTTGGCTTCAATCAAATGTTGGATTTTGATGTAAAAGGGGATTTTGCCATAGCCGATTGTCCGGGT
TGGCAAGGAGTCGCTCCCAAGTCCCAGATCTGCAAGGATGGGTGGACTGGCCGCGCTTATTGGCTAACGTCCTCTGGCGT
CGAACCCGGCGTCATTGGTAGGGGATTCGCCTTTTGTTTCACCGCGTGCGGCGATTCCGGGTCCCCAGTGATCACCGAGG
CCGGAGAGCTTGTCGGAGTCCACACGGGATCAAACAAACAAGGAGGAGGCATTGTCACGCGCCCTTCAGGCCAGTTTTGT
AATGTGACACCCACCAAACTAAGTGAATTGAGTGAATTCTTCGCCGGACCCAGGGTCCCGCTTGGTGATGTGAAGGTTGG
CAACCACATAATCAAAGATACAGATGAGGTGCCCTCAGATCTTTGCGCCTTGCTTGCTGCCAAGCCCGAGTTGGAAGGAG
GCCTCTCCACCGTTCAACTTCTGTGCGTGTTTTTTCTCCTATGGAGAATGATGGGACATGCCTGGACGCCCTTGGTTGCT
GTTGGTTTTTTCATCTTGAATGARATCCTCCCAGCGGTCCTGGTCCGGAGTGTTTTCTCCTTTGGAATGTTYGYKCTRTC
YTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCGGCGGGTCAGTTTATCGAGGCCGCTTATGCGAAAGCGATCAGGGTGGAACTTGCCCAGT
TAGTGCAGGTCGACAAGGTTCGGGGTGTTTTAGCCAAACTTGAAGCTTTTGCTGACACCGTGGCGCCCCATCTTTCACCC
GGCGACATTGTTGTTGTTCTTGGTCATACGCCCGTTGGCAGCATCTTTGACTTAAAGATTGGCRATGCCAAGCACACCCT
ACAAGCCATCGAGACCAGAGTCCTTGCTGGGTCCAGGATGACCGTGGCGCGTGTCGTTGATCCGACTCCCGCGCCGCCAC
CCGTACCCGTGCCCGTTCCTCTCCCACCGAAAGTTTTAGAGAACGGCCCCAGTGCCTGGGGGGATGAAGACCGCCTGAAC
AAAAAGAAGCGGCGCAAGATGGAAGCCGTTGGCGTTTACGTCATGGGCGGGAAAAAGTACCAGAAATTTTGGGATAAGAA
TTCTGGTGATGTGTTCTATGAGGAAGTCCACGACAACACAGATGCGTGGGAATGCCTTAGAGCTGACGACCCTGCCGACT
TGGATCCTGAGAGGGGAACCTTGTGTGGACACGTCACCATAGAGAATAGGCCTTACCATGTTTACGCCTCCCCGTCTGGT
AGGAAGTTCCTGGTCCCTGCCGACCCAGAGAATGGGAAAGCCCAGTGGGAAGCTGCAAAGCTTTCCATAGAGCAGGCCCT
TGGTATGATGAACGTTGACGGCGAGCTGACCGCCAAAGAACTGGAGAAATTGAAGAGAATAATTGACAAACTCCAGGGCC
TGACTAAGGAGCAGTGTTTAAACTGTTAGCCGCCAGCGGCTTGACCCGCTGTGGTCGCGGCGGCTTGGTTATTACTGAGA
CAGCGGTAAAAATAGTCAGATTCCACAATCGGACCTTCACCCTGGGGCCTGTGAATTTGAAAGTGGCCAGCGAAGTTGAG
TTGAAAGACGCCGTCGAGCACAACCAACACCCGGTTGCAAGACCAGTTGACGGTGGCGTTGTGCTCCTGCGCTCTGCAGT
TCCTTCGCTTATAGACGTCTTGATCTCCGGTGCCGACGCATCTCCCCAGTTGCTCGCCCATCACGGTCCAGGAAACACTG
```

Fig. 1E-3

```
GGATTGATGGCACGCTCTGGGATTTTGAGTCCGTAGCCACTAAAGAGGAAGTCGCACTTAGTGCACAAATAATACAGGCT
TGTGGCATTAGGCGTGGCGATGCTCCTGAGATTGGCCTCCCTTACAAGCTGCACCCTGTTAGGGACAACCCTGAACGTGT
AAAAGGGGTTTTGAAAAACACAAGGTTTGGAGACATACCTTACAAGACCCCTAGCGACACTGGGAGCCCAGTACATGCGG
CCGCCTGCCTTACGCCTAATGCCACCCCGGTGACTGATGGGCGCTCCGTCTTGGCCACGACTATGCCCTCCGGGTTTGAG
TTGTATGTGCCGACCATTCCAGCGTCTGTCCTTGATTACCTTGATTCCAGGCCAGACTGCCCTAAACAGTTGACGGAGCA
CGGGTGTGAAAATGCTGCATTGAGAGACCTCTCCAAATATGACTTGTCCACCCAAGGTTTTGTTTTGCCCGGAGTCCTCC
GCCTCGTGCGGAAATACTTGTTTGCCCACGTGGGCAAGTGCCCACCTGTCCATCGGCCCTCCACCTACCCGGCCAAGAAT
TCCATGGCTGGAATAAACGGGAATAGGTTCCCGACCAAGGACATTCAGAGCATCCCTGAGATCGACGTTCTGTGTGCACA
GGCTGTACGAGAGAACTGGCAGACCGTTACCCCTTGCACCCTCAAGAAGCAGTATTGCGGGAAGAAGAAAACCAGGACCA
TACTCGGTACCAATAACTTCATTGCGCTGGCCCACCGGGCAGCACTGAGTGGTGTCACCCAGGGCTTCATGAAAAAGGCG
TTTAACTCGCCCATCGCCCTCGGGAAGAACAAATTCAAGGAGCTACAGACTCCGGTCCTGGGCAGATGTCTTGAGGCTGA
TCTTGCCTCTTGCGATCGGTCCACTCCCGCGATTGTCCGCTGGTTTGCCGCCCATCTCCTTTATGAACTTGCCTGCGCTG
AGGAGCACCTACCGTCGTATGTGCTGAATTGCTGCCATGACCTATTGGTCACGCAGTCCGGTGCGGTGACTAAGAGAGGT
GGCCTGTCATCTGGTGATCCGATCACCTCTGTATCCAACACCATTTACAGTCTGGTAATTTATGCGCAGCACATGGTGCT
CAGTTACTTCAAAAGTGGTCACCCACATGGTCTCCTGTATCTCCAGGACCAGCTAAAGTTTGAGGACATGCTTAAGGTTC
AGCCCCTGATYGTCTACTCGGATGATCTTGTGCTGTATGCCGAGTCCCCCACCATGCCAAACTACCACTGGTGGGTTGAG
CATCTGAACTTGATGCTAGGGTTTCAGACGGACCCAAAGAAGACAACCATTACTGACTCGCCATCTTTTCTGGGCTGTAG
GATAATGAATGGGCGTCAGCTAGTCCCAAACCGTGACAGGTTCTCGCAGCTCTTGCCTACCACATGAAGGCGAATAATG
TTTCTGAGTACTACGCCTCCGCTGCTGCAATACTCATGGACAGTTGTGCTTGTCTGGAGTACGACCCTGAATGGTTTGAA
GAACTTGTGGTTGGAATGGCGCTATGCGCCCGCAAGGACGGCTATAGCTTCCCCGGCCCGCCGTTCTTCTTATCCATGTG
GGAGAAACTTAAGTCCAATTATGAGGGGAAGAAGTCAAGGGTATGTGGGTACTGCGGAGCTTCGGCCCCGTATGCCACTG
CCTGTGGTCTTGACGTCTGTGTTTACCACACTCACTTTCACCAGCATTGTCCAGTCATAATCTGGTGTGGCCACCCTGCA
GGTTCCAGGTCCTGTGATGAGTGCAAATCCCCCATAGGGAAAGGCACAAGCCCTCTGGATGAGGTTTTGAGACAAGTCCC
GTATAAGCCTCCACGGACCGTCCTCATGCATGTGGAGCAGGGCCTCACCCCCCTTGACCCAGGCAGATATCAGACCCGCC
GTGGGTTGGTTGCCGTTAGGCGCGGGATCAGGGGAAATGAAGTTGACCTACCAGATGGTGATTATGCTAGCACCGCCTTA
CTCCCAACCTGTAAAGAGATCAACATGGTTGCTGTTGCTTCTAATGTGTTGCGCAGCAGATTTATCATCGGTCCACCCGG
TGCTGGGAAAACATACTGGCTCCTTCAACAGGTCCAGGATGGTGATGTCATATACACACCGACCCATCAGACCATGCTTG
ACATGATCAAAGCTTTRGGGACGTGCCGGTTTAACGTCCCGGCAGGCACAACGCTGCAATTCCCCGTCCCCTCCCGCACC
GGTCCGTGGGTTCGCATCCTGGCCGGCGGGTGGTGTCCTGGCAAAAACTCCTTCCTGGACGAAGCTGCGTATTGTAATCA
TCTTGATGTCTTGAGGCTTCTTAGCAAAACCACTCTCACCTGTTTGGGGACTTCAAACAACTCCACCCAGTGGGTTTTG
ATTCTCATTGCTATGTCTTTGACATTATGCCTCAGACTCAATTGAAGACCATCTGGAGATTTGGACAGAACATCTGTGAT
GCCATCCAACCAGACTACAGAGACAAGCTTATGTCCATGGTCAACACAACTCGTGTAACTTATGTGGAAAAACCTGTCAA
ATATGGGCAAGTCCTCACCCCTTACCATAGGGACCGAGAGGATAGCGCCATTACCATTGACTCCAGTCAAGGCGCCACAT
TTGATGTGGTTACACTGCATTTGCCCACGAAAGATTCACTCAACAAACAAAGGGCCCTTGTTGCTATTACCAGGGCAAGA
CATGCCATCTTTGTGTATGACCCATATAGGCAACTGCAGAGCCTATTTGATCTTCCTGCAAAAAGCACGCCCGTCAACTT
GGCCGTGCACCACGATGGGCAACTGATTGTGCTAGATAGAAATAACAAAGAATGCACGGTTGCCCAAGCTCTGGGTAATG
GTGACAAATTTAGGGCCACAGACAAGCGCGTTGTGGATTCTCTCCGCGCCATTTGTGCTGACCTAGAAGGGTCGAGCTCT
CCACTCCCCAAGGTTGCACATAATTTGGGGTTTTATTTCTCACCTGATTTGATACAGTTTGCCAAGCTTCCAATAGAACT
TGCGCCACACTGGCCAGTAGTGACGACCCAAGACAATAAAAACTGGCCAGATCGGCTGGTTGCCAGCCTACGCCCTATTC
ACAAACATAGCCGTGCGTGTATCGGTGCCGGCTATATGGTGGGCCCCTCGGTGTTTTTAGGCACCCCTGGGGTTGTGTCA
TACTATCTTACAAAATTTGTTAAGGGCGAGGCTCAAGTGCTTCCGGAAACGGTCTTCAGTACCGGCCGAATTGAGGTGGA
TTGCCGGGAATATCTTGACGACCGGGAGCGGGAAGTTGCAGCGTCCCTCCCACACGCCTTTATCGGCGACGTCAAAGGCA
CTACCGTCGGAGGGTGTCATCACATCACCTCCAAATACCTTCCGCGCTTCCTCCCCAAGGAATCAGTTGCGGTAGTCGGG
GTTTCAAGCCCCGGAAAAGCAGCGAAAGCAGTGTGTACATTGACAGATGTGTACCTCCCAGACCTTGAAGCTTACCTCCA
TCCTAAGACCCTGTCCAAGTGCTGGAAAATGATGTTGGACTTCAAAGAAGTTCGGCTGATGGTCTGGAAGGACAAGACGG
CCTATTTCCAACTCGAAGGTCGCCATTTCACCTGGTATCAACTTGCTAGCTATGCCTCGTACATCCGTGTTCCTTTAAAC
TCCACGGTGTACCTGGACCCCTGCATGGGCCCCGCCCTTTGCAACAGAAAAGTTGTTGGGTCCACTCATTGGGGAGCTGA
CCTCGCAGTCACCCCTTATGATTATGGGCAAGAATTATTTTGTCTAGTGCGTACCATGGTGAGATGCCTCCTGGGTACA
```

*Fig. 1E-4*

```
AGATTCTGGCGTGCGCGGAGTTCTCGCTGGACGACCCAGTCAGATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCCTAGACTGAA
ATGAAATGGGGCTGTGCAGAGCCTATTTGATAAAATTGGCCAACTGTTTGTGGACGCTTTCACGGAGTTCTTGGTGTCC
ATTGTTGATATCATCATATTTTTGGCCATTTTGTTCGGCTTCACAATCGCCGGTTGGCTGGTGGTCTTTTGCATCAGATT
GGTTTGCTCCGCGATACTCCGTTCGCGCTCTGCCGTTCACCCTGAGCAATTACAGAAGATCCTATGAGGCATTTCTCTCC
CAGTGCCGGACGGAYATTCCCACCTGGGGAACTAAACATCCCTTGGGGATGCTCTGGCACCACAAGGTGTCGACCCTAAT
TGATGAAATGGTGTCGCGTCGAATGTACCGCATCATGGAACAAGCAGGGCAGGCTGCCTGGAAACAGGTGGTGACCGAGG
CAACGTTGTCTCGTATTAGTAGCTTGGATGTGGTGGCTCATTTCCAGCACCTTGCCGCCATAGAAGCCGAGACTTGTAAA
TACTTGGCCTCCCGGCTGCCAATGCTGCACAACCTGCGCATGACAGGGTCAAATGTAACCATAGTGTATAATAGCTCTCT
AGAACAGGTGTTTGCTGTTTTCCCGACCCTCAGTTCCCGGCCAAAGCTTCATGATTTTCGGCAATGGCTAATAGCTGTGC
ATTCCTCCATATTCTCTTCTGTTGCGGCTTCCTGTACCCTTTTCGTCGTGCTGTGGTTGCGGCTTCCAATAATACGTACT
GTTTTTGGTTTCCACTGGTTAGGGGCAATTTTTCCTTCGAGCTCACAGTGAACTACACGGTGTGTCCTCCCTGCCTCACC
CGGCAGGCGGCCGCAGAGATCTACGAACCTAGTGGGTCTCTTTGGTGCAGGATAGGGCACGATCGATGCTCGGAGGACGA
TCACGACGAGCTAGGATTTCTGGTGCCGCCTGGCCTCTCCAGCGAAGGCCACTTGACCAGTGTTTACGCCTGGTTGGCGT
TCTTGTCCTTCAGTTACACGGCCCAGTTTCACCCCGAGATATTCGGGATAGGGAATGTGAGTAAAGTTTATGTTGACATC
AAGCATCAATTTATTTGCGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTCTCAGACATTAAGACCAACA
CCACCGCAGCTGCAGGCTTTGCTGTCCTCCAAGACATCAGTTGTCTTAGGCATGGCCACTCGTCCTCTGAGGCGACTCGC
AAAAGCCGTCAATGTCGCACGGCGATAGGAACGCCCGTATACATTACTGTCACAGCCAATGTAACAGATGAGAATTATTT
GCATTCCTCTGACCTTCTCATGCTTTCCTCTTGCCTTTTCTACGCTTCCGAGATGAGTGAAAAGGGATTTGAAGTGATAT
TTGGCAATGTGTCAGGCATAGTGGCTGTGTGTCAACTTTACCAGCTATGTCCAACATGTCAAGGAGTTCACCCAGCGC
TCCTTGGTGGTTGACCATGTGCGGTTACTTCATTTTATGACACCTGAGACTATGAGGTGGGCGACCGTTTTAGCCTGTCT
TTTTGCCATTCTGTTGGCCATTTGAATGTTCAGATATGTTGGGGAAATGCTTGACCGCGGGCTATTGCTCGCAATTGCTT
TTTTTGTGGTGTATCGTGCCGTTCTGTCTTGCTGCGCTCGTCAACGCCGACAGCAACAGCAGCTCCCATTTACAGTTGAT
TTATAAMTTAACGATATGTGAGCTGAATGGCACAGACTGGCTGAACAATCATTTTAGTTGGGCAGTGGAGACTTTCGTTA
TCTTTCCTGTGTTGACTCATATTGTTTCCTACGGCGCCCTCACTACCAGCCACCTCCTTGACACGGTCGGCCTGATCACT
GTGTCCACCGCCGGATACTGCCATAAGCGGTATGTCTTGAGTAGCATCTATGCTGTCTGCGCCCTGGCTGCGCTGATTTG
CTTCGTCATCAGGTTGACGAAAAATTGTATGTCCTGGCGCTACTCATGTACCAGATATACCAACTTTCTTCTGGACACCA
AGGGCAGACTCTATCGCTGGCGGTCACCCGTCATCATAGAGAAAAGGGGTAAAATTGAGGTTGGAGGTGACCTGATCGAC
CTCAAGAGAGTTGTGCTTGATGGTTCCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTTCTATCACCTACACACCAGTGATGATATATGC
CCTAAAGGTGAGTCGTGGCCGGCTGCTAGGGCTTTTACACCTTTTGATTTTTYTAAACTGTGCTTTTACCTTCGGGTATA
TGACATTTGTGCACTTTCAGAGCACAAACAGAGTTGCACTCACTATGGGAGCAGTAGTCGCGCTCCTTTGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGAGAGTGCCGCAGGCTTTCATCCGATTGCGGCAAGTGATAACCACGCATTTGTCGTCCGGCGTCCCGGTT
CCACTACGGTTAACGGCACATTGGTGCCCGGGTTGAAAAGCCTCGTGTTGGGTGGCAGAAGAGCTGTCAAACGGGGAGTG
GTAAACCTCGTTAAATATGCCAAATAACAACGGCAGGCAGCAGAAGAAAAAGAAAGGGGACGGCCAGCCAGTCAATCAGC
TGTGCCAAATGTTGGGCAGGATCATCGCCCAGCAAAACCAGTCCAGAGGTAAGGGACCGGGGAAGAAAAGTAAGAAGAAA
AGCCCGGAGAAGCCCCATTTTCCTCTCGCGACTGAAGATGACGTTAGACATCACTTCACCCCTAGTGAGCGGCAATTGTG
TCTGTCGTCAATCCAGACTGCCTTTAACCAAGGCGCTGGAACTTGTACCCTGTCGGATTCAGGGAGAATAAGTTACGCTG
TGGAGTTTAGTTTGCCTACGCATCATACTGTGCGCCTAATTCGCGTCACAGCATCACCCTCAGCATGATGAGCTGGCATT
CTTGAGACATCCCAGTGTTTGAATTGGAAGGATGTGTGGTGAATGGCACTGATTGATATTGTGCCTYAAGTCACCTATT
CAATTAGGGCGACCGTATGGGGGTAATATTTAATTGGCGTGAACCATGCGGCCGAAATT
```

Fig. 1F-1

>MN184B_DQ176020.seq
ATGACGTATAGGTGTTGGCTCTATGCCACGACATTTGTATTGTCAGGAGCTGTGACCACTGGCACAGCCCAAAGCTTGCT
GCACAGAAACACCCTTCTGTGACGGCCTCCTTCAGGGGAGTTTAGGGGTTTGTCCCTAGCACCTTGTTTCTGGAGTTGCA
CTGCTTTACGGTCTCTCCACCCCTTTAACCATGTCTGGGATTCTTGATCGGTGCACGTGCACCCCCAATGCCAGGGTGTT
TATGGCAGAGGGCCAAGTCTACTGCACACGATGTCTCAGTGCACGGTCCCTCCTTCCCCTGAATCTCCAAGTCTCTGAGC
TCGGAGTGTTGGGCTTGTTTTATAGGCCTGAAGAGCCGCTCCGGTGGACGTTGCCACGCGCATTCCCCACTGTTGAGTGC
TCCCCTGCTGGGGCTTGTTGGCTTTCTGCAATTTTTCCAATTGCACGAATGACCAGTGGAAACCTGAACTTTCAACAAAG
ATTAGTGCGGGTCGCAGCTGAGCTTTACAAAGCCGGCTGCCTCACCCCTACAGTCCTAAAGAGTCTACAAGTCTATGAAC
GGGGTTGCCGCTGGTACCCCATCGTTGGACCTGTCCCTGGAGTTGCCGTTTTCGCCAACTCCCTACATGTGAGTGATAGA
CCTTTCCCAGGTGCTACTCACGTGCTAACCAACCTGCCGCTCCCGCAGAGACCTAAGCCTGAAGATTTTTGCCCCTTTGA
GTGTGCTATGGCTGCCGTCTATGACATTGGTCATGACGCCGTTATGTTCGTGGCCGAAGGGAGAGTCTCTTGGGCTCCGC
GTGGTGGGGAAAAAGGAAAATTTGAAACTGTTCCCGAGGAGTTGGGGTTGATTGCAGAGCAACTTTATACCTCCTTCCCG
CCCCACCACTTGGTGGACATGTCGAAATTCACCTTTACGGCCCCTGAGTGTGGTGCTTCCATGCGAGTCGAACGCCAGTA
TGGCTGCCTCCCCGCTGGCACTGTCCCTGACGGCAATTGCTGGTGGAGCTTGTTTAGCTCGCTCCCATTGGAAGTCCAGT
ATAAAGAAATTCGCTACGCCACCCAATTTGGCTATCAAACTAAGCATGGCGTTGCTGGCAAGTACCTACAGCGGAGGCTG
CAAATTAATGGTCTCCGAGCAGTGGTTGACTCGAATGGACCCATCGTCATACAGTACTTCTCTGTTAAGGAGAGCTGGAT
CCGCCACGTGAAACTGGCGGAAGAGTTTGACTACCCTGGGTTTGAGGATCTCCTCAGGATAAGAGTCGAGCCCAACACGT
TGCCATTGTCCAACAAGGACGAGAAAATCTTCCGGTTTGGTGGGTGCAAGTGGTACGGTGCTGGGAAGAGGGCAAGGAGG
GCACGTGCAAGTGCAGTCACCGCAGTCGCCGGTCACGCTCCGCCTACTCGTGAAACCCAGCAAGCCAAGAAACACGAAGC
TGCTAGTGCCAACAAGGCTGAGCTTCTTGAACGCTACTCCCGCCTGCTGAAGGGAATTGCGGCTGGCACTGTATCTCCG
CCATCGCCAACCGGATGGTRAATTCYAARTTTGAAACYRCCCTTCCCGAAAGAGTGAGACCTCCAGATGACTGGGCTACT
GACGAGGATCTTGTGAATGCCATCCAAATCCTCAGACTCCCTGCGGCCTTAGACAGGAACGGTGCTTGTACTAGCGCCAA
GTACGTACTTAAGCTGGAAGGTGAGCATTGGACTGTCACTGTGACCCCTGGGATGTCCCCTTCTTTGCTCCCTCTTGAAT
GTGTTCAGGGCTGTTGTGGGCACAAGGGCGGTCTTGGTTCCCCAGATGCAGTCGAGGTCTCCGGATTTGACCCTGCCTGC
CTTGACCGGCTGGCTGAGGTGATGCACCTGCCTAGCAGTGCTATCCCAGCCGCTCTGGCCGAAATGTCTGGCGATTCCGA
TCGTTCGGCTTCTCCGGTCACCACCGTGTGGACTGTTTCGCAGTTCTTTGCCCGTCACAGCGGAGGGAATCACCCTGACC
AAGTGCGCTTAGGGAAAATTATCAGCCTTTGTCAGGTGATTGAGGACTGCTGCTGTTCCCAGAACAAAACCAACCGGGTC
ACCCCGGAGGAGGTCGCAGCAAAGATTGAYCAGTACCTTTTTGGTGCAGCAAGTCTTGAAGAATGCTTGGCCAGGCTTGA
RAAAGCTCGCCCGCCAAGCGTATTARACACCTCCTTTGATTGGGATGTTGTGCTCCCTGGTGTCGGGGCGGCTGCTCAAG
CAGCAAAACTGCCCCTCACCAACCAGCGTCACGCTCTAGCCACTGTTGTGACTCAAAGGTCTTTGCCGAAATTTCAACCT
CGAAAAGCGGAGTCTGTCAAGAGCCTACCAGAGAGCAGGCCCCTCCCTGCCCCGCGCAAAAAGATTGGGTCCAGGTGTGG
TAGTCCGATTTCATTGGGCGGCAATCTCCCTGACAGCCGGGAAGACTTGGCCGGTGGTTCCTTTGATTTCCCAACCCTAC
CTGAGTTGGTGGCAAGCTCGAGCGAGCCTGTGCCTGTCCCTGCACCGCGCAGGGTTGTGTCCCGATTAGTGTCGTCTCCG
ATAGTGTCGACCCCTGTGCCCGCACCACGACGTGGGCTTCGGCAGGTGGAGGGAATGAATTTGGCGGCGGTGACTCTAGC
GTGCCAGGACGAGCCCCTCGATTTGTCTGCGTCCTCGCAGACTGAATATGAGGCGTCCCCCTTGGCATTGCCGCTGAGTG
AGGATGTCCTGGCGGTGGAGAGACGAGAAGTTGAAGAAGTCCTGAGCGGAATATCGGGCATGCCAGATGACATCAGGTTG
GCGCCCGTGTCATCAAGTAGCTCCCTGTCAAGCATAGAGATCACACGTCCAAAGTACTCAGCTCAAGCCATCATTAACTC
AGGTGGGCCCTGTTGTGGGCACCTCCAGGAGGTAAAAGAGAAATACCTTAATGTGATGCGTGAGGCATGTGATGCGACCA
AGCTTGATGACCCTGCCACGCAAGAATGGCTTTCCCGCATGTGGGATAGGGTAGACATGCTAACCTGGCGCAACACGTCC
ATTTTTCAGGCGCCTTTCACCTTGGCTGACAAGTTTAAGACCCTCCCGAAGATGATACTCGAAACACCGCCGCCCTACCC
TTGTGGGTTTGTGATGATGCCCCGCACGCCTGCACCTTCTGTAGGTGCGGAGAGCGACCTCACCGTTGGCTCAGTTGCTA
CTGAGGATGTCCCGCGCATTCTCGGGAATGTACAAGGTGTTGGCGAAACGACCGACCAGGGACCCTTGGCACCCTTCGCA
GACGAATTGGCAGATGACCAACTTGCTAGAGAACCCCGGACACAAACCCCTCCTGCAAGCACAGGTGGCGCCGGCTTGGT
TTCGGATTCTGGAAGGTCGCCGGAGCTCACTGACCTGCCGCTTTCAAACGGTACAGACGCGGGCGGAGGGGGGCCGTTAC
ACACGGTCAAGAAGAAAGCTGAGAGGTGCTTTGACCAGCTGAGCCGTCGGGTTTTTGACATTGTCTCCCATCTCCCTGTT
TTCTTCTCACGCCTTTTCAAGCCTGACAGTCACTACTCTTCGGGTGACTGGAGTTTTGCAGCTTTTACTTTATTGTGCCT
CTTTCTATGTTACAGTTACCCAGCCTTTGGTGTTGCTCCCCTATTGGGTGTATTTTCTGGGTCTTCTCGGCGCGTTCGCA
TGGGGGTTTTTGGCTGCTGGTTGGCTTTCGCTGTTGGTTTGTTCAAGCCTGCACCCGACCCAGTCGGTGCTGCTTGTGAG

Fig. 1F-2

```
TTTGATTCGCCAGAGTGTAGAGACATCCTTCATTCTTTTGAGCTTCTGCAACCTTGGGACCCTGTTCGCAGCCTTGTGGT
GGGGCCCGTCGGTCTCGGTCTTGCCATTATTGGCAGGTTACTGGGCGGGGCACGCTACGTCTGGCTGCTTTTGCTTAGGC
TTGGCATCGTTTCAGACTGTATCTTGGCTGGAGCTTATGTGCTTTCGCAAGGTAGGTGTAAAAAGTGTTGGGGATCTTGT
ATAAGAACTGCTCCCAGTGAGGTCGCCTTCAATGTGTTTCCCTTCACACGTGCAACCAGATCGTCACTTGTCGACCTGTG
CGACCGGTTTTGTGCGCCCAAGGGCATGGACCCCATCTTCCTCGCCACTGGATGGCGCGGATGTTGGTCCGGCCAGAGCC
CCATTGAGCAACCCACTGAGAAACCCATTGCGTTCGCCCAGTTGGATGAAAAGAAAATCACGGCAAGGACTGTGGTTGCC
CAACCTTATGACCCCAACCAAGCTGTGAAGTGCTTACGAGTCTTGCAGGCGGGTGGGGCGATGGTGGCTGAGGCGGTTCC
AAAAGTGGTTAAGGTCTCTGCTGTCCCATTTCGAGCCCCCTTCTTCCCCGCCGGAGTGAAAGTTGATCCTGAATGCAGGG
TCGTGGTTGACCCAGACACCTTCACAACTGCTCTCCGGTCCGGCTACTCCACCACAAACCTCATTCTTGGTATGGGGAT
TTTGCCCAACTGAATGGGTTGAAAATCAGACAAATTTCCAAGCCTTCAGGAGGTGGTCCATACCTCATGGCGGCCTTACA
TGTCGCTTGCTCGATGGCCTTGCACATGCTCGTTGGGATTTATGTTACCGCGGTGGGTTCTTGTGGTTCTGGCACTAACG
ATCCGTGGTGCACTAACCCGTTTGCCGTCCCTGTCTACGGGCCTGGCTCTCTTTGCACGTCCAGGTTGTGCATCTCCCAG
CATGGCCTTACTCTGCCTTTAACAGCGCTTGTGGCGGGGTTTGGCATTCAGGAAGTTGCTTTGGTTGTTTTAATCTTTAC
TTCCATCGGGGTATGGCTCACAGGTTGAGCTGCAAGGCCGATGTGCTCTGTGTATTCTGCTTGCAATTGCCAGCTATGTTT
GGGTACCCTTCACCTGGTTGCTTTGTGTGTTTCCTTGCTGGTTGCGCTGGTTTTCTTTGCATCCCCTCACCATTCTATGG
TTGGTGTTTTTCTTGATTTCTGTGAACATGCCCTCAGGAATCTTGGCTTTAGTGTTGTTGATCTCTCTCTGGCTCCTTGG
TCGCTATACCAATGTCGCTGGCCTTGTCACCCCTTATGACATTCACCATTACACCAACGGCCCCCGCGGCGTTGCCGCCT
TGGCCACTGCCCCGGATGGGACCTATTTGGCTGCTGTCCGCCGCGCTGCGTTGACTGGCCGCACCATGCTGTTTACCCCG
TCTCAACTTGGGTCACTCCTTGAGGGCGCCTTTAGAACCCAAAAGCCTTCACTGAATACCGTCAATGTGGTTGGGTCCTC
CATGGGCTCCGGCGGGGTGTTCACCATTGACGGGAAAATTAAGTGCGTGACCGCCGCACATATCCTCACGGGTAACTCTG
CTAGGGTCTCTGGGGTTGGCTTCAATCARATGTTGGATTTTGATGTAAAAGGGGATTTTGCCATAGCCGATTGTCCGGGT
TGGCAGGGAGTCGCTCCCAAGTCCCAGTTCTGCAAGGATGGGTGGACTGGCCGCGCTTATTGGCTAACGTCCTCTGGCGT
CGAACCCGGCGTCATTGGTAGGGGATTCGCCTTTTGTTTCACCGCGTGCGGCGATTCCGGGTCCCCAGTGATCACCGAGG
CCGGAGAGCTTGTCGGAGTCCACACGGGATCAAACAAACAAGGAGGAGGCATTGTCACGCGCCCTTCAGGCCAGTTTTGT
AATGTGRCACCCAYCAARYTAAGYGAATTRAGTGAATTCTTYGCYGGRCCTARGGTCCCGCTYGGTGAYGTGAAGGTCGG
CAGCCACATAATTAAAGACATAAGCGAGGTGCCTTCAGATCTTTGTGCCTTGCTTGCTGCCAAACCTGAACTGGAAGGAG
GCCTCTCCACCGTCCAACTTCTTTGTGTGTTTTTTCTCCTGTGGAGAATGATGGGACATGCCTGGACGCCCTTGGTTGCT
GTGAGTTTCTTTATTTTGAATGAGGTTCTCCCAGCCGTCCTGGTCCGGAGTGTTTTCTCCTTTGGAATGTTTGTGCTATC
CTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCAGCGGGTCARTTTATCGAGGCYGCCTATGCGAAAGCGATCAGGGTGGAACTTGCCCAGT
TAGTGCAGGTCGACAAGGTTCGGGGTGTTTTAGCCAAACTTGAAGCTTTTGCTGACACCGTGGCGCCCCATCTTTCACCC
GGCGACATTGTTGTTGTTCTTGGTCATACGCCCGTTGGCAGCATCTTTGACTTAAAGATTGGCAATGCCAAGCACACCCT
ACAAGCCATCGAGACCAGAGTCCTTGCTGGGTCCAGGATGACCGTGGCGCGTGTCGTTGATCCGACTCCCGCGCCGCCAC
CCGTACCCGTGCCCGTTCCTCTCCCACCGAAAGTTTTAGAGAACGGCCCCAGTGCCTGGGGGGATGAAGACCGCCTGAAC
AAAAAGAAGCGGCGCAAGATGGAAGCCGTTGGCATTTACGTTATGGGCGGGAAAAAGTACCAGAAATTTTGGGATAAGAA
TTCTGGTGATGTGTTCTATGAGGAAGTCCACGACAACACAGATGCGTGGGAATGCCTTAGAGCTGACGACCCCGCCGACT
TGGATCCTGAGAGGGGAACCTTGTGTGGACACGTCACCATAGAGAATAGGCCTTACCATGTTTATGCCTCCCCGTCTGGT
AGGAAGTTCCTGGTCCCTGCCGACCCAGAGAATGGGAAAGCCCAGTGGGAAGCTGCAAAGCTTTCCATGGAGCAGGCCCT
TGGTATGATGAACGTTGACGGCGAGCTGACCGCCAAAGAACTGGAGAAATTGAAGAGAATAATTGACAAACTCCAGGGCC
TGACTAAGGAGCAGTGTTTAAACTGTTAGCCGCCAGCGGCTTGACCCGCTGTGGTCGCGGCGGCTTGGTTATTACTGAGA
CAGCGGTAAAAATAGTCAGATTCCACAATCGGACCTTCACCCTGGGGCCTGTGAATTTGAAAGTGGCCAGCGAAGTTGAG
TTGAAAGACGCCGTCGAGCACAACCAACACCCGGTTGCAAGACCAGTTGACGGTGGCGTTGTGCTCCTGCGCTCTGCAGT
TCCTTCGCTTATAGACGTCTTGATCTCCGGTGCCGACGCATCTCCCCAGTTGCTCGCCCATCACGGGCCAGGAAACACTG
```

Fig. 1F-3

```
GGATTGATGGCACGCTCTGGGATTTTGAGTCCGTAGCCACTAAAGAGGAAGTCGCACTTAGTGCACAAATAATACAGGCT
TGTGGCATTAGGCGTGGCGATGCTCCTGAGATTGGCCTCCCTTACAAGCTGCACCCTGTTAGGGGCAACCCTGAACGTGT
GAAAGGGGTTTTGAAAAACACAAGGTTTGGAGACATACCTTACAGGACCCCTAGCGACACTGGGAGCCCAGTACATGCGG
CCGCCTGCCTTACGCCTAACGCCACCCCGGTGACTGATGGGCGCTCCGTCTTGGCCACGACTATGCCCTCCGGGTTTGAG
TTGTATGTGCCGACCATTCCAGCATCTGTCCTTGATTACCTTGATTCCAGGCCAGACTGCCCTAAACAGTTGACGGAGCA
CGGGTGTGAAGATGCTGCATTGAGAGACCTCTCCAAATATGACTTGTCCRCCCAAGGTTTTGTTTTGCCCGGAGTCCTCC
GCCTCGTGCGAAATACTTGTTTGCCCACGTGGGCAAGTGCCCACCTGTCCATCGGCCCTCCACCTACCCGGCCAAGAAT
TCCATGGCTGGAATAAACGGGAATAGGTTCCCAACCAAGGACATTCAGAGCATCCCTGAGATCGACGTTCTGTGTGCACA
GGCTGTACGAGAGAACTGGCAGACCGTTACCCCTTGCACCCTCAAGAAGCAGTATTGCGGGAAGAAGAAAACCAGGACCA
TACTCGGTACCAATAACTTCATTGCGCTGGCCCACCGGGCAGCACTGAGTGGTGTCACCCAGGGCTTCATGAAAAAGGCG
TTTAACTCGCCCATCGCCCTCGGGAAGAACAAATTCAAGGAGCTACAGACTCCGGTCCTGGGCAGATGCCTTGAGGCTGA
TCTTGCCTCTTGCGATCGATCCACTCCCGCGATTGTCCGCTGGTTTGCCGCCCATCTCCTTTATGAACTTGCCTGCGCTG
AGGAACACCTACCGTCGTATGTGCTGAATTGCTGCCATGACCTATTGGTCACGCAGTCCGGTGCGGTGACTAAGAGAGGT
GGCCTGTCATCTGGTGATCCGATCACCTCGGTATCCAACACCATTTACAGTCTGGTGATTTATGCGCAGCACATGGTGCT
CAGTTATTTCAAAAGTGGTCACCCACATGGTCTCCTGTTTCTCCAGGACCAGCTAAAGTTTGAGGACATGCTTAAGGTTC
AGCCCCTGATTGTCTACTCGGATGATCTTGTGCTGTATGCCGAGTCTCCCACCATGCCAAACTATCACTGGTGGGTTGAG
CATCTGAACTTGATGCTAGGGTTTCAGACGGACCCAAAGAAGACAACCATTACTGACTCGCCATCTTTTCTGGGCTGTAG
GATAATGAATGGGCGTCAGCTAGTCCCAAACCGTGATAGGATTCTCGCAGCTCTTGCCTACCACATGAAGGCGAATAATG
TTTCTGAGTACTACGCCTCCGCTGCTGCAATACTCATGGACAGTTGTGCTTGTCTGGAGTACGACCCTGAATGGTTTGAA
GAACTTGTGGTTGGAATGGCGCAATGCGCCCGCAAGGACGGCTATAGCTTCCCCGGCCCGCCGTTCTTCTTATCCATGTG
GGAGAAACTCAGGTCCAATTATGAGGGGAAGAAGTCAAGGGTGTGTGGGTACTGCGGAGCTTCGGCCCCGTATGCCACTG
CCTGTGGTCTTGACGTCTGTGTTTACCACACTCACTTTCACCAGCATTGTCCAGTCATAATCTGRTGTGGCCACCCTGCA
GGTTCCAGGTCCTGTGATGAGTGCAAATCCCCCATAGGGAAAGGTACAAGCCCTCTGGATGAGGTTTTAAGACAAGTCCC
GTATAAGCCTCCACGGACCGTCCTCATGCATGTGGAGCAGGGCCTCACCCCCCTTGACCCAGGCAGATATCAGACCCGCC
GTGGGTTGGTTGCCGTTAGGCGCGGGATCAGGGGAAATGAAGTTGACCTACCAGATGGTGATTATGCTAGCACCGCCTTA
CTCCCAACCTGTAAAGAGATCAACATGGTTGCTGTTGCTTCTAATGTGTTGCGCAGCAGATTTATCATCGGTCCACCCGG
TGCTGGGAAAACATACTGGCTCCTTCAACAGGTCCAGGATGGTGATGTCATATACACACCGACCCATCAGACCATGCTTG
ACATGATCAAAGCTTTGGGGACGTGCCGGTTTAACGTCCCGGCAGGCACAACGCTGCAATTCCCCGCCCCTTCCCGCACT
GGCCCGTGGGTTCGCATCCTGGCCGGCGGGTGGTGTCCTGGCAAAAACTCCTTCCTGGACGAAGCTGCGTATTGTAATCA
TCTTGATGTCTTGAGGCTTCTTAGCAAAACCACTCTCACCTGTTTAGGGGACTTCAAACAACTCCACCCAGTGGGTTTTG
ATTCTCATTGCTATGTCTTTGACATTATGCCTCAGACTCAACTGAAGACCATCTGGAGATTTGGACAGAACATCTGTGAT
GCCATCCAACCAGACTACAGAGACAAGCTTATGTCCATGGTCAAACACAACTCGTGTAACTTATGTGGAAAAACCTGTCAA
ACATGGGCAAGTCCTCACCCCCTTACCATAGGGACCGAGAGGATAGCGCCATTACCATTGACTCCAGTCAAGGCGCCACAT
TTGATGTGGTTACACTGCATTTGCCCACGAAAGATTCACTCAACAAACAAAGGGCCCTTGTTGCTATTRCCAGGGCAAGA
CATGCCATCTTTGTGTATGACCCACATAGGCAACTGCAGAGCCTATTTGATCTTCCTGCAAAAAGCACGCCCGTCAACTT
GGCCGTGCACCACGATGGRCAACTGATTGTGCTAGATAGAAATAACAAAGAATGCACGGTTGCCCAAGCTCTGGGTAATG
GTGACAAATTTAGGGCCACAGACAAGCGCGTTGTGGATTCTCTCCGCGCCATTTGTGCTGACCTAGAAGGGTCGAGCTCT
CCACTCCCCAAGGTTGCACATAATTTGGGGTTTTATTTCTCACCTGATTTGACACAGTTTGCCAAGCTTCCAATAGAACT
TGCGCCACACTGGCCAGTAGTGACGACCCAAGACAATAAAAACTGGCCAGATCGGCTGGTTGCCAGCCTGCGCCCTATTC
ACAAACATAGCCGTGCGTGCATCGGTGCCGGCTATATGGTGGGCCCCTCGGTGTTTTAGGCACCCCTGGGGTTGTGTCA
TACTATCTTACAAAATTTGTTAAGGGCGAGGCTCAAGTGCTTCCGGAAACGGTCTTCAGTACTGGCCGAATTGAGGTAGA
TTGCCGGGAATATCTTGACGACCGGGAGCGGGAAGTTGCAGCGTCCCTCCCACACGCCTTTATCGGCGACGTCAAAGGCA
CTACCGTCGGAGGGTGTCATCACATCACCTCCAAATACCTTCCGCGCTTCCTCCCCAAGGAATCAGTTGCGGTAGTCGGG
GTTTCAAGCCCCGGAAAAGCAGCGAAAGCAGTGTGTACATTGACAGATGTGTACCTCCCAGACCTTGAAGCTTACCTCCA
TCCTAAGACCCCTGTCCAAGTGCTGGAAAATGATGTTGGACTTCAAAGAAGTTCGGCTGATGGTCTGGAAGGACAAGACGG
CCTATTTCCAACTCGAAGGTCGCCATTTCACCTGGTATCAACTTGCTAGCTATGCCTCGTACATCCGTGTTCCTTTAAAC
TCCACGGTGTACCTGGACCCCTGCATGGGCCCCGCCCTTTGCAACAGAAAAGTCGTTGGGTCCACTCATTGGGGAGCTGA
CCTCGCAGTCACCCCTTATGATTATGGGGCAAGAATTATTTTGTCTAGTGCGTACCATGGTGAGATGCCTCCTGGGTACA
```

Fig. 1F-4

```
AGATTCTGGCGTGCGCGGAGTTCTCGCTGGACGACCCAGTCAGATACAAGCACACTTGGGGGTTTGAGTCGGATACAGCG
TACTTGTACGAGTTCACTGGAAACGGTGAGGACTGGGAGGATTATAACGACGCGTTTCGTGCGCGACAGAAAGGAAAGAT
TTACAAGGCCACTGCCACCAGCCTGAAGTTCCATTTTCCTCCGGGTCATACCGTTGAACCAACTTTGGGCTTAGACTGAA
ATGAAATGGGGGCTGTGCAGAGCCTATTTGATAAAATTGGCCAACTGTTTGTGGACGCTTTCACGGAGTTCTTGGTATCC
ATTGTTGATATCATCATATTTTTGGCCATTTTGTTCGGCTTCACAATCGCCGGTTGGCTGGTGGTCTTTTGCATCAGATT
GGTTTGCTCCGCGATACTCCGTTCGCGCTCTGCCGTTCACCCTGAGCAATTACAGAAGATCCTATGAGGCATTTCTCTCC
CAGTGCCGGACGGACATTCCCACCTGGGGAACTAAACATCCCTTGGGGATGCTCTGGCACCACAAGGTGTCGACCCTAAT
TGATGAAATGGTGTCGCGTCGAATGTACCGCACCATGGAACAAGCAGGGCAGGCTGCCTGGAGACAGGTGGTGACCGAGG
CAACGTTGTCTCGTATTAGTAACTTGGATGTGGTGGCTCATTTCCAGCACCTTGCCGCCATAGAAGCCGAGACTTGTAAA
TACTTGGCCTCCCGGCTGCCAATGCTGCACAACCTGCGCATGACAGGGTCAAATGTAACCATAGTGTATAATAGCTCTCT
AGAACAGGTGTTTGCTATTTTCCCGACCCTCGATTCCCGGCCAAAGCTTCATGATTTTCGGCAATGGCTAATAGCTGTGC
ATTCCTCCATATTCTCTTCTGTTGCGGCTTCCTGTACCCTTTTCGTCGTGCTGTGGTTGCGGCTTCCAATAATACGTACT
GTTTTTGGTTTCCACTGGTCAGGGGCAATTTTTCCTTCGAGCTCACAGTGAACTACACGGTGTGTCCTCCCTGCCTCACC
CGGCAGGCGGCCGCAGAGATCTACGAACCTGGTGGGTCTCTTTGGTGCAGGATAGGGCACGATCGATGCTCGGAGGACGA
TCACGACGAGCTAGGATTTCTGGTGCCGCCTGGCCTCTCCAGCGAAGGCCACTTGACCAGTGTTTACGCCTGGTTGGCGT
TCTTGTCCTTCAGTTACACGGCCCAGTTTCACCCCGAGATATTCGGAATAGGGAATGTGAGCCAAGTTTATGTTGACATC
AAGCATCAATTTATTTGTGCTGTTCATGACGGGCAAAACACCACCTTGCCTCGCCATGACAACGTCTCAGCCGTGTTCCA
GACTTATTACCAGCATCAGGTCGACGGCGGCAATTGGTTTCACCTGGAATGGCTGCGCCCCTTCTTCTCCTCCTGGTTGG
TTTTGAACGTCTCTTGGTTTCTCAGGCGTTCGCCTGTAAGCCGTGTTTCAGTTCGAGTCTTTCAGACATTAAGACCAACA
CCACCGCAGCTGCAGGCTTTGCTGTCCTCCAAGACATCAGCTGTCTTAGGCATGGCCACTCGTCCTCTGAGGCGACTCGC
AAAGGCCGCCAATGCCGCACGGCGATAGGAACGCCCGTATACATTACTGTCACAGCCAATGTAACAGATGAGAATTATTT
GCATTCCTCTGACCTTCTCATGCTTTCCTCTTGCCTTTTCTACGCTTCCGAGATGAGTGAAAAGGGATTTGAGGTGATAT
TTGGCAATGTGTCAGGCATAGTGGCTGTGTGTGTCAACTTTACCAGCTATGTCCAACATGTTAAGGAGTTCACCCAGCGC
TCCTTGGTGGTTGACCATGTGCGGTTACTTCATTTTGTGACACCTGAGACTATGAGGTGGGCGACCGTTTTAGCCTGTCT
TTTTGCCATTCTGTTGGCCATTTGAATGTTCAGATATGTTGGGGAAATGCTTGACCGCGGGCTATTGCTCGCAATTGCCT
TTTTTGTGGTGTATCGTGCCGTTCTGTCTTGCTGCGCTCGTCAACGCCAGCAGCAACAGCAGCTCCCACTTACAGTTGAT
TTATAACTTAACGATATGTGAGCTGAATGGCACAGACTGGCTGAATGATCATTTTAGTTGGGCAGTGGAGACTTTCGTTA
TCTTTCCTGTGTTGACTCACATTGTTTCCTACGGCGCCCTCACTACCAGCCACTTCCTTGACACGGTCGGCCTGATCACT
GTGTCCACCGCCGGATACTACCATGCGCGGTATGTCTTGAGTAGCATCTATGCCGTCTGCGCCCTGGCTGCGCTGATTTG
CTTCGTCATCAGGTTGACGAAAAATTGTATGTCCTGGCGCTACTCATGTACCAGATATACCAACTTTCTTCTGGACACCA
AGGGCAGACTCTATCGCTGGCGGTCACCCGTCATCATAGAGAAAAGGGGTAAAATTGAGGTTGGAGGTGACCTGATCGAC
CTCAAGAGAGTTGTGCTTGATGGCTCCGCGGCAACCCCTGTAACCAAAGTTTCAGCGGAACAATGGGGTCGTCCTTAGAC
GACTTCTGCAATGACAGCACGGCTCCACAAAAGGTGATCTTGGCATTTTCTATCACCTACACTCCAGTGATGATATATGC
CCTAAAGGTGAGTCGTGGCCGGCTGCTAGGGCTTTTACACCTTTTGATTTTTCTAAACTGTGCTTTTACCTTCGGGTATA
TGACATTTGTGCACTTTCAGAGCACAAACAGAGTTGCACTCACTATGGAGCAGTAGTCGCGCTCCTTTGGGGGGTGTAC
TCAGCTATAGAAACCTGGAAATTCATCACTTCCAGATGCCGTTTGTGCTTGCTAGGCCGCAAGTACATTCTGGCCCCTGC
CCACCACGTTGAGAGTGCCGCAGGCTTTCATCCGATTGCGGCAAGTGATAACCACGCATTTGTCGTCCGGCGTCCCGGTT
CCACTACGGTTAACGGCACATTGGTTCCCGGGTTGAAAAGCCTCGTGTTGGGTGGCAGAAGAGCTGTCAAACGGGGAGTG
GTAAACCCTCGTTAAATATGCCAAATAACAACGGCAGGCAGCAGAAGAAGAAGAAAGGGGACGGCCAGCCAGTCAATCAGC
TGTGCCAAATGTTGGGCAGGATCATCGCCCAGCAAAACCAGTCCAGAGGTAAGGGACCGGGGAAGAAAAGTAAGAAGAAA
AGCCTGGAGAAGCCCCATTTTCCTCTCGCGACTGAAGATGACGTTAGACATCACTTCACCCCTAGTGAGCGGCAATTGTG
TCTGTCGTCAATCCAGACTGCCTTTAACCAAGGCGCTGGAACTTGTACCCTGTCGGATTCAGGGAGAATAAGTTACACTG
CGGAGTTTAGTTTGCCTACGCATCATACTGTGCGCCTAATTCGCGTCACAGCATCACCCTCAGCATGATGAGCTGGCATT
CTTGAGACATCCCAGTGTTTGAATTGGAAGGATGTGTGGTGAATGGCACTGATTGATATTGTGCCTYAAGTCACCTATT
CAATTAGGGCGACCGTATGGGGGTAATATTTAATTGGCGTGAACCATGCGGCCGAAAYT
```

Fig. 1G-1

>V7-Nsp2d324-434.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGCCAAAAGTTCAGCCTC
GAAAAACGAAGCCTGTCAAGAGCTTGCCGGAGAGAAAGCCTGTCCCCGCCCCGCGCAGGAAGGTTGGGTCCGATTGTGGC
AGCCCGGTTTCATTAGGCGGCGATGTCCCTAACAGTTGGGAAGATTTGGCTGTTAGTAGCCCCTTTGATCTCCCGACCCC
ACCTGAGCCGGCAACACCTTCAAGTGAGCTGGTGATTGTGTCCTCACCGCAATGCATCTTCAGGCCGGCGACACCCTTGA
GTGAGCCGGCTCCAATTCCCGCACCTCGCGGAACTGTGTCTCGACCGGTGACACCCTTGAGTGAGCCGATCCCTGTGCCC
GCACCGCGGCGTAAGTTTCAGCAGGTGAAAAGATTGAGTTCGGCGGCGGCAATCCCACCGTACCAGGACGAGCCCCTGGA
TTTGTCTGCTTCCTCACAGACTGAATATGAGGCCTCTCCCCCAGCACCGCCGCAGAGCGGGGGCGTTCTGGGAGTAGAGG
GGCATGAAGCTGAGGAAACCCTGAGTGAAATCTCGGACATGTCGGGTAACATTAAACCTGCGTCCGTGTCATCAAGCAGC
TCCTTGTCCAGCGTGAGAATCACACGCCCAAAATACTCAGCTCAAGCCATCATCGACTCGGGCGGGCCCTGCAGTGGGCA
TCTCCAAGAGGTAAAGGAAACATGCCTTAGTGTCATGCGCGAGGCATGTGATGCGACTAAGCTTGATGACCCTGCTACGC
AGGAATGGCTTTCTCGCATGTGGGATCGGGTGGACATGCTGACTTGGCGCAACACGTCTGTTTACCAGGCGATTTGCACC
TTAGATGGCAGGTTAAAGTTCCTCCCAAAAATGATACTCGAGACACCGCCGCCCTATCCGTGAGTTTGTGATGATGCC
TCACACGCCTGCACCTTCCGTAGGTGCGGAGAGCGACCTTACCATTGGCTCAGTTGCTACTGAAGATGTTCCACGCATCC
TCGAGAAAATAGAAAATGTCGGCGAGATGGCCAACCAGGGACCCTTGGCCTTCTCCGAGGATAAACCGGTAGATGACCAA
CTTGTCAACGACCCCCGGATATCGTCGCGGAGGCCTGACGAGAGCACATCAGCTCCGTCCGCAGGCACAGGTGGCGCCGG
CTCTTTTACCGATTTGCCGCCTTCAGATGGCGCGGATGCGGACGGGGGGGGCCGTTTCGGACGGTAAAAAGAAAAGCTG
AAAGGCTCTTTGACCAACTGAGCCGTCAGGTTTTTGACCTCGTCTCCCATCTCCCTGTTTTCTTCTCACGCCTTTTCTAC
CCTGGCGGTGGTTATTCTCCGGGTGATTGGGGTTTTGCAGCTTTTACTCTATTGTGCCTCTTTTTATGTTACAGTTACCC
AGCCTTTGGTATTGCTCCCCTCTTGGGTGTGTTTTCTGGGTCTTCTCGGCGCGTTCGAATGGGGGTTTTTGGCTGCTGGT
TGGCTTTTGCTGTTGGTCTGTTCAAGCCTGTGTCCGACCCAGTCGGCGCTGCTTGTGAGTTTGACTCGCCAGAGTGTAGA
AACATCCTTCATTCTTTTGAGCTTCTCAAACCTTGGGACCCTGTTCGCAGCCTTGTTGTGGGCCCCGTCGGTCTCGGTCT

*Fig. 1G-2*

```
TGCCATTCTTGGCAGGTTACTGGGCGGGGCACGCTGCATCTGGCACTTTTTGCTTAGGCTTGGCATTGTTGCAGACTGTA
TCTTGGCTGGAGCTTACGTGCTTTCTCAAGGTAGGTGTAAAAAGTGCTGGGGATCTTGTATAAGAACTGCTCCCAATGAG
GTCGCTTTTAACGTGTTTCCTTTCACACGTGCGACCAGGTCGTCACTTATCGACCTGTGCGATCGGTTTTGTGCGCCAAA
AGGAATGGACCCCATTTTTCTCGCCACTGGGTGGCGCGGGTGCTGGGCCGGCCGAAGCCCCATTGAGCAACCCTCTGAAA
AACCCATCGCGTTTGCCCAGTTGGATGAAAAGAAGATTACGGCTAGGACTGTGGTCGCCCAGCCTTATGACCCCAACCAA
GCCGTAAAGTGCTTGCGGGTATTGCAGGCGGGTGGGGCGATGGTGGCTAAGGCGGTCCCAAAAGTGGTCAAGGTTTCCGC
TGTTCCATTCCGAGCCCCCTTCTTTCCCACTGGAGTGAAAGTTGACCCTGATTGCAGGGTCGTGGTTGACCCTGACACTT
TCACTGCAGCTCTCCGGTCTGGCTACTCCACCACAAACCTCGTCCTTGGTGTGGGGGACTTTGCCCAGCTGAATGGATTA
AAAATCAGGCAAATTTCCAAGCCTTCAGGGGGAGGCCCACATCTCATGGCTGCCCTGCATGTTGCCTGCTCGATGGCTCT
GCACATGCTTGCTGGATTTATGTGACTGCGGTGGGTTCTTGCGGCACCGGCACCAACGACCCGTGGTGCGCTAACCCGT
TTGCCGTCCCTGGCTACGGACCTGGCTCTCTCTGCACGTCCAGATTGTGCATTTCCCAACACGGCCTTACCCTGCCCTTG
ACAGCACTTGTGGCGGGATTCGGTATTCAAGAAATTGCCTTGGTCGTTTTGATTTTTGTTTCCATCGGAGGCATGGCTCA
TAGGTTGAGCTGTAAGGCTGACATGCTGTGTGTCTTGCTTGCAATTGCCAGCTATGTTTGGGTACCTCTTACCTGGTTGC
TTTGTGTGTTTCCTTGCTGGTTGCGCTGTTTTTCTTTGCACCCCCTCACCATCCTATGGTTGGTGTTTTTCTTGATTTCT
GTGAATATGCCTTCAGGAATCTTGGCCATGGTGTTGTTGGTTTCTCTTTGGCTTCTTGGTCGTTATACTAATGTTGCTGG
CCTTGTCACCCCCTACGACATTCATCATTACACCAGTGGCCCCGCGGTGTTGCCGCCTTGGCTACCGCACCAGATGGGA
CCTACTTGGCCGCTGTCCGCCGCGCTGCGTTGACTGGCCGCACCATGCTGTTTACCCCGTCCCAGCTTGGGTCTCTTCTT
GAGGGTGCTTTCAGAACTCGAAAGCCCTCACTGAACACCGTCAATGTGATCGGGTCCTCCATGGGCTCTGGCGGGGTGTT
TACCATCGACGGGAAAGTCAAGTGCGTAACTGCCGCACATGTCCTTACGGGCAATTCAGCTCGGGTTTCCGGGGTCGGCT
TCAATCAAATGCTTGACTTTGACGTAAAGGGAGATTTCGCTATAGCTGATTGCCCGAATTGGCAAGGGGCTGCCCCCAAG
ACCCAATTCTGCACGGATGGATGGACTGGCCGTGCCTATTGGCTAACATCCTCTGGCGTCGAACCCGGCGTCATTGGAAA
AGGATTCGCCTTCTGCTTCACCGCATGTGGCGATTCCGGGTCCCCAGTGATCACCGAGGCCGGTGAGCTTGTCGGCGTTC
ACACGGGATCGAATAAACAAGGGGGGGGCATTGTTACGCGCCCCTCAGGCCAGTTTTGTAATGTGGCACCCATCAAGCTA
AGCGAATTAAGTGAATTCTTTGCTGGGCCTAAGGTCCCGCTCGGTGATGTGAAGGTCGGCAGCCACATAATTAAAGACAT
AAGCGAGGTGCCTTCAGATCTTTGTGCCTTGCTTGCTGCCAAACCTGAACTGGAAGGAGGCCTCTCCACCGTCCAACTTC
TTTGTGTGTTTTTTCTCCTGTGGAGAATGATGGGACATGCCTGGACGCCCTTGGTTGCTGTGAGTTTCTTTATTTTGAAT
GAGGTTCTCCCAGCCGTCCTGGTCCGGAGTGTTTTCTCCTTTGGAATGTTTGTGCTATCCTGGCTCACGCCATGGTCTGC
GCAAGTTCTGATGATCAGGCTTCTGACAGCAGCTCTTAACAGGAACAGATGGTCACTTGCCTTTTTCAGCCTCGGTGCAG
TGACCGGTTTTGTCGCAGATCTTGCGGCCACTCAGGGGCATCCTTGCAGGCAGTGATGAATTTGAGCACCTATGCATTC
CTGCCTCGGATGATGGTTGTGACCTCACCAGTCCCAGTGATCACGTGTGGTGTCGTGCACCTACTTGCCATCATTTTGTA
CTTGTTTAAGTACCGTGGCCTGCACCATATCCTTGTTGGCGATGGAGTGTTCTCTGCGGCTTTCTTCTTGAGATACTTTG
CCGAGGGAAAGTTGAGGGAAGGGGTGTCGCAATCCTGCGGAATGAATCATGAGTCTCTGACTGGTGCCCTCGCTATGAGA
CTCAATGACGAGGACTTGGATTTCCTTATGAAATGGACTGATTTTAAGTGCTTTGTTTCTGCGTCCAACATGAGGAATGC
AGCGGGTCAATTTATCGAGGCTGCCTATGCTAAAGCACTTAGAGTAGAACTGGCCCAGTTGGTGCAGGTTGATAAAGTTC
GAGGTACTTTGGCCAAACTTGAAGCTTTTGCTGATACCGTGGCACCTCAACTCTCGCCCGGTGACATTGTTGTCGCTCTC
GGCCACACGCCTGTTGGCAGTATCTTCGACCTAAAGGTTGGTAGCACCAAGCATACCCTCCAAGCCATTGAGACCAGAGT
CCTTGCTGGGTCCAAAATGACCGTGGCGCGCGTCGTCGACCCGACCCCCACGCCCCACCCGCACCCGTGCCCATCCCCC
TCCCACCGAAAGTTCTGGAGAATGGCCCCAACGCTTGGGGGGATGAGGACCGTTTGAATAAGAAGAAGAGGCGCAGGATG
GAAGCCCTCGGCATCTATGTTATGGGCGGGAAAAAATACCAGAAATTTTGGGACAAGAATTCCGGTGATGTGTTTTATGA
GGAGGTCCATAATAACACAGATGAGTGGGAGTGTCTCAGAGTTGGCGACCCTGCCGACTTTGACCCTGAGAAGGGAACTC
TGTGTGGACATGTCACCATTGAAAACAAGGCTTACCATGTTTACACCTCCCCATCTGGTAAGAAGTTCTTGGTCCCCGTC
AACCCAGAGAATGGAAGAGTCCAATGGGAAGCTGCAAAGCTTTCCGTGGAGCAGGCCCTAGGTATGATGAATGTCGACGG
CGAACTGACTGCCAAAGAACTGGAGAAACTGAAAAGAATAATTGACAAACTCCAGGGCCTGACTAAGGAGCAGTGTTTAA
ACTGCTAGCCGCCAGCGACTTGACCCGCTGTGGTCGCGGCGGCTTGGTTGTTACTGAAACAGCGGTAAAAATAGTCAAAT
TTCACAACCGGACCTTCACCCTGGGACCTGTGAATTTAAAAGTGGCCAGTGAGGTTGAGCTAAAAGACGCGGTTGAGCAC
AACCAACACCCGGTTGCGAGACCGATCGATGGTGGAGTTGTGCTCCTGCGTTCCGCGGTTCCTTCGCTTATAGACGTCTT
GATCTCCGGTGCTGATGCATCTCCCAAGTTACTTGCCCATCACGGGCCGGGAAAACACTGGGATCGATGGCACGCTCTGGG
ATTTTGAGTCCGAAGCCACTAAAGAGGAAGTCGCACTCAGTGCGCAAATAATACAGGCTTGTGACATTAGGCGCGGCGAC
GCTCCTGAAATTGGTCTCCCTTACAAGCTGTACCCTGTTAGGGGTAACCCTGAGCGGGTGAAAGGAGTTCTGCAGAATAC
AAGGTTTGGAGACATACCTTACAAAACCCCCAGTGACACTGGAAGCCCAGTGCACGCGGCTGCCTGCCTTACGCCCAACG
```

Fig. 1G-3

```
CCACTCCGGTGACTGATGGGCGCTCCGTCTTGGCCACGACCATGCCCCCCGGGTTTGAGTTATATGTACCGACCATACCA
GCGTCTGTCCTTGATTACCTTGACTCTAGGCCTGACTGCCCTAAACAGCTGACAGAGCACGGCTGCGAAGATGCCGCACT
GAAAGACCTCTCTAAATATGACTTGTCCACCCAAGGCTTTGTTTTACCTGGAGTTCTTCGCCTTGTGCGGAAATACCTGT
TTGCCCATGTAGGTAAGTGCCCACCCGTTCATCGGCCTTCTACTTACCCTGCTAAGAATTCTATGGCTGGAATAAATGGG
AACAGGTTCCCAACCAAGGACATTCAGAGCGTCCCTGAAATCGACGTTCTGTGCGCACAGGCTGTGCGAGAAAACTGGCA
AACTGTCACCCCTTGTACTCTTAAGAAACAGTATTGCGGGAAGAAGAAGACTAGGACCATACTCGGCACCAATAACTTCA
TCGCACTAGCCCACCGAGCAGTGTTGAGTGGTGTTACCCAGGGCTTCATGAAAAAGGCGTTTAACTCGCCCATCGCCCTC
GGAAAGAACAAGTTTAAGGAGCTACAGACTCCGGTCCTGGGCAGGTGCCTTGAAGCTGATCTCGCATCCTGCGATCGATC
CACGCCTGCAATTGTCCGCTGGTTTGCCGCCAACCTTCTTTATGAACTTGCCTGTGCTGAAGAGCATCTACCGTCGTACG
TGCTGAACTGCTGCCACGACTTACTGGTCACGCAGTCCGGCGCAGTGACTAAGAGAGGTGGCCTGTCGTCTGGCGACCCG
ATCACCTCTGTGTCTAACACCATTTATAGTTTGGTGATCTATGCACAGCATATGGTGCTTAGTTACTTCAAAAGTGGTCA
CCCCCATGGCCTTCTGTTCTTACAAGACCAGCTAAAGTTTGAGGACATGCTCAAGGTTCAACCCCTGATCGTCTATTCGG
ACGACCTCGTGCTGTATGCCGAGTCTCCCACCATGCCAAACTATCACTGGTGGGTTGAACATCTGAATTTGATGCTGGGG
TTTCAGACGGACCCAAAGAAGACAGCAATAACAGACTCGCCATCATTTCTAGGCTGTAGAATAATAAATGGGCGCCAGCT
AGTCCCCAACCGTGACAGGATCCTCGCGGCCCTCGCCTATCACATGAAGGCGAGTAATGTTTCTGAATACTATGCCTCAG
CGGCTGCAATACTCATGGACAGCTGTGCTTGTTTGGAGTATGATCCTGAATGGTTTGAAGAACTTGTAGTTGGAATAGCG
CAGTGCGCCCGCAAGGACGGCTACAGCTTTCCCGGCACGCCGTTCTTCATGTCCATGTGGGAAAAACTCAGGTCCAATTA
TGAGGGGAAGAAGTCGAGAGTGTGCGGGTACTGCGGGGCCCCGGCCCCGTACGCTACTGCCTGTGGCCTCGACGTCTGCA
TTTACCACACCCACTTCCACCAGCATTGTCCAGTCACAATCTGGTGTGGCCATCCAGCGGGTTCTGGTTCTTGTAGTGAG
TGCAAATCCCCTGTAGGGAAAGGCACAAGCCCTTTAGACGAGGTGCTGGAACAAGTCCCGTATAAGCCCCCACGGACCGT
TATCATGCATGTGGAGCAGGGTCTCACCCCCCTTGATCCAGGTAGATACCAAACTCGCCGCGGATTAGTCTCTGTCAGGC
GTGGAATTAGGGGAAATGAAGTTGGACTACCAGACGGTGATTATGCTAGCACCGCCTTGCTCCCTACCTGCAAAGAGATC
AACATGGTCGCTGTCGCTTCCAATGTATTGCGCAGCAGGTTCATCATCGGCCCACCCGGTGCTGGGAAAACATACTGGCT
CCTTCAACAGGTCCAGGATGGTGATGTTATTTACACACCAACTCACCAGACCATGCTTGACATGATTAGGGCTTTGGGGA
CGTGCCGGTTCAACGTCCCGGCAGGCACAACGCTGCAATTCCCCGTCCCCTCCCGCACCGGTCCGTGGGTTCGCATCCTA
GCCGGCGGTTGGTGTCCTGGCAAGAATTCCTTCCTAGATGAAGCAGCGTATTGCAATCACCTTGATGTTTTGAGGCTTCT
TAGTAAAACTACCCTCACCTGTCTAGGAGACTTCAAGCAACTCCACCCAGTGGGTTTTGATTCTCATTGCTATGTTTTTG
ACATCATGCCTCAAACTCAACTGAAGACCATCTGGAGGTTTGGACAGAATATCTGTGATGCCATTCAGCCAGATTACAGG
GACAAACTCATGTCCATGGTCAACACAACCCGTGTGACCTACGTGGAAAAACCTGTCAGGTATGGGCAGGTCCTCACCCC
CTACCACAGGGACCGAGAGGACGACGCCATCACTATTGACTCCAGTCAAGGCGCCACATTCGATGTGGTTACATTGCATT
TGCCCACTAAAGATTCACTCAACAGGCAAAGAGCCCTTGTTGCTATCACCAGGGCAAGACACGCTATCTTTGTGTATGAC
CCACACAGGCAGCTGCAGGGCTTGTTTGATCTTCCTGCAAAAGGCACGCCCGTCAACCTCGCAGTGCACTGCGACGGGCA
GCTGATCGTGCTGGATAGAAATAACAAAGAATGCACGGTTGCTCAGGCTCTAGGCAACGGGGATAAATTTAGGGCCACAG
ACAAGCGTGTTGTAGATTCTCTCCGCGCCATTTGTGCTGATCTAGAAGGGTCGAGCTCTCCGCTCCCCAAGGTCGCACAC
AACTTGGGATTTTATTTCTCACCTGATTTAACACAGTTTGCTAAACTCCCAGTAGAACTTGCACCTCACTGGCCCGTGGT
GTCAACCCAGAACAATGAAAAGTGGCCGGATCGGCTGGTTGCCAGCCTTCGCCCTATCCATAAATACAGCCGCGCGTGCA
TCGGTGCCGGCTATATGGTGGGCCCTTCGGTGTTTCTAGGCACTCCTGGGGTCGTGTCATACTATCTCACAAAATTTGTT
AAGGGCGGGGCTCAAGTGCTTCCGGAGACGGTTTTCAGCACCGGCCGAATTGAGGTAGACTGCCGGGAATATCTTGATGA
TCGGGAGCGAGAAGTTGCTGCGTCCCTCCCACACGCTTTCATTGGCGACGTCAAAGGCACTACCGTTGGAGGATGTCATC
ATGTCACCTCCAGATACCTCCCGCGCGTCCTTCCCAAGGAATCAGTTGCGGTAGTCGGGGTTTCAAGCCCCGGAAAAGCC
GCGAAAGCATTGTGCACACTGACAGATGTGTACCTCCCAGATCTTGAAGCCTATCTCCACCCGGAGACCCAGTCCAAGTG
CTGGAAAATGATGTTGGACTTCAAAGAAGTTCGACTAATGGTCTGGAAAGACAAAACAGCCTATTTCCAACTTGAAGGTC
GCTATTTCACCTGGTATCAGCTTGCCAGCTATGCCTCGTACATCCGTGTTCCCGTCAACTCTACGGTGTACTTGGACCCC
TGCATGGGCCCCGCCCTTTGCAACAGGAGAGTCGTCGGGTCCACCCACTGGGGGCTGACCTCGCGGTCACCCCTTATGA
TTACGGCGCTAAAATTATCCTGTCTAGCGCGTACCATGGTGAAATGCCCCCCGGATACAAAATTCTGGCGTGCGCGGAGT
TCTCGTTGGATGACCCAGTTAAGTACAAACATACCTGGGGGTTTGAATCGGATACAGCGTATCTGTATGAGTTCACCGGA
AACGGTGAGGACTGGGAGGATTACAATGATGCGTTTCGTGCGCGCCAGGAAGGGAAAATTTATAAGGCCACTGCCACCAG
CTTGAAGTTTTATTTTCCCCCGGGCCCTGTCATTGAACCAACTTTAGGCCTGAATTGAAATGAAATGGGGTCCATGCAAA
GCCTTTTTGACAAAATTGGCCAACTTTTTGTGGATGCTTTCACGGAGTTCTTGGTGTCCATTGTTGATATCATTATATTT
TTGGCCATTTTGTTTGGCTTCACCATCGCCGGTTGGCTGGTGGTCTTTTGCATCAGATTGGTTTGCTCCGCGATACTCCG
```

Fig. 1G-4

```
TACGCGCCCTGCCATTCACTCTGAGCAATTACAGAAGATCTTATGAGGCCTTTCTTTCCCAGTGCCAAGTGGACATTCCC
ACCTGGGGAACTAAACATCCTTTGGGGATGCTTTGGCACCATAAGGTGTCAACCCTGATTGATGAAATGGTGTCGCGTCG
AATGTACCGCATCATGGAAAAAGCAGGGCAGGCTGCCTGGAAACAGGTGGTGAGCGAGGCTACGCTGTCTCGCATTAGTA
GTTTGGATGTGGTGGCTCATTTTCAGCATCTAGCCGCCATTGAAGCCGAGACCTGTAAATATTTGGCCTCCCGGCTGCCC
ATGCTACACAACCTGCGCATGACAGGGTCAAATGTAACCATAGTGTATAATAGCACTTTGAATCAGGTGTTTGCTATTTT
TCCAACCCCTGGTTCCCGGCCAAAGCTTCATGATTTTCAGCAATGGTTAATAGCTGTACATTCCTCCATATTTTCCTCTG
TTGCAGCTTCTTGTACTCTTTTTGTTGTGCTGTGGTTGCGGGTTCCAATACTACGTACTGTTTTTGGTTTCCGCTGGTTA
GGGGCAATTTTTCTTTCGAACTCACAGTGAATTACACGGTGTGTCCACCTTGCCTCACCCGGCAAGCAGCCACAGAGATC
TACGAACCCGGTAGGTCTCTTTGGTGCAGGATAGGGTATGACCGATGTGGGGAGGACGATCATGACGAGCTAGGGTTTAT
GATACCGCCTGGCCTCTCCAGCGAAGGCCACTTGACTGGTGTTTACGCCTGGTTGGCGTTCTTGTCCTTCAGCTACACGG
CCCAGTTCCATCCCGAGATATTCGGGATAGGGAATGTGAGTCGAGTTTATGTTGACATCAAACATCAACTCATCTGCGCC
GAACATGACGGGCAGAACACCACCTTGCCTCGTCATGACAACATTTCAGCCGTGTTTCAGACCTATTACCAACATCAAGT
CGACGGCGGCAATTGGTTTCACCTAGAATGGCTTCGTCCCTTCTTTTCCTCGTGGTTGGTTTTAAATGTCTCTTGGTTTC
TCAGGCGTTCGCCTGCAAACCATGTTTCAGTTCGAGTCTTGCAGATATTAAGACCAACACCACCGCAGCGGCAAGCTTTG
CTGTCCTCCAAGACATCAGTTGCCTTAGGCATCGCGACTCGGCCTCTGAGGCGATTCGCAAAATCCCTCAGTGCCGTACG
GCGATAGGGACACCCGTGTATGTTACCATCACAGCCAATGTGACAGATGAGAATTATTTACATTCTTCTGATCTCCTCAT
GCTTTCTTCTTGCCTTTTCTATGCTTCTGAGATGAGTGAAAAGGGATTTAAGGTGGTATTTGGCAATGTGTCAGGCATCG
TGGCTGTGTGTGTCAATTTTACCAGCTACGTCCAACATGTCAAGGAGTTTACCCAACGCTCCCTGGTGGTCGACCATGTG
CGGTTGCTCCATTTCATGACACCTGAGACCATGAGGTGGGCAACTGTTTTAGCCTGTCTTTTTGCCATTCTGTTGGCAAT
TTGAATGTTTAAGTATGTTGGAGAAATGCTTGACCGCGGGCTGTTGCTCGCGATTGCTTTCTTTGTGGTGTATCGTGCCG
TTCTGTTTTGCTGTGCTCGCCAACGCCAGCAACGACAGCAGCTCCCATCTACAGCTGATTTACAACTTGACGCTATGTGA
GCTGAATGGCACAGATTGGCTAGCTAACAAATTTGATTGGGCAGTGGAGAGTTTTGTCATCTTTCCCGTTTTGACTCACA
TTGTCTCCTATGGTGCCCTCACTACCAGCCATTTCCTTGACACAGTCGCTTTAGTCACTGTGTCTACCGCCGGGTTTGTT
CACGGGCGGTATGTCCTAAGTAGCATCTACGCGGTCTGTGCCCTGGCTGCGTTGACTTGCTTCGTCATTAGGTTTGCAAA
GAATTGCATGTCCTGGCGCTACGCGTGTACCAGATATACCAACTTTCTTCTGGACACTAAGGGCAGACTCTATCGTTGGC
GGTCGCCTGTCATCATAGAGAAAAGGGGCAAAGTTGAGGTCGAAGGTCATCTGATCGACCTCAAAAGAGTTGTGCTTGAT
GGCTCCGTGGCAACCCCTATAACCAGAGTTTCAGCGGAACAATGGGGTCGTCCTTAGATGACTTCTGTCACGATAGCACG
GCTCCACAAAAGGTGCTTTTGGCGTTTTCTATTACCTACACGCCAGTGATGATATATGCCCTAAAGGTGAGTCGCGGCCG
ACTGCTAGGGCTTCTGCACCTTTTGATCTTCCTGAATTGTGCTTTCACCTTCGGGTACATGACTTTCGCGCACTTTCAGA
GTACAAATAAGGTCGCGCTCACTATGGAGCAGTAGTTGCACTCCTTTGGGGGGTGTACTCAGCCATAGAAACCTGGAAA
TTCATCACCTCCAGATGCCGTTTTGTGCTTGCTAGGCCGCAAGTACATTCTGGCCCCTGCCCACCACGTTGAAAGTGCCGC
AGGCTTTCATCCGATTGCGGCAAATGATAACCACGCATTTGTCGTCCGGCGTCCCGGCTCCACTACGGTCAACGGCACAT
TGGTGCCCGGGTTAAAAAGCCTCGTGTTGGGTGGCAGAAAAGCTGTTAAACAGGGAGTGGTAAACCTTGTCAAATATGCC
AAATAACAACGGCAAGCAGCAGAAGAGAAAGAAGGGGGATGGCCAGCCAGTCAATCAGCTGTGCCAGATGCTGGGTAAGA
TCATCGCTCAGCAAAACCAGTCCAGAGGCAAGGGACCGGGAAAGAAAAATAAGAAGAAAAACCCGGAGAAGCCCCATTTT
CCTCTAGCGACTGAAGATGATGTCAGACATCACTTTACCCCTAGTGAGCGGCAATTGTGTCTGTCGTCAATCCAGACCGC
CTTTAATCAAGGCGCTGGGACTTGCACCCTGTCAGATTCAGGGAGGATAAGTTACACTGTGGAGTTTAGTTTGCCTACGC
ATCATACTGTGCGCCTGATCCGCGTCACAGCATCACCCTCAGCATGATGGGCTGGCATTCTTGAGGCATCTCAGTGTTTG
AATTGGAAGAATGTGTGGTGAATGGCACTGATTGACATTGTGCCTCTAAGTCACCTATTCAATTAGGGCGACCGTGTGGG
GGTGAGATTTAATTGGCGAGAACCATGCGGCCGAAATTAAAAAAAA
```

*Fig. 1H-1*

```
>V7-Nsp2d324-523.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGCCAATTCCCGCACCTC
GCGGAACTGTGTCTCGACCGGTGACACCCTTGAGTGAGCCGATCCCTGTGCCCGCACCGCGGCGTAAGTTTCAGCAGGTG
AAAAGATTGAGTTCGGCGGCGGCAATCCCACCGTACCAGGACGAGCCCCTGGATTTGTCTGCTTCCTCACAGACTGAATA
TGAGGCCTCTCCCCCAGCACCGCCGCAGAGCGGGGGCGTTCTGGGAGTAGAGGGGCATGAAGCTGAGGAAACCCTGAGTG
AAATCTCGGACATGTCGGGTAACATTAAACCTGCGTCCGTGTCATCAAGCAGCTCCTTGTCCAGCGTGAGAATCACACGC
CCAAAATACTCAGCTCAAGCCATCATCGACCTCGGGCGGGCCCTGCAGTGGGCATCTCCAAGAGGTAAAGGAAACATGCCT
TAGTGTCATGCGCGAGGCATGTGATGCGACTAAGCTTGATGACCCTGCTACGCAGGAATGGCTTTCTCGCATGTGGGATC
GGGTGGACATGCTGACTTGGCGCAACACGTCTGTTTACCAGGCGATTTGCACCTTAGATGGCAGGTTAAAGTTCCTCCCA
AAAATGATACTCGAGACACCGCCGCCCTATCCGTGTGAGTTTGTGATGATGCCTCACACGCCTGCACCTTCCGTAGGTGC
GGAGAGCGACCTTACCATTGGCTCAGTTGCTACTGAAGATGTTCCACGCATCCTCGAGAAAATAGAAAATGTCGGCGAGA
TGGCCAACCAGGGACCCTTGGCCTTCTCCGAGGATAAACCGGTAGATGACCAACTTGTCAACGACCCCCGGATATCGTCG
CGGAGGCCTGACGAGAGCACATCAGCTCCGTCCGCAGGCACAGGTGGCGCCGGCTCTTTTACCGATTTGCCGCCTTCAGA
TGGCGCGGATGCGGACGGGGGGGGCCGTTTCGGACGGTAAAAAGAAAAGCTGAAAGGCTCTTTGACCAACTGAGCCGTC
AGGTTTTTGACCTCGTCTCCCATCTCCCTGTTTTCTTCTCACGCCTTTTCTACCCTGGCGGTGGTTATTCTCCGGGTGAT
TGGGGTTTTGCAGCTTTTACTCTATTGTGCCTCTTTTTATGTTACAGTTACCCAGCCTTTGGTATTGCTCCCCTCTTGGG
TGTGTTTTCTGGGTCTTCTCGGCGCGTTCGAATGGGGGTTTTTGGCTGCTGGTTGGCTTTTGCTGTTGGTCTGTTCAAGC
CTGTGTCCGACCCAGTCGGCGCTGCTTGTGAGTTTGACTCGCCAGAGTGTAGAAACATCCTTCATTCTTTTGAGCTTCTC
AAACCTTGGGACCCTGTTCGCAGCCTTGTTGTGGGCCCCGTCGGTCTCGGTCTTGCCATTCTTGGCAGGTTACTGGGCGG
GGCACGCTGCATCTGGCACTTTTTGCTTAGGCTTGGCATTGTTGCAGACTGTATCTTGGCTGGAGCTTACGTGCTTTCTC
AAGGTAGGTGTAAAAAGTGCTGGGGATCTTGTATAAGAACTGCTCCCAATGAGGTCGCTTTTAACGTGTTTCCTTTCACA
CGTGCGACCAGGTCGTCACTTATCGACCTGTGCGATCGGTTTTGTGCGCCAAAAGGAATGGACCCCATTTTTCTCGCCAC
```

Fig. 1H-2

```
TGGGTGGCGCGGGTGCTGGGCCGGCCGAAGCCCCATTGAGCAACCCTCTGAAAAACCCATCGCGTTTGCCCAGTTGGATG
AAAAGAAGATTACGGCTAGGACTGTGGTCGCCCAGCCTTATGACCCCAACCAAGCCGTAAAGTGCTTGCGGGTATTGCAG
GCGGGTGGGGCGATGGTGGCTAAGGCGGTCCCAAAAGTGGTCAAGGTTTCCGCTGTTCCATTCCGAGCCCCCTTCTTTCC
CACTGGAGTGAAAGTTGACCCTGATTGCAGGGTCGTGGTTGACCCTGACACTTTCACTGCAGCTCTCCGGTCTGGCTACT
CCACCACAAACCTCGTCCTTGGTGTGGGGGACTTTGCCCAGCTGAATGGATTAAAAATCAGGCAAATTTCCAAGCCTTCA
GGGGGAGGCCCACATCTCATGGCTGCCCTGCATGTTGCCTGCTCGATGGCTCTGCACATGCTTGCTGGGATTTATGTGAC
TGCCGGTGGGTTCTTGCGGCACCGGCACCAACGACCCGTGGTGCGCTAACCCGTTTGCCGTCCCTGGCTACGGACCTGGCT
CTCTCTGCACGTCCAGATTGTGCATTTCCCAACACGGCCTTACCCTGCCCTTGACAGCACTTGTGGCGGGATTCGGTATT
CAAGAAATTGCCTTGGTCGTTTTGATTTTTGTTTCCATCGGAGGCATGGCTCATAGGTTGAGCTGTAAGGCTGACATGCT
GTGTGTCTTGCTTGCAATTGCCAGCTATGTTTGGGTACCTCTTACCTGGTTGCTTTGTGTGTTTCCTTGCTGGTTGCGCT
GTTTTTCTTTGCACCCCCTCACCATCCTATGGTTGGTGTTTTTCTTGATTTCTGTGAATATGCCTTCAGGAATCTTGGCC
ATGGTGTTGTTGGTTTCTCTTTGGCTTCTTGGTCGTTATACTAATGTTGCTGGCCTTGTCACCCCCTACGACATTCATCA
TTACACCAGTGGCCCCCGCGGTGTTGCCGCCTTGGCTACCGCACCAGATGGGACCTACTTGGCCGCTGTCCGCCGCGCTG
CGTTGACTGGCCGCACCATGCTGTTTACCCCGTCCCAGCTTGGGTCTCTTCTTGAGGGTGCTTTCAGAACTCGAAAGCCC
TCACTGAACACCGTCAATGTGATCGGGTCCTCCATGGGCTCTGGCGGGGTGTTTACCATCGACGGGAAAGTCAAGTGCGT
AACTGCCGCACATGTCCTTACGGGCAATTCAGCTCGGGTTTCCGGGGTCGGCTTCAATCAAATGCTTGACTTTGACGTAA
AGGGAGATTTCGCTATAGCTGATTGCCCGAATTGGCAAGGGGCTGCCCCCAAGACCCAATTCTGCACGGATGGATGGACT
GGCCGTGCCTATTGGCTAACATCCTCTGGCGTCGAACCCGGCGTCATTGGAAAAGGATTCGCCTTCTGCTTCACCGCATG
TGGCGATTCCGGGTCCCCAGTGATCACCGAGGCCGGTGAGCTTGTCGGCGTTCACACGGGATCGAATAAACAAGGGGGGG
GCATTGTTACGCGCCCCTCAGGCCAGTTTTGTAATGTGGCACCCATCAAGCTAAGCGAATTAAGTGAATTCTTTGCTGGG
CCTAAGGTCCCGCTCGGTGATGTGAAGGTCGGCAGCCACATAATTAAAGACATAAGCGAGGTGCCTTCAGATCTTTGTGC
CTTGCTTGCTGCCAAACCTGAACTGGAAGGAGGCCTCTCCACCGTCCAACTTCTTTGTGTGTTTTTTCTCCTGTGGAGAA
TGATGGGACATGCCTGGACGCCCTTGGTTGCTGTGAGTTTCTTTATTTTGAATGAGGTTCTCCCAGCCGTCCTGGTCCGG
AGTGTTTTCTCCTTTGGAATGTTTGTGCTATCCTGGCTCACGCCATGGTCTGCGCAAGTTCTGATGATCAGGCTTCTGAC
AGCAGCTCTTAACAGGAACAGATGGTCACTTGCCTTTTTCAGCCTCGGTGCAGTGACCGGTTTTGTCGCAGATCTTGCGG
CCACTCAGGGGCATCCGTTGCAGGCAGTGATGAATTTGAGCACCTATGCATTCCTGCCTCGGATGATGGTTGTGACCTCA
CCAGTCCCAGTGATCACGTGTGGTGTCGTGCACCTACTTGCCATCATTTTGTACTTGTTTAAGTACCGTGGCCTGCACCA
TATCCTTGTTGGCGATGGAGTGTTCTCTGCGGCTTTCTTCTTGAGATACTTTGCCGAGGGAAAGTTGAGGGAAGGGGTGT
CGCAATCCTGCGGAATGAATCATGAGTCTCTGACTGGTGCCCTCGCTATGAGACTCAATGACGAGGACTTGGATTTCCTT
ATGAAATGGACTGATTTTAAGTGCTTTGTTTCTGCGTCCAACATGAGGAATGCAGCGGGTCAATTTATCGAGGCTGCCTA
TGCTAAAGCACTTAGAGTAGAACTGGCCCAGTTGGTGCAGGTTGATAAAGTTCGAGGTACTTTGGCCAAACTTGAAGCTT
TTGCTGATACCGTGGCACCTCAACTCTCGCCCGGTGACATTGTTGTCGCTCTCGGCCACACGCCTGTTGGCAGTATCTTC
GACCTAAAGGTTGGTAGCACCAAGCATACCCTCCAAGCCATTGAGACCAGAGTCCTTGCTGGGTCCAAAATGACCGTGGC
GCGCGTCGTCGACCCGACCCCCACGCCCCCACCCGCACCCGTGCCCATCCCCCTCCCACCGAAAGTTCTGGAGAATGGCC
CCAACGCTTGGGGGGATGAGGACCGTTTGAATAAGAAGAAGAGGCGCAGGATGGAAGCCCTCGGCATCTATGTTATGGGC
GGGAAAAAATACCAGAAATTTTGGGACAAGAATTCCGGTGATGTGTTTTATGAGGAGGTCCATAATAACACAGATGAGTG
GGAGTGTCTCAGAGTTGGCGACCCTGCCGACTTTGACCCTGAGAAGGGAACTCTGTGTGGACATGTCACCATTGAAAACA
AGGCTTACCATGTTTACACCTCCCCATCTGGTAAGAAGTTCTTGGTCCCCGTCAACCCAGAGAATGGAAGAGTCCAATGG
GAAGCTGCAAAGCTTTCCGTGGAGCAGGCCCTAGGTATGATGAATGTCGACGGCGAACTGACTGCCAAAGAACTGGAGAA
ACTGAAAAGAATAATTGACAAACTCCAGGGCCTGACTAAGGAGCAGTGTTTAAACTGCTAGCCGCCAGCGACTTGACCCG
CTGTGGTCGCGGCGGCTTGGTTGTTACTGAAACAGCGGTAAAAATAGTCAAATTTCACAACCGGACCTTCACCCTGGGAC
CTGTGAATTTAAAAGTGGCCAGTGAGGTTGAGCTAAAAGACCGGTTGAGCACAACCACCCCGGTTGCAGACCGATC
GATGGTGGAGTTGTGCTCCTGCGTTCCGCGGTTCCTTCGCTTATAGACGTCTTGATCTCCGGTGCTGATGCATCTCCCAA
GTTACTTGCCCATCACGGGCCGGGAAACACTGGGATCGATGGCACGCTCTGGGATTTTGAGTCCGAAGCCACTAAAGAGG
AAGTCGCACTCAGTGCGCAAATAATACAGGCTTGTGACATTAGGCGCGGCGACGCTCCTGAAATTGGTCTCCCTTACAAG
CTGTACCCTGTTAGGGGTAACCCTGAGCGGGTGAAAGGAGTTCTGCAGAATACAAGGTTTGGAGACATACCTTACAAAAC
CCCCAGTGACACTGGAAGCCCAGTGCACGCGGCTGCCTGCCTTACGCCCAACGCCACTCCGGTGACTGATGGGCGCTCCG
TCTTGGCCACGACCATGCCCCCCGGGTTTGAGTTATATGTACCGACCATACCAGCGTCTGTCCTTGATTACCTTGACTCT
AGGCCTGACTGCCCTAAACAGCTGACAGAGCACGGCTGCGAAGATGCCGCACTGAAAGACCTCTCTAAATATGACTTGTC
CACCCAAGGCTTTGTTTTACCTGGAGTTCTTCGCCTTGTGCGGAAATACCTGTTTGCCCATGTAGGTAAGTGCCCACCCG
```

Fig. 1H-3

```
TTCATCGGCCTTCTACTTACCCTGCTAAGAATTCTATGGCTGGAATAAATGGGAACAGGTTCCCAACCAAGGACATTCAG
AGCGTCCCTGAAATCGACGTTCTGTGCGCACAGGCTGTGCGAGAAAACTGGCAAACTGTCACCCCTTGTACTCTTAAGAA
ACAGTATTGCGGGAAGAAGAAGACTAGGACCATACTCGGCACCAATAACTTCATCGCACTAGCCCACCGAGCAGTGTTGA
GTGGTGTTACCCAGGGCTTCATGAAAAAGGCGTTTAACTCGCCCATCGCCCTCGGAAAGAACAAGTTTAAGGAGCTACAG
ACTCCGGTCCTGGGCAGGTGCCTTGAAGCTGATCTCGCATCCTGCGATCGATCCACGCCTGCAATTGTCCGCTGGTTTGC
CGCCAACCTTCTTTATGAACTTGCCTGTGCTGAAGAGCATCTACCGTCGTACGTGCTGAACTGCTGCCACGACTTACTGG
TCACGCAGTCCGGCGCAGTGACTAAGAGAGGTGGCCTGTCGTCTGGCGACCCGATCACCTCTGTGTCTAACACCATTTAT
AGTTTGGTGATCTATGCACAGCATATGGTGCTTAGTTACTTCAAAAGTGGTCACCCCCATGGCCTTCTGTTCTTACAAGA
CCAGCTAAAGTTTGAGGACATGCTCAAGGTTCAACCCCTGATCGTCTATTCGGACGACCTCGTGCTGTATGCCGAGTCTC
CCACCATGCCAAACTATCACTGGTGGGTTGAACATCTGAATTTGATGCTGGGGTTTCAGACGGACCCAAAGAAGACAGCA
ATAACAGACTCGCCATCATTTCTAGGCTGTAGAATAATAAATGGGCGCCAGCTAGTCCCCAACCGTGACAGGATCCTCGC
GGCCCTCGCCTATCACATGAAGGCGAGTAATGTTTCTGAATACTATGCCTCAGCGGCTGCAATACTCATGGACAGCTGTG
CTTGTTTGGAGTATGATCCTGAATGGTTTGAAGAACTTGTAGTTGGAATAGCGCAGTGCGCCCGCAAGGACGGCTACAGC
TTTCCCGGCACGCCGTTCTTCATGTCCATGTGGGAAAAACTCAGGTCCAATTATGAGGGGAAGAAGTCGAGAGTGTGCGG
GTACTGCGGGGCCCCGGCCCCGTACGCTACTGCCTGTGGCCTCGACGTCTGCATTTACCACACCCACTTCCACCAGCATT
GTCCAGTCACAATCTGGTGTGGCCATCCAGCGGGTTCTGGTTCTTGTAGTGAGTGCAAATCCCCTGTAGGGAAAGGCACA
AGCCCTTTAGACGAGGTGCTGGAACAAGTCCCGTATAAGCCCCACGGACCGTTATCATGCATGTGGAGCAGGGTCTCAC
CCCCCTTGATCCAGGTAGATACCAAACTCGCCGCGGATTAGTCTCTGTCAGGCGTGGAATTAGGGGAAATGAAGTTGGAC
TACCAGACGGTGATTATGCTAGCACCGCCTTGCTCCCTACCTGCAAAGAGATCAACATGGTCGCTGTCGCTTCCAATGTA
TTGCGCAGCAGGTTCATCATCGGCCCACCCGGTGCTGGGAAAACATACTGGCTCCTTCAACAGGTCCAGGATGGTGATGT
TATTTACACACCAACTCACCAGACCATGCTTGACATGATTAGGGCTTTGGGGACGTGCCGGTTCAACGTCCCGGCAGGCA
CAACGCTGCAATTCCCCGTCCCCTCCCGCACCGGTCCGTGGGTTCGCATCCTAGCCGGCGGTTGGTGTCCTGGCAAGAAT
TCCTTCCTAGATGAAGCAGCGTATTGCAATCACCTTGATGTTTTGAGGCTTCTTAGTAAAACTACCCTCACCTGTCTAGG
AGACTTCAAGCAACTCCACCCAGTGGGTTTTGATTCTCATTGCTATGTTTTTGACATCATGCCTCAAACTCAACTGAAGA
CCATCTGGAGGTTTGGACAGAATATCTGTGATGCCATTCAGCCAGATTACAGGGACAAACTCATGTCCATGGTCAACACA
ACCCGTGTGACCTACGTGGAAAAACCTGTCAGGTATGGGCAGGTCCTCACCCCCTACCACAGGGACCGAGAGGACGACGC
CATCACTATTGACTCCAGTCAAGGCGCCACATTCGATGTGGTTACATTGCATTTGCCCACTAAAGATTCACTCAACAGGC
AAAGAGCCCTTGTTGCTATCACCAGGGCAAGACACGCTATCTTTGTGTATGACCCACACAGGCAGCTGCAGGGCTTGTTT
GATCTTCCTGCAAAAGGCACGCCCGTCAACCTCGCAGTGCACTGCGACGGGCAGCTGATCGTGCTGGATAGAAATAACAA
AGAATGCACGGTTGCTCAGGCTCTAGGCAACGGGGATAAATTTAGGGCCACAGACAAGCGTGTTGTAGATTCTCTCCGCG
CCATTTGTGCTGATCTAGAAGGGTCGAGCTCTCCGCTCCCCAAGGTCGCACACAACTTGGGATTTTATTTCTCACCTGAT
TTAACACAGTTTGCTAAACTCCCAGTAGAACTTGCACCTCACTGGCCCGTGGTGTCAACCCAGAACAATGAAAAGTGGCC
GGATCGGCTGGTTGCCAGCCTTCGCCCTATCCATAAATACAGCCGCGCGTGCATCGGTGCCGGCTATATGGTGGGCCCTT
CGGTGTTTCTAGGCACTCCTGGGGTCGTGTCATACTATCTCACAAAATTTGTTAAGGGCGGGGCTCAAGTGCTTCCGGAG
ACGGTTTTCAGCACCGGCCGAATTGAGGTAGACTGCCGGGAATATCTTGATGATCGGGAGCGAGAAGTTGCTGCGTCCCT
CCCACACGCTTTCATTGGCGACGTCAAAGGCACTACCGTTGGAGGATGTCATCATGTCACCTCCAGATACCTCCCGCGCG
TCCTTCCCAAGGAATCAGTTGCGGTAGTCGGGGTTTCAAGCCCGGAAAAGCCGCGAAAGCATTGTGCACACTGACAGAT
GTGTACCTCCAGATCTTGAAGCCTATCTCCACCCGGAGACCCAGTCCAAGTGCTGGAAAATGATGTTGGACTTCAAAGA
AGTTCGACTAATGGTCTGGAAAGACAAAACAGCCTATTTCCAACTTGAAGGTCGCTATTTCACCTGGTATCAGCTTGCCA
GCTATGCCTCGTACATCCGTGTTCCCGTCAACTCTACGGTGTACTTGGACCCCTGCATGGGCCCCGCCCTTTGCAACAGG
AGAGTCGTCGGGTCCACCCACTGGGGGGCTGACCTCGCGGTCACCCCTTATGATTACGGCGCTAAAATTATCCTGTCTAG
CGCGTACCATGGTGAAATGCCCCCCGGATACAAAATTCTGGCGTGCGCGGAGTTCTCGTTGGATGACCCAGTTAAGTACA
AACATACCTGGGGGTTTGAATCGGATACAGCGTATCTGTATGAGTTCACCGGAAACGGTGAGGACTGGGAGGATTACAAT
GATGCGTTTCGTGCGCGCCAGGAAGGGAAAATTTATAAGGCCACTGCCACCAGCTTGAAGTTTTATTTTCCCCGGGCCC
TGTCATTGAACCAACTTTAGGCCTGAATTGAAATGAAATGGGGTCCATGCAAAGCCTTTTTGACAAAATTGGCCAACTTT
TTGTGGATGCTTTCACGGAGTTCTTGGTGTCCATTGTTGATATCATTATATTTTTGGCCATTTTGTTTGGCTTCACCATC
GCCGGTTGGCTGGTGGTCTTTTGCATCAGATTGGTTTGCTCCGCGATACTCCGTACGCGCCCTGCCATTCACTCTGAGCA
ATTACAGAAGATCTTATGAGGCCTTTCTTTCCCAGTGCCAAGTGGACATTCCCACCTGGGGAACTAAACATCCTTTGGGG
ATGCTTTGGCACCATAAGGTGTCAACCCTGATTGATGAAATGGTGTCGCGTCGAATGTACCGCATCATGGAAAAAGCAGG
GCAGGCTGCCTGGAAACAGGTGGTGAGCGAGGCTACGCTGTCTCGCATTAGTAGTTTGGATGTGGTGGCTCATTTTCAGC
```

Fig. 1H-4

```
ATCTAGCCGCCATTGAAGCCGAGACCTGTAAATATTTGGCCTCCCGGCTGCCCATGCTACACAACCTGCGCATGACAGGG
TCAAATGTAACCATAGTGTATAATAGCACTTTGAATCAGGTGTTTGCTATTTTTCCAACCCCTGGTTCCCGGCCAAAGCT
TCATGATTTTCAGCAATGGTTAATAGCTGTACATTCCTCCATATTTTCCTCTGTTGCAGCTTCTTGTACTCTTTTTGTTG
TGCTGTGGTTGCGGGTTCCAATACTACGTACTGTTTTTGGTTTCCGCTGGTTAGGGGCAATTTTTCTTTCGAACTCACAG
TGAATTACACGGTGTGTCCACCTTGCCTCACCCGGCAAGCAGCCACAGAGATCTACGAACCCGGTAGGTCTCTTTGGTGC
AGGATAGGGTATGACCGATGTGGGGAGGACGATCATGACGAGCTAGGGTTTATGATACCGCCTGGCCTCTCCAGCGAAGG
CCACTTGACTGGTGTTTACGCCTGGTTGGCGTTCTTGTCCTTCAGCTACACGGCCCAGTTCCATCCCGAGATATTCGGGA
TAGGGAATGTGAGTCGAGTTTATGTTGACATCAAACATCAACTCATCTGCGCCGAACATGACGGGCAGAACACCACCTTG
CCTCGTCATGACAACATTTCAGCCGTGTTTCAGACCTATTACCAACATCAAGTCGACGGCGGCAATTGGTTTCACCTAGA
ATGGCTTCGTCCCTTCTTTTCCTCGTGGTTGGTTTTAAATGTCTCTTGGTTTCTCAGGCGTTCGCCTGCAAACCATGTTT
CAGTTCGAGTCTTGCAGATATTAAGACCAACACCACCGCAGCGGCAAGCTTTGCTGTCCTCCAAGACATCAGTTGCCTTA
GGCATCGCGACTCGGCCTCTGAGGCGATTCGCAAAATCCCTCAGTGCCGTACGGCGATAGGGACACCCGTGTATGTTACC
ATCACAGCCAATGTGACAGATGAGAATTATTTACATTCTTCTGATCTCCTCATGCTTTCTTCTTGCCTTTTCTATGCTTC
TGAGATGAGTGAAAAGGGATTTAAGGTGGTATTTGGCAATGTGTCAGGCATCGTGGCTGTGTGTGTCAATTTTACCAGCT
ACGTCCAACATGTCAAGGAGTTTACCCAACGCTCCCTGGTGGTCGACCATGTGCGGTTGCTCCATTTCATGACACCTGAG
ACCATGAGGTGGGCAACTGTTTTAGCCTGTCTTTTTGCCATTCTGTTGGCAATTTGAATGTTTAAGTATGTTGGAGAAAT
GCTTGACCGCGGGCTGTTGCTCGCGATTGCTTTCTTTGTGGTGTATCGTGCCGTTCTGTTTTGCTGTGCTCGCCAACGCC
AGCAACGACAGCAGCTCCCATCTACAGCTGATTTACAACTTGACGCTATGTGAGCTGAATGGCACAGATTGGCTAGCTAA
CAAATTTGATTGGGCAGTGGAGAGTTTTGTCATCTTTCCCGTTTTGACTCACATTGTCTCCTATGGTGCCCTCACTACCA
GCCATTTCCTTGACACAGTCGCTTTAGTCACTGTGTCTACCGCCGGGTTTGTTCACGGGCGGTATGTCCTAAGTAGCATC
TACGCGGTCTGTGCCCTGGCTGCGTTGACTTGCTTCGTCATTAGGTTTGCAAAGAATTGCATGTCCTGGCGCTACGCGTG
TACCAGATATACCAACTTTCTTCTGGACACTAAGGGCAGACTCTATCGTTGGCGGTCGCCTGTCATCATAGAGAAAAGGG
GCAAAGTTGAGGTCGAAGGTCATCTGATCGACCTCAAAAGAGTTGTGCTTGATGGCTCCGTGGCAACCCCTATAACCAGA
GTTTCAGCGGAACAATGGGTCGTCCTTAGATGACTTCTGTCACGATAGCACGGCTCCACAAAAGGTGCTTTTGGCGTTT
TCTATTACCTACACGCCAGTGATGATATATGCCCTAAAGGTGAGTCGCGGCCGACTGCTAGGGCTTCTGCACCTTTTGAT
CTTCCTGAATTGTGCTTTCACCTTCGGGTACATGACTTTCGCGCACTTTCAGAGTACAAATAAGGTCGCGCTCACTATGG
GAGCAGTAGTTGCACTCCTTTGGGGGGTGTACTCAGCCATAGAAACCTGGAAATTCATCACCTCCAGATGCCGTTTGTGC
TTGCTAGGCCGCAAGTACATTCTGGCCCCTGCCCACCACGTTGAAAGTGCCGCAGGCTTTCATCCGATTGCGGCAAATGA
TAACCACGCATTTGTCGTCCGGCGTCCCGGCTCCACTACGGTCAACGGCACATTGGTGCCCGGGTTAAAAAGCCTCGTGT
TGGGTGGCAGAAAAGCTGTTAAACAGGGAGTGGTAAACCTTGTCAAATATGCCAAATAACAACGGCAAGCAGCAGAAGAG
AAAGAAGGGGGATGGCCAGCCAGTCAATCAGCTGTGCCAGATGCTGGGTAAGATCATCGCTCAGCAAAACCAGTCCAGAG
GCAAGGGACCGGGAAAGAAAAATAAGAAGAAAAACCCGGAGAAGCCCCATTTTCCTCTAGCGACTGAAGATGATGTCAGA
CATCACTTTACCCCTAGTGAGCGGCAATTGTGTCTGTCGTCAATCCAGACCGCCTTTAATCAAGGCGCTGGGACTTGCAC
CCTGTCAGATTCAGGGAGGATAAGTTACACTGTGGAGTTTAGTTTGCCTACGCATCATACTGTGCGCCTGATCCGCGTCA
CAGCATCACCCTCAGCATGATGGCTGGCATTCTTGAGGCATCTCAGTGTTTGAATTGGAAGAATGTGTGGTGAATGGCA
CTGATTGACATTGTGCCTCTAAGTCACCTATTCAATTAGGGCGACCGTGTGGGGGTGAGATTTAATTGGCGAGAACCATG
CGGCCGAAATTAAAAAAAA
```

Fig. 1I-1

```
>V7-Nsp2d543-632.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTGAGAAGAATATGGGCTCATGCCAACCGAGCCTGGTCCACGGCCCACACTGCC
ACGCGGGCTCGACGAACTCAAAGACCAAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCGCGGTGGACACCACCACCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCACACGCCCAAAATACTCAGCTCAAGCCATCATCGACTCGGGCGGGCCCTGCAGTGGGCATCTCCAAGAGGTAAAGG
AAACATGCCTTAGTGTCATGCGCGAGGCATGTGATGCGACTAAGCTTGATGACCCTGCTACGCAGGAATGGCTTTCTCGC
ATGTGGGATCGGTGGACATGCTGACTTGGCGCAACACGTCTGTTTACCAGGCGATTTGCACCTTAGATGGCAGGTTAAA
GTTCCTCCCAAAAATGATACTCGAGACACCGCCGCCCTATCCGTGTGAGTTTGTGATGATGCCTCACACGCCTGCACCTT
CCGTAGGTGCGGAGAGCGACCTTACCATTGGCTCAGTTGCTACTGAAGATGTTCCACGCATCCTCGAGAAAATAGAAAAT
GTCGGCGAGATGGCCAACCAGGGACCCTTGGCCTTCTCCGAGGATAAACCGGTAGATGACCAACTTGTCAACGACCCCG
GATATCGTCGCGAGGCCTGACGAGAGCACATCAGCTCCGTCCGCAGGCACAGGTGGCGCCGGCTCTTTTACCGATTTGC
CGCCTTCAGATGGCGCGGATGCGGACGGGGGGGGGCCGTTTCGGACGGTAAAAAGAAAAGCTGAAAGGCTCTTTGACCAA
CTGAGCCGTCAGGTTTTTGACCTCGTCTCCCATCTCCCTGTTTTCTTCTCACGCCTTTTCTACCCTGGCGGTGGTTATTC
TCCGGGTGATTGGGGTTTTGCAGCTTTTACTCTATTGTGCCTCTTTTTATGTTACAGTTACCCAGCCTTTGGTATTGCTC
CCCTCTTGGGTGTGTTTTCTGGGTCTTCTCGGCGCGTTCGAATGGGGGTTTTTGGCTGCTGGTTGGCTTTTGCTGTTGGT
CTGTTCAAGCCTGTGTCCGACCCAGTCGGCGCTGCTTGTGAGTTTGACTCGCCAGAGTGTAGAAACATCCTTCATTCTTT
```

Fig. 1I-2

```
TGAGCTTCTCAAACCTTGGGACCCTGTTCGCAGCCTTGTTGTGGGCCCCGTCGGTCTCGGTCTTGCCATTCTTGGCAGGT
TACTGGGCGGGGCACGCTGCATCTGGCACTTTTTGCTTAGGCTTGGCATTGTTGCAGACTGTATCTTGGCTGGAGCTTAC
GTGCTTTCTCAAGGTAGGTGTAAAAAGTGCTGGGGATCTTGTATAAGAACTGCTCCCAATGAGGTCGCTTTTAACGTGTT
TCCTTTCACACGTGCGACCAGGTCGTCACTTATCGACCTGTGCGATCGGTTTTGTGCGCCAAAAGGAATGGACCCCATTT
TTCTCGCCACTGGGTGGCGCGGGTGCTGGGCCGGCCGAAGCCCCATTGAGCAACCCTCTGAAAAACCCATCGCGTTTGCC
CAGTTGGATGAAAAGAAGATTACGGCTAGGACTGTGGTCGCCCAGCCTTATGACCCAACCAAGCCGTAAAGTGCTTGCG
GGTATTGCAGGCGGGTGGGGCGATGGTGGCTAAGGCGGTCCCAAAAGTGGTCAAGGTTTCCGCTGTTCCATTCCGAGCCC
CCTTCTTTCCCACTGGAGTGAAAGTTGACCCTGATTGCAGGGTCGTGGTTGACCCTGACACTTTCACTGCAGCTCTCCGG
TCTGGCTACTCCACCACAAACCTCGTCCTTGGTGTGGGGGACTTTGCCCAGCTGAATGGATTAAAAATCAGGCAAATTTC
CAAGCCTTCAGGGGGAGGCCCACATCTCATGGCTGCCCTGCATGTTGCCTGCTCGATGGCTCTGCACATGCTTGCTGGGA
TTTATGTGACTGCGGTGGGTTCTTGCGGCACCGGCACCAACGACCCGTGGTGCGCTAACCCGTTTGCCGTCCCTGGCTAC
GGACCTGGCTCTCTCTGCACGTCCAGATTGTGCATTTCCAACACGGCCTTACCCTGCCCTTGACAGCACTTGTGGCGGG
ATTCGGTATTCAAGAAATTGCCTTGGTCGTTTTGATTTTTGTTTCCATCGGAGGCATGGCTCATAGGTTGAGCTGTAAGG
CTGACATGCTGTGTGTCTTGCTTGCAATTGCCAGCTATGTTGGGTACCTCTTACCTGGTTGCTTTGTGTGTTTCCTTGC
TGGTTGCGCTGTTTTTCTTTGCACCCCCTCACCATCCTATGGTTGGTGTTTTTCTTGATTTCTGTGAATATGCCTTCAGG
AATCTTGGCCATGGTGTTGTTGGTTTCTCTTTGGCTTCTTGGTCGTTATACTAATGTTGCTGGCCTTGTCACCCCCTACG
ACATTCATCATTACACCAGTGGCCCCCGCGGTGTTGCCGCCTTGGCTACCGCACCAGATGGGACCTACTTGGCCGCTGTC
CGCCGCGCTGCGTTGACTGGCCGCACCATGCTGTTTACCCCGTCCCAGCTTGGGTCTCTTCTTGAGGGTGCTTTCAGAAC
TCGAAAGCCCTCACTGAACACCGTCAATGTGATCGGGTCCTCCATGGGCTCTGGCGGGGTGTTTACCATCGACGGGAAAG
TCAAGTGCGTAACTGCCGCACATGTCCTTACGGGCAATTCAGCTCGGGTTTCCGGGGTCGGCTTCAATCAAATGCTTGAC
TTTGACGTAAAGGGAGATTTCGCTATAGCTGATTGCCCGAATTGGCAAGGGGCTGCCCCCAAGACCCAATTCTGCACGGA
TGGATGGACTGGCCGTGCCTATTGGCTAACATCCTCTGGCGTCGAACCCGGCGTCATTGGAAAAGGATTCGCCTTCTGCT
TCACCGCATGTGGCGATTCCGGGTCCCCAGTGATCACCGAGGCCGGTGAGCTTGTCGGCGTTCACACGGGATCGAATAAA
CAAGGGGGGGCATTGTTACGCGCCCCTCAGGCCAGTTTTGTAATGTGGCACCCATCAAGCTAAGCGAATTAAGTGAATT
CTTTGCTGGGCCTAAGGTCCCGCTCGGTGATGTGAAGGTCGGCAGCCACATAATTAAAGACATAAGCGAGGTGCCTTCAG
ATCTTTGTGCCTTGCTTGCTGCCAAACCTGAACTGGAAGGAGGCCTCTCCACCGTCCAACTTCTTTGTGTGTTTTTTCTC
CTGTGGAGAATGATGGGACATGCCTGGACGCCCTTGGTTGCTGTGAGTTTCTTTATTTTGAATGAGGTTCTCCCAGCCGT
CCTGGTCCGGAGTGTTTTCTCCTTTGGAATGTTTGTGCTATCCTGGCTCACGCCATGGTCTGCGCAAGTTCTGATGATCA
GGCTTCTGACAGCAGCTCTTAACAGGAACAGATGGTCACTTGCCTTTTTCAGCCTCGGTGCAGTGACCGGTTTTGTCGCA
GATCTTGCGGCCACTCAGGGGCATCCGTTGCAGGCAGTGATGAATTTGAGCACCTATGCATTCCTGCCTCGGATGATGGT
TGTGACCTCACCAGTCCCAGTGATCACGTGTGGTGTCGTGCACCTACTTGCCATCATTTTGTACTTGTTTAAGTACCGTG
GCCTGCACCATATCCTTGTTGGCGATGGAGTGTTCTCTGCGGCTTTCTTCTTGAGATACTTTGCCGAGGGAAAGTTGAGG
GAAGGGGTGTCGCAATCCTGCGGAATGAATCATGAGTCTCTGACTGGTGCCCTCGCTATGAGACTCAATGACGAGGACTT
GGATTTCCTTATGAAATGGACTGATTTTAAGTGCTTTGTTTCTGCGTCCAACATGAGGAATGCAGCGGGTCAATTTATCG
AGGCTGCCTATGCTAAAGCACTTAGAGTAGAACTGGCCCAGTTGGTGCAGGTTGATAAAGTTCGAGGTACTTTGGCCAAA
CTTGAAGCTTTTGCTGATACCGTGGCACCTCAACTCTCGCCCGGTGACATTGTTGTCGCTCTCGGCCACACGCCTGTTGG
CAGTATCTTCGACCTAAAGGTTGGTAGCACCAAGCATACCCTCCAAGCCATTGAGACCAGAGTCCTTGCTGGGTCCAAAA
TGACCGTGGCGCGCGTCGTCGACCCGACCCCCACGCCCCCACCCGCACCCGTGCCCATCCCCCTCCCACCGAAAGTTCTG
GAGAATGGCCCCAACGCTTGGGGGGATGAGGACCGTTTGAATAAGAAGAAGAGGCGCAGGATGGAAGCCCTCGGCATCTA
TGTTATGGGCGGAAAAAATACCAGAAATTTTGGGACAAGAATTCCGGTGATGTGTTTTATGAGGAGGTCCATAATAACA
CAGATGAGTGGGAGTGTCTCAGAGTTGGCGACCCTGCCGACTTTGACCCTGAGAAGGGAACTCTGTGTGGACATGTCACC
ATTGAAAACAAGGCTTACCATGTTTACACCTCCCCATCTGGTAAGAAGTTCTTGGTCCCCGTCAACCCAGAGAATGGAAG
AGTCCAATGGGAAGCTGCAAAGCTTTCCGTGGAGCAGGCCCTAGGTATGATGAATGTCGACGGCGAACTGACTGCCAAAG
AACTGGAGAAACTGAAAAGAATAATTGACAAACTCCAGGGCCTGACTAAGGAGCAGTGTTTAAACTGCTAGCCGCCAGCG
ACTTGACCCGCTGTGGTCGCGGCGGCTTGGTTGTTACTGAAACAGCGGTAAAAATAGTCAAATTTCACAACCGGACCTTC
ACCCTGGGACCTGTGAATTTAAAAGTGGCCAGTGAGGTTGAGCTAAAAGACGCGGTTGAGCACAACCAACACCCGGTTGC
GAGACCGATCGATGGTGGAGTTGTGCTCCTGCGTTCCGCGGTTCCTTCGCTTATAGACGTCTTGATCTCCGGTGCTGATG
CATCTCCCAAGTTACTTGCCCATCACGGGCCGGGAAACACTGGGATCGATGGCACGCTCTGGGATTTTGAGTCCGAAGCC
ACTAAAGAGGAAGTCGCACTCAGTGCGCAAATAATACAGGCTTGTGACATTAGGCGCGGCGACGCTCCTGAAATTGGTCT
CCCTTACAAGCTGTACCCTGTTAGGGGTAACCCTGAGCGGGTGAAAGGAGTTCTGCAGAATACAAGGTTTGGAGACATAC
```

*Fig. 1I-3*

```
CTTACAAAACCCCCAGTGACACTGGAAGCCCAGTGCACGCGGCTGCCTGCCTTACGCCCAACGCCACTCCGGTGACTGAT
GGGCGCTCCGTCTTGGCCACGACCATGCCCCCCGGGTTTGAGTTATATGTACCGACCATACCAGCGTCTGTCCTTGATTA
CCTTGACTCTAGGCCTGACTGCCCTAAACAGCTGACAGAGCACGGCTGCGAAGATGCCGCACTGAAAGACCTCTCTAAAT
ATGACTTGTCCACCCAAGGCTTTGTTTTACCTGGAGTTCTTCGCCTTGTGCGGAAATACCTGTTTGCCCATGTAGGTAAG
TGCCCACCCGTTCATCGGCCTTCTACTTACCCTGCTAAGAATTCTATGGCTGGAATAAATGGGAACAGGTTCCCAACCAA
GGACATTCAGAGCGTCCCTGAAATCGACGTTCTGTGCGCACAGGCTGTGCGAGAAAACTGGCAAACTGTCACCCCTTGTA
CTCTTAAGAAACAGTATTGCGGGAAGAAGAAGACTAGGACCATACTCGGCACCAATAACTTCATCGCACTAGCCCACCGA
GCAGTGTTGAGTGGTGTTACCCAGGGCTTCATGAAAAAGGCGTTTAACTCGCCCATCGCCCTCGGAAAGAACAAGTTTAA
GGAGCTACAGACTCCGGTCCTGGGCAGGTGCCTTGAAGCTGATCTCGCATCCTGCGATCGATCCACGCCTGCAATTGTCC
GCTGGTTTGCCGCCAACCTTCTTTATGAACTTGCCTGTGCTGAAGAGCATCTACCGTCGTACGTGCTGAACTGCTGCCAC
GACTTACTGGTCACGCAGTCCGGCGCAGTGACTAAGAGAGGTGGCCTGTCGTCTGGCGACCCGATCACCTCTGTGTCTAA
CACCATTTATAGTTTGGTGATCTATGCACAGCATATGGTGCTTAGTTACTTCAAAAGTGGTCACCCCCATGGCCTTCTGT
TCTTACAAGACCAGCTAAAGTTTGAGGACATGCTCAAGGTTCAACCCCTGATCGTCTATTCGGACGACCTCGTGCTGTAT
GCCGAGTCTCCCACCATGCCAAACTATCACTGGTGGGTTGAACATCTGAATTTGATGCTGGGGTTTCAGACGGACCCAAA
GAAGACAGCAATAACAGACTCGCCATCATTTCTAGGCTGTAGAATAATAAATGGGCGCCAGCTAGTCCCCAACCGTGACA
GGATCCTCGCGGCCCTCGCCTATCACATGAAGGCGAGTAATGTTTCTGAATACTATGCCTCAGCGGCTGCAATACTCATG
GACAGCTGTGCTTGTTTGGAGTATGATCCTGAATGGTTTGAAGAACTTGTAGTTGGAATAGCGCAGTGCGCCCGCAAGGA
CGGCTACAGCTTTCCCGGCACGCCGTTCTTCATGTCCATGTGGGAAAAACTCAGGTCCAATTATGAGGGGAAGAAGTCGA
GAGTGTGCGGGTACTGCGGGGCCCCGGCCCCGTACGCTACTGCCTGTGGCCTCGACGTCTGCATTTACCACACCCACTTC
CACCAGCATTGTCCAGTCACAATCTGGTGTGGCCATCCAGCGGGTTCTGGTTCTTGTAGTGAGTGCAAATCCCCTGTAGG
GAAAGGCACAAGCCCTTTAGACGAGGTGCTGGAACAAGTCCCGTATAAGCCCCACGGACCGTTATCATGCATGTGGAGC
AGGGTCTCACCCCCCTTGATCCAGGTAGATACCAAACTCGCCGCGGATTAGTCTCTGTCAGGCGTGGAATTAGGGGAAAT
GAAGTTGGACTACCAGACGGTGATTATGCTAGCACCGCCTTGCTCCCTACCTGCAAAGAGATCAACATGGTCGCTGTCGC
TTCCAATGTATTGCGCAGCAGGTTCATCATCGGCCCACCCGGTGCTGGGAAAACATACTGGCTCCTTCAACAGGTCCAGG
ATGGTGATGTTATTTACACACCAACTCACCAGACCATGCTTGACATGATTAGGGCTTTGGGGACGTGCCGGTTCAACGTC
CCGGCAGGCACAACGCTGCAATTCCCCGTCCCTCCCGCACCGGTCCGTGGGTTCGCATCCTAGCCGGCGGTTGGTGTCC
TGGCAAGAATTCCTTCCTAGATGAAGCAGCGTATTGCAATCACCTTGATGTTTTGAGGCTTCTTAGTAAAACTACCCTCA
CCTGTCTAGGAGACTTCAAGCAACTCCACCCAGTGGGTTTTGATTCTCATTGCTATGTTTTTGACATCATGCCTCAAACT
CAACTGAAGACCATCTGGAGGTTTGGACAGAATATCTGTGATGCCATTCAGCCAGATTACAGGGACAAACTCATGTCCAT
GGTCAACACAACCCGTGTGACCTACGTGGAAAAACCTGTCAGGTATGGGCAGGTCCTCACCCCCTACCACAGGGACCGAG
AGGACGACGCCATCACTATTGACTCCAGTCAAGGCGCCACATTCGATGTGGTTACATTGCATTTGCCCACTAAAGATTCA
CTCAACAGGCAAAGAGCCCTTGTTGCTATCACCAGGGCAAGACACGCTATCTTTGTGTATGACCCACACAGGCAGCTGCA
GGGCTTGTTTGATCTTCCTGCAAAAGGCACGCCCGTCAACCTCGCAGTGCACTGCGACGGGCAGCTGATCGTGCTGGATA
GAAATAACAAAGAATGCACGGTTGCTCAGGCTCTAGGCAACGGGGATAAATTTAGGGCCACAGACAAGCGTGTTGTAGAT
TCTCTCCGCGCCATTTGTGCTGATCTAGAAGGGTCGAGCTCTCCGCTCCCCAAGGTCGCACACAACTTGGGATTTTATTT
CTCACCTGATTTAACACAGTTTGCTAAACTCCCAGTAGAACTTGCACCTCACTGGCCCGTGGTGTCAACCCAGAACAATG
AAAAGTGGCCGGATCGGCTGGTTGCCAGCCTTCGCCCTATCCATAAATACAGCCGCGCGTGCATCGGTGCCGGCTATATG
GTGGGCCCTTCGGTGTTTCTAGGCACTCCTGGGGTCGTGTCATACTATCTCACAAAATTTGTTAAGGGCGGGGCTCAAGT
GCTTCCGGAGACGGTTTTCAGCACCGGCCGAATTGAGGTAGACTGCCGGGAATATCTTGATGATCGGGAGCGAGAAGTTG
CTGCGTCCCTCCCACACGCTTTCATTGGCGACGTCAAAGGCACTACCGTTGGAGGATGTCATCATGTCACCTCCAGATAC
CTCCCGCGCGTCCTTCCCAAGGAATCAGTTGCGGTAGTCGGGGTTTCAAGCCCCGGAAAAGCCGCGAAAGCATTGTGCAC
ACTGACAGATGTGTACCTCCCAGATCTTGAAGCCTATCTCCACCCGGAGACCCAGTCCAAGTGCTGGAAAATGATGTTGG
ACTTCAAAGAAGTTCGACTAATGGTCTGGAAAGACAAAACAGCCTATTTCCAACTTGAAGGTCGCTATTTCACCTGGTAT
CAGCTTGCCAGCTATGCCTCGTACATCCGTGTTCCCGTCAACTCTACGGTGTACTTGGACCCCTGCATGGGCCCCGCCCT
TTGCAACAGGAGAGTCGTCGGGTCCACCCACTGGGGGCTGACCTCGCGGTCACCCCTTATGATTACGGCGCTAAAATTA
TCCTGTCTAGCGCGTACCATGGTGAAATGCCCCCCGGATACAAAATTCTGGCGTGCGCGGAGTTCTCGTTGGATGACCCA
GTTAAGTACAAACATACCTGGGGGTTTGAATCGGATACAGCGTATCTGTATGAGTTCACCGGAAACGGTGAGGACTGGGA
GGATTACAATGATGCGTTTCGTGCGCGCCAGGAAGGGAAAATTTATAAGGCCACTGCCACCAGCTTGAAGTTTTATTTTC
CCCCGGGCCCTGTCATTGAACCAACTTTAGGCCTGAATTGAAATGAAATGGGGTCCATGCAAAGCCTTTTTGACAAAATT
GGCCAACTTTTTGTGGATGCTTTCACGGAGTTCTTGGTGTCCATTGTTGATATCATTATATTTTTGGCCATTTTGTTTGG
```

*Fig. 1I-4*

```
CTTCACCATCGCCGGTTGGCTGGTGGTCTTTTGCATCAGATTGGTTTGCTCCGCGATACTCCGTACGCGCCCTGCCATTC
ACTCTGAGCAATTACAGAAGATCTTATGAGGCCTTTCTTTCCCAGTGCCAAGTGGACATTCCCACCTGGGGAACTAAACA
TCCTTTGGGGATGCTTTGGCACCATAAGGTGTCAACCCTGATTGATGAAATGGTGTCGCGTCGAATGTACCGCATCATGG
AAAAAGCAGGGCAGGCTGCCTGGAAACAGGTGGTGAGCGAGGCTACGCTGTCTCGCATTAGTAGTTTGGATGTGGTGGCT
CATTTTCAGCATCTAGCCGCCATTGAAGCCGAGACCTGTAAATATTTGGCCTCCCGGCTGCCCATGCTACACAACCTGCG
CATGACAGGGTCAAATGTAACCATAGTGTATAATAGCACTTTGAATCAGGTGTTTGCTATTTTTCCAACCCCTGGTTCCC
GGCCAAAGCTTCATGATTTTCAGCAATGGTTAATAGCTGTACATTCCTCCATATTTTCCTCTGTTGCAGCTTCTTGTACT
CTTTTTGTTGTGCTGTGGTTGCGGGTTCCAATACTACGTACTGTTTTTGGTTTCCGCTGGTTAGGGGCAATTTTTCTTTC
GAACTCACAGTGAATTACACGGTGTGTCCACCTTGCCTCACCCGGCAAGCAGCCACAGAGATCTACGAACCCGGTAGGTC
TCTTTGGTGCAGGATAGGGTATGACCGATGTGGGGAGGACGATCATGACGAGCTAGGGTTTATGATACCGCCTGGCCTCT
CCAGCGAAGGCCACTTGACTGGTGTTTACGCCTGGTTGGCGTTCTTGTCCTTCAGCTACACGGCCCAGTTCCATCCCGAG
ATATTCGGGATAGGGAATGTGAGTCGAGTTTATGTTGACATCAAACATCAACTCATCTGCGCCGAACATGACGGGCAGAA
CACCACCTTGCCTCGTCATGACAACATTTCAGCCGTGTTTCAGACCTATTACCAACATCAAGTCGACGGCGGCAATTGGT
TTCACCTAGAATGGCTTCGTCCCTTCTTTTCCTCGTGGTTGGTTTTAAATGTCTCTTGGTTTCTCAGGCGTTCGCCTGCA
AACCATGTTTCAGTTCGAGTCTTGCAGATATTAAGACCAACACCACCGCAGCGGCAAGCTTTGCTGTCCTCCAAGACATC
AGTTGCCTTAGGCATCGCGACTCGGCCTCTGAGGCGATTCGCAAAATCCCTCAGTGCCGTACGGCGATAGGGACACCCGT
GTATGTTACCATCACAGCCAATGTGACAGATGAGAATTATTTACATTCTTCTGATCTCCTCATGCTTTCTTCTTGCCTTT
TCTATGCTTCTGAGATGAGTGAAAAGGGATTTAAGGTGGTATTTGGCAATGTGTCAGGCATCGTGGCTGTGTGTGTCAAT
TTTACCAGCTACGTCCAACATGTCAAGGAGTTTACCCAACGCTCCCTGGTGGTCGACCATGTGCGGTTGCTCCATTTCAT
GACACCTGAGACCATGAGGTGGGCAACTGTTTTAGCCTGTCTTTTTGCCATTCTGTTGGCAATTTGAATGTTTAAGTATG
TTGGAGAAATGCTTGACCGCGGGCTGTTGCTCGCGATTGCTTTCTTTGTGGTGTATCGTGCCGTTCTGTTTTGCTGTGCT
CGCCAACGCCAGCAACGACAGCAGCTCCCATCTACAGCTGATTTACAACTTGACGCTATGTGAGCTGAATGGCACAGATT
GGCTAGCTAACAAATTTGATTGGGCAGTGGAGAGTTTTGTCATCTTTCCCGTTTTGACTCACATTGTCTCTCCTATGGTGCC
CTCACTACCAGCCATTTCCTTGACACAGTCGCTTTAGTCACTGTGTCTACCGCCGGGTTTGTTCACGGGCGGTATGTCCT
AAGTAGCATCTACGCGGTCTGTGCCCTGGCTGCGTTGACTTGCTTCGTCATTAGGTTTGCAAAGAATTGCATGTCCTGGC
GCTACGCGTGTACCAGATATACCAACTTTCTTCTGGACACTAAGGGCAGACTCTATCGTTGGCGGTCGCCTGTCATCATA
GAGAAAAGGGGCAAAGTTGAGGTCGAAGGTCATCTGATCGACCTCAAAAGAGTTGTGCTTGATGGCTCCGTGGCAACCCC
TATAACCAGAGTTTCAGCGGAACAATGGGTCGTCCTTAGATGACTTCTGTCACGATAGCACGGCTCCACAAAAGGTGCT
TTTGGCGTTTTCTATTACCTACACGCCAGTGATGATATATGCCCTAAAGGTGAGTCGCGGCCGACTGCTAGGGCTTCTGC
ACCTTTTGATCTTCCTGAATTGTGCTTTCACCTTCGGGTACATGACTTTCGCGCACTTTCAGAGTACAAATAAGGTCGCG
CTCACTATGGGAGCAGTAGTTGCACTCCTTTGGGGGGTGTACTCAGCCATAGAAACCTGGAAATTCATCACCTCCAGATG
CCGTTTGTGCTTGCTAGGCCGCAAGTACATTCTGGCCCCTGCCCACCACGTTGAAAGTGCCGCAGGCTTTCATCCGATTG
CGGCAAATGATAACCACGCATTTGTCGTCCGGCGTCCCGGCTCCACTACGGTCAACGGCACATTGGTGCCCGGGTTAAAA
AGCCTCGTGTTGGGTGGCAGAAAAGCTGTTAAACAGGGAGTGGTAAACCTTGTCAAATATGCCAAATAACAACGGCAAGC
AGCAGAAGAGAAAGAAGGGGGATGGCCAGCCAGTCAATCAGCTGTGCCAGATGCTGGGTAAGATCATCGCTCAGCAAAAC
CAGTCCAGAGGCAAGGGACCGGGAAAGAAAAATAAGAAGAAAAACCCGGAGAAGCCCCATTTTCCTCTAGCGACTGAAGA
TGATGTCAGACATCACTTTACCCCTAGTGAGCGGCAATTGTGTCTGTCGTCAATCCAGACCGCCTTTAATCAAGGCGCTG
GGACTTGCACCCTGTCAGATTCAGGGAGGATAAGTTACACTGTGGAGTTTAGTTTGCCTACGCATCATACTGTGCGCCTG
ATCCGCGTCACAGCATCACCCTCAGCATGATGGGCTGGCATTCTTGAGGCATCTCAGTGTTTGAATTGGAAGAATGTGTG
GTGAATGGCACTGATTGACATTGTGCCTCTAAGTCACCTATTCAATTAGGGCGACCGTGTGGGGGTGAGATTTAATTGGC
GAGAACCATGCGGCCGAAATTAAAAAAAA
```

Fig. 1J-1

```
>V7-Nsp2d633-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAACCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGATGTGAGTTTGTGATGATGCCTCACACGCCTGCACCTTCCGTAGGTGCGG
AGAGCGACCTTACCATTGGCTCAGTTGCTACTGAAGATGTTCCACGCATCCTCGAGAAAATAGAAAATGTCGGCGAGATG
GCCAACCAGGGACCCTTGGCCTTCTCCGAGGATAAACCGGTAGATGACCAACTTGTCAACGACCCCCGGATATCGTCGCG
GAGGCCTGACGAGAGCACATCAGCTCCGTCCGCAGGCACAGGTGGCGCCGGCTCTTTTACCGATTTGCCGCCTTCAGATG
GCGCGGATGCGGACGGGGGGGGCCGTTTCGGACGGTAAAAAGAAAAGCTGAAAGGCTCTTTGACCAACTGAGCCGTCAG
GTTTTTGACCTCGTCTCCCATCTCCCTGTTTTCTTCTCACGCCTTTTCTACCCTGGCGGTGGTTATTCTCCGGGTGATTG
GGGTTTTGCAGCTTTTACTCTATTGTGCCTCTTTTTATGTTACAGTTACCCAGCCTTTGGTATTGCTCCCCTCTTGGGTG
```

Fig. 1J-2

```
TGTTTTCTGGGTCTTCTCGGCGCGTTCGAATGGGGGTTTTTGGCTGCTGGTTGGCTTTTGCTGTTGGTCTGTTCAAGCCT
GTGTCCGACCCAGTCGGCGCTGCTTGTGAGTTTGACTCGCCAGAGTGTAGAAACATCCTTCATTCTTTTGAGCTTCTCAA
ACCTTGGGACCCTGTTCGCAGCCTTGTTGTGGGCCCCGTCGGTCTCGGTCTTGCCATTCTTGGCAGGTTACTGGGCGGGG
CACGCTGCATCTGGCACTTTTTGCTTAGGCTTGGCATTGTTGCAGACTGTATCTTGGCTGGAGCTTACGTGCTTTCTCAA
GGTAGGTGTAAAAAGTGCTGGGGATCTTGTATAAGAACTGCTCCCAATGAGGTCGCTTTTAACGTGTTTCCTTTCACACG
TGCGACCAGGTCGTCACTTATCGACCTGTGCGATCGGTTTTGTGCGCCAAAAGGAATGGACCCCATTTTTCTCGCCACTG
GGTGGCGCGGGTGCTGGGCCGGCCGAAGCCCCATTGAGCAACCCTCTGAAAAACCCATCGCGTTTGCCCAGTTGGATGAA
AAGAAGATTACGGCTAGGACTGTGGTCGCCCAGCCTTATGACCCCAACCAAGCCGTAAAGTGCTTGCGGGTATTGCAGGC
GGGTGGGGCGATGGTGGCTAAGGCGGTCCCAAAAGTGGTCAAGGTTTCCGCTGTTCCATTCCGAGCCCCCTTCTTTCCCA
CTGGAGTGAAAGTTGACCCTGATTGCAGGGTCGTGGTTGACCCTGACACTTTCACTGCAGCTCTCCGGTCTGGCTACTCC
ACCACAAACCTCGTCCTTGGTGTGGGGACTTTGCCCAGCTGAATGGATTAAAAATCAGGCAAATTTCCAAGCCTTCAGG
GGGAGGCCCACATCTCATGGCTGCCCTGCATGTTGCCTGCTCGATGGCTCTGCACATGCTTGCTGGGATTTATGTGACTG
CGGTGGGTTCTTGCGGCACCGGCACCAACGACCCGTGGTGCGCTAACCCGTTTGCCGTCCCTGGCTACGGACCTGGCTCT
CTCTGCACGTCCAGATTGTGCATTTCCCAACACGGCCTTACCCTGCCCTTGACAGCACTTGTGGCGGGATTCGGTATTCA
AGAAATTGCCTTGGTCGTTTTGATTTTTGTTTCCATCGGAGGCATGGCTCATAGGTTGAGCTGTAAGGCTGACATGCTGT
GTGTCTTGCTTGCAATTGCCAGCTATGTTTGGGTACCTCTTACCTGGTTGCTTTGTGTGTTTCCTTGCTGGTTGCGCTGT
TTTTCTTTGCACCCCCTCACCATCCTATGGTTGGTGTTTTTCTTGATTTCTGTGAATATGCCTTCAGGAATCTTGGCCAT
GGTGTTGTTGGTTTCTCTTTGGCTTCTTGGTCGTTATACTAATGTTGCTGGCCTTGTCACCCCCTACGACATTCATCATT
ACACCAGTGGCCCCCGCGGTGTTGCCGCCTTGGCTACCGCACCAGATGGGACCTACTTGGCCGCTGTCCGCCGCGCTGCG
TTGACTGGCCGCACCATGCTGTTTACCCCGTCCCAGCTTGGGTCTCTTCTTGAGGGTGCTTTCAGAACTCGAAAGCCCTC
ACTGAACACCGTCAATGTGATCGGGTCCTCCATGGGCTCTGGCGGGGTGTTTACCATCGACGGGAAAGTCAAGTGCGTAA
CTGCCGCACATGTCCTTACGGGCAATTCAGCTCGGGTTTCCGGGGTCGGCTTCAATCAAATGCTTGACTTTGACGTAAAG
GGAGATTTCGCTATAGCTGATTGCCCGAATTGGCAAGGGGCTGCCCCCAAGACCCAATTCTGCACGGATGGATGGACTGG
CCGTGCCTATTGGCTAACATCCTCTGGCGTCGAACCCGGCGTCATTGGAAAAGGATTCGCCTTCTGCTTCACCGCATGTG
GCGATTCCGGGTCCCCAGTGATCACCGAGGCCGGTGAGCGTTGTCGGCGTTCACACGGGATCGAATAAACAAGGGGGGGC
ATTGTTACGCGCCCCTCAGGCCAGTTTTGTAATGTGGCACCCATCAAGCTAAGCGAATTAAGTGAATTCTTTGCTGGGCC
TAAGGTCCCGCTCGGTGATGTGAAGGTCGGCAGCCACATAATTAAAGACATAAGCGAGGTGCCTTCAGATCTTTGTGCCT
TGCTTGCTGCCAAACCTGAACTGGAAGGAGGCCTCTCCACCGTCCAACTTCTTTGTGTGTTTTTCTCCTGTGGAGAATG
ATGGGACATGCCTGGACGCCCTTGGTTGCTGTGAGTTTCTTTATTTTGAATGAGGTTCTCCCAGCCGTCCTGGTCCGGAG
TGTTTTCTCCTTTGGAATGTTTGTGCTATCCTGGCTCACGCCATGGTCTGCGCAAGTTCTGATGATCAGGCTTCTGACAG
CAGCTCTTAACAGGAACAGATGGTCACTTGCCTTTTTCAGCCTCGGTGCAGTGACCGGTTTTGTCGCAGATCTTGCGGCC
ACTCAGGGGCATCCGTTGCAGGCAGTGATGAATTTGAGCACCTATGCATTCCTGCCTCGGATGATGGTTGTGACCTCACC
AGTCCCAGTGATCACGTGTGGTGTCGTGCACCTACTTGCCATCATTTTGTACTTGTTTAAGTACCGTGGCCTGCACCATA
TCCTTGTTGGCGATGGAGTGTTCTCTGCGGCTTTCTTCTTGAGATACTTTGCCGAGGGAAAGTTGAGGGAAGGGGTGTCG
CAATCCTGCGGAATGAATCATGAGTCTCTGACTGGTGCCCTCGCTATGAGACTCAATGACGAGGACTTGGATTTCCTTAT
GAAATGGACTGATTTTAAGTGCTTTGTTTCTGCGTCCAACATGAGGAATGCAGCGGGTCAATTTATCGAGGCTGCCTATG
CTAAAGCACTTAGAGTAGAACTGGCCCAGTTGGTGCAGGTTGATAAAGTTCGAGGTACTTTGGCCAAACTTGAAGCTTTT
GCTGATACCGTGGCACCTCAACTCTCGCCCGGTGACATTGTTGTCGCTCTCGGCCACACGCCTGTTGGCAGTATCTTCGA
CCTAAAGGTTGGTAGCACCAAGCATACCCTCCAAGCCATTGAGACCAGAGTCCTTGCTGGGTCCAAAATGACCGTGGCGC
GCGTCGTCGACCCGACCCCCACGCCCCCACCCGCACCCGTGCCCATCCCCCTCCCACCGAAAGTTCTGGAGAATGGCCCC
AACGCTTGGGGGGATGAGGACCGTTTGAATAAGAAGAAGAGGCGCAGGATGGAAGCCCTCGGCATCTATGTTATGGGCGG
GAAAAAATACCAGAAATTTTGGGACAAGAATTCCGGTGATGTGTTTTATGAGGAGGTCCATAATAACACAGATGAGTGGG
AGTGTCTCAGAGTTGGCGACCCTGCCGACTTTGACCCTGAGAAGGGAACTCTGTGTGGACATGTCACCATTGAAAACAAG
GCTTACCATGTTTACACCTCCCCATCTGGTAAGAAGTTCTTGGTCCCCGTCAACCCAGAGAATGGAAGAGTCCAATGGGA
AGCTGCAAAGCTTTCCGTGGAGCAGGCCCTAGGTATGATGAATGTCGACGGCGAACTGACTGCCAAAGAACTGGAGAAAC
TGAAAAGAATAATTGACAAACTCCAGGGCCTGACTAAGGAGCAGTGTTTAAACTGCTAGCCGCCAGCGACTTGACCCGCT
GTGGTCGCGGCGGCTTGGTTGTTACTGAAACAGCGGTAAAAATAGTCAAATTTCACAACCGGACCTTCACCCTGGGACCT
GTGAATTTAAAAGTGGCCAGTGAGGTTGAGCTAAAAGACGCGGTTGAGCACAACCAACACCCGGTTGCGAGACCGATCGA
```

Fig. 1J-3

```
TGGTGGAGTTGTGCTCCTGCGTTCCGCGGTTCCTTCGCTTATAGACGTCTTGATCTCCGGTGCTGATGCATCTCCCAAGT
TACTTGCCCATCACGGGCCGGGAAACACTGGGATCGATGGCACGCTCTGGGATTTTGAGTCCGAAGCCACTAAAGAGGAA
GTCGCACTCAGTGCGCAAATAATACAGGCTTGTGACATTAGGCGCGGCGACGCTCCTGAAATTGGTCTCCCTTACAAGCT
GTACCCTGTTAGGGGTAACCCTGAGCGGGTGAAAGGAGTTCTGCAGAATACAAGGTTTGGAGACATACCTTACAAAACCC
CCAGTGACACTGGAAGCCCAGTGCACGCGGCTGCCTGCCTTACGCCCAACGCCACTCCGGTGACTGATGGGCGCTCCGTC
TTGGCCACGACCATGCCCCCCGGGTTTGAGTTATATGTACCGACCATACCAGCGTCTGTCCTTGATTACCTTGACTCTAG
GCCTGACTGCCCTAAACAGCTGACAGAGCACGGCTGCGAAGATGCCGCACTGAAAGACCTCTCTAAATATGACTTGTCCA
CCCAAGGCTTTGTTTTACCTGGAGTTCTTCGCCTTGTGCGGAAATACCTGTTTGCCCATGTAGGTAAGTGCCCACCCGTT
CATCGGCCTTCTACTTACCCTGCTAAGAATTCTATGGCTGGAATAAATGGGAACAGGTTCCCAACCAAGGACATTCAGAG
CGTCCCTGAAATCGACGTTCTGTGCGCACAGGCTGTGCGAGAAAACTGGCAAACTGTCACCCCTTGTACTCTTAAGAAAC
AGTATTGCGGGAAGAAGAAGACTAGGACCATACTCGGCACCAATAACTTCATCGCACTAGCCCACCGAGCAGTGTTGAGT
GGTGTTACCCAGGGCTTCATGAAAAAGGCGTTTAACTCGCCCATCGCCCTCGGAAAGAACAAGTTTAAGGAGCTACAGAC
TCCGGTCCTGGGCAGGTGCCTTGAAGCTGATCTCGCATCCTGCGATCGATCCACGCCTGCAATTGTCCGCTGGTTTGCCG
CCAACCTTCTTTATGAACTTGCCTGTGCTGAAGAGCATCTACCGTCGTACGTGCTGAACTGCTGCCACGACTTACTGGTC
ACGCAGTCCGGCGCAGTGACTAAGAGAGGTGGCCTGTCGTCTGGCGACCCGATCACCTCTGTGTCTAACACCATTTATAG
TTTGGTGATCTATGCACAGCATATGGTGCTTAGTTACTTCAAAAGTGGTCACCCCCATGGCCTTCTGTTCTTACAAGACC
AGCTAAAGTTTGAGGACATGCTCAAGGTTCAACCCCTGATCGTCTATTCGGACGACCTCGTGCTGTATGCCGAGTCTCCC
ACCATGCCAAACTATCACTGGTGGGTTGAACATCTGAATTTGATGCTGGGGTTTCAGACGGACCCAAAGAAGACAGCAAT
AACAGACTCGCCATCATTTCTAGGCTGTAGAATAATAAATGGGCGCCAGCTAGTCCCCAACCGTGACAGGATCCTCGCGG
CCCTCGCCTATCACATGAAGGCGAGTAATGTTTCTGAATACTATGCCTCAGCGGCTGCAATACTCATGGACAGCTGTGCT
TGTTTGGAGTATGATCCTGAATGGTTTGAAGAACTTGTAGTTGGAATAGCGCAGTGCGCCCGCAAGGACGGCTACAGCTT
TCCCGGCACGCCGTTCTTCATGTCCATGTGGGAAAAACTCAGGTCCAATTATGAGGGGAAGAAGTCGAGAGTGTGCGGGT
ACTGCGGGCCCCGGCCCCGTACGCTACTGCCTGTGGCCTCGACGTCTGCATTTACCACACCCACTTCCACCAGCATTGT
CCAGTCACAATCTGGTGTGGCCATCCAGCGGGTTCTGGTTCTTGTAGTGAGTGCAAATCCCCTGTAGGGAAAGGCACAAG
CCCTTTAGACGAGGTGCTGGAACAAGTCCCGTATAAGCCCCACGGACCGTTATCATGCATGTGGAGCAGGGTCTCACCC
CCCTTGATCCAGGTAGATACCAAACTCGCCGCGGATTAGTCTCTGTCAGGCGTGGAATTAGGGGAAATGAAGTTGGACTA
CCAGACGGTGATTATGCTAGCACCGCCTTGCTCCCTACCTGCAAAGAGATCAACATGGTCGCTGTCGCTTCCAATGTATT
GCGCAGCAGGTTCATCATCGGCCCACCCGGTGCTGGGAAAACATACTGGCTCCTTCAACAGGTCCAGGATGGTGATGTTA
TTTACACACCAACTCACCAGACCATGCTTGACATGATTAGGGCTTTGGGGACGTGCCGGTTCAACGTCCCGGCAGGCACA
ACGCTGCAATTCCCCGTCCCCTCCCGCACCGGTCCGTGGGTTCGCATCCTAGCCGGCGGTTGGTGTCCTGGCAAGAATTC
CTTCCTAGATGAAGCAGCGTATTGCAATCACCTTGATGTTTTGAGGCTTCTTAGTAAAACTACCCTCACCTGTCTAGGAG
ACTTCAAGCAACTCCACCCAGTGGGTTTTGATTCTCATTGCTATGTTTTTGACATCATGCCTCAAACTCAACTGAAGACC
ATCTGGAGGTTTGGACAGAATATCTGTGATGCCATTCAGCCAGATTACAGGGACAAACTCATGTCCATGGTCAACACAAC
CCGTGTGACCTACGTGGAAAAACCTGTCAGGTATGGGCAGGTCCTCACCCCCCTACCACAGGGACCGAGAGGACGACGCCA
TCACTATTGACTCCAGTCAAGGCGCCACATTCGATGTGGTTACATTGCATTTGCCCACTAAAGATTCACTCAACAGGCAA
AGAGCCCTTGTTGCTATCACCAGGGCAAGACACGCTATCTTTGTGTATGACCCACACAGGCAGCTGCAGGGCTTGTTTGA
TCTTCCTGCAAAAGGCACGCCCGTCAACCTCGCAGTGCACTGCGACGGGCAGCTGATCGTGCTGGATAGAAATAACAAAG
AATGCACGGTTGCTCAGGCTCTAGGCAACGGGGATAAATTTAGGGCCACAGACAAGCGTGTTGTAGATTCTCTCCGCGCC
ATTTGTGCTGATCTAGAAGGGTCGAGCTCTCCGCTCCCCAAGGTCGCACACAACTTGGGATTTTATTTCTCACCTGATTT
AACACAGTTTGCTAAACTCCCAGTAGAACTTGCACCTCACTGGCCCGTGGTGTCAACCCAGAACAATGAAAAGTGGCCGG
ATCGGCTGGTTGCCAGCCTTCGCCCTATCCATAAATACAGCCGCGCGTGCATCGGTGCCGGCTATATGGTGGGCCCTTCG
GTGTTTCTAGGCACTCCTGGGGTCGTGTCATACTATCTCACAAAATTTGTTAAGGGCGGGGCTCAAGTGCTTCCGGAGAC
GGTTTTCAGCACCGGCCGAATTGAGGTAGACTGCCGGGAATATCTTGATGATCGGGAGCGAGAAGTTGCTGCGTCCCTCC
CACACGCTTTCATTGGCGACGTCAAAGGCACTACCGTTGGAGGATGTCATCATGTCACCTCCAGATACCTCCCGCGCGTC
CTTCCCAAGGAATCAGTTGCGGTAGTCGGGGTTTCAAGCCCCGGAAAAGCCGCGAAAGCATTGTGCACACTGACAGATGT
GTACCTCCAGATCTTGAAGCCTATCTCCACCCGGAGACCCAGTCCAAGTGCTGGAAAATGATGTTGGACTTCAAAGAAG
TTCGACTAATGGTCTGGAAAGACAAAACAGCCTATTTCCAACTTGAAGGTCGCTATTTCACCTGGTATCAGCTTGCCAGC
TATGCCTCGTACATCCGTGTTCCCGTCAACTCTACGGTGTACTTGGACCCCTGCATGGGCCCCGCCCTTTGCAACAGGAG
```

Fig. 1J-4

```
AGTCGTCGGGTCCACCCACTGGGGGGCTGACCTCGCGGTCACCCCTTATGATTACGGCGCTAAAATTATCCTGTCTAGCG
CGTACCATGGTGAAATGCCCCCCGGATACAAAATTCTGGCGTGCGCGGAGTTCTCGTTGGATGACCCAGTTAAGTACAAA
CATACCTGGGGGTTTGAATCGGATACAGCGTATCTGTATGAGTTCACCGGAAACGGTGAGGACTGGGAGGATTACAATGA
TGCGTTTCGTGCGCGCCAGGAAGGGAAAATTTATAAGGCCACTGCCACCAGCTTGAAGTTTTATTTTCCCCCGGGCCCTG
TCATTGAACCAACTTTAGGCCTGAATTGAAATGAAATGGGGTCCATGCAAAGCCTTTTTGACAAAATTGGCCAACTTTTT
GTGGATGCTTTCACGGAGTTCTTGGTGTCCATTGTTGATATCATTATATTTTTGGCCATTTTGTTTGGCTTCACCATCGC
CGGTTGGCTGGTGGTCTTTTGCATCAGATTGGTTTGCTCCGCGATACTCCGTACGCGCCCTGCCATTCACTCTGAGCAAT
TACAGAAGATCTTATGAGGCCTTTCTTTCCCAGTGCCAAGTGGACATTCCCACCTGGGGAACTAAACATCCTTTGGGGAT
GCTTTGGCACCATAAGGTGTCAACCCTGATTGATGAAATGGTGTCGCGTCGAATGTACCGCATCATGGAAAAAGCAGGGC
AGGCTGCCTGGAAACAGGTGGTGAGCGAGGCTACGCTGTCTCGCATTAGTAGTTTGGATGTGGTGGCTCATTTTCAGCAT
CTAGCCGCCATTGAAGCCGAGACCTGTAAATATTTGGCCTCCCGGCTGCCCATGCTACACAACCTGCGCATGACAGGGTC
AAATGTAACCATAGTGTATAATAGCACTTTGAATCAGGTGTTTGCTATTTTTCCAACCCCTGGTTCCCGGCCAAAGCTTC
ATGATTTTCAGCAATGGTTAATAGCTGTACATTCCTCCATATTTTCCTCTGTTGCAGCTTCTTGTACTCTTTTTGTTGTG
CTGTGGTTGCGGGTTCCAATACTACGTACTGTTTTTGGTTTCCGCTGGTTAGGGGCAATTTTTCTTTCGAACTCACAGTG
AATTACACGGTGTGTCCACCTTGCCTCACCCGGCAAGCAGCCACAGAGATCTACGAACCCGGTAGGTCTCTTTGGTGCAG
GATAGGGTATGACCGATGTGGGGAGGACGATCATGACGAGCTAGGGTTTATGATACCGCCTGGCCTCTCCAGCGAAGGCC
ACTTGACTGGTGTTTACGCCTGGTTGGCGTTCTTGTCCTTCAGCTACACGGCCCAGTTCCATCCCGAGATATTCGGGATA
GGGAATGTGAGTCGAGTTTATGTTGACATCAAACATCAACTCATCTGCGCCGAACATGACGGGCAGAACACCACCTTGCC
TCGTCATGACAACATTTCAGCCGTGTTTCAGACCTATTACCAACATCAAGTCGACGGCGGCAATTGGTTTCACCTAGAAT
GGCTTCGTCCCTTCTTTTCCTCGTGGTTGGTTTTAAATGTCTCTTGGTTTCTCAGGCGTTCGCCTGCAAACCATGTTTCA
GTTCGAGTCTTGCAGATATTAAGACCAACACCACCGCAGCGGCAAGCTTTGCTGTCCTCCAAGACATCAGTTGCCTTAGG
CATCGCGACTCGGCCTCTGAGGCGATTCGCAAAATCCCTCAGTGCCGTACGGCGATAGGGACACCCGTGTATGTTACCAT
CACAGCCAATGTGACAGATGAGAATTATTTACATTCTTCTGATCTCCTCATGCTTTCTTCTTGCCTTTTCTATGCTTCTG
AGATGAGTGAAAAGGGATTTAAGGTGGTATTTGGCAATGTGTCAGGCATCGTGGCTGTGTGTGTCAATTTTACCAGCTAC
GTCCAACATGTCAAGGAGTTTACCCAACGCTCCCTGGTGGTCGACCATGTGCGGTTGCTCCATTTCATGACACCTGAGAC
CATGAGGTGGGCAACTGTTTTAGCCTGTCTTTTTGCCATTCTGTTGGCAATTTGAATGTTTAAGTATGTTGGAGAAATGC
TTGACCGCGGGCTGTTGCTCGCGATTGCTTTCTTTGTGGTGTATCGTGCCGTTCTGTTTTGCTGTGCTCGCCAACGCCAG
CAACGACAGCAGCTCCCATCTACAGCTGATTTACAACTTGACGCTATGTGAGCTGAATGGCACAGATTGGCTAGCTAACA
AATTTGATTGGGCAGTGGAGAGTTTTGTCATCTTTCCCGTTTTGACTCACATTGTCTCCTATGGTGCCCTCACTACCAGC
CATTTCCTTGACACAGTCGCTTTAGTCACTGTGTCTACCGCCGGGTTTGTTCACGGGCGGTATGTCCTAAGTAGCATCTA
CGCGGTCTGTGCCCTGGCTGCGTTGACTTGCTTCGTCATTAGGTTTGCAAAGAATTGCATGTCCTGGCGCTACGCGTGTA
CCAGATATACCAACTTTCTTCTGGACACTAAGGGCAGACTCTATCGTTGGCGGTCGCCTGTCATCATAGAGAAAAGGGGC
AAAGTTGAGGTCGAAGGTCATCTGATCGACCTCAAAAGAGTTGTGCTTGATGGCTCCGTGGCAACCCCTATAACCAGAGT
TTCAGCGGAACAATGGGGTCGTCCTTAGATGACTTCTGTCACGATAGCACGGCTCCACAAAAGGTGCTTTTGGCGTTTTC
TATTACCTACACGCCAGTGATGATATATGCCCTAAAGGTGAGTCGCGGCCGACTGCTAGGGCTTCTGCACCTTTTGATCT
TCCTGAATTGTGCTTTCACCTTCGGGTACATGACTTTCGCGCACTTTCAGAGTACAAATAAGGTCGCGCTCACTATGGGA
GCAGTAGTTGCACTCCTTTGGGGGTGTACTCAGCCATAGAAACCTGGAAATTCATCACCTCCAGATGCCGTTTGTGCTT
GCTAGGCCGCAAGTACATTCTGGCCCCTGCCCACCACGTTGAAAGTGCCGCAGGCTTTCATCCGATTGCGGCAAATGATA
ACCACGCATTTGTCGTCCGGCGTCCCGGCTCCACTACGGTCAACGGCACATTGGTGCCCGGGTTAAAAAGCCTCGTGTTG
GGTGGCAGAAAAGCTGTTAAACAGGGAGTGGTAAACCTTGTCAAATATGCCAAATAACAACGGCAAGCAGCAGAAGAGAA
AGAAGGGGATGGCCAGCCAGTCAATCAGCTGTGCCAGATGCTGGGTAAGATCATCGCTCAGCAAAACCAGTCCAGAGGC
AAGGGACCGGGAAAGAAAAATAAGAAGAAAAACCCGGAGAAGCCCCATTTTCCTCTAGCGACTGAAGATGATGTCAGACA
TCACTTTACCCCTAGTGAGCGGCAATTGTGTCTGTCGTCAATCCAGACCGCCTTTAATCAAGGCGCTGGGACTTGCACCC
TGTCAGATTCAGGGAGGATAAGTTACACTGTGGAGTTTAGTTTGCCTACGCATCATACTGTGCGCCTGATCCGCGTCACA
GCATCACCCTCAGCATGATGGGCTGGCATTCTTGAGGCATCTCAGTGTTTGAATTGGAAGAATGTGTGGTGAATGGCACT
GATTGACATTGTGCCTCTAAGTCACCTATTCAATTAGGGCGACCGTGTGGGGGTGAGATTTAATTGGCGAGAACCATGCG
GCCGAAATTAAAAAAAA
```

Fig. 1K-1

```
>V7-Nsp2d543-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GTGTGAGTTTGTGATGATGCCTCACACGCCTGCACCTTCCGTAGGTGCGGAGAGCGACCTTACCATTGGCTCAGTTGCTA
CTGAAGATGTTCCACGCATCCTCGAGAAAATAGAAAATGTCGGCGAGATGGCCAACCAGGGACCCTTGGCCTTCTCCGAG
GATAAACCGGTAGATGACCAACTTGTCAACGACCCCCGGATATCGTCGCGGAGGCCTGACGAGAGCACATCAGCTCCGTC
CGCAGGCACAGGTGGCGCCGGCTCTTTTACCGATTTGCCGCCTTCAGATGGCGCGGATGCGGACGGGGGGGGCCGTTTC
GGACGGTAAAAAGAAAAGCTGAAAGGCTCTTTGACCAACTGAGCCGTCAGGTTTTTGACCTCGTCTCCCATCTCCCTGTT
TTCTTCTCACGCCTTTTCTACCCTGGCGGTGGTTATTCTCCGGGTGATTGGGGTTTTGCAGCTTTTACTCTATTGTGCCT
CTTTTTATGTTACAGTTACCCAGCCTTTGGTATTGCTCCCCTCTTGGGTGTGTTTTCTGGGTCTTCTCGGCGCGTTCGAA
TGGGGGTTTTTGGCTGCTGGTTGGCTTTTGCTGTTGGTCTGTTCAAGCCTGTGTCCGACCCAGTCGGCGCTGCTTGTGAG
TTTGACTCGCCAGAGTGTAGAAACATCCTTCATTCTTTTTGAGCTTCTCAAACCTTGGGACCCTGTTCGCAGCCTTGTTGT
GGGCCCCGTCGGTCTCGGTCTTGCCATTCTTGGCAGGTTACTGGGCGGGGCACGCTGCATCTGGCACTTTTTGCTTAGGC
```

Fig. 1K-2

```
TTGGCATTGTTGCAGACTGTATCTTGGCTGGAGCTTACGTGCTTTCTCAAGGTAGGTGTAAAAAGTGCTGGGGATCTTGT
ATAAGAACTGCTCCCAATGAGGTCGCTTTTAACGTGTTTCCTTTCACACGTGCGACCAGGTCGTCACTTATCGACCTGTG
CGATCGGTTTTGTGCGCCAAAAGGAATGGACCCCATTTTTCTCGCCACTGGGTGGCGCGGGTGCTGGGCCGGCCGAAGCC
CCATTGAGCAACCCTCTGAAAAACCCATCGCGTTTGCCCAGTTGGATGAAAAGAAGATTACGGCTAGGACTGTGGTCGCC
CAGCCTTATGACCCCAACCAAGCCGTAAAGTGCTTGCGGGTATTGCAGGCGGGTGGGGCGATGGTGGCTAAGGCGGTCCC
AAAAGTGGTCAAGGTTTCCGCTGTTCCATTCCGAGCCCCCTTCTTTCCCACTGGAGTGAAAGTTGACCCTGATTGCAGGG
TCGTGGTTGACCCTGACACTTTCACTGCAGCTCTCCGGTCTGGCTACTCCACCACAAACCTCGTCCTTGGTGTGGGGGAC
TTTGCCCAGCTGAATGGATTAAAAATCAGGCAAATTTCCAAGCCTTCAGGGGGAGGCCCACATCTCATGGCTGCCCTGCA
TGTTGCCTGCTCGATGGCTCTGCACATGCTTGCTGGGATTTATGTGACTGCGGTGGGTTCTTGCGGCACCGGCACCAACG
ACCCGTGGTGCGCTAACCCGTTTGCCGTCCCTGGCTACGGACCTGGCTCTCTCTGCACGTCCAGATTGTGCATTTCCCAA
CACGGCCTTACCCTGCCCTTGACAGCACTTGTGGCGGGATTCGGTATTCAAGAAATTGCCTTGGTCGTTTTGATTTTTGT
TTCCATCGGAGGCATGGCTCATAGGTTGAGCTGTAAGGCTGACATGCTGTGTGTCTTGCTTGCAATTGCCAGCTATGTTT
GGGTACCTCTTACCTGGTTGCTTTGTGTGTTTCCTTGCTGGTTGCGCTGTTTTCTTTGCACCCCCTCACCATCCTATGG
TTGGTGTTTTTCTTGATTTCTGTGAATATGCCTTCAGGAATCTTGGCCATGGTGTTGTTGGTTTCTCTTTGGCTTCTTGG
TCGTTATACTAATGTTGCTGGCCTTGTCACCCCCTACGACATTCATCATTACACCAGTGGCCCCCGCGGTGTTGCCGCCT
TGGCTACCGCACCAGATGGGACCTACTTGGCCGCTGTCCGCCGCGCTGCGTTGACTGGCCGCACCATGCTGTTTACCCCG
TCCCAGCTTGGGTCTCTTCTTGAGGGTGCTTTCAGAACTCGAAAGCCCTCACTGAACACCGTCAATGTGATCGGGTCCTC
CATGGGCTCTGGCGGGGTGTTTACCATCGACGGGAAAGTCAAGTGCGTAACTGCCGCACATGTCCTTACGGGCAATTCAG
CTCGGGTTTCCGGGGTCGGCTTCAATCAAATGCTTGACTTTGACGTAAAGGGAGATTTCGCTATAGCTGATTGCCCGAAT
TGGCAAGGGGCTGCCCCCAAGACCCAATTCTGCACGGATGGATGGACTGGCCGTGCCTATTGGCTAACATCCTCTGGCGT
CGAACCCGGCGTCATTGGAAAAGGATTCGCCTTCTGCTTCACCGCATGTGGCGATTCCGGGTCCCCAGTGATCACCGAGG
CCGGTGAGCTTGTCGGCGTTCACACGGGATCGAATAAACAAGGGGGGGGCATTGTTACGCGCCCCTCAGGCCAGTTTTGT
AATGTGGCACCCATCAAGCTAAGCGAATTAAGTGAATTCTTTGCTGGGCCTAAGGTCCCGCTCGGTGATGTGAAGGTCGG
CAGCCACATAATTAAAGACATAAGCGAGGTGCCTTCAGATCTTTGTGCCTTGCTTGCTGCCAAACCTGAACTGGAAGGAG
GCCTCTCCACCGTCCAACTTCTTTGTGTGTTTTTCTCCTGTGGAGAATGATGGGACATGCCTGGACGCCCTTGGTTGCT
GTGAGTTTCTTTATTTTGAATGAGGTTCTCCCAGCCGTCCTGGTCCGGAGTGTTTTCTCCTTTGGAATGTTTGTGCTATC
CTGGCTCACGCCATGGTCTGCGCAAGTTCTGATGATCAGGCTTCTGACAGCAGCTCTTAACAGGAACAGATGGTCACTTG
CCTTTTTCAGCCTCGGTGCAGTGACCGGTTTTGTCGCAGATCTTGCGGCCACTCAGGGGCATCCGTTGCAGGCAGTGATG
AATTTGAGCACCTATGCATTCCTGCCTCGGATGATGGTTGTGACCTCACCAGTCCCAGTGATCACGTGTGGTGTCGTGCA
CCTACTTGCCATCATTTTGTACTTGTTTAAGTACCGTGGCCTGCACCATATCCTTGTTGGCGATGGAGTGTTCTCTGCGG
CTTTCTTCTTGAGATACTTTGCCGAGGGAAAGTTGAGGGAAGGGGTGTCGCAATCCTGCGGAATGAATCATGAGTCTCTG
ACTGGTGCCCTCGCTATGAGACTCAATGACGAGGACTTGGATTTCCTTATGAAATGGACTGATTTTAAGTGCTTTGTTTC
TGCGTCCAACATGAGGAATGCAGCGGGTCAATTTATCGAGGCTGCCTATGCTAAAGCACTTAGAGTAGAACTGGCCCAGT
TGGTGCAGGTTGATAAAGTTCGAGGTACTTTGGCCAAACTTGAAGCTTTTGCTGATACCGTGGCACCTCAACTCTCGCCC
GGTGACATTGTTGTCGCTCTCGGCCACACGCCTGTTGGCAGTATCTTCGACCTAAAGGTTGGTAGCACCAAGCATACCCT
CCAAGCCATTGAGACCAGAGTCCTTGCTGGGTCCAAAATGACCGTGGCGCGCGTCGTCGACCCGACCCCCACGCCCCCAC
CCGCACCCGTGCCCATCCCCCTCCCACCGAAAGTTCTGGAGAATGGCCCCAACGCTTGGGGGGATGAGGACCGTTTGAAT
AAGAAGAAGAGGCGCAGGATGGAAGCCCTCGGCATCTATGTTATGGGCGGGAAAAAATACCAGAAATTTTGGGACAAGAA
TTCCGGTGATGTGTTTTATGAGGAGGTCCATAATAACACAGATGAGTGGGAGTGTCTCAGAGTTGGCGACCCTGCCGACT
TTGACCCTGAGAAGGGAACTCTGTGTGGACATGTCACCATTGAAAACAAGGCTTACCATGTTTACACCTCCCCATCTGGT
AAGAAGTTCTTGGTCCCCGTCAACCCAGAGAATGGAAGAGTCCAATGGGAAGCTGCAAAGCTTTCCGTGGAGCAGGCCCT
AGGTATGATGAATGTCGACGGCGAACTGACTGCCAAAGAACTGGAGAAACTGAAAAGAATAATTGACAAACTCCAGGGCC
TGACTAAGGAGCAGTGTTTAAACTGCTAGCCGCCAGCGACTTGACCCGCTGTGGTCGCGGCGGCTTGGTTGTTACTGAAA
CAGCGGTAAAAATAGTCAAATTTCACAACCGGACCTTCACCCTGGGACCTGTGAATTTAAAAGTGGCCAGTGAGGTTGAG
CTAAAAGACGCGGTTGAGCACAACCAACACCCGGTTGCGAGACCGATCGATGGTGGAGTTGTGCTCCTGCGTTCCGCGGT
TCCTTCGCTTATAGACGTCTTGATCTCCGGTGCTGATGCATCTCCCAAGTTACTTGCCCATCACGGGCCGGGAAACACTG
GGATCGATGGCACGCTCTGGGATTTTGAGTCCGAAGCCACTAAAGAGGAAGTCGCACTCAGTGCGCAAATAATACAGGCT
TGTGACATTAGGCGCGGCGACGCTCCTGAAATTGGTCTCCCTTACAAGCTGTACCCTGTTAGGGGTAACCCTGAGCGGGT
```

*Fig. 1K-3*

```
GAAAGGAGTTCTGCAGAATACAAGGTTTGGAGACATACCTTACAAAACCCCCAGTGACACTGGAAGCCCAGTGCACGCGG
CTGCCTGCCTTACGCCCAACGCCACTCCGGTGACTGATGGGCGCTCCGTCTTGGCCACGACCATGCCCCCCGGGTTTGAG
TTATATGTACCGACCATACCAGCGTCTGTCCTTGATTACCTTGACTCTAGGCCTGACTGCCCTAAACAGCTGACAGAGCA
CGGCTGCGAAGATGCCGCACTGAAAGACCTCTCTAAATATGACTTGTCCACCCAAGGCTTTGTTTTACCTGGAGTTCTTC
GCCTTGTGCGGAAATACCTGTTTGCCCATGTAGGTAAGTGCCCACCCGTTCATCGGCCTTCTACTTACCCTGCTAAGAAT
TCTATGGCTGGAATAAATGGGAACAGGTTCCCAACCAAGGACATTCAGAGCGTCCCTGAAATCGACGTTCTGTGCGCACA
GGCTGTGCGAGAAAACTGGCAAACTGTCACCCCTTGTACTCTTAAGAAACAGTATTGCGGGAAGAAGAAGACTAGGACCA
TACTCGGCACCAATAACTTCATCGCACTAGCCCACCGAGCAGTGTTGAGTGGTGTTACCCAGGGCTTCATGAAAAAGGCG
TTTAACTCGCCCATCGCCCTCGGAAAGAACAAGTTTAAGGAGCTACAGACTCCGGTCCTGGGCAGGTGCCTTGAAGCTGA
TCTCGCATCCTGCGATCGATCCACGCCTGCAATTGTCCGCTGGTTTGCCGCCAACCTTCTTTATGAACTTGCCTGTGCTG
AAGAGCATCTACCGTCGTACGTGCTGAACTGCTGCCACGACTTACTGGTCACGCAGTCCGGCGCAGTGACTAAGAGAGGT
GGCCTGTCGTCTGGCGACCCGATCACCTCTGTGTCTAACACCATTTATAGTTTGGTGATCTATGCACAGCATATGGTGCT
TAGTTACTTCAAAAGTGGTCACCCCCATGGCCTTCTGTTCTTACAAGACCAGCTAAAGTTTGAGGACATGCTCAAGGTTC
AACCCCTGATCGTCTATTCGGACGACCTCGTGCTGTATGCCGAGTCTCCCACCATGCCAAACTATCACTGGTGGGTTGAA
CATCTGAATTTGATGCTGGGGTTTCAGACGGACCCAAAGAAGACAGCAATAACAGACTCGCCATCATTTCTAGGCTGTAG
AATAATAAATGGGCGCCAGCTAGTCCCCAACCGTGACAGGATCCTCGCGGCCCTCGCCTATCACATGAAGGCGAGTAATG
TTTCTGAATACTATGCCTCAGCGGCTGCAATACTCATGGACAGCTGTGCTTGTTTGGAGTATGATCCTGAATGGTTTGAA
GAACTTGTAGTTGGAATAGCGCAGTGCGCCCGCAAGGACGGCTACAGCTTTCCCGGCACGCCGTTCTTCATGTCCATGTG
GGAAAAACTCAGGTCCAATTATGAGGGGAAGAAGTCGAGAGTGTGCGGGTACTGCGGGCCCCGGCCCCGTACGCTACTG
CCTGTGGCCTCGACGTCTGCATTTACCACACCCACTTCCACCAGCATTGTCCAGTCACAATCTGGTGTGGCCATCCAGCG
GGTTCTGGTTCTTGTAGTGAGTGCAAATCCCCTGTAGGGAAAGGCACAAGCCCTTTAGACGAGGTGCTGGAACAAGTCCC
GTATAAGCCCCCACGGACCGTTATCATGCATGTGGAGCAGGGTCTCACCCCCCTTGATCCAGGTAGATACCAAACTCGCC
GCGGATTAGTCTCTGTCAGGCGTGGAATTAGGGGAAATGAAGTTGGACTACCAGACGGTGATTATGCTAGCACCGCCTTG
CTCCCTACCTGCAAAGAGATCAACATGGTCGCTGTCGCTTCCAATGTATTGCGCAGCAGGTTCATCATCGGCCCACCCGG
TGCTGGGAAAACATACTGGCTCCTTCAACAGGTCCAGGATGGTGATGTTATTTACACACCAACTCACCAGACCATGCTTG
ACATGATTAGGGCTTTGGGGACGTGCCGGTTCAACGTCCCGGCAGGCACAACGCTGCAATTCCCCGTCCCCTCCCGCACC
GGTCCGTGGGTTCGCATCCTAGCCGGCGGTTGGTGTCCTGGCAAGAATTCCTTCCTAGATGAAGCAGCGTATTGCAATCA
CCTTGATGTTTTGAGGCTTCTTAGTAAAACTACCCTCACCTGTCTAGGAGACTTCAAGCAACTCCACCCAGTGGGTTTTG
ATTCTCATTGCTATGTTTTTGACATCATGCCTCAAACTCAACTGAAGACCATCTGGAGGTTTGGACAGAATATCTGTGAT
GCCATTCAGCCAGATTACAGGGACAAACTCATGTCCATGGTCAACACAACCCGTGTGACCTACGTGGAAAAACCTGTCAG
GTATGGGCAGGTCCTCACCCCCTACCACAGGGACCGAGAGGACGACGCCATCACTATTGACTCCAGTCAAGGCGCCACAT
TCGATGTGGTTACATTGCATTTGCCCACTAAAGATTCACTCAACAGGCAAAGAGCCCTTGTTGCTATCACCAGGGCAAGA
CACGCTATCTTTGTGTATGACCCACACAGGCAGCTGCAGGGCTTGTTTGATCTTCCTGCAAAAGGCACGCCCGTCAACCT
CGCAGTGCACTGCGACGGGCAGCTGATCGTGCTGGATAGAAATAACAAAGAATGCACGGTTGCTCAGGCTCTAGGCAACG
GGGATAAATTTAGGGCCACAGACAAGCGTGTTGTAGATTCTCTCCGCGCCATTTGTGCTGATCTAGAAGGGTCGAGCTCT
CCGCTCCCCAAGGTCGCACACAACTTGGGATTTTATTTCTCACCTGATTTAACACAGTTTGCTAAACTCCCAGTAGAACT
TGCACCTCACTGGCCCGTGGTGTCAACCCAGAACAATGAAAAGTGGCCGGATCGGCTGGTTGCCAGCCTTCGCCCTATCC
ATAAATACAGCCGCGCGTGCATCGGTGCCGGCTATATGGTGGGCCCTTCGGTGTTTCTAGGCACTCCTGGGGTCGTGTCA
TACTATCTCACAAAATTTGTTAAGGGCGGGGCTCAAGTGCTTCCGGAGACGGTTTTCAGCACCGGCCGAATTGAGGTAGA
CTGCCGGGAATATCTTGATGATCGGGAGCGAGAAGTTGCTGCGTCCCTCCCACACGCTTTCATTGGCGACGTCAAAGGCA
CTACCGTTGGAGGATGTCATCATGTCACCTCCAGATACCTCCCGCGCGTCCTTCCCAAGGAATCAGTTGCGGTAGTCGGG
GTTTCAAGCCCCGGAAAAGCCGCGAAAGCATTGTGCACACTGACAGATGTGTACCTCCCAGATCTTGAAGCCTATCTCCA
CCCCGGAGACCCAGTCCAAGTGCTGGAAAATGATGTTGGACTTCAAAGAAGTTCGACTAATGGTCTGGAAAGACAAAACAG
CCTATTTCCAACTTGAAGGTCGCTATTTCACCTGGTATCAGCTTGCCAGCTATGCCTCGTACATCCGTGTTCCCGTCAAC
TCTACGGTGTACTTGGACCCCTGCATGGGCCCCGCCCTTTGCAACAGGAGAGTCGTCGGGTCCACCCACTGGGGGCTGA
CCTCGCGGTCACCCCTTATGATTACGGCGCTAAAATTATCCTGTCTAGCGCGTACCATGGTGAAATGCCCCCCGGATACA
AAATTCTGGCGTGCGCGGAGTTCTCGTTGGATGACCCAGTTAAGTACAAACATACCTGGGGGTTTGAATCGGATACAGCG
TATCTGTATGAGTTCACCGGAAACGGTGAGGACTGGGAGGATTACAATGATGCGTTTCGTGCGCGCCAGGAAGGGAAAAT
```

Fig. 1K-4

```
TTATAAGGCCACTGCCACCAGCTTGAAGTTTTATTTTCCCCCGGGCCCTGTCATTGAACCAACTTTAGGCCTGAATTGAA
ATGAAATGGGGTCCATGCAAAGCCTTTTTGACAAAATTGGCCAACTTTTTGTGGATGCTTTCACGGAGTTCTTGGTGTCC
ATTGTTGATATCATTATATTTTTGGCCATTTTGTTTGGCTTCACCATCGCCGGTTGGCTGGTGGTCTTTTGCATCAGATT
GGTTTGCTCCGCGATACTCCGTACGCGCCCTGCCATTCACTCTGAGCAATTACAGAAGATCTTATGAGGCCTTTCTTTCC
CAGTGCCAAGTGGACATTCCCACCTGGGGAACTAAACATCCTTTGGGGATGCTTTGGCACCATAAGGTGTCAACCCTGAT
TGATGAAATGGTGTCGCGTCGAATGTACCGCATCATGGAAAAAGCAGGGCAGGCTGCCTGGAAACAGGTGGTGAGCGAGG
CTACGCTGTCTCGCATTAGTAGTTTGGATGTGGTGGCTCATTTTCAGCATCTAGCCGCCATTGAAGCCGAGACCTGTAAA
TATTTGGCCTCCCGGCTGCCCATGCTACACAACCTGCGCATGACAGGGTCAAATGTAACCATAGTGTATAATAGCACTTT
GAATCAGGTGTTTGCTATTTTTCCAACCCCTGGTTCCCGGCCAAAGCTTCATGATTTTCAGCAATGGTTAATAGCTGTAC
ATTCCTCCATATTTTCCTCTGTTGCAGCTTCTTGTACTCTTTTTGTTGTGCTGTGGTTGCGGGTTCCAATACTACGTACT
GTTTTTGGTTTCCGCTGGTTAGGGGCAATTTTTTCTTTCGAACTCACAGTGAATTACACGGTGTGTCCACCTTGCCTCACC
CGGCAAGCAGCCACAGAGATCTACGAACCCGGTAGGTCTCTTTGGTGCAGGATAGGGTATGACCGATGTGGGGAGGACGA
TCATGACGAGCTAGGGTTTATGATACCGCCTGGCCTCTCCAGCGAAGGCCACTTGACTGGTGTTTACGCCTGGTTGGCGT
TCTTGTCCTTCAGCTACACGGCCCAGTTCCATCCCGAGATATTCGGGATAGGGAATGTGAGTCGAGTTTATGTTGACATC
AAACATCAACTCATCTGCGCCGAACATGACGGGCAGAACACCACCTTGCCTCGTCATGACAACATTTCAGCCGTGTTTCA
GACCTATTACCAACATCAAGTCGACGGCGGCAATTGGTTTCACCTAGAATGGCTTCGTCCCTTCTTTTCCTCGTGGTTGG
TTTTAAATGTCTCTTGGTTTCTCAGGCGTTCGCCTGCAAACCATGTTTCAGTTCGAGTCTTGCAGATATTAAGACCAACA
CCACCGCAGCGGCAAGCTTTGCTGTCCTCCAAGACATCAGTTGCCTTAGGCATCGCGACTCGGCCTCTGAGGCGATTCGC
AAAATCCCTCAGTGCCGTACGGCGATAGGGACACCCGTGTATGTTACCATCACAGCCAATGTGACAGATGAGAATTATTT
ACATTCTTCTGATCTCCTCATGCTTTCTTCTTGCCTTTTCTATGCTTCTGAGATGAGTGAAAAGGGATTTAAGGTGGTAT
TTGGCAATGTGTCAGGCATCGTGGCTGTGTGTCAATTTTACCAGCTACGTCCAACATGTCAAGGAGTTTACCCAACGC
TCCCTGGTGGTCGACCATGTGCGGTTGCTCCATTTCATGACACCTGAGACCATGAGGTGGGCAACTGTTTTAGCCTGTCT
TTTTGCCATTCTGTTGGCAATTTGAATGTTTAAGTATGTTGGAGAAATGCTTGACCGCGGGCTGTTGCTCGCGATTGCTT
TCTTTGTGGTGTATCGTGCCGTTCTGTTTTGCTGTGCTCGCCAACGCCAGCAACGACAGCAGCTCCCATCTACAGCTGAT
TTACAACTTGACGCTATGTGAGCTGAATGGCACAGATTGGCTAGCTAACAAATTTGATTGGGCAGTGGAGAGTTTTGTCA
TCTTTCCCGTTTTGACTCACATTGTCTCCTATGGTGCCCTCACTACCAGCCATTTCCTTGACACAGTCGCTTTAGTCACT
GTGTCTACCGCCGGGTTTGTTCACGGGCGGTATGTCCTAAGTAGCATCTACGCGGTCTGTGCCCTGGCTGCGTTGACTTG
CTTCGTCATTAGGTTTGCAAAGAATTGCATGTCCTGGCGCTACGCGTGTACCAGATATACCAACTTTCTTCTGGACACTA
AGGGCAGACTCTATCGTTGGCGGTCGCCTGTCATCATAGAGAAAAGGGCAAAGTTGAGGTCGAAGGTCATCTGATCGAC
CTCAAAAGAGTTGTGCTTGATGGTCCGTGGCAACCCCTATAACCAGAGTTTCAGCGGAACAATGGGGTCGTCCTTAGAT
GACTTCTGTCACGATAGCACGGCTCCACAAAAGGTGCTTTTGGCGTTTTCTATTACCTACACGCCAGTGATGATATATGC
CCTAAAGGTGAGTCGCGGCCGACTGCTAGGGCTTCTGCACCTTTTGATCTTCCTGAATTGTGCTTTCACCTTCGGGTACA
TGACTTTCGCGCACTTTCAGAGTACAAATAAGGTCGCGCTCACTATGGGAGCAGTAGTTGCACTCCTTTGGGGGGTGTAC
TCAGCCATAGAAACCTGGAAATTCATCACCTCCAGATGCCGTTTGTGCTTGCTAGGCCGCAAGTACATTCTGGCCCCTGC
CCACCACGTTGAAAGTGCCGCAGGCTTTCATCCGATTGCGGCAAATGATAACCACGCATTTGTCGTCCGGCGTCCCGGCT
CCACTACGGTCAACGGCACATTGGTGCCCGGGTTAAAAAGCCTCGTGTTGGGTGGCAGAAAAGCTGTTAAACAGGGAGTG
GTAAACCTTGTCAAATATGCCAAATAACAACGGCAAGCAGCAGAAGAGAAAGAAGGGGGATGGCCAGCCAGTCAATCAGC
TGTGCCAGATGCTGGGTAAGATCATCGCTCAGCAAAACCAGTCCAGAGGCAAGGGACCGGGAAAGAAAAATAAGAAGAAA
AACCCGGAGAAGCCCCATTTTCCTCTAGCGACTGAAGATGATGTCAGACATCACTTTACCCCTAGTGAGCGGCAATTGTG
TCTGTCGTCAATCCAGACCGCCTTTAATCAAGGCGCTGGGACTTGCACCCTGTCAGATTCAGGGAGGATAAGTTACACTG
TGGAGTTTAGTTTGCCTACGCATCATACTGTGCGCCTGATCCGCGTCACAGCATCACCCTCAGCATGATGGGCTGGCATT
CTTGAGGCATCTCAGTGTTTGAATTGGAAGAATGTGTGGTGAATGGCACTGATTGACATTGTGCCTCTAAGTCACCTATT
CAATTAGGGCGACCGTGTGGGGGTGAGATTTAATTGGCGAGAACCATGCGGCCGAAATTAAAAAAAA
```

Fig. 1L-1

```
>V7-Nsp2d727-813.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAACACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGGACAACAACTCGGTCC
CCCTGACCGCCTTTTCACTGGCTAACTACTACTACCGTGCGCAAGGTGACGAAGTTCGTCACCGTGAAAGACTAACCGCC
GTGCTCTCCAAGTTGGAAAAGGTTGTTCGAGAAGAATATGGGCTCATGCCAACCGAGCCTGGTCCACGGCCCACACTGCC
ACGCGGGCTCGACGAACTCAAAGACCAGATGGAGGAGGACTTGCTGAAACTGGCTAACGCCCAGACGACTTCGGACATGA
TGGCCTGGGCAGTCGAGCAGGTTGACCTAAAAACTTGGGTCAAGAACTACCCGCGGTGGACACCACCACCCCCTCCGCCA
AAAGTTCAGCCTCGAAAAACGAAGCCTGTCAAGAGCTTGCCGGAGAGAAAGCCTGTCCCCGCCCCGCGCAGGAAGGTTGG
GTCCGATTGTGGCAGCCCGGTTTCATTAGGCGGCGATGTCCCTAACAGTTGGGAAGATTTGGCTGTTAGTAGCCCCTTTG
ATCTCCCGACCCCACCTGAGCCGGCAACACCTTCAAGTGAGCTGGTGATTGTGTCCTCACCGCAATGCATCTTCAGGCCG
GCGACACCCTTGAGTGAGCCGGCTCCAATTCCCGCACCTCGCGGAACTGTGTCTCGACCGGTGACACCCTTGAGTGAGCC
GATCCCTGTGCCCGCACCGCGGCGTAAGTTTCAGCAGGTGAAAAGATTGAGTTCGGCGGCGGCAATCCCACCGTACCAGG
ACGAGCCCCTGGATTTGTCTGCTTCCTCACAGACTGAATATGAGGCCTCTCCCCCAGCACCGCCGCAGAGCGGGGGCGTT
CTGGGAGTAGAGGGGCATGAAGCTGAGGAAACCCTGAGTGAAATCTCGGACATGTCGGGTAACATTAAACCTGCGTCCGT
GTCATCAAGCAGCTCCTTGTCCAGCGTGAGAATCACACGCCCAAAATACTCAGCTCAAGCCATCATCGACTCGGGCGGGC
CCTGCAGTGGGCATCTCCAAGAGGTAAAGGAAACATGCCTTAGTGTCATGCGCGAGGCATGTGATGCGACTAAGCTTGAT
GACCCTGCTACGCAGGAATGGCTTTCTCGCATGTGGGATCGGGTGGACATGCTGACTTGGCGCAACACGTCTGTTTACCA
GGCGATTTGCACCTTAGATGGCAGGTTAAAGTTCCTCCCAAAAATGATACTCGAGACACCGCCGCCCTATCCGTCTTTTA
CCGATTTGCCGCCTTCAGATGGCGCGGATGCGGACGGGGGGGGCCGTTTCGGACGGTAAAAAGAAAAGCTGAAAGGCTC
TTTGACCAACTGAGCCGTCAGGTTTTTGACCTCGTCTCCCATCTCCCTGTTTTCTTCTCACGCCTTTTCTACCCTGGCGG
TGGTTATTCTCCGGGTGATTGGGGTTTTGCAGCTTTTACTCTATTGTGCCTCTTTTTATGTTACAGTTACCCAGCCTTTG
GTATTGCTCCCCTCTTGGGTGTGTTTTCTGGGTCTTCTCGGCGCGTTCGAATGGGGGTTTTTGGCTGCTGGTTGGCTTTT
```

Fig. 1L-2

```
GCTGTTGGTCTGTTCAAGCCTGTGTCCGACCCAGTCGGCGCTGCTTGTGAGTTTGACTCGCCAGAGTGTAGAAACATCCT
TCATTCTTTTGAGCTTCTCAAACCTTGGGACCCTGTTCGCAGCCTTGTTGTGGGCCCCGTCGGTCTCGGTCTTGCCATTC
TTGGCAGGTTACTGGGCGGGGCACGCTGCATCTGGCACTTTTTGCTTAGGCTTGGCATTGTTGCAGACTGTATCTTGGCT
GGAGCTTACGTGCTTTCTCAAGGTAGGTGTAAAAAGTGCTGGGGATCTTGTATAAGAACTGCTCCCAATGAGGTCGCTTT
TAACGTGTTTCCTTTCACACGTGCGACCAGGTCGTCACTTATCGACCTGTGCGATCGGTTTTGTGCGCCAAAAGGAATGG
ACCCCATTTTTCTCGCCACTGGGTGGCGCGGGTGCTGGGCCGGCCGAAGCCCCATTGAGCAACCCTCTGAAAAACCCATC
GCGTTTGCCCAGTTGGATGAAAAGAAGATTACGGCTAGGACTGTGGTCGCCCAGCCTTATGACCCCAACCAAGCCGTAAA
GTGCTTGCGGGTATTGCAGGCGGGTGGGGCGATGGTGGCTAAGGCGGTCCCAAAAGTGGTCAAGGTTTCCGCTGTTCCAT
TCCGAGCCCCCTTCTTTCCCACTGGAGTGAAAGTTGACCCTGATTGCAGGGTCGTGGTTGACCCTGACACTTTCACTGCA
GCTCTCCGGTCTGGCTACTCCACCACAAACCTCGTCCTTGGTGTGGGGGACTTTGCCCAGCTGAATGGATTAAAAATCAG
GCAAATTTCCAAGCCTTCAGGGGGAGGCCCACATCTCATGGCTGCCCTGCATGTTGCCTGCTCGATGGCTCTGCACATGC
TTGCTGGGATTTATGTGACTGCGGTGGGTTCTTGCGGCACCGGCACCAACGACCCGTGGTGCGCTAACCCGTTTGCCGTC
CCTGGCTACGGACCTGGCTCTCTCTGCACGTCCAGATTGTGCATTTCCCAACACGGCCTTACCCTGCCCTTGACAGCACT
TGTGGCGGGATTCGGTATTCAAGAAATTGCCTTGGTCGTTTTGATTTTTGTTTCCATCGGAGGCATGGCTCATAGGTTGA
GCTGTAAGGCTGACATGCTGTGTGTCTTGCTTGCAATTGCCAGCTATGTTTGGGTACCTCTTACCTGGTTGCTTTGTGTG
TTTCCTTGCTGGTTGCGCTGTTTTTCTTTGCACCCCCTCACCATCCTATGGTTGGTGTTTTTCTTGATTTCTGTGAATAT
GCCTTCAGGAATCTTGGCCATGGTGTTGTTGGTTTCTCTTTGGCTTCTTGGTCGTTATACTAATGTTGCTGGCCTTGTCA
CCCCCTACGACATTCATCATTACACCAGTGGCCCCCGCGGTGTTGCCGCCTTGGCTACCGCACCAGATGGGACCTACTTG
GCCGCTGTCCGCCGCGCTGCGTTGACTGGCCGCACCATGCTGTTTACCCCGTCCCAGCTTGGGTCTCTTCTTGAGGGTGC
TTTCAGAACTCGAAAGCCCTCACTGAACACCGTCAATGTGATCGGGTCCTCCATGGGCTCTGGCGGGGTGTTTACCATCG
ACGGGAAAGTCAAGTGCGTAACTGCCGCACATGTCCTTACGGGCAATTCAGCTCGGGTTTCCGGGGTCGGCTTCAATCAA
ATGCTTGACTTTGACGTAAAGGGAGATTTCGCTATAGCTGATTGCCCGAATTGGCAAGGGGCTGCCCCCAAGACCCAATT
CTGCACGGATGGATGGACTGGCCGTGCCTATTGGCTAACATCCTCTGGCGTCGAACCCGGCGTCATTGGAAAAGGATTCG
CCTTCTGCTTCACCGCATGTGGCGATTCCGGGTCCCCAGTGATCACCGAGGCCGGTGAGCTTGTCGGCGTTCACACGGGA
TCGAATAAACAAGGGGGGGGGCATTGTTACGCGCCCCTCAGGCCAGTTTTGTAATGTGGCACCCATCAAGCTAAGCGAATT
AAGTGAATTCTTTGCTGGGCCTAAGGTCCCGCTCGGTGATGTGAAGGTCGGCAGCCACATAATTAAAGACATAAGCGAGG
TGCCTTCAGATCTTTGTGCCTTGCTTGCTGCCAAACCTGAACTGGAAGGAGGCCTCTCCACCGTCCAACTTCTTTGTGTG
TTTTTTCTCCTGTGGAGAATGATGGGACATGCCTGGACGCCCTTGGTTGCTGTGAGTTTCTTTATTTTGAATGAGGTTCT
CCCCAGCCGTCCTGGTCCGGAGTGTTTTCTCCTTTGGAATGTTTGTGCTATCCTGGCTCACGCCATGGTCTGCGCAAGTTC
TGATGATCAGGCTTCTGACAGCAGCTCTTAACAGGAACAGATGGTCACTTGCCTTTTTCAGCCTCGGTGCAGTGACCGGT
TTTGTCGCAGATCTTGCGGCCACTCAGGGGCATCCGTTGCAGGCAGTGATGAATTTGAGCACCTATGCATTCCTGCCTCG
GATGATGGTTGTGACCTCACCAGTCCCAGTGATCACGTGTGGTGTCGTGCACCTACTTGCCATCATTTTGTACTTGTTTA
AGTACCGTGGCCTGCACCATATCCTTGTTGGCGATGGAGTGTTCTCTGCGGCTTTCTTCTTGAGATACTTTGCCGAGGGA
AAGTTGAGGGAAGGGGTGTCGCAATCCTGCGGAATGAATCATGAGTCTCTGACTGGTGCCCTCGCTATGAGACTCAATGA
CGAGGACTTGGATTTCCTTATGAAATGGACTGATTTTAAGTGCTTTGTTTCTGCGTCCAACATGAGGAATGCAGCGGGTC
AATTTATCGAGGCTGCCTATGCTAAAGCACTTAGAGTAGAACTGGCCCAGTTGGTGCAGGTTGATAAAGTTCGAGGTACT
TTGGCCAAACTTGAAGCTTTTGCTGATACCGTGGCACCTCAACTCTCGCCCGGTGACATTGTTGTCGCTCTCGGCCACAC
GCCTGTTGGCAGTATCTTCGACCTAAAGGTTGGTAGCACCAAGCATACCCTCCAAGCCATTGAGACCAGAGTCCTTGCTG
GGTCCAAAATGACCGTGGCGCGCGTCGTCGACCCGACCCCCACGCCCCCACCCGCACCCGTGCCCATCCCCCTCCCACCG
AAAGTTCTGGAGAATGGCCCCAACGCTTGGGGGATGAGGACCGTTTGAATAAGAAGAAGAGGCGCAGGATGGAAGCCCT
CGGCATCTATGTTATGGGCGGGAAAAAATACCAGAAATTTTGGGACAAGAATTCCGGTGATGTGTTTTATGAGGAGGTCC
ATAATAACACAGATGAGTGGGAGTGTCTCAGAGTTGGCGACCCTGCCGACTTTGACCCTGAGAAGGGAACTCTGTGTGGA
CATGTCACCATTGAAAACAAGGCTTACCATGTTTACACCTCCCCATCTGGTAAGAAGTTCTTGGTCCCCGTCAACCCAGA
GAATGGAAGAGTCCAATGGGAAGCTGCAAAGCTTTCCGTGGAGCAGGCCCTAGGTATGATGAATGTCGACGGCGAACTGA
CTGCCAAAGAACTGGAGAAACTGAAAAGAATAATTGACAAACTCCAGGGCCTGACTAAGGAGCAGTGTTTAAACTGCTAG
CCGCCAGCGACTTGACCCGCTGTGGTCGCGGCGGCTTGGTTGTTACTGAAACAGCGGTAAAAATAGTCAAATTTCACAAC
CGGACCTTCACCCTGGGACCTGTGAATTTAAAAGTGGCCAGTGAGGTTGAGCTAAAAGACGCGGTTGAGCACAACCAACA
CCCGGTTGCGAGACCGATCGATGGTGGAGTTGTGCTCCTGCGTTCCGCGGTTCCTTCGCTTATAGACGTCTTGATCTCCG
GTGCTGATGCATCTCCCAAGTTACTTGCCCATCACGGGCCGGGAAACACTGGGATCGATGGCACGCTCTGGGATTTTGAG
```

Fig. 1L-3

```
TCCGAAGCCACTAAAGAGGAAGTCGCACTCAGTGCGCAAATAATACAGGCTTGTGACATTAGGCGCGGCGACGCTCCTGA
AATTGGTCTCCCTTACAAGCTGTACCCTGTTAGGGGTAACCCTGAGCGGGTGAAAGGAGTTCTGCAGAATACAAGGTTTG
GAGACATACCTTACAAAACCCCCAGTGACACTGGAAGCCCAGTGCACGCGGCTGCCTGCCTTACGCCCAACGCCACTCCG
GTGACTGATGGGCGCTCCGTCTTGGCCACGACCATGCCCCCCGGGTTTGAGTTATATGTACCGACCATACCAGCGTCTGT
CCTTGATTACCTTGACTCTAGGCCTGACTGCCCTAAACAGCTGACAGAGCACGGCTGCGAAGATGCCGCACTGAAAGACC
TCTCTAAATATGACTTGTCCACCCAAGGCTTTGTTTTACCTGGAGTTCTTCGCCTTGTGCGGAAATACCTGTTTGCCCAT
GTAGGTAAGTGCCCACCCGTTCATCGGCCTTCTACTTACCCTGCTAAGAATTCTATGGCTGGAATAAATGGGAACAGGTT
CCCAACCAAGGACATTCAGAGCGTCCCTGAAATCGACGTTCTGTGCGCACAGGCTGTGCGAGAAAACTGGCAAACTGTCA
CCCCTTGTACTCTTAAGAAACAGTATTGCGGGAAGAAGAAGACTAGGACCATACTCGGCACCAATAACTTCATCGCACTA
GCCCACCGAGCAGTGTTGAGTGGTGTTACCCAGGGCTTCATGAAAAAGGCGTTTAACTCGCCCATCGCCCTCGGAAAGAA
CAAGTTTAAGGAGCTACAGACTCCGGTCCTGGGCAGGTGCCTTGAAGCTGATCTCGCATCCTGCGATCGATCCACGCCTG
CAATTGTCCGCTGGTTTGCCGCCAACCTTCTTTATGAACTTGCCTGTGCTGAAGAGCATCTACCGTCGTACGTGCTGAAC
TGCTGCCACGACTTACTGGTCACGCAGTCCGGCGCAGTGACTAAGAGAGGTGGCCTGTCGTCTGGCGACCCGATCACCTC
TGTGTCTAACACCATTTATAGTTTGGTGATCTATGCACAGCATATGGTGCTTAGTTACTTCAAAAGTGGTCACCCCCATG
GCCTTCTGTTCTTACAAGACCAGCTAAAGTTTGAGGACATGCTCAAGGTTCAACCCCTGATCGTCTATTCGGACGACCTC
GTGCTGTATGCCGAGTCTCCCACCATGCCAAACTATCACTGGTGGGTTGAACATCTGAATTTGATGCTGGGGTTTCAGAC
GGACCCAAAGAAGACAGCAATAACAGACTCGCCATCATTTCTAGGCTGTAGAATAATAAATGGGCGCCAGCTAGTCCCCA
ACCGTGACAGGATCCTCGCGGCCCTCGCCTATCACATGAAGGCGAGTAATGTTTCTGAATACTATGCCTCAGCGGCTGCA
ATACTCATGGACAGCTGTGCTTGTTTGGAGTATGATCCTGAATGGTTTGAAGAACTTGTAGTTGGAATAGCGCAGTGCGC
CCGCAAGGACGGCTACAGCTTTCCCGGCACGCCGTTCTTCATGTCCATGTGGGAAAAACTCAGGTCCAATTATGAGGGA
AGAAGTCGAGAGTGTGCGGGTACTGCGGGGCCCCGGCCCCGTACGCTACTGCCTGTGGCCTCGACGTCTGCATTTACCAC
ACCCACTTCCACCAGCATTGTCCAGTCACAATCTGGTGTGGCCATCCAGCGGGTTCTGGTTCTTGTAGTGAGTGCAAATC
CCCTGTAGGGAAAGGCACAAGCCCTTTAGACGAGGTGCTGGAACAAGTCCCGTATAAGCCCCCACGGACCGTTATCATGC
ATGTGGAGCAGGGTCTCACCCCCCTTGATCCAGGTAGATACCAAACTCGCCGCGGATTAGTCTCTGTCAGGCGTGGAATT
AGGGGAAATGAAGTTGGACTACCAGACGGTGATTATGCTAGCACCGCCTTGCTCCCTACCTGCAAAGAGATCAACATGGT
CGCTGTCGCTTCCAATGTATTGCGCAGCAGGTTCATCATCGGCCCACCCGGTGCTGGGAAAACATACTGGCTCCTTCAAC
AGGTCCAGGATGGTGATGTTATTTACACACCAACTCACCAGACCATGCTTGACATGATTAGGGCTTTGGGGACGTGCCGG
TTCAACGTCCCGGCAGGCACAACGCTGCAATTCCCCGTCCCCTCCCGCACCGGTCCGTGGGTTCGCATCCTAGCCGGCGG
TTGGTGTCCTGGCAAGAATTCCTTCCTAGATGAAGCAGCGTATTGCAATCACCTTGATGTTTTGAGGCTTCTTAGTAAAA
CTACCCTCACCTGTCTAGGAGACTTCAAGCAACTCCACCCAGTGGGTTTTGATTCTCATTGCTATGTTTTTGACATCATG
CCTCAAACTCAACTGAAGACCATCTGGAGGTTTGGACAGAATATCTGTGATGCCATTCAGCCAGATTACAGGGACAAACT
CATGTCCATGGTCAACACAACCCGTGTGACCTACGTGGAAAAACCTGTCAGGTATGGGCAGGTCCTCACCCCCTACCACA
GGGACCGAGAGGACGACGCCATCACTATTGACTCCAGTCAAGGCGCCACATTCGATGTGGTTACATTGCATTTGCCCACT
AAAGATTCACTCAACAGGCAAAGAGCCCTTGTTGCTATCACCAGGGCAAGACACGCTATCTTTGTGTATGACCCACACAG
GCAGCTGCAGGGCTTGTTTGATCTTCCTGCAAAAGGCACGCCCGTCAACCTCGCAGTGCACTGCGACGGGCAGCTGATCG
TGCTGGATAGAAATAACAAAGAATGCACGGTTGCTCAGGCTCTAGGCAACGGGGATAAATTTAGGGCCACAGACAAGCGT
GTTGTAGATTCTCTCCGCGCCATTTGTGCTGATCTAGAAGGGTCGAGCTCTCCGCTCCCAAGGTCGCACACAACTTGGG
ATTTTATTTCTCACCTGATTTAACACAGTTTGCTAAACTCCCAGTAGAACTTGCACCTCACTGGCCCGTGGTGTCAACCC
AGAACAATGAAAAGTGGCCGGATCGGCTGGTTGCCAGCCTTCGCCCTATCCATAAATACAGCCGCGCGTGCATCGGTGCC
GGCTATATGGTGGGCCCTTCGGTGTTTCTAGGCACTCCTGGGGTCGTGTCATACTATCTCACAAAATTTGTTAAGGGCGG
GGCTCAAGTGCTTCCGGAGACGGTTTTCAGCACCGGCCGAATTGAGGTAGACTGCCGGGAATATCTTGATGATCGGGAGC
GAGAAGTTGCTGCGTCCCTCCCACACGCTTTCATTGGCGACGTCAAAGGCACTACCGTTGGAGGATGTCATCATGTCACC
TCCAGATACCTCCCGCGCGTCCTTCCCAAGGAATCAGTTGCGGTAGTCGGGGTTTCAAGCCCCGGAAAAGCCGCGAAAGC
ATTGTGCACACTGACAGATGTGTACCTCCCAGATCTTGAAGCCTATCTCCACCCGGAGACCCAGTCCAAGTGCTGGAAAA
TGATGTTGGACTTCAAAGAAGTTCGACTAATGGTCTGGAAAGACAAAACAGCCTATTTCCAACTTGAAGGTCGCTATTTC
ACCTGGTATCAGCTTGCCAGCTATGCCTCGTACATCCGTGTTCCCGTCAACTCTACGGTGTACTTGGACCCCTGCATGGG
CCCCGCCCTTTGCAACAGGAGAGTCGTCGGGTCCACCCACTGGGGGGCTGACCTCGCGGTCACCCCTTATGATTACGGCG
CTAAAATTATCCTGTCTAGCGCGTACCATGGTGAAATGCCCCCCGGATACAAAATTCTGGCGTGCGCGGAGTTCTCGTTG
GATGACCCAGTTAAGTACAAACATACCTGGGGGTTTGAATCGGATACAGCGTATCTGTATGAGTTCACCGGAAACGGTGA
```

Fig. 1L-4

```
GGACTGGGAGGATTACAATGATGCGTTTCGTGCGCGCCAGGAAGGGAAAATTTATAAGGCCACTGCCACCAGCTTGAAGT
TTTATTTTCCCCCGGGCCCTGTCATTGAACCAACTTTAGGCCTGAATTGAAATGAAATGGGGTCCATGCAAAGCCTTTTT
GACAAAATTGGCCAACTTTTTGTGGATGCTTTCACGGAGTTCTTGGTGTCCATTGTTGATATCATTATATTTTTGGCCAT
TTTGTTTGGCTTCACCATCGCCGGTTGGCTGGTGGTCTTTTGCATCAGATTGGTTTGCTCCGCGATACTCCGTACGCGCC
CTGCCATTCACTCTGAGCAATTACAGAAGATCTTATGAGGCCTTTCTTTCCCAGTGCCAAGTGGACATTCCCACCTGGGG
AACTAAACATCCTTTGGGGATGCTTTGGCACCATAAGGTGTCAACCCTGATTGATGAAATGGTGTCGCGTCGAATGTACC
GCATCATGGAAAAAGCAGGGCAGGCTGCCTGGAAACAGGTGGTGAGCGAGGCTACGCTGTCTCGCATTAGTAGTTTGGAT
GTGGTGGCTCATTTTCAGCATCTAGCCGCCATTGAAGCCGAGACCTGTAAATATTTGGCCTCCCGGCTGCCCATGCTACA
CAACCTGCGCATGACAGGGTCAAATGTAACCATAGTGTATAATAGCACTTTGAATCAGGTGTTTGCTATTTTTCCAACCC
CTGGTTCCCGGCCAAAGCTTCATGATTTTCAGCAATGGTTAATAGCTGTACATTCCTCCATATTTTCCTCTGTTGCAGCT
TCTTGTACTCTTTTTGTTGTGCTGTGGTTGCGGGTTCCAATACTACGTACTGTTTTGGTTTCCGCTGGTTAGGGGCAAT
TTTTCTTTCGAACTCACAGTGAATTACACGGTGTGTCCACCTTGCCTCACCCGGCAAGCAGCCACAGAGATCTACGAACC
CGGTAGGTCTCTTTGGTGCAGGATAGGGTATGACCGATGTGGGGAGGACGATCATGACGAGCTAGGGTTTATGATACCGC
CTGGCCTCTCCAGCGAAGGCCACTTGACTGGTGTTTACGCCTGGTTGGCGTTCTTGTCCTTCAGCTACACGGCCCAGTTC
CATCCCGAGATATTCGGGATAGGGAATGTGAGTCGAGTTTATGTTGACATCAAACATCAACTCATCTGCGCCGAACATGA
CGGGCAGAACACCACCTTGCCTCGTCATGACAACATTTCAGCCGTGTTTCAGACCTATTACCAACATCAAGTCGACGGCG
GCAATTGGTTTCACCTAGAATGGCTTCGTCCCTTCTTTTCCTCGTGGTTGGTTTTAAATGTCTCTTGGTTTCTCAGGCGT
TCGCCTGCAAACCATGTTTCAGTTCGAGTCTTGCAGATATTAAGACCAACACCACCGCAGCGGCAAGCTTTGCTGTCCTC
CAAGACATCAGTTGCCTTAGGCATCGCGACTCGGCCTCTGAGGCGATTCGCAAAATCCCTCAGTGCCGTACGGCGATAGG
GACACCCGTGTATGTTACCATCACAGCCAATGTGACAGATGAGAATTATTTACATTCTTCTGATCTCCTCATGCTTTCTT
CTTGCCTTTTCTATGCTTCTGAGATGAGTGAAAAGGGATTTAAGGTGGTATTTGGCAATGTGTCAGGCATCGTGGCTGTG
TGTGTCAATTTTACCAGCTACGTCCAACATGTCAAGGAGTTTACCCAACGCTCCCTGGTGGTCGACCATGTGCGGTTGCT
CCATTTCATGACACCTGAGACCATGAGGTGGGCAACTGTTTTAGCCTGTCTTTTTGCCATTCTGTTGGCAATTTGAATGT
TTAAGTATGTTGGAGAAATGCTTGACCGCGGGCTGTTGCTCGCGATTGCTTTCTTTGTGGTGTATCGTGCCGTTCTGTTT
TGCTGTGCTCGCCAACGCCAGCAACGACAGCAGCTCCCATCTACAGCTGATTTACAACTTGACGCTATGTGAGCTGAATG
GCACAGATTGGCTAGCTAACAAATTTGATTGGGCAGTGGAGAGTTTTGTCATCTTTCCCGTTTTGACTCACATTGTCTCC
TATGGTGCCCTCACTACCAGCCATTTCCTTGACACAGTCGCTTTAGTCACTGTGTCTACCGCCGGGTTTGTTCACGGGCG
GTATGTCCTAAGTAGCATCTACGCGGTCTGTGCCCTGGCTGCGTTGACTTGCTTCGTCATTAGGTTTGCAAAGAATTGCA
TGTCCTGGCGCTACGCGTGTACCAGATATACCAACTTTCTTCTGGACACTAAGGGCAGACTCTATCGTTGGCGGTCGCCT
GTCATCATAGAGAAAAGGGGCAAAGTTGAGGTCGAAGGTCATCTGATCGACCTCAAAAGAGTTGTGCTTGATGGCTCCGT
GGCAACCCCTATAACCAGAGTTTCAGCGGAACAATGGGGTCGTCCTTAGATGACTTCTGTCACGATAGCACGGCTCCACA
AAAGGTGCTTTTGGCGTTTTCTATTACCTACACGCCAGTGATGATATATGCCCTAAAGGTGAGTCGCGGCCGACTGCTAG
GGCTTCTGCACCTTTTGATCTTCCTGAATTGTGCTTTCACCTTCGGGTACATGACTTTCGCGCACTTTCAGAGTACAAAT
AAGGTCGCGCTCACTATGGGAGCAGTAGTTGCACTCCTTTGGGGGGTGTACTCAGCCATAGAAACCTGGAAATTCATCAC
CTCCAGATGCCGTTTGTGCTTGCTAGGCCGCAAGTACATTCTGGCCCCTGCCCACCACGTTGAAAGTGCCGCAGGCTTTC
ATCCGATTGCGGCAAATGATAACCACGCATTTGTCGTCCGGCGTCCCGGCTCCACTACGGTCAACGGCACATTGGTGCCC
GGGTTAAAAAGCCTCGTGTTGGGTGGCAGAAAAGCTGTTAAACAGGGAGTGGTAAACCTTGTCAAATATGCCAAATAACA
ACGGCAAGCAGCAGAAGAGAAAGAAGGGGGATGGCCAGCCAGTCAATCAGCTGTGCCAGATGCTGGGTAAGATCATCGCT
CAGCAAAACCAGTCCAGAGGCAAGGGACCGGGAAAGAAAAATAAGAAGAAAAACCCGGAGAAGCCCCATTTTCCTCTAGC
GACTGAAGATGATGTCAGACATCACTTTACCCCTAGTGAGCGGCAATTGTGTCTGTCGTCAATCCAGACCGCCTTTAATC
AAGGCGCTGGGACTTGCACCCTGTCAGATTCAGGGAGGATAAGTTACACTGTGGAGTTTAGTTTGCCTACGCATCATACT
GTGCGCCTGATCCGCGTCACAGCATCACCCTCAGCATGATGGGCTGGCATTCTTGAGGCATCTCAGTGTTTGAATTGGAA
GAATGTGTGGTGAATGGCACTGATTGACATTGTGCCTCTAAGTCACCTATTCAATTAGGGCGACCGTGTGGGGGTGAGAT
TTAATTGGCGAGAACCATGCGGCCGAAATTAAAAAAAA
```

Fig. 1M-1

```
>V7-Nsp2d324-726.seq
ATGACGTATAGGTGTTGGCTCTATGCCTTGGCATTTGTATTGTCAGGAGCTGTGACCATTGGCACAGCCCAAAACTTGCT
GCACAGAAACACCCTTCTGTGATAGCCTCCTTCAGGGGAGCTTAGGGTTTGTCCCTAGCACCTTGCTTCCGGAGTTGCAC
TGCTTTACGGTCTCTCCACCCCTTTAACCATGTCTGGGATACTTGATCGGTGCACGTGTACCCCCAATGCCAGGGTGTTT
ATGGCGGAGGGCCAAGTCTACTGCACACGATGCCTCAGTGCACGGTCTCTCCTTCCCCTGAACCTCCAGGTTTCTGAGCT
CGGGGTGCTAGGCCTATTCTACAGGCCCGAAGAGCCACTCCGGTGGACGTTGCCACGTGCATTCCCCACTGTTGAGTGCT
CCCCCGCCGGGGCCTGCTGGCTTTCTGCAATCTTTCCAATCGCACGAATGACCAGTGGAAACCTGAACTTCCAACAAAGA
ATGGTACGGGTCGCAGCTGAGCTTTACAGAGCCGGCCAGCTCACCCCTGCAGTCTTGAAGGCTCTACAAGTTTATGAACG
GGGTTGCCGCTGGTACCCCATTGTTGGACCTGTCCCTGGAGTGGCCGTTTTCGCCAATTCCCTACATGTGAGTGATAAAC
CCTTCCCGGGAGCAACTCACGTGTTGACCAACCTGCCGCTCCCGCAGAGACCCAAGCCTGAAGACTTTTGCCCCTTTGAG
TGTGCTATGGCTACTGTCTATGACATTGGTCATGACGCCGTCATGTATGTGGCCGAAAGGAAAGTCTCCTGGGCCCCTCG
TGGCGGGGATGAAGTGAAATTTGAAGCTGTCCCCGGGGAGTTGAAGTTGATTGCGAACCGGCTCCGCACCTCCTTCCCGC
CCCACCACACAGTGGACATGTCTAAGTTCGCCTTCACAGCCCCTGGGTGTGGTGTTTCTATGCGGGTCGAACGCCAACAC
GGCTGCCTTCCCGCTGACACTGTCCCTGAAGGCAACTGCTGGTGGAGCTTGTTTGACTTGCTTCCACTGGAAGTTCAGAA
CAAAGAAATTCGCCATGCTAACCAATTTGGCTACCAGACCAAGCATGGTGTCTCTGGCAAGTACCTGCAGCGGAGGCTGC
AAGTTAATGGTCTCCGAGCAGTAACTGACCTAAACGGACCTATCGTCGTACAGTACTTCTCCGTTAAGGAGAGTTGGATC
CGCCATTTGAAACTGGCGGGAGAACCCAGCTACTCTGGGTTTGAGGACCTCCTCAGAATAAGGGTTGAGCCTAACACGTC
GCCATTGGCTGACAAGGAAGAAAAATTTTCCGGTTTGGCAGTCACAAGTGGTACGGCGCTGGAAAGAGAGCAAGAAAAG
CACGCTCTTGTGCGACTGCTACAGTCGCTGGCCGCGCTTTGTCCGTTCGTGAAACCCGGCAGGCCAAGGAGCACGAGGTT
GCCGGCGCCAACAAGGCTGAGCACCTCAAAACTACTCCCCGCCTGCCGAAGGGAATTGTGGTTGGCACTGCATTTCCGC
CATCGCCAACCGGATGGTGAATTCCAAATTTGAAACCACCCTTCCCGAAAGAGTGAGACCTCCAGATGACTGGGCTACTG
ACGAGGATCTTGTGAATGCCATCCAAATCCTCAGACTCCCTGCGGCCTTAGACAGGAACGGTGCTTGTACTAGCGCCAAG
TACGTACTTAAGCTGGAAGGTGAGCATTGGACTGTCACTGTGACCCCTGGGATGTCCCCTTCTTTGCTCCCTCTTGAATG
TGTTCAGGGCTGTTGTGGGCACAAGGGCGGTCTTGGTTCCCCAGATGCAGTCGAGGTCTCCGGATTTGACCCTGCCTGCC
TTGACCGGCTGGCTGAGGTGATGCACCTGCCTAGCAGTGCTATCCCAGCCGCTCTGGCCGAAATGTCTGGCGATTCCGAT
CGTTCGGCTTCTCCGGTCACCACCGTGTGGACTGTTTCGCAGTTCTTTGCCCGTCACAGCGGAGGGAATCACCCTGACCA
AGTGCGCTTAGGGAAAATTATCAGCCTTTGTCAGGTGATTGAGGACTGCTGCTGTTCCCAGAACAAAACCAACCGGGTCA
CCCCGGAGGAGGTCGCAGCAAAGATTGACCTGTACCTCCGTGGTGCAACAAATCTTGAAGAATGCTTGGCCAGGCTTGAG
AAAGCGCGCCCGCCACGCGTAATCGACACCTCCTTTGATTGGGATGTTGTGCTCCCTGGGGTTGAGGCGGCAACCCAGAC
GATCAAGCTGCCCCAGGTCAACCAGTGTCGTGCTCTGGTCCCTGTTGTGACTCAAAAGTCCTTGTGTGAGTTTGTGATGA
TGCCTCACACGCCTGCACCTTCCGTAGGTGCGGAGAGCGACCTTACCATTGGCTCAGTTGCTACTGAAGATGTTCCACGC
ATCCTCGAGAAAATAGAAAATGTCGGCGAGATGGCCAACCAGGGACCCTTGGCCTTCTCCGAGGATAAACCGGTAGATGA
CCAACTTGTCAACGACCCCCGGATATCGTCGCGGAGGCCTGACGAGAGCACATCAGCTCCGTCCGCAGGCACAGGTGGCG
CCGGCTCTTTTACCGATTTGCCGCCTTCAGATGGCGCGGATGCGGACGGGGGGGGGCCGTTTCGGACGGTAAAAAGAAAA
GCTGAAAGGCTCTTTGACCAACTGAGCCGTCAGGTTTTTGACCTCGTCTCCCATCTCCCTGTTTTCTTCTCACGCCTTTT
CTACCCTGGCGGTGGTTATTCTCCGGGTGATTGGGGTTTTGCAGCTTTTACTCTATTGTGCCTCTTTTTATGTTACAGTT
ACCCAGCCTTTGGTATTGCTCCCCTCTTGGGTGTGTTTTCTGGGTCTTCTCGGCGCGTTCGAATGGGGGTTTTTGGCTGC
TGGTTGGCTTTTGCTGTTGGTCTGTTCAAGCCTGTGTCCGACCCAGTCGGCGCTGCTTGTGAGTTTGACTCGCCAGAGTG
TAGAAACATCCTTCATTCTTTTGAGCTTCTCAAACCTTGGGACCCTGTTCGCAGCCTTGTTGTGGGCCCCGTCGGTCTCG
GTCTTGCCATTCTTGGCAGGTTACTGGGCGGGGCACGCTGCATCTGGCACTTTTTGCTTAGGCTTGGCATTGTTGCAGAC
TGTATCTTGGCTGGAGCTTACGTGCTTTCTCAAGGTAGGTGTAAAAAGTGCTGGGGATCTTGTATAAGAACTGCTCCCAA
TGAGGTCGCTTTTAACGTGTTTCCTTTCACACGTGCGACCAGGTCGTCACTTATCGACCTGTGCGATCGGTTTTGTGCGC
CAAAAGGAATGGACCCCATTTTTCTCGCCACTGGGTGGCGCGGGTGCTGGGCCGGCCGAAGCCCCATTGAGCAACCCTCT
GAAAAACCCATCGCGTTTGCCCAGTTGGATGAAAAGAAGATTACGGCTAGGACTGTGGTCGCCCAGCCTTATGACCCCAA
CCAAGCCGTAAAGTGCTTGCGGGTATTGCAGGCGGGTGGGGCGATGGTGGCTAAGGCGGTCCCAAAAGTGGTCAAGGTTT
CCGCTGTTCCATTCCGAGCCCCCTTCTTTCCCACTGGAGTGAAAGTTGACCCTGATTGCAGGGTCGTGGTTGACCCTGAC
ACTTTCACTGCAGCTCTCCGGTCTGGCTACTCCACCACAAACCTCGTCCTTGGTGTGGGGACTTTGCCCAGCTGAATGG
ATTAAAAAATCAGGCAAATTTCCAAGCCTTCAGGGGGAGGCCCACATCTCATGGCTGCCCTGCATGTTGCCTGCTCGATGG
CTCTGCACATGCTTGCTGGGATTTATGTGACTGCGGTGGGTTCTTGCGGCACCGGCACCAACGACCCGTGGTGCGCTAAC
```

Fig. 1M-2

```
CCGTTTGCCGTCCCTGGCTACGGACCTGGCTCTCTCTGCACGTCCAGATTGTGCATTTCCCAACACGGCCTTACCCTGCC
CTTGACAGCACTTGTGGCGGGATTCGGTATTCAAGAAATTGCCTTGGTCGTTTTGATTTTTGTTTCCATCGGAGGCATGG
CTCATAGGTTGAGCTGTAAGGCTGACATGCTGTGTGTCTTGCTTGCAATTGCCAGCTATGTTTGGGTACCTCTTACCTGG
TTGCTTTGTGTGTTTCCTTGCTGGTTGCGCTGTTTTTCTTTGCACCCCCTCACCATCCTATGGTTGGTGTTTTTCTTGAT
TTCTGTGAATATGCCTTCAGGAATCTTGGCCATGGTGTTGTTGGTTTCTCTTTGGCTTCTTGGTCGTTATACTAATGTTG
CTGGCCTTGTCACCCCCTACGACATTCATCATTACACCAGTGGCCCCCGCGGTGTTGCCGCCTTGGCTACCGCACCAGAT
GGGACCTACTTGGCCGCTGTCCGCCGCGCTGCGTTGACTGGCCGCACCATGCTGTTTACCCCGTCCCAGCTTGGGTCTCT
TCTTGAGGGTGCTTTCAGAACTCGAAAGCCCTCACTGAACACCGTCAATGTGATCGGGTCCTCCATGGGCTCTGGCGGGG
TGTTTACCATCGACGGGAAAGTCAAGTGCGTAACTGCCGCACATGTCCTTACGGGCAATTCAGCTCGGGTTTCCGGGGTC
GGCTTCAATCAAATGCTTGACTTTGACGTAAAGGGAGATTTCGCTATAGCTGATTGCCCGAATTGGCAAGGGGCTGCCCC
CAAGACCCAATTCTGCACGGATGGATGGACTGGCCGTGCCTATTGGCTAACATCCTCTGGCGTCGAACCCGGCGTCATTG
GAAAAGGATTCGCCTTCTGCTTCACCGCATGTGGCGATTCCGGGTCCCAGTGATCACCGAGGCCGGTGAGCTTGTCGGC
GTTCACACGGGATCGAATAAACAAGGGGGGGGCATTGTTACGCGCCCTCAGGCCAGTTTTGTAATGTGGCACCCATCAA
GCTAAGCGAATTAAGTGAATTCTTTGCTGGGCCTAAGGTCCCGCTCGGTGATGTGAAGGTCGGCAGCCACATAATTAAAG
ACATAAGCGAGGTGCCTTCAGATCTTTGTGCCTTGCTTGCTGCCAAACCTGAACTGGAAGGAGGCCTCTCCACCGTCCAA
CTTCTTTGTGTGTTTTTTCTCCTGTGGAGAATGATGGGACATGCCTGGACGCCCTTGGTTGCTGTGAGTTTCTTTATTTT
GAATGAGGTTCTCCCAGCCGTCCTGGTCCGGAGTGTTTTCTCCTTTGGAATGTTTGTGCTATCCTGGCTCACGCCATGGT
CTGCGCAAGTTCTGATGATCAGGCTTCTGACAGCAGCTCTTAACAGGAACAGATGGTCACTTGCCTTTTTCAGCCTCGGT
GCAGTGACCGGTTTTGTCGCAGATCTTGCGGCCACTCAGGGGCATCCGTTGCAGGCAGTGATGAATTTGAGCACCTATGC
ATTCCTGCCTCGGATGATGGTTGTGACCTCACCAGTCCCAGTGATCACGTGTGGTGTCGTGCACCTACTTGCCATCATTT
TGTACTTGTTTAAGTACCGTGGCCTGCACCATATCCTTGTTGGCGATGGAGTGTTCTCTGCGGCTTTCTTCTTGAGATAC
TTTGCCGAGGGAAAGTTGAGGGAAGGGGTGTCGCAATCCTGCGGAATGAATCATGAGTCTCTGACTGGTGCCCTCGCTAT
GAGACTCAATGACGAGGACTTGGATTTCCTTATGAAATGGACTGATTTTAAGTGCTTTGTTTCTGCGTCCAACATGAGGA
ATGCAGCGGGTCAATTTATCGAGGCTGCCTATGCTAAAGCACTTAGAGTAGAACTGGCCCAGTTGGTGCAGGTTGATAAA
GTTCGAGGTACTTTGGCCAAACTTGAAGCTTTTGCTGATACCGTGGCACCTCAACTCTCGCCCGGTGACATTGTTGTCGC
TCTCGGCCACACGCCTGTTGGCAGTATCTTCGACCTAAAGGTTGGTAGCACCAAGCATACCCTCCAAGCCATTGAGACCA
GAGTCCTTGCTGGGTCCAAAATGACCGTGGCGCGCGTCGTCGACCCGACCCCCACGCCCCCACCCGCACCCGTGCCCATC
CCCCTCCCACCGAAAGTTCTGGAGAATGGCCCCAACGCTTGGGGGGATGAGGACCGTTTGAATAAGAAGAAGAGGCGCAG
GATGGAAGCCCTCGGCATCTATGTTATGGGCGGGAAAAAATACCAGAAATTTTGGGACAAGAATTCCGGTGATGTGTTTT
ATGAGGAGGTCCATAATAACACAGATGAGTGGGAGTGTCTCAGAGTTGGCGACCCTGCCGACTTTGACCCTGAGAAGGGA
ACTCTGTGTGGACATGTCACCATTGAAAACAAGGCTTACCATGTTTACACCTCCCCATCTGGTAAGAAGTTCTTGGTCCC
CGTCAACCCAGAGAATGGAAGAGTCCAATGGGAAGCTGCAAAGCTTTCCGTGGAGCAGGCCCTAGGTATGATGAATGTCG
ACGGCGAACTGACTGCCAAAGAACTGGAGAAACTGAAAAGAATAATTGACAAACTCCAGGGCCTGACTAAGGAGCAGTGT
TTAAACTGCTAGCCGCCAGCGACTTGACCCGCTGTGGTCGCGGCGGCTTGGTTGTTACTGAAACAGCGGTAAAAATAGTC
AAATTTCACAACCGGACCTTCACCCTGGGACCTGTGAATTTAAAAGTGGCCAGTGAGGTTGAGCTAAAAGACGCGGTTGA
GCACAACCAACACCCGGTTGCGAGACCGATCGATGGTGGAGTTGTGCTCCTGCGTTCCGCGGTTCCTTCGCTTATAGACG
TCTTGATCTCCGGTGCTGATGCATCTCCCAAGTTACTTGCCCATCACGGGCCGGGAAACACTGGGATCGATGGCACGCTC
TGGGATTTTGAGTCCGAAGCCACTAAAGAGGAAGTCGCACTCAGTGCGCAAATAATACAGGCTTGTGACATTAGGCGCGG
CGACGCTCCTGAAATTGGTCTCCCTTACAAGCTGTACCCTGTTAGGGGTAACCCTGAGCGGGTGAAAGGAGTTCTGCAGA
ATACAAGGTTTGGAGACATACCTTACAAAACCCCAGTGACACTGGAAGCCCAGTGCACGCGGCTGCCTGCCTTACGCCC
AACGCCACTCCGGTGACTGATGGGCGCTCCGTCTTGGCCACGACCATGCCCCCGGGTTTGAGTTATATGTACCGACCAT
ACCAGCGTCTGTCCTTGATTACCTTGACTCTAGGCCTGACTGCCCTAAACAGCTGACAGAGCACGGCTGCGAAGATGCCG
CACTGAAAGACCTCTCTAAATATGACTTGTCCACCCAAGGCTTTGTTTTACCTGGAGTTCTTCGCCTTGTGCGGAAATAC
CTGTTTGCCCATGTAGGTAAGTGCCCACCCGTTCATCGGCCTTCTACTTACCCTGCTAAGAATTCTATGGCTGGAATAAA
TGGGAACAGGTTCCCAACCAAGGACATTCAGAGCGTCCCTGAAATCGACGTTCTGTGCGCACAGGCTGTGCGAGAAAACT
GGCAAACTGTCACCCCTTGTACTCTTAAGAAACAGTATTGCGGGAAGAAGAAGACTAGGACCATACTCGGCACCAATAAC
TTCATCGCACTAGCCCACCGAGCAGTGTTGAGTGGTGTTACCCAGGGCTTCATGAAAAAGGCGTTTAACTCGCCCATCGC
CCTCGGAAAGAACAAGTTTAAGGAGCTACAGACTCCGGTCCTGGGCAGGTGCCTTGAAGCTGATCTCGCATCCTGCGATC
GATCCACGCCTGCAATTGTCCGCTGGTTTGCCGCCAACCTTCTTTATGAACTTGCCTGTGCTGAAGAGCATCTACCGTCG
```

*Fig. 1M-3*

```
TACGTGCTGAACTGCTGCCACGACTTACTGGTCACGCAGTCCGGCGCAGTGACTAAGAGAGGTGGCCTGTCGTCTGGCGA
CCCGATCACCTCTGTGTCTAACACCATTTATAGTTTGGTGATCTATGCACAGCATATGGTGCTTAGTTACTTCAAAAGTG
GTCACCCCCATGGCCTTCTGTTCTTACAAGACCAGCTAAAGTTTGAGGACATGCTCAAGGTTCAACCCCTGATCGTCTAT
TCGGACGACCTCGTGCTGTATGCCGAGTCTCCCACCATGCCAAACTATCACTGGTGGGTTGAACATCTGAATTTGATGCT
GGGGTTTCAGACGGACCCAAAGAAGACAGCAATAACAGACTCGCCATCATTTCTAGGCTGTAGAATAATAAATGGGCGCC
AGCTAGTCCCCAACCGTGACAGGATCCTCGCGGCCCTCGCCTATCACATGAAGGCGAGTAATGTTTCTGAATACTATGCC
TCAGCGGCTGCAATACTCATGGACAGCTGTGCTTGTTTGGAGTATGATCCTGAATGGTTTGAAGAACTTGTAGTTGGAAT
AGCGCAGTGCGCCCGCAAGGACGGCTACAGCTTTCCCGGCACGCCGTTCTTCATGTCCATGTGGGAAAAACTCAGGTCCA
ATTATGAGGGGAAGAAGTCGAGAGTGTGCGGGTACTGCGGGGCCCCGGCCCCGTACGCTACTGCCTGTGGCCTCGACGTC
TGCATTTACCACACCCACTTCCACCAGCATTGTCCAGTCACAATCTGGTGTGGCCATCCAGCGGGTTCTGGTTCTTGTAG
TGAGTGCAAATCCCCTGTAGGGAAAGGCACAAGCCCTTTAGACGAGGTGCTGGAACAAGTCCCGTATAAGCCCCACGGA
CCGTTATCATGCATGTGGAGCAGGGTCTCACCCCCCTTGATCCAGGTAGATACCAAACTCGCCGCGGATTAGTCTCTGTC
AGGCGTGGAATTAGGGGAAATGAAGTTGGACTACCAGACGGTGATTATGCTAGCACCGCCTTGCTCCCTACCTGCAAAGA
GATCAACATGGTCGCTGTCGCTTCCAATGTATTGCGCAGCAGGTTCATCATCGGCCCACCCGGTGCTGGGAAAACATACT
GGCTCCTTCAACAGGTCCAGGATGGTGATGTTATTTACACACCAACTCACCAGACCATGCTTGACATGATTAGGGCTTTG
GGGACGTGCCGGTTCAACGTCCCGGCAGGCACAACGCTGCAATTCCCCGTCCCCTCCCGCACCGGTCCGTGGGTTCGCAT
CCTAGCCGGCGGTTGGTGTCCTGGCAAGAATTCCTTCCTAGATGAAGCAGCGTATTGCAATCACCTTGATGTTTTGAGGC
TTCTTAGTAAAACTACCCTCACCTGTCTAGGAGACTTCAAGCAACTCCACCCAGTGGGTTTTGATTCTCATTGCTATGTT
TTTGACATCATGCCTCAAACTCAACTGAAGACCATCTGGAGGTTTGGACAGAATATCTGTGATGCCATTCAGCCAGATTA
CAGGGACAAACTCATGTCCATGGTCAACACAACCCGTGTGACCTACGTGGAAAAACCTGTCAGGTATGGGCAGGTCCTCA
CCCCCTACCACAGGGACCGAGAGGACGACGCCATCACTATTGACTCCAGTCAAGGCGCCACATTCGATGTGGTTACATTG
CATTTGCCCACTAAAGATTCACTCAACAGGCAAAGAGCCCTTGTTGCTATCACCAGGGCAAGACACGCTATCTTTGTGTA
TGACCCACACAGGCAGCTGCAGGGCTTGTTTGATCTTCCTGCAAAAGGCACGCCCGTCAACCTCGCAGTGCACTGCGACG
GGCAGCTGATCGTGCTGGATAGAAATAACAAAGAATGCACGGTTGCTCAGGCTCTAGGCAACGGGGATAAATTTAGGGCC
ACAGACAAGCGTGTTGTAGATTCTCTCCGCGCCATTTGTGCTGATCTAGAAGGGTCGAGCTCTCCGCTCCCAAGGTCGC
ACACAACTTGGGATTTTATTTCTCACCTGATTTAACACAGTTTGCTAAACTCCCAGTAGAACTTGCACCTCACTGGCCCG
TGGTGTCAACCCAGAACAATGAAAAGTGGCCGGATCGGCTGGTTGCCAGCCTTCGCCCTATCCATAAATACAGCCGCGCG
TGCATCGGTGCCGGCTATATGGTGGGCCCTTCGGTGTTTCTAGGCACTCCTGGGGTCGTGTCATACTATCTCACAAAATT
TGTTAAGGGCGGGGCTCAAGTGCTTCCGGAGACGGTTTTCAGCACCGGCCGAATTGAGGTAGACTGCCGGGAATATCTTG
ATGATCGGGAGCGAGAAGTTGCTGCGTCCCTCCCACACGCTTTCATTGGCGACGTCAAAGGCACTACCGTTGGAGGATGT
CATCATGTCACCTCCAGATACCTCCCGCGCGTCCTTCCCAAGGAATCAGTTGCGGTAGTCGGGGTTTCAAGCCCGGAAA
AGCCGCGAAAGCATTGTGCACACTGACAGATGTGTACCTCCCAGATCTTGAAGCCTATCTCCACCCGGAGACCCAGTCCA
AGTGCTGGAAAATGATGTTGGACTTCAAAGAAGTTCGACTAATGGTCTGGAAAGACAAAACAGCCTATTTCCAACTTGAA
GGTCGCTATTTCACCTGGTATCAGCTTGCCAGCTATGCCTCGTACATCCGTGTTCCCGTCAACTCTACGGTGTACTTGGA
CCCCCTGCATGGGCCCCGCCCTTTGCAACAGGAGAGTCGTCGGGTCCACCCACTGGGGGGCTGACCTCGCGGTCACCCCTT
ATGATTACGGCGCTAAAATTATCCTGTCTAGCGCGTACCATGGTGAAATGCCCCCCGGATACAAAATTCTGGCGTGCGCG
GAGTTCTCGTTGGATGACCCAGTTAAGTACAAACATACCTGGGGGTTTGAATCGGATACAGCGTATCTGTATGAGTTCAC
CGGAAACGGTGAGGACTGGGAGGATTACAATGATGCGTTTCGTGCGCGCCAGGAAGGGAAAATTTATAAGGCCACTGCCA
CCAGCTTGAAGTTTTATTTTCCCCCGGGCCCTGTCATTGAACCAACTTTAGGCCTGAATTGAAATGAAATGGGGTCCATG
CAAAGCCTTTTTGACAAAATTGGCCAACTTTTTGTGGATGCTTTCACGGAGTTCTTGGTGTCCATTGTTGATATCATTAT
ATTTTTGGCCATTTTGTTTGGCTTCACCATCGCCGGTTGGCTGGTGGTCTTTTGCATCAGATTGGTTTGCTCCGCGATAC
TCCGTACGCGCCCTGCCATTCACTCTGAGCAATTACAGAAGATCTTATGAGGCCTTTCTTTCCCAGTGCCAAGTGGACAT
TCCCACCTGGGGAACTAAACATCCTTTGGGGATGCTTTGGCACCATAAGGTGTCAACCCTGATTGATGAAATGGTGTCGC
GTCGAATGTACCGCATCATGGAAAAAGCAGGGCAGGCTGCCTGGAAACAGGTGGTGAGCGAGGCTACGCTGTCTCGCATT
AGTAGTTTGGATGTGGTGGCTCATTTTCAGCATCTAGCCGCCATTGAAGCCGAGACCTGTAAATATTTGGCCTCCCGGCT
GCCCATGCTACACAACCTGCGCATGACAGGGTCAAATGTAACCATAGTGTATAATAGCACTTTGAATCAGGTGTTTGCTA
TTTTTTCCAACCCCTGGTTCCCGGCCAAAGCTTCATGATTTTCAGCAATGGTTAATAGCTGTACATTCCTCCATATTTTCC
TCTGTTGCAGCTTCTTGTACTCTTTTTGTTGTGCTGTGGTTGCGGGTTCCAATACTACGTACTGTTTTTGGTTTCCGCTG
GTTAGGGGCAATTTTTCTTTCGAACTCACAGTGAATTACACGGTGTGTCCACCTTGCCTCACCCGGCAAGCAGCCACAGA
```

*Fig. 1M-4*

```
GATCTACGAACCCGGTAGGTCTCTTTGGTGCAGGATAGGGTATGACCGATGTGGGGAGGACGATCATGACGAGCTAGGGT
TTATGATACCGCCTGGCCTCTCCAGCGAAGGCCACTTGACTGGTGTTTACGCCTGGTTGGCGTTCTTGTCCTTCAGCTAC
ACGGCCCAGTTCCATCCCGAGATATTCGGGATAGGGAATGTGAGTCGAGTTTATGTTGACATCAAACATCAACTCATCTG
CGCCGAACATGACGGGCAGAACACCACCTTGCCTCGTCATGACAACATTTCAGCCGTGTTTCAGACCTATTACCAACATC
AAGTCGACGGCGGCAATTGGTTTCACCTAGAATGGCTTCGTCCCTTCTTTTCCTCGTGGTTGGTTTTAAATGTCTCTTGG
TTTCTCAGGCGTTCGCCTGCAAACCATGTTTCAGTTCGAGTCTTGCAGATATTAAGACCAACACCACCGCAGCGGCAAGC
TTTGCTGTCCTCCAAGACATCAGTTGCCTTAGGCATCGCGACTCGGCCTCTGAGGCGATTCGCAAAATCCCTCAGTGCCG
TACGGCGATAGGGACACCCGTGTATGTTACCATCACAGCCAATGTGACAGATGAGAATTATTTACATTCTTCTGATCTCC
TCATGCTTTCTTCTTGCCTTTTCTATGCTTCTGAGATGAGTGAAAAGGGATTTAAGGTGGTATTTGGCAATGTGTCAGGC
ATCGTGGCTGTGTGTGTCAATTTTACCAGCTACGTCCAACATGTCAAGGAGTTTACCCAACGCTCCCTGGTGGTCGACCA
TGTGCGGTTGCTCCATTTCATGACACCTGAGACCATGAGGTGGGCAACTGTTTTAGCCTGTCTTTTTGCCATTCTGTTGG
CAATTTGAATGTTTAAGTATGTTGGAGAAATGCTTGACCGCGGGCTGTTGCTCGCGATTGCTTTCTTTGTGGTGTATCGT
GCCGTTCTGTTTTGCTGTGCTCGCCAACGCCAGCAACGACAGCAGCTCCCATCTACAGCTGATTTACAACTTGACGCTAT
GTGAGCTGAATGGCACAGATTGGCTAGCTAACAAATTTGATTGGGCAGTGGAGAGTTTTGTCATCTTTCCCGTTTTGACT
CACATTGTCTCCTATGGTGCCCTCACTACCAGCCATTTCCTTGACACAGTCGCTTTAGTCACTGTGTCTACCGCCGGGTT
TGTTCACGGGCGGTATGTCCTAAGTAGCATCTACGCGGTCTGTGCCCTGGCTGCGTTGACTTGCTTCGTCATTAGGTTTG
CAAAGAATTGCATGTCCTGGCGCTACGCGTGTACCAGATATACCAACTTTCTTCTGGACACTAAGGGCAGACTCTATCGT
TGGCGGTCGCCTGTCATCATAGAGAAAAGGGGCAAAGTTGAGGTCGAAGGTCATCTGATCGACCTCAAAAGAGTTGTGCT
TGATGGCTCCGTGGCAACCCCTATAACCAGAGTTTCAGCGGAACAATGGGGTCGTCCTTAGATGACTTCTGTCACGATAG
CACGGCTCCACAAAAGGTGCTTTTGGCGTTTTCTATTACCTACACGCCAGTGATGATATATGCCCTAAAGGTGAGTCGCG
GCCGACTGCTAGGGCTTCTGCACCTTTTGATCTTCCTGAATTGTGCTTTCACCTTCGGGTACATGACTTTCGCGCACTTT
CAGAGTACAAATAAGGTCGCGCTCACTATGGGAGCAGTAGTTGCACTCCTTTGGGGGGTGTACTCAGCCATAGAAACCTG
GAAATTCATCACCTCCAGATGCCGTTTGTGCTTGCTAGGCCGCAAGTACATTCTGGCCCCTGCCCACCACGTTGAAAGTG
CCGCAGGCTTTCATCCGATTGCGGCAAATGATAACCACGCATTTGTCGTCCGGCGTCCCGGCTCCACTACGGTCAACGGC
ACATTGGTGCCCGGGTTAAAAAGCCTCGTGTTGGGTGGCAGAAAAGCTGTTAAACAGGGAGTGGTAAACCTTGTCAAATA
TGCCAAATAACAACGGCAAGCAGCAGAAGAGAAAGAAGGGGGATGGCCAGCCAGTCAATCAGCTGTGCCAGATGCTGGGT
AAGATCATCGCTCAGCAAAACCAGTCCAGAGGCAAGGGACCGGGAAAGAAAAATAAGAAGAAAAACCCGGAGAAGCCCCA
TTTTCCTCTAGCGACTGAAGATGATGTCAGACATCACTTTACCCCTAGTGAGCGGCAATTGTGTCTGTCGTCAATCCAGA
CCGCCTTTAATCAAGGCGCTGGGACTTGCACCCTGTCAGATTCAGGGAGGATAAGTTACACTGTGGAGTTTAGTTTGCCT
ACGCATCATACTGTGCGCCTGATCCGCGTCACAGCATCACCCTCAGCATGATGGGCTGGCATTCTTGAGGCATCTCAGTG
TTTGAATTGGAAGAATGTGTGGTGAATGGCACTGATTGACATTGTGCCTCTAAGTCACCTATTCAATTAGGGCGACCGTG
TGGGGGTGAGATTTAATTGGCGAGAACCATGCGGCCGAAATTAAAAAAAA
```

| | wt VR2332 | Sw612 | VR-HN | VR-V5-2 | VR-V5G7475A | VR-V6 | VR-V6G7475A | Mock |
|---|---|---|---|---|---|---|---|---|
| Viral Titer | $2.5 \times 10^5$ | $9.8 \times 10^4$ | $1.5 \times 10^4$

| | wt VR2332 | Sw612 | VR-HN | VR-V5 | VR-V5G7475A | VR-V6 | VR-V6G7475A | Mock |
|---|---|---|---|---|---|---|---|---|
| Viral Titer | $8.12 \times 10^4$ | $2.0 \times 10^5$ | $5.5 \times 10^3$ | $5.0 \times 10^3$ | $2.5 \times 10^4$ | $4.4 \times 10^3$ | $1.9 \times 10^4$ | |

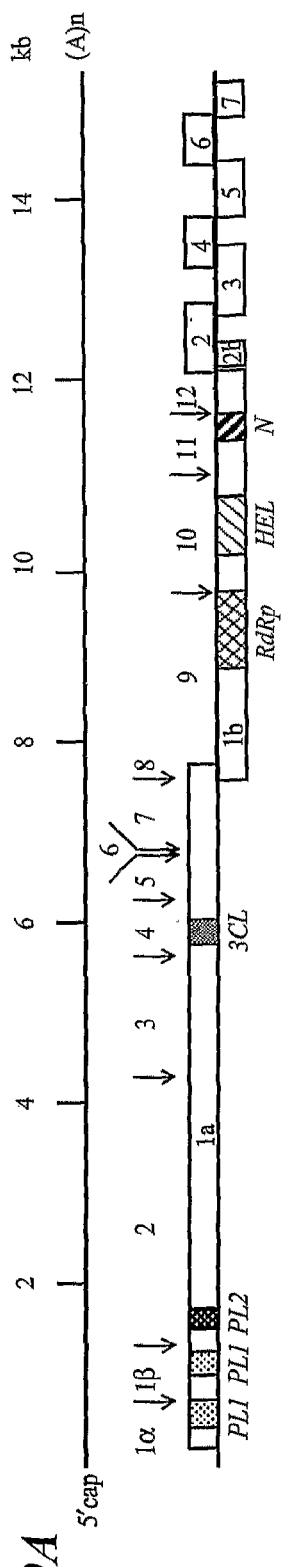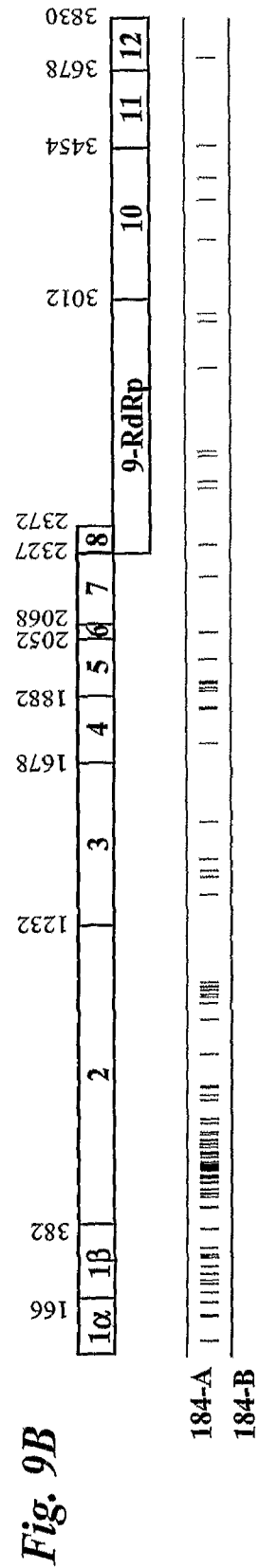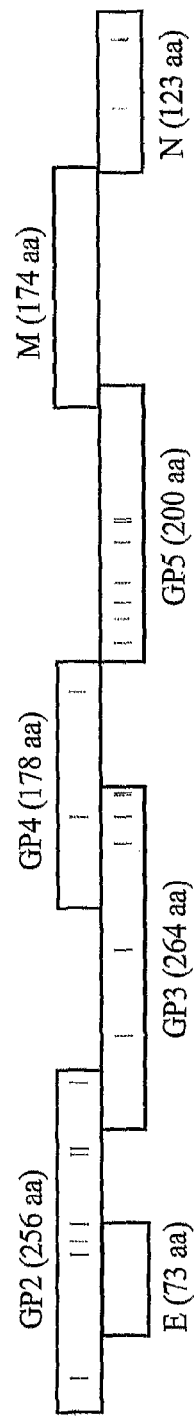
Fig. 9A
Fig. 9B
Fig. 9C

| | | |
|---|---|---|
| EuroPRRSV | IVDDRGGVHRWMKSPIVVEKLGKADIDGSLVTIKHVVLEGVKAQPLTRTSAEQW-EA | 201 |
| Lelystad | IVDDRGRVHRWMKSPIVVEKLGKAEVDGNIVTIKHVVLEGVKAQPLTRTSAEQW-EA | 201 |
| MN184A | LLDTKGRLYRWRSPVIIEKRGKIEVGGDLIDLKRVVLDGSAATPVTKVSAEQWGRP | 200 |
| MN184B | LLDTKGRLYRWRSPVIIEKRGKIEVGGDLIDLKRVVLDGSAATPVTKVSAEQWGRP | 200 |
| 98-3298 | LLDTKGRLYRWRSPVIIEKGGKVEVEGHLIDLKRVVLDGSAATPVTKVSAERWGRP | 200 |
| 98-3403 | LLDTKGRLYRWRSPVIIEKGGKVEVEGHLIDLKRVVLDGSAATPVTKVSAERWGRP | 200 |
| 99-3584 | LLDTKGRLYRWRSPVIIEKGGKVEVEGHLIDLKRVVLDGSAATPVTKVSAERWGRP | 200 |
| IAF-93-653 | LLDTKGKLYRWRSPVIIERQGKVEVEGHLIDLKRVVLDGSAATPVTKVSAEQWCRP | 200 |
| IAF-Klop | LLDSKGKLYRWRSPVIIEKGGKVEVDGHLIDLKRVVLDGSAATPVTKVSAEQWGRP | 200 |
| Ingelvac | LLDTKGGLYRWRSPVIIEKRGKVEVEGHLIDLKRVVLDGSVATPITRVSAEQWGRP | 200 |
| BJ-4 | LLDTKGGLYRWRSPVIIEKRGKVEVEGHLIDLKRVVLDGSVATPITRVSAEQWGRP | 200 |
| VR-2332 | LLDTKGRLYRWRSPVIIEKRGKVEVEGHLIDLKRVVLDGSVATPITRVSAEQWGRP | 200 |
| PL97-1 | LLDTKGRLYRWRSPVIIEKRGKVEVEGHLIDLKRVVLDGSVATPITRVSAEQWGRP | 200 |
| 16244B | LLDTKGRLYRWRSPVIIEKRGKVEVEGHLIDLKRVVLDGSVATPITRVSAEQWGRP | 200 |
| HN1 | LLDTKGRLYRWRSPVIIEKRGKVEVEGHLIDLKRVVLDGSVATPITRVSAEQWGRP | 200 |
| PA-8 | LLDTKGRLYRWRSPVIIEKRGKVEVEGHLIDLKRVVLDGSVATPITRVSAEQWGRP | 200 |
| JA142 | LLDTKGRLYRWRSPVIIEKGGKVEVEGHLIDLKRVVLDGSVATPLTRVSAEQWGRL | 200 |
| CH-1 | LLDTKGRLYRWRSPVIVEKGGKVEVEGHLIDLKRVVLDGSVATPLTRVSAEQWGRL | 200 |
| P129 | LLDTKGRLYRWRSPVIIEKGGKVEVEGHLIDLKRVVLDGSVATPLTRVSAEQWGRL | 200 |
| SP | LLDTKGRLYRWRSPVIIEKGGKVEVESHLIDLKRVVLDGSAATPLTRVSAEQWGRP | 200 |
| HB-2 | LLDTKGRLYRWRPPVVEKGGKVEVEGHLIDLKRVVLDGSVATPLTRVSAEQWGRL | 200 |
| HB-1 | LLDTKGKLYRWRSPVIVEKGGKVEVEGHLIDLKRVVLDGSVATPLTRVSAEQWGRL | 200 |

*Intravirion*

Figure 11

| | | |
|---|---|---|
| EuroPRRSV | QACRQPFCPFEEAHSGVYRWKKFVIFSDSPLNGQSR IMWTPKSDDSAALEELPPELERQVE ILIRSFPAHHPVNL | 75 |
| Lelystad | QACRQPFCPFEEAHSSVYRWKKFVVFTDSSLNGRSR MWTPESDDSAALEVLPPELERQVE ILIRSFPAHHPVDL | 75 |
| MN184A | RPKPEDFCPFECAMAXVVDIGHDAVM----FVAEGRVSWAPRGGGKGKFETVPEELRLIAEQLYTSFPPHHVVDM | 71 |
| MN184B | RPKPEDFCPFECAMAAVVDIGHDAVM----FVAEGRVSWAPRGGEKGKFETVPEELXLIAEQLYTSFPPHHLVDM | 71 |
| Ingelvac | RPKPEDFCPFECAMATVVDIGHDAVM----YVAERKISWAPRGGDEVKFEAVPGELKLIANRLRTSFPPHHTVDM | 71 |
| VR-2332 | RPKPEDFCPFECAMATVVDIGHDAVM----YVAERKVSWAPRGGDEVKFEAVPGELKLIANRLRTSFPPHHTVDM | 71 |
| PL97-1 | RPKPEDFCPFECAMATVVDIGHDAVM----YVAERKISWAPRGGDEVKFEAVPGELKLIANRLRTSFPPHHTVDM | 71 |
| HN1 | RPKPEDFCPFECAMATVVDIGHDAVM----YVAERKVSWAPRGGDEVKFEAVPGELKLIADQLRTSFPPHHTVDV | 71 |
| 16244B | RPKPEDFCPFECAMATVVDIGHDAVM----YVAGMKISWAPRGGDEVKFEAVPGELKLIANRLRTSFPPHHTVDM | 71 |
| PA-8 | RPKPEDFCPFECAMATVVDIGHDAVM----YVAEGKISWAPRGGDEVKFEAVPGELKLIANRLRTSFPPHHAVDM | 71 |
| SP | RPKPDDFCPFECAMATVVDIGHDAVM----YVAEEKVSWAPRGGDEVKFEPVPGELKLIANRLRTSFPPHHAVDM | 71 |
| JA142 | RPKPEDFCPFECAMADVVDIGHGAVM----YVAKGKVSWAPRGGDEAKFETVPRELKLIANQLHISFPPHHAVDM | 71 |
| CH-1 | RPKPEDFCPFECAMADVVDIGRDAVM----YVARGKVSWAPRGGDEVKFETVPEELKLIANRLHISFPPHHAVDM | 71 |
| P129 | RPKPEDFCPFECAMADVVDISHDAVM----YVARGKVSWAPRGGDEVKFETVPEELKLIANRLHISFPPYHAVDM | 71 |
| HB-2 | RPKPEDFCPFECAMADVVDIGHGAVM----FVAGGKVSWAPRGGDEVRFETVPEELKLIANRLHISFPPHHLVDM | 71 |
| HB-1 | RPKPEDFCPFECAMADVVDIGRGAVM----YVAGGKVSWAPRGGDEVKFEPVPKELKLVANRLHTSFPPHHVVDM | 71 |

Figure 11 (continued)

| | | | |
|---|---|---|---|
| EuroPRRSV | ADWELTGSPENGFSFNTSHSCGHLVRNSNVEDGKCWLTCFLGQSVEVRCHEEHLANAFGYQTKWGVHGKYLQRRL | 150 |
| Lelystad  | ADWELTESPENGFSFNTSHSCGHLVQNPDVEDGKCWLSCFLGQSVEVRCHEEHLADAFGYQTKWGVHGKYLQRRL | 150 |
| MN184A    | SKFTFT-APECGASMRVERHYGCLPAGT-VPDGNCWWSLFSSLPLEIQYKEIRHATQFGYQTKHGVAGKYLQRRL | 144 |
| MN184B    | SKFTFT-APECGASMRVERQYGCLPAGT-VPDGNCWWSLFSSLPLEVQYKEIRYATQFGYQTKHGVAGKYLQRRL | 144 |
| Ingelvac  | SKFAFT-APGCGVSMRVERQHGCLPADT-VPEGNCWWSLFDLLPLEVQNKEIRHANQFGYQTKHGVSGKYLQRRL | 144 |
| VR-2332   | SKFAFT-APGCGVSMRVERQHGCLPADT-VPEGNCWWSLFDLLPLEVQNKEIRHANQFGYQTKHGVSGKYLQRRL | 144 |
| PL97-1    | SKFAFT-APGCGVSMRVERQHGCLPADT-VPEGNCWWSLFDLLPLEVQNKEIRHANQFGYQTKHGVSGKYLQRRL | 144 |
| HN1       | SKFAFT-APGCGVSMRVERQHGCLPADT-VPEGNCWWSLFDLLPLEVKNKEIRHANQFGYQTKHGVSGKYLQRRL | 144 |
| 16244B    | SKFAFT-ALGCGVSMRVERQHGCLPADT-VPEGNCWWSLFDLLPLEVQDKEIRHANQFGYQTKHGVSGKYLQRRL | 144 |
| PA-8      | SKFAFT-APGCGVSMRVERQHGCLPADT-VPEGNCWWSLFDLLPLEVQNKEIRYANQFGYQTKHGVSGKYLQRRL | 144 |
| SP        | SKFTFT-APGRGVSMRVERQHGCLPADT-VPEGNCWWSLFNLLPLEVQNKEIRHAGQFGYQTKHGVSGKYLQRRL | 144 |
| JA142     | SKFVFI-APGSGVSMRVECPHGCLPADT-VPEGNCWWRLFDSLPLDVQNKEIRRANQFGYQTKHGVAGKYLQRRL | 144 |
| CH-1      | SKFAFI-APGSGVSLRVEYQHGCLPADT-VPEGNCWWRLFDLLPPEVQNKEIRYANQFGYQTKHGVSGKYLQRRL | 144 |
| P129      | SEFAFI-APGSGVSLRVEHQHGCLPADT-VPEGNCWWCLFDLLPPEVQNKEIRRANQFGYQTKHGVSGKYLQRRL | 144 |
| HB-2      | SKFAFI-VPGSGVSLRVEHQHGCLPADI-VPKGNCWWCLFDLLPPGVQNREIRYANQFGYQTKHGVPGKYLQRRL | 144 |
| HB-1      | SKFTFM-TPGSGVSMRVEYQYGCLPADT-VPEGNCWWRLFDLLPPEVQNKEIRHANQFGYQTKHGVPGKYLQRRL | 144 |

Figure 11 (continued)

```
EuroPRRSV  QVRGIRAVDPDGPIHVEALSCSQSWIRHLTLNDDVT-PGFVRLTSIRIVPNTEPTTS---QIFRFGAHKWYG  219
Lelystad   QVRGIRAVDPDGPIHVEALSCPQSWIRHLTLDDDVT-PGFVRLTSLRIVPNTEPTTS---RIFRFGAHKWYG  219
MN184A     QVNGLRAVDSNGPIVIQYFSVKESWIRHVKLAEEFDYPGFEDLLRIRVEPNTLPLSNKDEKIFRFGGCKWYG  217
MN184B     QINGLRAVDSNGPIVIQYFSVKESWIRHVKLAEEFDYPGFEDLLRIRVEPNTXPLSNKDEKIFRFGGCKWYG  217
Ingelvac   QVNGLRAVTDLNGPIVVQYFFVKESWIRHLKLAGEPSYSGFEDLLRIRVEPNTSPLADKEEKIFRFGSHKWYG  217
VR-2332    QVNGLRAVTDLNGPIVVQYFSVKESWIRHLKLAGEPSYSGFEDLLRIRVEPNTSPLADKEEKIFRFGSHKWYG  217
PL97-1     QVNGLRAVTDPNGPIVVQYFSVKESWIRHLKLAGEPSYPGFEDLLRIRVEHNTSPLADKEEKIFRFGSHKWYG  217
HN1        QVNGLRAVTDPNGPIVVQYFSVKESWIRHLRLAGEPSYPGFEDLLRIRVEPNTSPLADKEEKIFRFGSHKWYG  217
16244B     QVNGLRAVTDLNGPIVVQYFSVKESWIRHLKLAGEPSYSGFEDLLRIRVEPNTSPLANTEGKIFRFGSHKWYG  217
PA-8       QVNGLRAVTDSNGPIVVQYFSVKESWIRHLKLAEEPSYPGFEDLLRIRVEPNTSPLADKDEKIFRFGNHKWYG  217
SP         QVNGLRAVTDLNGPIVVQCFSVKESWIRHLKLAEEPSYPGFEDLLRIRVEPNTSPLSDKGGKIFRFGSHKWYG  217
JA142      QANGLRAVTDTDGPIVVQYFSVRESWIRHFRLAEEPSLPGFEDLLRIRVEPNTSPLPGFEDKGKIFRFGSHKWYG  217
CH-1       QVNGLRAVTDTDGPIVVQYFSVEESWIRHFRLAGEPSLPGFEDLLRIRVEPNTSPLAEKDGKIFRFGSHKWYG  217
P129       QVNGLRAVTDTDGPIVVQYFSVRESWIRHFRLAGEPSLPGFEDLLRIRVEPNTSPLGGKGEKIFRFGSHKWYG  217
HB-2       QINGLRAVTDTHGPIVVQYFSVKESWIRHLKLAEEPSLPGFEDLLRIRVESNTSPLADKDEKIFRFGSHKWYG  217
HB-1       QVNGLRAVTDTHGPIVIQYFSVKESWIRHLKPVEEPSLPGFEDLLRIRVEPNTSPLAGKNEKIFRFGSHKWYG  217
```

Figure 12

| | | |
|---|---|---|
| MN184A | GAGKRARRARASAVTAVAGHAPPTRETQQAKKHEAASANKAELLERYSPPAEGNCGWHCISAIANRMVNSKFETA | 75 |
| MN184B | GAGKRARRARASAVTAVAGHAPPTRETQQAKKHEAASANKAELXXYSPPAEGNCGWHCISAIANRMVNSKFETX | 75 |
| VR-2332 | GAGKRARKARSCATATVAGRALSVRETRQAKEHEVAGANKAEHLKHYSPPAEGNCGWHCISAIANRMVNSKFETT | 75 |
| Ingelvac | GAGKRARKARSCATATVAGRALSVRETRQAKEHEVAGANKAEHLKHYSPPAEGNCGWHCISAIANRMVNSKFETT | 75 |
| 01NP1.2 | GAGKRARKARSCATATVAGRALSVRETRQAKEHEVAGANKAEHLKHYSPPAEGNCGWHCISAIANRMVNSKFETT | 75 |
| PL97-1 | GAGKRARKARSCATATVAGRALSVRETRQAKEHEVAGANKAEHLKHYSPPAEGNCGWHCISAIANRMVNSKFETT | 75 |
| SP | GAGKRARKARSSATATVAGRALPVRETRQVEEHEVAGANKAEHLKHYSPPAEGNCGWHCISAIGNRMLNSKFETT | 75 |
| PA-8 | GAGKRARKARSCATATVAGRALSVRETRQAKEHEVAGANKAEHLKHYSPPAEGNCGWHCISAIANRMVNSKFETT | 75 |
| BJ-4 | GAGKRARKARSCATATVAGRALSVRETRQAKEHEVAREHEVAGANKAEHLKHYSPPAEGNCGWHCISAIANRMVNSKFETT | 75 |
| HN1 | GAGKRARKARSCATATVAGRALSVCETRQAKEHEVAGTNKAEHLKHYSPPAEGNCGWHCISAIANRMVNSIFETT | 75 |
| 16244B | GAGKRARKARSCATATVAGRALSVRETRQAKKHEGADANKAEHLEHYSPPAEGNCGWHCISAIANRMVNSFETT | 75 |
| CH-1 | GAGKRARKARSGATTMVAHRALSARETRQAKKHEGVDANNAAHLEHYSPPAEGNCGWHCISAIVNRMVNSFETT | 75 |
| HB-2 | GAGKRARKARSGATTVAHRASSARETRQAKKHEGVDANNAAHLEHYSPPAEGNCGWHCISAIVNRMVNSFETT | 75 |
| P129 | GAGKRARKARSGATATVAHCALPAREAQQAKLEVASANRAEHLKYSPPADGNCGWHCISAITNRMVNSKFETT | 75 |
| JA142 | GAGKRARKARSGMTTVAHRALPAREIQQAKKHEDAGADKAVHLRHYSPPADGNCGWHCISAIANRMVNSKFETT | 75 |
| HB-1 | GAGKRARKARSGATTMVAHRASSAHETRQATKHEGAGANKAEHLKLYSPPAEGNCGWHCISAIVNRMVNSNFETT | 75 |
| SDPRRS-01-08 | AAGKRARARAKR------ATKSGKDSALAPKIAPPVPTCGITTYSPPTDGSCGWHVLAAIVNRMINGDFTSP | 64 |
| EuroPRRSV | AAGKRARARAK Figure 12 (continued)

| | | |
|---|---|---|
| MN184A | LPERVRSPEDWATDEDLVNTIQILRLPAALDRNGACASAKYILKLEGEHWTVSVIPGMXPSLLPLECVQGCCEHK | 150 |
| MN184B | LPERVRXPXDWATDEDLVNXIQILRLPAALDRNGACXSAKYXLKLEGEHWTVXXVXPGMSPSLLPLECVQGCCGHK | 150 |
| VR-2332 | LPERVRPPDDWATDEDLVNAIQILRLPAALDRNGACTSAKYVLKLEGEHWTVTPGMSPSLLPLECVQGCCGHK | 150 |
| Ingelvac | LPERVRPPDDWATDEDLVNTIQILRLPAALDRNGACTSAKYVLKLEGEHWTVTVTPGMSPSLLPLECVQGCCGHK | 150 |
| 01NP1.2 | LPERVRPPDDWATDEDLVNTIQILRLPAALDRNGACTSAKYVLKLEGEHWTVTVTPGMSPSLLPLECVQGCCGHK |

Figure 12 (continued)

| | | |
|---|---|---|
| MN184 | GNLGSPNAVGVFGFDPASLDRLAGVMHLPSSAIPAALAELSGDLDRPTSPAATVWTVSQFYARHSGGEHPDQKCL | 225 |
| MN184B | GGLGSPDAVEVSGFDPACLDRLAXVMHLPSSAIPAALAEXSGDXDRXXSPXXTVWTVSQFYARHSGGXHPDQXXL | 225 |
| VR-2332 | GGLGSPDAVEVSGFDPACLDRLAEVMHLPSSAIPAALAEMSGDSDRSASPVTTVWTVSQFFARHSGGNHPDQVRL | 225 |
| Ingelvac | GGLGSPDAVEVSGFDPACLDRLAEVMHLPSSAIPAALAEMSGDSDRSASPVTTVWTVSQFFARHSGGNHPDQVRL | 225 |
| 01NP1.2 | GGLGSPDAVEVSGFDPACLDRLAEVMHLPSSAIPAALAEMSGDSDRSASPVTTVWTVSQFFARHSGGNHPDQVRL | 225 |
| PL97-1 | GGLGSPDAVEVSGFDPACLDRLAEVMHLPSSAIPAALAEMSGDSDRSASPVTTVWTVSQFFARHSGGNHPDQVRL | 225 |
| SP | GGLGSPDAVEVFGFDPACLDWLAEVMHLPSSNAIPAALAEMSGDSNRPASPVTTVWTVSQFLARHNGGNHPDQIRL | 225 |
| PA-8 | GGLGSPDAVEVSGFDPACLDRLAEVMHLPSSAIPAALAEMSGDSDRSASPVTTVWTVSQFFARHSGGNHPDQVRL | 225 |
| BJ-4 | GGLGSPDAVEVSGFDPACLDRLAEVMHLPSSAIPAALAEVSGDSDRSASPVTTVWTVSQFFARHSGGNHPDQVRL | 225 |
| HN1 | GGLGSPDAVEVSGFDPACLDRLAEVMHLPSSAIPAALAEMSGDSDRSASPVTTVWTVSQFFARHSGGNHPDQVRL | 225 |
| 16244B | GGLGSPDAIEVSGFDPACLDWLAEVMHLPSSAIPAALAEMSGDSDRSASPVTTVWTVSQFFARHSGGNHPDQVRL | 225 |
| CH-1 | GGLGSPDAVEVSGFDPACLDRLAEVMHLPSSAIPAALAEMPVDSNRPASPVTTAWTVSQFYARHRGGNHRDQVCL | 225 |
| HB-2 | GGLGSPDAVEVSGFDPTCLDRLAEVMHLPSSVIPAALAEMSNNSDRPASLVNTAWTVSQFYARHTGGNHPDQVRL | 225 |
| P129 | SGLGFPDVVEVSGFDPACLDRLAEIMHLPSSVIPAALAEMSDDFNRLASPAATVWTVSQFFARHRGGEHPDQVCL | 225 |
| JA142 | SGLGPPDAVEVFGFDPACLDRLAEVMHLPSSVIPAALAEMSGDFNCPASPVTTVWTVSQFFARHRGGEHPDQVRL | 225 |
| HB-1 | GGLGSPDAVEVSGFDPACLDRLLQVMHLPSSTIPAALAELSDDSNRPVSPAAATWTVSQSYARHRGGNHHDQVCL | 225 |
| SDPRRS-01-08 | ----CVAPPYPADGLPKRALEALASAYRLPSDCVSSGIADPPPQEFWTLDKMLTSPSPERSGFSSLYKLLLE | 211 |
| EuroPRRSV | ----CVAPPYPADGLPKRALEAIEALASAYRLPSDCVCSGIADFLANPPPQEFWTLDKMLTSPSPERSGFSSLYNLLLE | 211 |
| Lelystad | ----CVAPPYPADGLPKRALEALASAYRLPSDCVSSGIADFLANPPPQEFWTLDKMLTSPSPERSGFSSLYKLLLE | 211 |

Figure 12 (continued)

```
MN184A          KKIISLCEVIESCCCSXNKTNRVTPEEVTAKIDLYLFGAASLEECLARLEKARPPSVLXTSFDWDVVLPGVGXAA 300
MN184B          XKIISLCXVIEXCCCSXNKTNRVTPEEVXAKIDQYLFGAASLEECLARLEKARPPSVLDTSFDWDVVLPGVGAAA 300
VR-2332         GKIISLCQVIEDCCCSQNKTNRVTPEEVAAKIDLYLYLRGATNLEECLARLEKARPPRVIDTSFDWDVVLPGVEAAT 300
Ingelvac        GKIISLCQVIEDCCCSQNKTNRVTPEEVAAKIDLYLYLRGATNLEECLARLEKARPPRVIDTFFDWDVVLPGVEAAT 300
01NP1.2         GKIISLCQVIEDCCCSQNKTNRVTPEEVAAKIDLYLYLRGATNLEECLARLEKARPPRVIDTFFDWDVVLPGVEAAT 300
PL97-1          GKIISLCQVIEDCCCSQNKTNRVTPEEVAAKIDLYLYLRGATNLEECLARLEKARPPRVIDTFFDWDVVLPGVEAAT 300
SP              GKIISLCQVIEDCCCSQNKTNRVTPEEVAAKIDLYLYLRGATNLEECLARLEKARPPRVMDTSFDWDVVLPGVEAAT 300
PA-8            GKIISLCQVIEDCCCSQNKTNRVTPEEVAAKIDLYLYLRGATNLEECLARLEKARPPRVIDTFFDWDVVLPGVEAAT 300
BJ-4            GKIISLCQVIEDCCCSQNKTNRVTPEEVAAKFDLYLYLRGATNLEECLARLEKARPPRVIDTFFDWDVVLPGVEAAT 300
HN1             GKIISLCQVIEDCCCSQNKTNRVTPEEVAAKIDLYLYLRGATNLEECLARLEKARPPRVIDTSFDWDVVLPGVEAAT 300
16244B          GKIISLCQVIEDCCCSQNKTNRVTPEEVAAKIDLYLYLRGAASLEECLARLEKARPPRVIDTSFDWDVVLPGVEAAT 300
CH-1            GKIISLCQVIEDCCCHQNKTNRATPEEVAAKIDQYLRGATSLEECLIKLERVSPPSAADTSFDWNVLPGVEAAN 300
HB-2            GKIISLCQVIEECCCHQNKTNRATPEEVAAKIDQYLRGATSLEECLIKLERVSPPSAADTSFDWNVVLPGVEAAG 300
P129            GKIINLCQVIEECCCSRNKANRATPEEVAAKVDQYLRGAASIGECLAKLERARPPSAMDTSFDWNVVLPGVETAD 300
JA142           GKIISLCQVVEECCCHQNKTNRATPEEVAARIDQYLHGATSLEECLIRLERVCPPSAADTFFDWNVVLPGVGAST 300
HB-1            GKIISLCQVIEDCCCHQNKTNRATPEEVAAKIDQYLRGATSLEECLAKLERVSPPGAADTSFDWNVLPGVEAAH 300
SDPRRS-01-08    VVPQKCGATEGAFVYAVERMLKDCPSPEQAMALLAKIKVPSSKAPSVSLDECFPAGVPADFEPAFQERPRSPGAA 286
EuroPRRSV       VVPQKCGVTEGAFTYAVERMLMDCPSSEQAMALLAKIKVPSSKAPSVSLDECFPADVPADFEPTSQKRPQSSGAA 286
Lelystad        VVPQKCGATEGAFIYAVERMLKDCPSSKQAMALLAKIKVPSSKAPSVSLDECFPTDVLADFEPASQERPQSSGAA 286
```

Figure 12 (continued)

| | | |
|---|---|---|
| MN184A | QAAKLPLTNQRHALATVVTQRSL---:------------------------------------------------------- | 323 |
| MN184B | QAAKLPLTNQRHALATVVTQRSL--*:------------------------------------------------------- | 323 |
| VR-2332 | QTIKLPQVNQCRALVPVVTQKSLDNNSVPLTAFSLANYYYRAQGDEVRHRERLTAVLSKLEKVVREEYGLMPTEP | 375 |
| Ingelvac | QTIKLPQVNQCRALVPVVTQKSLDNNSVPLTAFSLANYYYRAQGDEVRHRERLTAVLSKLEKVVREEYGLMPTEP | 375 |
| 01NP1.2 | QTIKLPQVNQCRALVPVVTQKSLDNNSVPLTAFSLANYYYRAQGDEVRHRERLTAVLSKLEKVVREEYGLMPTEP | 375 |
| PL97-1 | QTIKLPQVNQCRALVPVVTQKSLDNNSVPLTAFSLANHYYRAQGDEVRHRERLTAVLSNLEKVVREEYGLMPTEP | 375 |
| SP | QTTELPQVNQCRALVPVVTQKSLDNNSVPLTAFSLANYYYRAQGDEVRHRERLTAVLSKLEGVVREEYGLMPTGP | 375 |
| PA-8 | QTIKLPQVNQCRALVPVVTQKSLDNNSVPLTAFSLANYYYRAQGDEVRHRERLTAVLSKLEKVVREEYGLMPTKP | 375 |
| BJ-4 | QTLKLPQVNQCRALVPVVTQKSLDNNSVPLTAFSLANYYYRAQGDEVRHRERLTAVLSNLEKVVREEYGLMPTEP | 375 |
| HN1 | QMIKLPQVNQCRALVPVVTQKSLDNNSVPLTAFSLANYYYRAQGDEVRHRERLTAVLSKLEKVVREEYGLVPTEP | 375 |
| 16244B | QTNKLPQVNQCRALVPVVTQKSLDNNSVPLTAFSLSNCYYPAQGDEVRHRERLNSVLSKLEGVVLEEYGLMPTEP | 375 |
| CH-1 | QTTKQLHVNQCRALVPVVTQEPLDKDSVPLTAFSLSNCYYPAQGDEVRHRERLNSVLSKLEVVLEEYGLMPTGL | 375 |
| HB-2 | PTTEQPHANQCCAPVPVVTQEPLDKDSVPLTAFSLSNCYYPAQGDEVRHRERLNSVLSKLEGVVREEYGLTPTGP | 375 |
| P129 | QTTKQLHVNQCRALVPVVTQEPLDRDSVPLTAFSLSNCYYPAQGDEVRHRERLNSVLSKLEGVVREEYGLTPTGP | 375 |
| JA142 | QTTKQLHVNQCRALVPVVTQEPLDKDSVPLTAFSLSNCYYPAQGDEVRHRERLNSVLSKLEGVVREEYGLTPTEP | 375 |
| HB-1 | QTTEQLHVNPCRTLVPPVTQEPLGKDSVPLTAFSLSNCYYPAQGNEVRHRERLNSVLSKLEEVVLEEYGLMSTGL | 375 |
| SDPRRS-01-08 | VALCSPDAKGFEGTASEEAQESGHKAVHAVPLAEGPNNEQVQVVAGEQLELGGCGLAIGSAQS--- | 349 |
| EuroPRRSV | VALCSSDAEGFEEAAPEGVQERGHKAVHSALFAKGPNNEQVQVVAGEQQKLGGCGLAIGNAQS--- | 349 |
| Lelystad | VVLCSPDAKEFEEAAPEEVQESGHKAVHSALLAEGPNNEQVQVVAGEQLKIGGCGLAVGNAHEG--- | 350 |

Figure 12 (continued)

| | | | |
|---|---|---|---|
| MN184A | ------------------------------------------------------------ | ---------------PKFQPRKAESVKSLPE | 339 |
| MN184B | ------------------------------------------------------------ | ---------------PKFQPRKAESVKSLPE | 339 |
| VR-2332 | GPRPTLPRGLDELKDQMEEDLLKLANAQTTSDMMAWAVEQVDLKTWVKNYPRWTPPPPPKVQPRKTKPVKSLPE | 450 |
| Ingelvac | GPRPTLPRGLDELKDQMEEDLLKLANAQTTSDMMAWAVEQVDLKTWVKNYPRWTPPPPPKVQPRKTKPVKSLPE | 450 |
| 01NP1.2 | GPRPTLPRGLDELKAQMEEDLLKLANAQTTSDMMAWAVEQVDLKTWVKNYPRWTPPPPPKVQPRKTKPVKSLPE | 450 |
| PL97-1 | GPRPTLPRGLDELKDQMEEDLLKLANAQTTSDMMAWAVEQVDLKTWVKNYPRWTPPPPPKVQPRKTKPVKSLPE | 450 |
| SP | GPRPTLPRGLDELKDQMEVDLLKLANAQMTSDMMAWAVEQVDLKTWVKNYPRWTPPPPPIVQPRKTKLVKSLPE | 450 |
| PA-8 | GPRPTLPRGLDELKDQMEEDLLKLANAQTTSDMMAWAAEQVDLKTWVKNYPRWTPPPESPKVQLRKTKPVKSLPK | 450 |
| BJ-4 | GPRPTLPRGLDELKDQMEEDLLKLANAQTTSDMMAWAVEQVDLKTWVKNYPRWTPPPPPKVQPRKTKPVKSLPE | 450 |
| HN1 | GPQPTLPRGLDELKDQMEEDLLKLRLANAQTTSDMMAWAVEQVDLKTWVKNYPRWTPPPPPKVQPRKTKPVKSLPE | 450 |
| 16244B | GPRPVLPSGLDELKDQMEEDLLKLANAQATSEMMAWAAEQVDLKAWVKSYPRWTPPPPPKVQPRKTKPVKSLPE | 450 |
| CH-1 | GPRPVLPSGLDELKDQMEEDLLKLANAQATSEMMALAAEQVDLKAWVKSYPRWIPPPPPEKVQPRMKPVKSLPE | 450 |
| HB-2 | GPRPALPNGLDELKDQMEEDLLKLANAQATSEMMAWAAAEQVDLKAWVKNYPRWTPPPPPRVQPRKTKSVKSLLE | 450 |
| P129 | GPRPALPNGLVELKDQMEEDLLKLVNAQATSEMMAWAAEQVDLKAWVKNYPRWTPPPPPRVQPRKTKSVKSLPG | 450 |
| JA142 | GPRPVLPSGLDELKDQMEEDLLKLANTQATSEMMAWAAEQVDLKAWVKSYPRWTPPPPPRVQPRKTKSVKSLPE | 450 |
| HB-1 | GPRPVLPSGLDELKDQMEEDLLKLANTQATSEMMAWAAEQVDLKAWVKSYPRWTPPPPPRVQPRKTKSVKSLPE | 450 |
| SDPRRS-01-08 | ------------------------------------------------------------ | --- | 349 |
| EuroPRRSV | ------------------------------------------------------------ | --- | 349 |
| Lelystad | ------------------------------------------------------------ | -------ALVSAGLINLVGGNL | 365 |

Figure 12 (continued)

```
MN184A         SRPLPAPRKKIRSRCGSPISLGGNLPDSQEDLAGG-SFDFPTLPELVVSSSESV---------------PV  394
MN184B         SRPLPAPRKKIGSRCGSPISLGGNLPDSREDLAGG-SFDFPTLPELVASSSEPV---------------PV  394
VR-2332        RKPVPAPRRKVGSDCGSPVSLGGDVPNSWEDLAVSSPFDLPTPPEPATPSSELVIVSSPQCIFRPATPLSEPAPI  525
Ingelvac       RKPVPAPRRKVGSDCGSPVSLGGDVPNSWEDLAVSSPFDLPTPPEPATPSSELVIVSSPQCIFRPATPLSEPAPI  525
01NP1.2        RKPVPAPRRKVGSDCGSPVSLGGDVPNSWEDLAVSSPFDLPTPPEPATPSSELVIVSSPQCIFRPATPLSEPAPI  525
PL97-1         RKPVPAPRRKVGSDCGSPVSLGGDVPNSWEDLAVSSPFDLPTPPEPATPSSELVIVSSPQCIFRPATPLSEPAPI  525
SP             SKPVPAPRRKVRSDCDCPTLSGNNLPDSWEDLAVGCPSDLPTSPEPVTPLSEPASVSAPRRSFRPVKFLSEPVPV  525
PA-8           RKPVPAPRRKVGSDCGSPVSLGGDVPNSWEDLAVSSPFDLPTPPEPAIPSSELVIVSSPQCIFRPATPLSEPAPI  525
BJ-4           RKPVPAPRRKVGSDCGSPVSLGGDVPNSWEDLAVSSPFDLPTPPPELATPSSELVIVSSPQCIFRPATPLSEPAPI  525
HN1            RKPVPAPRRKVGSDCGSPVSLGGDVPNSWEDLAVSSPFDLPTPPEPATPSSELVIVSSPQCIFRPATPLSEPAPI  525
16244B         RKPVPAPRRKVGPDCGSPVSLGGDVPNSWEDLAVSSPLDLPTPPEPATLSSELVIVSSPQCIFRPATPLSEPAPI  525
CH-1           NKPVPAPRRKVGSDCGSPILMGDNVPNGWEDFAVGGPLDFPTPSEPMTPLSEPVLMPASQHIPRPVTPLSGPAPV  525
HB-2           NKPVPAPRRKVRSDP------------GKSILAVGGPLNFSTPSELVTPLGEPVLMPASQHVSRPVTPLSEPAPV  513
P129           NKPVPAPRRKVRSDYGSPILMGDNVPNGWEDSTVGGPLDLSAPSEPMTPLSEPVLI------SRPVTSLSVPAPV  519
JA142          NKPVPAPRRKVRSDCGSPILMGDNVPDGREDLTVGGPLDLSTPSEPMTPLSEPALMPALQYISRPVTSLSVLAPV  525
HB-1           DKPVPAPRRKVRSGCGSPVLMGDNVPNGSEDLTVGGPLNFPTPSEPMTPMSEPVLTPALQRVPKLMTPLDGSAPV  525
SDPRRS-01-08   -SSDSKRENMHNSREDEPLDLSHPAPAATTTLVGEQTPDNPGSDASALPIAVRGFVPTGPIILRHVEHCGTESGDS  423
EuroPRRSV      -PLNSMKENMRSSREDEPLDLSQPAPVAATTLEREQTPDNPGSDAGALPATVRESVPTGPMLRHVEHCGTESGDS  423
Lelystad       SPSDPMKENMLNSREDEPLDLSQPAPASTTTLVREQTPDNPGSDAGALPVTVREFVPTGPILCHVEHCGTESGDS  440
```

Figure 12 (continued)

| | | |
|---|---|---|
| MN184A | PAPRRVVSRLVSSPIVSTPVPAPRRGLRQVEGMNLAAVTLACQDEPLDLSASSQTEYEASPLALPLSEDVLAVER | 469 |
| MN184B | PAPRRVVSRLVSSPIVSTPVPAPRRGLRQVEGMNLAAVTLACQDEPLDLSASSQTEYEASPLALPLSEDVLAVER | 469 |
| VR-2332 | PAPRGTVSRPVTPLSEPIPVPAPRRKFQQVKRLSSAAAIPPYQDEPLDLSASSQTEYEASPPAPPQSGGVLGVEG | 600 |
| Ingelvac | PAPRGTVSRPVTPLSEPIPVPAPRRKFQQVKRLSSAAAIPPYQNEPLDLSASSQTEYEASPPAPPQSGGVLGVEG | 600 |
| 01NP1.2 | PAPRGTVSRPVTPLSEPIPVPAPRRKFQQVKRLSSAAAIPPYQNEPLDLSASSQTEYEASPPAPPQSGGVLGVEG | 600 |
| PL97-1 | PAPRGTVSRPVTPLSEPIPVPAPRRKFQQVEKVNPAAATLGCQDEFPDLSASSHTEYEASPIVLPQNGDVLEVEE | 600 |
| SP | PAPRKTVSRPATPLSEPIPVPAPRRKFQQVEKVNPAAATLGCQDEFPDLSASSHTEYEASPIVLPQNGDVLEVEE | 600 |
| PA-8 | PAPRGTVSRPVTPLSEPIPVPAPRRKFQQVKRLSSAAAIPPYQNEPLDLSASSQTEYEASPPAPPQSGGVLGVEG | 600 |
| BJ-4 | PAPRGTVSRPVTPLSEPIPVPAPRRKFQQVKRLSSAAAIPPYQNEPLDLSASSQTEYEASPPAPPQSGGVLGVEG | 600 |
| HN1 | PAPRGTVSRPVTPLSEPIPVPAPRRKFQQVKRLSSAAAIPPYQNEPLDLSASSQTEYEASPPAPPQSGGVLGVEG | 600 |
| 16244B | PAPRGTVSRPVTPLSEPIPVPAPRRKFQQVKRLSSAAAVPLHQNEPLDLSASSQTEYEASPSAPPQSGGVLGVEG | 600 |
| CH-1 | PAPRRTVSRPMTPLSEPIFVSAPRHKFQQVEEANPAATTLTYQDEPLDLSAFSQTECEASPLAPLQNMGILEAGG | 600 |
| HB-2 | PAPRRIVSRPMTPLSEPTFVFAPWRKSQQVEEANPAAATLTCQDEPLDLSASSQTEYEAYPLAPLENIGVILEAGG | 588 |
| P129 | PAPRRAVSRPMTPSSEPIFVSALRHKFQQVEKANLAAAAPMYQDEPLDLSASSQTEYGASPITPPQNVGILEVRG | 594 |
| JA142 | PAPRRTVSRPVTPLSEPIFVSAPRHKFQQVEEANLAATTLTHQDEPLDLSASSQTEYEASPITPLQNMGILEVGG | 600 |
| HB-1 | PAPRRTVSRPMTPLSEPIFLSAPRHKFQQVEEANPATTLTHQNEPLDLSASSQNMSILEAGG | 600 |
| SDPRRS-01-08 | SSPLDLSFAQTLDQPLDLSLAAWPVKATASDPGWVRGRCEPVFLKPRKAFSDGDSALQFGELSESSS----VIEF | 494 |
| EuroPRRSV | SSPLDLSYAQTLDQPLDLSLAVWPVKATASDPGWVHGRREPVFVKPRKAFSDSDSAFQFGKLSESGS----VIEF | 494 |
| Lelystad | SSPLDLSDAQTLDQPLNLSLAAWPVRATASDPGWVHGRREPVFVKPRNAFSDGDSALQFGELSESSS----VIEF | 511 |
| | * | |

Figure 12 (continued)

| | | |
|---|---|---|
| MN184A | REVEEVLSGISGMSDDIRLAPVSSSSSLSSIEITRPKYSAQAIINSGGPCCGHLQEVKEKYLNVMREACDATKLD | 544 |
| MN184B | REVEEVLSGISGMPDDIRLAPVSSSSSLSSIEITRPKYSAQAIINSGGPCCGHLQEVKEKYLNVMREACDATKLD | 544 |
| VR-2332 | HEAEETLSEISDMSGNIKPASVSSSSSLSSVRITRPKYSAQAIIDSGGPCSGHLQEVKETCLSVMREACDATKLD | 675 |
| Ingelvac | HEAEETLSEISDMSGNIKPASVSSSSSLSSVRITRPKYSAQAIIDSGGPCSGHLQEVKETCLSVMREACDATKLD | 675 |
| 01NP1.2 | HEAEETLSEISDMSGNIKPASVSSSSSLSSVRITRPKYSAQAIIDSGGPCSGHLQEVKETCLSVMREACDATKLD | 675 |
| PL97-1 | HEAEETLSEISDMSGNIKPASVSSSSSLSSVRITRPKYSAQAIIDSGGPCSGHLQEVKEACLSVMREACDATKLD | 675 |
| SP | REAEEILSGISDILDAIKPASASASSSSLSSVAITRPKYSAQAIIDSGGPYSGHLQEVKETCLSIMSEACDVTKLD | 675 |
| PA-8 | HEAEETLSEISDMSGNIKPASVSSSSSLSSVRITRPKYSAQAIIDSGGPCSGHLQEVKETCLSVMREACDATKLD | 675 |
| BJ-4 | HEAEETLSEISDMSGNIKPASVSSSSSLSSVRITRPKYSAQAIIDSGGPCSGHLQEVKETCLSVMREACDATKLD | 675 |
| HN1 | HEAEETLSEISDMSGNIKPASVSSSSSLSSVRVTRPKYSAQAIIDSGGPCSGHLQEVKETCLSVMREACDATKLD | 675 |
| 16244B | HEAEETLSEISDMSGNIKPASVSSSSSLSSVEITRPKYSAQAIIDSGGPCSGHLQGVKETCLSVMREACDATKLD | 675 |
| CH-1 | QEAEEVLSGISDILNDINPAPVSSSSSLSSVKITRPKYSAQAIIDSGGPCSGHLQREKEACLSIMREACDAAKLS | 675 |
| HB-2 | QEAEEVLSGISDILDNTNPAPVSSSSSLSSVKITRPKYSAQAIIDSGGPCSGHLQKEKEACLRIMREACDAARLG | 663 |
| P129 | QEAEEVLSEISDILNDTNPAPVSSSSSLSSVRITRPKYSAQAIIDLGGPCSGHLQREKEACLRIMREACDAAKLS | 669 |
| JA142 | QEAEEVLSEISDTLNDINPAPVSSSSSLSSVKITRPKHSAQAIIDSGGPCSGHLRREKEACLSIMREACDAAKLS | 675 |
| HB-1 | QEAEEVLSEISDILNDTSPAPVSSSSSLSSVKITRPKYSAQAIIDSGGPCSGHLQKEKEACLSIMREACDASKLS | 675 |
| SDPRRS-01-08 | DQTKDTLVADAPVDLTTSNEALSAVDPSEFVELRRPRHSAQALIDRGGPLADVHAKIKNRVYEQCLQACEPGSRA | 569 |
| EuroPRRSV | DRTKDAPVVDAPVGSTTSNEALSIADPFEFAELKRPRFSAQALIDRGGPLADVHAKIKNRVYERCLQACEPGSRA | 569 |
| Lelystad | DRTKDAPVVDAPVDLTTSNEALSVVDPFEFAELKRPRFSAQALIDRGGPLADVHAKIKNRVYEQCLQACEPGSRA | 586 |

Figure 12 (continued)

| | | |
|---|---|---|
| MN184A | DPATQEWLSRMWDRVDMLTWRNTSIFQAPFTLADKFKSLPKMILETPPYPCGFVMMPRTPAPSVGAESDLTVGS | 619 |
| MN184B | DPATQEWLSRMWDRVDMLTWRNTSIFQAPFTLADKFKTLPKMILETPPYPCGFVMMPRTPAPSVGAESDLTVGS | 619 |
| VR-2332 | DPATQEWLSRMWDRVDMLTWRNTSVYQAICTLDGRLKFLPKMILETPPYPCEFVMMPHTPAPSVGAESDLTIGS | 750 |
| Ingelvac | DPATQEWLSRMWDRVDMLTWRNTSVYQAICTLNGRLKFLPKMILETPPYPCEFVMMPHTPAPSVGAESDLTIGS | 750 |
| 01NP1.2 | DPATQEWLSRMWDRVDMLTWRNTSVYQAICTLDGRLKFLPKMILETPPYPCEFVMMPHTPAPSVGAESDLTIGS | 750 |
| PL97-1 | DPATQEWLSRMWDRVDMLTWRNTSVYQAICTLDGRLKFLPKMILETPPYPCGFVMMPRTPAPSVGAESDLTIGS | 750 |
| SP | DPATQEWLSRMWDRVDMLTWRNTSVHQASRTLDDRFKFLPKMILETPPYPCEFVMMPHTPAPSVGAESDLTIGS | 750 |
| PA-8 | DPATQEWLSRMWDRVDMLTWRNTSVYQVICTLDGMLKFLPKMILETPPYPCEFVMMPHTPAPSVGAESDLTIGS | 750 |
| BJ-4 | DPATQEWLSRMWDRVDMLTCN-TSVYQAICTLDGRLKFLPKLILETPPYPCEFVMMPHTPAPSVGAESDLTIGS | 749 |
| HN1 | DPATQEWLSRMWDRVDMLTWRNTSAYQAICTLDGRLKFLPKMILETPPYPCEFVMMPHTPAPSVGAESDLTIGS | 750 |
| 16244B | DPATQEWLSRMWDRVDMLTWRNTSVCQAIRTLDGRLKFLPKMILETPPYPCEFVMMPHTPAPSVGAESDLTIGS | 750 |
| CH-1 | DPATQEWLSRMWDRVDMLTWRNTSAYQALHTLDGRSGFLPKMILETPPHPCGFVMLPHTPAPSVSAKSDLTIGS | 750 |
| HB-2 | DPATQEWLSHMWDRVDVLTWRNTSVYQAFRTLDGRFGFLPKMILETPPYPCGFVMLPHTPTPSVSAESDLTIGS | 738 |
| P129 | DPATQEWLSRMWDRVDMLTWRNTSAYQAFRTLDGRFGFLPKMILETPPYPCGFVMLPHTPAPSVSAESDLTIGS | 744 |
| JA142 | DPATQEWLSRMWDRVDMLTWRNTSAYQAFRILDGRFEFLPKMILETPPYPCGFVMLPHTPAPSVGAESDLTIGS | 750 |
| HB-1 | DPATQEWLSRMWDRVDMLTWRNTSAYQAFRTLNGRFEFLPKMILETPPHPCGFVMLPHTPAPSVSAESDLTIGS | 750 |
| SDPRRS-01-08 | TPATREWLDKMWDKTWRCTSQFQAGRILAS-LKFLPDMIQDTPPPVPRKNRASDNAGLKQLVARWDKKLSV | 643 |
| EuroPRRSV | TPATKEWLDKMWDRVDMKIWCCTSQFQAGRILAS-LKFLPDMIQDTPPPVPRKNRASDNADLKQLVAQWDRKLSM | 643 |
| Lelystad | TPATREWLDKMWDRVDMKTWRCTSQFQAGRILAS-LKFLPDMIQDTPPPVPRKNRASDNAGLKQLVAQWDRKLSV | 660 |

Figure 12 (continued)

```
MN184A       VATEDVPRIILGKVQGVGETTDQGPLALFADELADDQPAREPRTQTPPASAGGAGLVLDSGGSP------------------------  682
MN184B       VATEDVPRIILGNVQGVGETTDQGPLAPFADELADDQLAREPRTQTPPASTGGAGLVSDSGRSP------------------------  682
VR-2332      VATEDVPRILEKIENVGEMANQGPLAFSEDKPVDDQLVNDPRISSRRPDESTSAPSAGTGGAG------------------------  813
Ingelvac     VATEDVPRILEKIENVGEMANQGPLAFSEDKPVDDQLVNDPRISSRRPDESTSAPSAGTGGAG------------------------  813
01NP1.2      VATEDVPRILEKIENVGEMANQGPLAFSEDKPVDDQLVNDPRISSRRPDESTSAPSAGTGGAG------------------------  813
PL97-1       VATEDVPRILEKIENVGEMANQGPLAFSEDKPVDDQLVNDPRISSRRPDESTSAPSAGTGGAG------------------------  813
SP           VATEDVPRIFGKVNDVCKMIDQRPLVLFENELADDQPARDPRTSSQRFDGSTPAPPAGTDGTGLASGPGVREVDS-------------  825
PA-8         VTTEDVPRILEKIGNVGEMANQGPLAFSEDKPVDDQLVNDPRISSRRPDESTSAPSAGTGGAG------------------------  813
BJ-4         VATEDVPRILEKTENVGEMANQGPLAFSEDKPVDDQLVNDPRISSRRPDESTSAPSAGTGGAG------------------------  812
HN1          VATEDVPRILEKMENVGEMANQGPLAFSEDKPVDDQLVNDPRISSRRPDESTSAPSAGTGGSG------------------------  813
16244B       VATEDVPRILEKIENVGEMANQEPSAFSEDKPVDDQLVNDPRISSRRPDESTAAPSAGTGGAG------------------------  813
CH-1         VATEDVPRILGKIENTGEMLNQGPLAPFEEEPVCDPSRISSRGSGESTTAPSADTGGAG------------------------  813
HB-2         VATEDVPRILGKTENTGNVLNQKPLALFEEEPVCDQPAKDSRTLSRESGDSTTAPPVGTGGAG------------------------  801
P129         VATEDIPRILGKIENTGEMINQGPLASSEEEPVYNQPAKDSRISSRGSDESTAAPSAGTGGAG------------------------  807
JA142        VATEDVPRIIGKIENAGEMPNQGLITSFGEEPVCDQPVKDSWMSSRGFDESTTAPSAGTGGAD------------------------  813
HB-1         VATEDVPRIILGIGDTGELLNQGPSAPFKGGPVCDQPAKNSRMSPRESDESIIAPPADTGGAG------------------------  813
SDPRRS-01-08 TPPPKSAGLVLDQTVPPPTDIQQEDATPSDGLS---------------------------------------------------  676
EuroPRRSV    TPPQKPVEPVLDQTVSPPTDTQQEDVTPSDGPP---------------------------------------------------  676
Lelystad     TPPPKPVGPVLDQIVPPPTDIQQEDVTPSDGPP---------------------------------------------------  693
```

Figure 12 (continued)

| | | |
|---|---|---|
| MN184A | ------------ELTDLPLPXGTDAGGGGPLHTVKKKAERCFDQLSRRVFDIVSHLPVFFSRL | 733 |
| MN184B | ------------ELTDLPLSNGTDAGGGGPLHTVKKKAERCFDQLSRRVFDIVSHLPVFFSRL | 733 |
| VR-2332 | ------------SFTDLPPSDGADADGGGPFRTVKRKAERLFDQLSRQVFDLVSHLPVFFSRL | 864 |
| Ingelvac | ------------SFTDLPPSDGADADGGGPFRTVKRKAERLFDQLSRQVFDLVSHLPVFFSRL | 864 |
| 01NP1.2 | ------------SFTDLPPSDGADADGGGPFRTVKRKAERLFDQLSRQVFDLVSHLPVFFSRL | 864 |
| PL97-1 | ------------FFTDLPPSDGADADGGGPFRTVKRKAERLFDQLSRQVFDLVSHLPVFFSRL | 864 |
| SP | CEASSTEKIEQPFVLNGGASTQASTFFNLPPPGGIDAGGSGPLQTVRKKAERFFDLLSRQVFNLVSHLPVFFSRL | 900 |
| PA-8 | ------------SFTDLPPSDGADADGGGPFRTVKRKAERLFDQLSRQVFDLVSHLPVFFSRL | 864 |
| BJ-4 | ------------SFTDLPPSDGADADGGGPFRTVKRKAERLFDQLSRQVFDLVSHLPVFFSRL | 863 |
| HN1 | ------------SFTDLPPSDGADADGGGPFRTAKRKAERLFDQLSRQVFDLVSHLPVFFSRL | 864 |
| 16244B | ------------SFTDLPSSDGADADGGGPFRTAKRKAERLFDQLSRQVFNLVSHLPVFFSRL | 864 |
| CH-1 | ------------LFTDLLPSDGMDADGGGPLRTVKKTEKLFDQLSRQVFNIVSHLPVFFSHL | 864 |
| HB-2 | ------------LPTDLPPLDGVDADGGGLLRTAKGKAERFFDQLSRQVFNIVSHLPVFFSHL | 852 |
| P129 | ------------LFTDLPPSDGVDADGGGPLQTVRKKAERLFDQLSRQVFNLVSHLPVFFSHL | 858 |
| JA142 | ------------LPTDLPPSDGLDADEWGPLRTVRKKAERLFDQLSRQVFNLVSHLPVFFSHL | 864 |
| HB-1 | ------------SFTDLPSSDSVDANGGGPLRTVKTKAGRLLDQLSCQVFSLVSHLPVFFSHL | 864 |
| SDPRRS-01-08 | ------------HASDFSSRVSTSWSWKGLMLSGTRLAGSAGQRLMTWVFEVYSHLPAFILTL | 727 |
| EuroPRRSV | ------------HAPDFPSRVSTGGSWKDLMCSGTRLAGSISQRLMTWVFEVFSHLPAFMLTL | 727 |
| Lelystad | ------------HAPDFPSRVSTGGSWKGLMLSGTRLAGSISQRLMTWVFEVFSHLPAFMLTL | 744 |

Figure 12 (continued)

| | | |
|---|---|---|
| MN184A | FKPDSHYSSGDWSFAAFTLLCLFLCYSYPAFGVAPLLGVFSGSSRRVRMGVFGCWLAFAVGLFKPAPDPVGAACE | 808 |
| MN184B | FKPDSHYSSGDWSFAAFTLLCLFLCYSYPAFGVAPLLGVFSGSSRRVRMGVFGCWLAFAVGLFKPAPDPVGAACE | 808 |
| VR-2332 | FYPGGGYSPGDWGFAAFTLLCLFLCYSYPAFGIAPLLGVFSGSSRRVRMGVFGCWLAFAVGLFKPVSDPVGAACE | 939 |
| Ingelvac | FYPGGGYSPGDWGFAAFTLLCLFLCYSYPAFGIAPLLGVFSGSSRRVRMGVFGCWLAFAVGLFKPVSDPVGAACE | 939 |
| 01NP1.2 | FYPGGGYSPGDWGFAAFTLLCLFLCYSYPAFGIAPLLGVFSGSSRRVRMGVFGCWLAFAVGLFKPVSDPVGAACE | 939 |
| PL97-1 | FCPGGGYSPGDWGFAALTLICLFLCYSYPAFGIAPLLGVFSGSSRRVRMGVFGCWLAFAVGLFKPVSDPVGAACE | 975 |
| SP | FKPGGDYSPGDWGFAAFTLLCLFLCYSYPAFGAVPLLGVFSGSSRRVRMGFFGCWLAFAVSLFKPVSDPVGAACE | 939 |
| PA-8 | FYPGGGYSPGDWGFAAFTLLCLFLCYSYPAFGIAPLLGVFSGSSRRVRMGVFGCWLAFAVGLFKPVSDPVGAACE | 938 |
| BJ-4 | FYPGGGYSPGDWGFAAFTLLCLFLCYSYPAFGIAPLLGVFSGSSRRVRMGVFGCWLAFAVGLFKPVSDPVGAACE | 939 |
| HN1 | FHPGGGYSPGDWGFAAFTLLCLFLCYSYPAFGIAPLLGVFSGSSRRVRMGVFGCWLAFAVGLFKPVSDPVGAACE | 939 |
| 16244B | FHPGGGYSTGDWGFAAFTLLCLFLCYSYPAFGIAPLLGVFSGTSRRVRMGVFGCWLAFAVGLFKPVSDPVGTACE | 939 |
| CH-1 | FKSDSGYSSGDWSFAAFTLECLFLCYSYPFFGFAPLLGVFSGSSRRVRMGVFGCWLAFAVGLFKPVSDPVGAACE | 939 |
| HB-2 | FKSDSGYSPGDWGFAAFTLECLFLCYSYPFFGFVPLLGVFSGSSRRVRMGVFGCWLAFAVGLFKPVSDPVGAACE | 927 |
| P129 | FKSDSGYSPGDWGFAAFTLECLFLCYSYPFFGFELPLLGVFSGSSRRVRMGVFGCWLAFAVGLFKPVSDPVGTACE | 933 |
| JA142 | FKSDSGYSPGDWGFAAFTLECLFLCYSYPFFGFAPLLGVFSGSSRRVRMGVFGCWLAFAVGLFKPVSDPVGTACE | 939 |
| HB-1 | FKSDSGYSPGDWGFAAFTLECLFLCYSYPFFGFAPLLGVFSGSSRRVRMGVFGCWLAFAVGLFKPVSDPVGTACE | 939 |
| SDPRRS-01-08 | FSPRGSMAPGDWLFAGVVLLALLLCRSYPILGCLPLLGVFSGSLRRVRLGVFGSWMAFAVFLFSTPSNPVGSSCD | 802 |
| EuroPRRSV | FSPRGSMAPGDWLFAGVVLLALLLCHSYPILGCLPLLGVFSGSLRRVRLGVFGSWMAFAVFLFSTPSNPVGSSCD | 802 |
| Lelystad | FSPRGSMAPGDWLFAGVVLLALLLCRSYPILGCLPLLGVFSGSLRRVRLGVFGSWMAFAVFLFSTPSNPVGSSCD | 821 |

Figure 12 (continued)

| | | |
|---|---|---|
| MN184A | FDSPECRDILHSFELLQPWDPVRSLVVGPVGLGLAIIGRLLGGARYVWLLLLRLGIVSDCILAGAYVLSQGRCKK | 885 |
| MN184B | FDSPECRDILHSFELLQPWDPVRSLVVGPVGLGLAIIGRLLGGARYVWLLLLRLGIVSDCILAGAYVLSQGRCKK | 885 |
| VR-2332 | FDSPECRNILHSFELLKPWDPVRSLVVGPVGLGLAILGRLLGGARCIWHFLLRLGIVADCILAGAYVLSQGRCKK | 1014 |
| Ingelvac | FDSPECRNILHSFELLKPWDPVRSLVVGPVGLGLAILGRLLGGARCIWHFLLRLGIVADCILAGAYVLSQGRCKK | 1014 |
| 01NP1.2 | FDSPECRNILHSFELLKPWDPVRSLVVGPVGLGLAILGRLLGGARCIWHFLLRLGIVADCILAGAYVLSQGRCKK | 1014 |
| PL97-1 | FDSPECRNILHSFELLKPWDPVRSLVVGPVGLGLAILGRLLGGARCIWHFLLRLGIVADCILAGAYVLSQGRCKK | 1014 |
| SP | FDSPECRNILHSFELLKPWDPVRGLVVGPYGISLAIFGRLLGGARHIWHFLLRFGIVADCILAGAYVLSQGRCKK | 1050 |
| PA-8 | FDSPECRNILHSFELLKPWDPVRSLVVGPVGLGLAILGRLLGGARCIWHFLLRLGIVADCILAGAYVLSQGRCKK | 1014 |
| BJ-4 | FDSPECRNILHSFELLKPWDPVRSLVVGPVGLGLAILGRLLGGARCIWHFLLRLGIVADCILAGAYVLSQGRCKK | 1013 |
| HN1 | FDSPECRNILHSFELLKPWDPVRSLVVGPVGLGLAILGRLLGGARCIWHFLLRLGIVADCILAGAYVLSQGRCKK | 1014 |
| 16244B | FDSPECRNILHSFELLKPWDPVRGLVVGPVGLGLAILGRLLGGARCIWHFLLRLGIVADCILAGAYVLSQGRCKK | 1014 |
| CH-1 | FDSPECRNVLHSFELLKPWDPVRSLVVGPVGLGLAILGRLLGGARCIWHFLLRLGIVADCILAGAYVLSQGRCKK | 1014 |
| HB-2 | FDSPECRNVLHSFELLKPWDPVRSLVVGPVGLGLAILGRLLGGARYIWHFLLRLGIVADCILAGAYVLSQGRCKK | 1002 |
| P129 | FDSPECRNVLHSFELLKPWDPVRSLVVGPVGLGLAILGRLLGGARYIWHFLLRLGIVADCILAGAYVLSQGRCKK | 1008 |
| JA142 | FDSPECRNVLHSFELLKPWDPVRSLVVGPVGLGLAILGRLLGGARYIWHFLLRLGIVADCILAGAYVLSQGRCKK | 1014 |
| HB-1 | FDSPECRNVLHSFELLKPWDPVRSLVVGPVGLGLAILGRLLGGARYVWHFLLRFGIVADCILAGAYVLSQGRCKK | 1014 |
| SDPRRS-01-08 | HDSPECHAELLALEQRQLWEPVRGLVVGPSGLLCVILGKLIGGSSRHLWHVILRICMLTDLALSLVYVVSQGRCHK | 877 |
| EuroPRRSV | HDSPECHAELLALEQRQLWEPVRGIVVGPSGLLCVILGKLIGGSSRYLWHIILRICMLTDLALSIVYVVSQGRCHK | 877 |
| Lelystad | HDSPECHAELLALEQRQLWEPVRGLVVGPSGLLCVILGKLIGGSSRYLWHVLLRICMLADLALSIVYVVSQGRCHK | 894 |

Figure 12 (continued)

| | | |
|---|---|---|
| MN184A | CWGSCIRTAPSEVAFNVFPFTRATRSSLVDLCDRFCAPKGMDPIFLATGWRGCWSGQSPVEQPTEKPIAFAQLDE | 960 |
| MN184B | CWGSCIRTAPSEVAFNVFPFTRATRSSIVDLCDRFCAPKGMDPIFLATGWRGCWSGQSPIEQPTEKPIAFAQLDE | 960 |
| VR-2332 | CWGSCIRTAPNEVAFNVFPFTRATRSSLIDLCDRFCAPKGMDPIFLATGWRGCWAGRSPIEQPSEKPIAFAQLDE | 1089 |
| Ingelvac | CWGSCIRTAPNEVAFNVFPFTRATRSSLIDLCDRFCAPKGMDPIFLATGWRGCWAGRSPIEQPSEKPIAFAQLDE | 1089 |
| 01NP1.2 | CWGSCIRTAPNEVAFNVFPFTRATRSSLIDLCDRFCAPKGMDPIFLATGWRGCWAGRSPIEQPSEKPIAFAQLDE | 1089 |
| PL97-1 | CWGSCIRTAPNEVAFNVFPFTRATRSSLIDLCDRFCAPKGMDPIFLATGWRGCWAGRSPIEQPSEKPIAFAQLDE | 1089 |
| SP | CWGSCIRTAPNEVAFNVFPFTRATRSSLIDLCNRFCAPKGMDPIFFATGWRGCWTGRSPIEQPSEKPIAFAQLDE | 1125 |
| PA-8 | CWGSCIRTAPNEVAFNVFPFTRATRSSLIDLCDRFCAPKGMDPIFLATGWRGCWAGRSPIEQPSEKPIAFAQLDE | 1089 |
| BJ-4 | CWGSCIRTAPNEVAFNVFPFTRATRSSLIDLCDRFCAPKGMDPIFLATGWRGCWAGRSPIEQPSEKPIAFAQLDE | 1088 |
| HN1 | CWGSCIRTAPNEVAFNVFPFTRATRSSLIDLCDRLCAPKGMDPISLATGWRGCWAGRSPIEQPSEKPIAFAQLDE | 1089 |
| 16244B | CWGSCIRTAPNEVAFNVFPFTRATRSSLIDLCDRFCAPKGMDPIFLATGWRGCWAGRSPIEQPSEKPIAFAQLDE | 1089 |
| CH-1 | CWGSCVRTAPNEIAFNVFPFTRATRSSLIDLCDRFCAPKCMDPIFLATGWRGCWTGRSPIEQPSEKPIAFAQLDE | 1089 |
| HB-2 | CWGSCIRTAPNEIAFNVFPFTRATRSSLIDLCDRFCAPKGMDPIFLATGWRGCWTGQSPIEQPSEKPIAFAQLDE | 1077 |
| P129 | CWGSCVRTAPNEIAFNVFPFTRATRSSLIDLCDRFCAPKGMDPIFLATGWRGCWTGRSPIEQPSEKPIAFAQLDE | 1083 |
| JA142 | CWGSCIRTAPNEIAFNVFPFTRATRSSLIDLCDRFCAPKGMDPIFLATGWRGCWTGRSPIEQPSEKPIAFAQLDE | 1089 |
| HB-1 | CWGSCVRTAPNEIAFNVFPFTRATRSSLIDLCDRFCAPKGMDPIFLATVWRGCWTGRSPIEQPSEKPIAFAQLDE | 1089 |
| SDPRRS-01-08 | CWGKCIRTAPAEVALNVFPFSRATRNSLTSLCDRFQTPKGVDPVHLATGWRGESPIHQPHQKPIAYANLDE | 952 |
| EuroPRRSV | CWGKCIRTAPTEVALNVFPFTRATRSSLVSLCDRFQTPKGVDPVHLATGWRGGSPVHQPHQKPIAYANLDE | 952 |
| Lelystad | CWGKCIRTAPAEVALNVFPFSRATRVSLVSLCDRFQTPKGVDPVHLATGWRGESPIHQPHQKPIAYANLDE | 969 |

| | | |
|---|---|---|
| MN184A | KKITARTVVAQPYDPNQAVKCLRVLQAGGAMVAEAIPKVVKVSAVPFRAPFFPTGVKVDPECRVVVDPDTFTTAL | 1035 |
| MN184B | KKITARTVVAQPYDPNQAVKCLRVLQAGGAMVAEAVPKVVKVSAVPFRAPFFPAGVKVDPECRVVVDPDTFTTAL | 1035 |
| VR-2332 | KKITARTVVAQPYDPNQAVKCLRVLQSGGAMVAKAVPKVVKVSAVPFRAPFFPTGVKVDPDCRVVVDPDTFTAAL | 1164 |
| Ingelvac | KKITARTVVAQPYDPNQAVKCLRVLQAGGAMVAKAVPKVVKVSAVPFRAPFFPTGVKVDPDCRVVVDPDTFTAAL | 1164 |
| 01NP1.2 | KKITARTVVAQPYDPNQAVKCLRVLQAGGAMVAKAVPKVVKVSAVPFRAPFFPTGVKVDPDCRVVVDPDTFTAAL | 1164 |
| PL97-1 | KKITARTVVAQPYDPNQAVKCLRVLQAGGAMVAKAVPKVVKVSAVPFRAPFFPTGVKVDPDCRVVVDPDTFTAAL | 1164 |
| SP | KKITARTVVAQPYDPNQAVKCLRVLQAGGVMVAEAVPKVVKVSAVPFRAPFFPTGVKVDPECRIVVDPDTFTAAL | 1200 |
| PA-8 | KKITARTVVAQPYDPNQAVKCLRVLQAGGAMVAEAVPKVVKVSAVPFRAPFFPTGVKVDPNCRVVVDPDTFTAAL | 1164 |
| BJ-4 | KKITARTVVAQPYDPNQAVKCLRVLQAGGAMVAKAVPKVVKVSAVPFRAPFFPTGVKVDPDCRVVVDPDTFTAAL | 1163 |
| HN1 | KKITARTVAAQPYDPNQAVKCLRVLQAGGAMVAEAVPKVVKVSAVPFRAPFFPTGVKVDPDCRVVVDPDTFTAAL | 1164 |
| 16244B | KKITARTVVAQPYDPNQAVKCLRVLQAGGAMVAEAVPKVVKVSAVPFRAPFFPTGVKVDPDCRVVVDPDTFTAAL | 1164 |
| CH-1 | KKITARTVVAQPYDPNQAVKCLRVLQAGGAMVAEAVPKVVKVSAIPFRAPFFPTGVKVDPECRIVVDPDTFTTAL | 1164 |
| HB-2 | KRITARTVVSQPYDPNQAVKCLRVLQAGGAMVAEAVPKVVKVSAIPFRAPFFPTGVKVDPECRIVVDPDTFTTAL | 1152 |
| P129 | KRITARTVVAQPYDPNQAVKCLRVLQAGGAMVAEAVPKVVKVSAIPFRAPFFPTGVKVDPECRIVVDPDTFTTAL | 1158 |
| JA142 | KRITARTVGAQPYDPNQAVKCLRVLQAGGAIVAEAVPKVVKVSAIPFRAPFFPTGVKVDPECRIVVDPDTFTTAL | 1164 |
| HB-1 | KRITARTVVAQPYDPNQAVKCLRVLQAGGAMVAEAVPKVVKVSAIPFRAPPFPAGVKVDPECRIVVDPDTFTTAL | 1164 |
| SDPRRS-01-08 | KKISAQTVVAVPYDPSQAIKCLKVLQAGGAIVDQPTPEVVRVSEIPFSAPFFPK-VPVNPDCRIVVDSDTFVAAV | 1026 |
| EuroPRRSV | KKISAQTVVAVPYDPSQAIKCLKVLQAGGAIVDQPTPEVVRVSEIPFSAPFFPK-VPVNPDCRVVVDSDTFVAAV | 1026 |
| Lelystad | KKMSAQTVVAVPYDPSQAIKCLKVLQAGGAIVDQPTPEVVRVSEIPFSAPFFPK-VPVNPDCRVVVDSDTFVAAV | 1043 |

Figure 12 (continued)

| | | | |
|---|---|---|---|
| MN184A | RSGYSTTNLILGVGDFAQLNGLKIRQ--- | ---ISKPSGG | 1068 |
| MN184B | RSGYSTTNLILGMGDFAQLNGLKIRQ--- | ---ISKPSGG | 1068 |
| VR-2332 | RSGYSTTNLVLGVGDFAQLNGLKIRQ--- | ---ISKPSGG | 1197 |
| Ingelvac | RSGYSTTNLVLGVGDFAQLNGLKIRQ--- | ---ISKPSGG | 1197 |
| 01NP1.2 | RSGYSTTNLVLGVGDFAQLNGLKIRQ--- | ---ISKPSGG | 1197 |
| PL97-1 | RSGYSTTNLVLGVGDFAQLNGLKIRQ--- | ---ISKPSGG | 1233 |
| SP | RSGYSTTNLVLGVGDFAQLNGLKIRQ--- | ---ISKPSGG | 1197 |
| PA-8 | RSGYSTTNLLLVGVGDFAQLNGLKIRQ--- | ---ISKPSGG | 1196 |
| BJ-4 | RSGYPTTNLVVGVGDFAQLNGLKIRQ--- | ---ISKPSGG | 1197 |
| HN1 | RSGYSTTNLVVGVGDFAQLNGLKIRQ--- | ---ISKPSGG | 1197 |
| 16244B | RSGYSTTNLVVGVGDFAQLNGLKIRQ--- | ---ISKPSGG | 1197 |
| CH-1 | RSGYSTTNLVVGVGDFAQLNGLKIRQ--- | ---ISKPSGG | 1185 |
| HB-2 | RSGYSTTNLVVGVGDFAQLNGLKIRQ--- | ---ISKPSGG | 1191 |
| P129 | RSGYSTTNLVVGVGDFAQLNGLKIRQ--- | ---ISKPSGG | 1197 |
| JA142 | RSGYSTTNLVVGVGDFAQLNGLKIRQ--- | ---ISKPSGG | 1197 |
| HB-1 | RSGYSTTNLVVGMGDFAQLNGLKIRQ--- | ---ISKPSGG | 1197 |
| SDPRRS-01-08 | RCGYSTAQLVLGRGNFAKLNQTPLRDSASTKTTGG | | 1061 |
| EuroPRRSV | RCGYSTAQLVLGQGNFAKLNQTPPRNSTSTKTTGG | | 1061 |
| Lelystad | RCGYSTAQLVLGRGNFAKLNQTPPRNSISTKTTGG | | 1078 |

SEQUENCE LISTING

```
<160> NUMBER OF SEQ ID NOS: 90

<210> SEQ ID NO 1
<211> LENGTH: 15419
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 1
atgacgtata ggtgttggct ctatgccttg gcatttgtat tgtcaggagc tgtgaccatt        60
ggcacagccc aaaacttgct gcacagaaac acccttctgt gatagcctcc ttcaggggag       120
cttagggttt gtccctagca ccttgcttcc ggagttgcac tgctttacgg tctctccacc       180
cctttaacca tgtctgggat acttgatcgg tgcacgtgta ccccaatgc cagggtgttt        240 atggcggagg gccaagtcta ctgcacacga tgcctcagtg cacggtctct ccttcccctg       300
aacctccagg tttctgagct cggggtgcta ggcctattct acaggcccga agagccactc       360
cggtggacgt tgccacgtgc attccccact gttgagtgct ccccgccgg ggcctgctgg        420 ctttctgcaa tctttccaat cgcacgaatg accagtggaa acctgaactt ccaacaaaga       480
atggtacggg tcgcagctga gctttacaga gccggccagc tcaccctgc agtcttgaag        540 gctctacaag tttatgaacg gggttgccgc tggtacccca ttgttggacc tgtccctgga       600
gtggccgttt tcgccaattc cctacatgtg agtgataaac ccttcccggg agcaactcac       660
gtgttgacca acctgccgct cccgcagaga cccaagcctg aagactttg cccctttgag       720 tgtgctatgg ctactgtcta tgacattggt catgacgccg tcatgtatgt ggccgaaagg       780
aaagtctcct gggcccctcg tggcgggat gaagtgaaat ttgaagctgt ccccggggag        840
ttgaagttga ttgcgaaccg gctccgcacc tccttcccgc cccaccacac agtggacatg       900
tctaagttcg ccttcacagc ccctgggtgt ggtgtttcta tgcgggtcga acgccaacac       960
ggctgccttc ccgctgacac tgtccctgaa ggcaactgct ggtggagctt gtttgacttg      1020
cttccactgg aagttcagaa caaagaaatt cgccatgcta accaatttgg ctaccagacc      1080
```

```
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccctgg gatgtcccct   1740 tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc   2400
gtgctctcca gttggaaaaa ggttgttcga gaagaatatg ggctcatgcc aaccgagcct   2460
ggtccacggc ccacactgcc acgcgggctc gacgaactca agaccagat ggaggaggac   2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agcccctttg atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt   3120 ctggagtag agggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
```

```
cgcaacacgt ctgtttacca ggcgatttgc accttagatg gcaggttaaa gttcctccca    3480
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg    3720
cggaggcctg acgagagcac atcagctccg tccgcaggca caggtggcgc cggctctttt    3780
accgatttgc cgccttcaga tggcgcggat gcggacgggg ggggccgtt tcggacggta    3840
aaaagaaaag ctgaaaggct ctttgaccaa ctgagccgtc aggtttttga cctcgtctcc    3900
catctccctg ttttcttctc acgccttttc taccctggcg gtggttattc tccgggtgat    3960
tggggttttg cagcttttac tctattgtgc ctcttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt ccttttcaca    4440
cgtgcgacca ggtcgtcact tatcgacctg tgcgatcggt tttgtgcgcc aaaaggaatg    4500
gacccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca cttttcactgc agctctccgg tctggctact ccaccacaaa cctcgtcctt    4860
ggtgtggggg actttgcccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gtttccttgc tggttgcgct gttttctttt gcacccctc    5340
accatcctat ggtggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggccccccgcg tgttgccgc cttggctacc    5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cggcaattc agctcggtt    5760
tccggggtcg gcttcaatca aatgcttgac tttgacgtaa agggagattt cgctatagct    5820
```

```
gattgcccga attggcaagg ggctgccccc aagacccaat tctgcacgga tggatggact   5880
ggccgtgcct attggctaac atcctctggc gtcgaacccg gcgtcattgg aaaaggattc   5940
gccttctgct tcaccgcatg tggcgattcc gggtccccag tgatcaccga ggccggtgag   6000
cttgtcggcg ttcacacggg atcgaataaa caagggggg gcattgttac gcgcccctca    6060
ggccagtttt gtaatgtggc acccatcaag ctaagcgaat taagtgaatt ctttgctggg   6120
cctaaggtcc cgctcggtga tgtgaaggtc ggcagccaca taattaaaga cataagcgag   6180
gtgccttcag atctttgtgc cttgcttgct gccaaacctg aactggaagg aggcctctcc   6240
accgtccaac ttctttgtgt gttttttctc ctgtggagaa tgatgggaca tgcctggacg   6300
cccttggttg ctgtgagttt ctttattttg aatgaggttc tcccagccgt cctggtccgg   6360
agtgttttct cctttggaat gtttgtgcta tcctggctca cgccatggtc tgcgcaagtt   6420
ctgatgatca ggcttctgac agcagctctt aacaggaaca gatggtcact tgcctttttc   6480
agcctcggtg cagtgaccgg ttttgtcgca gatcttgcgg ccactcaggg gcatccgttg   6540
caggcagtga tgaatttgag cacctatgca ttcctgcctc ggatgatggt tgtgacctca   6600
ccagtcccag tgatcacgtg tggtgtcgtg cacctacttg ccatcatttt gtacttgttt   6660
aagtaccgtg gcctgcacca tatccttgtt ggcgatggag tgttctctgc ggctttcttc   6720
ttgagatact ttgccgaggg aaagttgagg aaggggtgt cgcaatcctg cggaatgaat    6780
catgagtctc tgactggtgc cctcgctatg agactcaatg acgaggactt ggatttcctt   6840
atgaaatgga ctgattttaa gtgctttgtt tctgcgtcca acatgaggaa tgcagcgggt   6900
caatttatcg aggctgccta tgctaaagca cttagagtag aactggccca gttggtgcag   6960
gttgataaag ttcgaggtac tttggccaaa cttgaagctt ttgctgatac cgtggcacct   7020
caactctcgc ccggtgacat tgttgtcgct ctcggccaca cgcctgttgg cagtatcttc   7080
gacctaaagg ttggtagcac caagcatacc ctccaagcca ttgagaccag agtccttgct   7140
gggtccaaaa tgaccgtggc gcgcgtcgtc gacccgaccc ccacgccccc acccgcaccc   7200
gtgcccatcc ccctcccacc gaaagttctg gagaatggcc ccaacgcttg gggggatgag   7260
gaccgtttga ataagaagaa gaggcgcagg atggaagccc tcggcatcta tgttatgggc   7320
gggaaaaaat accagaaatt ttgggacaag aattccggtg atgtgtttta tgaggaggtc   7380
cataataaca cagatgagtg ggagtgtctc agagttggcg accctgccga ctttgacccc   7440
gagaagggaa ctctgtgtgg acatgtcacc attgaaaaca aggcttacca tgtttacacc   7500
tccccatctg gtaagaagtt cttggtcccc gtcaacccag agaatggaag agtccaatgg   7560
gaagctgcaa agcttccgt ggagcaggcc ctaggtatga tgaatgtcga cggcgaactg    7620
actgccaaag aactggagaa actgaaaaga ataattgaca aactccaggg cctgactaag   7680
gagcagtgtt taaactgcta gccgccagcg acttgacccg ctgtggtcgc ggcggcttgg   7740
ttgttactga aacagcggta aaaatagtca aatttcacaa ccggaccttc accctgggac   7800
ctgtgaattt aaaagtggcc agtgaggttg agctaaaaga cgcggttgag cacaaccaac   7860
acccggttgc gagaccgatc gatggtggag ttgtgctcct gcgttccgcg gttccttcgc   7920
ttatagacgt cttgatctcc ggtgctgatg catctcccaa gttacttgcc catcacgggc   7980
cgggaaacac tggatcgat ggcacgctct gggattttga gtccgaagcc actaaagagg    8040
aagtcgcact cagtgcgcaa ataatacagg cttgtgacat taggcgcggc gacgctcctg   8100
aaattggtct cccttacaag ctgtaccctg ttaggggtaa ccctgagcgg gtgaaaggag   8160
```

```
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaagga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcacccccat ggccttctgt tcttacaaga ccagctaaag tttgaggaca    9180
tgctcaaggt tcaacccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc    9840
ccccacggac cgttatcatg catgtggagc agggtctcac ccccccttgat ccaggtagat    9900
accaaactcg ccgcggatta gtctctgtca ggcgtggaat taggggaaat gaagttggac    9960
taccagacgt tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggcttggg gacgtgccg gttcaacgtc ccggcaggca    10200
caacgctgca attccccgtc ccctcccgca ccggtccgtg ggttcgcatc ctagccggcg    10260
gttggtgtcc tggcaagaat tccttcctag atgaagcagc gtattgcaat caccttgatg    10320
ttttgaggct tcttagtaaa actaccctca cctgtctagg agacttcaag caactccacc    10380
cagtgggttt tgattctcat tgctatgttt ttgacatcat gcctcaaact caactgaaga    10440
ccatctggag gtttgacagg aatatctgtg atgccattca gccagattac agggacaaac    10500
tcatgtccat ggtcaacaca acccgtgtga cctacgtgga aaaacctgtc aggtatgggc    10560
```

```
aggtcctcac ccoctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggcccctt   11160 cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga gttcgacta atggtctgga   11580 aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcaccccctta tgattacggc gctaaaatta tcctgtctag cgcgtaccat ggtgaaatgc   11820 cccccgata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttatttc ccccgggccc tgtcattgaa ccaactttag   12060
gcctgaattg aaatgaaatg gggtccatgc aaagccttt tgacaaaatt ggccaacttt   12120
ttgtggatgc tttcacggag ttcttggtgt ccattgttga tatcattata tttttggcca   12180
ttttgtttgg cttcaccatc gccggttggc tggtggtctt tgcatcaga ttggtttgct   12240 ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct catttcagc atctagccgc cattgaagcc   12540
gagacctgta atatttggc ctccggctg ccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact cttttttgttg tgctgtggtt gcgggttcca   12780
atactacgta ctgttttgg tttccgctgg ttaggggcaa ttttttcttc gaactcacag   12840
tgaattacac ggtgtgtcca ccttgcctca cccggcaagc agccacagag atctacgaac   12900
```

```
ccggtaggtc tctttggtgc aggatagggt atgaccgatg tggggaggac gatcatgacg    12960
agctagggtt tatgataccg cctggcctct ccagcgaagg ccacttgact ggtgtttacg    13020
cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttgcca ttctgttggc aatttgaatg tttaagtatg ttggagaaat     13800
gcttgaccgc gggctgttgc tcgcgattgc tttcttgtg gtgtatcgtg ccgttctgtt     13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggctccg    14340
tggcaacccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc acctttggat    14520
cttcctgaat tgtgctttca ccttcgggta catgactttc gcgcactttc agagtacaaa    14580
taaggtcgcg ctcactatgg gagcagtagt tgcactcctt tgggggtgt actcagccat     14640 agaaacctgg aaattcatca cctccagatg ccgtttgtgc ttgctaggcc gcaagtacat    14700 tctggccct gcccaccacg ttgaaagtgc cgcaggcttt catccgattg cggcaaatga     14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa aataagaaga aaacccgga gaagccccat tttcctctag    15060
cgactgaaga tgatgtcaga catcactta ccctagtga gcggcaattg tgtctgtcgt     15120
caatccagac cgccttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
```

```
agaatgtgtg gtgaatggca ctgattgaca ttgtgcctct aagtcaccta ttcaattagg   15360
gcgaccgtgt gggggtgaga tttaattggc gagaaccatg cggccgaaat taaaaaaaa    15419

<210> SEQ ID NO 2
<211> LENGTH: 15458
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 2
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta ccccaatgc cagggtgttt     240 atggcggagg gccaagtcta ctgcacacga tgcctcagtg cacggtctct ccttcccctg    300
aacctccagg tttctgagct cggggtgcta ggcctattct acaggcccga gagccactc    360 cggtggacgt tgccacgtgc attccccact gttgagtgct ccccgccgg ggcctgctgg    420 ctttctgcaa tctttccaat cgcacgaatg accagtggaa acctgaactt ccaacaaaga   480
atggtacggg tcgcagctga gctttacaga gccggccagc tcacccctgc agtcttgaag    540
gctctacaag tttatgaacg gggttgccgc tggtacccca ttgttggacc tgtccctgga   600
gtggccgttt cgccaattc cctacatgtg agtgataaac ccttcccggg agcaactcac   660
gtgttgacca acctgccgct cccgcagaga cccaagcctg aagacttttg cccctttgag    720
tgtgctatgg ctactgtcta tgacattggt catgacgccg tcatgtatgt ggccgaaagg    780
aaagtctcct gggccctcg tggcggggat gaagtgaaat tgaagctgt ccccggggag     840 ttgaagttga ttgcgaaccg gctccgcacc tccttcccgc ccaccacac agtggacatg    900 tctaagttcg ccttcacagc ccctgggtgt ggtgtttcta tgcgggtcga acgccaacac   960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc    1200
cgccatttga actggcggg agaaccagc tactctgggt ttgaggacct cctcagaata    1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag    1680 tacgtactta agctggaagg tgagcattgg actgtcactg tgaccctggg gatgtccct    1740 tctttgctcc ctcttgaatg tgttcagggc tgttgtgggc acaagggcgg tcttggttcc   1800
ccagatgcag tcgaggtctc cggatttgac cctgcctgcc ttgacggct ggctgaggtg    1860 atgcacctgc ctagcagtgc tatcccagcc gctctggccg aaatgtctgg cgattccgat   1920
```

```
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca agttggaaaa ggttgttcga aagaatatg ggctcatgcc aaccgagcct     2460
ggtccacggc ccacactgcc acgcgggctc gacgaactca aagaccagat ggaggaggac    2520
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac cccacctgag     2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggcgtt    3120
ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgcccat ccgtgtgagt ttgtgatgat gcctcacacg      3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg      3720
cggaggcctg acgagagcac atcagctccg tccgcaggca caggtggcgc cggctctttt    3780
accgatttgc cgccttcaga tggcgcggat gcggacgggg gggggccgtt tcggacggta    3840
aaagaaaag ctgaaaggct cttttgaccaa ctgagccgtc aggttttga cctcgtctcc      3900
catctccctg ttttcttctc acgccttttc taccctggcg gtggttattc tccgggtgat    3960
tggggttttg cagcttttac tctattgtgc ctcttttat gttacagtta cccagccttt      4020
ggtattgctc cctcttgggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
```

```
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tccttttcaca   4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc cagttggatg aaaagaagat tacgctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgtcttg cttgcaattg ccagctatgt ttgggtacct    5280
cttacctggt tgctttgtgt gttttccttgc tggttgcgct gttttctctt gcaccccctc    5340
accatcctat ggtggtgtt tttcttgatt tctgtgaata tgccttcagg aatcttggcc    5400
atggtgttgt tggtttctct ttggcttctt ggtcgttata ctaatgttgc tggccttgtc    5460
acccccctacg acattcatca ttacaccagt ggccccgcg tgttgccgc cttggctacc    5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cggcaattc agctcgggtt    5760
tccggggtcg gcttcaatca aatgcttgac tttgacgtaa agggagattt cgctatagct    5820
gattgcccga attggcaagg ggctgccccc aagacccaat tctgcaccgga tggatggact    5880
ggccgtgcct attggctaac atcctctggc gtcgaacccg gcgtcattgg aaaaggattc    5940
gccttctgct tcaccgcatg tggcgattcc gggtccccag tgatcaccga ggccggtgag    6000
cttgtcggcg ttcacacggg atcgaataaa caagggggg gcattgttac gcgccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactgaagg aggcctctcc    6240
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480
agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
```

```
aagtaccgtg gcctgcacca tatccttgtt ggcgatggag tgttctctgc ggctttcttc    6720
ttgagatact ttgccgaggg aaagttgagg aagggtgt cgcaatcctg cggaatgaat      6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc cctcccacc gaaagttctg gagaatggcc caacgcttg ggggatgag       7260 gaccgtttga ataagaagaa gaggcgcagg atggaagccc tcggcatcta tgttatgggc    7320
gggaaaaaat accagaaatt ttgggacaag aattccggtg atgtgtttta tgaggaggtc    7380
cataataaca cagatgagtg ggagtgtctc agagttggcg accctgccga ctttgaccct    7440
gagaagggaa ctctgtgtgg acatgtcacc attggaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga acagcggta aaatagtca atttcacaa ccggaccttc accctgggac       7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaggag    8160 ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc ccccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaagaa    8820
acaagtttaa ggagctacag actccggtcc tgggcaggtg ccttgaagct gatctcgcat    8880
cctgcgatcg atccacgcct gcaattgtcc gctggtttgc cgccaaccct ctttatgaac    8940
ttgcctgtgc tgaagagcat ctaccgtcgt acgtgctgaa ctgctgccac gacttactgg    9000
```

```
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca     9180
tgctcaaggt tcaaccctg atcgtctatt cggacgacct cgtgctgtat gccgagtctc     9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg     9480
cttgttttgga gtatgatcct gaatggtttg aagaacttgt agttggaata gcgcagtgcg    9540
cccgcaagga cggctacagc tttcccggca cgccgttctt catgtccatg tgggaaaaac     9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agccctttag acgaggtgct ggaacaagtc ccgtataagc    9840
ccccacggac cgttatcatg catgtggagc agggtctcac cccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attcccgtc ccctcccgca ccggtccgtg ggttcgcatc ctagccggcg    10260
gttggtgtcc tggcaagaat tccttcctag atgaagcagc gtattgcaat caccttgatg   10320
tttttgaggct tctagtaaa actaccctca cctgtcctagg agacttcaag caactccacc    10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gccgtcaac ctcgcagtgc    10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggccccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgttcct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcc   11340
acgtcaaagg cactaccgtt ggaggatgtc atcatgtcac ctccagatac ctcccgcgcg   11400
```

```
tccttcccaa ggaatcagtt gcggtagtcg gggtttcaag ccccggaaaa gccgcgaaag    11460
cattgtgcac actgacagat gtgtacctcc cagatcttga agcctatctc cacccggaga    11520
cccagtccaa gtgctggaaa atgatgttgg acttcaaaga agttcgacta atggtctgga    11580
aagacaaaac agcctatttc caacttgaag gtcgctattt cacctggtat cagcttgcca    11640
gctatgcctc gtacatccgt gttcccgtca actctacggt gtacttggac ccctgcatgg    11700
gccccgccct ttgcaacagg agagtcgtcg ggtccaccca ctgggggggct gacctcgcgg    11760 tcacccctta tgattacggc gctaaaatta tcctgtctag cgcgtaccat ggtgaaatgc    11820
cccccggata caaaattctg gcgtgcgcgg agttctcgtt ggatgaccca gttaagtaca    11880
aacatacctg ggggtttgaa tcggatacag cgtatctgta tgagttcacc ggaaacggtg    11940
aggactggga ggattacaat gatgcgtttc gtgcgcgcca ggaagggaaa atttataagg    12000
ccactgccac cagcttgaag ttttatttt ccccgggccc tgtcattgaa ccaactttag    12060
gcctgaattg aaatgaaatg gggtccatgc aaagcctttt tgacaaaatt ggccaacttt    12120
ttgtggatgc tttcacggag ttcttggtgt ccattgttga tatcattata ttttggcca    12180 ttttgtttgg cttcaccatc gccggttggc tggtggtctt ttgcatcaga ttggtttgct    12240
ccgcgatact ccgtacgcgc cctgccattc actctgagca attacagaag atcttatgag    12300
gcctttcttt cccagtgcca agtggacatt cccacctggg gaactaaaca tcctttgggg    12360
atgctttggc accataaggt gtcaaccctg attgatgaaa tggtgtcgcg tcgaatgtac    12420
cgcatcatgg aaaaagcagg gcaggctgcc tggaaacagg tggtgagcga ggctacgctg    12480
tctcgcatta gtagtttgga tgtggtggct cattttcagc atctagccgc cattgaagcc    12540
gagacctgta aatatttggc ctcccggctg cccatgctac acaacctgcg catgacaggg    12600
tcaaatgtaa ccatagtgta aatagcact ttgaatcagg tgtttgctat ttttccaacc    12660
cctggttccc ggccaaagct tcatgatttt cagcaatggt taatagctgt acattcctcc    12720
atattttcct ctgttgcagc ttcttgtact cttttgttg tgctgtggtt gcgggttcca    12780
atactacgta ctgtttttgg tttccgctgg ttaggggcaa ttttttcttc gaactcacag    12840
tgaattacac ggtgtgtcca ccttgcctca cccggcaagc agccacagag atctacgaac    12900
ccggtaggtc tctttggtgc aggataggggt atgaccgatg tggggaggac gatcatgacg    12960
agctagggtt tatgataccg cctggcctct ccagcgaagg ccactgact ggtgtttacg    13020 cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
```

-continued

```
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtc   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catctttccc gttttgactc acattgtctc ctatggtgcc ctcactacca   14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac taagggcaga ctctatcgtt ggcggtcgcc tgtcatcata gagaaaaggg   14280
gcaaagttga ggtcgaaggt catctgatcg acctcaaaag agttgtgctt gatggctccg   14340
tggcaacccc tataaccaga gtttcagcgg aacaatgggg tcgtccttag atgacttctg   14400
tcacgatagc acggctccac aaaaggtgct tttggcgttt tctattacct acacgccagt   14460
gatgatatat gccctaaagg tgagtcgcgg ccgactgcta gggcttctgc accttttgat   14520
cttcctgaat tgtgctttca ccttcgggta catgactttc gcgcactttc agagtacaaa   14580
taaggtcgcg ctcactatgg gagcagtagt tgcactcctt tgggggtgt actcagccat   14640
agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtcccgg ctccactacg gtcaacggca cattggtgcc   14820
cgggttaaaa agcctcgtgt tgggtggcag aaaagctgtt aaacagggag tggtaaacct   14880
tgtcaaatat gccaaataac aacggcaagc agcagaagag aaagaagggg gatggccagc   14940
cagtcaatca gctgtgccag atgctgggta agatcatcac tcagcaaaac cagtccagag   15000
gcaagggacc gggaaagaaa aataagaaga aaaacccgga gaagccccat tttcctctag   15060
cgactgaaga tgatgtcaga catcactta ccccctagtga gcggcaattg tgtctgtcgt   15120
caatccagac cgcctttaat caaggcgctg ggacttgcac cctgtcagat tcaggagga   15180
taagttacac tgtggagttt agtttgccta cgcatcatac tgtgcgcctg atccgcgtca   15240
cagcatcacc ctcagcatga tgggctggca ttcttgaggc atctcagtgt ttgaattgga   15300
agaatgtgtg gtgaatggca ctgattgaca ttgtgcctct aagtcaccta ttcaattagg   15360
gcgaccgtgt gggggtgaga tttaattggc gagaaccatg cggccgaaat taaaaaaaaa   15420
aaaaaaaaa aaaaaaaaa aaaaaaaaaa aaaaaaa                              15458
```

<210> SEQ ID NO 3
<211> LENGTH: 15460
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 3

```
atgacgtata ggtgttggct ctatgccttg gcatttgtat tgtcaggagc tgtgaccatt     60
ggcacagccc aaaacttgct gcacagaaac acccttctgt gatagcctcc ttcagggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
atggcggagg ccaagtctta ctgcacacga tgcctcagtg cacggtctct ccttcccctg    300
```

```
aacctccagg tttctgagct cggggtgcta ggcctattct acaggcccga agagccactc    360
cggtggacgt tgccacgtgc attccccact gttgagtgct ccccgccgg ggcctgctgg     420 cttctctgcaa tctttccaat cgcacgaatg accagtggaa acctgaactt ccaacaaaga   480
atggtacggg tcgcagctga gctttacaga gccggccagc tcaccccctgc agtcttgaag   540 gctctacaag tttatgaacg gggttgccgc tggtaccccca ttgttggacc tgtccctgga   600
gtggccgttt tcgccaattc cctacatgtg agtgataaac ccttcccggg agcaactcac    660
gtgttgacca acctgccgct cccgcagaga cccaagcctg aagactttg cccctttgag    720 tgtgctatgg ctactgtcta tgacattggt catgacgccg tcatgtatgt ggccgaaagg   780
aaagtctcct gggcccctcg tggcggggat gaagtgaaat ttgaagctgt ccccggggag   840
ttgaagttga ttcgcaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga aactggcggg agaacccagc tactctgggt ttgaggacct cctcagaata   1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg tgcttgtac tagcgccaag   1680 tacgtactta agctggaagg tgagcattgg actgtcactg tgaccccctgg gatgtcccct   1740 tctttgctcc ctcttgaatg tgttcagggc tgttgtgggc gcaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca atcttgaag aatgcttggc caggcttgag   2160
aaagcgcgcc cgccacgcgt aatcgacacc tcctttgatt gggatgttgt gctccctggg   2220
gttgaggcgg caaccagac gatcaagctg ccccaggtca accagtgtcg tgctctggtc   2280
cctgttgtga ctcaaaagtc cttggacaac aactcggtcc cctgaccgc cttttcactg   2340 gctaactact actaccgtgc gcaaggtgac gaagttcgtc accgtgaaag actaaccgcc   2400
gtgctctcca agttggaaaa ggttgttcga aagaatatg ggctcatgcc aaccgagcct   2460
ggtccacggc ccacactgcc acgcgggctc gacgaactca agaccagat ggaggaggac   2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
```

```
gccccgcgca ggaaggttgg gtccgattgt ggcagcccgg tttcattagg cggcgatgtc    2760
cctaacagtt gggaagattt ggctgttagt agccccttty atctcccgac cccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cgggggcgtt    3120
ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgcccaat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg    3720 cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct ctttgaccaa ctgagccgtc aggtttttga cctcgtctcc    3900
catctccctg ttttcttctc acgccttttc taccctggcg gtggttattc tccgggtgat    3960
tggggttttg cagcttttac tctattgtgc ctcttttttat gttacagtta cccagccttt    4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tgggaatctt gtataagaac tgctcccaat gaggtcgctt ttaacgtgtt ccttttcaca    4440
cgtgcgacca ggtcgtcact tatcgacctg tgcgatcggt tttgtgcgcc aaaaggaatg    4500
gaccccattt tcctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860 ggtgtgggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
```

```
tgcgctaacc cgtttgccgt ccctggctac ggacctggct ctctctgcac gtccagattg   5100
tgcatttccc aacacggcct taccctgccc ttgacagcac ttgtggcggg attcggtatt   5160
caagaaattg ccttggtcgt tttgattttt gtttccatcg gaggcatggc tcataggttg   5220
agctgtaagg ctgacatgct gtgtgtcttg cttgcaattg ccagctatgt ttgggtacct   5280
cttacctggt tgctttgtgt gtttccttgc tggttgcgct gtttttcttt gcaccccctc   5340
accatcctat ggtggtgtt tttcttgatt tctgtgaata tgccttcagg aatcttggcc    5400
atggtgttgt tggtttctct ttggcttctt ggtcgttata ctaatgttgc tggccttgtc   5460
accccctacg acattcatca ttacaccagt ggccccgcg tgttgccgc cttggctacc     5520
gcaccagatg ggacctactt ggccgctgtc cgccgcgctg cgttgactgg ccgcaccatg   5580
ctgtttaccc cgtcccagct tgggtctctt cttgagggtg ctttcagaac tcgaaagccc   5640
tcactgaaca ccgtcaatgt gatcgggtcc tccatgggct ctggcggggt gtttaccatc   5700
gacgggaaag tcaagtgcgt aactgccgca catgtcctta cggcaattc agctcgggtt    5760
tccgggtcg gcttcaatca aatgcttgac tttgacgtaa agggagattt cgctatagct    5820
gattgcccga attggcaagg ggctgccccc aagacccaat tctgcacgga tggatggact   5880
ggccgtgcct attggctaac atcctctggc gtcgaacccg cgtcattgg aaaaggattc    5940
gccttctgct tcaccgcatg tggcgattcc gggtccccag tgatcaccga ggccggtgag   6000
cttgtcggcg ttcacacggg atcgaataaa caagggggg gcattgttac gcgcccctca    6060
ggccagtttt gtaatgtggc acccatcaag ctaagcgaat taagtgaatt ctttgctggg   6120
cctaaggtcc cgctcggtga tgtgaaggtc ggcagccaca taattaaaga cataagcgag   6180
gtgccttcag atctttgtgc cttgcttgct gccaaacctg aactggaagg aggcctctcc   6240
accgtccaac ttctttgtgt gttttttctc ctgtggagaa tgatgggaca tgcctggacg   6300
cccttggttg ctgtgagttt ctttattttg aatgaggttc tcccagccgt cctggtccgg   6360
agtgttttct cctttggaat gtttgtgcta tcctggctca cgccatggtc tgcgcaagtt   6420
ctgatgatca ggcttctgac agcagctctt aacaggaaca gatggtcact tgccttttc    6480
agcctcggtg cagtgaccgg ttttgtcgca gatcttgcgg ccactcaggg gcatccgttg   6540
caggcagtga tgaatttgag cacctatgca ttcctgcctc ggatgatggt tgtgacctca   6600
ccagtcccag tgatcacgtg tggtgtcgtg cacctacttg ccatcatttt gtacttgttt   6660
aagtaccgtg gcctgcacca tatccttgtt ggcgatggag tgttctctgc ggctttcttc   6720
ttgagatact tgccgagggg aaagttgagg aaggggtgt cgcaatcctg cggaatgaat   6780
catgagtctc tgactggtgc cctcgctatg agactcaatg acgaggactt ggatttcctt   6840
atgaaatgga ctgattttaa gtgctttgtt tctgcgtcca acatgaggaa tgcagcgggt   6900
caatttatcg aggctgccta tgctaaagca cttagagtag aactggccca gttggtgcag   6960
gttgataaag ttcgaggtac tttggccaaa cttgaagctt ttgctgatac cgtggcacct   7020
caactctcgc ccggtgacat tgttgtcgct ctcggccaca cgcctgttgg cagtatcttc   7080
gacctaaagg ttggtagcac caagcatacc ctccaagcca ttgagaccag agtccttgct   7140
gggtccaaaa tgaccgtggc gcgcgtcgtc gacccgaccc ccacgccccc acccgcaccc   7200
gtgcccatcc ccctcccacc gaaagttctg gagaatggcc caacgcttg ggggatgag    7260
gaccgtttga ataagaagaa gaggcgcagg atgaagccc tcggcatcta tgttatgggc   7320
gggaaaaat accagaaatt ttgggacaag aattccggtg atgtgtttta tgaggaggtc   7380
cataataaca cagatgagtg ggagtgtctc agagttggcg accctgccga ctttgaccct   7440
```

```
gagaagggaa ctctgtgtgg acatgtcacc attgaaaaca aggcttacca tgtttacacc    7500
tccccatctg gtaagaagtt cttggtcccc gtcaacccag agaatggaag agtccaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga aacagcggta aaatagtcaa atttcacaa ccggaccttc accctgggac     7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaaccct ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaacccctg atcgtctatt cggacgacct cgtgctgtat gccgagtctc    9240
ccaccatgcc aaactatcac tggtgggttg aacatctgaa tttgatgctg ggtttcaga    9300 cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480 cttgttttgga gtatgatcct gaatggtttg aagaacttgt agttggaata gcgcagtgcg    9540
cccgcaagga cggctacagc tttccgggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
```

```
ccctgtagg gaaaggcaca agcccttag acgaggtgct ggaacaagtc ccgtataagc    9840
ccccacggac cgttatcatg catgtggagc agggtctcac ccccttgat ccaggtagat     9900
accaaactcg ccgcggatta gtctctgtca ggcgtggaat taggggaaat gaagttggac   9960
taccagacgg tgattatgct agcaccgcct tgctccctac ctgcaaagag atcaacatgg  10020
tcgctgtcgc ttccaatgta ttgcgcagca ggttcatcat cggcccaccc ggtgctggga  10080
aaacatactg gctccttcaa caggtccagg atggtgatgt tatttacaca ccaactcacc  10140
agaccatgct tgacatgatt agggctttgg ggacgtgccg gttcaacgtc ccggcaggca  10200
caacgctgca attccccgtc ccctcccgca ccggtccgtg ggttcgcatc ctagccggcg  10260
gttggtgtcc tggcaagaat tccttcctag atgaagcagc gtattgcaat caccttgatg  10320
ttttgaggct tcttagtaaa actaccctca cctgtctagg agacttcaag caactccacc  10380
cagtgggttt tgattctcat tgctatgttt ttgacatcat gcctcaaact caactgaaga  10440
ccatctggag gtttggacag aatatctgtg atgccattca gccagattac agggacaaac  10500
tcatgtccat ggtcaacaca acccgtgtga cctacgtgga aaaacctgtc aggtatgggc  10560
aggtcctcac cccctaccac agggaccgag aggacgacgc catcactatt gactccagtc  10620
aaggcgccac attcgatgtg gttacattgc atttgcccac taaagattca ctcaacaggc  10680
aaagagccct tgttgctatc accagggcaa gacacgctat ctttgtgtat gacccacaca  10740
ggcagctgca gggcttgttt gatcttcctg caaaaggcac gcccgtcaac ctcgcagtgc  10800
actgcgacgg gcagctgatc gtgctggata gaaataacaa agaatgcacg gttgctcagg  10860
ctctaggcaa cggggataaa tttagggcca cagacaagcg tgttgtagat tctctccgcg  10920
ccatttgtgc tgatctagaa gggtcgagct ctccgctccc caaggtcgca cacaacttgg  10980
gattttattt ctcacctgat ttaacacagt ttgctaaact cccagtagaa cttgcacctc  11040
actggcccgt ggtgtcaacc cagaacaatg aaaagtggcc ggatcggctg gttgccagcc  11100
ttcgccctat ccataaatac agccgcgcgt gcatcggtgc cggctatatg gtgggccctt  11160
cggtgtttct aggcactcct ggggtcgtgt catactatct cacaaaattt gttaagggcg  11220
gggctcaagt gcttccggag acggttttca gcaccggccg aattgaggta gactgccggg  11280
aatatcttga tgatcgggag cgagaagttg ctgcgtccct cccacacgct ttcattggcg  11340
acgtcaaagg cactaccgtt ggaggatgtc atcatgtcac ctccagatac ctcccgcgcg  11400
tccttcccaa ggaatcagtt gcggtagtcg gggtttcaag cccggaaaa gccgcgaaag  11460
cattgtgcac actgacagat gtgtacctcc cagatcttga agcctatctc cacccggaga  11520
cccagtccaa gtgctggaaa atgatgttgg acttcaaaga agttcgacta atggtctgga  11580
aagacaaaac agcctatttc caacttgaag gtcgctattt cacctggtat cagcttgcca  11640
gctatgcctc gtacatccgt gttcccgtca actctacggt gtacttggac ccctgcatgg  11700
gcccccgccct ttgcaacagg agagtcgtcg ggtccaccca ctgggggggct gacctcgcgg  11760
tcacccctta tgattacggc gctaaaatta tcctgtctag cgcgtaccat ggtgaaatgc  11820
cccccggata caaaattctg gcgtgcgcgg agttctcgtt ggatgaccca gttaagtaca  11880
aacatacctg gggggtttgaa tcggatacag cgtatctgta tgagttcacc ggaaacggtt  11940
aggactggga ggattacaat gatgcgtttc gtgcgcgcca ggaagggaaa atttataagg  12000
ccactgccac cagcttgaag ttttattttc cccgggccc tgtcattgaa ccaactttag  12060
gcctgaattg aaatgaaatg gggtccatgc aaagcctttt tgacaaaatt ggccaacttt  12120
ttgtggatgc tttcacggag ttcttggtgt ccattgttga tatcattata ttttggcca   12180
```

```
ttttgtttgg cttcaccatc gccggttggc tggtggtctt ttgcatcaga ttggtttgct    12240
ccgcgatact ccgtacgcgc cctgccattc actctgagca attacagaag atcttatgag    12300
gcctttcttt cccagtgcca agtggacatt cccacctggg gaactaaaca tcctttgggg    12360
atgctttggc accataaggt gtcaaccctg attgatgaaa tggtgtcgcg tcgaatgtac    12420
cgcatcatgg aaaaagcagg gcaggctgcc tggaaacagg tggtgagcga ggctacgctg    12480
tctcgcatta gtagtttgga tgtggtggct cattttcagc atctagccgc cattgaagcc    12540
gagacctgta aatatttggc ctcccggctg cccatgctac acaacctgcg catgacaggg    12600
tcaaatgtaa ccatagtgta taatagcact ttgaatcagg tgtttgctat ttttccaacc    12660
cctggttccc ggccaaagct tcatgatttt cagcaatggt taatagctgt acattcctcc    12720
atattttcct ctgttgcagc ttcttgtact ctttttgttg tgctgtggtt gcggttcca    12780 atactacgta ctgttttgg tttccgctgg ttaggggcaa ttttctttc gaactcacag    12840 tgaattacac ggtgtgtcca ccttgcctca cccggcaagc agccacagag atctacgaac    12900
ccggtaggtc tctttggtgc aggatagggt atgaccgatg tggggaggac gatcatgacg    12960
agctagggtt tatgataccg cctggcctct ccagcgaagg ccacttgact ggtgtttacg    13020
cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcaaata ttaagaccaa caccaccgca gcggcaagct ttgctgtcct    13380
ccaagacatc agttgcctta ggcatcgcga ctcggcctct gaggcgattc gcaaaatccc    13440
tcagtgccgt acggcgatag ggacacccgt gtatgttacc atcacagcca atgggacaga    13500
tgagaattat ctacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttttgcca ttctgttggc aatttgaatg tttaagtatg ttggagaaat    13800
gcttgaccgc gggctgttgc tcgcgattgc tttctttgtg gtgtatcgtg ccgttctgtc    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggctccg    14340
tggcaacccc tataaccaga gtttcagcgg aacaatgggg tcgtccttag atgacttctg    14400
tcacgatagc acggctccac aaaaggtgct tttggcgttt tctattacct acacgccagt    14460
gatgatatat gccctaaagg tgagtcgcgg ccgactgcta gggcttctgc acctttgat    14520
```

```
cttcctgaat tgtgctttca ccttcgggta catgactttc gcgcactttc agagtacaaa  14580
taaggtcgcg ctcactatgg gagcagtagt tgcactcctt tggggggtgt actcagccat  14640
agaaacctgg aaattcatca cctccagatg ccgtttgtgc ttgctaggcc gcaagtacat  14700
tctggcccct gcccaccacg ttgaaagtgc cgcaggcttt catccgattg cggcaaatga  14760
taaccacgca tttgtcgtcc ggcgtcccgg ctccactacg gtcaacggca cattggtgcc  14820
cgggttaaaa agcctcgtgt tgggtggcag aaaagctgtt aaacagggag tggtaaacct  14880
tgtcaaatat gccaaataac aacggcaagc agcagaagag aaagaagggg gatggccagc  14940
cagtcaatca gctgtgccag atgctgggta agatcatcac tcagcaaaac cagtccagag  15000
gcaagggacc gggaaagaaa aataagaaga aaaacccgga gaagccccat tttcctctag  15060
cgactgaaga tgatgtcaga catcacttta cccctagtga gcggcaattg tgtctgtcgt  15120
caatccagac cgcctttaat caaggcgctg ggacttgcac cctgtcagat tcagggagga  15180
taagttacac tgtggagttt agtttgccta cgcatcatac tgtgcgcctg atccgcgtca  15240
cagcatcacc ctcagcatga tgggctggca ttcttgaggc atctcagtgt ttgaattgga  15300
agaatgtgtg gtgaatggca ctgattgaca ttgtgcctct aagtcaccta ttcaattagg  15360
gcgaccgtgt gggggtgaga tttaattggc gagaaccatg cggccgaaat taaaaaaaaa  15420
aaaaaaaaaa aaaaaaaaaa aaaaaaaaaa aaaaaaaccc                        15460
```

```

<210> SEQ ID NO 4
<211> LENGTH: 15456
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 4
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttgcac tgctttacgg tctctccacc    180
cctttaacca tgtctgggat acttgatcgg tgcacgtgta cccccaatgc cagggtgttt    240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct cccccgccgg ggcctgctgg    420
ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg ggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg cccctttgag    720
tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc cccaccacac agtggacatg    900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
```

```
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt ttgaggacct cctcagaata    1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcattccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccccctgg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaaagcgcgc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca gttggaaaa ggttgttcga gaagaatatg ggctcatgcc aaccgagcct    2460
ggtccacggc ccacactgcc acgcgggctc gacgaactca agaccagat ggaggaggac    2520
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac ccacctgag    2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct cccccagcac cgccgcagag cggggcgtt    3120
ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gacccctgcta cgcaggaatg gctttctcgc atgtgggatc ggtggacat gctgacttgg    3420
cgcaacacgt ctgtttacca ggcgatttgc accttagatg gcaggttaaa gttcctccca    3480
```

```
aaaatgatac tcgagacacc gccgccctat ccgtgtgagt ttgtgatgat gcctcacacg    3540
cctgcacctt ccgtaggtgc ggagagcgac cttaccattg gctcagttgc tactgaagat    3600
gttccacgca tcctcgagaa aatagaaaat gtcggcgaga tggccaacca gggacccttg    3660
gccttctccg aggataaacc ggtagatgac caacttgtca acgaccccg gatatcgtcg     3720 cggaggcctg acgagagcac atcagctccg tccgcaggca caggtggcgc cggctctttt    3780
accgatttgc cgccttcaga tggcgcggat gcggacgggg gggggccgtt tcggacggta    3840
aaaagaaaag ctgaaaggct ctttgaccaa ctgagccgtc aggttttga cctcgtctcc      3900 catctccctg ttttcttctc acgccttttc taccctggcg gtggttattc tccgggtgat    3960
tggggttttg cagcttttac tctattgtgc ctcttttat gttacagtta cccagccttt     4020
ggtattgctc ccctcttggg tgtgttttct gggtcttctc ggcgcgttcg aatgggggtt    4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcccaat gaggtcgctt ttaacgtgtt tcctttcaca    4440
cgtgcgacca ggtcgtcact tatcgacctg tgcgatcggt tttgtgcgcc aaaaggaatg    4500
gaccccattt ttctcgccac tgggtggcgc gggtgctggg ccggccgaag ccccattgag    4560
caaccctctg aaaaacccat cgcgtttgcc cagttggatg aaaagaagat tacggctagg    4620
actgtggtcg cccagcctta tgaccccaac caagccgtaa agtgcttgcg ggtattgcag    4680
gcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca cttttcactgc agctctccgg tctggctact ccaccacaaa cctcgtcctt    4860
ggtgtggggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccagattg    5100
tgcatttccc aacacggcct taccctgccc ttgacagcac ttgtggcggg attcggtatt    5160
caagaaattg ccttggtcgt tttgatttt gtttccatcg gaggcatggc tcataggttg      5220
agctgtaagg ctgacatgct gtgtgtcttg cttgcaattg ccagctatgt ttgggtacct    5280
cttacctggt tgctttgtgt gtttccttgc tggttgcgct gttttctttt gcacccctc      5340 accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggccccgcg gtgttgccgc cttggctacc       5520
gcaccagatg ggacctactt ggccgctgtc cgccgcgctg cgttgactgg ccgcaccatg    5580
ctgtttaccc cgtcccagct tgggtctctt cttgagggtc tttcagaac tcgaaagccc     5640 tcactgaaca ccgtcaatgt gatcgggtcc tccatgggct ctggcggggt gtttaccatc    5700
gacgggaaag tcaagtgcgt aactgccgca catgtcctta cggcaattc agctcgggtt      5760 tccggggtcg gcttcaatca aatgcttgac tttgacgtaa agggagattt cgctatagct    5820
```

```
gattgcccga attggcaagg ggctgcccce aagacccaat tctgcacgga tggatggact      5880
ggccgtgcct attggctaac atcctctggc gtcgaacccg gcgtcattgg aaaaggattc      5940
gccttctgct tcaccgcatg tggcgattcc gggtccccag tgatcaccga ggccggtgag      6000
cttgtcggcg ttcacacggg atcgaataaa caagggggg gcattgttac gcgcccctca       6060
ggccagtttt gtaatgtggc acccatcaag ctaagcgaat taagtgaatt ctttgctggg      6120
cctaaggtcc cgctcggtga tgtgaaggtc ggcagccaca taattaaaga cataagcgag      6180
gtgccttcag atctttgtgc cttgcttgct gccaaacctg aactggaagg aggcctctcc      6240
accgtccaac ttctttgtgt gttttttctc ctgtggagaa tgatgggaca tgcctggacg      6300
cccttggttg ctgtgagttt ctttattttg aatgaggttc tcccagccgt cctggtccgg      6360
agtgttttct cctttggaat gtttgtgcta tcctggctca cgccatggtc tgcgcaagtt      6420
ctgatgatca ggcttctgac agcagctctt aacaggaaca gatggtcact tgccttttc      6480
agcctcggtg cagtgaccgg ttttgtcgca gatcttgcgg ccactcaggg gcatccgttg      6540
caggcagtga tgaatttgag cacctatgca ttcctgcctc ggatgatggt tgtgacctca      6600
ccagtcccag tgatcacgtg tggtgtcgtg cacctacttg ccatcatttt gtacttgttt      6660
aagtaccgtg gcctgcacca tatccttgtt ggcgatgag tgttctctgc ggcttcttc       6720
ttgagatact tgccgaggg aaagttgagg aagggtgt cgcaatcctg cggaatgaat         6780
catgagtctc tgactggtgc cctcgctatg agactcaatg acgaggactt ggatttcctt      6840
atgaaatgga ctgattttaa gtgctttgtt tctgcgtcca acatgaggaa tgcagcgggt      6900
caatttatcg aggctgccta tgctaaagca cttagagtag aactggccca gttggtgcag      6960
gttgataaag ttcgaggtac tttggccaaa cttgaagctt tgctgatac cgtggcacct      7020
caactctcgc ccggtgacat tgttgtcgct ctcggccaca cgcctgttgg cagtatcttc      7080
gacctaaagg ttggtagcac caagcatacc ctccaagcca ttgagaccag agtccttgct      7140
gggtccaaaa tgaccgtggc gcgcgtcgtc gacccgaccc ccacgccccc acccgcaccc      7200
gtgcccatcc ccctcccacc gaaagttctg gagaatggcc caacgcttg gggggatgag      7260
gaccgtttga ataagaagaa gaggcgcagg atggaagccc tcggcatcta tgttatgggc      7320
gggaaaaaat accagaaatt ttgggacaag aattccggtg atgtgtttta tgaggaggtc      7380
cataataaca cagatgagtg ggagtgtctc agagttggcg accctgccga ctttgacccct     7440
gagaagggaa ctctgtgtgg acatgtcacc attggaaaca aggcttacca tgtttacacc      7500
tccccatctg gtaagaagtt cttggtcccc gtcaacccag agaatggaag agtccaatgg      7560
gaagctgcaa agctttccgt ggagcaggcc ctaggtatga tgaatgtcga cggcgaactg      7620
actgccaaag aactggagaa actgaaaaga ataattgaca aactccaggg cctgactaag      7680
gagcagtgtt taaactgcta gccgccagcg acttgacccg ctgtggtcgc ggcggcttgg      7740
ttgttactga aacagcggta aaaatagtca aatttcacaa ccggaccttc acccctgggac      7800
ctgtgaattt aaaagtggcc agtgaggttg agctaaaaga cgcggttgag cacaaccaac      7860
acccggttgc gagaccgatc gatggtggag ttgtgctcct gcgttccgcg gttccttcgc      7920
ttatagacgt cttgatctcc ggtgctgatg catctcccaa gttacttgcc catcacgggc      7980
cgggaaacac tgggatcgat ggcacgctct gggattttga gtccgaagcc actaaagagg      8040
aagtcgcact cagtgcgcaa ataatacagg cttgtgacat taggcgcggc gacgctcctg      8100
aaattggtct cccttacaag ctgtaccctg ttagggtaa ccctgagcgg gtgaaaggag       8160
ttctgcagaa tacaaggttt ggagacatac cttacaaaac ccccagtgac actggaagcc      8220
```

```
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc acccctttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaaccctg atcgtctatt cggacgacct cgtgctgtat gccgagtctc    9240
ccaccatgcc aaactatcac tggtgggttg aacatctgaa tttgatgctg gggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480 cttgttttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc    9840
ccccacggac cgttatcatg catgtggagc agggtctcac ccccttgat ccaggtagat    9900 accaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc cctcccgca ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gttggacag aatatctgtg atgccattca gccagattac agggacaaac   10500
tcatgtccat ggtcaacaca acccgtgtga cctacgtgga aaaacctgtc aggtatgggc   10560
```

```
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacgct ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc caccggagaa   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcaccccctta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc cccggggccc tgtcattgaa ccaactttag   12060
gcctgaattg aaatgaaatg gggtccatgc aaagcctttt tgacaaaatt ggccaacttt   12120 tgtggatgc tttcacggag ttcttggtgt ccattgttga tatcattata ttttggcca   12180 ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tccttgggg   12360 atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact tgaatcagg tgtttgctat ttttccaacc   12660
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgttttggg tttccgctgg ttaggggcaa ttttttcttc gaactcacag   12840
tgaattacac ggtgtgtcca ccttgcctca cccggcaagc agccacagag atctacgaac   12900
ccggtaggtc tctttggtgc aggataaggt atgaccgatg tggggaggac gatcatgacg   12960
```

```
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct ttgctgtcct   13380
ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgtcaaggag tttacccaac gctccctggt   13680
ggtcgaccat gtgcggttgc tccatttcat gacacctgag accatgaggt gggcaactgt   13740
tttagcctgt cttttttgcca ttctgttggc aatttgaatg tttaagtatg ttggagaaat   13800
gcttgaccgc gggctgttgc tcgcgattgc tttctttgtg gtgtatcgtg ccgttctgtt   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catctttccc gttttgactc acattgtctc ctatggtgcc ctcactacca   14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac taagggcaga ctctatcgtt ggcggtcgcc tgtcatcata gagaaaaggg   14280
gcaaagttga ggtcgaaggt catctgatcg acctcaaaag agttgtgctt gatggctccg   14340
tggcaacccc tataaccaga gtttcagcgg aacaatgggg tcgtccttag atgacttctg   14400
tcacgatagc acggctccac aaaaggtgct ttggcgtttt tctattacct acacgccagt   14460
gatgatatat gccctaaagg tgagtcgcgg ccgactgcta gggcttctgc acctttgat    14520 cttcctgaat tgtgctttca ccttcgggta catgactttc gcgcactttc agagtacaaa   14580
taaggtcgcg ctcactatgg gagcagtagt tgcactcctt tgggggtgt actcagccat    14640 agaaacctgg aaattcatca cctccagatg ccgtttgtgc ttgctaggcc gcaagtacat   14700
tctggcccct gcccaccacg ttgaaagtgc cgcaggcttt catccgattg cggcaaatga   14760
taaccacgca tttgtcgtcc ggcgtccggg ctccactacg gtcaacggca cattggtgcc   14820
cgggttaaaa agcctcgtgt tgggtggcag aaaagctgtt aaacagggag tggtaaacct   14880
tgtcaaatat gccaaataac aacggcaagc agcagaagag aaagaagggg gatgccagc    14940 cagtcaatca gctgtgccag atgctgggta agatcatcgc tcagcaaaac cagtccagag   15000
gcaagggacc gggaaagaaa aataagaaga aaacccgga gaagccccat tttcctctag    15060
cgactgaaga tgatgtcaga catcacttta cccctagtga gcggcaattg tgtctgtcgt   15120
caatccagac cgcctttaat caaggcgctg ggacttgcac cctgtcagat tcaggagga    15180 taagttacac tgtggagttt agtttgccta cgcatcatac tgtgcgcctg atccgcgtca   15240
cagcatcacc ctcagcatga tgggctggca ttcttgaggc atctcagtgt ttgaattgga   15300
```
agaatgtgtg gtgaatggca ctgattgaca ttgtgcctct aagtcaccta ttcaattagg     15360
gcgaccgtgt gggggtgaga tttaattggc gagaaccatg cggccgaaat taaaaaaaaa     15420
aaaaaaaaaa aaaaaaaaaa aaaaaaaaaa aaaaaa                               15456

```
<210> SEQ ID NO 5
<211> LENGTH: 15019
<212> TYPE: DNA
<213> ORGANISM: Artificial Sequence
<220> FEATURE:
<223> OTHER INFORMATION: Porcine reproductive and respiratory syndrome
      virus, strain MN184A
<220> FEATURE:
<221> NAME/KEY: misc_feature
<222> LOCATION: (654)..(654)
<223> OTHER INFORMATION: S = C or G
<220> FEATURE:
<221> NAME/KEY: misc_feature
<222> LOCATION: (735)..(735)
<223> OTHER INFORMATION: M = A or C
<220> FEATURE:
<221> NAME/KEY: misc_feature
<222> LOCATION: (745)..(745)
<223> OTHER INFORMATION: Y = C or T
<220> FEATURE:
<221> NAME/KEY: misc_feature
<222> LOCATION: (1627)..(1627)
<223> OTHER INFORMATION: R = A or G
<220> FEATURE:
<221> NAME/KEY: misc_feature
<222> LOCATION: (1642)..(1642)
<223> OTHER INFORMATION: Y = C or T
<220> FEATURE:
<221> NAME/KEY: misc_feature
<222> LOCATION: (1736)..(1736)
<223> OTHER INFORMATION: Y = C or T
<220> FEATURE:
<221> NAME/KEY: misc_feature
<222> LOCATION: (1987)..(1987)
<223> OTHER INFORMATION: R = A or G
<220> FEATURE:
<221> NAME/KEY: misc_feature
<222> LOCATION: (2061)..(2061)
<223> OTHER INFORMATION: R = A or G
<220> FEATURE:
<221> NAME/KEY: misc_feature
<222> LOCATION: (2161)..(2161)
<223> OTHER INFORMATION: R = A or G
<220> FEATURE:
<221> NAME/KEY: misc_feature
<222> LOCATION: (2186)..(2186)
<223> OTHER INFORMATION: R = A or G
<220> FEATURE:
<221> NAME/KEY: misc_feature
<222> LOCATION: (2228)..(2228)
<223> OTHER INFORMATION: R = A or G
<220> FEATURE:
<221> NAME/KEY: misc_feature
<222> LOCATION: (2293)..(2293)
<223> OTHER INFORMATION: Y = C or T
<220> FEATURE:
<221> NAME/KEY: misc_feature
<222> LOCATION: (3407)..(3407)
<223> OTHER INFORMATION: R = A or G
<220> FEATURE:
<221> NAME/KEY: misc_feature
<222> LOCATION: (5992)..(5992)
<223> OTHER INFORMATION: Y = C or T
<220> FEATURE:
<221> NAME/KEY: misc_feature
<222> LOCATION: (5994)..(5994)
<223> OTHER INFORMATION: Y = C or T        R = A or G
<220> FEATURE:
<221> NAME/KEY: misc_feature
<222> LOCATION: (5995)..(5995)
<223> OTHER INFORMATION: K= G or T
<220> FEATURE:
```

```
<221> NAME/KEY: misc_feature
<222> LOCATION: (5998)..(5998)
<223> OTHER INFORMATION: R = A or G
<220> FEATURE:
<221> NAME/KEY: misc_feature
<222> LOCATION: (6001)..(6001)
<223> OTHER INFORMATION: Y = C or T
<220> FEATURE:
<221> NAME/KEY: misc_feature
<222> LOCATION: (6704)..(6704)
<223> OTHER INFORMATION: R = A or G
<220> FEATURE:
<221> NAME/KEY: misc_feature
<222> LOCATION: (8811)..(8811)
<223> OTHER INFORMATION: Y = C or T
<220> FEATURE:
<221> NAME/KEY: misc_feature
<222> LOCATION: (9777)..(9777)
<223> OTHER INFORMATION: R = A or G
<220> FEATURE:
<221> NAME/KEY: misc_feature
<222> LOCATION: (11935)..(11935)
<223> OTHER INFORMATION: Y = C or T
<220> FEATURE:
<221> NAME/KEY: misc_feature
<222> LOCATION: (13527)..(13527)
<223> OTHER INFORMATION: M = A or C
<220> FEATURE:
<221> NAME/KEY: misc_feature
<222> LOCATION: (14133)..(14133)
<223> OTHER INFORMATION: Y = C or T
<220> FEATURE:
<221> NAME/KEY: misc_feature
<222> LOCATION: (14947)..(14947)
<223> OTHER INFORMATION: Y = C or T

<400> SEQUENCE: 5
atgacgtata ggtgttggct ctatgccacg acatttgtat tgtcaggagc tgtgaccact      60
ggcacagccc aaagcttgct gcacagaaac acccttctgt gacggcctcc ttcaggggag     120
tttaggggtt tatccctagc accttgtttc tggagttgca ctgctttacg gtctctccac     180 cccttaacc atgtctggga ttcttgatcg gtgcacgtgc accccaatg ccagggtgtt      240 tatggcagag ggccaagtct actgcacacg atgtctcagt gcacggtccc tccttcccct     300
gaatctccaa gtccctgagc tcggagtgtt gggcttgttt tataggcccg aagagccgct     360
ccggtggacg ttgccacgcg cattccccac tgttgagtgc tcccctgctg gggcttgttg     420
gctttctgca attttccaa ttgcacgaat gaccagtgga aacctgaact ttcaacaaag      480
attagtgcgg gtcgcagctg agctttacaa agccggctgc ctcaccccta gtcctaaa       540 gaatctacaa gtctatgaac ggggttgccg atggtacccc atcgttggac ctgtccctgg     600
agttgccgtt ttcgccaact ccctacatgt gagtgataga cctttcccag gggstactca     660
cgtgctaacc aacctgccgc tcccgcagag acctaagcct gaagatttt gccccttga      720 gtgtgctatg gctgmcgtct atgayattgg tcatgacgcc gttatgttcg tggccgaagg     780
gagagtctcc tgggctccgc gtggtggggg aaaaggaaaa tttgaaactg ttcccgagga     840
gttgaggttg attgcagagc aactttatac ctccttcccg ccccaccacg tggtggacat     900
gtcgaaattc acctttacgg cccctgagtg tggtgcttcc atgcgagtcg aacgccatta     960
tggctgcctc cccgccggca ctgtccctga cggcaattgc tggtggagtt tgtttagctc    1020
gctcccattg gaaatccagt acaaagaaat tcgccacgcc acccaatttg gctatcaaac    1080
taagcatggc gttgctggca agtacctaca gcggaggctg caagttaatg gtctccgagc    1140
agtggttgac tcgaatggac ctatcgtcat acagtacttc tctgttaagg agagctggat    1200
ccgccacgtg aaactggcgg aagagtttga ctaccctggg tttgaggatc tcctcaggat    1260
```

```
aagagtcgag cccaacacgt tgccattgtc aacaaggac gagaaaatct tccggtttgg   1320
tgggtgcaag tggtacggtg ctgggaagag ggcaaggagg gcacgtgcaa gtgcagtcac   1380
cgcagtcgcc ggtcacgctc cgcctactcg tgaaacccag caagccaaga aacacgaggc   1440
tgctagtgcc aacaaggctg agcttcttga acgctactcc ccgcctgctg aagggaattg   1500
cggctggcac tgtatttccg ccatcgccaa tcggatggta aattctaagt ttgagactgc   1560
ccttcccgaa agagtgagat ccccagaaga ctgggctact gatgaggatc ttgtgaatac   1620
tatccaratc ctcaggctcc cygcggcctt agacaggaac ggcgcctgtg caagcgccaa   1680
gtacatcctt aagctggaag gtgagcactg gactgtttca gtgattcccg gaatgycccc   1740
ttccttgctc ccccttgaat gcgttcaggg ttgctgtgag cataagggta atcttggttc   1800
tccgaacgcg gtcggggttt ttggattcga ccctgccagc cttgaccgac ttgctggggt   1860
gatgcacctg cccagcagtg ccatcccagc cgctctggcc gagttgtctg gcgaccttga   1920
tcgtccaact tccccggccg ccactgtgtg gactgtctcg cagttttatg ctcgtcatag   1980
tggaggrgag catcctgatc aaaagtgttt aaaaaaaatt atcagtctct gtgaggtgat   2040
cgagagttgt tgctgttctc rgaacaaaac taaccgggtc accccggaag aggtcacagc   2100
aaagattgat ctgtaccttt ttggtgcagc aagtcttgaa gaatgcttgg ccaggcttga   2160
raaagctcgc ccgccaagcg tattaracac ctcctttgat tgggatgttg tgctccctgg   2220
tgttgggrcg gctgctcaag cagcaaaact gcccctcacc aaccagcgtc acgctctagc   2280
cactgttgtg acycaaaggt ctttgccgaa atttcaacct cgaaaagcgg agtctgtcaa   2340
gagcctacca gagagcaggc cactccctgc cccgcgcaaa aagattaggt ccaggtgtgg   2400
tagtccgatt tcattgggcg gcaatctccc tgacagccag gaagacttgg ccggtggttc   2460
ctttgatttc ccaaccctac ctgagttggt ggtaagctcg agtgagtctg tgcctgtccc   2520
tgcaccgcgc agggttgtgt cccgattagt gtcgtctccg atagtgtcga cccctgtgcc   2580
cgcaccacga cgtgggcttc ggcaggtgga gggaatgaat ttggcggcag tgactctagc   2640
gtgccaggac gagcccctcg atttgtctgc gtcctcgcag actgaatatg aggcgtcccc   2700
cttggcattg ccgctgagtg aggatgtcct ggcggtggag agacgagaag ttgaagaagt   2760
cctgagcgga atatcgggca tgtcagatga catcaggttg gcgcccgtgt catcaagtag   2820
ctccctgtca agcatagaga tcacacgtcc aaagtactca gctcaagcca tcattaactc   2880
aggtgggccc tgttgtgggc acctccagga ggtgaaagag aaataccttac atgtgatgcg   2940
tgaggcatgt gatgcgacca agcttgatga ccctgccacg caagaatggc tttcccgtat   3000
gtgggatagg gtagacatgc taacctggcg caacacgtcc attttcagg cgcctttcac   3060
cttggctgac aagtttaagt ccctcccgaa gatgatactc gaaacaccgc cgccctaccc   3120
ttgtgggttt gtgatgatgc cccgcacgcc tgcaccttct gtaggtgcgg agagcgacct   3180
caccgttggc tcagttgcta ctgaagatgt ccgcgcgatt tcggggaagg tacaaggtgt   3240
tggcgaaacg accgaccagg gaccctgggc actcttcgca gatgaattgg cagatgacca   3300
acctgctaga gaaccccgga cacaaacccc tcctgcaagc gcaggtggcg ccggcttagt   3360
tttggattct ggagggtcgc cggagctcac tgacctgccg cttccaracg gtacagacgc   3420
gggcggaggg ggaccgttac acacggtcaa gaagaaagct gagaggtgct ttgaccagct   3480
gagccgtcgg gttttttgaca ttgtctccca tctccctgtc ttcttctcac gccttttcaa   3540
gcctgacagt cactactctt cgggtgactg gagttttgca gcttttactt tattgtgcct   3600
```

```
ctttctatgt tacagttacc cggcctttgg tgttgctccc ctattgggtg tattttctgg    3660
gtcttctcgg cgcgttcgca tgggggtttt tggctgctgg ttggctttcg ctgttggttt    3720
gttcaagcct gcacccgacc cagtcggtgc tgcttgtgag tttgattcgc cagagtgtag    3780
agacatcctt cattcttttg agctcctgca accttgggat cctgttcgca gccttgtggt    3840
gggacccgtc ggtctcggtc ttgccattat tggcaggtta ctgggcgggg cacgctacgt    3900
ctggctgctt ttgcttaggc ttggcatcgt ttcagactgt atcttggctg agcttacgt    3960
gctttcgcaa ggtaggtgta aaaagtgttg gggatcttgt ataagaactg cccccagtga    4020
ggtcgccttc aatgtgtttc ccttcacacg tgcaaccaga tcgtcacttg tcgacctgtg    4080
cgaccggttt tgtgcgccca agggcatgga ccccatcttc ctcgccactg gatggcgcgg    4140
atgctggtcc ggccagagcc ccgttgagca acccactgag aaacccattg cattcgccca    4200
gttggatgag aagaaaatca cggcaaggac tgtggttgcc caaccttatg accccaacca    4260
agctgtgaag tgcttacgag tcttgcaggc gggtggggcg atggtggctg aggcgattcc    4320
aaaagtggtt aaggtctctg ctgtcccatt tcgagccccc ttcttcccca ccggagtgaa    4380
agttgatcct gaatgcaggg tcgtggttga cccagacacc ttcacaactg ctctccggtc    4440
cggctactcc accacaaacc tcattcttgg tgtggggat ttttgcccagc tgaatgggtt    4500
gaaaatcaga caaatttcca agccttcagg aggaggccca tacctcatgg cggccttaca    4560
tgtcgcttgc tcgatggcct tgcacatgct cgttgggatt tatgttaccg cggtgggttc    4620
ttgtggttct ggcactaacg atccgtggtg cactaacccg tttgccgtcc ctgtctacgg    4680
gcctggctct ctttgcacgt ccaggttgtg catctcccag catggcctta ctctgccttt    4740
aacagcgctt gtggcggggt ttggtattca ggaagttgct ttggttgttt taatctttgc    4800
ttccatcggg ggtatggctc acaggttgag ttgcaaggcc gatgtgctgt gcattctgct    4860
tgcaattgcc agctatgttt gggtacccct cacctggttg cttttgtgtgt tccttgctg    4920
gttgcgctgg ttttctttgc atcccctcac cattctatgg ttggtgtttt ttttgatttc    4980
tgtgaacatg ccctcaggaa tcttggcttt agtgttgttg atctctctct ggctccttgg    5040
tcgctatacc aatgtcgctg gccttgtcac cccttatgac attcaccatt acaccaacgg    5100
cccccgcggc gttgccgcct tggccactgc cccggatggg acctatttgg ctgctgtccg    5160
ccgcgctgcg ttgactggcc gtaccatgct gtttaccccg tctcaacttg gtcactcct    5220
tgagggcgcc tttagaaccc aaaagccttc actgaatacc gtcaatgtgg ttgggtcctc    5280
catgggctcc ggcggggtgt tcaccattga cgggaaaatt aaatgcgtga ccgccgcaca    5340
tatcctcacg ggtaactctg ctagggtctc tggggttggc ttcaatcaaa tgttggattt    5400
tgatgtaaaa gggatttttg ccatagccga ttgtccgggt tggcaaggag tcgctcccaa    5460
gtcccagatc tgcaaggatg ggtggactgg ccgcgcttat tggctaacgt cctctggcgt    5520
cgaaccggc gtcattggta ggggattcgc cttttgtttc accgcgtgcg gcgattccgg    5580
gtccccagtg atcaccgagg ccggagagct tgtcggagtc cacacgggat caaacaaaca    5640
aggaggaggc attgtcacgc gcccttcagg ccagttttgt aatgtgacac ccaccaaact    5700
aagtgaattg agtgaattct cgccggacc cagggtcccg cttggtgatg tgaaggttgg    5760
caaccacata atcaaagata cagatgaggt gccctcagat ctttgcgcct tgcttgctgc    5820
caagcccgag ttgaaggag gcctctccac cgttcaactt ctgtgcgtgt ttttctcct    5880
atggagaatg atgggacatg cctggacgcc cttggttgct gttggttttt tcatcttgaa    5940
tgaratcctc ccagcggtcc tggtccggag tgttttctcc tttggaatgt tygykctrtc    6000
```

```
ytggctcacg ccatggtctg cgcaagttct gatgatcagg cttctgacag cagctcttaa    6060
caggaacaga tggtcacttg ccttttttcag cctcggtgca gtgaccggtt ttgtcgcaga   6120
tcttgcggcc actcaggggc atccgttgca ggcagtgatg aatttgagca cctatgcatt   6180
cctgcctcgg atgatggttg tgacctcacc agtcccagtg atcacgtgtg gtgtcgtgca   6240
cctacttgcc atcattttgt acttgtttaa gtaccgtggc ctgcaccata tccttgttgg   6300
cgatggagtg ttctctgcgg ctttcttctt gagatacttt gccgagggaa agttgaggga   6360
aggggtgtcg caatcctgcg gaatgaatca tgagtctctg actggtgccc tcgctatgag   6420
actcaatgac gaggacttgg atttccttat gaaatggact gattttaagt gctttgtttc   6480
tgcgtccaac atgaggaatg cggcgggtca gtttatcgag gccgcttatg cgaaagcgat   6540
cagggtggaa cttgcccagt tagtgcaggt cgacaaggtt cggggtgttt tagccaaact   6600
tgaagctttt gctgacaccg tggcgcccca tctttcaccc ggcgacattg ttgttgttct   6660
tggtcatacg cccgttggca gcatctttga cttaaagatt ggcratgcca agcacaccct   6720
acaagccatc gagaccagag tccttgctgg gtccaggatg accgtggcgc gtgtcgttga   6780
tccgactccc gcgccgccac ccgtacccgt gcccgttcct ctcccaccga aagttttaga   6840
gaacggcccc agtgcctggg gggatgaaga ccgcctgaac aaaaagaagc ggcgcaagat   6900
ggaagccgtt ggcgtttacg tcatgggcgg gaaaaagtac cagaaattt gggataagaa    6960
ttctggtgat gtgttctatg aggaagtcca cgacaacaca gatgcgtggg aatgccttag   7020
agctgacgac cctgccgact ggatcctga gaggggaacc ttgtgtggac acgtcaccat    7080
agagaatagg ccttaccatg tttacgcctc cccgtctggt aggaagttcc tggtccctgc   7140
cgacccagag aatgggaaag cccagtggga agctgcaaag cttccatag agcaggccct    7200
tggtatgatg aacgttgacg gcgagctgac cgccaaagaa ctggagaaat tgaagagaat   7260
aattgacaaa ctccagggcc tgactaagga gcagtgttta aactgttagc cgccagcggc   7320
ttgacccgct gtggtcgcgg cggcttggtt attactgaga cagcggtaaa aatagtcaga   7380
ttccacaatc ggaccttcac cctgggggcct gtgaatttga aagtggccag cgaagttgag   7440
ttgaaagacg ccgtcgagca caaccaacac ccggttgcaa gaccagttga cggtggcgtt   7500
gtgctcctgc gctctgcagt tccttcgctt atagacgtct tgatctccgg tgccgacgca   7560
tctcccagt gctcgccca tcacggtcca ggaaacactg ggattgatgg cacgctctgg    7620
gattttgagt ccgtagccac taaagaggaa gtcgcactta gtgcacaaat aatacaggct   7680
tgtggcatta ggcgtggcga tgctcctgag attggcctcc cttacaagct gcaccctgtt   7740
agggacaacc ctgaacgtgt aaaaggggtt ttgaaaaaca caaggtttgg agacatacct   7800
tacaagaccc ctagcgacac tgggagccca gtacatgcgg ccgcctgcct tacgcctaat   7860
gccaccccgg tgactgatgg cgcctccgtc ttggccacga ctatgccctc cgggtttgag   7920
ttgtatgtgc cgaccattcc agcgtctgtc cttgattacc ttgattccag ccagactgc    7980
cctaaacagt tgacggagca cgggtgtgaa aatgctgcat tgagagacct ctccaaatat   8040
gacttgtcca cccaaggttt tgttttgccc ggagtcctcc gcctcgtgcg gaaatacttg   8100
tttgcccacg tgggcaagtg cccacctgtc atcggccct ccacctaccc ggccaagaat    8160
tccatggctg gaataaacgg gaataggttc ccgaccaagg acattcagag catccctgag   8220
atcgacgttc tgtgtgcaca ggctgtacga gagaactggc agaccgttac cccttgcacc   8280
ctcaagaagc agtattgcgg gaagaagaaa accaggacca tactcggtac caataacttc   8340
```

```
attgcgctgg cccaccgggc agcactgagt ggtgtcaccc agggcttcat gaaaaaggcg      8400
tttaactcgc ccatcgccct cgggaagaac aaattcaagg agctacagac tccggtcctg      8460
ggcagatgtc ttgaggctga tcttgcctct tgcgatcggt ccactcccgc gattgtccgc      8520
tggtttgccg cccatctcct ttatgaactt gcctgcgctg aggagcacct accgtcgtat      8580
gtgctgaatt gctgccatga cctattggtc acgcagtccg gtgcggtgac taagagaggt      8640
ggcctgtcat ctggtgatcc gatcacctct gtatccaaca ccatttacag tctggtaatt      8700
tatgcgcagc acatggtgct cagttacttc aaaagtggtc acccacatgg tctcctgtat      8760
ctccaggacc agctaaagtt tgaggacatg cttaaggttc agcccctgat ygtctactcg      8820
gatgatcttg tgctgtatgc cgagtccccc accatgccaa actaccactg gtgggttgag      8880
catctgaact tgatgctagg gtttcagacg gacccaaaga agacaaccat tactgactcg      8940
ccatcttttc tgggctgtag gataatgaat gggcgtcagc tagtcccaaa ccgtgacagg      9000
attctcgcag ctcttgccta ccacatgaag gcgaataatg tttctgagta ctacgcctcc      9060
gctgctgcaa tactcatgga cagttgtgct tgtctggagt acgaccctga atggtttgaa      9120
gaacttgtgg ttggaatggc gctatgcgcc cgcaaggacg gctatagctt ccccggcccg      9180
ccgttcttct tatccatgtg ggagaaactt aagtccaatt atgaggggaa gaagtcaagg      9240
gtatgtgggt actgcggagc ttcggccccg tatgccactg cctgtggtct tgacgtctgt      9300
gtttaccaca ctcactttca ccagcattgt ccagtcataa tctggtgtgg ccaccctgca      9360
ggttccaggt cctgtgatga gtgcaaatcc ccatagggaa aaggcacaag ccctctggat      9420
gaggttttga gacaagtccc gtataagcct ccacggaccg tcctcatgca tgtggagcag      9480
ggcctcaccc cccttgaccc aggcagatat cagacccgcc gtgggttggt tgccgttagg      9540
cgcgggatca ggggaaatga agttgaccta ccagatggtg attatgctag caccgcctta      9600
ctcccaacct gtaaagagat caacatggtt gctgttgctt ctaatgtgtt gcgcagcaga      9660
tttatcatcg gtccacccgg tgctgggaaa acatactggc tccttcaaca ggtccaggat      9720
ggtgatgtca tatacacacc gacccatcag accatgcttg acatgatcaa gcttttrggg      9780
acgtgccggt taacgtccc ggcaggcaca acgctgcaat tccccgtccc ctcccgcacc      9840
ggtccgtggg ttcgcatcct ggccggcggg tggtgtcctg gcaaaaactc cttcctggac      9900
gaagctgcgt attgtaatca tcttgatgtc ttgaggcttc ttagcaaaac cactctcacc      9960
tgtttggggg acttcaaaca actccaccca gtgggttttg attctcattg ctatgtcttt     10020
gacattatgc ctcagactca attgaagacc atctggagat ttggacagaa catctgtgat     10080
gccatccaac cagactacag agacaagctt atgtccatgg tcaacacaac tcgtgtaact     10140
tatgtggaaa aacctgtcaa atatgggcaa gtcctcaccc cttaccatag ggaccgagag     10200
gatagcgcca ttaccattga ctccagtcaa ggcgccacat tgatgtggt tacactgcat     10260
ttgcccacga aagattcact caacaaacaa agggcccttg ttgctattac agggcaaga     10320
catgccatct ttgtgtatga cccatatagg caactgcaga gcctatttga tcttcctgca     10380
aaaagcacgc ccgtcaactt ggccgtgcac cacgatgggc aactgattgt gctagataga     10440
aataacaaag aatgcacggt tgcccaagct ctggtaatg gtgacaaatt tagggccaca     10500
gacaagcgcg ttgtggattc tctccgcgcc atttgtgctg acctagaagg gtcgagctct     10560
ccactcccca aggttgcaca taatttgggg ttttatttct cacctgattt gatacagttt     10620
gccaagcttc caatagaact tgcgccacac tggccagtag tgacgaccca agacaataaa     10680
aactggccag atcggctggt tgccagccta cgccctattc acaaacatag ccgtgcgtgt     10740
```

```
atcggtgccg gctatatggt gggcccctcg gtgttttag gcaccctgg ggttgtgtca    10800 tactatctta caaaatttgt taagggcgag gctcaagtgc ttccggaaac ggtcttcagt    10860
accggccgaa ttgaggtgga ttgccgggaa tatcttgacg accgggagcg ggaagttgca    10920
gcgtccctcc cacacgcctt tatcggcgac gtcaaaggca ctaccgtcgg agggtgtcat    10980
cacatcacct ccaaataccct tccgcgcttc ctccccaagg aatcagttgc ggtagtcggg    11040
gtttcaagcc ccgaaaagc agcgaaagca gtgtgtacat tgacagatgt gtacctccca    11100
gaccttgaag cttacctcca tcctaagacc ctgtccaagt gctggaaaat gatgttggac    11160
ttcaaagaag ttcggctgat ggtctggaag gacaagacgg cctatttcca actcgaaggt    11220
cgccatttca cctggtatca acttgctagc tatgcctcgt acatccgtgt tcctttaaac    11280
tccacggtgt acctggaccc ctgcatgggc ccgcccttt gcaacagaaa agttgttggg    11340
tccactcatt ggggagctga cctcgcagtc accccttatg attatggggc aagaattatt    11400
ttgtctagtg cgtaccatgg tgagatgcct cctgggtaca agattctggc gtgcgcggag    11460
ttctcgctgg acgacccagt cagatacaag cacacttggg ggtttgagtc ggatacagcg    11520
tacttgtacg agttcactgg aaacggtgag gactgggagg attataacga cgcgtttcgt    11580
gcgcgacaga aggaaagat ttacaaggcc actgccacca gcctgaagtt ccattttcct    11640
ccgggtcata ccgttgaacc aactttgggc ctagactgaa atgaaatggg ggctgtgcag    11700
agcctatttg ataaaattgg ccaactgttt gtggacgctt tcacggagtt cttggtgtcc    11760
attgttgata tcatcatatt tttggccatt ttgttcggct tcacaatcgc cggttggctg    11820
gtggtctttt gcatcagatt ggtttgctcc gcgatactcc gttcgcgctc tgccgttcac    11880
cctgagcaat tacagaagat cctatgaggc atttctctcc cagtgccgga cggayattcc    11940
cacctgggga actaaacatc ccttggggat gctctggcac cacaaggtgt cgaccctaat    12000
tgatgaaatg gtgtcgcgtc gaatgtaccg catcatggaa caagcagggc aggctgcctg    12060
gaaacaggtg gtgaccgagg caacgttgtc tcgtattagt agcttggatg tggtggctca    12120
tttccagcac cttgccgcca tagaagccga gacttgtaaa tacttggcct cccggctgcc    12180
aatgctgcac aacctgcgca tgacagggtc aaatgtaacc atagtgtata atagctctct    12240
agaacaggtg tttgctgttt tcccgaccct cagttcccgg ccaaagcttc atgattttcg    12300
gcaatggcta atagctgtgc attcctccat attctcttct gttgcggctt cctgtaccct    12360
tttcgtcgtg ctgtggttgc ggcttccaat aatacgtact gttttggtt tccactggtt    12420 aggggcaatt tttccttcga gctcacagtg aactacacgg tgtgtcctcc ctgcctcacc    12480
cggcaggcgg ccgcagagat ctacgaacct agtgggtctc tttggtgcag ataggggcac    12540
gatcgatgct cggaggacga tcacgacgag ctaggatttc tggtgccgcc tggcctctcc    12600
agcgaaggcc acttgaccag tgtttacgcc tggttggcgt tcttgtcctt cagttacacg    12660
gcccagtttc accccgagat attcgggata gggaatgtga gtaaagttta tgttgacatc    12720
aagcatcaat ttatttgcgc tgttcatgac gggcaaaaca ccaccttgcc tcgccatgac    12780
aacgtctcag ccgtgttcca gacttattac cagcatcagg tcgacggcgg caattggttt    12840
cacctggaat ggctgcgccc cttcttctcc tcctggttgg ttttgaacgt ctcttggttt    12900
ctcaggcgtt cgcctgtaag ccgtgtttca gttcgagtct ctcagacatt aagaccaaca    12960
ccaccgcagc tgcaggcttt gctgtcctcc aagacatcag ttgtcttagg catggccact    13020
cgtcctctga ggcgactcgc aaaagccgtc aatgtcgcac ggcgatagga acgcccgtat    13080
```

```
acattactgt cacagccaat gtaacagatg agaattattt gcattcctct gaccttctca   13140
tgctttcctc ttgccttttc tacgcttccg agatgagtga aaagggattt gaagtgatat   13200
ttggcaatgt gtcaggcata gtggctgtgt gtgtcaactt taccagctat gtccaacatg   13260
tcaaggagtt cacccagcgc tccttggtgg ttgaccatgt gcggttactt cattttatga   13320
cacctgagac tatgaggtgg gcgaccgttt tagcctgtct ttttgccatt ctgttggcca   13380
tttgaatgtt cagatatgtt ggggaaatgc ttgaccgcgg gctattgctc gcaattgctt   13440 ttttgtggt gtatcgtgcc gttctgtctt gctgcgctcg tcaacgccga cagcaacagc   13500
agctcccatt tacagttgat ttataamtta acgatatgtg agctgaatgg cacagactgg   13560
ctgaacaatc attttagttg ggcagtggag actttcgtta tctttcctgt gttgactcat   13620
attgtttcct acggcgccct cactaccagc cacctccttg acacggtcgg cctgatcact   13680
gtgtccaccg ccggatactg ccataagcgg tatgtcttga gtagcatcta tgctgtctgc   13740
gccctggctg cgctgatttg cttcgtcatc aggttgacga aaaattgtat gtcctggcgc   13800
tactcatgta ccagatatac caactttctt ctggacacca agggcagact ctatcgctgg   13860
cggtcacccg tcatcataga gaaaaggggt aaaattgagg ttggaggtga cctgatcgac   13920
ctcaagagag ttgtgcttga tggttccgcg gcaacccctg taaccaaagt tcagcggaa   13980 caatggggtc gtccttagac gacttctgca atgacagcac ggctccacaa aaggtgatct   14040
tggcattttc tatcacctac acaccagtga tgatatatgc cctaaaggtg agtcgtggcc   14100
ggctgctagg gcttttacac cttttgattt ttytaaactg tgcttttacc ttcgggtata   14160
tgacatttgt gcactttcag agcacaaaca gagttgcact cactatggga gcagtagtcg   14220
cgctcctttg gggggtgtac tcagctatag aaacctggaa attcatcact tccagatgcc   14280
gtttgtgctt gctaggccgc aagtacattc tggcccctgc ccaccacgtt gagagtgccg   14340
caggctttca tccgattgcg gcaagtgata accacgcatt tgtcgtccgg cgtcccggtt   14400
ccactacggt taacggcaca ttggtgcccg ggttgaaaag cctcgtgttg ggtggcagaa   14460
gagctgtcaa acggggagtg gtaaacctcg ttaaatatgc caaataacaa cggcaggcag   14520
cagaagaaaa agaaagggga cggccagcca gtcaatcagc tgtgccaaat gttgggcagg   14580
atcatcgccc agcaaaacca gtccagaggt aagggaccgg ggaagaaaag taagaagaaa   14640
agcccggaga agccccattt tcctctcgcg actgaagatg acgttagaca tcacttcacc   14700
cctagtgagc ggcaattgtg tctgtcgtca atccagactg cctttaacca aggcgctgga   14760
acttgtaccc tgtcggattc agggagaata agttacgctg tggagtttag tttgcctacg   14820
catcatactg tgcgcctaat tcgcgtcaca gcatcaccct cagcatgatg agctggcatt   14880
cttgagacat cccagtgttt gaattggaag gatgtgtggt gaatggcact gattgatatt   14940
gtgcctytaa gtcacctatt caattagggc gaccgtatgg gggtaatatt taattggcgt   15000
gaaccatgcg gccgaaatt                                                15019
```

<210> SEQ ID NO 6
<211> LENGTH: 15019
<212> TYPE: DNA
<213> ORGANISM: Artificial Sequence
<220> FEATURE:
<223> OTHER INFORMATION: Porcine reproductive and respiratory syndrome virus, strain MN184B
<220> FEATURE:
<221> NAME/KEY: misc_feature
<222> LOCATION: (1540)..(1540)
<223> OTHER INFORMATION: R = A or G
<220> FEAT -continued

```
<221> NAME/KEY: misc_feature
<222> LOCATION: (1546)..(1546)
<223> OTHER INFORMATION: Y = C or T
<220> FEATURE:
<221> NAME/KEY: misc_feature
<222> LOCATION: (1549)..(1549)
<223> OTHER INFORMATION: R = C or A
<220> FEATURE:
<221> NAME/KEY: misc_feature
<222> LOCATION: (1558)..(1558)
<223> OTHER INFORMATION: Y = C or T
<220> FEATURE:
<221> NAME/KEY: misc_feature
<222> LOCATION: (1559)..(1559)
<223> OTHER INFORMATION: R = C or A
<220> FEATURE:
<221> NAME/KEY: misc_feature
<222> LOCATION: (2110)..(2110)
<223> OTHER INFORMATION: Y = C or T
<220> FEATURE:
<221> NAME/KEY: misc_feature
<222> LOCATION: (2161)..(2161)
<223> OTHER INFORMATION: R = C or A
<220> FEATURE:
<221> NAME/KEY: misc_feature
<222> LOCATION: (2186)..(2186)
<223> OTHER INFORMATION: R = C or A
<220> FEATURE:
<221> NAME/KEY: misc_feature
<222> LOCATION: (5389)..(5389)
<223> OTHER INFORMATION: R = C or A
<220> FEATURE:
<221> NAME/KEY: misc_feature
<222> LOCATION: (5687)..(5687)
<223> OTHER INFORMATION: R = C or A
<220> FEATURE:
<221> NAME/KEY: misc_feature
<222> LOCATION: (5694)..(5694)
<223> OTHER INFORMATION: Y = C or T
<220> FEATURE:
<221> NAME/KEY: misc_feature
<222> LOCATION: (5698)..(5698)
<223> OTHER INFORMATION: R = C or A
<220> FEATURE:
<221> NAME/KEY: misc_feature
<222> LOCATION: (5699)..(5699)
<223> OTHER INFORMATION: Y = C or T
<220> FEATURE:
<221> NAME/KEY: misc_feature
<222> LOCATION: (5704)..(5704)
<223> OTHER INFORMATION: Y = C or T
<220> FEATURE:
<221> NAME/KEY: misc_feature
<222> LOCATION: (5710)..(5710)
<223> OTHER INFORMATION: R = C or A
<220> FEATURE:
<221> NAME/KEY: misc_feature
<222> LOCATION: (5722)..(5722)
<223> OTHER INFORMATION: Y = C or T
<220> FEATURE:
<221> NAME/KEY: misc_feature
<222> LOCATION: (5724)..(5724)
<223> OTHER INFORMATION: Y = C or T
<220> FEATURE:
<221> NAME/KEY: misc_feature
<222> LOCATION: (5728)..(5728)
<223> OTHER INFORMATION: R = C or A
<220> FEATURE:
<221> NAME/KEY: misc_feature
<222> LOCATION: (5733)..(5733)
<223> OTHER INFORMATION: R = C or A
<220> FEATURE:
<221> NAME/KEY: misc_feature
<222> LOCATION: (5743)..(5743)
<223> OTHER INFORMATION: Y = C or T
<220> FEATURE:
<221> NAME/KEY: misc_feature
<222> LOCATION: (5749)..(5749)
<223> OTHER INFORMATION: Y = C or T
```

```
<220> FEATURE:
<221> NAME/KEY: misc_feature
<222> LOCATION: (6511)..(6511)
<223> OTHER INFORMATION: R = C or A
<220> FEATURE:
<221> NAME/KEY: misc_feature
<222> LOCATION: (6523)..(6523)
<223> OTHER INFORMATION: Y = C or T
<220> FEATURE:
<221> NAME/KEY: misc_feature
<222> LOCATION: (8050)..(8050)
<223> OTHER INFORMATION: R = C or A
<220> FEATURE:
<221> NAME/KEY: misc_feature
<222> LOCATION: (9345)..(9345)
<223> OTHER INFORMATION: R = C or A
<220> FEATURE:
<221> NAME/KEY: misc_feature
<222> LOCATION: (10309)..(10309)
<223> OTHER INFORMATION: R = C or A
<220> FEATURE:
<221> NAME/KEY: misc_feature
<222> LOCATION: (10419)..(10419)
<223> OTHER INFORMATION: R = C or A
<220> FEATURE:
<221> NAME/KEY: misc_feature
<222> LOCATION: (14947)..(14947)
<223> OTHER INFORMATION: Y = C or T
<220> FEATURE:
<221> NAME/KEY: misc_feature
<222> LOCATION: (15018)..(15018)
<223> OTHER INFORMATION: Y = C or T

<400> SEQUENCE: 6
atgacgtata ggtgttggct ctatgccacg acatttgtat tgtcaggagc tgtgaccact        60
ggcacagccc aaagcttgct gcacagaaac acccttctgt gacggcctcc ttcaggggag       120
tttaggggtt tgtccctagc accttgtttc tggagttgca ctgctttacg gtctctccac       180 cccctttaacc atgtctggga ttcttgatcg gtgcacgtgc accccaatg ccagggtgtt       240 tatggcagag ggccaagtct actgcacacg atgtctcagt gcacggtccc tccttcccct       300
gaatctccaa gtctctgagc tcggagtgtt gggcttgttt tataggcctg aagagccgct       360
ccggtggacg ttgccacgcg cattcccac tgttgagtgc tcccctgctg ggcttgttg        420 gctttctgca attttccaa ttgcacgaat gaccagtgga aacctgaact ttcaacaaag       480
attagtgcgg gtcgcagctg agctttacaa agccggctgc ctcaccccta cagtcctaaa       540
gagtctacaa gtctatgaac gggggttgccg ctggtacccc atcgttggac ctgtccctgg       600
agttgccgtt ttcgccaact ccctacatgt gagtgataga cctttcccag gtgctactca       660
cgtgctaacc aacctgccgc tcccgcagag acctaagcct gaagattttt gccccttga       720 gtgtgctatg gctgccgtct atgacattgg tcatgacgcc gttatgttcg tggccgaagg       780
gagagtctct tgggctccgc gtggtgggga aaaaggaaaa tttgaaactg ttcccgagga       840
gttggggttg attgcagagc aactttatac ctccttcccg ccccaccact ggtggacat        900 gtcgaaattc acctttacgg cccctgagtg tggtgcttcc atgcgagtcg aacgccagta       960
tggctgcctc cccgctggca ctgtccctga cggcaattgc tggtggagct tgtttagctc      1020
gctcccattg gaagtccagt ataaagaat tcgctacgcc acccaatttg gctatcaaac       1080
taagcatggc gttgctggca agtacctaca gcggaggctg caattaatg gtctccgagc       1140 agtggttgac tcgaatggac ccatcgtcat acagtacttc tctgttaagg agagctggat      1200
ccgccacgtg aaactggcgg aagagtttga ctaccctggg tttgaggatc tcctcaggat      1260
aagagtcgag cccaacacgt tgccattgtc caacaaggac gagaaaatct tccggtttgg      1320
```

-continued

```
tgggtgcaag tggtacggtg ctgggaagag ggcaaggagg gcacgtgcaa gtgcagtcac    1380
cgcagtcgcc ggtcacgctc cgcctactcg tgaaacccag caagccaaga aacacgaagc    1440
tgctagtgcc aacaaggctg agcttcttga acgctactcc ccgcctgctg aagggaattg    1500
cggctggcac tgtatctccg ccatcgccaa ccggatggtr aattcyaart ttgaaacyrc    1560
ccttcccgaa agagtgagac ctccagatga ctgggctact gacgaggatc ttgtgaatgc    1620
catccaaatc ctcagactcc ctgcggcctt agacaggaac ggtgcttgta ctagcgccaa    1680
gtacgtactt aagctggaag gtgagcattg gactgtcact gtgacccctg ggatgtcccc    1740
ttctttgctc cctcttgaat gtgttcaggg ctgttgtggg caagggcg tcttggttc       1800
cccagatgca gtcgaggtct ccggatttga ccctgcctgc cttgaccggc tggctgaggt    1860
gatgcacctg cctagcagtg ctatcccagc cgctctggcc gaaatgtctg gcgattccga    1920
tcgttcggct tctccggtca ccaccgtgtg gactgtttcg cagttctttg cccgtcacag    1980
cggagggaat caccctgacc aagtgcgctt agggaaaatt atcagccttt gtcaggtgat    2040
tgaggactgc tgctgttccc agaacaaaac caaccgggtc accccggagg aggtcgcagc    2100
aaagattgay cagtaccttt ttggtgcagc aagtcttgaa gaatgcttgg ccaggcttga    2160
raaagctcgc ccgccaagcg tattaracac ctcctttgat tgggatgttg tgctccctgg    2220
tgtcggggcg gctgctcaag cagcaaaact gcccctcacc aaccagcgtc acgctctagc    2280
cactgttgtg actcaaaggt cttgccgaa atttcaacct cgaaaagcgg agtctgtcaa     2340
gagcctacca gagagcaggc ccctccctgc cccgcgcaaa aagattgggt ccaggtgtgg    2400
tagtccgatt tcattgggcg gcaatctccc tgacagccgg gaagacttgg ccggtggttc    2460
ctttgatttc ccaaccctac ctgagttggt ggcaagctcg agcgagcctg tgcctgtccc    2520
tgcaccgcgc agggttgtgt cccgattagt gtcgtctccg atagtgtcga cccctgtgcc    2580
cgcaccacga cgtgggcttc ggcaggtgga gggaatgaat ttggcggcgg tgactctagc    2640
gtgccaggac gagccctcg atttgtctgc gtcctcgcag actgaatatg aggcgtcccc    2700
cttggcattg ccgctgagtg aggatgtcct ggcggtggag agacgagaag ttgaagaagt    2760
cctgagcgga atatcgggca tgccagatga catcaggttg gcgcccgtgt catcaagtag    2820
ctccctgtca agcatagaga tcacacgtcc aaagtactca gctcaagcca tcattaactc    2880
aggtgggccc tgttgtgggc acctccagga ggtaaaagag aaatacctta atgtgatgcg    2940
tgaggcatgt gatgcgacca agcttgatga ccctgccacg caagaatggc tttcccgcat    3000
gtgggatagg gtagacatgc taacctggcg caacacgtcc atttttcagg cgcctttcac    3060
cttggctgac aagtttaaga ccctcccgaa gatgatactc gaaacaccgc cgccctaccc    3120
ttgtgggttt gtgatgatgc cccgcacgcc tgcaccttct gtaggtgcgg agagcgacct    3180
caccgttggc tcagttgcta ctgaggatgt cccgcgcatt ctcgggaatg tacaaggtgt    3240
tggcgaaacg accgaccagg gacccttggc acccttcgca gacgaattgg cagatgacca    3300
acttgctaga gaaccccgga cacaaacccc tcctgcaagc acaggtggcg ccggcttggt    3360
ttcggattct ggaaggtcgc cggagctcac tgacctgccg ctttcaaacg gtacagacgc    3420
gggcggaggg gggccgttac acacggtcaa gaagaaagct gagaggtgct ttgaccagct    3480
gagccgtcgg gttttgaca ttgtctccca tctccctgtt ttcttctcac gccttttcaa     3540
gcctgacagt cactactctt cgggtgactg gagttttgca gcttttactt tattgtgcct    3600
cttttctatgt tacagttacc cagcctttgg tgttgctccc ctattgggtg tatttttctgg  3660
gtcttctcgg cgcgttcgca tgggggttttt tggctgctgg ttggctttcg ctgttggttt   3720
```

```
gttcaagcct gcacccgacc cagtcggtgc tgcttgtgag tttgattcgc cagagtgtag    3780
agacatcctt cattcttttg agcttctgca accttggac  cctgttcgca gccttgtggt    3840
ggggcccgtc ggtctcggtc ttgccattat tggcaggtta ctgggcgggg cacgctacgt    3900
ctggctgctt ttgcttaggc ttggcatcgt ttcagactgt atcttggctg gagcttatgt    3960
gctttcgcaa ggtaggtgta aaaagtgttg gggatcttgt ataagaactg ctcccagtga    4020
ggtcgccttc aatgtgtttc ccttcacacg tgcaaccaga tcgtcacttg tcgacctgtg    4080
cgaccggttt tgtgcgccca agggcatgga ccccatcttc ctcgccactg gatggcgcgg    4140
atgttggtcc ggccagagcc ccattgagca acccactgag aaacccattg cgttcgccca    4200
gttggatgaa aagaaaatca cggcaaggac tgtggttgcc caaccttatg accccaacca    4260
agctgtgaag tgcttacgag tcttgcaggc gggtggggcg atggtggctg aggcggttcc    4320
aaaagtggtt aaggtctctg ctgtcccatt tcgagccccc ttcttccccg ccggagtgaa    4380
agttgatcct gaatgcaggg tcgtggttga cccagacacc ttcacaactg ctctccggtc    4440
cggctactcc accacaaacc tcattcttgg tatgggggat tttgcccaac tgaatgggtt    4500
gaaaatcaga caaatttcca agccttcagg aggtggtcca tacctcatgg cggccttaca    4560
tgtcgcttgc tcgatggcct tgcacatgct cgttgggatt tatgttaccg cggtgggttc    4620
ttgtggttct ggcactaacg atccgtggtg cactaacccg tttgccgtcc ctgtctacgg    4680
gcctggctct ctttgcacgt ccaggttgtg catctcccag catggcctta ctctgccttt    4740
aacagcgctt gtggcggggt ttggcattca ggaagttgct ttggttgttt taatcttttac   4800 ttccatcggg ggtatggctc acaggttgag ctgcaaggcc gatgtgctgt gtattctgct    4860
tgcaattgcc agctatgttt gggtaccctt cacctggttg ctttgtgtgt tccttgctg    4920 gttgcgctgg ttttctttgc atcccctcac cattctatgg ttggtgtttt cttgatttc    4980 tgtgaacatg ccctcaggaa tcttggcttt agtgttgttg atctctctct ggctccttgg    5040
tcgctatacc aatgtcgctg gccttgtcac cccttatgac attcaccatt acaccaacgg    5100
cccccgcggc gttgccgcct tggccactgc cccggatggg acctatttgg ctgctgtccg    5160
ccgcgctgcg ttgactggcc gcaccatgct gtttaccccg tctcaacttg gtcactcct    5220 tgagggcgcc tttagaaccc aaaagccttc actgaatacc gtcaatgtgg ttgggtcctc    5280
catgggctcc ggcggggtgt tcaccattga cgggaaaatt aagtgcgtga ccgccgcaca    5340
tatcctcacg ggtaactctg ctagggtctc tggggttggc ttcaatcara tgttggattt    5400
tgatgtaaaa ggggattttg ccatagccga ttgtccgggt tggcagggag tcgctcccaa    5460
gtcccagttc tgcaaggatg ggtggactgg ccgcgcttat tggctaacgt cctctggcgt    5520 cgaaccggc  gtcattggta ggggattcgc cttttgtttc accgcgtgcg gcgattccgg    5580
gtccccagtg atcaccgagg ccggagagct tgtcggagtc cacacgggat caaacaaaca    5640
aggaggaggc attgtcacgc gcccttcagg ccagttttgt aatgtgrcac ccaycaaryt    5700
aagygaattr agtgaattct tygcyggrcc targgtcccg ctyggtgayg tgaaggtcgg    5760
cagccacata attaaagaca taagcgaggt gccttcagat cttgtgcct  tgcttgctgc    5820 caaacctgaa ctggaaggag gcctctccac cgtccaactt cttgtgtgt  ttttctcct   5880 gtggagaatg atgggacatg cctggacgcc cttggttgct gtgagtttct ttattttgaa    5940
tgaggttctc ccagccgtcc tggtccggag tgttttctcc tttggaatgt tgtgctatc    6000 ctggctcacg ccatggtctg cgcaagttct gatgatcagg cttctgacag cagctcttaa    6060
```

```
caggaacaga tggtcacttg ccttttcag cctcggtgca gtgaccggtt ttgtcgcaga    6120
tcttgcggcc actcagggc atccgttgca ggcagtgatg aatttgagca cctatgcatt    6180
cctgcctcgg atgatggttg tgacctcacc agtcccagtg atcacgtgtg gtgtcgtgca    6240
cctacttgcc atcattttgt acttgtttaa gtaccgtggc ctgcaccata tccttgttgg    6300
cgatggagtg ttctctgcgg cttcttctt gagatacttt gccgagggaa agttgaggga    6360
aggggtgtcg caatcctgcg gaatgaatca tgagtctctg actggtgccc tcgctatgag    6420
actcaatgac gaggacttgg atttccttat gaaatggact gattttaagt gctttgtttc    6480
tgcgtccaac atgaggaatg cagcgggtca rtttatcgag gcygcctatg cgaaagcgat    6540
cagggtggaa cttgcccagt tagtgcaggt cgacaaggtt cggggtgttt tagccaaact    6600
tgaagctttt gctgacaccg tggcgcccca tctttcaccc ggcgacattg ttgttgttct    6660
tggtcatacg cccgttggca gcatctttga cttaaagatt ggcaatgcca agcacaccct    6720
acaagccatc gagaccagag tccttgctgg gtccaggatg accgtggcgc gtgtcgttga    6780
tccgactccc gcgccgccac ccgtacccgt gcccgttcct ctcccaccga agttttaga    6840 gaacggcccc agtgcctggg gggatgaaga ccgcctgaac aaaaagaagc ggcgcaagat    6900
ggaagccgtt ggcatttacg ttatgggcgg gaaaaagtac cagaaatttt gggataagaa    6960
ttctggtgat gtgttctatg aggaagtcca cgacaacaca gatgcgtggg aatgccttag    7020
agctgacgac cccgccgact ggatcctga gggggaacc ttgtgtggac acgtcaccat    7080
agagaatagg ccttaccatg tttatgcctc cccgtctggt aggaagttcc tggtccctgc    7140
cgacccagag aatgggaaag cccagtggga agctgcaaag ctttccatgg agcaggccct    7200
tggtatgatg aacgttgacg gcgagctgac cgccaaagaa ctggagaaat tgaagagaat    7260
aattgacaaa ctccagggcc tgactaagga gcagtgttta aactgttagc cgccagcggc    7320
ttgacccgct gtggtcgcgg cggcttggtt attactgaga cagcggtaaa aatagtcaga    7380
ttccacaatc ggaccttcac cctggggcct gtgaatttga agtggccag cgaagttgag    7440 ttgaaagacg ccgtcgagca caaccaacac ccggttgcaa gaccagttga cggtggcgtt    7500
gtgctcctgc gctctgcagt tccttcgctt atagacgtct tgatctccgg tgccgacgca    7560
tctccccagt tgctcgccca tcacgggcca ggaaacactg ggattgatgg cacgctctgg    7620
gattttgagt ccgtagccac taaagaggaa gtcgcactta gtgcacaaat aatacaggct    7680
tgtggcatta ggcgtggcga tgctcctgag attggcctcc cttacaagct gcaccctgtt    7740
aggggcaacc ctgaacgtgt gaaagggtt ttgaaaaaca caaggtttgg agacatacct    7800
tacaggaccc ctagcgacac tgggagccca gtacatgcgg ccgcctgcct tacgcctaac    7860 gccacccgg tgactgatgg cgctccgtc ttggccacga ctatgccctc cgggtttgag    7920
ttgtatgtgc cgaccattcc agcatctgtc cttgattacc ttgattccag gccagactgc    7980
cctaaacagt tgacggagca cgggtgtgaa gatgctgcat tgagagacct ctccaaatat    8040
gacttgtccr cccaaggttt tgttttgccc ggagtcctcc gcctcgtgcg gaaatacttg    8100
tttgcccacg tgggcaagtg cccacctgtc catcggccct ccacctaccc ggccaagaat    8160
tccatggctg gaataaacgg gaataggttc ccaaccaagg acattcagag catccctgag    8220
atcgacgttc tgtgtgcaca ggctgtacga gagaactggc agaccgttac cccttgcacc    8280
ctcaagaagc agtattgcgg gaagaagaaa accaggacca tactcggtac caataacttc    8340
attgcgctgg cccaccgggc agcactgagt ggtgtcaccc agggcttcat gaaaaggcg    8400 tttaactcgc ccatcgccct cgggaagaac aaattcaagg agctacagac tccggtcctg    8460
```

```
ggcagatgcc ttgaggctga tcttgcctct tgcgatcgat ccactcccgc gattgtccgc    8520
tggtttgccg cccatctcct ttatgaactt gcctgcgctg aggaacacct accgtcgtat    8580
gtgctgaatt gctgccatga cctattggtc acgcagtccg gtgcggtgac taagagaggt    8640
ggcctgtcat ctggtgatcc gatcacctcg gtatccaaca ccatttacag tctggtgatt    8700
tatgcgcagc acatggtgct cagttatttc aaaagtggtc acccacatgg tctcctgttt    8760
ctccaggacc agctaaagtt tgaggacatg cttaaggttc agcccctgat tgtctactcg    8820
gatgatcttg tgctgtatgc cgagtctccc accatgccaa actatcactg gtgggttgag    8880
catctgaact tgatgctagg gtttcagacg gacccaaaga agacaaccat tactgactcg    8940
ccatcttttc tgggctgtag gataatgaat gggcgtcagc tagtcccaaa ccgtgatagg    9000
attctcgcag ctcttgccta ccacatgaag gcgaataatg tttctgagta ctacgcctcc    9060
gctgctgcaa tactcatgga cagttgtgct tgtctggagt acgaccctga atggtttgaa    9120
gaacttgtgg ttggaatggc gcaatgcgcc cgcaaggacg gctatagctt ccccggcccg    9180
ccgttcttct tatccatgtg ggagaaactc aggtccaatt atgagggga gaagtcaagg    9240
gtgtgtgggg actgcggagc ttcggccccg tatgccactg cctgtggtct tgacgtctgt    9300
gtttaccaca ctcactttca ccagcattgt ccagtcataa tctgrtgtgg ccaccctgca    9360
ggttccaggt cctgtgatga gtgcaaatcc cccatagga aaggtacaag ccctctggat    9420
gaggttttaa gacaagtccc gtataagcct ccacggaccg tcctcatgca tgtggagcag    9480
ggcctcaccc cccttgaccc aggcagatat cagacccgcc gtgggttggt tgccgttagg    9540
cgcgggatca ggggaaatga agttgaccta ccagatggtg attatgctag caccgcctta    9600
ctcccaacct gtaaagagat caacatggtt gctgttgctt ctaatgtgtt gcgcagcaga    9660
tttatcatcg gtccacccgg tgctgggaaa acatactggc tccttcaaca ggtccaggat    9720
ggtgatgtca tatacacacc gacccatcag accatgcttg acatgatcaa gctttgggg    9780
acgtgccggt ttaacgtccc ggcaggcaca acgctgcaat tccccgcccc ttcccgcact    9840
ggcccgtggg ttcgcatcct ggccggcggg tggtgtcctg gcaaaaactc cttcctggac    9900
gaagctgcgt attgtaatca tcttgatgtc ttgaggcttc ttagcaaaac cactctcacc    9960
tgtttagggg acttcaaaca actccaccca gtgggttttg attctcattg ctatgtcttt   10020
gacattatgc ctcagactca actgaagacc atctggagat ttggacagaa catctgtgat   10080
gccatccaac cagactacag agacaagctt atgtccatgg tcaacacaac tcgtgtaact   10140
tatgtggaaa aacctgtcaa acatgggcaa gtcctcaccc cttaccatag ggaccgagag   10200
gatagcgcca ttaccattga ctccagtcaa ggcgccacat tgatgtggt tacactgcat   10260
ttgcccacga aagattcact caacaaacaa agggcccttg ttgctattrc cagggcaaga   10320
catgccatct ttgtgtatga cccacatagg caactgcaga gcctatttga tcttcctgca   10380
aaaagcacgc ccgtcaactt ggccgtgcac cacgatggrc aactgattgt gctagataga   10440
aataacaaag aatgcacggt tgcccaagct ctgggtaatg gtgacaaatt tagggccaca   10500
gacaagcgcg ttgtggattc tctccgcgcc atttgtgctg acctagaagg gtcgagctct   10560
ccactcccca aggttgcaca taatttgggg ttttatttct cacctgattt gacacagttt   10620
gccaagcttc caatagaact tgcgccacac tggccagtag tgacgaccca agacaataaa   10680
aactggccag atcggctggt tgccagcctg cgcctattc acaaacatag ccgtgcgtgc   10740
atcggtgccg gctatatggt gggccctcg gtgtttttag gcaccctgg ggttgtgtca   10800
```

```
tactatctta caaaatttgt taagggcgag gctcaagtgc ttccggaaac ggtcttcagt   10860
actggccgaa ttgaggtaga ttgccgggaa tatcttgacg accggagcg ggaagttgca    10920
gcgtccctcc cacacgcctt tatcggcgac gtcaaaggca ctaccgtcgg agggtgtcat   10980
cacatcacct ccaaatacct tccgcgcttc ctccccaagg aatcagttgc ggtagtcggg   11040
gtttcaagcc ccggaaaagc agcgaaagca gtgtgtacat tgacagatgt gtacctccca   11100
gaccttgaag cttacctcca tcctaagacc ctgtccaagt gctggaaaat gatgttggac   11160
ttcaaagaag ttcggctgat ggtctggaag gacaagacgg cctatttcca actcgaaggt   11220
cgccatttca cctggtatca acttgctagc tatgcctcgt acatccgtgt tcctttaaac   11280
tccacggtgt acctggaccc ctgcatgggc ccgccctttt gcaacagaaa agtcgttggg   11340
tccactcatt ggggagctga cctcgcagtc accccttatg attatggggc aagaattatt   11400
ttgtctagtg cgtaccatgg tgagatgcct cctgggtaca agattctggc gtgcgcggag   11460
ttctcgctgg acgacccagt cagatacaag cacacttggg ggtttgagtc ggatacagcg   11520
tacttgtacg agttcactgg aaacggtgag gactgggagt attataacga cgcgtttcgt   11580
gcgcgacaga aggaaagat ttacaaggcc actgccacca gcctgaagtt ccattttcct    11640
ccgggtcata ccgttgaacc aactttgggc ttagactgaa atgaaatggg ggctgtgcag   11700
agcctatttg ataaaattgg ccaactgttt gtggacgctt tcacggagtt cttggtatcc   11760
attgttgata tcatcatatt tttggccatt ttgttcggct tcacaatcgc cggttggctg   11820
gtggtctttt gcatcagatt ggtttgctcc gcgatactcc gttcgcgctc tgccgttcac   11880
cctgagcaat tacagaagat cctatgaggc atttctctcc cagtgccgga cggacattcc   11940
cacctgggga actaaacatc ccttggggat gctctggcac acaaggtgt cgaccctaat    12000
tgatgaaatg gtgtcgcgtc gaatgtaccg caccatggaa caagcagggc aggctgcctg   12060
gagacaggtg gtgaccgagg caacgttgtc tcgtattagt aacttggatg tggtggctca   12120
tttccagcac cttgccgcca tagaagccga gacttgtaaa tacttggcct cccggctgcc   12180
aatgctgcac aacctgcgca tgacagggtc aaatgtaacc atagtgtata atagctctct   12240
agaacaggtg tttgctattt tcccgaccct cgattcccgg ccaaagcttc atgattttcg   12300
gcaatggcta atagctgtgc attcctccat attctcttct gttgcggctt cctgtaccct   12360
tttcgtcgtg ctgtggttgc ggcttccaat aatacgtact gttttttggtt tccactggtc   12420
agggggcaatt tttccttcga gctcacagtg aactacacgg tgtgtcctcc ctgcctcacc   12480
cggcaggcgg ccgcagagat ctacgaacct ggtgggtctc tttggtgcag gatagggcac   12540
gatcgatgct cggaggacga tcacgacgag ctaggatttc tggtgccgcc tggcctctcc   12600
agcgaaggcc acttgaccag tgtttacgcc tggttggcgt tcttgtcctt cagttacacg   12660
gcccagtttc accccgagat attcggaata gggaatgtga gccaagttta tgttgacatc   12720
aagcatcaat ttatttgtgc tgttcatgac gggcaaaaca ccaccttgcc tcgccatgac   12780
aacgtctcag ccgtgttcca gacttattac cagcatcagg tcgacggcgg caattggttt   12840
cacctggaat ggctgcgccc cttcttctcc tcctggttgg ttttgaacgt ctcttggttt   12900
ctcaggcgtt cgcctgtaag ccgtgtttca gttcgagtct ttcagacatt aagaccaaca   12960
ccaccgcagc tgcaggcttt gctgtcctcc aagacatcag ctgtcttagg catggccact   13020
cgtcctctga ggcgactcgc aaaggccgcc aatgccgcac ggcgatagga acgcccgtat   13080
acattactgt cacagccaat gtaacagatg agaattattt gcattcctct gaccttctca   13140
tgctttcctc ttgccttttc tacgcttccg agatgagtga aaagggattt gaggtgatat   13200
```

```
ttggcaatgt gtcaggcata gtggctgtgt gtgtcaactt taccagctat gtccaacatg    13260
ttaaggagtt cacccagcgc tccttggtgg ttgaccatgt gcggttactt cattttgtga    13320
cacctgagac tatgaggtgg gcgaccgttt tagcctgtct ttttgccatt ctgttggcca    13380
tttgaatgtt cagatatgtt ggggaaatgc ttgaccgcgg gctattgctc gcaattgcct    13440
tttttgtggt gtatcgtgcc gttctgtctt gctgcgctcg tcaacgccag cagcaacagc    13500
agctcccact tacagttgat ttataactta acgatatgtg agctgaatgg cacagactgg    13560
ctgaatgatc attttagttg ggcagtggag actttcgtta tctttcctgt gttgactcac    13620
attgtttcct acggcgccct cactaccagc cacttccttg acacggtcgg cctgatcact    13680
gtgtccaccg ccggatacta ccatgcgcgg tatgtcttga gtagcatcta tgccgtctgc    13740
gccctggctg cgctgatttg cttcgtcatc aggttgacga aaaattgtat gtcctggcgc    13800
tactcatgta ccagatatac caactttctt ctggacacca agggcagact ctatcgctgg    13860
cggtcacccg tcatcataga gaaaggggt aaaattgagg ttggaggtga cctgatcgac    13920
ctcaagagag ttgtgcttga tggctccgcg gcaaccctg taaccaaagt ttcagcggaa    13980
caatggggtc gtccttagac gacttctgca atgcagcac ggctccacaa aaggtgatct    14040
tggcattttc tatcacctac actccagtga tgatatatgc cctaaaggtg agtcgtggcc    14100
ggctgctagg gcttttacac cttttgattt ttctaaactg tgcttttacc ttcgggtata    14160
tgacatttgt gcactttcag agcacaaaca gagttgcact cactatggga gcagtagtcg    14220
cgctcctttg gggggtgtac tcagctatag aaacctggaa attcatcact tccagatgcc    14280
gtttgtgctt gctaggccgc aagtacattc tggcccctgc ccaccacgtt gagagtgccg    14340
caggctttca tccgattgcg gcaagtgata accacgcatt tgtcgtccgg cgtcccggtt    14400
ccactacggt taacggcaca ttggttcccg ggttgaaaag cctcgtgttg ggtggcagaa    14460
gagctgtcaa acggggagtg gtaaacctcg ttaaatatgc caaataacaa cggcaggcag    14520
cagaagaaga agaaggggga cggccagcca gtcaatcagc tgtgccaaat gttgggcagg    14580
atcatcgccc agcaaaacca gtccagaggt aagggaccgg ggaagaaaag taagaagaaa    14640
agcctggaga agccccattt tcctctcgcg actgaagatg acgttagaca tcacttcacc    14700
cctagtgagc ggcaattgtg tctgtcgtca atccagactg cctttaacca aggcgctgga    14760
acttgtaccc tgtcggattc agggagaata agttacactg cggagtttag tttgcctacg    14820
catcatactg tgcgcctaat tcgcgtcaca gcatcaccct cagcatgatg agctggcatt    14880
cttgagacat cccagtgttt gaattggaag gatgtgtggt gaatggcact gattgatatt    14940
gtgcctytaa gtcacctatt caattagggc gaccgtatgg gggtaatatt taattggcgt    15000
gaaccatgcg gccgaaayt                                                 15019
```

<210> SEQ ID NO 7
<211> LENGTH: 15086
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 7

```
atgacgtata ggtgttggct ctatgccttg gcatttgtat tgtcaggagc tgtgaccatt     60
ggcacagccc aaaacttgct gcacagaaac acccttctgt gatagcctcc ttcagggag    120
cttagggttt gtccctagca ccttgcttcc ggagttgcac tgctttacgg tctctccacc   180
```

```
cctttaacca tgtctgggat acttgatcgg tgcacgtgta cccccaatgc cagggtgttt    240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct ccccgccgg ggcctgctgg     420
ctttctgcaa tctttccaat cgcacgaatg accagtggaa acctgaactt ccaacaaaga    480
atggtacggg tcgcagctga gctttacaga gccggccagc tcaccctgc agtcttgaag     540
gctctacaag tttatgaacg gggttgccgc tggtacccca ttgttggacc tgtccctgga    600
gtggccgttt cgccaattc cctacatgtg agtgataaac ccttcccggg agcaactcac     660
gtgttgacca acctgccgct cccgcagaga cccaagcctg aagactttg ccctttgag      720
tgtgctatgg ctactgtcta tgacattggt catgacgccg tcatgtatgt ggccgaaagg    780
aaagtctcct gggcccctcg tggcgggat gaagtgaaat ttgaagctgt ccccggggag     840
ttgaagttga ttgcgaaccg gctccgcacc tccttcccgc ccaccacac agtggacatg     900
tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga actggcggg agaacccagc tactctgggt ttgaggacct cctcagaata     1260
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccctgg gatgtcccct     1740
tctttgctcc ctcttgaatg tgttcaggc tgttgtgggc acaagggcgg tcttggttcc     1800
ccagatgcag tcgaggtctc cggatttgac cctgcctgcc ttgaccggct ggctgaggtg    1860
atgcacctgc tagcagtgc tatcccagcc gctctggccg aaatgtctgg cgattccgat     1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttgccaaaa gttcagcctc gaaaaacgaa gcctgtcaag    2340
agcttgccgg agagaaagcc tgtccccgcc ccgcgcagga aggttgggtc gattgtggc     2400
agcccggttt cattaggcgg cgatgtccct aacagtgggg aagatttggc tgttagtagc    2460
ccctttgatc tcccgacccc acctgagccg gcaacacctt caagtgagct ggtgattgtg    2520
```

```
tcctcaccgc aatgcatctt caggccggcg acacccttga gtgagccggc tccaattccc    2580
gcacctcgcg gaactgtgtc tcgaccggtg acacccttga gtgagccgat ccctgtgccc    2640
gcaccgcggc gtaagtttca gcaggtgaaa agattgagtt cggcggcggc aatcccaccg    2700
taccaggacg agcccctgga tttgtctgct tcctcacaga ctgaatatga ggcctctccc    2760
ccagcaccgc cgcagagcgg gggcgttctg ggagtagagg ggcatgaagc tgaggaaacc    2820
ctgagtgaaa tctcggacat gtcgggtaac attaaacctg cgtccgtgtc atcaagcagc    2880
tccttgtcca gcgtgagaat cacacgccca aaatactcag ctcaagccat catcgactcg    2940
ggcgggccct gcagtgggca tctccaagag gtaaaggaaa catgccttag tgtcatgcgc    3000
gaggcatgtg atgcgactaa gcttgatgac cctgctacgc aggaatggct ttctcgcatg    3060
tgggatcggg tggacatgct gacttggcgc aacacgtctg tttaccaggc gatttgcacc    3120
ttagatggca ggttaaagtt cctcccaaaa atgatactcg acaccgcc gccctatccg    3180
tgtgagtttg tgatgatgcc tcacacgcct gcaccttccg taggtgcgga gagcgacctt    3240
accattggct cagttgctac tgaagatgtt ccacgcatcc tcgagaaaat agaaaatgtc    3300
ggcgagatgg ccaaccaggg acccttggcc ttctccgagg ataaaccggt agatgaccaa    3360
cttgtcaacg accccggat atcgtcgcgg aggcctgacg agagcacatc agctccgtcc    3420
gcaggcacag gtggcgccgg ctcttttacc gatttgccgc cttcagatgg cgcggatgcg    3480
gacgggggg ggccgtttcg gacgtaaaa agaaaagctg aaaggctctt tgaccaactg    3540
agccgtcagg tttttgacct cgtctcccat ctccctgttt tcttctcacg ccttttctac    3600
cctggcggtg gttattctcc gggtgattgg ggttttgcag cttttactct attgtgcctc    3660
tttttatgtt acagttaccc agcctttggt attgctcccc tcttgggtgt gttttctggg    3720
tcttctcggc gcgttcgaat gggggttttt ggctgctggt tggcttttgc tgttggtctg    3780
ttcaagcctg tgtccgaccc agtcggcgct gcttgtgagt ttgactcgcc agagtgtaga    3840
aacatccttc attcttttga gcttctcaaa ccttgggacc ctgttcgcag ccttgttgtg    3900
ggccccgtcg gtctcggtct tgccattctt ggcaggttac tgggcggggc acgctgcatc    3960
tggcactttt tgcttaggct tggcattgtt gcagactgta tcttggctgg agcttacgtg    4020
cttttctcaag gtaggtgtaa aaagtgctgg ggatcttgta taagaactgc tcccaatgag    4080
gtcgcttta acgtgtttcc tttcacacgt gcgaccaggt cgtcacttat cgacctgtgc    4140
gatcggtttt gtgcgccaaa aggaatggac cccattttc tcgccactgg gtggcgcggg    4200
tgctgggccg gccgaagccc cattgagcaa ccctctgaaa acccatcgc gtttgcccag    4260
ttggatgaaa agaagattac ggctaggact gtggtcgccc agcctttatga ccccaaccaa    4320
gccgtaaagt gcttgcgggt attgcaggcg ggtggggcga tggtggctaa ggcggtccca    4380
aaagtggtca aggtttccgc tgttccattc cgagccccct tctttcccac tggagtgaaa    4440
gttgaccctg attgcagggt cgtggttgac cctgacactt tcactgcagc tctccggtct    4500
ggctactcca ccacaaacct cgtccttggt gtggggact tgcccagct gaatggatta    4560
aaaatcaggc aaatttccaa gccttcaggg ggaggcccac atctcatggc tgccctgcat    4620
gttgcctgct cgatggctct gcacatgctt gctgggattt atgtgactgc ggtgggttct    4680
tgcggcaccg gcaccaacga cccgtggtgc gctaacccgt ttgccgtccc tggctacgga    4740
cctggctctc tctgcacgtc cagattgtgc atttcccaac acggccttac cctgcccttg    4800
acagcacttg tggcgggatt cggtattcaa gaaattgcct tggtcgtttt gatttttgtt    4860
tccatcggag gcatggctca taggttgagc tgtaaggctg acatgctgtg tgtcttgctt    4920
```

```
gcaattgcca gctatgtttg ggtacctctt acctggttgc tttgtgtgtt tccttgctgg   4980
ttgcgctgtt tttctttgca cccccctcacc atcctatggt tggtgttttt cttgatttct   5040
gtgaatatgc cttcaggaat cttggccatg gtgttgttgg tttctctttg gcttcttggt   5100
cgttatacta atgttgctgg ccttgtcacc ccctacgaca ttcatcatta caccagtggc   5160
ccccgcggtg ttgccgcctt ggctaccgca ccagatggga cctacttggc cgctgtccgc   5220
cgcgctgcgt tgactggccg caccatgctg tttaccccgt cccagcttgg gtctcttctt   5280
gagggtgctt tcagaactcg aaagccctca ctgaacaccg tcaatgtgat cgggtcctcc   5340
atgggctctg gcggggtgtt taccatcgac gggaaagtca agtgcgtaac tgccgcacat   5400
gtccttacgg gcaattcagc tcgggtttcc ggggtcggct tcaatcaaat gcttgacttt   5460
gacgtaaagg gagatttcgc tatagctgat tgcccgaatt ggcaaggggc tgcccccaag   5520
acccaattct gcacggatgg atggactggc cgtgcctatt ggctaacatc ctctggcgtc   5580
gaacccggcg tcattggaaa aggattcgcc ttctgcttca ccgcatgtgg cgattccggg   5640
tccccagtga tcaccgaggc cggtgagctt gtcggcgttc acacgggatc gaataaacaa   5700
ggggggggca ttgttacgcg cccctcaggc cagttttgta atgtggcacc catcaagcta   5760
agcgaattaa gtgaattctt tgctgggcct aaggtcccgc tcggtgatgt gaaggtcggc   5820
agccacataa ttaaagacat aagcgaggtg ccttcagatc tttgtgcctt gcttgctgcc   5880
aaacctgaac tggaaggagg cctctccacc gtccaacttc tttgtgtgtt ttttctcctg   5940
tggagaatga tgggacatgc ctggacgccc ttggttgctg tgagtttctt tatttttgaat   6000 gaggttctcc cagccgtcct ggtccggagt gtttttctcct ttggaatgtt tgtgctatcc   6060
tggctcacgc catggtctgc gcaagttctg atgatcaggc ttctgacagc agctcttaac   6120
aggaacagat ggtcacttgc cttttttcagc ctcggtgcag tgaccggttt tgtcgcagat   6180
cttgcggcca ctcaggggca tccgttgcag gcagtgatga atttgagcac ctatgcattc   6240
ctgcctcgga tgatggttgt gacctcacca gtcccagtga tcacgtgtgg tgtcgtgcac   6300
ctacttgcca tcattttgta cttgtttaag taccgtggcc tgcaccatat ccttgttggc   6360
gatggagtgt tctctgcggc tttcttcttg agatactttg ccgagggaaa gttgagggaa   6420
ggggtgtcgc aatcctgcgg aatgaatcat gagtctctga ctggtgccct cgctatgaga   6480
ctcaatgacg aggacttgga tttccttatg aaatggactg attttaagtg ctttgtttct   6540
gcgtccaaca tgaggaatgc agcgggtcaa tttatcgagg ctgcctatgc taaagcactt   6600
agagtagaac tggcccagtt ggtgcaggtt gataaagttc gaggtactt ggccaaactt   6660 gaagcttttg ctgataccgt ggcacctcaa ctctcgcccg gtgacattgt tgtcgctctc   6720
ggccacacgc ctgttggcag tatcttcgac ctaaaggttg gtagcaccaa gcatacccctc   6780 caagccattg agaccagagt ccttgctggg tccaaaatga ccgtggcgcg cgtcgtcgac   6840 ccgacccca cgcccccacc cgcacccgtg cccatccccc tcccaccgaa agttctggag   6900
aatggcccca acgcttgggg ggatgaggac cgtttgaata agaagaagag gcgcaggatg   6960
gaagccctcg gcatctatgt tatgggcggg aaaaaatacc agaaattttg ggacaagaat   7020
tccggtgatg tgttttatga ggaggtccat aataacacag atgagtggga gtgtctcaga   7080
gttggcgacc ctgccgactt tgaccctgag aagggaactc tgtgtggaca tgtcaccatt   7140
gaaaacaagg cttaccatgt ttacacctcc ccatctggta agaagttctt ggtccccgtc   7200
aacccagaga atggaagagt ccaatgggaa gctgcaaagc tttccgtgga gcaggcccta   7260
```

```
ggtatgatga atgtcgacgg cgaactgact gccaagaaac tggagaaact gaaaagaata    7320
attgacaaac tccagggcct gactaaggag cagtgtttaa actgctagcc gccagcgact    7380
tgacccgctg tggtcgcggc ggcttggttg ttactgaaac agcggtaaaa atagtcaaat    7440
ttcacaaccg gaccttcacc ctgggacctg tgaatttaaa agtggccagt gaggttgagc    7500
taaaagacgc ggttgagcac aaccaacacc cggttgcgag accgatcgat ggtggagttg    7560
tgctcctgcg ttccgcggtt ccttcgctta tagacgtctt gatctccggt gctgatgcat    7620
ctcccaagtt acttgcccat cacgggccgg gaaacactgg gatcgatggc acgctctggg    7680
attttgagtc cgaagccact aaagaggaag tcgcactcag tgcgcaaata atacaggctt    7740
gtgacattag gcgcggcgac gctcctgaaa ttggtctccc ttacaagctg taccctgtta    7800
ggggtaaccc tgagcgggtg aaaggagttc tgcagaatac aaggtttgga gataccctt    7860
acaaaacccc cagtgacact ggaagcccag tgcacgcggc tgcctgcctt acgcccaacg    7920
ccactccggt gactgatggg cgctccgtct tggccacgac catgcccccc gggtttgagt    7980
tatatgtacc gaccatacca gcgtctgtcc ttgattacct tgactctagg cctgactgcc    8040
ctaaacagct gacagagcac ggctgcgaag atgccgcact gaaagacctc tctaaatatg    8100
acttgtccac ccaaggcttt gttttacctg gagttcttcg ccttgtgcgg aaatacctgt    8160
ttgcccatgt aggtaagtgc ccacccgttc atcggccttc tacttaccct gctaagaatt    8220
ctatggctgg aataaatggg aacaggttcc caaccaagga cattcagagc gtccctgaaa    8280
tcgacgttct gtgcgcacag gctgtgcgag aaaactggca aactgtcacc ccttgtactc    8340
ttaagaaaca gtattgcggg aagaagaaga ctaggaccat actcggcacc aataacttca    8400
tcgcactagc ccaccgagca gtgttgagtg tgttaccca gggcttcatg aaaaaggcgt    8460
ttaactcgcc catcgccctc ggaaagaaca gtttaagga gctacagact ccggtcctgg    8520
gcaggtgcct tgaagctgat ctcgcatcct gcgatcgatc cacgcctgca attgtccgct    8580
ggtttgccgc caaccttctt tatgaacttg cctgtgctga agagcatcta ccgtcgtacg    8640
tgctgaactg ctgccacgac ttactggtca cgcagtccgg cgcagtgact aagagaggtg    8700
gcctgtcgtc tggcgacccg atcacctctg tgtctaacac catttatagt ttggtgatct    8760
atgcacagca tatggtgctt agttacttca aaagtggtca cccccatggc cttctgttct    8820
tacaagacca gctaaagttt gaggacatgc tcaaggttca acccctgatc gtctattcgg    8880
acgacctcgt gctgtatgcc gagtctccca ccatgccaaa ctatcactgg tgggttgaac    8940
atctgaattt gatgctgggg tttcagacgg acccaaagaa gacagcaata acagactcgc    9000
catcatttct aggctgtaga ataataaatg gcgccagct agtccccaac cgtgacagga    9060
tcctcgcggc cctcgcctat cacatgaagg cgagtaatgt ttctgaatac tatgcctcag    9120
cggctgcaat actcatggac agctgtgctt gtttggagta tgatcctgaa tggtttgaag    9180
aacttgtagt tggaatagcg cagtgcgccc gcaaggacgg ctacagcttt cccggcacgc    9240
cgttcttcat gtccatgtgg gaaaaactca ggtccaatta tgagggaag aagtcgagag    9300
tgtgcgggta ctgcggggcc ccggccccgt acgctactgc ctgtggcctc gacgtctgca    9360
tttaccacac ccacttccac cagcattgtc cagtcacaat ctggtgtggc catccagcgg    9420
gttctggttc ttgtagtgag tgcaaatccc ctgtagggaa aggcacaagc ccttagacg    9480
aggtgctgga acaagtcccg tataagcccc cacggaccgt tatcatgcat gtggagcagg    9540
gtctcacccc ccttgatcca ggtagatacc aaactcgccg cggattagtc tctgtcaggc    9600
gtggaattag gggaaatgaa gttggactac cagacggtga ttatgctagc accgccttgc    9660
```

```
tccctacctg caaagagatc aacatggtcg ctgtcgcttc caatgtattg cgcagcaggt   9720
tcatcatcgg cccacccggt gctgggaaaa catactggct ccttcaacag gtccaggatg   9780
gtgatgttat ttacacacca actcaccaga ccatgcttga catgattagg gctttgggga   9840
cgtgccggtt caacgtcccg gcaggcacaa cgctgcaatt ccccgtcccc tcccgcaccg   9900
gtccgtgggt tcgcatccta gccggcggtt ggtgtcctgg caagaattcc ttcctagatg   9960
aagcagcgta ttgcaatcac cttgatgttt tgaggcttct tagtaaaact accctcacct  10020
gtctaggaga cttcaagcaa ctccacccag tgggttttga ttctcattgc tatgttttg  10080 acatcatgcc tcaaactcaa ctgaagacca tctggaggtt tggacagaat atctgtgatg  10140
ccattcagcc agattacagg gacaaactca tgtccatggt caacacaacc cgtgtgacct  10200
acgtggaaaa acctgtcagg tatgggcagg tcctcacccc ctaccacagg gaccgagagg  10260
acgacgccat cactattgac tccagtcaag gcgccacatt cgatgtggtt acattgcatt  10320
tgcccactaa agattcactc aacaggcaaa gagcccttgt tgctatcacc agggcaagac  10380
acgctatctt tgtgtatgac ccacacaggc agctgcaggg cttgtttgat cttcctgcaa  10440
aaggcacgcc cgtcaacctc gcagtgcact gcgacgggca gctgatcgtg ctggatagaa  10500
ataacaaaga atgcacggtt gctcaggctc taggcaacgg ggataaattt agggccacag  10560
acaagcgtgt tgtagattct ctccgcgcca tttgtgctga tctagaaggg tcgagctctc  10620
cgctccccaa ggtcgcacac aacttgggat tttatttctc acctgattta acacagtttg  10680
ctaaactccc agtagaactt gcacctcact ggcccgtggt gtcaacccag aacaatgaaa  10740
agtggccgga tcggctggtt gccagccttc gccctatcca taaatacagc cgcgcgtgca  10800
tcggtgccgg ctatatggtg ggcccttcgg tgtttctagg cactcctggg gtcgtgtcat  10860
actatctcac aaaatttgtt aagggcgggg ctcaagtgct tccggagacg gttttcagca  10920
ccggccgaat tgaggtagac tgccgggaat atcttgatga tcgggagcga gaagttgctg  10980
cgtccctccc acacgctttc attggcgacg tcaaaggcac taccgttgga ggatgtcatc  11040
atgtcacctc cagatacctc ccgcgcgtcc ttcccaagga atcagttgcg gtagtcgggg  11100
tttcaagccc cggaaaagcc gcgaaagcat tgtgcacact gacagatgtg tacctcccag  11160
atcttgaagc ctatctccac ccggagaccc agtccaagtg ctggaaaatg atgttggact  11220
tcaaagaagt tcgactaatg gtctggaaag acaaaacagc ctatttccaa cttgaaggtc  11280
gctatttcac ctggtatcag cttgccagct atgcctcgta catccgtgtt cccgtcaact  11340
ctacggtgta cttggacccc tgcatgggcc ccgccctttg caacaggaga gtcgtcgggt  11400
ccacccactg gggggctgac ctcgcggtca cccttatga ttacggcgct aaaattatcc  11460
tgtctagcgc gtaccatggt gaaatgcccc ccggatacaa aattctggcg tgcgcggagt  11520
tctcgttgga tgacccagtt aagtacaaac atacctgggg gtttgaatcg gatacagcgt  11580
atctgtatga gttcaccgga aacggtgagg actgggagga ttacaatgat gcgtttcgtg  11640
cgcgccagga agggaaaatt tataaggcca ctgccaccag cttgaagttt tattttccc  11700 cgggccctgt cattgaacca actttaggcc tgaattgaaa tgaaatgggg tccatgcaaa  11760 gccttttga caaaattggc caacttttg tggatgcttt cacggagttc ttggtgtcca  11820
ttgttgatat cattatattt ttggccattt gtttggctt caccatcgcc ggttggctgg  11880
tggtcttttg catcagattg gtttgctccg cgatactccg tacgcgccct gccattcact  11940
ctgagcaatt acagaagatc ttatgaggcc tttctttccc agtgccaagt ggacattccc  12000
```

```
acctggggaa ctaaacatcc tttggggatg ctttggcacc ataaggtgtc aaccctgatt    12060
gatgaaatgg tgtcgcgtcg aatgtaccgc atcatggaaa aagcagggca ggctgcctgg    12120
aaacaggtgg tgagcgaggc tacgctgtct cgcattagta gtttggatgt ggtggctcat    12180
tttcagcatc tagccgccat tgaagccgag acctgtaaat atttggcctc ccggctgccc    12240
atgctacaca acctgcgcat gacagggtca aatgtaacca tagtgtataa tagcactttg    12300
aatcaggtgt ttgctatttt tccaacccct ggttcccggc caaagcttca tgattttcag    12360
caatggttaa tagctgtaca ttcctccata ttttcctctg ttgcagcttc ttgtactctt    12420
tttgttgtgc tgtggttgcg ggttccaata ctacgtactg ttttggttt ccgctggtta    12480 ggggcaattt ttcttcgaa ctcacagtga attacacggt gtgtccacct tgcctcaccc    12540
ggcaagcagc cacagagatc tacgaacccg gtaggtctct ttggtgcagg atagggtatg    12600
accgatgtgg ggaggacgat catgacgagc tagggtttat gataccgcct ggcctctcca    12660
gcgaaggcca cttgactggt gtttacgcct ggttggcgtt cttgtccttc agctacacgg    12720
cccagttcca tcccgagata ttcgggatag ggaatgtgag tcgagtttat gttgacatca    12780
aacatcaact catctgcgcc gaacatgacg ggcagaacac caccttgcct cgtcatgaca    12840
acatttcagc cgtgttttcag acctattacc aacatcaagt cgacggcggc aattggtttc    12900
acctagaatg gcttcgtccc ttcttttcct cgtggttggt tttaaatgtc tcttggtttc    12960
tcaggcgttc gcctgcaaac catgtttcag ttcgagtctt gcagatatta agaccaacac    13020
caccgcagcg gcaagctttg ctgtcctcca agacatcagt tgccttaggc atcgcgactc    13080
ggcctctgag gcgattcgca aaatccctca gtgccgtacg gcgataggga cacccgtgta    13140
tgttaccatc acagccaatg tgacagatga gaattattta cattcttctg atctcctcat    13200
gctttcttct tgccttttct atgcttctga gatgagtgaa aagggattta aggtggtatt    13260
tggcaatgtg tcaggcatcg tggctgtgtg tgtcaatttt accagctacg tccaacatgt    13320
caaggagttt acccaacgct ccctggtggt cgaccatgtg cggttgctcc atttcatgac    13380
acctgagacc atgaggtggg caactgtttt agcctgtctt tttgccattc tgttggcaat    13440
ttgaatgttt aagtatgttg gagaaatgct tgaccgcggg ctgttgctcg cgattgcttt    13500
ctttgtggtg tatcgtgccg ttctgttttg ctgtgctcgc caacgccagc aacgacagca    13560
gctcccatct acagctgatt tacaacttga cgctatgtga gctgaatggc acagattggc    13620
tagctaacaa atttgattgg gcagtggaga gttttgtcat ctttcccgtt ttgactcaca    13680
ttgtctccta tggtgccctc actaccagcc atttccttga cacagtcgct ttagtcactg    13740
tgtctaccgc cgggtttgtt cacgggcggt atgtcctaag tagcatctac gcggtctgtg    13800
ccctggctgc gttgacttgc ttcgtcatta ggtttgcaaa gaattgcatg tcctggcgct    13860
acgcgtgtac cagatatacc aactttcttc tggacactaa gggcagactc tatcgttggc    13920
ggtcgcctgt catcatagag aaaagggggca aagttgaggt cgaaggtcat ctgatcgacc    13980
tcaaaagagt tgtgcttgat ggctccgtgg caaccctat aaccgagtt tcagcggaac    14040 aatggggtcg tccttagatg acttctgtca cgatagcacg gctccacaaa aggtgctttt    14100
ggcgttttct attacctaca cgccagtgat gatatatgcc ctaaaggtga gtcgcggccg    14160
actgctaggg cttctgcacc ttttgatctt cctgaattgt gctttcacct tcgggtacat    14220
gactttcgcg cactttcaga gtacaaataa ggtcgcgctc actatgggag cagtagttgc    14280 actccttttgg ggggtgtact cagccataga aacctggaaa ttcatcacct ccagatgccg    14340
tttgtgcttg ctaggccgca agtacattct ggcccctgcc caccacgttg aaagtgccgc    14400
```

```
aggctttcat ccgattgcgg caaatgataa ccacgcattt gtcgtccggc gtcccggctc    14460
cactacggtc aacggcacat tggtgcccgg gttaaaaagc ctcgtgttgg gtggcagaaa    14520
agctgttaaa cagggagtgg taaaccttgt caaatatgcc aaataacaac ggcaagcagc    14580
agaagagaaa gaagggggat ggccagccag tcaatcagct gtgccagatg ctgggtaaga    14640
tcatcgctca gcaaaaccag tccagaggca agggaccggg aaagaaaaat aagaagaaaa    14700
acccggagaa gccccatttt cctctagcga ctgaagatga tgtcagacat cactttaccc    14760
ctagtgagcg gcaattgtgt ctgtcgtcaa tccagaccgc cttaatcaa ggcgctggga    14820 cttgcaccct gtcagattca ggaggataa gttacactgt ggagtttagt ttgcctacgc    14880
atcatactgt gcgcctgatc cgcgtcacag catcaccctc agcatgatgg gctggcattc    14940
ttgaggcatc tcagtgtttg aattggaaga atgtgtggtg aatggcactg attgacattg    15000
tgcctctaag tcacctattc aattagggcg accgtgtggg ggtgagattt aattggcgag    15060
aaccatgcgg ccgaaattaa aaaaaa                                         15086
```

<210> SEQ ID NO 8
<211> LENGTH: 14819
<212> TYPE: DNA
<213> ORGANISM: Artificial Sequence
<220> FEATURE:
<223> OTHER INFORMATION: Porcine reproductive and respiratory syndrome virus

<400> SEQUENCE: 8

```
atgacgtata ggtgttggct ctatgccttg gcatttgtat tgtcaggagc tgtgaccatt      60
ggcacagccc aaaacttgct gcacagaaac acccttctgt gatagcctcc ttcaggggag     120
cttagggttt gtccctagca ccttgcttcc ggagttgcac tgctttacgg tctctccacc     180
cctttaacca tgtctgggat acttgatcgg tgcacgtgta cccccaatgc caggggtgttt    240 atggcggagg ccaagtcta ctgcacacga tgcctcagtg cacggtctct cctcccctg       300 aacctccagg tttctgagct cggggtgcta ggcctattct acaggcccga agagccactc     360
cggtggacgt tgccacgtgc attccccact gttgagtgct cccccgccgg ggcctgctgg    420 cttttctgcaa tctttccaat cgcacgaatg accagtggaa acctgaactt ccaacaaaga   480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagactttg ccccttgag     720 tgtgctatgg ctactgtcta tgacattggt catgacgccg tcatgtatgt ggccgaaagg    780
aaagtctcct gggcccctcg tggcggggat gaagtgaaat ttgaagctgt ccccggggag    840
ttgaagttga ttgcgaaccg gctccgcacc tccttcccgc ccaccacac agtggacatg      900 tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc    1080
aagcatggtg tctctggcaa gtacctgcag cggaggctgc aagttaatgg tctccgagca    1140
gtaactgacc taaacggacc tatcgtcgta cagtacttct ccgttaagga gagttggatc    1200
cgccatttga aactgcgggg agaacccagc tactctgggt tgaggaccct cctcagaata    1260
agggttgagc ctaacacgtc gccattggct gacaaggaag aaaaaattt ccggtttggc    1320
```

```
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccccctgg gatgtcccct    1740
tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca gtgcgcttag ggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca accagtgtcg tgctctggtc    2280
cctgttgtga ctcaaaagtc cttgccaatt cccgcacctc gcggaactgt gtctcgaccg    2340
gtgacaccct tgagtgagcc gatccctgtg cccgcaccgc ggcgtaagtt tcagcaggtg    2400
aaaagattga gttcggcggc ggcaatccca ccgtaccagg acgagcccct ggatttgtct    2460
gcttcctcac agactgaata tgaggcctct cccccagcac cgccgcagag cggggcgtt    2520
ctgggagtag aggggcatga agctgaggaa accctgagtg aaatctcgga catgtcgggt    2580
aacattaaac ctgcgtccgt gtcatcaagc agctccttgt ccagcgtgag aatcacacgc    2640
ccaaaatact cagctcaagc catcatcgac tcgggcgggc cctgcagtgg gcatctccaa    2700
gaggtaaagg aaacatgcct tagtgtcatg cgcgaggcat gtgatgcgac taagcttgat    2760
gaccctgcta cgcaggaatg gctttctcgc atgtgggatc gggtggacat gctgacttgg    2820
cgcaacacgt ctgtttacca ggcgatttgc accttagatg gcaggttaaa gttcctccca    2880
aaaatgatac tcgagacacc gccgcccat cgtgtgagt ttgtgatgat gcctcacacg    2940
cctgcacctt ccgtaggtgc ggagagcgac cttaccattg gctcagttgc tactgaagat    3000
gttccacgca tcctcgagaa aatagaaaat gtcggcgaga tggccaacca gggacccttg    3060
gccttctccg aggataaacc ggtagatgac caacttgtca acgaccccg gatatcgtcg    3120
cggaggcctg acgagagcac atcagctccg tccgcaggca caggtggcgc cggctctttt    3180
accgatttgc cgccttcaga tggcgcggat gcggacgggg gggggccgtt tcggacggta    3240
aaaagaaaag ctgaaaggct cttttgaccaa ctgagccgtc aggtttttga cctcgtctcc    3300
catctcccctg ttttcttctc acgccttttc taccctggcg gtggttattc tccgggtgat    3360
tggggttttg cagcttttac tctattgtgc ctcttttat gttacagtta cccagccttt    3420
ggtattgctc cctctcttggg tgtgttttct gggtcttctc ggcgcgttcg aatgggggtt    3480
tttggctgct ggttggcttt tgctgttggt ctgttcaagc ctgtgtccga cccagtcggc    3540
gctgcttgtg agtttgactc gccagagtgt agaaacatcc ttcattcttt tgagcttctc    3600
aaaccttggg accctgttcg cagccttgtt gtgggccccg tcggtctcgg tcttgccatt    3660
```

```
cttggcaggt tactgggcgg ggcacgctgc atctggcact ttttgcttag gcttggcatt    3720
gttgcagact gtatcttggc tggagcttac gtgctttctc aaggtaggtg taaaaagtgc    3780
tggggatctt gtataagaac tgctcccaat gaggtcgctt ttaacgtgtt tccttttcaca   3840 cgtgcgacca ggtcgtcact tatcgacctg tgcgatcggt tttgtgcgcc aaaaggaatg    3900
gaccccattt ttctcgccac tgggtggcgc gggtgctggg ccggccgaag ccccattgag    3960
caaccctctg aaaacccat cgcgtttgcc cagttggatg aaaagaagat tacgctagg     4020 actgtggtcg cccagcctta tgaccccaac caagccgtaa agtgcttgcg ggtattgcag    4080
gcgggtgggg cgatggtggc taaggcggtc ccaaaagtgg tcaaggtttc cgctgttcca    4140
ttccgagccc ccttctttcc cactggagtg aaagttgacc ctgattgcag ggtcgtggtt    4200
gaccctgaca ctttcactgc agctctccgg tctggctact ccaccacaaa cctcgtcctt    4260
ggtgtggggg actttgccca gctgaatgga ttaaaaatca ggcaaatttc caagccttca    4320
gggggaggcc cacatctcat ggctgccctg catgttgcct gctcgatggc tctgcacatg    4380
cttgctggga tttatgtgac tgcggtgggt tcttgcggca ccggcaccaa cgacccgtgg    4440
tgcgctaacc cgtttgccgt ccctggctac ggacctggct ctctctgcac gtccagattg    4500
tgcatttccc aacacggcct taccctgccc ttgacagcac ttgtggcggg attcggtatt    4560
caagaaattg ccttggtcgt tttgattttt gtttccatcg gaggcatggc tcataggttg    4620
agctgtaagg ctgacatgct gtgtgtcttg cttgcaattg ccagctatgt ttgggtacct    4680
cttacctggt tgctttgtgt gtttccttgc tggttgcgct gttttctttt gcaccccctc    4740
accatcctat ggttggtgtt tttcttgatt tctgtgaata tgccttcagg aatcttggcc    4800
atggtgttgt tggtttctct ttggcttctt ggtcgttata ctaatgttgc tggccttgtc    4860 acccccctacg acattcatca ttacaccagt ggccccgcg tgttgccgc cttggctacc     4920 gcaccagatg ggacctactt ggccgctgtc cgccgcgctg cgttgactgg ccgcaccatg    4980
ctgtttaccc cgtcccagct tgggtctctt cttgagggtg ctttcagaac tcgaaagccc    5040
tcactgaaca ccgtcaatgt gatcgggtcc tccatgggct ctggcggggt gtttaccatc    5100
gacgggaaag tcaagtgcgt aactgccgca catgtcctta cgggcaattc agctcgggtt    5160
tccggggtcg gcttcaatca aatgcttgac tttgacgtaa agggagattt cgctatagct    5220
gattgcccga attggcaagg ggctgccccc aagacccaat tctgcacgga tggatggact    5280
ggccgtgcct attggctaac atcctctggc gtcgaacccg gcgtcattgg aaaaggattc    5340
gccttctgct tcaccgcatg tggcgattcc ggtccccag tgatcaccga ggccggtgag    5400
cttgtcggcg ttcacacggg atcgaataaa caagggggggg gcattgttac gcgcccctca    5460
ggccagtttt gtaatgtggc acccatcaag ctaagcgaat taagtgaatt ctttgctggg    5520
cctaaggtcc cgctcggtga tgtgaaggtc ggcagccaca taattaaaga cataagcgag    5580
gtgccttcag atctttgtgc cttgcttgct gccaaacctg aactgaagg aggcctctcc    5640 accgtccaac ttctttgtgt gttttttctc ctgtggagaa tgatgggaca tgcctggacg    5700
cccttggttg ctgtgagttt ctttattttg aatgaggttc tcccagccgt cctggtccgg    5760
agtgttttct cctttggaat gtttgtgcta tcctggctca cgccatggtc tgcgcaagtt    5820
ctgatgatca ggcttctgac agcagctctt aacaggaaca gatggtcact tgccttttcc    5880
agcctcggtg cagtgaccgg ttttgtcgca gatcttgcgg ccactcaggg gcatccgttg    5940
caggcagtga tgaatttgag cacctatgca ttcctgcctc ggatgatggt tgtgacctca    6000
ccagtcccag tgatcacgtg tggtgtcgtg cacctacttg ccatcatttt gtacttgttt    6060
```

```
aagtaccgtg gcctgcacca tatccttgtt ggcgatggag tgttctctgc ggctttcttc   6120
ttgagatact ttgccgaggg aaagttgagg aagggggtgt cgcaatcctg cggaatgaat   6180
catgagtctc tgactggtgc cctcgctatg agactcaatg acgaggactt ggatttcctt   6240
atgaaatgga ctgattttaa gtgctttgtt tctgcgtcca acatgaggaa tgcagcgggt   6300
caatttatcg aggctgccta tgctaaagca cttagagtag aactggccca gttggtgcag   6360
gttgataaag ttcgaggtac tttggccaaa cttgaagctt ttgctgatac cgtggcacct   6420
caactctcgc ccggtgacat tgttgtcgct ctcggccaca cgcctgttgg cagtatcttc   6480
gacctaaagg ttggtagcac caagcatacc ctccaagcca ttgagaccag agtccttgct   6540
gggtccaaaa tgaccgtggc gcgcgtcgtc gacccgaccc ccacgccccc acccgcaccc   6600
gtgcccatcc cctcccacc gaaagttctg gagaatggcc caacgcttg ggggatgag    6660 gaccgtttga ataagaagaa gaggcgcagg atggaagccc tcggcatcta tgttatgggc   6720
gggaaaaaat accagaaatt ttgggacaag aattccggtg atgtgttta tgaggaggtc    6780 cataataaca cagatgagtg ggagtgtctc agagttggcg accctgccga ctttgacctt   6840
gagaagggaa ctctgtgtgg acatgtcacc attgaaaaca aggcttacca tgtttacacc   6900
tccccatctg gtaagaagtt cttggtcccc gtcaacccag agaatggaag agtccaatgg   6960
gaagctgcaa gctttccgt ggagcaggcc ctaggtatga tgaatgtcga cggcgaactg    7020
actgccaaag aactggagaa actgaaaaga ataattgaca aactccaggg cctgactaag   7080
gagcagtgtt taaactgcta gccgccagcg acttgacccg ctgtggtcgc ggcggcttgg   7140
ttgttactga aacagcggta aaaatagtca aatttcacaa ccggaccttc accctgggac   7200
ctgtgaattt aaaagtggcc agtgaggttg agctaaaaga cgcggttgag cacaaccaac   7260
acccggttgc gagaccgatc gatggtggag ttgtgctcct gcgttccgcg gttccttcgc   7320
ttatagacgt cttgatctcc ggtgctgatg catctcccaa gttacttgcc catcacgggc   7380
cgggaaacac tgggatcgat ggcacgctct gggattttga gtccgaagcc actaaagagg   7440
aagtcgcact cagtgcgcaa ataatacagg cttgtgacat taggcgcggc gacgctcctg   7500
aaattggtct cccttacaag ctgtaccctg ttagggtaa ccctgagcgg gtgaaaggag    7560
ttctgcagaa tacaaggttt ggagacatac cttacaaaac ccccagtgac actggaagcc   7620
cagtgcacgc ggctgcctgc cttacgccca acgccactcc ggtgactgat gggcgctccg   7680
tcttggccac gaccatgccc cccgggtttg agttatatgt accgaccata ccagcgtctg   7740
tccttgatta ccttgactct aggcctgact gccctaaaca gctgacagag cacggctgcg   7800
aagatgccgc actgaaagac ctctctaaat atgacttgtc cacccaaggc tttgttttac   7860
ctggagttct tcgccttgtg cggaaatacc tgtttgccca tgtaggtaag tgcccacccg   7920
ttcatcggcc ttctacttac cctgctaaga attctatggc tggaataaat gggaacaggt   7980
tcccaaccaa ggacattcag agcgtccctg aaatcgacgt tctgtgcgca caggctgtgc   8040
gagaaaactg gcaaactgtc acccccttgta ctcttaagaa acagtattgc gggaagaaga   8100
agactaggac catactcggc accaataact tcatcgcact agcccaccga gcagtgttga   8160
gtggtgttac ccagggcttc atgaaaaagg cgtttaactc gcccatcgcc ctcggaaaga   8220
acaagtttaa ggagctacag actccggtcc tgggcaggtg ccttgaagct gatctcgcat   8280
cctgcgatcg atccacgcct gcaattgtcc gctggtttgc cgccaacctt ctttatgaac   8340
ttgcctgtgc tgaagagcat ctaccgtcgt acgtgctgaa ctgctgccac gacttactgg   8400
```

```
tcacgcagtc cggcgcagtg actaagagag gtggcctgtc gtctggcgac ccgatcacct   8460
ctgtgtctaa caccatttat agtttggtga tctatgcaca gcatatggtg cttagttact   8520
tcaaaagtgg tcaccccat ggccttctgt tcttacaaga ccagctaaag tttgaggaca    8580
tgctcaaggt tcaaccctg atcgtctatt cggacgacct cgtgctgtat gccgagtctc    8640
ccaccatgcc aaactatcac tggtgggttg aacatctgaa tttgatgctg gggtttcaga   8700
cggacccaaa gaagacagca ataacagact cgccatcatt tctaggctgt agaataataa   8760
atgggcgcca gctagtcccc aaccgtgaca ggatcctcgc ggccctcgcc tatcacatga   8820
aggcgagtaa tgtttctgaa tactatgcct cagcggctgc aatactcatg acagctgtg    8880
cttgttttgga gtatgatcct gaatggtttg aagaacttgt agttggaata gcgcagtgcg  8940
cccgcaagga cggctacagc tttcccggca cgccgttctt catgtccatg tgggaaaaac   9000
tcaggtccaa ttatgagggg aagaagtcga gagtgtgcgg gtactgcggg gccccggccc  9060
cgtacgctac tgcctgtggc ctcgacgtct gcatttacca cacccacttc caccagcatt   9120
gtccagtcac aatctggtgt ggccatccag cgggttctgg ttcttgtagt gagtgcaaat   9180
cccctgtagg gaaaggcaca agccctttag acgaggtgct ggaacaagtc ccgtataagc   9240
ccccacggac cgttatcatg catgtggagc agggtctcac ccccccttgat ccaggtagat  9300
accaaactcg ccgcggatta gtctctgtca ggcgtggaat taggggaaat gaagttggac   9360
taccagacgg tgattatgct agcaccgcct tgctccctac ctgcaaagag atcaacatgg   9420
tcgctgtcgc ttccaatgta ttgcgcagca ggttcatcat cggcccaccc ggtgctggga   9480
aaacatactg gctccttcaa caggtccagg atggtgatgt tatttacaca ccaactcacc   9540
agaccatgct tgacatgatt agggctttgg ggacgtgccg gttcaacgtc ccggcaggca   9600
caacgctgca attccccgtc ccctcccgca ccggtccgtg ggttcgcatc ctagccggcg   9660
gttggtgtcc tggcaagaat tccttcctag atgaagcagc gtattgcaat caccttgatg   9720
ttttgaggct tcttagtaaa actaccctca cctgtctagg agacttcaag caactccacc   9780
cagtgggttt tgattctcat tgctatgttt ttgacatcat gcctcaaact caactgaaga   9840
ccatctggag gttggacag aatatctgtg atgccattca gccagattac agggacaaac    9900
tcatgtccat ggtcaacaca acccgtgtga cctacgtgga aaaacctgtc aggtatgggc   9960
aggtcctcac cccctaccac agggaccgag aggacgacgc catcactatt gactccagtc  10020
aaggcgccac attcgatgtg gttacattgc atttgcccac taaagattca ctcaacaggc  10080
aaagagccct tgttgctatc accagggcaa gacacgctat ctttgtgtat gacccacaca  10140
ggcagctgca gggcttgttt gatcttcctg caaaaggcac gcccgtcaac ctcgcagtgc  10200
actgcgacgg gcagctgatc gtgctggata gaaataacaa agaatgcacg gttgctcagg  10260
ctctaggcaa cggggataaa tttagggcca cagacaagcg tgttgtagat tctctccgcg  10320
ccatttgtgc tgatctagaa gggtcgagct ctccgctccc caaggtcgca cacaacttgg  10380
gattttattt ctcacctgat ttaacacagt ttgctaaact cccagtagaa cttgcacctc  10440
actggccgt ggtgtcaacc cagaacaatg aaaagtggcc ggatcggctg gttgccagcc    10500
ttcgccctat ccataaatac agccgcgcgt gcatcggtgc cggctatatg gtgggccctt  10560
cggtgtttct aggcactcct ggggtcgtgt catactatct cacaaaattt gttaagggcg  10620
gggctcaagt gcttccggag acggttttca gcaccggccg aattgaggta gactgccggg  10680
aatatcttga tgatcgggag cgagaagttg ctgcgtccct cccacacgct ttcattggcc  10740
acgtcaaagg cactaccgtt ggaggatgtc atcatgtcac ctccagatac ctcccgcgcg  10800
```

```
tccttcccaa ggaatcagtt gcggtagtcg gggtttcaag cccccggaaaa gccgcgaaag   10860
cattgtgcac actgacagat gtgtacctcc cagatcttga agcctatctc cacccggaga   10920
cccagtccaa gtgctggaaa atgatgttgg acttcaaaga agttcgacta atggtctgga   10980
aagacaaaac agcctatttc caacttgaag gtcgctattt cacctggtat cagcttgcca   11040
gctatgcctc gtacatccgt gttcccgtca actctacggt gtacttggac ccctgcatgg   11100
gccccgccct ttgcaacagg agagtcgtcg ggtccaccca ctgggggggct gacctcgcgg   11160
tcaccccta tgattacggc gctaaaatta tcctgtctag cgcgtaccat ggtgaaatgc   11220
cccccggata caaaattctg gcgtgcgcgg agttctcgtt ggatgaccca gttaagtaca   11280
aacatacctg ggggtttgaa tcggatacag cgtatctgta tgagttcacc ggaaacggtg   11340
aggactggga ggattacaat gatgcgtttc gtgcgcgcca ggaagggaaa atttataagg   11400
ccactgccac cagcttgaag ttttatttc cccccgggccc tgtcattgaa ccaactttag   11460
gcctgaattg aaatgaaatg gggtccatgc aaagcctttt tgacaaaatt ggccaacttt   11520
ttgtggatgc tttcacggag ttcttggtgt ccattgttga tatcattata tttttggcca   11580
ttttgtttgg cttcaccatc gccggttggc tggtggtctt ttgcatcaga ttggtttgct   11640
ccgcgatact ccgtacgcgc cctgccattc actctgagca attacagaag atcttatgag   11700
gcctttcttt cccagtgcca agtggacatt cccacctggg gaactaaaca tcctttgggg   11760
atgctttggc accataaggt gtcaaccctg attgatgaaa tggtgtcgcg tcgaatgtac   11820
cgcatcatgg aaaaagcagg gcaggctgcc tggaaacagg tggtgagcga ggctacgctg   11880
tctcgcatta gtagtttgga tgtggtggct catttcagc atctagccgc cattgaagcc   11940
gagacctgta aatatttggc ctcccggctg cccatgctac acaacctgcg catgacaggg   12000
tcaaatgtaa ccatagtgta taatagcact ttgaatcagg tgtttgctat ttttccaacc   12060
cctggttccc ggccaaagct tcatgatttt cagcaatggt taatagctgt acattcctcc   12120
atattttcct ctgttgcagc ttcttgtact cttttttgttg tgctgtggtt gcgggttcca   12180
atactacgta ctgttttttgg tttccgctgg ttagggggcaa ttttttctttc gaactcacag   12240
tgaattacac ggtgtgtcca ccttgcctca cccggcaagc agccacagag atctacgaac   12300
ccggtaggtc tctttggtgc aggatagggt atgaccgatg tggggaggac gatcatgacg   12360
agctagggtt tatgataccg cctggcctct ccagcgaagg ccactgact ggtgtttacg   12420
cctggttggc gttcttgtcc ttcagctaca cggcccagtt ccatcccgag atattcggga   12480
tagggaatgt gagtcgagtt tatgttgaca tcaaacatca actcatctgc gccgaacatg   12540
acgggcagaa caccaccttg cctcgtcatg acaacatttc agccgtgttt cagacctatt   12600
accaacatca agtcgacggc ggcaattggt ttcacctaga atggcttcgt cccttctttt   12660
cctcgtggtt ggttttaaat gtctcttggt ttctcaggcg ttcgcctgca accatgtttt   12720
cagttcgagt cttgcagata ttaagaccaa caccaccgca cgcgcaagct tgctgtcct   12780
ccaagacatc agttgcctta ggcatcgcga ctcggcctct gaggcgattc gcaaaatccc   12840
tcagtgccgt acggcgatag ggacacccgt gtatgttacc atcacagcca atgtgacaga   12900
tgagaattat ttcattctt ctgatctcct catgctttct tcttgccttt tctatgcttc   12960
tgagatgagt gaaaagggat ttaaggtggt atttggcaat gtgtcaggca tcgtggctgt   13020
gtgtgtcaat tttaccagct acgtccaaca tgtcaaggag tttacccaac gctccctggt   13080
ggtcgaccat gtgcggttgc tccatttcat gacacctgag accatgaggt gggcaactgt   13140
```

```
tttagcctgt cttttttgcca ttctgttggc aatttgaatg tttaagtatg ttggagaaat   13200
gcttgaccgc gggctgttgc tcgcgattgc tttctttgtg gtgtatcgtg ccgttctgtt   13260
ttgctgtgct cgccaacgcc agcaacgaca gcagctccca tctacagctg atttacaact   13320
tgacgctatg tgagctgaat ggcacagatt ggctagctaa caaatttgat tgggcagtgg   13380
agagttttgt catctttccc gttttgactc acattgtctc ctatggtgcc ctcactacca   13440
gccatttcct tgacacagtc gctttagtca ctgtgtctac cgccgggttt gttcacgggc   13500
ggtatgtcct aagtagcatc tacgcggtct gtgccctggc tgcgttgact tgcttcgtca   13560
ttaggtttgc aaagaattgc atgtcctggc gctacgcgtg taccagatat accaactttc   13620
ttctggacac taagggcaga ctctatcgtt ggcggtcgcc tgtcatcata gagaaaaggg   13680
gcaaagttga ggtcgaaggt catctgatcg acctcaaaag agttgtgctt gatggctccg   13740
tggcaacccc tataaccaga gtttcagcgg aacaatgggg tcgtccttag atgacttctg   13800
tcacgatagc acggctccac aaaaggtgct tttggcgttt tctattacct acacgccagt   13860
gatgatatat gccctaaagg tgagtcgcgg ccgactgcta gggcttctgc acctttgat   13920 cttcctgaat tgtgctttca ccttcgggta catgactttc gcgcactttc agagtacaaa   13980
taaggtcgcg ctcactatgg gagcagtagt tgcactcctt ggggggtgt actcagccat   14040 agaaacctgg aaattcatca cctccagatg ccgtttgtgc ttgctaggcc gcaagtacat   14100
tctggcccct gcccaccacg ttgaaagtgc cgcaggcttt catccgattg cggcaaatga   14160
taaccacgca tttgtcgtcc ggcgtcccgg ctccactacg gtcaacggca cattggtgcc   14220
cgggttaaaa agcctcgtgt tgggtggcag aaaagctgtt aaacagggag tggtaaacct   14280
tgtcaaatat gccaaataac aacggcaagc agcagaagag aaagaagggg gatggccagc   14340
cagtcaatca gctgtgccag atgctgggta agatcatcgc tcagcaaaac cagtccagag   14400
gcaagggacc gggaaagaaa aataagaaga aaaacccgga gaagccccat tttcctctag   14460
cgactgaaga tgatgtcaga catcactttta cccctagtga gcggcaattg tgtctgtcgt   14520
caatccagac cgccttaat caaggcgctg ggacttgcac cctgtcagat tcaggggga   14580 taagttacac tgtggagttt agtttgccta cgcatcatac tgtgcgcctg atccgcgtca   14640
cagcatcacc ctcagcatga tgggctggca ttcttgaggc atctcagtgt ttgaattgga   14700
agaatgtgtg gtgaatggca ctgattgaca ttgtgcctct aagtcaccta ttcaattagg   14760
gcgaccgtgt gggggtgaga tttaattggc gagaaccatg cggccgaaat taaaaaaaa   14819
```

<210> SEQ ID NO 9
<211> LENGTH: 15149
<212> TYPE: DNA
<213> ORGANISM: Artificial Sequence
<220> FEATURE:
<223> OTHER INFORMATION: Porcine reproductive and respiratory syndrome virus

<400> SEQUENCE: 9

```
atgacgtata ggtgttggct ctatgccttg gcatttgtat tgtcaggagc tgtgaccatt     60
ggcacagccc aaaacttgct gcacagaaac acccttctgt gatagcctcc ttcaggggag    120
cttagggttt gtccctagca ccttgcttcc ggagttcac tgctttacgg tctctccacc    180 ccttttaacca tgtctgggat acttgatcgg tgcacgtgta cccccaatgc cagggtgttt    240
atggcggagg ccaagtcta ctgcacacga tgcctcagtg cacggtctct cctccccctg    300
aacctccagg tttctgagct cggggtgcta ggcctattct acaggcccga agagccactc    360
```

```
cggtggacgt tgccacgtgc attccccact gttgagtgct cccccgccgg ggcctgctgg      420
ctttctgcaa tctttccaat cgcacgaatg accagtggaa acctgaactt ccaacaaaga      480
atggtacggg tcgcagctga gctttacaga gccggccagc tcacccctgc agtcttgaag      540
gctctacaag tttatgaacg gggttgccgc tggtacccca ttgttggacc tgtccctgga      600
gtggccgttt tcgccaattc cctacatgtg agtgataaac ccttcccggg agcaactcac      660
gtgttgacca acctgccgct cccgcagaga cccaagcctg aagacttttg ccccttgag       720 tgtgctatgg ctactgtcta tgacattggt catgacgccg tcatgtatgt ggccgaaagg      780
aaagtctcct gggcccctcg tggcggggat gaagtgaaat ttgaagctgt ccccggggag      840
ttgaagttga ttgcgaaccg gctccgcacc tccttcccgc ccaccacac agtggacatg       900 tctaagttcg ccttcacagc ccctgggtgt ggtgtttcta tgcgggtcga acgccaacac      960
ggctgccttc ccgctgacac tgtccctgaa ggcaactgct ggtggagctt gtttgacttg     1020
cttccactgg aagttcagaa caaagaaatt cgccatgcta accaatttgg ctaccagacc     1080
aagcatggtg tctctggcaa gtacctgcag cggaggctgc aagttaatgg tctccgagca     1140
gtaactgacc taaacggacc tatcgtcgta cagtacttct ccgttaagga gagttggatc     1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct     1380
acagtcgctg gccgcgcttt gtccgttcgt gaaacccggc aggccaagga gcacgaggtt     1440
gccggcgcca acaaggctga gcacctcaaa cactactccc cgcctgccga agggaattgt     1500
ggttggcact gcatttccgc catcgccaac cggatggtga attccaaatt tgaaaccacc     1560
cttcccgaaa gagtgagacc tccagatgac tgggctactg acgaggatct tgtgaatgcc     1620
atccaaatcc tcagactccc tgcggcctta gacaggaacg tgcttgtac tagcgccaag      1680 tacgtactta agctgaagg tgagcattgg actgtcactg tgaccccctgg gatgtcccct     1740 tctttgctcc ctcttgaatg tgttcagggc tgttgtgggc acaagggcgg tcttggttcc     1800
ccagatgcag tcgaggtctc cggatttgac cctgcctgcc ttgaccggct ggctgaggtg     1860
atgcacctgc ctagcagtgc tatcccagcc gctctggccg aaatgtctgg cgattccgat     1920
cgttcggctt ctccggtcac caccgtgtgg actgtttcgc agttctttgc ccgtcacagc     1980
ggagggaatc accctgacca agtgcgctta gggaaaatta tcagcctttg tcaggtgatt     2040
gaggactgct gctgttccca gaacaaaacc aaccgggtca ccccgaggga ggtcgcagca     2100
aagattgacc tgtacctccg tggtgcaaca aatcttgaag aatgcttggc caggcttgag     2160
aaagcgcgcc cgccacgcgt aatcgacacc tcctttgatt gggatgttgt gctccctggg     2220
gttgaggcgg caacccagac gatcaagctg ccccaggtca accagtgtcg tgctctggtc     2280
cctgttgtga ctcaaaagtc cttggacaac aactcggtcc ccctgaccgc cttttcactg     2340
gctaactact actaccgtgc gcaaggtgac gaagttcgtc accgtgaaag actaaccgcc     2400
gtgctctcca gttggaaaa ggttgttcga gaagaatatg gcctcatgcc aaccgagcct      2460
ggtccacggc ccacactgcc acgcgggctc gacgaactca agaccagat ggaggaggac      2520 ttgctgaaac tggctaacgc ccagacgact tcggacatga tggcctgggc agtcgagcag     2580
gttgacctaa aaacttgggt caagaactac ccgcggtgga caccaccacc ccctccgcca     2640
aaagttcagc ctcgaaaaac gaagcctgtc aagagcttgc cggagagaaa gcctgtcccc     2700
gccccgcgca ggaaggttgg gtccgattgt ggcagcccgg tttcattagg cggcgatgtc     2760
```

| | |
|---|---|
| cctaacagtt gggaagattt ggctgttagt agcccctttg atctcccgac cccacctgag | 2820 |
| ccggcaacac cttcaagtga gctggtgatt gtgtcctcac cgcaatgcat cttcaggccg | 2880 |
| gcgacaccct tgagtgagcc ggctccaatt cccgcacctc gcggaactgt gtctcgaccg | 2940 |
| gtgacaccct tgagtgagcc gatcacacgc ccaaaatact cagctcaagc catcatcgac | 3000 |
| tcgggcgggc cctgcagtgg gcatctccaa gaggtaaagg aaacatgcct tagtgtcatg | 3060 |
| cgcgaggcat gtgatgcgac taagcttgat gaccctgcta cgcaggaatg gctttctcgc | 3120 |
| atgtgggatc gggtggacat gctgacttgg cgcaacacgt ctgtttacca ggcgatttgc | 3180 |
| accttagatg gcaggttaaa gttcctccca aaaatgatac tcgagacacc gccgccctat | 3240 |
| ccgtgtgagt ttgtgatgat gcctcacacg cctgcacctt ccgtaggtgc ggagagcgac | 3300 |
| cttaccattg gctcagttgc tactgaagat gttccacgca tcctcgagaa aatagaaaat | 3360 |
| gtcggcgaga tggccaacca gggacccttg gccttctccg aggataaacc ggtagatgac | 3420 |
| caacttgtca acgaccccg gatatcgtcg cggaggcctg acgagagcac atcagctccg | 3480 |
| tccgcaggca caggtggcgc cggctctttt accgatttgc cgccttcaga tggcgcggat | 3540 |
| gcggacgggg ggggccgtt tcggacggta aaaagaaaag ctgaaaggct ctttgaccaa | 3600 |
| ctgagccgtc aggttttga cctcgtctcc catctccctg ttttcttctc acgcttttc | 3660 |
| taccctggcg gtggttattc tccgggtgat tggggttttg cagcttttac tctattgtgc | 3720 |
| ctcttttat gttacagtta cccagccttt ggtattgctc ccctcttggg tgtgttttct | 3780 |
| gggtcttctc ggcgcgttcg aatgggggtt tttggctgct ggttggcttt tgctgttggt | 3840 |
| ctgttcaagc ctgtgtccga cccagtcggc gctgcttgtg agtttgactc gccagagtgt | 3900 |
| agaaacatcc ttcattcttt tgagcttctc aaaccttggg accctgttcg cagccttgtt | 3960 |
| gtgggccccg tcggtctcgg tcttgccatt cttggcaggt tactgggcgg ggcacgctgc | 4020 |
| atctggcact ttttgcttag gcttggcatt gttgcagact gtatcttggc tggagcttac | 4080 |
| gtgctttctc aaggtaggtg taaaaagtgc tggggatctt gtataagaac tgctcccaat | 4140 |
| gaggtcgctt ttaacgtgtt tccttttcaca cgtgcgacca ggtcgtcact tatcgacctg | 4200 |
| tgcgatcggt tttgtgcgcc aaaaggaatg gaccccattt ttctcgccac tgggtggcgc | 4260 |
| gggtgctggg ccggccgaag ccccattgag caaccctctg aaaaacccat cgcgtttgcc | 4320 |
| cagttggatg aaaagaagat tacggctagg actgtggtcg cccagcctta tgaccccaac | 4380 |
| caagccgtaa agtgcttgcg ggtattgcag gcgggtgggg cgatggtggc taaggcggtc | 4440 |
| ccaaaagtgg tcaaggtttc cgctgttcca ttccgagccc ccttctttcc cactggagtg | 4500 |
| aaagttgacc ctgattgcag ggtcgtggtt gaccctgaca ctttcactgc agctctccgg | 4560 |
| tctggctact ccaccacaaa cctcgtcctt ggtgtggggg actttgccca gctgaatgga | 4620 |
| ttaaaaatca ggcaaatttc caagccttca ggggaggcc cacatctcat ggctgccctg | 4680 |
| catgttgcct gctcgatggc tctgcacatg cttgctggga tttatgtgac tgcggtgggt | 4740 |
| tcttgcggca ccggcaccaa cgacccgtgg tgcgctaacc cgtttgccgt ccctggctac | 4800 |
| ggacctggct ctctctgcac gtccagattg tgcatttccc aacacggcct taccctgccc | 4860 |
| ttgacagcac ttgtggcggg attcggtatt caagaaattg ccttggtcgt tttgattttt | 4920 |
| gtttccatcg gaggcatggc tcataggttg agctgtaagg ctgacatgct gtgtgtcttg | 4980 |
| cttgcaattg ccagctatgt ttgggtacct cttacctggt tgctttgtgt gtttccttgc | 5040 |
| tggttgcgct gttttcttt gcaccccctc accatcctat ggttggtgtt tttcttgatt | 5100 |

```
tctgtgaata tgccttcagg aatcttggcc atggtgttgt tggtttctct ttggcttctt      5160
ggtcgttata ctaatgttgc tggccttgtc accccctacg acattcatca ttacaccagt      5220
ggcccccgcg gtgttgccgc cttggctacc gcaccagatg ggacctactt ggccgctgtc      5280
cgccgcgctg cgttgactgg ccgcaccatg ctgtttaccc cgtcccagct tgggtctctt      5340
cttgagggtg ctttcagaac tcgaaagccc tcactgaaca ccgtcaatgt gatcgggtcc      5400
tccatgggct ctggcggggt gtttaccatc gacgggaaag tcaagtgcgt aactgccgca      5460
catgtcctta cgggcaattc agctcgggtt ccggggtcg gcttcaatca aatgcttgac       5520
tttgacgtaa agggagattt cgctatagct gattgcccga attggcaagg gctgccccc       5580 aagacccaat tctgcacgga tggatggact ggccgtgcct attggctaac atcctctggc      5640
gtcgaacccg cgtcattgg aaaaggattc gccttctgct tcaccgcatg tggcgattcc       5700
gggtccccag tgatcaccga ggccggtgag cttgtcggcg ttcacacggg atcgaataaa      5760 caagggggg gcattgttac gcgcccctca ggccagtttt gtaatgtggc acccatcaag       5820
ctaagcgaat taagtgaatt ctttgctggg cctaaggtcc cgctcggtga tgtgaaggtc      5880
ggcagccaca taattaaaga cataagcgag gtgccttcag atctttgtgc cttgcttgct      5940
gccaaacctg aactggaagg aggcctctcc accgtccaac ttctttgtgt gttttttctc      6000
ctgtggagaa tgatgggaca tgcctggacg cccttggttg ctgtgagttt ctttattttg      6060
aatgaggttc tcccagccgt cctggtccgg agtgttttct cctttggaat gtttgtgcta      6120
tcctggctca cgccatggtc tgcgcaagtt ctgatgatca ggcttctgac agcagctctt      6180
aacaggaaca gatggtcact tgccttttc agcctcggtg cagtgaccgg ttttgtcgca       6240
gatcttgcgg ccactcaggg gcatccgttg caggcagtga tgaatttgag cacctatgca      6300
ttcctgcctc ggatgatggt tgtgacctca ccagtcccag tgatcacgtg tggtgtcgtg      6360
cacctacttg ccatcatttt gtacttgttt aagtaccgtg gcctgcacca tatccttgtt      6420
ggcgatggag tgttctctgc ggcttttctt ttgagatact ttgccgaggg aaagttgagg      6480
gaaggggtgt cgcaatcctg cggaatgaat catgagtctc tgactggtgc cctcgctatg      6540
agactcaatg acgaggactt ggatttcctt atgaaatgga ctgattttaa gtgctttgtt      6600
tctgcgtcca acatgaggaa tgcagcgggt caatttatcg aggctgccta tgctaaagca      6660
cttagagtag aactggccca gttggtgcag gttgataaag ttcgaggtac tttggccaaa      6720
cttgaagctt ttgctgatac cgtggcacct caactctcgc ccggtgacat tgttgtcgct      6780
ctcggccaca cgcctgttgg cagtatcttc gacctaaagg ttggtagcac caagcatacc      6840
ctccaagcca ttgagaccag agtccttgct gggtccaaaa tgaccgtggc gcgcgtcgtc      6900
gacccgaccc ccacgccccc acccgcaccc gtgccatcc cctcccacc gaaagttctg       6960 gagaatggcc ccaacgcttg ggggatgag gaccgtttga ataagaagaa gaggcgcagg       7020
atggaagccc tcgcatcta tgttatgggc gggaaaaaat accagaaatt ttgggacaag      7080
aattccggtg atgtgttta tgaggaggtc cataataaca cagatgagtg ggagtgtctc      7140
agagttggcg accctgccga ctttgaccct gagaagggaa ctctgtgtgg acatgtcacc      7200
attgaaaaca aggcttacca tgtttacacc tccccatctg gtaagaagtt cttggtcccc      7260
gtcaacccag agaatggaag agtccaatgg gaagctgcaa agctttccgt ggagcaggcc      7320
ctaggtatga tgaatgtcga cggcgaactg actgccaaag aactggagaa actgaaaaga      7380
ataattgaca aactccaggg cctgactaag gagcagtgtt taaactgcta gccgccagcg      7440
acttgacccg ctgtggtcgc ggcggcttgg ttgttactga aacagcggta aaaatagtca      7500
```

```
aatttcacaa ccggaccttc accctgggac ctgtgaattt aaaagtggcc agtgaggttg    7560
agctaaaaga cgcggttgag cacaaccaac acccggttgc gagaccgatc gatggtggag    7620
ttgtgctcct gcgttccgcg gttccttcgc ttatagacgt cttgatctcc ggtgctgatg    7680
catctcccaa gttacttgcc catcacgggc cgggaaacac tgggatcgat ggcacgctct    7740
gggattttga gtccgaagcc actaagagg aagtcgcact cagtgcgcaa ataatacagg    7800
cttgtgacat taggcgcggc gacgctcctg aaattggtct cccttacaag ctgtaccctg    7860
ttaggggtaa ccctgagcgg gtgaaaggag ttctgcagaa tacaaggttt ggagacatac    7920
cttacaaaac ccccagtgac actggaagcc cagtgcacgc ggctgcctgc cttacgccca    7980
acgccactcc ggtgactgat gggcgctccg tcttggccac gaccatgccc ccgggtttg     8040 agttatatgt accgaccata ccagcgtctg tccttgatta ccttgactct aggcctgact    8100
gccctaaaca gctgacagag cacggctgcg aagatgccgc actgaaagac ctctctaaat    8160
atgacttgtc cacccaaggc tttgttttac ctggagttct tcgccttgtg cggaaatacc    8220
tgtttgccca tgtaggtaag tgcccacccg ttcatcggcc ttctacttac cctgctaaga    8280
attctatggc tggaataaat gggaacaggt tcccaaccaa ggacattcag agcgtccctg    8340
aaatcgacgt tctgtgcgca caggctgtgc gagaaaactg gcaaactgtc acccttgta    8400 ctcttaagaa acagtattgc gggaagaaga agactaggac catactcggc accaataact    8460
tcatcgcact agcccaccga gcagtgttga gtggtgttac ccagggcttc atgaaaaagg    8520
cgtttaactc gcccatcgcc ctcggaaaga acaagtttaa ggagctacag actccggtcc    8580
tgggcaggtg ccttgaagct gatctcgcat cctgcgatcg atccacgcct gcaattgtcc    8640
gctggtttgc cgccaacctt ctttatgaac ttgcctgtgc tgaagagcat ctaccgtcgt    8700
acgtgctgaa ctgctgccac gacttactgg tcacgcagtc cggcgcagtg actaagagag    8760
gtggcctgtc gtctggcgac ccgatcacct ctgtgtctaa caccatttat agtttggtga    8820
tctatgcaca gcatatggtg cttagttact tcaaaagtgg tcaccccat ggccttctgt    8880 tcttacaaga ccagctaaag tttgaggaca tgctcaaggt tcaacccctg atcgtctatt    8940
cggacgacct cgtgctgtat gccgagtctc ccaccatgcc aaactatcac tggtgggttg    9000
aacatctgaa tttgatgctg ggtttcaga cggacccaaa gaagacagca ataacagact    9060
cgccatcatt tctaggctgt agaataataa atgggcgcca gctagtcccc aaccgtgaca    9120
ggatcctcgc ggccctcgcc tatcacatga aggcgagtaa tgtttctgaa tactatgcct    9180
cagcggctgc aatactcatg gacagctgtg cttgtttgga gtatgatcct gaatggtttg    9240
aagaacttgt agttggaata gcgcagtgcg cccgcaagga cggctacagc tttcccggca    9300
cgccgttctt catgtccatg tgggaaaaac tcaggtccaa ttatgagggg aagaagtcga    9360
gagtgtgcgg gtactgcggg gccccggccc cgtacgctac tgcctgtggc ctcgacgtct    9420
gcatttacca cacccactc caccagcatt gtccagtcac aatctggtgt ggccatccag    9480
cgggttctgg ttcttgtagt gagtgcaaat ccctgtagg gaaaggcaca agcccctttag    9540 acgaggtgct ggaacaagtc ccgtataagc ccccacggac cgttatcatg catgtggagc    9600
agggtctcac ccccccttgat ccaggtagat accaaactcg ccgcggatta gtctctgtca    9660
ggcgtggaat taggggaaat gaagttggac taccagacgg tgattatgct agcaccgcct    9720
tgctccctac ctgcaaagag atcaacatgg tcgctgtcgc ttccaatgta ttgcgcagca    9780
ggttcatcat cggcccaccc ggtgctggga aaacatactg gctccttcaa caggtccagg    9840
```

-continued

```
atggtgatgt tatttacaca ccaactcacc agaccatgct tgacatgatt agggctttgg    9900
ggacgtgccg gttcaacgtc ccggcaggca caacgctgca attccccgtc ccctcccgca    9960
ccggtccgtg ggttcgcatc ctagccggcg gttggtgtcc tggcaagaat tccttcctag   10020
atgaagcagc gtattgcaat caccttgatg ttttgaggct tcttagtaaa actaccctca   10080
cctgtctagg agacttcaag caactccacc cagtgggttt tgattctcat tgctatgttt   10140
ttgacatcat gcctcaaact caactgaaga ccatctggag gtttggacag aatatctgtg   10200
atgccattca gccagattac agggacaaac tcatgtccat ggtcaacaca acccgtgtga   10260
cctacgtgga aaaacctgtc aggtatgggc aggtcctcac ccctaccac agggaccgag     10320
aggacgacgc catcactatt gactccagtc aaggcgccac attcgatgtg gttacattgc   10380
atttgcccac taaagattca ctcaacaggc aaagagccct tgttgctatc accagggcaa   10440
gacacgctat ctttgtgtat gacccacaca ggcagctgca gggcttgttt gatcttcctg   10500
caaaaggcac gcccgtcaac ctcgcagtgc actgcgacgg gcagctgatc gtgctggata   10560
gaaataacaa agaatgcacg gttgctcagg ctctaggcaa cggggataaa tttagggcca   10620
cagacaagcg tgttgtagat tctctccgcg ccatttgtgc tgatctagaa gggtcgagct   10680
ctccgctccc caaggtcgca cacaacttgg gattttattt ctcacctgat ttaacacagt   10740
ttgctaaact cccagtagaa cttgcacctc actggcccgt ggtgtcaacc cagaacaatg   10800
aaaagtggcc ggatcggctg gttgccagcc ttcgccctat ccataaatac agccgcgcgt   10860
gcatcggtgc cggctatatg gtgggcccctt cggtgtttct aggcactcct ggggtcgtgt   10920
catactatct cacaaaattt gttaagggcg gggctcaagt gcttccggag acggttttca   10980
gcaccggccg aattgaggta gactgccggg aatatcttga tgatcgggag cgagaagttg   11040
ctgcgtccct cccacacgct ttcattggcg acgtcaaagg cactaccgtt ggaggatgtc   11100
atcatgtcac ctccagatac ctcccgcgcg tccttcccaa ggaatcagtt gcggtagtcg   11160
gggtttcaag ccccggaaaa gccgcgaaag cattgtgcac actgacagat gtgtacctcc   11220
cagatcttga agcctatctc cacccggaga cccagtccaa gtgctggaaa atgatgttgg   11280
acttcaaaga agttcgacta atggtctgga aagacaaaac agcctatttc caacttgaag   11340
gtcgctattt cacctggtat cagcttgcca gctatgcctc gtacatccgt gttcccgtca   11400
actctacggt gtacttggac ccctgcatgg gccccgccct ttgcaacagg agagtcgtcg   11460
ggtccaccca ctgggggct gacctcgcgg tcaccccctta tgattacggc gctaaaatta   11520
tcctgtctag cgcgtaccat ggtgaaatgc ccccccggata caaaattctg gcgtgcgcgg   11580
agttctcgtt ggatgaccca gttaagtaca acatacctg ggggtttgaa tcggatacag     11640
cgtatctgta tgagttcacc ggaaacggtg aggactggga ggattacaat gatgcgtttc   11700
gtgcgcgcca ggaagggaaa atttataagg ccactgccac cagcttgaag ttttatttc    11760
cccgggccc tgtcattgaa ccaactttag gcctgaattg aaatgaaatg gggtccatgc    11820
aaagcctttt tgacaaaatt ggccaacttt ttgtggatgc tttcacgag ttcttggtgt     11880
ccattgttga tatcattata ttttttggcca ttttgtttgg cttccacatc gccggttggc   11940
tggtggtctt ttgcatcaga ttggtttgct ccgcgatact ccgtacgcgc cctgccattc   12000
actctgagca attacagaag atcttatgag gcctttcttt cccagtgcca agtggacatt   12060
cccacctggg gaactaaaca tcctttgggg atgctttggc accataaggt gtcaaccctg   12120
attgatgaaa tggtgtcgcg tcgaatgtac cgcatcatga aaaagcagg gcaggctgcc   12180
tggaaacagg tggtgagcga ggctacgctg tctcgcatta gtagtttgga tgtggtggct   12240
```

```
cattttcagc atctagccgc cattgaagcc gagacctgta aatatttggc ctcccggctg   12300
cccatgctac acaacctgcg catgacaggg tcaaatgtaa ccatagtgta taatagcact   12360
ttgaatcagg tgtttgctat ttttccaacc cctggttccc ggccaaagct tcatgatttt   12420
cagcaatggt taatagctgt acattcctcc atattttcct ctgttgcagc ttcttgtact   12480 cttttttgttg tgctgtggtt gcgggttcca atactacgta ctgttttttgg tttccgctgg   12540 ttaggggcaa tttttctttc gaactcacag tgaattacac ggtgtgtcca ccttgcctca   12600
cccggcaagc agccacagag atctacgaac ccggtaggtc tctttggtgc aggatagggt   12660
atgaccgatg tggggaggac gatcatgacg agctagggtt tatgataccg cctggcctct   12720
ccagcgaagg ccacttgact ggtgtttacg cctggttggc gttcttgtcc ttcagctaca   12780
cggcccagtt ccatcccgag atattcggga tagggaatgt gagtcgagtt tatgttgaca   12840
tcaaacatca actcatctgc gccgaacatg acgggcagaa caccaccttg cctcgtcatg   12900
acaacatttc agccgtgttt cagacctatt accaacatca agtcgacggc ggcaattggt   12960
ttcacctaga atggcttcgt cccttctttt cctcgtggtt ggttttaaat gtctcttggt   13020
ttctcaggcg ttcgcctgca aaccatgttt cagttcgagt cttgcagata ttaagaccaa   13080
caccaccgca gcggcaagct ttgctgtcct ccaagacatc agttgcctta ggcatcgcga   13140
ctcggcctct gaggcgattc gcaaaatccc tcagtgccgt acggcgatag ggacacccgt   13200
gtatgttacc atcacagcca atgtgacaga tgagaattat ttacattctt ctgatctcct   13260 catgcttttct tcttgccttt tctatgcttc tgagatgagt gaaaagggat ttaaggtggt   13320
atttggcaat gtgtcaggca tcgtggctgt gtgtgtcaat tttaccagct acgtccaaca   13380
tgtcaaggag tttacccaac gctccctggt ggtcgaccat gtgcggttgc tccatttcat   13440
gacacctgag accatgaggt gggcaactgt tttagcctgt cttttttgcca ttctgttggc   13500 aatttgaatg tttaagtatg ttggagaaat gcttgaccgc gggctgttgc tcgcgattgc   13560
tttctttgtg gtgtatcgtg ccgttctgtt ttgctgtgct cgccaacgcc agcaacgaca   13620
gcagctccca tctacagctg atttacaact tgacgctatg tgagctgaat ggcacagatt   13680
ggctagctaa caaatttgat tgggcagtgg agagttttgt catctttccc gttttgactc   13740
acattgtctc ctatggtgcc ctcactacca gccatttcct tgacacagtc gctttagtca   13800
ctgtgtctac cgccgggttt gttcacgggc ggtatgtcct aagtagcatc tacgcggtct   13860
gtgccctggc tgcgttgact tgcttcgtca ttaggtttgc aaagaattgc atgtcctggc   13920
gctacgcgtg taccagatat accaactttc ttctggacac taagggcaga ctctatcgtt   13980
ggcggtcgcc tgtcatcata gagaaaggg gcaaagttga ggtcgaaggt catctgatcg   14040
acctcaaaag agttgtgctt gatggctccg tggcaacccc tataaccaga gtttcagcgg   14100
aacaatgggg tcgtccttag atgacttctg tcacgatagc acggctccac aaaaggtgct   14160
tttggcgttt tctattacct acacgccagt gatgatatat gccctaaagg tgagtcgcgg   14220
ccgactgcta gggcttctgc accttttgat cttcctgaat tgtgctttca ccttcgggta   14280
catgactttc gcgcactttt cagtacaaa taaggtcgcg ctcactatgg gagcagtagt   14340
tgcactcctt tgggggtgt actcagccat agaaacctgg aaattcatca cctccagatg   14400
ccgtttgtgc ttgctaggcc gcaagtacat tctggcccct gcccaccacg ttgaaagtgc   14460
cgcaggcttt catccgattg cggcaaatga taaccacgca tttgtcgtcc ggcgtcccgg   14520
ctccactacg gtcaacggca cattggtgcc cgggttaaaa agcctcgtgt tgggtggcag   14580
```

| | |
|---|---|
| aaaagctgtt aaacagggag tggtaaacct tgtcaaatat gccaaataac aacggcaagc | 14640 |
| agcagaagag aaagaagggg gatggccagc cagtcaatca gctgtgccag atgctgggta | 14700 |
| agatcatcgc tcagcaaaac cagtccagag gcaagggacc gggaagaaa aataagaaga | 14760 |
| aaaacccgga gaagccccat tttcctctag cgactgaaga tgatgtcaga catcacttta | 14820 |
| cccctagtga gcggcaattg tgtctgtcgt caatccagac cgcctttaat caaggcgctg | 14880 |
| ggacttgcac cctgtcagat tcagggagga taagttacac tgtggagttt agtttgccta | 14940 |
| cgcatcatac tgtgcgcctg atccgcgtca cagcatcacc ctcagcatga tgggctggca | 15000 |
| ttcttgaggc atctcagtgt ttgaattgga agaatgtgtg gtgaatggca ctgattgaca | 15060 |
| ttgtgcctct aagtcaccta ttcaattagg gcgaccgtgt gggggtgaga tttaattggc | 15120 |
| gagaaccatg cggccgaaat taaaaaaaa | 15149 |

<210> SEQ ID NO 10
<211> LENGTH: 15137
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 10

| | |
|---|---|
| atgacgtata ggtgttggct ctatgccttg gcatttgtat tgtcaggagc tgtgaccatt | 60 |
| ggcacagccc aaaacttgct gcacagaaac acccttctgt gatagcctcc ttcaggggag | 120 |
| cttaggggttt gtccctagca ccttgcttcc ggagttgcac tgctttacgg tctctccacc | 180 |
| cctttaacca tgtctgggat acttgatcgg tgcacgtgta cccccaatgc cagggtgttt | 240 |
| atggcggagg gccaagtcta ctgcacacga tgcctcagtg cacggtctct ccttcccctg | 300 |
| aacctccagg tttctgagct cggggtgcta ggcctattct acaggcccga agagccactc | 360 |
| cggtggacgt tgccacgtgc attcccact gttgagtgct ccccgccgg ggcctgctgg | 420 |
| cttttctgcaa tctttccaat cgcacgaatg accagtggaa acctgaactt ccaacaaaga | 480 |
| atggtacggg tcgcagctga gctttacaga gccggccagc tcacccctgc agtcttgaag | 540 |
| gctctacaag tttatgaacg gggttgccgc tggtacccca ttgttggacc tgtccctgga | 600 |
| gtggccgttt tcgccaattc cctacatgtg agtgataaac ccttcccggg agcaactcac | 660 |
| gtgttgacca acctgccgct cccgcagaga cccaagcctg aagactttg ccccctttgag | 720 |
| tgtgctatgg ctactgtcta tgacattggt catgacgccg tcatgtatgt ggccgaaagg | 780 |
| aaagtctcct gggcccctcg tggcggggat gaagtgaaat ttgaagctgt ccccggggag | 840 |
| ttgaagttga ttgcgaaccg gctccgcacc tccttcccgc cccaccacac agtggacatg | 900 |
| tctaagttcg ccttcacagc ccctgggtgt ggtgtttcta gcgggtcga acgccaacac | 960 |
| ggctgccttc ccgctgacac tgtccctgaa ggcaactgct ggtggagctt gtttgacttg | 1020 |
| cttccactgg aagttcagaa caaagaaatt cgccatgcta accaatttgg ctaccagacc | 1080 |
| aagcatggtg tctctggcaa gtacctgcag cggaggctgc aagttaatgg tctccgagca | 1140 |
| gtaactgacc taaacggacc tatcgtcgta cagtacttct ccgttaagga gagttggatc | 1200 |
| cgccatttga aactggcggg agaacccagc tactctgggt tgaggaccct cctcagaata | 1260 |
| agggttgagc ctaacacgtc gccattggct gacaaggaag aaaaaatttt ccggttggc | 1320 |
| agtcacaagt ggtacggcgc tggaaagaga gcaagaaaag cacgctcttg tgcgactgct | 1380 |
| acagtcgctg gccgcgcttt gtccgttcgt gaaacccggc aggccaagga gcacgaggtt | 1440 |

```
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgacccctgg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc ccctgaccgc ttttcactg   2340 gctaactact actaccgtgc gcaaggtgac gaagttcgtc accgtgaaag actaaccgcc   2400
gtgctctcca agttggaaaa ggttgttcga gaagaatatg gctcatgcc aaccgagcct   2460 ggtccacggc ccacactgcc acgcgggctc gacgaactca agaccagat ggaggaggac   2520 ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac cccacctgag   2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt   3120 ctgggagtag aggggcatga agctgaggaa accctgagtg aaatctcgga catgtcgggt   3180
aacattaaac ctgcgtccgt gtcatcaagc agctccttgt ccagcgtgag atgtgagttt   3240
gtgatgatgc ctcacacgcc tgcaccttcc gtaggtgcgg agagcgacct taccattggc   3300
tcagttgcta ctgaagatgt tccacgcatc ctcgagaaaa tagaaaatgt cggcgagatg   3360
gccaaccagg gacccttggc cttctccgag ataaaccgg tagatgacca acttgtcaac   3420
gaccccccga tatcgtcgcg gaggcctgac gagagcacat cagctccgtc cgcaggcaca   3480
ggtggcgccg gctcttttac cgatttgccg ccttcagatg gcgcggatgc ggacgggggg   3540
gggccgtttc ggacggtaaa aagaaaagct gaaaggctct tgaccaact gagccgtcag   3600 gttttttgacc tcgtctccca tctccctgtt ttcttctcac gccttttcta ccctggcggt   3660
ggttattctc cgggtgattg gggtttgca gctttactc tattgtgcct ctttttatgt   3720
tacagttacc cagcctttgg tattgctccc ctcttgggtg tgttttctgg gtcttctcgg   3780
cgcgttcgaa tggggttttt tggctgctgg ttggcttttg ctgttggtct gttcaagcct   3840
```

```
gtgtccgacc cagtcggcgc tgcttgtgag tttgactcgc cagagtgtag aaacatcctt    3900
cattcttttg agcttctcaa accttgggac cctgttcgca gccttgttgt gggccccgtc    3960
ggtctcggtc ttgccattct tggcaggtta ctgggcgggg cacgctgcat ctggcacttt    4020
ttgcttaggc ttggcattgt tgcagactgt atcttggctg gagcttacgt gctttctcaa    4080
ggtaggtgta aaaagtgctg gggatcttgt ataagaactg ctcccaatga ggtcgctttt    4140
aacgtgtttc ctttcacacg tgcgaccagg tcgtcactta tcgacctgtg cgatcggttt    4200
tgtgcgccaa aaggaatgga ccccattttt ctcgccactg ggtggcgcgg tgctgggcc     4260 ggccgaagcc ccattgagca accctctgaa aaacccatcg cgtttgccca gttggatgaa    4320
aagaagatta cggctaggac tgtggtcgcc cagccttatg accccaacca agccgtaaag    4380
tgcttgcggg tattgcaggc gggtgggggcg atggtggcta aggcggtccc aaaagtggtc    4440
aaggtttccg ctgttccatt ccgagccccc ttctttccca ctggagtgaa agttgaccct    4500
gattgcaggg tcgtggttga ccctgacact ttcactgcag ctctccggtc tggctactcc    4560
accacaaacc tcgtccttgg tgtggggac tttgcccagc tgaatggatt aaaaatcagg    4620
caaatttcca agccttcagg gggagggccca catctcatgg ctgccctgca tgttgcctgc    4680
tcgatggctc tgcacatgct tgctgggatt tatgtgactg cggtgggttc ttgcggcacc    4740
ggcaccaacg accccgtggtg cgctaacccg tttgccgtcc ctggctacgg acctggctct    4800
ctctgcacgt ccagattgtg catttcccaa cacggcctta cctgcccctt gacagcactt    4860
gtggcgggat tcggtattca agaaaattgcc ttggtcgttt tgattttgt ttccatcgga    4920 ggcatggctc ataggttgag ctgtaaggct gacatgctgt gtgtcttgct tgcaattgcc    4980
agctatgttt gggtacctct tacctggttg ctttgtgtgt ttccttgctg gttgcgctgt    5040
ttttctttgc acccctcac catcctatgg ttggtgtttt tcttgattc tgtgaatatg      5100 ccttcaggaa tcttggccat ggtgttgttg gtttctcttt ggcttcttgg tcgttatact    5160
aatgttgctg gccttgtcac cccctacgac attcatcatt acaccagtgg cccccgcggt    5220
gttgccgcct tggctaccgc accagatggg acctacttgg ccgctgtccg ccgcgctgcg    5280
ttgactggcc gcaccatgct gtttaccccg tcccagcttg gtctcttct tgagggtgct     5340 ttcagaactc gaaagccctc actgaacacc gtcaatgtga tcgggtcctc catgggctct    5400
ggcggggtgt ttaccatcga cgggaaagtc aagtgcgtaa ctgccgcaca tgtccttacg    5460
ggcaattcag ctcgggtttc cggggtcggc ttcaatcaaa tgcttgactt tgacgtaaag    5520
ggagatttcg ctatagctga ttgcccgaat tggcaagggg ctgcccccaa gacccaattc    5580
tgcacggatg gatggactgg ccgtgcctat tggctaacat cctctggcgt cgaacccggc    5640
gtcattggaa aaggattcgc cttctgcttc accgcatgtg gcgattccgg tccccagtg     5700 atcaccgagg ccggtgagct tgtcggcgtt cacacgggat cgaataaaca agggggggc     5760 attgttacgc gcccctcagg ccagttttgt aatgtgcac ccatcaagct aagcgaatta     5820
agtgaattct tgctgggcc taaggtcccg ctcggtgatg tgaaggtcgg cagccacata    5880
attaaagaca taagcgaggt gccttcagat ctttgtgcct tgcttgctgc caaacctgaa    5940
ctggaaggag gcctctccac cgtccaactt cttttgtgtg ttttttctcct gtggagaatg   6000 atgggacatg cctggacgcc cttggttgct gtgagtttct ttattttgaa tgaggttctc    6060
ccagccgtcc tggtccggag tgttttctcc tttggaatgt ttgtgctatc ctggctcacg   6120
ccatggtctg cgcaagttct gatgatcagg cttctgacag cagctcttaa caggaacaga    6180
```

```
tggtcacttg cctttttcag cctcggtgca gtgaccggtt ttgtcgcaga tcttgcggcc    6240
actcaggggc atccgttgca ggcagtgatg aatttgagca cctatgcatt cctgcctcgg    6300
atgatggttg tgacctcacc agtcccagtg atcacgtgtg gtgtcgtgca cctacttgcc    6360
atcattttgt acttgtttaa gtaccgtggc ctgcaccata tccttgttgg cgatggagtg    6420
ttctctgcgg ctttcttctt gagatacttt gccgagggaa agttgaggga aggggtgtcg    6480
caatcctgcg gaatgaatca tgagtctctg actggtgccc tcgctatgag actcaatgac    6540
gaggacttgg atttccttat gaaatggact gattttaagt gctttgtttc tgcgtccaac    6600
atgaggaatg cagcgggtca atttatcgag gctgcctatg ctaaagcact tagagtagaa    6660
ctggcccagt tggtgcaggt tgataaagtt cgaggtactt tggccaaact tgaagctttt    6720
gctgataccg tggcacctca actctcgccc ggtgacattg ttgtcgctct cggccacacg    6780
cctgttggca gtatcttcga cctaaaggtt ggtagcacca agcatacect ccaagccatt    6840 gagaccagag tccttgctgg gtccaaaatg accgtggcgc gcgtcgtcga cccgaccccc    6900
acgcccccac ccgcacccgt gcccatcccc ctcccaccga aagttctgga gaatggcccc    6960
aacgcttggg gggatgagga ccgttttgaat aagaagaaga ggcgcaggat ggaagccctc    7020
ggcatctatg ttatgggcgg gaaaaaatac cagaaatttt gggacaagaa ttccggtgat    7080
gtgttttatg aggaggtcca taataacaca gatgagtggg agtgtctcag agttggcgac    7140
cctgccgact tgaccctga aagggaact ctgtgtggac atgtcaccat tgaaaacaag    7200
gcttaccatg tttacacctc cccatctggt aagaagttct tggtcccgt caacccagag    7260 aatgaaagag tccaatggga agctgcaaag ctttccgtgg agcaggccct aggtatgatg    7320
aatgtcgacg gcgaactgac tgccaaagaa ctggagaaac tgaaaagaat aattgacaaa    7380 ctccaggggcc tgactaagga gcagtgttta aactgctagc cgccagcgac ttgacccgct    7440
gtggtcgcgg cggcttggtt gttactgaaa cagcggtaaa aatagtcaaa tttcacaacc    7500
ggaccttcac cctgggacct gtgaatttaa agtggccag tgaggttgag ctaaagacg    7560 cggttgagca caaccaacac ccggttgcga accgatcga tggtggagtt gtgctcctgc    7620
gttccgcggt tccttcgctt atagacgtct tgatctccgg tgctgatgca tctcccaagt    7680
tacttgccca tcacgggccg ggaaacactg ggatcgatgg cacgctctgg gattttgagt    7740
ccgaagccac taaagaggaa gtcgcactca gtgcgcaaat aatacaggct tgtgacatta    7800
ggcgcggcga cgctcctgaa attggtctcc cttacaagct gtaccctgtt aggggtaacc    7860
ctgagcgggt gaaaggagtt ctgcagaata caaggtttgg agacatacct tacaaaaccc    7920
ccagtgacac tggaagccca gtgcacgcgg ctgcctgcct tacgcccaac gccactccgg    7980
tgactgatgg cgctccgtc ttggccacga ccatgcccc cgggtttgag ttatatgtac    8040
cgaccatacc agcgtctgtc cttgattacc ttgactctag gctgactgc cctaaacagc    8100 tgacagagca cggctgcgaa gatgccgcac tgaaagacct ctctaaatat gacttgtcca    8160
cccaaggctt tgttttacct ggagttcttc gccttgtgcg gaaatacctg tttgcccatg    8220
taggtaagtg cccaccegtt catcggcctt ctacttaccc tgctaagaat tctatggctg    8280
gaataaatgg gaacaggttc ccaaccaagg acattcagag cgtccctgaa atcgacgttc    8340
tgtgcgcaca ggctgtgcga gaaactggc aaactgtcac cccttgtact cttaagaaac    8400
agtattgcgg gaagaagaag actaggacca tactcggcac caataacttc atcgcactag    8460
cccaccgagc agtgttgagt ggtgttaccc agggcttcat gaaaaaggcg tttaactcgc    8520
ccatcgccct cggaaagaac aagtttaagg agctacagac tccggtcctg ggcaggtgcc    8580
```

```
ttgaagctga tctcgcatcc tgcgatcgat ccacgcctgc aattgtccgc tggtttgccg    8640
ccaaccttct ttatgaactt gcctgtgctg aagagcatct accgtcgtac gtgctgaact    8700
gctgccacga cttactggtc acgcagtccg gcgcagtgac taagagaggt ggcctgtcgt    8760
ctggcgaccc gatcacctct gtgtctaaca ccatttatag tttggtgatc tatgcacagc    8820
atatggtgct tagttacttc aaaagtggtc accccatgg ccttctgttc ttacaagacc     8880
agctaaagtt tgaggacatg ctcaaggttc aacccctgat cgtctattcg gacgacctcg    8940
tgctgtatgc cgagtctccc accatgccaa actatcactg gtgggttgaa catctgaatt    9000
tgatgctggg gtttcagacg gacccaaaga agacagcaat aacagactcg ccatcatttc    9060
taggctgtag aataataaat gggcgccagc tagtccccaa ccgtgacagg atcctcgcgg    9120
ccctcgccta tcacatgaag gcgagtaatg tttctgaata ctatgcctca gcggctgcaa    9180
tactcatgga cagctgtgct tgtttggagt atgatcctga atggtttgaa gaacttgtag    9240 ttgaatagc gcagtgcgcc cgcaaggacg gctacagctt tcccggcacg ccgttcttca     9300
tgtccatgtg ggaaaaactc aggtccaatt atgagggaa gaagtcgaga gtgtgcgggt     9360
actgcggggc cccggccccg tacgctactg cctgtggcct cgacgtctgc atttaccaca    9420
cccacttcca ccagcattgt ccagtcacaa tctggtgtgg ccatccagcg ggttctggtt    9480
cttgtagtga gtgcaaatcc cctgtaggga aaggcacaag cccttagac gaggtgctgg     9540 aacaagtccc gtataagccc ccacggaccg ttatcatgca tgtggagcag ggtctcaccc    9600
cccttgatcc aggtagatac caaactcgcc gcggattagt ctctgtcagg cgtggaatta    9660
ggggaaatga agttggacta ccagacggtg attatgctag caccgccttg ctccctacct    9720
gcaaagagat caactggtc gctgtcgctt ccaatgtatt gcgcagcagg ttcatcatcg      9780
gcccacccgg tgctgggaaa acatactggc tccttcaaca ggtccaggat ggtgatgtta    9840
tttacacacc aactcaccag accatgcttg acatgattag gctttgggg acgtgccggt     9900 tcaacgtccc ggcaggcaca acgctgcaat tccccgtccc ctcccgcacc ggtccgtggg    9960
ttcgcatcct agccggcggt tggtgtcctg gcaagaattc cttcctagat gaagcagcgt    10020
attgcaatca ccttgatgtt ttgaggcttc ttagtaaaac taccctcacc tgtctaggag    10080
acttcaagca actccaccca gtgggttttg attctcattg ctatgttttt gacatcatgc    10140
ctcaaactca actgaagacc atctggaggt ttggacagaa tatctgtgat gccattcagc    10200
cagattacag ggacaaactc atgtccatgg tcaacacaac ccgtgtgacc tacgtggaaa    10260
aacctgtcag gtatgggcag gtcctcaccc cctaccacag ggaccgagag gacgacgcca    10320
tcactattga ctccagtcaa ggcgccacat tcgatgtggt tacattgcat ttgcccacta    10380
aagattcact caacaggcaa agagcccttg ttgctatcac cagggcaaga cacgctatct    10440
ttgtgtatga cccacacagg cagctgcagg cttgtttga tcttcctgca aaaggcacgc     10500
ccgtcaacct cgcagtgcac tgcgacgggc agctgatcgt gctggataga aataacaaag    10560
aatgcacggt tgctcaggct ctaggcaacg gggataaatt tagggccaca gacaagcgtg    10620
ttgtagattc tctccgcgcc atttgtgctg atctagaagg gtcgagctct ccgctcccca    10680
aggtcgcaca caacttggga ttttatttct cacctgattt aacacagttt gctaaactcc    10740
cagtagaact tgcacctcac tggcccgtgg tgtcaaccca gaacaatgaa agtggccgg     10800 atcggctggt tgccagcctt cgccctatcc ataaatacag ccgcgcgtgc atcggtgccg    10860
gctatatggt gggcccttcg gtgtttctag gcactcctgg ggtcgtgtca tactatctca    10920
```

```
caaaatttgt taagggcggg gctcaagtgc ttccggagac ggttttcagc accggccgaa   10980
ttgaggtaga ctgccgggaa tatcttgatg atcgggagcg agaagttgct gcgtccctcc   11040
cacacgcttt cattggcgac gtcaaaggca ctaccgttgg aggatgtcat catgtcacct   11100
ccagatacct cccgcgcgtc cttcccaagg aatcagttgc ggtagtcggg gtttcaagcc   11160
ccggaaaagc cgcgaaagca ttgtgcacac tgacagatgt gtacctccca gatcttgaag   11220
cctatctcca cccggagacc cagtccaagt gctggaaaat gatgttggac ttcaaagaag   11280
ttcgactaat ggtctggaaa gacaaaacag cctatttcca acttgaaggt cgctatttca   11340
cctggtatca gcttgccagc tatgcctcgt acatccgtgt tcccgtcaac tctacggtgt   11400
acttggaccc ctgcatgggc cccgcccttt gcaacaggag agtcgtcggg tccacccact   11460
gggggggctga cctcgcggtc acccctattatg attacggcgc taaaattatc ctgtctagcg   11520
cgtaccatgg tgaaatgccc cccggataca aaattctggc gtgcgcggag ttctcgttgg   11580
atgacccagt taagtacaaa catacctggg ggtttgaatc ggatacagcg tatctgtatg   11640
agttcaccgg aaacggtgag gactgggagg attacaatga tgcgtttcgt gcgcgccagg   11700
aagggaaaat ttataaggcc actgccacca gcttgaagtt ttatttttccc ccgggccctg   11760
tcattgaacc aactttaggc ctgaattgaa atgaaatggg gtccatgcaa agccttttg    11820
acaaaattgg ccaacttttt gtggatgctt tcacggagtt cttggtgtcc attgttgata   11880
tcattatatt tttggccatt ttgtttggct tcaccatcgc cggttggctg gtggtctttt   11940
gcatcagatt ggtttgctcc gcgatactcc gtacgcgccc tgccattcac tctgagcaat   12000
tacagaagat cttatgaggc cttctcttcc cagtgccaag tggacattcc cacctgggga   12060
actaaacatc ctttggggat gctttggcac cataaggtgt caaccctgat tgatgaaatg   12120
gtgtcgcgtc gaatgtaccg catcatgaa aaagcagggc aggctgcctg gaaacaggtg   12180
gtgagcgagg ctacgctgtc tcgcattagt agtttggatg tggtggctca ttttcagcat   12240
ctagccgcca ttgaagccga gacctgtaaa tatttggcct cccggctgcc catgctacac   12300
aacctgcgca tgacagggtc aaatgtaacc atagtgtata atagcacttt gaatcaggtg   12360
tttgctatttt ttccaacccc tggttccgg ccaaagcttc atgattttca gcaatggtta   12420
atagctgtac attcctccat attttcctct gttgcagctt cttgtactct ttttgttgtg   12480
ctgtggttgc gggttccaat actacgtact gttttttggtt tccgctggtt aggggcaatt   12540
tttctttcga actcacagtg aattacacgg tgtgtccacc ttgcctcacc cggcaagcag   12600
ccacagagat ctacgaaccc ggtaggtctc tttggtgcag atagggtat gaccgatgtg   12660
gggaggacga tcatgacgag ctagggttta tgataccgcc tggcctctcc agcgaaggcc   12720
acttgactgg tgtttacgcc tggttggcgt tcttgtcctt cagctacacg gcccagttcc   12780
atcccgagat attcgggata gggaatgtga gtcgagttta tgttgacatc aaacatcaac   12840
tcatctgcgc cgaacatgac gggcagaaca ccaccttgcc tcgtcatgac aacatttcag   12900
ccgtgtttca gacctattac caacatcaag tcgacggcgg caattggttt cacctagaat   12960
ggcttcgtcc cttctttttcc tcgtggttgg ttttaaatgt ctcttggttt ctcaggcgtt   13020
cgcctgcaaa ccatgtttca gttcgagtct tgcagatatt aagaccaaca ccaccgcagc   13080
ggcaagcttt gctgtcctcc aagacatcag ttgccttagg catcgcgact cggcctctga   13140
ggcgattcgc aaaatccctc agtgccgtac ggcgataggg acaccgtgt atgttaccat   13200
cacagccaat gtgacagatg agaattattt acattcttct gatctcctca tgctttcttc   13260
ttgcctttct tatgcttctg agatgagtga aaagggattt aaggtggtat ttggcaatgt   13320
```

```
gtcaggcatc gtggctgtgt gtgtcaattt taccagctac gtccaacatg tcaaggagtt   13380
tacccaacgc tccctggtgg tcgaccatgt gcggttgctc catttcatga cacctgagac   13440
catgaggtgg gcaactgttt tagcctgtct ttttgccatt ctgttggcaa tttgaatgtt   13500
taagtatgtt ggagaaatgc ttgaccgcgg gctgttgctc gcgattgctt tctttgtggt   13560
gtatcgtgcc gttctgtttt gctgtgctcg ccaacgccag caacgacagc agctcccatc   13620
tacagctgat ttacaacttg acgctatgtg agctgaatgg cacagattgg ctagctaaca   13680
aatttgattg ggcagtggag agttttgtca tcttttcccgt tttgactcac attgtctcct   13740
atggtgccct cactaccagc catttccttg acacagtcgc tttagtcact gtgtctaccg   13800
ccgggtttgt tcacgggcgg tatgtcctaa gtagcatcta cgcggtctgt gccctggctg   13860
cgttgacttg cttcgtcatt aggtttgcaa agaattgcat gtcctggcgc tacgcgtgta   13920
ccagatatac caactttctt ctggacacta agggcagact ctatcgttgg cggtcgcctg   13980
tcatcataga gaaagggggc aaagttgagg tcgaaggtca tctgatcgac ctcaaaagag   14040
ttgtgcttga tggctccgtg gcaaccccta taaccagagt ttcagcggaa caatggggtc   14100
gtccttagat gacttctgtc acgatagcac ggctccacaa aaggtgcttt tggcgttttc   14160
tattacctac acgccagtga tgatatatgc cctaaaggtg agtcgcggcc gactgctagg   14220
gcttctgcac cttttgatct tcctgaattg tgctttcacc ttcgggtaca tgactttcgc   14280
gcactttcag agtacaaata aggtcgcgct cactatggga gcagtagttg cactccttg   14340 gggggtgtac tcagccatag aaacctggaa attcatcacc tccagatgcc gtttgtgctt   14400
gctaggccgc aagtacattc tggcccctgc ccaccacgtt gaaagtgccg caggctttca   14460
tccgattgcg gcaaatgata accacgcatt tgtcgtccgg cgtcccggct ccactacggt   14520
caacggcaca ttggtgcccg ggttaaaaag cctcgtgttg ggtggcagaa aagctgttaa   14580
acagggagtg gtaaaccttg tcaaatatgc caaataacaa cggcaagcag cagaagagaa   14640
agaaggggga tggccagcca gtcaatcagc tgtgccagat gctgggtaag atcatcgctc   14700
agcaaaacca gtccagaggc aagggaccgg gaaagaaaaa taagaagaaa acccgggaga   14760
agccccattt tcctctagcg actgaagatg atgtcagaca tcactttacc cctagtgagc   14820
ggcaattgtg tctgtcgtca atccagaccg ccttttaatca aggcgctggg acttgcaccc   14880
tgtcagattc agggaggata agttacactg tggagtttag tttgcctacg catcatactg   14940
tgcgcctgat ccgcgtcaca gcatcaccct cagcatgatg ggctggcatt cttgaggcat   15000
ctcagtgttt gaattggaag aatgtgtggt gaatggcact gattgacatt gtgcctctaa   15060
gtcacctatt caattagggc gaccgtgtgg gggtgagatt taattggcga gaaccatgcg   15120
gccgaaatta aaaaaaa                                                   15137
```

<210> SEQ ID NO 11
<211> LENGTH: 14867
<212> TYPE: DNA
<213> ORGANISM: Artificial Sequence
<220> FEATURE:
<223> OTHER INFORMATION: Porcine reproductive and respiratory syndrome
      virus

<400> SEQUENCE: 11

```
atgacgtata ggtgttggct ctatgccttg gcatttgtat tgtcaggagc tgtgaccatt    60
ggcacagccc aaaacttgct gcacagaaac acccttctgt gatagcctcc ttcagggag   120 cttagggttt gtccctagca ccttgcttcc ggagttgcac tgctttacgg tctctccacc   180
```

-continued

```
cctttaacca tgtctgggat acttgatcgg tgcacgtgta cccccaatgc cagggtgttt    240
atggcggagg gccaagtcta ctgcacacga tgcctcagtg cacggtctct ccttcccctg    300
aacctccagg tttctgagct cggggtgcta ggcctattct acaggcccga agagccactc    360
cggtggacgt tgccacgtgc attccccact gttgagtgct cccccgccgg ggcctgctgg    420
ctttctgcaa tctttccaat cgcacgaatg accagtggaa acctgaactt ccaacaaaga    480
atggtacggg tcgcagctga gctttacaga gccggccagc tcacccctgc agtcttgaag    540
gctctacaag tttatgaacg gggttgccgc tggtacccca ttgttggacc tgtccctgga    600
gtggccgttt tcgccaattc cctacatgtg agtgataaac ccttcccggg agcaactcac    660
gtgttgacca acctgccgct cccgcagaga cccaagcctg aagacttttg ccctttgag     720 tgtgctatgg ctactgtcta tgacattggt catgacgccg tcatgtatgt ggccgaaagg    780
aaagtctcct gggcccctcg tggcgggat gaagtgaaat ttgaagctgt ccccggggag     840
ttgaagttga ttgcgaaccg gctccgcacc tccttcccgc ccaccacac agtgacatg      900 tctaagttcg ccttcacagc ccctgggtgt ggtgtttcta tgcgggtcga acgccaacac    960
ggctgccttc ccgctgacac tgtccctgaa ggcaactgct ggtggagctt gtttgacttg   1020
cttccactgg aagttcagaa caaagaaatt cgccatgcta accaatttgg ctaccagacc   1080
aagcatggtg tctctggcaa gtacctgcag cggaggctgc aagttaatgg tctccgagca   1140
gtaactgacc taaacggacc tatcgtcgta cagtacttct ccgttaagga gagttggatc   1200
cgccatttga actggcggg agaacccagc tactctgggt ttgaggacct cctcagaata    1260
agggttgagc ctaacacgtc gccattggct gacaaggaag aaaaaatttt ccggtttggc   1320
agtcacaagt ggtacggcgc tggaaagaga gcaagaaaag cacgctcttg tgcgactgct   1380
acagtcgctg gccgcgcttt gtccgttcgt gaaacccggc aggccaagga gcacgaggtt   1440
gccggcgcca acaaggctga gcacctcaaa cactactccc cgcctgccga agggaattgt   1500
ggttggcact gcatttccgc catcgccaac cggatggtga attccaaatt tgaaaccacc   1560
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctgaaggt tgagcattgg actgtcactg tgaccccatg gatgtcccct   1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg    2340 gctaactact actaccgtgc gcaaggtgac gaagttcgtc accgtgaaag actaaccgcc   2400
gtgctctcca gttggaaaaa ggttgttcga gaagaatatg gctcatgcc aaccgagcct    2460 ggtccacggc ccacactgcc acgcgggctc gacgaactca aagaccagat ggaggaggac   2520
```

```
ttgctgaaac tggctaacgc ccagacgact tcggacatga tggcctgggc agtcgagcag    2580
gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agccccttg atctcccgac cccacctgag     2820
ccggcaacac cttcaagtga gctggtgatt gtgtcctcac cgcaatgcat cttcaggccg    2880
gcgacaccct tgagtgagcc ggctccaatt cccgcacctc gcggaactgt gtctcgaccg    2940
gtgcacccct tgagtgagcc gtgtgagttt gtgatgatgc ctcacacgcc tgcaccttcc    3000
gtaggtgcgg agagcgacct taccattggc tcagttgcta ctgaagatgt tccacgcatc    3060
ctcgagaaaa tagaaaatgt cggcgagatg gccaaccagg gacccttggc cttctccgag    3120
gataaaccgg tagatgacca acttgtcaac gaccccggga tatcgtcgcg gaggcctgac    3180
gagagcacat cagctccgtc cgcaggcaca ggtggcgccg gctcttttac cgatttgccg    3240
ccttcagatg gcgcggatgc ggacgggggg gggccgtttc ggacggtaaa aagaaaagct    3300
gaaaggctct ttgaccaact gagccgtcag gttttgacc tcgtctccca tctccctgtt     3360
ttcttctcac gccttttcta ccctggcggt ggttattctc cgggtgattg gggttttgca    3420
gcttttactc tattgtgcct cttttatgt tacagttacc cagcctttgg tattgctccc     3480
ctcttgggtg tgttttctgg gtcttctcgg cgcgttcgaa tgggggtttt tggctgctgg    3540
ttggcttttg ctgttggtct gttcaagcct gtgtccgacc cagtcggcgc tgcttgtgag    3600
tttgactcgc cagagtgtag aaacatcctt cattcttttg agcttctcaa accttgggac    3660
cctgttcgca gccttgttgt gggccccgtc ggtctcggtc ttgccattct tggcaggtta    3720
ctgggcgggg cacgctgcat ctggcacttt ttgcttaggc ttggcattgt tgcagactgt    3780
atcttggctg gagcttacgt gctttctcaa ggtaggtgta aaagtgctg gggatcttgt     3840
ataagaactg ctcccaatga ggtcgctttt aacgtgtttc ctttcacacg tgcgaccagg    3900
tcgtcactta tcgacctgtg cgatcggttt tgtgcgccaa aaggaatgga ccccattttt    3960
ctcgccactg gtggcgcgg gtgctgggcc ggccgaagcc ccattgagca accctctgaa     4020
aaacccatcg cgtttgccca gttggatgaa aagaagatta cggctaggac tgtggtcgcc    4080
cagccttatg accccaacca agccgtaaag tgcttgcggg tattgcaggc gggtggggcg    4140
atggtggcta aggcggtccc aaaagtggtc aaggtttccg ctgttccatt ccgagccccc    4200
ttctttccca ctggagtgaa agttgaccct gattgcaggg tcgtggttga ccctgacact    4260
ttcactgcag ctctccggtc tggctactcc accacaaacc tcgtccttgg tgtgggggac    4320
tttgcccagc tgaatggatt aaaaatcagg caaatttcca agccttcagg gggaggccca    4380
catctcatgg ctgccctgca tgttgcctgc tcgatggctc tgcacatgct tgctgggatt    4440
tatgtgactg cggtgggttc ttgcggcacc ggcaccaacg accgtggtg cgctaacccg     4500
tttgccgtcc ctggctacgg acctggctct ctctgcacgt ccagattgtg catttcccaa    4560
cacggcctta ccctgcccct tgacagcact tgtggcggga tcggtattca agaaattgcc    4620
ttggtcgttt tgattttgt ttccatcgga ggcatggctc ataggttgag ctgtaaggct     4680
gacatgctgt gtgtcttgct tgcaattgcc agctatgttt gggtacctct tacctggttg    4740
ctttgtgtgt tcccttgctg gttgcgctgt ttttctttgc acccctcac catcctatgg    4800
ttggtgtttt tcttgatttc tgtgaatatg ccttcaggaa tcttggccat ggtgttgttg    4860
gtttctcttt ggcttcttgg tcgttatact aatgttgctg gccttgtcac cccctacgac    4920
```

```
attcatcatt acaccagtgg cccccgcggt gttgccgcct tggctaccgc accagatggg    4980
acctacttgg ccgctgtccg ccgcgctgcg ttgactggcc gcaccatgct gtttaccccg    5040
tcccagcttg ggtctcttct tgagggtgct ttcagaactc gaaagccctc actgaacacc    5100
gtcaatgtga tcgggtcctc catgggctct ggcggggtgt ttaccatcga cgggaaagtc    5160
aagtgcgtaa ctgccgcaca tgtccttacg ggcaattcag ctcgggtttc cggggtcggc    5220
ttcaatcaaa tgcttgactt tgacgtaaag ggagatttcg ctatagctga ttgcccgaat    5280
tggcaagggg ctgcccccaa gacccaattc tgcacggatg gatggactgg ccgtgcctat    5340
tggctaacat cctctggcgt cgaacccggc gtcattggaa aaggattcgc cttctgcttc    5400
accgcatgtg gcgattccgg gtccccagtg atcaccgagg ccggtgagct tgtcggcgtt    5460
cacacgggat cgaataaaca aggggggggc attgttacgc gcccctcagg ccagttttgt    5520
aatgtggcac ccatcaagct aagcgaatta agtgaattct tgctgggcc taaggtcccg    5580
ctcggtgatg tgaaggtcgg cagccacata attaaagaca taagcgaggt gccttcagat    5640
ctttgtgcct tgcttgctgc caaacctgaa ctggaaggag gcctctccac cgtccaactt    5700
ctttgtgtgt tttttctcct gtggagaatg atgggacatg cctggacgcc cttggttgct    5760
gtgagtttct ttattttgaa tgaggttctc ccagccgtcc tggtccggag tgttttctcc    5820
tttggaatgt tgtgctatc ctggctcacg ccatggtctg cgcaagttct gatgatcagg    5880
cttctgacag cagctcttaa caggaacaga tggtcacttg ccttttttcag cctcggtgca    5940
gtgaccggtt ttgtcgcaga tcttgcggcc actcaggggc atccgttgca ggcagtgatg    6000
aatttgagca cctatgcatt cctgcctcgg atgatggttg tgacctcacc agtcccagtg    6060
atcacgtgtg gtgtcgtgca cctacttgcc atcattttgt acttgtttaa gtaccgtggc    6120
ctgcaccata tccttgttgg cgatggagtg ttctctgcgg ctttcttctt gagatacttt    6180
gccgagggaa agttgaggga aggggtgtcg caatcctgcg gaatgaatca tgagtctctg    6240
actggtgccc tcgctatgag actcaatgac gaggacttgg atttccttat gaaatggact    6300
gattttaagt gctttgtttc tgcgtccaac atgaggaatg cagcgggtca atttatcgag    6360
gctgcctatg ctaaagcact tagagtagaa ctggcccagt tggtgcaggt tgataaagtt    6420
cgaggtactt tggccaaact tgaagctttt gctgataccg tggcacctca actctcgccc    6480
ggtgacattg ttgtcgctct cggccacacg cctgttggca gtatcttcga cctaaaggtt    6540
ggtagcacca agcataccct ccaagccatt gagaccagag tccttgctgg gtccaaaatg    6600
accgtggcgc gcgtcgtcga cccgacccc acgcccccac ccgcacccgt gcccatcccc    6660
ctcccaccga aagttctgga gaatggcccc aacgcttggg gggatgagga ccgtttgaat    6720
aagaagaaga ggcgcaggat ggaagccctc ggcatctatg ttatgggcgg gaaaaaatac    6780
cagaaatttt gggacaagaa ttccggtgat gtgttttatg aggaggtcca taataacaca    6840
gatgagtggg agtgtctcag agttggcgac cctgccgact tgacccctga aagggaact    6900
ctgtgtggac atgtcaccat tgaaaacaag gcttaccatg tttacacctc cccatctggt    6960
aagaagttct tggtccccgt caacccagag aatggaagag tccaatggga agctgcaaag    7020
cttttccgtg agcaggccct aggtatgatg aatgtcgacg cgaactgac tgccaaagaa    7080
ctggagaaac tgaaaagaat aattgacaaa ctccagggcc tgactaagga gcagtgttta    7140
aactgctagc cgccagcgac ttgacccgct gtggtcgcgg cggcttggtt gttactgaaa    7200
cagcggtaaa aatagtcaaa tttcacaacc ggaccttcac cctgggacct gtgaatttaa    7260
```

```
aagtggccag tgaggttgag ctaaaagacg cggttgagca caaccaacac ccggttgcga   7320
gaccgatcga tggtggagtt gtgctcctgc gttccgcggt tccttcgctt atagacgtct   7380
tgatctccgg tgctgatgca tctcccaagt tacttgccca tcacgggccg ggaaacactg   7440
ggatcgatgg cacgctctgg gattttgagt ccgaagccac taaagaggaa gtcgcactca   7500
gtgcgcaaat aatacaggct tgtgacatta ggcgcggcga cgctcctgaa attggtctcc   7560
cttacaagct gtaccctgtt aggggtaacc ctgagcgggt gaaggagtt ctgcagaata    7620
caaggtttgg agacatacct tacaaaaccc ccagtgacac tggaagccca gtgcacgcgg   7680
ctgcctgcct tacgcccaac gccactccgg tgactgatgg gcgctccgtc ttggccacga   7740
ccatgccccc cgggtttgag ttatatgtac cgaccatacc agcgtctgtc cttgattacc   7800
ttgactctag gcctgactgc cctaaacagc tgacagagca cggctgcgaa gatgccgcac   7860
tgaaagacct ctctaaatat gacttgtcca cccaaggctt tgttttacct ggagttcttc   7920
gccttgtgcg gaaatacctg tttgcccatg taggtaagtg cccacccgtt catcggcctt   7980
ctacttaccc tgctaagaat tctatggctg aataaatgg gaacaggttc ccaaccaagg    8040
acattcagag cgtccctgaa atcgacgttc tgtgcgcaca ggctgtgcga gaaaactggc   8100
aaactgtcac cccttgtact cttaagaaac agtattgcgg gaagaagaag actaggacca   8160
tactcggcac caataacttc atcgcactag cccaccgagc agtgttgagt ggtgttaccc   8220
agggcttcat gaaaaggcg tttaactcgc ccatcgccct cggaaagaac aagtttaagg    8280
agctacagac tccggtcctg ggcaggtgcc ttgaagctga tctcgcatcc tgcgatcgat   8340
ccacgcctgc aattgtccgc tggtttgccg ccaaccttct ttatgaactt gcctgtgctg   8400
aagagcatct accgtcgtac gtgctgaact gctgccacga cttactggtc acgcagtccg   8460
gcgcagtgac taagagaggt ggcctgtcgt ctggcgaccc gatcacctct gtgtctaaca   8520
ccatttatag tttggtgatc tatgcacagc atatggtgct tagttacttc aaaagtggtc   8580
accccccatgg ccttctgttc ttacaagacc agctaaagtt tgaggacatg ctcaaggttc   8640
aaccccctgat cgtctattcg gacgacctcg tgctgtatgc cgagtctccc accatgccaa   8700
actatcactg gtggttgaa catctgaatt tgatgctggg gtttcagacg acccaaaga    8760
agacagcaat aacagactcg ccatcatttc taggctgtag aataataaat gggcgccagc   8820
tagtccccaa ccgtgacagg atcctcgcgg ccctcgccta tcacatgaag gcgagtaatg   8880
tttctgaata ctatgcctca gcggctgcaa tactcatgga cagctgtgct tgtttggagt   8940
atgatcctga atggttttgaa gaacttgtag ttggaatagc gcagtgcgcc cgcaaggacg   9000
gctacagctt tcccggcacg ccgttcttca tgtccatgtg ggaaaaactc aggtccaatt   9060
atgaggggaa gaagtcgaga gtgtgcgggt actgcggggc cccggcccg tacgctactg     9120
cctgtggcct cgacgtctgc atttaccaca cccacttcca ccagcattgt ccagtcacaa   9180
tctggtgtgg ccatccagcg ggttctggtt cttgtagtga gtgcaaatcc cctgtaggga   9240
aaggcacaag ccctttagac gaggtgctgg aacaagtccc gtataagccc ccacggaccg   9300
ttatcatgca tgtggagcag ggtctcaccc cccttgatcc aggtagatac caaactcgcc   9360
gcggattagt ctctgtcagg cgtggaatta ggggaaatga agttggacta ccagacggtg   9420
attatgctag caccgccttg ctccctacct gcaaagagat caacatggtc gctgtcgctt   9480
ccaatgtatt gcgcagcagg ttcatcatcg gcccacccgg tgctgggaaa acatactggc   9540
tccttcaaca ggtccaggat ggtgatgtta tttacacacc aactcaccag accatgcttg   9600
acatgattag ggctttgggg acgtgccggt tcaacgtccc ggcaggcaca acgctgcaat   9660
```

```
tcccgtccc  ctcccgcacc  ggtccgtggg  ttcgcatcct  agccggcggt  tggtgtcctg   9720
gcaagaattc  cttcctagat  gaagcagcgt  attgcaatca  ccttgatgtt  ttgaggcttc   9780
ttagtaaaac  taccctcacc  tgtctaggag  acttcaagca  actccaccca  gtgggttttg   9840
attctcattg  ctatgttttt  gacatcatgc  ctcaaactca  actgaagacc  atctggaggt   9900
ttggacagaa  tatctgtgat  gccattcagc  cagattacag  ggacaaactc  atgtccatgg   9960
tcaacacaac  ccgtgtgacc  tacgtggaaa  aacctgtcag  gtatgggcag  gtcctcaccc  10020
cctaccacag  ggaccgagag  gacgacgcca  tcactattga  ctccagtcaa  ggcgccacat  10080
tcgatgtggt  tacattgcat  ttgcccacta  aagattcact  caacaggcaa  agagcccttg  10140
ttgctatcac  cagggcaaga  cacgctatct  tgtgtatga   cccacacagg  cagctgcagg  10200
gcttgtttga  tcttcctgca  aaaggcacgc  ccgtcaacct  cgcagtgcac  tgcgacgggc  10260
agctgatcgt  gctggataga  aataacaaag  aatgcacggt  tgctcaggct  ctaggcaacg  10320
gggataaatt  tagggccaca  gacaagcgtg  ttgtagattc  tctccgcgcc  atttgtgctg  10380
atctagaagg  gtcgagctct  ccgctcccca  aggtcgcaca  caacttggga  ttttatttct  10440
cacctgattt  aacacagttt  gctaaactcc  cagtagaact  tgcacctcac  tggcccgtgg  10500
tgtcaaccca  gaacaatgaa  agtggccgg   atcggctggt  tgccagcctt  cgccctatcc  10560
ataaatacag  ccgcgcgtgc  atcggtgccg  gctatatggt  gggcccttcg  gtgtttctag  10620
gcactcctgg  ggtcgtgtca  tactatctca  caaaatttgt  taagggcggg  gctcaagtgc  10680
ttccggagac  ggttttcagc  accggccgaa  ttgaggtaga  ctgccgggaa  tatcttgatg  10740
atcgggagcg  agaagttgct  gcgtccctcc  cacacgcttt  cattggcgac  gtcaaaggca  10800
ctaccgttgg  aggatgtcat  catgtcacct  ccagatacct  cccgcgcgtc  cttcccaagg  10860
aatcagttgc  ggtagtcggg  gtttcaagcc  ccggaaaagc  cgcgaaagca  ttgtgcacac  10920
tgacagatgt  gtacctccca  gatcttgaag  cctatctcca  cccggagacc  cagtccaagt  10980
gctggaaaat  gatgttggac  ttcaaagaag  ttcgactaat  ggtctggaaa  gacaaaacag  11040
cctatttcca  acttgaaggt  cgctatttca  cctggtatca  gcttccagc   tatgcctcgt  11100 acatccgtgt  tcccgtcaac  tctacggtgt  acttggaccc  ctgcatgggc  cccgcccttt  11160
gcaacaggag  agtcgtcggg  tccacccact  gggggctga   cctcgcggtc  accccttatg  11220
attacggcgc  taaaattatc  ctgtctagcg  cgtaccatgt  tgaaatgccc  cccggataca  11280
aaattctggc  gtgcgcggag  ttctcgttgg  atgacccagt  taagtacaaa  catacctggg  11340
ggtttgaatc  ggatacagcg  tatctgtatg  agttcaccgg  aaacggtgag  gactgggagg  11400
attacaatga  tgcgtttcgt  gcgcgccagg  aagggaaaat  ttataaggcc  actgccacca  11460
gcttgaagtt  ttatttttcc  ccgggccctg  tcattgaacc  aacttaggc   ctgaattgaa  11520 atgaaatggg  gtccatgcaa  agccttttg   acaaaattgg  ccaactttt   gtggatgctt  11580 tcacggagtt  cttggtgtcc  attgttgata  tcattatatt  tttggccatt  ttgtttggct  11640
tcaccatcgc  cggttggctg  gtggtctttt  gcatcagatt  ggtttgctcc  gcgatactcc  11700
gtacgcgccc  tgccattcac  tctgagcaat  tacagaagat  cttatgaggc  ctttctttcc  11760
cagtgccaag  tggacattcc  cacctgggga  actaaacatc  ctttggggat  gctttggcac  11820
cataaggtgt  caaccctgat  tgatgaaatg  gtgtcgcgtc  gaatgtaccg  catcatggaa  11880
aaagcagggc  aggctgcctg  gaaacaggtg  gtgagcgagg  ctacgctgtc  tcgcattagt  11940
agtttggatg  tggtggctca  ttttcagcat  ctagccgcca  ttgaagccga  gacctgtaaa  12000
```

```
tatttggcct cccggctgcc catgctacac aacctgcgca tgacagggtc aaatgtaacc   12060
atagtgtata atagcacttt gaatcaggtg tttgctattt ttccaacccc tggttcccgg   12120
ccaaagcttc atgattttca gcaatggtta atagctgtac attcctccat attttcctct   12180
gttgcagctt cttgtactct ttttgttgtg ctgtggttgc gggttccaat actacgtact   12240
gttttttggtt tccgctggtt aggggcaatt tttctttcga actcacagtg aattacacgg   12300
tgtgtccacc ttgcctcacc cggcaagcag ccacagagat ctacgaaccc ggtaggtctc   12360
tttggtgcag atagggtat gaccgatgtg gggaggacga tcatgacgag ctagggttta    12420
tgataccgcc tggcctctcc agcgaaggcc acttgactgg tgtttacgcc tggttggcgt   12480
tcttgtcctt cagctacacg gcccagttcc atcccgagat attcgggata gggaatgtga   12540
gtcgagttta tgttgacatc aaacatcaac tcatctgcgc cgaacatgac gggcagaaca   12600
ccaccttgcc tcgtcatgac aacatttcag ccgtgtttca gacctattac caacatcaag   12660
tcgacggcgg caattggttt cacctagaat ggcttcgtcc cttcttttcc tcgtggttgg   12720
ttttaaatgt ctcttggttt ctcaggcgtt cgcctgcaaa ccatgtttca gttcgagtct   12780
tgcagatatt aagaccaaca ccaccgcagc ggcaagcttt gctgtcctcc aagacatcag   12840
ttgccttagg catcgcgact cggcctctga ggcgattcgc aaaatccctc agtgccgtac   12900
ggcgataggg acaccgtgt atgttaccat cacagccaat gtgacagatg agaattattt    12960
acattcttct gatctcctca tgctttcttc ttgccttttc tatgcttctg agatgagtga   13020
aaagggattt aaggtggtat ttggcaatgt gtcaggcatc gtggctgtgt gtgtcaattt   13080
taccagctac gtccaacatg tcaaggagtt tacccaacgc tccctggtgg tcgaccatgt   13140
gcggttgctc catttcatga cacctgagac catgaggtgg gcaactgttt tagcctgtct   13200
ttttgccatt ctgttggcaa tttgaatgtt taagtatgtt ggagaaatgc ttgaccgcgg   13260
gctgttgctc gcgattgctt tctttgtggt gtatcgtgcc gttctgtttt gctgtgctcg   13320
ccaacgccag caacgacagc agctcccatc tacagctgat ttacaacttg acgctatgtg   13380
agctgaatgg cacagattgg ctagctaaca aatttgattg ggcagtggag agttttgtca   13440
tctttcccgt tttgactcac attgtctcct atggtgccct cactaccagc catttccttg   13500
acacagtcgc tttagtcact gtgtctaccg ccgggtttgt tcacgggcgg tatgtcctaa   13560
gtagcatcta cgcggtctgt gccctggctg cgttgacttg cttcgtcatt aggttttgcaa  13620
agaattgcat gtcctggcgc tacgcgtgta ccagatatac caactttctt ctggacacta   13680
agggcagact ctatcgttgg cggtcgcctg tcatcataga gaaagggggc aaagttgagg   13740
tcgaaggtca tctgatcgac ctcaaaagag ttgtgcttga tggctccgtg caacccctaa   13800
taaccagagt ttcagcggaa caatgggtc gtccttagat gacttctgtc acgatagcac    13860
ggctccacaa aaggtgcttt tggcgttttc tattacctac acgccagtga tgatatatgc   13920
cctaaaggtg agtcgcggcc gactgctagg gcttctgcac cttttgatct tcctgaattg   13980
tgctttcacc ttcgggtaca tgactttcgc gcactttcag agtacaaaata aggtcgcgct  14040
cactatggga gcagtagttg cactcctttg gggggtgtac tcagccatag aaacctggaa   14100
attcatcacc tccagatgcc gtttgtgctt gctaggccgc aagtacattc tggccctgc    14160
ccaccacgtt gaaagtgccg caggctttca tccgattgcg gcaaatgata accacgcatt   14220
tgtcgtccgg cgtcccggct ccactacggt caacggcaca ttggtgcccg ggttaaaaag   14280
cctcgtgttg ggtggcagaa aagctgttaa acagggagtg gtaaacccttg tcaaatatgc  14340
caaataacaa cggcaagcag cagaagagaa agaagggggga tggccagcca gtcaatcagc   14400
```

-continued

| | |
|---|---|
| tgtgccagat gctgggtaag atcatcgctc agcaaaacca gtccagaggc aagggaccgg | 14460 |
| gaaagaaaaa taagaagaaa aacccggaga agccccattt tcctctagcg actgaagatg | 14520 |
| atgtcagaca tcactttacc cctagtgagc ggcaattgtg tctgtcgtca atccagaccg | 14580 |
| cctttaatca aggcgctggg acttgcaccc tgtcagattc agggaggata agttacactg | 14640 |
| tggagtttag tttgcctacg catcatactg tgcgcctgat ccgcgtcaca gcatcaccct | 14700 |
| cagcatgatg ggctggcatt cttgaggcat ctcagtgttt gaattggaag aatgtgtggt | 14760 |
| gaatggcact gattgacatt gtgcctctaa gtcacctatt caattagggc gaccgtgtgg | 14820 |
| gggtgagatt taattggcga gaaccatgcg gccgaaatta aaaaaaa | 14867 |

<210> SEQ ID NO 12
<211> LENGTH: 15158
<212> TYPE: DNA
<213> ORGANISM: Artificial Sequence
<220> FEATURE:
<223> OTHER INFORMATION: Porcine reproductive and respiratory syndrome virus

<400> SEQUENCE: 12

| | |
|---|---|
| atgacgtata ggtgttggct ctatgccttg gcatttgtat tgtcaggagc tgtgaccatt | 60 |
| ggcacagccc aaaacttgct gcacagaaac acccttctgt gatagcctcc ttcaggggag | 120 |
| cttagggttt gtccctagca ccttgcttcc ggagttgcac tgctttacgg tctctccacc | 180 |
| cctttaacca tgtctgggat acttgatcgg tgcacgtgta cccccaatgc cagggtgttt | 240 |
| atggcggagg gccaagtcta ctgcacacga tgcctcagtg cacggtctct ccttcccctg | 300 |
| aacctccagg tttctgagct cggggtgcta ggcctattct acaggcccga agagccactc | 360 |
| cggtggacgt tgccacgtgc attccccact gttgagtgct ccccgccgg ggcctgctgg | 420 |
| ctttctgcaa tctttccaat cgcacgaatg accagtggaa acctgaactt ccaacaaaga | 480 |
| atggtacggg tcgcagctga gctttacaga gccggccagc tcacccctgc agtcttgaag | 540 |
| gctctacaag tttatgaacg gggttgccgc tggtacccca ttgttggacc tgtccctgga | 600 |
| gtggccgttt cgccaattc cctacatgtg agtgataaac ccttcccggg agcaactcac | 660 |
| gtgttgacca acctgccgct cccgcagaga cccaagcctg aagactttg cccctttgag | 720 |
| tgtgctatgg ctactgtcta tgacattggt catgacgccg tcatgtatgt ggccgaaagg | 780 |
| aaagtctcct gggccccctcg tggcggggat gaagtgaaat ttgaagctgt ccccggggag | 840 |
| ttgaagttga ttgcgaaccg gctccgcacc tccttcccgc cccaccacac agtggacatg | 900 |
| tctaagttcg ccttcacagc ccctgggtgt ggtgtttcta tgcgggtcga acgccaacac | 960 |
| ggctgccttc ccgctgacac tgtccctgaa ggcaactgct ggtggagctt gtttgacttg | 1020 |
| cttccactgg aagttcagaa caaagaaatt cgccatgcta accaatttgg ctaccagacc | 1080 |
| aagcatggtg tctctggcaa gtacctgcag cggaggctgc aagttaatgg tctccgagca | 1140 |
| gtaactgacc taaacggacc tatcgtcgta cagtacttct ccgttaagga gagttggatc | 1200 |
| cgccatttga aactggcggg agaacccagc tactctgggt ttgaggacct cctcagaata | 1260 |
| agggttgagc ctaacacgtc gccattggct gacaaggaag aaaaaatttt ccggtttggc | 1320 |
| agtcacaagt ggtacggcgc tggaaagaga gcaagaaaag cacgctcttg tgcgactgct | 1380 |
| acagtcgctg gccgcgcttt gtccgttcgt gaaacccggc aggccaagga gcacgaggtt | 1440 |
| gccggcgcca acaaggctga gcacctcaaa cactactccc cgcctgccga agggaattgt | 1500 |
| ggttggcact gcatttccgc catcgccaac cggatggtga attccaaatt tgaaaccacc | 1560 |

```
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccgggg gatgtgccct    1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc cctgaccgc cttttcactg    2340
gctaactact actaccgtgc gcaaggtgac gaagttcgtc accgtgaaag actaaccgcc   2400
gtgctctcca gttggaaaa ggttgttcga gaagaatatg gctcatgcc aaccgagcct     2460
ggtccacggc ccacactgcc acgcgggctc gacgaactca aagaccagat ggaggaggac   2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac cccacctgag    2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggcgtt    3120
ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgcccta t ccgtctttta ccgatttgcc gccttcagat   3540
ggcgcggatg cggacggggg ggggccgttt cggacggtaa aagaaaagc tgaaaggctc    3600
tttgaccaac tgagccgtca ggttttgac ctcgtctccc atctccctgt tttcttctca    3660
cgccttttct accctggcgg tggttattct ccgggtgatt gggggttttgc agcttttact  3720
ctattgtgcc tcttttatg ttacagttac ccagcctttg gtattgctcc cctcttgggt    3780
gtgttttctg ggtcttctcg gcgcgttcga atggggtt ttggctgctg gttggctttt     3840
gctgttggtc tgttcaagcc tgtgtccgac ccagtcggcg ctgcttgtga gtttgactcg   3900
```

```
ccagagtgta gaaacatcct tcattctttt gagcttctca aaccttggga ccctgttcgc   3960
agccttgttg tgggccccgt cggtctcggt cttgccattc ttggcaggtt actgggcggg   4020
gcacgctgca tctggcactt tttgcttagg cttggcattg ttgcagactg tatcttggct   4080
ggagcttacg tgctttctca aggtaggtgt aaaaagtgct ggggatcttg tataagaact   4140
gctcccaatg aggtcgcttt taacgtgttt cctttcacac gtgcgaccag gtcgtcactt   4200
atcgacctgt gcgatcggtt ttgtgcgcca aaaggaatgg accccatttt tctcgccact   4260
gggtggcgcg ggtgctgggc cggccgaagc cccattgagc aaccctctga aaacccatc    4320
gcgtttgccc agttggatga aaagaagatt acggctagga ctgtggtcgc ccagccttat   4380
gaccccaacc aagccgtaaa gtgcttgcgg gtattgcagg cgggtggggc gatggtggct   4440
aaggcggtcc caaagtggt caaggttttcc gctgttccat tccgagcccc cttcttttccc   4500
actggagtga agttgaccc tgattgcagg gtcgtggttg accctgacac tttcactgca    4560
gctctccggt ctggctactc caccacaaac ctcgtccttg gtgtggggga ctttgcccag   4620
ctgaatggat taaaaatcag gcaaatttcc aagccttcag ggggaggccc acatctcatg   4680
gctgccctgc atgttgcctg ctcgatggct ctgcacatgc ttgctgggat ttatgtgact   4740
gcggtgggtt cttgcggcac cggcaccaac gacccgtggt gcgctaaccc gtttgccgtc   4800
cctggctacg gacctggctc tctctgcacg tccagattgt gcatttccca acacggcctt   4860
accctgccct tgacagcact tgtggcggga ttcggtattc aagaaattgc cttggtcgtt   4920
ttgattttttg tttccatcgg aggcatggct cataggttga gctgtaaggc tgacatgctg   4980
tgtgtcttgc ttgcaattgc cagctatgtt tgggtacctc ttacctggtt gctttgtgtg   5040
tttccttgct ggttgcgctg ttttctcttg caccccctca ccatcctatg gttggtgttt   5100
ttcttgattt ctgtgaatat gccttcagga atcttggcca tggtgttgtt ggtttctctt    5160
tggcttcttg gtcgttatac taatgttgct ggccttgtca ccccctacga cattcatcat   5220
tacaccagtg gccccgcgg tgttgccgcc ttggctaccg caccagatgg gacctacttg    5280
gccgctgtcc gccgcgctgc gttgactggc cgcaccatgc tgtttacccc gtcccagctt   5340
gggtctcttc ttgagggtgc tttcagaact cgaaagccct cactgaacac cgtcaatgtg   5400
atcgggtcct ccatgggctc tggcggggtg tttaccatcg acgggaaagt caagtgcgta   5460
actgccgcac atgtccttac gggcaattca gctcgggttt ccggggtcgg cttcaatcaa   5520
atgcttgact ttgacgtaaa gggagatttc gctatagctg attgcccgaa ttggcaaggg   5580
gctgccccca agacccaatt ctgcacggat ggatggactg gccgtgccta ttggctaaca   5640
tcctctggcg tcgaacccgg cgtcattgga aaaggattcg ccttctgctt caccgcatgt   5700
ggcgattccg ggtccccagt gatcaccgag gccggtgagc ttgtcggcgt tcacacggga   5760
tcgaataaac aagggggggg cattgttacg cgcccctcag gccagttttg taatgtggca   5820
cccatcaagc taagcgaatt aagtgaattc tttgctgggc ctaaggtccc gctcggtgat   5880
gtgaaggtcg gcagccacat aattaaagac ataagcgagg tgccttcaga tctttgtgcc   5940
ttgcttgctg ccaaacctga actggaagga ggcctctcca ccgtccaact tctttgtgtg   6000
tttttttctcc tgtggagaat gatgggacat gcctggacgc ccttggttgc tgtgagtttc   6060
tttatttttga atgaggttct cccagccgtc ctggtccgga gtgttttctc ctttggaatg   6120
tttgtgctat cctggctcac gccatggtct gcgcaagttc tgatgatcag gcttctgaca   6180
gcagctctta acaggaacag atggtcactt gccttttttca gcctcggtgc agtgaccggt   6240
tttgtcgcag atcttgcggc cactcagggg catccgttgc aggcagtgat gaatttgagc   6300
```

```
acctatgcat tcctgcctcg gatgatggtt gtgacctcac cagtcccagt gatcacgtgt    6360
ggtgtcgtgc acctacttgc catcattttg tacttgttta agtaccgtgg cctgcaccat    6420
atccttgttg gcgatggagt gttctctgcg gctttcttct tgagatactt tgccgaggga    6480
aagttgaggg aagggtgtc gcaatcctgc ggaatgaatc atgagtctct gactggtgcc    6540
ctcgctatga gactcaatga cgaggacttg gatttcctta tgaaatggac tgattttaag    6600
tgctttgttt ctgcgtccaa catgaggaat gcagcgggtc aatttatcga ggctgcctat    6660
gctaaagcac ttagagtaga actggcccag ttggtgcagg ttgataaagt tcgaggtact    6720
ttggccaaac ttgaagcttt tgctgatacc gtggcacctc aactctcgcc cggtgacatt    6780
gttgtcgctc tcggccacac gcctgttggc agtatcttcg acctaaaggt tggtagcacc    6840
aagcataccc tccaagccat tgagaccaga gtccttgctg gtccaaaat gaccgtggcg    6900
cgcgtcgtcg acccgacccc cacgccccca cccgcacccg tgcccatccc cctcccaccg    6960
aaagttctgg agaatggccc caacgcttgg ggggatgagg accgtttgaa taagaagaag    7020
aggcgcagga tggaagccct cggcatctat gttatgggcg ggaaaaaata ccagaaattt    7080
tgggacaaga attccggtga tgtgttttat gaggaggtcc ataataacac agatgagtgg    7140
gagtgtctca gagttggcga ccctgccgac tttgaccctg agaagggaac tctgtgtgga    7200
catgtcacca ttgaaaacaa ggcttaccat gtttacacct ccccatctgg taagaagttc    7260
ttggtccccg tcaacccaga gaatggaaga gtccaatggg aagctgcaaa gctttccgtg    7320
gagcaggccc taggtatgat gaatgtcgac ggcgaactga ctgccaaaga actggagaaa    7380
ctgaaaagaa taattgacaa actccagggc ctgactaagg agcagtgttt aaactgctag    7440
ccgccagcga cttgacccgc tgtggtcgcg gcggcttggt tgttactgaa acagcggtaa    7500
aaatagtcaa atttcacaac cggaccttca ccctgggacc tgtgaattta aaagtggcca    7560
gtgaggttga gctaaaagac gcggttgagc acaaccaaca cccggttgcg agaccgatcg    7620
atggtggagt tgtgctcctg cgttccgcgg ttccttcgct tatagacgtc ttgatctccg    7680
gtgctgatgc atctcccaag ttacttgccc atcacgggcc gggaaacact gggatcgatg    7740
gcacgctctg ggattttgag tccgaagcca ctaaagagga agtcgcactc agtgcgcaaa    7800
taatacaggc ttgtgacatt aggcgcggcg acgctcctga aattggtctc ccttacaagc    7860
tgtaccctgt tagggtaac cctgagcggg tgaaggagt tctgcagaat acaaggtttg    7920
gagacatacc ttacaaaacc cccagtgaca ctggaagccc agtgcacgcg gctgcctgcc    7980
ttacgcccaa cgccactccg gtgactgatg gcgctccgt cttggccacg accatgcccc    8040
ccgggtttga gttatatgta ccgaccatac cagcgtctgt ccttgattac cttgactcta    8100
ggcctgactg ccctaaacag ctgacagagc acggctgcga agatgccgca ctgaaagacc    8160
tctctaaata tgacttgtcc acccaaggct ttgttttacc tggagttctt cgccttgtgc    8220
ggaaatacct gtttgcccat gtaggtaagt gcccacccgt tcatcggcct tctacttacc    8280
ctgctaagaa ttctatggct ggaataaatg gaacaggtt cccaaccaag gacattcaga    8340
gcgtccctga aatcgacgtt ctgtgcgcac aggctgtgcg agaaaactgg caaactgtca    8400
ccccttgtac tcttaagaaa cagtattgcg ggaagaagaa gactaggacc atactcggca    8460
ccaataactt catcgcacta gcccaccgag cagtgttgag tggtgttacc cagggcttca    8520
tgaaaaaggc gtttaactcg cccatcgccc tcggaaagaa caagtttaag gagctacaga    8580
ctccggtcct gggcaggtgc cttgaagctg atctcgcatc ctgcgatcga tccacgcctg    8640
```

```
caattgtccg ctggtttgcc gccaaccttc tttatgaact tgcctgtgct gaagagcatc    8700
taccgtcgta cgtgctgaac tgctgccacg acttactggt cacgcagtcc ggcgcagtga    8760
ctaagagagg tggcctgtcg tctggcgacc cgatcacctc tgtgtctaac accatttata    8820
gtttggtgat ctatgcacag catatggtgc ttagttactt caaaagtggt cacccccatg    8880
gccttctgtt cttacaagac cagctaaagt ttgaggacat gctcaaggtt caaccctga    8940 tcgtctattc ggacgacctc gtgctgtatg ccgagtctcc caccatgcca aactatcact    9000
ggtgggttga acatctgaat ttgatgctgg ggtttcagac ggacccaaag aagacagcaa    9060
taacagactc gccatcattt ctaggctgta gaataataaa tgggcgccag ctagtcccca    9120
accgtgacag gatcctcgcg gccctcgcct atcacatgaa ggcgagtaat gtttctgaat    9180
actatgcctc agcggctgca atactcatgg acagctgtgc ttgtttggag tatgatcctg    9240
aatggtttga agaacttgta gttggaatag cgcagtgcgc ccgcaaggac ggctacagct    9300
ttcccggcac gccgttcttc atgtccatgt gggaaaaact caggtccaat tatgagggga    9360
agaagtcgag agtgtgcggg tactgcgggg ccccggcccc gtacgctact gcctgtggcc    9420
tcgacgtctg catttaccac acccacttcc accagcattg tccagtcaca atctggtgtg    9480
gccatccagc gggttctggt tcttgtagtg agtgcaaatc ccctgtaggg aaaggcacaa    9540 gcccttttaga cgaggtgctg aacaagtcc cgtataagcc cccacggacc gttatcatgc    9600
atgtggagca gggtctcacc cccttgatc caggtagata ccaaactcgc cgcggattag    9660
tctctgtcag gcgtggaatt aggggaaatg aagttggact accagacggt gattatgcta    9720
gcaccgcctt gctccctacc tgcaaagaga tcaacatggt cgctgtcgct tccaatgtat    9780
tgcgcagcag gttcatcatc ggcccacccg gtgctgggaa acatactgg ctccttcaac    9840 aggtccagga tggtgatgtt atttacacac caactcacca gaccatgctt gacatgatta    9900
gggctttggg gacgtgccgg ttcaacgtcc cggcaggcac aacgctgcaa ttccccgtcc    9960
cctcccgcac cggtccgtgg gttcgcatcc tagccggcgg ttggtgtcct ggcaagaatt   10020
ccttcctaga tgaagcagcg tattgcaatc accttgatgt tttgaggctt cttagtaaaa   10080
ctaccctcac ctgtctagga gacttcaagc aactccaccc agtgggtttt gattctcatt   10140
gctatgtttt tgacatcatg cctcaaactc aactgaagac catctggagg tttggacaga   10200
atatctgtga tgccattcag ccagattaca gggacaaact catgtccatg gtcaacacaa   10260
cccgtgtgac ctacgtggaa aaacctgtca ggtatgggca ggtcctcacc ccctaccaca   10320
gggaccgaga ggacgacgcc atcactattg actccagtca aggcgccaca ttcgatgtgg   10380
ttacattgca tttgcccact aaagattcac tcaacaggca aagagccctt gttgctatca   10440
ccagggcaag acacgctatc tttgtgtatg acccacacag gcagctgcag gcttgtttg    10500 atcttcctgc aaaaggcacg cccgtcaacc tcgcagtgca ctgcgacggg cagctgatcg   10560
tgctggatag aaataacaaa gaatgcacgg ttgctcaggc tctaggcaac ggggataaat   10620
ttagggccac agacaagcgt gttgtagatt ctctccgcgc catttgtgct gatctagaag   10680
ggtcgagctc tccgctcccc aaggtcgcac acaacttggg attttatttc tcacctgatt   10740
taacacagtt tgctaaactc ccagtagaac ttgcacctca ctggcccgtg gtgtcaaccc   10800
agaacaatga aaagtggccg gatcggctgg ttgccagcct tcgccctatc cataaataca   10860
gccgcgcgtg catcggtgcc ggctatatgg tgggcccttc ggtgtttcta ggcactcctg   10920
gggtcgtgtc atactatctc acaaaatttg ttaagggcgg ggctcaagtg cttccggaga   10980
cggttttcag caccggccga attgaggtag actgccggga atatcttgat gatcgggagc   11040
```

-continued

```
gagaagttgc tgcgtccctc ccacacgctt tcattggcga cgtcaaaggc actaccgttg   11100
gaggatgtca tcatgtcacc tccagatacc tcccgcgcgt ccttcccaag gaatcagttg   11160
cggtagtcgg ggtttcaagc cccggaaaag ccgcgaaagc attgtgcaca ctgacagatg   11220
tgtacctccc agatcttgaa gcctatctcc acccggagac ccagtccaag tgctggaaaa   11280
tgatgttgga cttcaaagaa gttcgactaa tggtctggaa agacaaaaca gcctatttcc   11340
aacttgaagg tcgctatttc acctggtatc agcttgccag ctatgcctcg tacatccgtg   11400
ttcccgtcaa ctctacggtg tacttggacc cctgcatggg ccccgcccct tgcaacagga   11460
gagtcgtcgg gtccacccac tgggggctg acctcgcgt caccccttat gattacggcg   11520
ctaaaattat cctgtctagc gcgtaccatg gtgaaatgcc ccccggatac aaaattctgg   11580
cgtgcgcgga gttctcgttg gatgacccag ttaagtacaa acatacctgg gggtttgaat   11640
cggatacagc gtatctgtat gagttcaccg gaaacggtga ggactgggag gattacaatg   11700
atgcgtttcg tgcgcgccag gaagggaaaa tttataaggc cactgccacc agcttgaagt   11760
tttattttcc cccgggccct gtcattgaac caactttagg cctgaattga aatgaaatgg   11820
ggtccatgca aagccttttt gacaaaattg gccaactttt tgtggatgct ttcacggagt   11880
tcttggtgtc cattgttgat atcattatat ttttggccat tttgtttggc ttcaccatcg   11940
ccggttggct ggtggtcttt tgcatcagat tggtttgctc cgcgatactc cgtacgcgcc   12000
ctgccattca ctctgagcaa ttacagaaga tcttatgagg cctttctttc ccagtgccaa   12060
gtggacattc ccacctgggg aactaaacat cctttgggga tgctttggca ccataaggtg   12120
tcaaccctga ttgatgaaat ggtgtcgcgt cgaatgtacc gcatcatgga aaaagcaggg   12180
caggctgcct ggaaacaggt ggtgagcgag gctacgctgt ctcgcattag tagtttggat   12240
gtggtggctc attttcagca tctagccgcc attgaagccg agacctgtaa atatttggcc   12300
tcccggctgc ccatgctaca caacctgcgc atgacagggt caaatgtaac catagtgtat   12360
aatagcactt tgaatcaggt gtttgctatt tttccaaccc ctggttcccg gccaaagctt   12420
catgattttc agcaatggtt aatagctgta cattcctcca tattttcctc tgttgcagct   12480
tcttgtactc ttttttgttgt gctgtggttg cgggttccaa tactacgtac tgtttttggt   12540
ttccgctggt tagggggcaat ttttctttcg aactcacagt gaattacacg gtgtgtccac   12600
cttgcctcac ccggcaagca gccacagaga tctacgaacc cggtaggtct ctttggtgca   12660
ggatagggta tgaccgatgt ggggaggacg atcatgacga gctagggttt atgataccgc   12720
ctggcctctc cagcgaaggc cacttgactg gtgtttacgc ctggttggcg ttcttgtcct   12780
tcagctacac ggcccagttc catcccgaga tattcgggat agggaatgtg agtcgagttt   12840
atgttgacat caaacatcaa ctcatctgcg ccgaacatga cggcagaac accaccttgc   12900 ctcgtcatga caacatttca gccgtgtttc agacctatta ccaacatcaa gtcgacggcg   12960
gcaattggtt tcacctagaa tggcttcgtc ccttcttttc ctcgtggttg gtttttaaatg   13020 tctcttggtt tctcaggcgt tcgcctgcaa accatgtttc agttcgagtc ttgcagatat   13080
taagaccaac accaccgcag cggcaagctt tgctgtcctc caagacatca gttgccttag   13140
gcatcgcgac tcggcctctg aggcgattcg caaaatccct cagtgccgta cggcgatagg   13200
gacacccgtg tatgttacca tcacagccaa tgtgacagat gagaattatt acattcttc   13260 tgatctcctc atgctttctt cttgcctttt ctatgcttct gagatgagtg aaaagggatt   13320
taaggtggta tttggcaatg tgtcaggcat cgtggctgtg tgtgtcaatt ttaccagcta   13380
```

-continued

```
cgtccaacat gtcaaggagt ttacccaacg ctccctggtg gtcgaccatg tgcggttgct    13440
ccatttcatg acacctgaga ccatgaggtg ggcaactgtt ttagcctgtc tttttgccat    13500
tctgttggca atttgaatgt ttaagtatgt tggagaaatg cttgaccgcg ggctgttgct    13560
cgcgattgct ttctttgtgg tgtatcgtgc cgttctgttt tgctgtgctc gccaacgcca    13620
gcaacgacag cagctcccat ctacagctga tttacaactt gacgctatgt gagctgaatg    13680
gcacagattg gctagctaac aaatttgatt gggcagtgga gagttttgtc atctttcccg    13740
ttttgactca cattgtctcc tatggtgccc tcactaccag ccatttcctt gacacagtcg    13800
ctttagtcac tgtgtctacc gccgggtttg ttcacgggcg gtatgtccta agtagcatct    13860
acgcggtctg tgccctggct gcgttgactt gcttcgtcat taggtttgca agaattgca    13920 tgtcctggcg ctacgcgtgt accagatata ccaactttct tctggacact aagggcagac    13980
tctatcgttg gcggtcgcct gtcatcatag agaaaagggg caaagttgag gtcgaaggtc    14040
atctgatcga cctcaaaaga gttgtgcttg atggctccgt ggcaacccct ataaccagag    14100
tttcagcgga acaatgggt cgtccttaga tgacttctgt cacgatagca cggctccaca    14160
aaaggtgctt ttggcgtttt ctattaccta cacgccagtg atgatatatg ccctaaaggt    14220
gagtcgcggc cgactgctag gcttctgca ccttttgatc ttcctgaatt gtgctttcac    14280
cttcgggtac atgactttcg cgcactttca gagtacaaat aaggtcgcgc tcactatggg    14340
agcagtagtt gcactccttt ggggggtgta ctcagccata gaaacctgga aattcatcac    14400
ctccagatgc cgtttgtgct tgctaggccg caagtacatt ctggcccctg cccaccacgt    14460
tgaaagtgcc gcaggctttc atccgattgc ggcaaatgat aaccacgcat tgtcgtccg    14520 gcgtcccggc tccactacgg tcaacggcac attggtgccc gggttaaaaa gcctcgtgtt    14580
gggtggcaga aaagctgtta aacagggagt ggtaaacctt gtcaaatatg ccaaataaca    14640
acggcaagca gcagaagaga aagaaggggg atggccagcc agtcaatcag ctgtgccaga    14700
tgctgggtaa gatcatcgct cagcaaaacc agtccagagg caagggaccg ggaaagaaaa    14760
ataagaagaa aaacccggag aagccccatt ttcctctagc gactgaagat gatgtcagac    14820
atcactttac ccctagtgag cggcaattgt gtctgtcgtc aatccagacc gcctttaatc    14880
aaggcgctgg gacttgcacc ctgtcagatt cagggaggat aagttacact gtggagttta    14940
gtttgcctac gcatcatact gtgcgcctga tccgcgtcac agcatcaccc tcagcatgat    15000
gggctggcat tcttgaggca tctcagtgtt tgaattggaa gaatgtgtgg tgaatggcac    15060
tgattgacat tgtgcctcta agtcacctat tcaattaggg cgaccgtgtg ggggtgagat    15120
ttaattggcg agaaccatgc ggccgaaatt aaaaaaaa                            15158
```

<210> SEQ ID NO 13
<211> LENGTH: 14210
<212> TYPE: DNA
<213> ORGANISM: Artificial Sequence
<220> FEATURE:
<223> OTHER INFORMATION: Porcine reproductive and respiratory syndrome virus

<400> SEQUENCE: 13

```
atgacgtata ggtgttggct ctatgccttg gcatttgtat tgtcaggagc tgtgaccatt       60
ggcacagccc aaaacttgct gcacagaaac acccttctgt gatagcctcc ttcaggggag      120
cttagggttt gtccctagca ccttgcttcc ggagttgcac tgctttacgg tctctccacc      180
cctttaacca tgtctgggat acttgatcgg tgcacgtgta cccccaatgc cagggtgttt      240
```

-continued

```
atggcggagg gccaagtcta ctgcacacga tgcctcagtg cacggtctct ccttcccctg      300
aacctccagg tttctgagct cggggtgcta ggcctattct acaggcccga agagccactc      360
cggtggacgt tgccacgtgc attccccact gttgagtgct ccccgccgg ggcctgctgg       420 ctttctgcaa tctttccaat cgcacgaatg accagtggaa acctgaactt ccaacaaaga      480
atggtacggg tcgcagctga gctttacaga gccggccagc tcacccctgc agtcttgaag      540
gctctacaag tttatgaacg gggttgccgc tggtacccca ttgttggacc tgtccctgga      600
gtggccgttt cgccaattc cctacatgtg agtgataaac ccttcccggg agcaactcac       660
gtgttgacca acctgccgct cccgcagaga cccaagcctg aagacttttg cccctttgag      720
tgtgctatgg ctactgtcta tgacattggt catgacgccg tcatgtatgt ggccgaaagg      780
aaagtctcct gggcccctcg tggcggggat gaagtgaaat ttgaagctgt ccccggggag      840
ttgaagttga ttgcgaaccg gctccgcacc tccttcccgc ccaccacac agtggacatg       900 tctaagttcg ccttcacagc ccctgggtgt ggtgtttcta tgcgggtcga acgccaacac      960
ggctgccttc ccgctgacac tgtccctgaa ggcaactgct ggtggagctt gtttgacttg     1020
cttccactgg aagttcagaa caaagaaatt cgccatgcta accaatttgg ctaccagacc     1080
aagcatggtg tctctggcaa gtacctgcag cggaggctgc aagttaatgg tctccgagca     1140
gtaactgacc taaacggacc tatcgtcgta cagtacttct ccgttaagga gagttggatc     1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct     1380
acagtcgctg gccgcgcttt gtccgttcgt gaaacccggc aggccaagga gcacgaggtt     1440
gccggcgcca acaaggctga gcacctcaaa cactactccc cgcctgccga agggaattgt     1500
ggttggcact gcatttccgc catcgccaac cggatggtga attccaaatt tgaaaccacc     1560
cttcccgaaa gagtgagacc tccagatgac tgggctactg acgaggatct tgtgaatgcc     1620
atccaaatcc tcagactccc tgcggcctta gacaggaacg gtgcttgtac tagcgccaag     1680
tacgtactta agctggaagg tgagcattgg actgtcactg tgaccccctgg gatgtcccct    1740 tctttgctcc ctcttgaatg tgttcagggc tgttgtgggc acaagggcgg tcttggttcc     1800
ccagatgcag tcgaggtctc cggatttgac cctgcctgcc ttgaccggct ggctgaggtg     1860
atgcacctgc ctagcagtgc tatcccagcc gctctggccg aaatgtctgg cgattccgat     1920
cgttcggctt ctccggtcac caccgtgtgg actgttcgc agttctttgc ccgtcacagc      1980
ggagggaatc accctgacca agtgcgctta gggaaaatta tcagcctttg tcaggtgatt     2040
gaggactgct gctgttccca gaacaaaacc aaccgggtca ccccggagga ggtcgcagca     2100
aagattgacc tgtacctccg tggtgcaaca atcttgaag aatgcttggc caggcttgag      2160
aaagcgcgcc cgccacgcgt aatcgacacc tcctttgatt gggatgttgt gctccctggg     2220
gttgaggcgg caacccagac gatcaagctg ccccaggtca ccagtgtcg tgctctggtc     2280 cctgttgtga ctcaaaagtc cttgtgtgag tttgtgatga tgcctcacac gcctgcacct     2340
tccgtaggtg cggagagcga ccttaccatt ggctcagttg ctactgaaga tgttccacgc     2400
atcctcgaga aaatagaaaa tgtcggcgag atggccaacc agggaccctt ggccttctcc     2460
gaggataaac cggtagatga ccaacttgtc aacgaccccc ggatatcgtc gcggaggcct     2520
gacgagagca catcagctcc gtccgcaggc acaggtggcg ccggctcttt taccgatttg     2580
ccgccttcag atggcgcgga tgcggacggg gggggccgt ttcggacggt aaaaagaaaa      2640
```

```
gctgaaaggc tctttgacca actgagccgt caggttttg  acctcgtctc ccatctccct   2700
gttttcttct cacgccttt  ctaccctggc ggtggttatt ctccgggtga ttggggtttt   2760
gcagcttta  ctctattgtg cctcttttta tgttacagtt acccagcctt tggtattgct   2820
cccctcttgg gtgtgttttc tgggtcttct cggcgcgttc gaatgggggt ttttggctgc   2880
tggttggctt tgctgttgg  tctgttcaag cctgtgtccg acccagtcgg cgctgcttgt   2940
gagtttgact cgccagagtg tagaaacatc cttcattctt ttgagcttct caaaccttgg   3000
gaccctgttc gcagccttgt tgtgggcccc gtcggtctcg gtcttgccat tcttggcagg   3060
ttactgggcg gggcacgctg catctggcac ttttgctta  ggcttggcat tgttgcagac   3120
tgtatcttgg ctggagctta cgtgctttct caaggtaggt gtaaaaagtg ctggggatct   3180
tgtataagaa ctgctcccaa tgaggtcgct tttaacgtgt ttcctttcac acgtgcgacc   3240
aggtcgtcac ttatcgacct gtgcgatcgg ttttgtgcgc caaaggaat  ggaccccatt   3300
tttctcgcca ctgggtggcg cgggtgctgg gccggccgaa gccccattga gcaaccctct   3360
gaaaaaccca tcgcgtttgc ccagttggat gaaaagaaga ttacggctag gactgtggtc   3420
gcccagcctt atgaccccaa ccaagccgta aagtgcttgc gggtattgca ggcgggtggg   3480
gcgatggtgg ctaaggcggt cccaaaagtg gtcaaggttt ccgctgttcc attccgagcc   3540
cccttctttc ccactggagt gaaagttgac cctgattgca gggtcgtggt tgaccctgac   3600
actttcactg cagctctccg gtctggctac tccaccacaa acctcgtcct tggtgtgggg   3660
gactttgccc agctgaatgg attaaaaatc aggcaaattt ccaagccttc aggggggagc   3720
ccacatctca tggctgccct gcatgttgcc tgctcgatgc tctgcacat  gcttgctggg   3780
atttatgtga ctgcggtggg ttcttgcggc accggcacca acgacccgtg gtgcgctaac   3840
ccgtttgccg tccctggcta cggacctggc tctctctgca cgtccagatt gtgcatttcc   3900
caacacggcc ttaccctgcc cttgacagca cttgtggcgg gattcggtat tcaagaaatt   3960
gccttggtcg ttttgatttt tgtttccatc ggaggcatgg ctcataggtt gagctgtaag   4020
gctgacatgc tgtgtgtctt gcttgcaatt gccagctatg tttgggtacc tcttacctgg   4080
ttgctttgtg tgtttccttg ctggttgcgc tgttttctt  tgcaccccct caccatccta   4140
tggttggtgt ttttcttgat ttctgtgaat atgccttcag gaatcttggc catggtgttg   4200
ttggtttctc tttggcttct tggtcgttat actaatgttg ctggccttgt cacccccta   4260
gacattcatc attacaccag tggccccgc  ggtgttgccg ccttggctac cgcaccagat   4320
gggacctact tggccgctgt ccgccgcgct gcgttgactg gccgcaccat gctgtttacc   4380
ccgtcccagc ttgggtctct tcttgagggt gctttcagaa ctcgaaagcc ctcactgaac   4440
accgtcaatg tgatcgggtc ctccatgggc tctggcgggg tgtttaccat cgacgggaaa   4500
gtcaagtgcg taactgccgc acatgtcctt acggcaatt  cagctcgggt ttccggggtc   4560
ggcttcaatc aaatgcttga ctttgacgta aaggagatt  cgctatagc  tgattgcccg   4620
aattggcaag gggctgcccc caagacccaa ttctgcacgg atggatggac tggccgtgcc   4680
tattggctaa catcctctgg cgtcgaaccc ggcgtcattg gaaaaggatt cgccttctgc   4740
ttcaccgcat gtggcgattc cgggtcccca gtgatcaccg aggccggtga gcttgtcggc   4800
gttcacacgg gatcgaataa acaagggggg ggcattgtta cgcgcccctc aggccagttt   4860
tgtaatgtgg cacccatcaa gctaagcgaa ttaagtgaat ctttgctgg  gcctaaggtc   4920
ccgctcggtg atgtgaaggt cggcagccac ataattaaag acataagcga ggtgccttca   4980
```

```
gatctttgtg ccttgcttgc tgccaaacct gaactggaag gaggcctctc caccgtccaa      5040
cttctttgtg tgttttttct cctgtggaga atgatgggac atgcctggac gcccttggtt      5100
gctgtgagtt tctttatttt gaatgaggtt ctcccagccg tcctggtccg gagtgttttc      5160
tcctttggaa tgtttgtgct atcctggctc acgccatggt ctgcgcaagt tctgatgatc      5220
aggcttctga cagcagctct taacaggaac agatggtcac ttgccttttt cagcctcggt      5280
gcagtgaccg ttttgtcgc agatcttgcg gccactcagg gcatccgtt gcaggcagtg      5340 atgaatttga gcacctatgc attcctgcct cggatgatgg ttgtgacctc accagtccca      5400
gtgatcacgt gtggtgtcgt gcacctactt gccatcattt tgtacttgtt taagtaccgt      5460
ggcctgcacc atatccttgt tggcgatgga gtgttctctg cggctttctt cttgagatac      5520
tttgccgagg gaaagttgag ggaaggggtg tcgcaatcct gcggaatgaa tcatgagtct      5580
ctgactggtg ccctcgctat gagactcaat gacgaggact tggatttcct tatgaaatgg      5640
actgatttta gtgctttgt ttctgcgtcc aacatgagga atgcagcggg tcaatttatc      5700
gaggctgcct atgctaaagc acttagagta gaactggccc agttggtgca ggttgataaa      5760
gttcgaggta ctttggccaa acttgaagct tttgctgata ccgtggcacc tcaactctcg      5820
cccggtgaca ttgttgtcgc tctcggccac acgcctgttg gcagtatctt cgacctaaag      5880
gttggtagca ccaagcatac cctccaagcc attgagacca gagtccttgc tgggtccaaa      5940
atgaccgtgg cgcgcgtcgt cgacccgacc cccacgcccc cacccgcacc cgtgcccatc      6000
cccctcccac cgaaagttct ggagaatggc cccaacgctt ggggggatga ggaccgtttg      6060
aataagaaga gaggcgcag gatggaagcc ctcggcatct atgttatggg cgggaaaaaa      6120
taccagaaat ttgggacaa gaattccggt gatgtgtttt atgaggaggt ccataataac      6180
acagatgagt gggagtgtct cagagttggc gaccctgccg actttgaccc tgagaaggga      6240
actctgtgtg acatgtcac cattgaaaac aaggcttacc atgtttacac ctccccatct      6300
ggtaagaagt tcttggtccc cgtcaaccca gagaatggaa gagtccaatg ggaagctgca      6360
aagctttccg tggagcaggc cctaggtatg atgaatgtcg acggcgaact gactgccaaa      6420
gaactggaga aactgaaaag aataattgac aaactccagg gcctgactaa ggagcagtgt      6480
ttaaactgct agccgccagc gacttgaccc gctgtggtcg cggcggcttg gttgttactg      6540
aaacagcggt aaaatagtc aaatttcaca accggacctt caccctggga cctgtgaatt      6600
taaaagtggc cagtgaggtt gagctaaaag acgcggttga gcacaaccaa cacccggttg      6660
cgagaccgat cgatggtgga gttgtgctcc tgcgttccgc ggttccttcg cttatagacg      6720
tcttgatctc cggtgctgat gcatctccca agttacttgc ccatcacggg ccgggaaaca      6780
ctgggatcga tggcacgctc tgggattttg agtccgaagc cactaaagag gaagtcgcac      6840
tcagtgcgca ataatacag gcttgtgaca ttaggcgcgg cgacgctcct gaaattggtc      6900
tcccttacaa gctgtaccct gttagggta accctgagcg ggtgaaagga gttctgcaga      6960
atacaaggtt tggagacata ccttacaaaa cccccagtga cactggaagc ccagtgcacg      7020
cggctgcctg ccttacgccc aacgccactc cggtgactga tgggcgctcc gtcttggcca      7080
cgaccatgcc ccccgggttt gagttatatg taccgaccat accagcgtct gtccttgatt      7140
accttgactc taggcctgac tgccctaaac agctgacaga gcacggctgc gaagatgccg      7200
cactgaaaga cctctctaaa tatgacttgt ccacccaagg ctttgtttta cctggagttc      7260
ttcgccttgt gcgaaatac ctgtttgccc atgtaggtaa gtgcccaccc gttcatcggc      7320
cttctactta ccctgctaag aattctatgg ctggaataaa tgggaacagg ttcccaacca      7380
```

```
aggacattca gagcgtccct gaaatcgacg ttctgtgcgc acaggctgtg cgagaaaact    7440
ggcaaactgt caccccttgt actcttaaga aacagtattg cgggaagaag aagactagga    7500
ccatactcgg caccaataac ttcatcgcac tagcccaccg agcagtgttg agtggtgtta    7560
cccagggctt catgaaaaag gcgtttaact cgcccatcgc cctcggaaag aacaagttta    7620
aggagctaca gactccggtc ctgggcaggt gccttgaagc tgatctcgca tcctgcgatc    7680
gatccacgcc tgcaattgtc cgctggtttg ccgccaacct tctttatgaa cttgcctgtg    7740
ctgaagagca tctaccgtcg tacgtgctga actgctgcca cgacttactg gtcacgcagt    7800
ccggcgcagt gactaagaga ggtggcctgt cgtctggcga cccgatcacc tctgtgtcta    7860
acaccattta tagtttggtg atctatgcac agcatatggt gcttagttac ttcaaaagtg    7920
gtcaccccca tggccttctg ttcttacaag accagctaaa gtttgaggac atgctcaagg    7980
ttcaacccct gatcgtctat tcggacgacc tcgtgctgta tgccgagtct cccaccatgc    8040
caaactatca ctggtgggtt gaacatctga atttgatgct ggggtttcag acggacccaa    8100
agaagacagc aataacagac tcgccatcat ttctaggctg tagaataata aatgggcgcc    8160
agctagtccc caaccgtgac aggatcctcg cggccctcgc ctatcacatg aaggcgagta    8220
atgtttctga atactatgcc tcagcggctg caatactcat ggacagctgt gcttgtttgg    8280
agtatgatcc tgaatggttt gaagaacttg tagttggaat agcgcagtgc gcccgcaagg    8340
acggctacag ctttcccggc acgccgttct tcatgtccat gtgggaaaaa ctcaggtcca    8400
attatgaggg gaagaagtcg agagtgtgcg ggtactgcgg ggccccggcc ccgtacgcta    8460
ctgcctgtgg cctcgacgtc tgcatttacc acacccactt ccaccagcat tgtccagtca    8520
caatctggtg tggccatcca gcgggttctg gttcttgtag tgagtgcaaa tcccctgtag    8580
ggaaaggcac aagccctta gacgaggtgc tggaacaagt cccgtataag cccccacgga    8640
ccgttatcat gcatgtggag cagggtctca ccccccttga tccaggtaga taccaaactc    8700
gccgcggatt agtctctgtc aggcgtggaa ttaggggaaa tgaagttgga ctaccagacg    8760
gtgattatgc tagcaccgcc ttgctcccta cctgcaaaga gatcaacatg gtcgctgtcg    8820
cttccaatgt attgcgcagc aggttcatca tcggcccacc cggtgctggg aaaacatact    8880
ggctccttca acaggtccag gatggtgatg ttatttacac accaactcac cagaccatgc    8940
ttgacatgat tagggctttg gggacgtgcc ggttcaacgt cccggcaggc acaacgctgc    9000
aattccccgt ccctcccgc accggtccgt gggttcgcat cctagccggc ggttggtgtc    9060
ctggcaagaa ttccttccta gatgaagcag cgtattgcaa tcaccttgat gttttgaggc    9120
ttcttagtaa aactaccctc acctgtctag gagacttcaa gcaactccac ccagtgggtt    9180
ttgattctca ttgctatgtt tttgacatca tgcctcaaac tcaactgaag accatctgga    9240
ggtttggaca gaatatctgt gatgccattc agccagatta cagggacaaa ctcatgtcca    9300
tggtcaacac aacccgtgtg acctacgtgg aaaaacctgt caggtatggg caggtcctca    9360 cccctacca cagggaccga gaggacgacg ccatcactat tgactccagt caaggcgcca    9420
cattcgatgt ggttacattg catttgccca ctaaagattc actcaacagg caaagagccc    9480
ttgttgctat caccagggca agacacgcta tctttgtgta tgacccacac aggcagctgc    9540
agggcttgtt tgatcttcct gcaaaaggca cgcccgtcaa cctcgcagtg cactgcgacg    9600
ggcagctgat cgtgctggat agaaataaca agaatgcac ggttgctcag gctctaggca    9660 acgggataa atttagggcc acagacaagc gtgttgtaga ttctctccgc gccatttgtg    9720
```

```
ctgatctaga agggtcgagc tctccgctcc ccaaggtcgc acacaacttg ggattttatt    9780
tctcacctga tttaacacag tttgctaaac tcccagtaga acttgcacct cactggcccg    9840
tggtgtcaac ccagaacaat gaaaagtggc cggatcggct ggttgccagc cttcgcccta    9900
tccataaata cagccgcgcg tgcatcggtg ccggctatat ggtgggccct tcggtgtttc    9960
taggcactcc tggggtcgtg tcatactatc tcacaaaatt tgttaagggc ggggctcaag   10020
tgcttccgga cacggttttc agcaccggcc gaattgaggt agactgccgg gaatatcttg   10080
atgatcggga gcgagaagtt gctgcgtccc tcccacacgc tttcattggc gacgtcaaag   10140
gcactaccgt tggaggatgt catcatgtca cctccagata cctcccgcgc gtccttccca   10200
aggaatcagt tgcggtagtc ggggtttcaa gccccggaaa agccgcgaaa gcattgtgca   10260
cactgacaga tgtgtacctc ccagatcttg aagcctatct ccaccggag acccagtcca    10320
agtgctggaa aatgatgttg gacttcaaag aagttcgact aatggtctgg aaagacaaaa   10380
cagcctattt ccaacttgaa ggtcgctatt tcacctggta tcagcttgcc agctatgcct   10440
cgtacatccg tgttcccgtc aactctacgg tgtacttgga cccctgcatg ggccccgccc   10500
tttgcaacag gagagtcgtc gggtccaccc actgggggc tgacctcgcg gtcaccccctt   10560
atgattacgg cgctaaaatt atcctgtcta gcgcgtacca tggtgaaatg ccccccggat   10620
acaaaattct ggcgtgcgcg gagttctcgt tggatgaccc agttaagtac aaacatacct   10680
gggggtttga atcggataca gcgtatctgt atgagttcac cggaaacggt gaggactggg   10740
aggattacaa tgatgcgttt cgtgcgcgcc aggaagggaa aatttataag gccactgcca   10800
ccagcttgaa gttttatttt ccccccgggcc ctgtcattga accaactta ggcctgaatt   10860
gaaatgaaat ggggtccatg caaagccttt ttgacaaaat tggccaactt tttgtggatg   10920
cttttcacgga gttcttggtg tccattgttg atatcattat atttttggcc attttgtttg   10980
gcttcaccat cgccggttgg ctggtggtct tttgcatcag attggtttgc tccgcgatac   11040
tccgtacgcg ccctgccatt cactctgagc aattacagaa gatcttatga ggcctttctt   11100
tcccagtgcc aagtggacat tcccacctgg ggaactaaac atcctttggg gatgctttgg   11160
caccataagg tgtcaaccct gattgatgaa atggtgtcgc gtcgaatgta ccgcatcatg   11220
gaaaaagcag ggcaggctgc ctggaaacag gtggtgagcg aggctacgct gtctcgcatt   11280
agtagtttgg atgtggtggc tcattttcag catctagccg ccattgaagc cgagacctgt   11340
aaatatttgg cctcccggct gcccatgcta cacaacctgc gcatgacagg gtcaaatgta   11400
accatagtgt ataatagcac tttgaatcag gtgtttgcta ttttttccaac ccctggttcc   11460
cggccaaagc ttcatgattt tcagcaatgg ttaatagctg tacattcctc catattttcc   11520
tctgttgcag cttcttgtac tctttttgtt gtgctgtggt tgcgggttcc aatactacgt   11580
actgttttgg gtttccgctg gttaggggca atttttcttt cgaactcaca gtgaattaca   11640
cggtgtgtcc accttgcctc acccggcaag cagccacaga gatctacgaa cccggtaggt   11700
ctctttggtg caggataggg tatgaccgat gtggggagga cgatcatgac gagctagggt   11760
ttatgatacc gcctggcctc tccagcgaag gccacttgac tggtgtttac gcctggttgg   11820
cgttcttgtc cttcagctac acggcccagt tccatcccga gatattcggg atagggaatg   11880
tgagtcgagt ttatgttgac atcaaacatc aactcatctg cgccgaacat gacgggcaga   11940
acaccacctt gcctcgtcat gacaacattt cagccgtgtt tcagacctat taccaacatc   12000
aagtcgacgg cggcaattgg tttcacctag aatggcttcg tcccttcttt tcctcgtggt   12060
tggttttaaa tgtctcttgg tttctcaggc gttcgcctgc aaaccatgtt tcagttcgag   12120
```

-continued

```
tcttgcagat attaagacca acaccaccgc agcggcaagc tttgctgtcc tccaagacat    12180
cagttgcctt aggcatcgcg actcggcctc tgaggcgatt cgcaaaatcc ctcagtgccg    12240
tacggcgata gggacacccg tgtatgttac catcacagcc aatgtgacag atgagaatta    12300
tttacattct tctgatctcc tcatgctttc ttcttgcctt ttctatgctt ctgagatgag    12360
tgaaaaggga tttaaggtgg tatttggcaa tgtgtcaggc atcgtggctg tgtgtgtcaa    12420
ttttaccagc tacgtccaac atgtcaagga gtttacccaa cgctccctgg tggtcgacca    12480
tgtgcggttg ctccatttca tgacacctga gaccatgagg tgggcaactg ttttagcctg    12540
tcttttgcc attctgttgg caatttgaat gtttaagtat gttggagaaa tgcttgaccg    12600
cgggctgttg ctcgcgattg ctttctttgt ggtgtatcgt gccgttctgt tttgctgtgc    12660
tcgccaacgc cagcaacgac agcagctccc atctacagct gatttacaac ttgacgctat    12720
gtgagctgaa tggcacagat tggctagcta acaaatttga ttgggcagtg gagagttttg    12780
tcatctttcc cgttttgact cacattgtct cctatggtgc cctcactacc agccatttcc    12840
ttgacacagt cgctttagtc actgtgtcta ccgccgggtt tgttcacggg cggtatgtcc    12900
taagtagcat ctacgcggtc tgtgccctgg ctgcgttgac ttgcttcgtc attaggtttg    12960
caaagaattg catgtcctgg cgctacgcgt gtaccagata taccaacttt cttctggaca    13020
ctaagggcag actctatcgt tggcggtcgc tgtcatcat agagaaaagg ggcaaagttg    13080
aggtcgaagg tcatctgatc gacctcaaaa gagttgtgct tgatggctcc gtggcaaccc    13140
ctataaccag agtttcagcg gaacaatggg gtcgtcctta gatgacttct gtcacgatag    13200
cacggctcca caaaaggtgc ttttggcgtt ttctattacc tacacgccag tgatgatata    13260
tgccctaaag gtgagtcgcg gccgactgct agggcttctg caccttttga tcttcctgaa    13320
ttgtgctttc accttcgggt acatgacttt cgcgcacttt cagagtacaa ataaggtcgc    13380
gctcactatg ggagcagtag ttgcactcct ttggggggtg tactcagcca tagaaacctg    13440
gaaattcatc acctccagat gccgtttgtg cttgctaggc cgcaagtaca ttctggcccc    13500
tgcccaccac gttgaaagtg ccgcaggctt tcatccgatt gcggcaaatg ataaccacgc    13560
atttgtcgtc cggcgtcccg gctccactac ggtcaacggc acattggtgc ccgggttaaa    13620
aagcctcgtg ttgggtggca gaaaagctgt taaacaggga gtggtaaacc ttgtcaaata    13680
tgccaaataa caacggcaag cagcagaaga gaaagaaggg ggatggccag ccagtcaatc    13740
agctgtgcca gatgctgggt aagatcatcg ctcagcaaaa ccagtccaga ggcaagggac    13800
cgggaaagaa aaataagaag aaaaacccgg agaagcccca ttttcctcta gcgactgaag    13860
atgatgtcag acatcacttt acccctagtg agcggcaatt gtgtctgtcg tcaatccaga    13920
ccgcctttaa tcaaggcgct gggacttgca ccctgtcaga ttcagggagg ataagttaca    13980
ctgtggagtt tagtttgcct acgcatcata ctgtgcgcct gatccgcgtc acagcatcac    14040
cctcagcatg atgggctggc attcttgagg catctcagtg tttgaattgg aagaatgtgt    14100
ggtgaatggc actgattgac attgtgcctc taagtcacct attcaattag ggcgaccgtg    14160
tgggggtgag atttaattgg cgagaaccat gcggccgaaa ttaaaaaaaa                14210
```

<210> SEQ ID NO 14
<211> LENGTH: 15111
<212> TYPE: DNA
<213> ORGANISM: Porcine Reproductive and Respiratory Syndrome Virus
<220> FEATURE:
<221> NAME/KEY: misc_feature
<223> OTHER INFORMATION: Lelystad strain

```
<300> PUBLICATION INFORMATION:
<308> DATABASE ACCESSION NUMBER: Genbank/M96262.2
<309> DATABASE ENTRY DATE: 2000-11-08
<313> RELEVANT RESIDUES IN SEQ ID NO: (1)..(15111)

<400> SEQUENCE: 14
atgatgtgta gggtattccc cctacataca cgacacttct agtgtttgtg taccttggag      60
gcgtgggtac agccccgccc caccccttgg ccctgttct agcccaacag gtatccttct     120
ctctcggggc gagtgcgccg cctgctgctc ccttgcagcg ggaaggacct cccgagtatt     180
tccggagagc acctgcttta cgggatctcc accctttaac catgtctggg acgttctccc     240
ggtgcatgtg caccccggct gcccgggtat tttggaacgc cggccaagtc ttttgcacac     300
ggtgtctcag tgcgcggtct cttctctctc cagagcttca ggacactgac ctcggtgcag     360
ttggcttgtt ttacaagcct agggacaagc ttcactggaa agtccctatc ggcatccctc     420
aggtggaatg tactccatcc gggtgctgtt ggctctcagc tgttttccct ttggcgcgta     480
tgacctccgg caatcacaac ttcctccaac gacttgtgaa ggttgctgat gttttgtacc     540
gtgacggttg cttggcacct cgacaccttc gtgaactcca agtttacgag cgcggctgca     600
actggtaccc gatcacgggg cccgtgcccg ggatgggttt gtttgcgaac tccatgcacg     660
tatccgacca gccgttccct ggtgccaccc atgtgttgac taactcgcct ttgcctcaac     720
aggcttgtcg gcagccgttc tgtccatttg aggaggctca ttctagcgtg tacaggtgga     780
agaaatttgt ggttttcacg gactcctccc tcaacggtcg atctcgcatg atgtggacgc     840
cggaatccga tgattcagcc gccctggagg tactaccgcc tgagttagaa cgtcaggtcg     900
aaatcctcat tcggagtttt cctgctcatc accctgtcga cctggccgac tgggagctca     960
ctgagtcccc tgagaacggt ttttccttca cacgtctca ttcttgcggt caccttgtcc    1020
agaaccccga cgtgtttgat ggcaagtgct ggctctcctg ctttttgggc cagtcggtcg    1080
aagtgcgctg ccatgaggaa catctagctg acgccttcgg ttaccaaacc aagtggggcg    1140
tgcatggtaa gtacctccag cgcaggcttc aagttcgcgg cattcgtgct gtagtcgatc    1200
ctgatggtcc cattcacgtt gaagcgctgt cttgccccca gtcttggatc aggcacctga    1260
ctctggatga tgatgtcacc ccaggattcg ttcgcctgac atcccttcgc attgtgccga    1320
acacagagcc taccacttcc cggatctttc ggtttggagc gcataagtgg tatggcgctg    1380
ccggcaaacg ggctcgtgct aagcgtgccg ctaaaagtga aaggattcg gctcccaccc    1440
ccaaggttgc cctgccggtc cccacctgtg gaattaccac ctactctcca ccgacagacg    1500
ggtcttgtgg ttggcatgtc cttgccgcca taatgaaccg gatgataaat ggtgacttca    1560
cgtcccctct gactcagtac aacagaccag aggatgattg gcttctgat tatgatcttg    1620
ttcaggcgat tcaatgtcta cgactgcctg ctaccgtggt tcggaatcgc gcctgtccta    1680
acgccaagta ccttataaaa cttaacggag ttcactggga ggtagaggtg aggtctggaa    1740
tggctcctcg ctcccttcct cgtgaatgtg tggttggcgt ttgctctgaa ggctgtgtcg    1800
caccgcctta tccagcagac gggctaccta aacgtgcact cgaggccttg gcgtctgctt    1860
acagactacc ctccgattgt gttagctctg gtattgctga ctttcttgct aatccacctc    1920
ctcaggaatt ctggaccctc gacaaaatgt tgacctcccc gtcaccagag cggtccggct    1980
tctctagttt gtataaatta ctattagagg ttgttccgca aaaatgcggt gccacggaag    2040
gggctttcat ctatgctgtt gagaggatgt tgaaggattg tccgagctcc aaacaggcca    2100
tggcccttct ggcaaaaatt aaagttccat cctcaaaggc cccgtctgtg tccctggacg    2160
```

-continued

```
agtgtttccc tacggatgtt ttagccgact tcgagccagc atctcaggaa aggccccaaa    2220
gttccggcgc tgctgttgtc ctgtgttcac cggatgcaaa agagttcgag gaagcagccc    2280
cggaagaagt tcaagagagt ggccacaagg ccgtccactc tgcactcctt gccgagggtc    2340
ctaacaatga gcaggtacag gtggttgccg gtgagcaact gaagctcggc ggttgtggtt    2400
tggcagtcgg gaatgctcat gaaggtgctc tggtctcagc tggtctaatt aacctggtag    2460
gcgggaattt gtcccctca gaccccatga aagaaaacat gctcaatagc cgggaagacg    2520
aaccactgga tttgtcccaa ccagcaccag cttccacaac gacccttgtg agagagcaaa    2580
cacccgacaa cccaggttct gatgccggtg ccctccccgt caccgttcga gaatttgtcc    2640
cgacggggcc tatactctgt catgttgagc actgcggcac ggagtcgggc gacagcagtt    2700
cgcctttgga tctatctgat gcgcaaaccc tggaccagcc tttaaatcta tccctggccg    2760
cttggccagt gagggccacc gcgtctgacc ctggctgggt ccacggtagg cgcgagcctg    2820
tctttgtaaa gcctcgaaat gctttctctg atggcgattc agcccttcag ttcggggagc    2880
tttctgaatc cagctctgtc atcgagtttg accggacaaa agatgctccg gtggttgacg    2940
cccctgtcga cttgacgact tcgaacgagg ccctctctgt agtcgatcct ttcgaatttg    3000
ccgaactcaa gcgcccgcgt ttctccgcac aagccttaat tgaccgaggc ggtccacttg    3060
ccgatgtcca tgcaaaaata aagaaccggg tatatgaaca gtgcctccaa gcttgtgagc    3120
ccggtagtcg tgcaaccca gccaccaggg agtggctcga caaaatgtgg gatagggtgg    3180
acatgaaaac ttggcgctgc acctcgcagt tccaagctgg tcgcattctt gcgtccctca    3240
aattcctccc tgacatgatt caagacacac cgcctcctgt tcccaggaag aaccgagcta    3300
gtgacaatgc cggcctgaag caactggtgg cacagtggga taggaaattg agtgtgaccc    3360
ccccccaaa accggttggg ccagtgcttg accagatcgt ccctccgcct acggatatcc    3420
agcaagaaga tgtcaccccc tccgatgggc caccccatgc gccggatttt cctagtcgag    3480
tgagcacggg cggagttgg aaaggcctta tgctttccgg cacccgtctc gcggggtcta    3540
tcagccagcg ccttatgaca tgggttttg aagttttctc ccacctccca gcttttatgc    3600
tcacactttt ctcgccgcgg ggctctatgg ctccaggtga ttggttgttt gcaggtgtcg    3660
ttttacttgc tctcttgctc tgtcgttctt accgatact cggatgcctt cccttattgg    3720
gtgtcttttc tggttctttg cggcgtgttc gtctgggtgt ttttggttct tggatggctt    3780
ttgctgtatt tttattctcg actccatcca acccagtcgg ttcttcttgt gaccacgatt    3840
cgccggagtg tcatgctgag cttttggctc ttgagcagcg ccaactttgg gaacctgtgc    3900
gcggccttgt ggtcggcccc tcaggcctct tatgtgtcat tcttggcaag ttactcggtg    3960
ggtcacgtta tctctggcat gttctcctac gtttatgcat gcttgcagat ttggcccttt    4020
ctcttgttta tgtggtgtcc caggggcgtt gtcacaagtg ttggggaaag tgtataagga    4080
cagctcctgc ggaggtggct cttaatgtat tcctttctc gcgcgccacc cgtgtctctc    4140
ttgtatcctt gtgtgatcga ttccaaacgc caaaggggt tgatcctgtg cacttggcaa    4200
cgggttggcg cgggtgctgg cgtggtgaga gccccatcca tcaaccacac caaaagccca    4260
tagcttatgc caatttggat gaaaagaaaa tgtctgccca acggtggtt gctgtcccat    4320
acgatcccag tcaggctatc aaatgcctga agttctgca ggcgggaggg gccatcgtgg    4380
accagcctac acctgaggtc gttcgtgtgt ccgagatccc cttctcagcc ccatttttcc    4440
caaaagttcc agtcaaccca gattgcaggg ttgtggtaga ttcggacact tttgtggctg    4500
cggttcgctg cggttactcg acagcacaac tggttctggg ccggggcaac tttgccaagt    4560
```

```
taaatcagac cccccccagg aactctatct ccaccaaaac gactggtggg gcctcttaca    4620
cccttgctgt ggctcaagtg tctgcgtgga ctcttgttca tttcatcctc ggtctttggt    4680
tcacatcacc tcaagtgtgt ggccgaggaa ccgctgaccc atggtgttca aatccttttt    4740
catatcctac ctatggcccc ggagttgtgt gctcctctcg actttgtgtg tctgccgacg    4800
gggtcaccct gccattgttc tcagccgtgg cacaactctc cggtagagag gtgggatttt    4860 ttatttggt gctcgtctcc ttgactgctt tggcccaccg catggctctt aaggcagaca     4920
tgttagtggt cttttcggct ttttgtgctt acgcctggcc catgagctcc tggttaatct    4980
gcttctttcc tatactcttg aagtgggtta cccttcaccc tcttactatg ctttgggtgc    5040
actcattctt ggtgttttgt ctgccagcag ccggcatcct ctcactaggg ataactggcc    5100
ttctttgggc aattggccgc tttacccagg ttgccggaat tattcacct tatgacatcc      5160 accagtacac ctctgggcca cgtggtgcag ctgctgtggc cacagcccca gaaggcactt    5220
atatggccgc cgtccggaga gctgcttaa ctgggcgaac tttaatcttc accccgtctg      5280
cagttggatc ccttctcgaa ggtgctttca ggactcataa accctgcctt aacaccgtga    5340
atgttgtagg ctcttccctt ggttccggag gggttttcac cattgatggc agaagaactg    5400
tcgtcactgc tgcccatgtg ttgaacggcg acacagctag agtcaccggc gactcctaca    5460
accgcatgca cactttcaag accaatggtg attatgcctg gtccatgct gatgactggc      5520 agggcgttgc ccctgtggtc aaggttgcga aggggtaccg cggtcgtgcc tactggcaaa    5580
catcaactgg tgtcgaaccc ggtatcattg gggaagggtt cgccttctgt tttactaact    5640
gcggcgattc ggggtcaccc gtcatctcag aatctggtga tcttattgga atccacaccg    5700
gttcaaacaa acttggttct ggtcttgtga caacccctga aggggagacc tgcaccatca    5760
aagaaaccaa gctctctgac cttttccagac attttgcagg cccaagcgtt cctcttgggg    5820
acattaaatt gagtccggcc atcatccctg atgtaacatc cattccgagt gacttggcat    5880
cgctcctagc ctccgtccct gtagtggaag gcggcctctc gaccgttcaa cttttgtgtg    5940
tctttttcct tctctggcgc atgatgggcc atgcctggac acccattgtt gccgtgggct    6000 tcttttgct gaatgaaatt cttccagcag ttttggtccg agccgtgttt tcttttgcac     6060
tctttgtgct tgcatgggcc accccctggt ctgcacaggt gttgatgatt agactcctca    6120
cggcatctct caaccgcaac aagctttctc tggcgttcta cgcactcggg ggtgtcgtcg    6180
gtttggcagc tgaaatcggg acttttgctg gcagattgtc tgaattgtct caagctcttt    6240
cgacatactg cttcttacct agggtccttg ctatgaccag ttgtgttccc accatcatca    6300
ttggtggact ccatacctc ggtgtgattc tgtggttatt caaataccgg tgcctccaca      6360
acatgctggt tggtgatggg agtttttcaa gcgccttctt cctacggtat tttgcagagg    6420
gtaatctcag aaaaggtgtt tcacagtcct gtggcatgaa taacgagtcc ctaacggctg    6480
ctttagcttg caagttgtca caggctgacc ttgattttt gtccagctta acgaacttca     6540
agtgctttgt atctgcttca aacatgaaaa atgctgccgg ccagtacatt gaagcagcgt    6600
atgccaaggc cctgcgccaa gagttggcct ctctagttca gattgacaaa atgaaaggag    6660
ttttgtccaa gctcgaggcc tttgctgaaa cagccacccc gtcccttgac ataggtgacg    6720
tgattgttct gcttgggcaa catcctcacg gatccatcct cgatattaat gtggggactg    6780
aaaggaaaac tgtgtccgtg caagagaccc ggagcctagg cggctccaaa ttcagtgttt    6840
gtactgtcgt gtccaacaca cccgtggacg ccttgaccgg catcccactc cagacaccaa    6900
```

| | |
|---|---|
| cccctcttt tgagaatggt ccgcgtcatc gcagcgagga agacgatctt aaagtcgaga | 6960 |
| ggatgaagaa acactgtgta tccctcggct tccacaacat caatggcaaa gtttactgca | 7020 |
| aaatttggga caagtctacc ggtgacacct tttacacgga tgattccgg tacacccaag | 7080 |
| accatgcttt tcaggacagg tcagccgact acagagacag ggactatgag ggtgtgcaaa | 7140 |
| ccaccccca cagggatttt gatccaaagt ctgaaacccc tgttggcact gttgtgatcg | 7200 |
| gcggtattac gtataacagg tatctgatca aaggtaagga ggttctggtc cccaagcctg | 7260 |
| acaactgcct tgaagctgcc aagctgtccc ttgagcaagc tctcgctggg atgggccaaa | 7320 |
| cttgcgacct tacagctgcc gaggtggaaa agctaaagcg catcattagt caactccaag | 7380 |
| gtttgaccac tgaacaggct ttaaactgtt agccgccagc ggcttgaccc gctgtggccg | 7440 |
| cggcggccta gttgtgactg aaacggcggt aaaaattata aataccaca gcagaacttt | 7500 |
| caccttaggc cctttagacc taaaagtcac ttccgaggtg gaggtaaaga aatcaactga | 7560 |
| gcagggccac gctgttgtgg caaacttatg ttccggtgtc atcttgatga acctcacccc | 7620 |
| accgtccctt gtcgacgttc ttctgaaacc cggacttgac acaatacccg gcattcaacc | 7680 |
| agggcatggg gccgggaata tgggcgtgga cggttctatt tgggattttg aaaccgcacc | 7740 |
| cacaaaggca gaactcgagt tatccaagca aataatccaa gcatgtgaag ttaggcgcgg | 7800 |
| ggacgccccg aacctccaac tcccttacaa gctctatcct gttagggggg atcctgagcg | 7860 |
| gcataaaggc cgccttatca ataccaggtt tggagattta ccttacaaaa ctcctcaaga | 7920 |
| caccaagtcc gcaatccacg cggcttgttg cctgcacccc aacggggccc ccgtgtctga | 7980 |
| tggtaaatcc acactaggta ccactcttca acatggtttc gagctttatg tccctactgt | 8040 |
| gccctatagt gtcatggagt accttgattc acgccctgac acccctttta tgtgtactaa | 8100 |
| acatggcact tccaaggctg ctgcagagga cctccaaaaa tacgacctat ccacccaagg | 8160 |
| atttgtcctg cctggggtcc tacgcctagt acgcagattc atctttggcc atattggtaa | 8220 |
| ggcgccgcca ttgttcctcc catcaaccta tcccgccaag aactctatgg cagggatcaa | 8280 |
| tggccagagg ttcccaacaa aggacgttca gagcatacct gaaattgatg aaatgtgtgc | 8340 |
| ccgcgctgtc aaggagaatt ggcaaactgt gacaccttgc accctcaaga aacagtactg | 8400 |
| ttccaagccc aaaaccagga ccatcctggg caccaacaac tttattgcct tggctcacag | 8460 |
| atcgcgctc agtggtgtca cccaggcatt catgaagaag gcttggaagt ccccaattgc | 8520 |
| cttggggaaa aacaaattca aggagctgca ttgcactgtc gccggcaggt gtcttgaggc | 8580 |
| cgacttggcc tcctgtgacc gcagcacccc cgccattgta agatggttg ttgccaacct | 8640 |
| cctgtatgaa cttgcaggat gtgaagagta cttgcctagc tatgtgctta attgctgcca | 8700 |
| tgacctcgtg gcaacacagg atggtgcctt cacaaaacgc ggtggcctgt cgtccgggga | 8760 |
| ccccgtcacc agtgtgtcca acccgtata ttcactggta atttatgccc agcacatggt | 8820 |
| attgtcggcc ttgaaaatgg gtcatgaaat tggtcttaag ttcctcgagg aacagctcaa | 8880 |
| gttcgaggac ctccttgaaa ttcagccat gttggtatac tctgatgatc ttgtcttgta | 8940 |
| cgctgaaaga cccacatttc ccaattacca ctggtgggtc gagcaccttg acctgatgct | 9000 |
| gggtttcaga acgacccaa agaaaaccgt cataactgat aaacccagct tcctcggctg | 9060 |
| cagaattgag gcagggcgac agctagtccc caatcgcgac cgcatcctgg ctgctcttgc | 9120 |
| atatcacatg aaggcgcaga acgcctcaga gtattatgcg tctgctgccg caatcctgat | 9180 |
| ggattcatgt gccttgcattg accatgaccc tgagtggtat gaggacctca tctgcggtat | 9240 |
| tgccccggtgc gcccgccagg atggttatag cttcccaggt ccggcatttt tcatgtccat | 9300 |

```
gtgggagaag ctgagaagtc ataatgaagg gaagaaattc cgccactgcg gcatctgcga   9360
cgccaaagcc gactatgcgt ccgcctgtgg gcttgatttg tgtttgttcc attcgcactt   9420
tcatcaacac tgccctgtca ctctgagctg cggtcaccat gccggttcaa aggaatgttc   9480
gcagtgtcag tcacctgttg gggctggcag atcccctctt gatgccgtgc taaaacaaat   9540
tccatacaaa cctcctcgta ctgtcatcat gaaggtgggt aataaaacaa cggccctcga   9600
tccggggagg taccagtccc gtcgaggtct cgttgcagtc aagagggta ttgcaggcaa   9660 tgaagttgat ctttctgatg ggactacca agtggtgcct cttttgccga cttgcaaaga   9720
cataaacatg gtgaaggtgg cttgcaatgt actactcagc aagttcatag tagggccacc   9780
aggttccgga aagaccacct ggctactgag tcaagtccag gacgatgatg tcatttacac   9840
acccacccat cagactatgt ttgatatagt cagtgctctc aaagtttgca ggtattccat   9900
tccaggagcc tcaggactcc ctttcccacc acctgccagg tccgggccgt gggttaggct   9960
tattgccagc gggcacgtcc ctggccgagt atcatacctc gatgaggctg atattgtaa   10020 tcatctggac attcttagac tgctttccaa acacccctt gtgtgtttgg gtgaccttca   10080
gcaacttcac cctgtcggct ttgattccta ctgttatgtg ttcgatcaga tgcctcagaa   10140
gcagctgacc actatttaca gatttggccc taacatctgc gcagccatcc agccttgtta   10200
cagggagaaa cttgaatcta aggctaggaa cactagggtg gttttacca cccgcctgt   10260 ggcctttggt caggtgctga caccatacca taaagatcgc atcggctctg cgataaccat   10320
agattcatcc caggggggcca cctttgatat tgtgacattg catctaccat cgccaaagtc   10380
cctaaataaa tcccgagcac ttgtagccat cactcgggca agacacgggt tgttcattta   10440
tgaccctcat aaccagctcc aggagttttt caacttaacc cctgagcgca ctgattgtaa   10500
ccttgtgttc agccgtgggg atgagctggt agttctgaat gcggataatg cagtcacaac   10560
tgtagcgaag gcccttgaga caggtccatc tcgatttcga gtatcagacc cgaggtgcaa   10620
gtctctctta gccgcttgtt cggccagtct ggaagggagc tgtatgccac taccgcaagt   10680
ggcacataac ctgggggtttt acttttcccc ggacagtcca acatttgcac ctctgccaaa   10740
agagttggcg ccacattggc cagtggttac ccaccagaat aatcgggcgt ggcctgatcg   10800
acttgtcgct agtatgcgcc caattgatgc ccgctacagc aagccaatgg tcggtgcagg   10860
gtatgtggtc gggccgtcca ccttttcttgg tactcctggt gtggtgtcat actatctcac   10920
actatacatc aggggtgagc cccaggcctt gccagaaaca ctcgtttcaa cagggcgtat   10980
agccacagat tgtcgggagt atctcgacgc ggctgaggaa gaggcagcaa aagaactccc   11040
ccacgcattc attggcgatg tcaaaggtac cacggttggg gggtgtcatc acattacatc   11100
aaaataccta cctaggtccc tgcctaagga ctctgttgcc gtagttggag taagttcgcc   11160
cggcagggct gctaaagccg tgtgcactct caccgatgtg tacctccccg aactccggcc   11220
atatctgcaa cctgagacgg catcaaaatg ctggaaactc aaattagact tcaggacgt   11280 ccgactaatg gtctggaaag gagccaccgc ctatttccag ttggaagggc ttacatggtc   11340
ggcgctgccc gactatgcca ggtttattca gctgcccaag gatgccgttg tatacattga   11400
tccgtgtata ggaccggcaa cagccaaccg taaggtcgtg cgaaccacag actgcgggc   11460 cgacctggca gtgacaccgt atgattacgg tgcccagaac attttgacaa cagcctggtt   11520
cgaggacctc gggccgcagt ggaagatttt ggggttgcag ccccttaggc gagcatttgg   11580 cttttgaaaac actgaggatt gggcaatcct tgcacgccgt atgaatgacg gcaaggacta   11640
```

```
cactgactat aactggaact gtgttcgaga acgcccacac gccatctacg ggcgtgctcg   11700
tgaccatacg tatcattttg ccoctggcac agaattgcag gtagagctag gtaaaccccg   11760
gctgccgcct gggcaagtgc cgtgaattcg gggtgatgca atggggtcac tgtggagtaa   11820
aatcagccag ctgttcgtgg acgccttcac tgagttcctt gttagtgtgg ttgatattgc   11880
cattttcctt gccatactgt ttgggttcac cgtcgcagga tggttactgg tctttcttct   11940
cagagtggtt tgctccgcgc ttctccgttc gcgctctgcc attcactctc ccgaactatc   12000
gaaggtccta tgaaggcttg ttgcccaact gcagaccgga tgtcccacaa tttgcagtca   12060
agcacccatt gggtatgttt tggcacatgc gagtttccca cttgattgat gagatggtct   12120
ctcgtcgcat ttaccagacc atggaacatt caggtcaagc ggcctggaag caggtggttg   12180
gtgaggccac tctcacgaag ctgtcagggc tcgatatagt tactcatttc caacacctgg   12240
ccgcagtgga ggcggattct tgccgctttc tcagctcacg actcgtgatg ctaaaaaatc   12300
ttgccgttgg caatgtgagc ctacagtaca acaccacgtt ggaccgcgtt gagctcatct   12360
tccccacgcc aggtacgagg cccaagttga ccgatttcag acaatggctc atcagtgtgc   12420
acgcttccat ttttcctct gtggcttcat ctgttacctt gttcatagtg ctttggcttc   12480
gaattccagc tctacgctat gttttttggtt tccattggcc cacggcaaca catcattcga   12540
gctgaccatc aactacacca tatgcatgcc ctgttctacc agtcaagcgg ctcgccaaag   12600
gctcgagccc ggtcgtaaca tgtggtgcaa aatagggcat gacaggtgtg aggagcgtga   12660
ccatgatgag ttgttaatgt ccatcccgtc cgggtacgac aacctcaaac ttgagggtta   12720
ttatgcttgg ctggctttt tgtcctttc ctacgcggcc caattccatc cggagttgtt   12780
cgggataggg aatgtgtcgc gcgtcttcgt ggacaagcga caccagttca tttgtgccga   12840
gcatgatgga cacaattcaa ccgtatctac cggacacaac atctccgcat tatatgcggc   12900
atattaccac caccaaatag acgggggcaa ttggttccat ttggaatggc tgcggccact   12960
cttttcttcc tggctggtgc tcaacatatc atggttctg aggcgttcgc ctgtaagccc   13020
tgtttctcga cgcatctatc agatattgag accaacacga ccgcggctgc cggtttcatg   13080
gtccttcagg acatcaattg tttccgacct cacggggtct cagcagcgca agagaaaatt   13140
tccttcggaa agtcgtccca atgtcgtgaa gccgtcggta ctccccagta catcacgata   13200
acggctaacg tgaccgacga atcatacttg tacaacgcgg acctgctgat gctttctgcg   13260
tgccttttct acgcctcaga aatgagcgag aaaggcttca agtcatctt tgggaatgtc   13320
tctggcgttg tttctgcttg tgtcaatttc acagattatg tggcccatgt gacccaacat   13380
acccagcagc atcatctggt aattgatcac attcggttgc tgcatttcct gacaccatct   13440
gcaatgaggt gggctacaac cattgcttgt tgttcgcca ttctcttggc aatatgagat   13500
gttctcacaa attgggcgt tcttgactc cgcactcttg cttctggtgg cttttttgc   13560
tgtgtaccgg cttgtcctgg tcctttgccg atggcaacgg cgacagctcg acataccaat   13620
acatatataa cttgacgata tgcgagctga atgggaccga ctggttgtcc agccattttg   13680
gttgggcagt cgagacccttt gtgctttacc cggttgccac tcatatcctc tcactgggtt   13740
ttctcacaac aagccatttt tttgacgcgc tcggtctcgg cgctgtatcc actgcaggat   13800
ttgttggcgg gcggtacgta ctctgcagcg tctacggcgc ttgtgctttc gcagcgttcg   13860
tatgttttgt catccgtgct gctaaaaatt gcatggcctg ccgctatgcc cgtacccggt   13920
ttaccaactt cattgtggac gaccggggga gagttcatcg atggaagtct ccaatagtgg   13980
tagaaaaatt gggcaaagcc gaagtcgatg gcaacctcgt caccatcaaa catgtcgtcc   14040
```

-continued

```
tcgaagggt  taaagctcaa  cccttgacga  ggacttcggc  tgagcaatgg  gaggcctaga     14100 cgattttgc   aacgatccta  tcgccgcaca  aaagctcgtg  ctagccttta  gcatcacata    14160
cacacctata  atgatatacg  cccttaaggt  gtcacgcggc  cgactcctgg  ggctgttgca    14220
catcctaata  tttctgaact  gttccttta   attcggatac  atgacatatg  tgcattttca    14280
atccaccaac  cgtgtcgcac  ttaccctggg  ggctgttgtc  gcccttctgt  ggggtgttta    14340
cagcttcaca  gagtcatgga  agtttatcac  ttcagatgc   agattgtgtt  gccttggccg    14400
gcgatacatt  ctggcccctg  cccatcacgt  agaaagtgct  gcaggtctcc  attcaatctc    14460
agcgtctggt  aaccgagcat  acgctgtgag  aaagcccgga  ctaacatcag  tgaacggcac    14520
tctagtacca  ggacttcgga  gcctcgtgct  gggcggcaaa  cgagctgtta  aacgaggagt    14580
ggttaacctc  gtcaagtatg  gccggtaaaa  accagagcca  aagaaaaag   aaagtacag    14640 ctccgatggg  gaatggccag  ccagtcaatc  aactgtgcca  gttgctgggt  gcaatgataa    14700
agtcccagcg  ccagcaacct  aggggaggac  aggccaaaaa  gaaaaagcct  gagaagccac    14760
attttcccct  ggctgctgaa  gatgacatcc  ggcaccacct  cacccagact  gaacgctccc    14820
tctgcttgca  atcgatccag  acggctttca  atcaaggcgc  aggaactgcg  tcgctttcat    14880
ccagcgggaa  ggtcagtttt  caggttgagt  ttatgctgcc  ggttgctcat  acagtgcgcc    14940
tgattcgcgt  gacttctaca  tccgccagtc  agggtgcaag  ttaatttgac  agtcaggtga    15000
atggccgcga  ttggcgtgtg  gcctctgagt  cacctattca  attagggcga  tcacatgggg    15060
gtcatactta  atcaggcagg  aaccatgtga  ccgaaattaa  aaaaaaaaa   a             15111
```

<210> SEQ ID NO 15
<211> LENGTH: 15411
<212> TYPE: DNA
<213> ORGANISM: Porcine Reproductive and Respiratory Syndrome Virus
<220> FEATURE:
<221> NAME/KEY: misc_feature
<223> OTHER INFORMATION: Strain VR-2332
<300> PUBLICATION INFORMATION:
<308> DATABASE ACCESSION NUMBER: Genbank/U87392.3
<309> DATABASE ENTRY DATE: 2000-11-17
<313> RELEVANT RESIDUES IN SEQ ID NO: (1)..(15411)

<400> SEQUENCE: 15

```
atgacgtata  ggtgttggct  ctatgccttg  gcatttgtat  tgtcaggagc  tgtgaccatt     60
ggcacagccc  aaaacttgct  gcacagaaac  acccttctgt  gatagcctcc  ttcaggggag    120
cttagggttt  gtccctagca  ccttgcttcc  ggagttgcac  tgctttacgg  tctctccacc    180
ccttaaccca  tgtctgggat  acttgatcgg  tgcacgtgta  cccccaatgc  cagggtgttt    240
atggcggagg  gccaagtcta  ctgcacacga  tgcctcagtg  cacggtctct  ccttcccctg    300
aacctccaag  tttctgagct  cggggtgcta  ggcctattct  acaggcccga  agagccactc    360
cggtggacgt  tgccacgtgc  attcccact   gttgagtgct  ccccgccgg   ggcctgctgg    420 ctttctgcaa  tctttccaat  cgcacgaatg  accagtggaa  acctgaactt  ccaacaaaga    480
atggtacggg  tcgcagctga  gctttacaga  gccggccagc  tcacccctgc  agtcttgaag    540
gctctacaag  tttatgaacg  gggttgccgc  tggtacccca  ttgttggacc  tgtccctgga    600
gtggccgttt  tcgccaattc  cctacatgtg  agtgataaac  ctttcccggg  agcaactcac    660
gtgttgacca  acctgccgct  cccgcagaga  cccaagcctg  aagacttttg  cccctttgag    720
tgtgctatgg  ctactgtcta  tgacattggt  catgacgccg  tcatgtatgt  ggccgaaagg    780
aaagtctcct  gggcccctcg  tggcggggat  gaagtgaaat  ttgaagctgt  ccccggggag    840
```

```
ttgaagttga ttgcgaaccg gctccgcacc tccttcccgc cccaccacac agtggacatg      900
tctaagttcg ccttcacagc ccctgggtgt ggtgtttcta tgcgggtcga acgccaacac      960
ggctgccttc ccgctgacac tgtccctgaa ggcaactgct ggtggagctt gtttgacttg     1020
cttccactgg aagttcagaa caagaaatt cgccatgcta accaatttgg ctaccagacc     1080
aagcatggtg tctctggcaa gtacctacag cggaggctgc aagttaatgg tctccgagca     1140
gtaactgacc taaacggacc tatcgtcgta cagtacttct ccgttaagga gagttggatc     1200
cgccatttga aactggcggg agaacccagc tactctgggt ttgaggacct cctcagaata     1260
agggttgagc ctaacacgtc gccattggct gacaaggaag aaaaaatttt ccggtttggc     1320
agtcacaagt ggtacggcgc tggaaagaga gcaagaaaag cacgctcttg tgcgactgct     1380
acagtcgctg gccgcgcttt gtccgttcgt gaaacccggc aggccaagga gcacgaggtt     1440
gccggcgcca acaaggctga gcacctcaaa cactactccc cgcctgccga agggaattgt     1500
ggttggcact gcattccgc catcgccaac cggatggtga attccaaatt tgaaaccacc     1560
cttcccgaaa gagtgagacc tccagatgac tgggctactg acgaggatct tgtgaatgcc     1620
atccaaatcc tcagactccc tgcggcctta gacaggaacg gtgcttgtac tagcgccaag     1680
tacgtactta agctggaagg tgagcattgg actgtcactg tgaccctgg gatgtcccct     1740 tctttgctcc ctcttgaatg tgttcagggc gttgtgggc acaagggcgg tcttggttcc     1800
ccagatgcag tcgaggtctc cggatttgac cctgcctgcc ttgaccggct ggctgaggtg     1860
atgcacctgc ctagcagtgc tatcccagcc gctctggccg aaatgtctgg cgattccgat     1920
cgttcggctt ctccggtcac caccgtgtgg actgtttcgc agttctttgc ccgtcacagc     1980
ggagggaatc accctgacca agtgcgctta gggaaaatta tcagcctttg tcaggtgatt     2040
gaggactgct gctgttccca gaacaaaacc aaccgggtca ccccggagga ggtcgcagca     2100
aagattgacc tgtacctccg tggtgcaaca atcttgaag aatgcttggc caggcttgag     2160
aaagcgcgcc cgccacgcgt aatcgacacc tcctttgatt gggatgttgt gctccctggg     2220
gttgaggcgg caacccagac gatcaagctg ccccaggtca accagtgtcg tgctctggtc     2280
cctgttgtga ctcaaaagtc cttggacaac aactcggtcc cctgaccgc cttttcactg     2340 gctaactact actaccgtgc gcaaggtgac gaagttcgtc accgtgaaag actaaccgcc     2400
gtgctctcca agttggaaaa ggttgttcga gaagaatatg gctcatgcc aaccgagcct     2460 ggtccacggc ccacactgcc acgcgggctc gacgaactca agaccagat ggaggaggac     2520 ttgctgaaac tggctaacgc ccagacgact tcggacatga tggcctgggc agtcgagcag     2580
gttgacctaa aaacttgggt caagaactac ccgcggtgga caccaccacc ccctccgcca     2640
aaagttcagc ctcgaaaaac gaagcctgtc aagagcttgc cggagagaaa gcctgtcccc     2700
gccccgcgca ggaaggttgg gtccgattgt ggcagcccgg tttcattagg cggcgatgtc     2760
cctaacagtt gggaagattt ggctgttagt agcccctttg atctcccgac ccacctgag     2820 ccggcaacac cttcaagtga gctggtgatt gtgtcctcac cgcaatgcat cttcaggccg     2880
gcgacaccct tgagtgagcc ggctccaatt cccgcacctc gcggaactgt gtctcgaccg     2940
gtgacaccct tgagtgagcc gatccctgtg cccgcaccgc ggcgtaagtt tcagcaggtg     3000
aaaagattga gttcggcggc ggcaatccca ccgtaccagg acgagcccct ggatttgtct     3060
gcttcctcac agactgaata tgaggcctct ccccagcac cgccgcagag cggggcgtt      3120 ctgggagtag aggggcatga agctgaggaa accctgagtg aaatctcgga catgtcgggt     3180
```

| | |
|---|---|
| aacattaaac ctgcgtccgt gtcatcaagc agctccttgt ccagcgtgag aatcacacgc | 3240 |
| ccaaaatact cagctcaagc catcatcgac tcgggcgggc cctgcagtgg gcatctccaa | 3300 |
| gaggtaaagg aaacatgcct tagtgtcatg cgcgaggcat gtgatgcgac taagcttgat | 3360 |
| gaccctgcta cgcaggaatg gctttctcgc atgtgggatc gggtggacat gctgacttgg | 3420 |
| cgcaacacgt ctgttttacca ggcgatttgc accttagatg gcaggttaaa gttcctccca | 3480 |
| aaaatgatac tcgagacacc gccgccctat ccgtgtgagt ttgtgatgat gcctcacacg | 3540 |
| cctgcacctt ccgtaggtgc ggagagcgac cttaccattg gctcagttgc tactgaagat | 3600 |
| gttccacgca tcctcgagaa aatagaaaat gtcggcgaga tggccaacca gggacccttg | 3660 |
| gccttctccg aggataaacc ggtagatgac caacttgtca acgaccccg gatatcgtcg | 3720 |
| cggaggcctg acgagagcac atcagctccg tccgcaggca caggtggcgc cggctctttt | 3780 |
| accgatttgc cgccttcaga tggcgcggat gcggacgggg gggggccgtt tcggacggta | 3840 |
| aaaagaaaag ctgaaaggct ctttgaccaa ctgagccgtc aggttttga cctcgtctcc | 3900 |
| catctccctg ttttcttctc acgccttttc taccctggcg gtggttattc tccgggtgat | 3960 |
| tgggttttg cagctttttac tctattgtgc ctctttttat gttacagtta cccagccttt | 4020 |
| ggtattgctc ccctcttggg tgtgttttct gggtcttctc ggcgcgttcg aatgggggtt | 4080 |
| tttggctgct ggttggcttt tgctgttggt ctgttcaagc ctgtgtccga cccagtcggc | 4140 |
| gctgcttgtg agtttgactc gccagagtgt agaaacatcc ttcattcttt tgagcttctc | 4200 |
| aaaccttggg accctgttcg cagccttgtt gtgggccccg tcggtctcgg tcttgccatt | 4260 |
| cttggcaggt tactgggcgg ggcacgctgc atctggcact ttttgcttag gcttggcatt | 4320 |
| gttgcagact gtatcttggc tggagcttac gtgctttctc aaggtaggtg taaaaagtgc | 4380 |
| tggggatctt gtataagaac tgctcctaat gaggtcgctt ttaacgtgtt tcctttcaca | 4440 |
| cgtgcgacca ggtcgtcact tatcgacctg tgcgatcggt tttgtgcgcc aaaaggaatg | 4500 |
| gaccccattt ttctcgccac tgggtggcgc gggtgctggg ccggccgaag ccccattgag | 4560 |
| caaccctctg aaaaacccat cgcgtttgcc caattggatg aaaagaagat tacggctagg | 4620 |
| actgtggtcg cccagcctta tgaccccaac caagccgtaa agtgcttgcg ggtattgcag | 4680 |
| tcgggtgggg cgatggtggc taaggcggtc ccaaaagtgg tcaaggtttc cgctgttcca | 4740 |
| ttccgagccc ccttctttcc cactggagtg aaagttgacc ctgattgcag ggtcgtggtt | 4800 |
| gaccctgaca cttttcactgc agctctccgg tctggctact ccaccacaaa cctcgtcctt | 4860 |
| ggtgtagggg actttgccca gctgaatgga ttaaaaatca ggcaaatttc caagccttca | 4920 |
| gggggaggcc cacatctcat ggctgccctg catgttgcct gctcgatggc tctgcacatg | 4980 |
| cttgctggga tttatgtgac tgcggtgggt tcttgcggca ccggcaccaa cgacccgtgg | 5040 |
| tgcgctaacc cgtttgccgt ccctggctac ggacctggct ctctctgcac gtccaggttg | 5100 |
| tgcatttccc aacacggcct taccctgccc ttgacagcac ttgtggcggg attcggtatt | 5160 |
| caagaaattg ccttggtcgt tttgattttt gtttccatcg gaggcatggc tcataggttt | 5220 |
| agctgtaagg ctgacatgct gtgtgttttg cttgcaattg ccagctatgt ttgggtacct | 5280 |
| cttacctggt tgctttgtgt gtttccttgc tggttgcgct gttttctttt gcaccccctc | 5340 |
| accatcctat ggttggtgtt tttcttgatt tctgtgaata tgccttcagg aatcttggcc | 5400 |
| atggtgttgt tggtttctct ttggcttctt ggtcgttata ctaatgttgc tggccttgtc | 5460 |
| acccccctacg acattcatca ttacaccagt ggccccgcg tgttgccgc cttggctacc | 5520 |
| gcaccagatg ggacctactt ggccgctgtc cgccgcgctg cgttgactgg ccgcaccatg | 5580 |

```
ctgtttaccc cgtcccagct tgggtctctt ctttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cgggcaattc agctcgggtt    5760
tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc    5940 gccttctgct tcaccgcatg tggcgattcc gggtccccag tgatcaccga ggccggtgag    6000
cttgtcggcg ttcacacggg atcgaataaa caagggggg gcattgttac gcgcccctca    6060
ggccagtttt gtaatgtggc acccatcaag ctaagcgaat taagtgaatt ctttgctggg    6120
cctaaggtcc cgctcggtga tgtgaaggtc ggcagccaca taattaaaga cataagcgag    6180
gtgccttcag atctttgtgc cttgcttgct gccaaacctg aactggaagg aggcctctcc    6240
accgtccaac ttctttgtgt gttttttctc ctgtggagaa tgatgggaca tgcctggacg    6300
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg gcatccgttg    6540
caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcccgcacca tatccttgtt ggcgatggag tgttctctgc ggctttcttc    6720
ttgagatact ttgccgaggg aaagttgagg aagggtgt cgcaatcctg cggaatgaat    6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcggccaca cgcctgttgg cagtatcttc    7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc caacgcttg ggggatgag    7260 gaccgtttga ataagaagaa gaggcgcagg atggaagccc tcggcatcta tgttatgggc    7320
gggaaaaagt accagaaatt tgggacaag aattccggtg atgtgttta tgaggaggtc    7380 cataataaca cagatgagtg ggagtgtctc agagttggcg accctgccga ctttgacccc    7440
gagaagggaa ctctgtgtgg acatgtcacc attgaaaaca aggcttacca tgtttacacc    7500
tccccatctg gtaagaagtt cttggtcccc gtcaacccag agaatggaag agttcaatgg    7560
gaagctgcaa agctttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccacg acttgacccg ctgtggtcgc ggcggcttgg    7740
ttgttactga acagcggta aaaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
```

```
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca    9180
tgctcaaggt tcaacccctg atcgtctatt cggacgacct cgtgctgtat gccgagtctc    9240
ccaccatgcc aaactatcac tggtgggttg aacatctgaa tttgatgctg ggtttcaga    9300 cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg gacagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc    9840
ccccacggac cgttatcatg catgtggagc agggtctcac cccccttgat ccaggtagat    9900
accaaactcg ccgcggatta gtctctgtca ggcgtggaat tagggggaat gaagttggac    9960
taccagacgg tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggcttttg ggacgtgccg gttcaacgtc ccggcaggca    10200
caacgctgca attccccgtc ccctcccgca ccggtccgtg ggtcgcatc ctagccggcg    10260 gttggtgtcc tggcaagaat tccttcctag atgaagcagc gtattgcaat caccttgatg    10320
```

```
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gtttggacag aatatctgtg atgccattca gccagattac agggacaaac   10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat cttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttatt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacggt ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctattttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760
tcacccctta tgattacggc gctaaaatta tcctgtctag cgcgtaccat ggtgaaatgc   11820
cccccggata caaaattctg gcgtgcgcgg agttctcgtt ggatgaccca gttaagtaca   11880
aacatacctg ggggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttatttc ccccgggccc tgtcattgaa ccaactttag   12060
gcctgaattg aaatgaaatg gggtccatgc aaagcctttt tgacaaaatt ggccaacttt   12120
ttgtggatgc tttcacggag ttcttggtgt ccattgttga tatcattata ttttggcca   12180
ttttgtttgg cttcaccatc gccggttggc tggtggtctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tcctttgggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact ttgaatcagg tgtttgctat ttttccaacc   12660
```

```
cctggttccc ggccaaagct tcatgatttt cagcaatggt taatagctgt acattcctcc   12720
atattttcct ctgttgcagc ttcttgtact ctttttgttg tgctgtggtt gcgggttcca   12780
atactacgta ctgttttggg tttccgctgg ttaggggcaa ttttctttc gaactcacag    12840 tgaattacac ggtgtgtcca ccttgcctca cccggcaagc agccacagag atctacgaac   12900
ccggtaggtc tctttggtgc aggatagggt atgaccgatg tggggaggac gatcatgacg   12960
agctagggtt tatgataccg cctggcctct ccagcgaagg ccacttgact ggtgtttacg   13020
cctggttggc gttcttgtcc ttcagctaca cggcccagtt ccatcccgag atattcggga   13080
tagggaatgt gagtcgagtt tatgttgaca tcaaacatca actcatctgc gccgaacatg   13140
acgggcagaa caccaccttg cctcgtcatg acaacatttc agccgtgttt cagacctatt   13200
accaacatca agtcgacggc ggcaattggt ttcacctaga atggcttcgt cccttctttt   13260
cctcgtggtt ggttttaaat gtctcttggt ttctcaggcg ttcgcctgca aaccatgttt   13320
cagttcgagt cttgcagata ttaagaccaa caccaccgca gcggcaagct ttgctgtcct   13380
ccaagacatc agttgcctta ggcatcgcga ctcggcctct gaggcgattc gcaaaatccc   13440
tcagtgccgt acggcgatag ggacacccgt gtatgttacc atcacagcca atgtgacaga   13500
tgagaattat ttacattctt ctgatctcct catgctttct tcttgccttt tctatgcttc   13560
tgagatgagt gaaaagggat ttaaggtggt atttggcaat gtgtcaggca tcgtggctgt   13620
gtgtgtcaat tttaccagct acgtccaaca tgtcaaggag tttacccaac gctccctggt   13680
ggtcgaccat gtgcggttgc tccatttcat gacacctgag accatgaggt gggcaactgt   13740
tttagcctgt cttttgcca ttctgttggc aatttgaatg tttaagtatg ttggagaaat    13800
gcttgaccgc gggctgttgc tcgcgattgc tttctttgtg gtgtatcgtg ccgttctgtt   13860
ttgctgtgct cgccaacgcc agcaacgaca gcagctccca tctacagctg atttacaact   13920
tgacgctatg tgagctgaat ggcacagatt ggctagctaa caaatttgat tgggcagtgg   13980
agagttttgt catcttccc gttttgactc acattgtctc ctatggtgcc ctcactacca    14040
gccatttcct tgacacagtc gctttagtca ctgtgtctac cgccgggttt gttcacgggc   14100
ggtatgtcct aagtagcatc tacgcggtct gtgccctggc tgcgttgact tgcttcgtca   14160
ttaggtttgc aaagaattgc atgtcctggc gctacgcgtg taccagatat accaactttc   14220
ttctggacac taagggcaga ctctatcgtt ggcggtcgcc tgtcatcata gagaaaaggg   14280
gcaaagttga ggtcgaaggt catctgatcg acctcaaaag agttgtgctt gatggttccg   14340
tggcaacccc tataaccaga gtttcagcgg aacaatgggg tcgtccttag atgacttctg   14400
tcatgatagc acggctccac aaaaggtgct tttggcgttt tctattacct acacgccagt   14460
gatgatatat gccctaaagg tgagtcgcgg ccgactgcta gggcttctgc accttttgat   14520
cttcctgaat tgtgctttca ccttcgggta catgactttc gcgcactttc agagtacaaa   14580
taaggtcgcg ctcactatgg gagcagtagt tgcactcctt tggggggtgt actcagccat   14640
agaaacctgg aaattcatca cctccagatg ccgtttgtgc ttgctaggcc gcaagtacat   14700
tctggcccct gccaccacg ttgaaagtgc cgcacggttt catccgattg cggcaaatga   14760
taaccacgca tttgtcgtcc ggcgtccgg ctccactacg gtcaacggca cattggtgcc   14820
cgggttaaaa agcctcgtgt tgggtggcag aaaagctgtt aaacagggag tggtaaacct   14880
tgtcaaatat gccaaataac aacggcaagc agcagaagag aaagaagggg gatggccagc   14940
cagtcaatca gctgtgccag atgctgggta agatcatcgc tcagcaaaac cagtccagag   15000
gcaagggacc gggaaagaaa aataagaaga aaacccggga gagcccat tttcctctag    15060
```

-continued

```
cgactgaaga tgatgtcaga catcacttta cccctagtga gcggcaattg tgtctgtcgt    15120
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat t             15411
```

<210> SEQ ID NO 16
<211> LENGTH: 17
<212> TYPE: DNA
<213> ORGANISM: Artificial Sequence
<220> FEATURE:
<223> OTHER INFORMATION: Synthetic Promoter

<400> SEQUENCE: 16

```
taatacgact cactata                                                   17
```

<210> SEQ ID NO 17
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 17

```
Glu Gln Lys Leu Ile Ser Glu Glu Asp Leu
1               5                   10
```

<210> SEQ ID NO 18
<211> LENGTH: 61
<212> TYPE: DNA
<213> ORGANISM: Artificial Sequence
<220> FEATURE:
<223> OTHER INFORMATION: Synthetic Primer

<400> SEQUENCE: 18

```
acatgcatgc ttaatacgac tcactatagt atgacgtata ggtgttggct ctatgccttg    60
g                                                                    61
```

<210> SEQ ID NO 19
<211> LENGTH: 19
<212> TYPE: DNA
<213> ORGANISM: Artificial Sequence
<220> FEATURE:
<223> OTHER INFORMATION: Synthetic Primer

<400> SEQUENCE: 19

```
ctgggcgacc acagtccta                                                 19
```

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20

```
cttctcggcg cgcccgaatg ggagt                                          25
```

<210> SEQ ID NO 21
<211> LENGTH: 26

```
<212> TYPE: DNA
<213> ORGANISM: Artificial Sequence
<220> FEATURE:
<223> OTHER INFORMATION: Synthetic Primer

<400> SEQUENCE: 21
tcatcatacc tagggcctgc tccacg                                          26

<210> SEQ ID NO 22
<211> LENGTH: 26
<212> TYPE: DNA
<213> ORGANISM: Artificial Sequence
<220> FEATURE:
<223> OTHER INFORMATION: Synthetic Primer

<400> SEQUENCE: 22
cgtggagcag gccctaggta tgatga                                          26

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
tgcaggcgaa cgcctgag                                                   18

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
gtgaggactg ggaggattac a                                               21

<210> SEQ ID NO 25
<211> LENGTH: 53
<212> TYPE: DNA
<213> ORGANISM: Artificial Sequence
<220> FEATURE:
<223> OTHER INFORMATION: Synthetic Primer

<400> SEQUENCE: 25
gtctttaatt aactagtttt ttttttttt tttttttttt tttttttaatt tcg            53

<210> SEQ ID NO 26
<211> LENGTH: 27
<212> TYPE: DNA
<213> ORGANISM: Artificial Sequence
<220> FEATURE:
<223> OTHER INFORMATION: Synthetic Primer

<400> SEQUENCE: 26
gatgcatgcc attaattaag ggtcggc                                         27

<210> SEQ ID NO 27
<211> LENGTH: 27
<212> TYPE: DNA
<213> ORGANISM: Artificial Sequence
<220> FEATURE:
<223> OTHER INFORMATION: Synthetic Primer

<400> SEQUENCE: 27
``` gccgacccttaattaatggcatgcatc 27

<210> SEQ ID NO 28
<211> LENGTH: 36
<212> TYPE: DNA
<213> ORGANISM: Artificial Sequence
<220> FEATURE:
<223> OTHER INFORMATION: Synthetic Primer

<400> SEQUENCE: 28
acatgcatgc ttaatacgac tcactatagg tatgac 36

<210> SEQ ID NO 29
<211> LENGTH: 25
<212> TYPE: DNA
<213> ORGANISM: Artificial Sequence
<220> FEATURE:
<223> OTHER INFORMATION: Synthetic Primer

<400> SEQUENCE: 29
ctgtgtggac atgtcaccat tgaaa 25

<210> SEQ ID NO 30
<211> LENGTH: 25
<212> TYPE: DNA
<213> ORGANISM: Artificial Sequence
<220> FEATURE:
<223> OTHER INFORMATION: Synthetic Primer

<400> SEQUENCE: 30
gtgtatcgtg ccgttctgtt ttgct 25

<210> SEQ ID NO 31
<211> LENGTH: 25
<212> TYPE: DNA
<213> ORGANISM: Artificial Sequence
<220> FEATURE:
<223> OTHER INFORMATION: Synthetic Primer

<400> SEQUENCE: 31
cagatgctgg gtaagatcat cgctc 25

<210> SEQ ID NO 32
<211> LENGTH: 39
<212> TYPE: DNA
<213> ORGANISM: Artificial Sequence
<220> FEATURE:
<223> OTHER INFORMATION: Synthetic Primer

<400> SEQUENCE: 32
gcacaatgtc aatcagtgcc attcaccaca cattcttcc 39

<210> SEQ ID NO 33
<211> LENGTH: 41
<212> TYPE: DNA
<213> ORGANISM: Artificial Sequence
<220> FEATURE:
<223> OTHER INFORMATION: Synthetic Primer

<400> SEQUENCE: 33
tagacttggc cctccgccat aaacaccctg gcattggggg t 41

<210> SEQ ID NO 34
<211> LENGTH: 201
<212> TYPE: PRT
<213> ORGANISM: Artificial Sequence

```
<220> FEATURE:
<223> OTHER INFORMATION: Porcine reproductive and respiratory syndrome
      virus; open reading frame 5 (ORF5)

<400> SEQUENCE: 34

Met Arg Cys Ser Tyr Lys Leu Gly Arg Ser Leu Ile Leu His Ser Cys
1               5                   10                  15

Ser Trp Trp Phe Phe Leu Leu Cys Thr Gly Leu Ser Trp Ser Phe Ala
            20                  25                  30

Asp Gly Asn Gly Asn Ser Thr Tyr Gln Tyr Ile Tyr Asn Leu Thr
        35                  40                  45

Ile Cys Glu Leu Asn Gly Thr Asn Trp Leu Ser Gly His Phe Asp Trp
50                  55                  60

Ala Val Glu Thr Phe Val Leu Tyr Pro Val Val Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Ile Asp Gly Arg Tyr Val Leu Ser Ser
            100                 105                 110

Ile Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
130                 135                 140

Asn Phe Ile Val Asp Asp Arg Gly Gly Val His Arg Trp Lys Ser Pro
145                 150                 155                 160

Ile Val Val Glu Lys Leu Gly Lys Ala Asp Ile Asp Gly Ser Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 35
<211> LENGTH: 201
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 35

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125
```

```
Ala Ala Lys Asn Cys Met Ala Cys Arg Tyr Ala Arg Thr Arg Phe Thr
        130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
            195                 200

<210> SEQ ID NO 36
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)
<220> FEATURE:
<221> NAME/KEY: MISC_FEATURE
<222> LOCATION: (44)..(44)
<223> OTHER INFORMATION: X = Xaa
<220> FEATURE:
<221> NAME/KEY: MISC_FEATURE
<222> LOCATION: (44)..(44)
<223> OTHER INFORMATION: Xaa = variable or unknown amino acid

<400> SEQUENCE: 36

Met Leu Gly Lys Cys Leu Thr Ala Gly Tyr Cys Ser Gln Leu Leu Phe
1               5                   10                  15

Leu Trp Cys Ile Val Pro Phe Cys Leu Ala Ala Leu Val Asn Ala Asp
                20                  25                  30

Ser Asn Ser Ser Ser His Leu Gln Leu Ile Tyr Xaa Leu Thr Ile Cys
            35                  40                  45

Glu Leu Asn Gly Thr Asp Trp Leu Asn Asn His Phe Ser Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Leu Leu Asp Thr Val Gly Leu Ile Thr Val
                85                  90                  95

Ser Thr Ala Gly Tyr Cys His Lys Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200

<210> SEQ ID NO 37
<211> LENGTH: 200
<212> TYPE: PRT
<213> ORGANISM: Artificial Sequence
```

<220> FEATURE:
<223> OTHER INFORMATION: Porcine reproductive and respiratory syndrome
      virus; open reading frame 5 (ORF5)

<400> SEQUENCE: 37

```
Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp His Phe Ser Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Ala Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200
```

<210> SEQ ID NO 38
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 38

```
Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125
```

Lys Asn Cys Met Ser Trp Arg Tyr Ser Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
            195                 200

<210> SEQ ID NO 39
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 39

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asp Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asn Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
            85                  90                  95

Ser Thr Ala Gly Tyr Tyr His Gly Arg Tyr Val Leu Ser Ser Ile Tyr
        100                 105                 110

Ala Val Cys Ala Leu Ala Ala Leu Ile Cys Phe Val Ile Arg Leu Thr
    115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
            195                 200

<210> SEQ ID NO 40
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 40

Met Leu Gly Lys Cys Leu Thr Ala Gly Cys Cys Ser Gln Leu Pro Phe
1               5                   10                  15

```
Leu Trp Cys Ile Val Pro Phe Cys Phe Ala Ala Leu Val Asn Ala Gly
            20                  25                  30

Ser Asn Ser Ser Ser His Leu Gln Leu Ile Tyr Asn Leu Thr Ile Cys
            35                  40                  45

Glu Leu Asn Gly Thr Asp Trp Leu Asn Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Tyr Tyr His Arg Arg Tyr Val Leu Ser Ser Ile Tyr
            100                 105                 110

Ala Val Cys Ala Leu Ala Ala Leu Ile Cys Phe Val Ile Arg Leu Thr
            115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Arg Trp Gly Arg Pro
            195                 200

<210> SEQ ID NO 41
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 41

Met Leu Gly Lys Cys Leu Thr Ala Gly Cys Cys Ser Gln Leu Pro Phe
 1               5                  10                  15

Leu Trp Cys Ile Val Pro Phe Cys Phe Val Ala Leu Val Asn Ala Asn
            20                  25                  30

Thr Asp Ser Ser Ser His Leu Gln Leu Ile Tyr Asn Leu Thr Ile Cys
            35                  40                  45

Glu Leu Asn Gly Thr Asp Trp Leu Asn Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Ala Ile Arg Leu Thr
            115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Ile Glu Arg Gln Gly Lys Val Glu Val Glu Gly His Leu Ile Asp Leu
```

```
                        165                 170                 175

Lys Arg Val Val Leu Asp Gly Ser Ala Ala Thr Pro Val Thr Arg Val
            180                 185                 190

Ser Ala Glu Arg Trp Gly Arg Pro
        195                 200

<210> SEQ ID NO 42
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 42

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Ser Ser Ser Ser Ser Gln Leu Gln Ser Ile Tyr Asn Leu Thr Ile Cys
        35                  40                  45

Glu Leu Asn Gly Thr Asp Trp Leu Asn Lys Asn Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr Val Leu Ser Ser Val Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Cys Arg Pro
        195                 200

<210> SEQ ID NO 43
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 43

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
```

```
Glu Ser Phe Val Ile Phe Pro Val Leu Thr His Ile Val Ser Tyr Gly
65                  70                  75                  80

Ala Le

<210> SEQ ID NO 45
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 45

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 46
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 46

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 47
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 47

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Ser Ser Ser His Leu Gln Leu Ile Tyr Asn Leu Thr Leu Cys
        35                  40                  45

Glu Leu Asn Gly Thr Asp Trp Leu Ala Asn Arg Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 48
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 48

Met Leu Glu Lys Cys Leu Thr Ala Gly Cys Cys Ser Gln Leu Leu Ser
1               5                   10                  15

Leu Trp Cys Ile Val Pro Phe Cys Phe Val Ala Leu Ala Asn Ala Asn
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Ala Cys Ala Leu Ala Ala Leu Thr Cys Phe Val Ile Arg Leu Ala
        115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
            195                 200

<210> SEQ ID NO 49
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 49

Met Leu Gly Lys Cys Leu Thr Ala Gly Trp Cys Ser Gln Leu Leu Ser
1               5                   10                  15

Leu Gly Cys Ile Val Pro Phe Cys Phe Ala Val Leu Ala Asn Ala Ser
            20                  25                  30

Asn Asp Ser Ser Ser His Val Gln Leu Ile Tyr Asn Leu Thr Leu Cys
        35                  40                  45

Glu Leu Asn Gly Thr Asp Trp Leu Ala Asn Lys Phe Asp Trp Ala Val
50 55 60

Glu Ser Phe Val Ile Phe Pro Val Leu Thr His Ile Val Ser Tyr Gly
65 70 75 80

Ala Leu Thr Thr Ser His Phe Leu Asp Thr Val Ala Leu Val Thr Val
85 90 95

Ser Thr Ala Gly Phe Val His Gly Arg Tyr Val Leu Ser Ser Ile Tyr
100 105 110

Ala Val Cys Ala Leu Ala Ala Leu Thr Cys Phe Val Ile Arg Phe Ala
115 120 125

Lys Asn Cys Met Ser Trp Arg Tyr Ala Cys Thr Arg Tyr Thr Asn Phe
130 135 140

```
Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 50
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 50

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 51
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 51

Met Leu Gly Lys Cys Leu Thr Thr Gly Cys Cys Ser Arg Leu Leu Ser
1               5                   10                  15

Leu Trp Cys Ile Val Pro Phe Cys Phe Ala Val Leu Val Asn Ala Asn
                20                  25                  30
```

Ser Asn Ser Ser Ser His Phe Gln Leu Ile Tyr Asn Leu Thr Leu Cys
        35                  40                  45

Glu Leu Asn Gly Thr Asp Trp Leu Ala Asn Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 52
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 52

Met Leu Gly Lys Cys Leu Thr Ala Gly Cys Cys Ser Arg Leu Leu Ser
1               5                  10                  15

Leu Trp Cys Ile Val Pro Phe Cys Phe Ala Val Leu Gly Ser Ala Asn
            20                  25                  30

Ser Ser Ser Ser Ser His Phe Gln Leu Ile Tyr Asn Leu Thr Leu Cys
        35                  40                  45

Glu Leu Asn Gly Thr Asp Trp Leu Ala Glu Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val

Ser Ala Glu Gln Trp Gly Arg Leu
        195                 200

<210> SEQ ID NO 53
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 53

Met Leu Gly Lys Cys Leu Thr Ala Gly Cys Cys Ser Arg Leu Leu Ser
1               5                   10                  15

Phe Trp Cys Ile Val Pro Phe Cys Phe Ala Val Leu Val Asn Ala Ser
            20                  25                  30

Tyr Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Ser His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Pro
        195                 200

<210> SEQ ID NO 54
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 54

Met Leu Gly Lys Cys Leu Thr Ala Gly Cys Tyr Ser Gln Leu Leu Ser
1               5                   10                  15

Leu Trp Cys Ile Val Pro Phe Cys Phe Ala Val Leu Val Asn Ala Ser
            20                  25                  30

Ser Asn Ser Ser Pro His Phe Gln Leu Ile Tyr Asn Leu Thr Leu Cys
        35                  40                  45

Glu Leu Asn Gly Thr Asp Trp Leu Ala Glu Arg Phe Asp Trp Ala Val
    50                  55                  60

Glu Thr Phe Val Ile Phe Pro Val Leu Thr His Ile Val Ser Tyr Gly

```
                65                  70                  75                  80
Ala Leu Thr Thr Ser His Phe Leu Asp Thr Val Gly Leu Ile Thr Val
                    85                  90                  95

Ser Thr Ala Gly Phe Tyr His Arg Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
            130                 135                 140

Leu Leu Asp Thr Lys Gly Arg Leu Tyr Arg Trp Arg Pro Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
                180                 185                 190

Ser Ala Glu Gln Trp Gly Arg Leu
            195                 200

<210> SEQ ID NO 55
<211> LENGTH: 200
<212> TYPE: PRT
<213> ORGANISM: Artificial Sequence
<220> FEATURE:
<223> OTHER INFORMATION: Porcine reproductive and respiratory syndrome
      virus; open reading frame 5 (ORF5)

<400> SEQUENCE: 55

Met Leu Gly Lys Cys Leu Thr Ala Gly Cys Cys Ser Arg Leu Leu Ser
1               5                   10                  15

Leu Trp Cys Ile Val Pro Phe Tyr Leu Ala Val Leu Val Asn Ala Ser
                20                  25                  30

Asn Asn Ser Ser Ser His Ile Gln Leu Ile Tyr Asn Leu Thr Leu Cys
            35                  40                  45

Glu Leu Asn Gly Thr Asp Trp Leu Ala Lys Asn Phe Asn Arg Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                    85                  90                  95

Ser Thr Ala Gly Tyr Tyr His Arg Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
            130                 135                 140

Leu Leu Asp Thr Lys Gly Lys Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
                180                 185                 190

Ser Ala Glu Gln Trp Gly Arg Leu
            195                 200

<210> SEQ ID NO 56
<211> LENGTH: 219
```

```
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 56

Gln Ala Cys Arg Gln Pro Phe Cys Pro Phe Glu Glu Ala His Ser Gly
1               5                   10                  15

Val Tyr Arg Trp Lys Lys Phe Val Ile Phe Ser Asp Ser Pro Leu Asn
            20                  25                  30

Gly G

```
Gly His Leu Val Gln Asn Pro Asp Val Phe Asp Gly Lys Cys Trp Leu
                100                 105                 110

Ser Cys Phe Leu Gly Gln Ser Val Glu Val Arg Cys His Glu Glu His
            115                 120                 125

Leu Ala Asp Ala Phe Gly Tyr Gln Thr Lys Trp Gly Val His Gly Lys
        130                 135                 140

Tyr Leu Gln Arg Arg Leu Gln Val Arg Gly Ile Arg Ala Val Val Asp
145                 150                 155                 160

Pro Asp Gly Pro Ile His Val Glu Ala Leu Ser Cys Pro Gln Ser Trp
                165                 170                 175

Ile Arg His Leu Thr Leu Asp Asp Val Thr Pro Gly Phe Val Arg
            180                 185                 190

Leu Thr Ser Leu Arg Ile Val Pro Asn Thr Glu Pro Thr Thr Ser Arg
            195                 200                 205

Ile Phe Arg Phe Gly Ala His Lys Trp Tyr Gly
            210                 215

<210> SEQ ID NO 58
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (16)..(16)
<223> OTHER INFORMATION: Xaa = variable or unknown amino acid

<400> SEQUENCE: 58

Arg Pro Lys Pro Glu Asp Phe Cys Pro Phe Glu Cys Ala Met Ala Xaa
1               5                   10                  15

Val Tyr Asp Ile Gly His Asp Ala Val Met Phe Val Ala Glu Gly Arg
            20                  25                  30

Val Ser Trp Ala Pro Arg Gly Gly Lys Gly Lys Phe Glu Thr Val
        35                  40                  45

Pro Glu Glu Leu Arg Leu Ile Ala Glu Gln Leu Tyr Thr Ser Phe Pro
50                  55                  60

Pro His His Val Val Asp Met Ser Lys Phe Thr Phe Thr Ala Pro Glu
65                  70                  75                  80

Cys Gly Ala Ser Met Arg Val Glu Arg His Tyr Gly Cys Leu Pro Ala
                85                  90                  95

Gly Thr Val Pro Asp Gly Asn Cys Trp Trp Ser Leu Phe Ser Ser Leu
            100                 105                 110

Pro Leu Glu Ile Gln Tyr Lys Glu Ile Arg His Ala Thr Gln Phe Gly
        115                 120                 125

Tyr Gln Thr Lys His Gly Val Ala Gly Lys Tyr Leu Gln Arg Arg Leu
130                 135                 140

Gln Val Asn Gly Leu Arg Ala Val Asp Ser Asn Gly Pro Ile Val
145                 150                 155                 160

Ile Gln Tyr Phe Ser Val Lys Glu Ser Trp Ile Arg His Val Lys Leu
            165                 170                 175

Ala Glu Glu Phe Asp Tyr Pro Gly Phe Glu Asp Leu Leu Arg Ile Arg
                180                 185                 190

Val Glu Pro Asn Thr Leu Pro Leu Ser Asn Lys Asp Glu Lys Ile Phe
            195                 200                 205

Arg Phe Gly Gly Cys Lys Trp Tyr Gly
```

<210> SEQ ID NO 59
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta
<220> FEATURE:
<221> NAME/KEY: MOD_RES
<222> LOCATION: (53)..(53)
<223> OTHER INFORMATION: Xaa = variable or unknown amino acid
<220> FEATURE:
<221> NAME/KEY: MOD_RES
<222> LOCATION: (198)..(198)
<223> OTHER INFORMATION: Xaa = variable or unknown amino acid

<400> SEQUENCE: 59

Arg Pro Lys Pro Glu Asp Phe Cys Pro Phe Glu Cys Ala Met Ala Ala
1               5                   10                  15

Val Tyr Asp Ile Gly His Asp Ala Val Met Phe Val Ala Glu Gly Arg
            20                  25                  30

Val Ser Trp Ala Pro Arg Gly Gly Glu Lys Gly Lys Phe Glu Thr Val
        35                  40                  45

Pro Glu Glu Leu Xaa Leu Ile Ala Glu Gln Leu Tyr Thr Ser Phe Pro
    50                  55                  60

Pro His His Leu Val Asp Met Ser Lys Phe Thr Phe Thr Ala Pro Glu
65                  70                  75                  80

Cys Gly Ala Ser Met Arg Val Glu Arg Gln Tyr Gly Cys Leu Pro Ala
                85                  90                  95

Gly Thr Val Pro Asp Gly Asn Cys Trp Trp Ser Leu Phe Ser Ser Leu
            100                 105                 110

Pro Leu Glu Val Gln Tyr Lys Glu Ile Arg Tyr Ala Thr Gln Phe Gly
        115                 120                 125

Tyr Gln Thr Lys His Gly Val Ala Gly Lys Tyr Leu Gln Arg Arg Leu
    130                 135                 140

Gln Ile Asn Gly Leu Arg Ala Val Val Asp Ser Asn Gly Pro Ile Val
145                 150                 155                 160

Ile Gln Tyr Phe Ser Val Lys Glu Ser Trp Ile Arg His Val Lys Leu
                165                 170                 175

Ala Glu Glu Phe Asp Tyr Pro Gly Phe Glu Asp Leu Leu Arg Ile Arg
            180                 185                 190

Val Glu Pro Asn Thr Xaa Pro Leu Ser Asn Lys Asp Glu Lys Ile Phe
        195                 200                 205

Arg Phe Gly Gly Cys Lys Trp Tyr Gly
    210                 215

<210> SEQ ID NO 60
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 60

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

```
Ile Ser Trp Ala Pro Arg Gly Gly Asp Glu Val Lys Phe Glu Ala Val
            35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
                100                 105                 110

Pro Leu Glu Val Gln Asn Lys Glu Ile Arg His Ala Asn Gln Phe Gly
                115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Phe Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
                180                 185                 190

Val Glu Pro Asn Thr Ser Pro Leu Ala Asp Lys Glu Glu Lys Ile Phe
                195                 200                 205

Arg Phe Gly Ser His Lys Trp Tyr Gly
    210                 215

<210> SEQ ID NO 61
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE:

```
                    165                 170                 175

Ala Gly Glu Pro Ser Tyr Ser Gly Phe Glu Asp Leu Leu Arg Ile Arg
                180                 185                 190

Val Glu Pro Asn Thr Ser Pro Leu Ala Asp Lys Glu Glu Lys Ile Phe
            195                 200                 205

Arg Phe Gly Ser His Lys Trp Tyr Gly
        210                 215

<210> SEQ ID NO 62
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 62

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Pro Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg His Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Pro Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Pro Gly Phe Glu Asp Leu Leu Arg Ile Arg
            180                 185                 190

Val Glu His Asn Thr Ser Pro Leu Ala Asp Lys Glu Glu Lys Ile Phe
        195                 200                 205

Arg Phe Gly Ser His Lys Trp Tyr Gly
    210                 215

<210> SEQ ID NO 63
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 63

Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Glu Arg Lys
```

```
                 20                  25                  30
Ile Ser Trp Ala Pro Arg Gly Gly Asp Glu Val Lys Phe Glu Ala Val
             35                  40                  45

Pro Gly Glu Leu Lys Leu Ile Ala Asp Gln Leu Arg Thr Ser Phe Pro
 50                  55                  60

Pro His His Thr Val Asp Val Ser Lys Phe Ala Phe Thr Ala Pro Gly
 65                  70                  75                  80

Cys Gly Val Ser Met Arg Val Glu Arg Gln His Gly Cys Leu Pro Ala
                 85                  90                  95

Asp Thr Val Pro Glu Gly Asn Cys Trp Trp Ser Leu Phe Asp Leu Leu
            100                 105                 110

Pro Leu Glu Val Lys Asn Lys Glu Ile Arg His Ala Asn Gln Phe Gly
            115                 120                 125

Tyr Gln Thr Lys His Gly Val Ser Gly Lys Tyr Leu Gln Arg Arg Leu
            130                 135                 140

Gln Val Asn Gly Leu Arg Ala Val Thr Asp Pro Asn Gly Pro Ile Val
145                 150                 155                 160

Val Gln Tyr Phe Ser Val Lys Glu Ser Trp Ile Arg His Leu Arg Leu
                165                 170                 175

Ala Gly Glu Pro Ser Tyr Pro Gly Phe Glu Asp Leu Leu Arg Ile Arg
            180                 185                 190

Val Glu Pro Asn Thr Ser Pro Leu Ala Asp Lys Glu Gly Lys Ile Phe
            195                 200                 205

Arg Phe Gly Ser His Lys Trp Tyr Gly
            210                 215
```

<210> SEQ ID NO 64
<211> LENGTH: 217
<212> TYPE: PRT
<213> ORGANISM: Artificial Sequence
<220> FEATURE:
<223> OTHER INFORMATION: Porcine reproductive and respiratory syndrome
virus; Nsp1 beta

<400> SEQUENCE: 64

```
Arg Pro Lys Pro Glu Asp Phe Cys Pro Phe Glu Cys Ala Met Ala Thr
 1               5                  10                  15

Val Tyr Asp Ile Gly His Asp Ala Val Met Tyr Val Ala Glu Gly Lys
                20                  25                  30

Ile Ser Trp Ala Pro Arg Gly Gly Asp Glu Val Lys Phe Glu Ala Val
             35                  40                  45

Pro Gly Glu Leu Lys Leu Ile Ala Asn Arg Leu Arg Thr Ser Phe Pro
 50                  55                  60

Pro His His Ala Val Asp Met Ser Lys Phe Ala Phe Thr Ala Pro Gly
 65                  70                  75                  80

Cys Gly Val Ser Met Arg Val Glu Arg Gln His Gly Cys Leu Pro Ala
                 85                  90                  95

Asp Thr Val Pro Glu Gly Asn Cys Trp Trp Ser Leu Phe Asp Leu Leu
            100                 105                 110

Pro Leu Glu Val Gln Asp Lys Glu Ile Arg His Ala Asn Gln Phe Gly
            115                 120                 125

Tyr Gln Thr Lys His Gly Val Ser Gly Lys Tyr Leu Gln Arg Arg Leu
            130                 135                 140

Gln Val Asn Gly Leu Arg Ala Val Thr Asp Ser Asn Gly Pro Ile Val
145                 150                 155                 160
```

```
Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asn Thr Glu Gly Lys Ile Phe
        195                 200                 205

Arg Phe Gly Ser His Lys Trp Tyr Gly
    210                 215
```

<210> SEQ ID NO 65
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 65

```
Arg Pro Lys Pro Glu Asp Phe Cys Pro Phe Glu Cys Ala Met Ala Thr
1               5                   10                  15

Val Tyr Asp Ile Gly His Asp Ala Val Met Tyr Val Ala Gly Met Lys
            20                  25                  30

Ile Ser Trp Ala Pro Arg Gly Gly Asp Glu Val Lys Phe Glu Ala Val
        35                  40                  45

Pro Gly Glu Leu Lys Leu Ile Ala Asn Arg Leu Arg Thr Ser Phe Pro
    50                  55                  60

Pro His His Thr Val Asp Met Ser Lys Phe Ala Phe Thr Ala Leu Gly
65                  70                  75                  80

Cys Gly Val Ser Met Arg Val Glu Arg Gln His Gly Cys Leu Pro Ala
                85                  90                  95

Asp Thr Val Pro Glu Gly Asn Cys Trp Trp Ser Leu Phe Asp Leu Leu
            100                 105                 110

Pro Leu Glu Val Gln Asn Lys Glu Ile Arg Tyr Ala Asn Gln Phe Gly
        115                 120                 125

Tyr Gln Thr Lys His Gly Val Ser Gly Lys Tyr Leu Gln Arg Arg Leu
    130                 135                 140

Gln Val Asn Gly Leu Arg Ala Val Thr Asp Leu Asn Gly Pro Ile Val
145                 150                 155                 160

Val Gln Tyr Phe Ser Val Lys Glu Ser Trp Ile Arg His Leu Lys Leu
                165                 170                 175

Ala Gly Glu Pro Ser Tyr Ser Gly Phe Glu Asp Leu Leu Arg Ile Arg
            180                 185                 190

Val Glu Pro Asn Thr Ser Pro Leu Ala Asp Lys Glu Glu Lys Ile Phe
        195                 200                 205

Arg Phe Gly Ser His Lys Trp Tyr Gly
    210                 215
```

<210> SEQ ID NO 66
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 66

```
Arg Pro Lys Pro Asp Asp Phe Cys Pro Phe Glu Cys Ala Met Ala Thr
1               5                   10                  15
```

Val Tyr Asp Ile Gly His Asp Ala Val Met Tyr Val Ala Glu Lys
                 20                  25                  30

Val Ser Trp Ala Pro Arg Gly Gly Asp Glu Val Lys Phe Glu Pro Val
         35                  40                  45

Pro Gly Glu Leu Lys Leu Ile Ala Asn Arg Leu Arg Thr Ser Phe Pro
     50                  55                  60

Pro His His Ala Val Asp Met Ser Lys Phe Thr Phe Thr Ala Pro Gly
65                  70                  75                  80

Arg Gly Val Ser Met Arg Val Glu Arg Gln His Gly Cys Leu Pro Ala
                 85                  90                  95

Asp Thr Val Pro Glu Gly Asn Cys Trp Trp Ser Leu Phe Asn Leu Leu
             100                 105                 110

Pro Leu Glu Val Gln Asn Lys Glu Ile Arg His Ala Gly Gln Phe Gly
         115                 120                 125

Tyr Gln Thr Lys His Gly Val Ser Gly Lys Tyr Leu Gln Arg Arg Leu
     130                 135                 140

Gln Val Asn Gly Leu Arg Ala Val Thr Asp Leu Asn Gly Pro Ile Val
145                 150                 155                 160

Val Gln Cys Phe Ser Val Lys Glu Ser Trp Ile Arg His Leu Lys Leu
                 165                 170                 175

Ala Glu Glu Pro Ser Tyr Pro Gly Phe Glu Asp Leu Leu Arg Ile Arg
             180                 185                 190

Val Glu Pro Asn Thr Ser Pro Leu Ala Asp Lys Asp Glu Lys Ile Phe
         195                 200                 205

Arg Phe Gly Asn His Lys Trp Tyr Gly
    210                 215

<210> SEQ ID NO 67
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 67

Arg Pro Lys Pro Glu Asp Phe Cys Pro Phe Glu Cys Ala Met Ala Asp
1               5                   10                  15

Val Tyr Asp Ile Gly His Gly Ala Val Met Tyr Val Ala Lys Gly Lys
                 20                  25                  30

Val Ser Trp Ala Pro Arg Gly Gly Asp Glu Ala Lys Phe Glu Thr Val
         35                  40                  45

Pro Arg Glu Leu Lys Leu Ile Ala Asn Gln Leu His Ile Ser Phe Pro
     50                  55                  60

Pro His His Ala Val Asp Met Ser Lys Phe Val Phe Ile Ala Pro Gly
65                  70                  75                  80

Ser Gly Val Ser Met Arg Val Glu Cys Pro His Gly Cys Leu Pro Ala
                 85                  90                  95

Asn Thr Val Pro Glu Gly Asn Cys Trp Trp Arg Leu Phe Asp Ser Leu
             100                 105                 110

Pro Leu Asp Val Gln Asn Lys Glu Ile Arg Arg Ala Asn Gln Phe Gly
         115                 120                 125

Tyr Gln Thr Lys His Gly Val Ala Gly Lys Tyr Leu Gln Arg Arg Leu
     130                 135                 140

Gln Ala Asn Gly Leu Arg Ala Val Thr Asp Thr Asp Gly Pro Ile Val
145                 150                 155                 160

```
Val Gln Tyr Phe Ser Val Arg Glu Ser Trp Ile Arg His Phe Arg Leu
            165                 170                 175

Ala Glu Glu Pro Ser Leu Pro Gly Phe Glu Asp Leu Leu Arg Ile Arg
            180                 185                 190

Val Glu Pro Asn Thr Ser Pro Leu Ser Asp Lys Gly Gly Lys Ile Phe
        195                 200                 205

Arg Phe Gly Ser His Lys Trp Tyr Gly
    210                 215

<210> SEQ ID NO 68
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 68

Arg Pro Lys Pro Glu Asp Phe Cys Pro Phe Glu Cys Ala Met Ala Asp
1               5                   10                  15

Val Tyr Asp Ile Gly Arg Asp Ala Val Met Tyr Val Ala Arg Gly Lys
            20                  25                  30

Val Ser Trp Ala Pro Arg Gly Gly Asp Glu Val Lys Phe Glu Thr Val
        35                  40                  45

Pro Glu Glu Leu Lys Leu Ile Ala Asn Arg Leu His Ile Ser Phe Pro
    50                  55                  60

Pro Tyr His Ala Val Asp Met Ser Lys Phe Ala Phe Ile Ala Pro Gly
65                  70                  75                  80

Ser Gly Val Ser Leu Arg Val Glu Tyr Gln His Gly Cys Leu Pro Ala
                85                  90                  95

Asp Thr Val Pro Glu Gly Asn Cys Trp Trp Arg Leu Phe Asp Leu Leu
            100                 105                 110

Pro Pro Glu Val Gln Asn Lys Glu Ile Arg Tyr Ala Asn Gln Phe Gly
        115                 120                 125

Tyr Gln Thr Lys His Gly Val Pro Gly Lys Tyr Leu Gln Arg Arg Leu
    130                 135                 140

Gln Val Asn Gly Leu Arg Ala Val Thr Asp Thr His Gly Pro Ile Val
145                 150                 155                 160

Ile Gln Tyr Phe Ser Val Gly Glu Ser Trp Ile Arg His Phe Arg Leu
                165                 170                 175

Ala Gly Glu Pro Ser Leu Pro Gly Phe Glu Asp Leu Leu Arg Ile Arg
            180                 185                 190

Val Glu Pro Asn Thr Ser Pro Leu Ala Glu Lys Asp Gly Lys Ile Phe
        195                 200                 205

Arg Phe Gly Ser His Lys Trp Tyr Gly
    210                 215

<210> SEQ ID NO 69
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 69

Arg Pro Lys Pro Glu Asp Phe Cys Pro Phe Glu Cys Ala Met Ala Asp
1               5                   10                  15
```

Val Tyr Asp Ile Ser His Asp Ala Val Met Tyr Val Ala Arg Gly Lys
            20                  25                  30

Val Ser Trp Ala Pro Arg Gly Gly Asp Glu Val Lys Phe Glu Thr Val
        35                  40                  45

Pro Glu Glu Leu Lys Leu Ile Ala Asn Arg Leu His Ile Ser Phe Pro
 50                  55                  60

Pro His His Ala Val Asp Met Ser Glu Phe Ala Phe Ile Ala Pro Gly
65                  70                  75                  80

Ser Gly Val Ser Leu Arg Val Glu His Gln His Gly Cys Leu Pro Ala
                85                  90                  95

Asp Thr Val Pro Glu Gly Asn Cys Trp Trp Cys Leu Phe Asp Leu Leu
            100                 105                 110

Pro Pro Glu Val Gln Asn Lys Glu Ile Arg Arg Ala Asn Gln Phe Gly
        115                 120                 125

Tyr Gln Thr Lys His Gly Val Pro Gly Lys Tyr Leu Gln Arg Arg Leu
130                 135                 140

Gln Val Asn Gly Leu Arg Ala Val Thr Asp Thr Asp Gly Pro Ile Val
145                 150                 155                 160

Val Gln Tyr Phe Ser Val Arg Glu Ser Trp Ile Arg His Phe Arg Leu
                165                 170                 175

Ala Glu Glu Pro Ser Leu Pro Gly Phe Glu Asp Leu Leu Arg Ile Arg
            180                 185                 190

Val Glu Pro Asn Thr Ser Pro Leu Gly Gly Lys Gly Glu Lys Ile Phe
        195                 200                 205

Arg Phe Gly Ser His Lys Trp Tyr Gly
        210                 215

<210> SEQ ID NO 70
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 70

Arg Pro Lys Pro Glu Asp Phe Cys Pro Phe Glu Cys Ala Met Ala Asp
1               5                   10                  15

Val Tyr Asp Ile Gly His Gly Ala Val Met Phe Val Ala Gly Gly Lys
            20                  25                  30

Val Ser Trp Ala Pro Arg Gly Gly Asp Glu Val Arg Phe Glu Thr Val
        35                  40                  45

Pro Glu Glu Leu Lys Leu Ile Ala Asn Arg Leu His Ile Ser Phe Pro
 50                  55                  60

Pro His His Leu Val Asp Met Ser Lys Phe Ala Phe Ile Val Pro Gly
65                  70                  75                  80

Ser Gly Val Ser Leu Arg Val Glu His Gln His Gly Cys Leu Pro Ala
                85                  90                  95

Asp Ile Val Pro Lys Gly Asn Cys Trp Trp Cys Leu Phe Asp Leu Leu
            100                 105                 110

Pro Pro Gly Val Gln Asn Arg Glu Ile Arg Tyr Ala Asn Gln Phe Gly
        115                 120                 125

Tyr Gln Thr Lys His Gly Val Ser Gly Lys Tyr Leu Gln Arg Arg Leu
130                 135                 140

Gln Ile Asn Gly Leu Arg Ala Val Thr Asp Thr His Gly Pro Ile Val

```
145                 150                 155                 160
Val Gln Tyr Phe Ser Val Lys Glu Ser Trp Ile Arg His Phe Arg Leu
                165                 170                 175

Ala Gly Glu Pro Ser Leu Pro Gly Phe Glu Asp Leu Leu Arg Ile Arg
                180                 185                 190

Val Glu Ser Asn Thr Ser Pro Leu Ala Asp Lys Asp Glu Lys Ile Phe
                195                 200                 205

Arg Phe Gly Ser His Lys Trp Tyr Gly
                210                 215

<210> SEQ ID NO 71
<211> LENGTH: 217
<212> TYPE: PRT
<213> ORGANISM: Artificial Sequence
<220> FEATURE:
<223> OTHER INFORMATION: Porcine reproductive and respiratory syndrome
      virus; Nsp1 beta

<400> SEQUENCE: 71

Arg Pro Lys Pro Glu Asp Phe Cys Pro Phe Glu Cys Ala Met Ala Asp
1               5                   10                  15

Val Tyr Asp Ile Gly Arg Gly Ala Val Met Tyr Val Ala Gly Gly Lys
                20                  25                  30

Val Ser Trp Ala Pro Arg Gly Gly Asp Glu Val Lys Phe Glu Pro Val
                35                  40                  45

Pro Lys Glu Leu Lys Leu Val Ala Asn Arg Leu His Thr Ser Phe Pro
            50                  55                  60

Pro His His Val Val Asp Met Ser Lys Phe Thr Phe Met Thr Pro Gly
65                  70                  75                  80

Ser Gly Val Ser Met Arg Val Glu Tyr Gln Tyr Gly Cys Leu Pro Ala
                85                  90                  95

Asp Thr Val Pro Glu Gly Asn Cys Trp Trp Arg Leu Phe Asp Leu Leu
                100                 105                 110

Pro Pro Glu Val Gln Asn Lys Glu Ile Arg His Ala Asn Gln Phe Gly
                115                 120                 125

Tyr Gln Thr Lys His Gly Val Pro Gly Lys Tyr Leu Gln Arg Arg Leu
                130                 135                 140

Gln Val Asn Gly Leu Arg Ala Val Thr Asp Thr His Gly Pro Ile Val
145                 150                 155                 160

Ile Gln Tyr Phe Ser Val Lys Glu Ser Trp Ile Arg His Leu Lys Pro
                165                 170                 175

Val Glu Glu Pro Ser Leu Pro Gly Phe Glu Asp Leu Leu Arg Ile Arg
                180                 185                 190

Val Glu Pro Asn Thr Ser Pro Leu Ala Gly Lys Asn Glu Lys Ile Phe
                195                 200                 205

Arg Phe Gly Ser His Lys Trp Tyr Gly
                210                 215

<210> SEQ ID NO 72
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (134)..(134)
<223> OTHER INFORMATION: Xaa = variable or unknown amino acid
```

```
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (284)..(284)
<223> OTHER INFORMATION: Xaa = variable or unknown amino acid
<220> FEATURE:
<221> NAME/KEY: MOD_RES
<222> LOCATION: (298)..(298)
<223> OTHER INFORMATION: Xaa = variable or unknown amino acid
<220> FEATURE:
<221> NAME/KEY: MOD_RES
<222> LOCATION: (691)..(691)
<223> OTHER INFORMATION: Xaa = variable or unknown amino acid

<400> SEQUENCE: 72

Gly Ala Gly Lys Arg Ala Arg Ala Arg Ala Ser Ala Val Thr Ala
1               5                   10                  15

Val Ala Gly His Ala Pro Pro Thr Arg Glu Thr Gln Gln Ala Lys Lys
            20                  25                  30

His Glu Ala Ala Ser Ala Asn Lys Ala Glu Leu Leu Glu Arg Tyr Ser
        35                  40                  45

Pro Pro Ala Glu Gly Asn Cys Gly Trp His Cys Ile Ser Ala Ile Ala
50                  55                  60

Asn Arg Met Val Asn Ser Lys Phe Glu Thr Ala Leu Pro Glu Arg Val
65                  70                  75                  80

Arg Ser Pro Glu Asp Trp Ala Thr Asp Glu Asp Leu Val Asn Thr Ile
            85                  90                  95

Gln Ile Leu Arg Leu Pro Ala Ala Leu Asp Arg Asn Gly Ala Cys Ala
        100                 105                 110

Ser Ala Lys Tyr Ile Leu Lys Leu Glu Gly Glu His Trp Thr Val Ser
    115                 120                 125

Val Ile Pro Gly Met Xaa Pro Ser Leu Leu Pro Leu Glu Cys Val Gln
130                 135                 140

Gly Cys Cys Glu His Lys Gly Asn Leu Gly Ser Pro Asn Ala Val Gly
145                 150                 155                 160

Val Phe Gly Phe Asp Pro Ala Ser Leu Asp Arg Leu Ala Gly Val Met
            165                 170                 175

His Leu Pro Ser Ser Ala Ile Pro Ala Ala Leu Ala Glu Leu Ser Gly
        180                 185                 190

Asp Leu Asp Arg Pro Thr Ser Pro Ala Ala Thr Val Trp Thr Val Ser
    195                 200                 205

Gln Phe Tyr Ala Arg His Ser Gly Gly Glu His Pro Asp Gln Lys Cys
210                 215                 220

Leu Lys Lys Ile Ile Ser Leu Cys Glu Val Ile Glu Ser Cys Cys Cys
225                 230                 235                 240

Ser Xaa Asn Lys Thr Asn Arg Val Thr Pro Glu Glu Val Thr Ala Lys
            245                 250                 255

Ile Asp Leu Tyr Leu Phe Gly Ala Ala Ser Leu Glu Glu Cys Leu Ala
        260                 265                 270

Arg Leu Glu Lys Ala Arg Pro Pro Ser Val Leu Xaa Thr Ser Phe Asp
    275                 280                 285

Trp Asp Val Val Leu Pro Gly Val Gly Xaa Ala Ala Gln Ala Ala Lys
290                 295                 300

Leu Pro Leu Thr Asn Gln Arg His Ala Leu Ala Thr Val Val Thr Gln
305                 310                 315                 320
```

-continued

```
Arg Ser Leu Pro Lys Phe Gln Pro Arg Lys Ala Glu Ser Val Lys Ser
            325                 330                 335

Leu Pro Glu Ser Arg Pro Leu Pro Ala Pro Arg Lys Lys Ile Arg Ser
        340                 345                 350

Arg Cys Gly Ser Pro Ile Ser Leu Gly Gly Asn Leu Pro Asp Ser Gln
        355                 360                 365

Glu Asp Leu Ala Gly Gly Ser Phe Asp Phe Pro Thr Leu Pro Glu Leu
        370                 375                 380

Val Val Ser Ser Ser Glu Ser Val Pro Val Pro Ala Pro Arg Arg Val
385                 390                 395                 400

Val Ser Arg Leu Val Ser Ser Pro Ile Val Ser Thr Pro Val Pro Ala
        405                 410                 415

Pro Arg Arg Gly Leu Arg Gln Val Glu Gly Met Asn Leu Ala Ala Val
        420                 425                 430

Thr Leu Ala Cys Gln Asp Glu Pro Leu Asp Leu Ser Ala Ser Ser Gln
        435                 440                 445

Thr Glu Tyr Glu Ala Ser Pro Leu Ala Leu Pro Leu Ser Glu Asp Val
        450                 455                 460

Leu Ala Val Glu Arg Arg Glu Val Glu Val Leu Ser Gly Ile Ser
465                 470                 475                 480

Gly Met Ser Asp Asp Ile Arg Leu Ala Pro Val Ser Ser Ser Ser
                485                 490                 495

Leu Ser Ser Ile Glu Ile Thr Arg Pro Lys Tyr Ser Ala Gln Ala Ile
                500                 505                 510

Ile Asn Ser Gly Gly Pro Cys Cys Gly His Leu Gln Glu Val Lys Glu
        515                 520                 525

Lys Tyr Leu Asn Val Met Arg Glu Ala Cys Asp Ala Thr Lys Leu Asp
        530                 535                 540

Asp Pro Ala Thr Gln Glu Trp Leu Ser Arg Met Trp Asp Arg Val Asp
545                 550                 555                 560

Met Leu Thr Trp Arg Asn Thr Ser Ile Phe Gln Ala Pro Phe Thr Leu
                565                 570                 575

Ala Asp Lys Phe Lys Ser Leu Pro Lys Met Ile Leu Glu Thr Pro Pro
                580                 585                 590

Pro Tyr Pro Cys Gly Phe Val Met Met Pro Arg Thr Pro Ala Pro Ser
            595                 600                 605

Val Gly Ala Glu Ser Asp Leu Thr Val Gly Ser Val Ala Thr Glu Asp
        610                 615                 620

Val Pro Arg Ile Leu Gly Lys Val Gln Gly Val Gly Glu Thr Thr Asp
625                 630                 635                 640

Gln Gly Pro Leu Ala Leu Phe Ala Asp Glu Leu Ala Asp Gln Pro
                645                 650                 655

Ala Arg Glu Pro Arg Thr Gln Thr Pro Pro Ala Ser Ala Gly Gly Ala
            660                 665                 670

Gly Leu Val Leu Asp Ser Gly Ser Pro Glu Leu Thr Asp Leu Pro
                675                 680                 685

Leu Pro Xaa Gly Thr Asp Ala Gly Gly Gly Gly Pro Leu His Thr Val
        690                 695                 700

Lys Lys Lys Ala Glu Arg Cys Phe Asp Gln Leu Ser Arg Arg Val Phe
705                 710                 715                 720

Asp Ile Val Ser His Leu Pro Val Phe Phe Ser Arg Leu Phe Lys Pro
                725                 730                 735

Asp Ser His Tyr Ser Ser Gly Asp Trp Ser Phe Ala Ala Phe Thr Leu
```

```
                    740                 745                 750

Leu Cys Leu Phe Leu Cys Tyr Ser Tyr Pro Ala Phe Gly Val Ala Pro
            755                 760                 765

Leu Leu Gly Val Phe Ser Gly Ser Arg Arg Val Arg Met Gly Val
    770                 775                 780

Phe Gly Cys Trp Leu Ala Phe Ala Val Gly Leu Phe Lys Pro Ala Pro
785                 790                 795                 800

Asp Pro Val Gly Ala Ala Cys Glu Phe Asp Ser Pro Glu Cys Arg Asp
                805                 810                 815

Ile Leu His Ser Phe Glu Leu Leu Gln Pro Trp Asp Pro Val Arg Ser
            820                 825                 830

Leu Val Val Gly Pro Val Gly Leu Gly Leu Ala Ile Ile Gly Arg Leu
            835                 840                 845

Leu Gly Gly Ala Arg Tyr Val Trp Leu Leu Leu Arg Leu Gly Ile
    850                 855                 860

Val Ser Asp Cys Ile Leu Ala Gly Ala Tyr Val Leu Ser Gln Gly Arg
865                 870                 875                 880

Cys Lys Lys Cys Trp Gly Ser Cys Ile Arg Thr Ala Pro Ser Glu Val
                885                 890                 895

Ala Phe Asn Val Phe Pro Phe Thr Arg Ala Thr Arg Ser Ser Leu Val
            900                 905                 910

Asp Leu Cys Asp Arg Phe Cys Ala Pro Lys Gly Met Asp Pro Ile Phe
            915                 920                 925

Leu Ala Thr Gly Trp Arg Gly Cys Trp Ser Gly Gln Ser Pro Val Glu
    930                 935                 940

Gln Pro Thr Glu Lys Pro Ile Ala Phe Ala Gln Leu Asp Glu Lys Lys
945                 950                 955                 960

Ile Thr Ala Arg Thr Val Val Ala Gln Pro Tyr Asp Pro Asn Gln Ala
                965                 970                 975

Val Lys Cys Leu Arg Val Leu Gln Ala Gly Gly Ala Met Val Ala Glu
            980                 985                 990

Ala Ile Pro Lys Val Val Lys Val Ser Ala Val Pro Phe Arg Ala Pro
            995                 1000                1005

Phe Phe Pro Thr Gly Val Lys Val Asp Pro Glu Cys Arg Val Val
    1010                1015                1020

Val Asp Pro Asp Thr Phe Thr Thr Ala Leu Arg Ser Gly Tyr Ser
    1025                1030                1035

Thr Thr Asn Leu Ile Leu Gly Val Gly Asp Phe Ala Gln Leu Asn
    1040                1045                1050

Gly Leu Lys Ile Arg Gln Ile Ser Lys Pro Ser Gly Gly
    1055                1060                1065
```

<210> SEQ ID NO 73
<211> LENGTH: 1066
<212> TYPE: PRT
<213> ORGANISM: Artificial Sequence
<220> FEATURE:
<223> OTHER INFORMATION: Porcine reproductive and respiratory syndrome
      virus; Nsp2
<220> FEATURE:
<221> NAME/KEY: MOD_RES
<222> LOCATION: (43)..(43)
<223> OTHER INFORMATION: Xaa = variable or unknown amino acid
<220> FEATURE:
<221> NAME/KEY: MOD_RES
<222> LOCATION: (45)..(46)
<223> OTHER INFORMATION: Xaa = variable or unknown amino acid
<220> FEATURE:

-continued

```
<221> NAME/KEY: MOD_RES
<222> LOCATION: (75)..(75)
<223> OTHER INFORMATION: Xaa = variable or unknown amino acid
<220> FEATURE:
<221> NAME/KEY: MOD_RES
<222> LOCATION: (82)..(82)
<223> OTHER INFORMATION: Xaa = variable or unknown amino acid
<220> FEATURE:
<221> NAME/KEY: MOD_RES
<222> LOCATION: (84)..(84)
<223> OTHER INFORMATION: Xaa = variable or unknown amino acid
<220> FEATURE:
<221> NAME/KEY: MOD_RES
<222> LOCATION: (95)..(95)
<223> OTHER INFORMATION: Xaa = variable or unknown amino acid
<220> FEATURE:
<221> NAME/KEY: MOD_RES
<222> LOCATION: (112)..(112)
<223> OTHER INFORMATION: Xaa = variable or unknown amino acid
<220> FEATURE:
<221> NAME/KEY: MOD_RES
<222> LOCATION: (117)..(117)
<223> OTHER INFORMATION: Xaa = variable or unknown amino acid
<220> FEATURE:
<221> NAME/KEY: MOD_RES
<222> LOCATION: (128)..(128)
<223> OTHER INFORMATION: Xaa = variable or unknown amino acid
<220> FEATURE:
<221> NAME/KEY: MOD_RES
<222> LOCATION: (130)..(130)
<223> OTHER INFORMATION: Xaa = variable or unknown amino acid
<220> FEATURE:
<221> NAME/KEY: MOD_RES
<222> LOCATION: (174)..(174)
<223> OTHER INFORMATION: Xaa = variable or unknown amino acid
<220> FEATURE:
<221> NAME/KEY: MOD_RES
<222> LOCATION: (190)..(190)
<223> OTHER INFORMATION: Xaa = variable or unknown amino acid
<220> FEATURE:
<221> NAME/KEY: MOD_RES
<222> LOCATION: (194)..(194)
<223> OTHER INFORMATION: Xaa = variable or unknown amino acid
<220> FEATURE:
<221> NAME/KEY: MOD_RES
<222> LOCATION: (197)..(198)
<223> OTHER INFORMATION: Xaa = variable or unknown amino acid
<220> FEATURE:
<221> NAME/KEY: MOD_RES
<222> LOCATION: (201)..(202)
<223> OTHER INFORMATION: Xaa = variable or unknown amino acid
<220> FEATURE:
<221> NAME/KEY: MOD_RES
<222> LOCATION: (218)..(218)
<223> OTHER INFORMATION: Xaa = variable or unknown amino acid
<220> FEATURE:
<221> NAME/KEY: MOD_RES
<222> LOCATION: (223)..(224)
<223> OTHER INFORMATION: Xaa = variable or unknown amino acid
<220> FEATURE:
<221> NAME/KEY: MOD_RES
<222> LOCATION: (226)..(226)
<223> OTHER INFORMATION: Xaa = variable or unknown amino acid
<220> FEATURE:
<221> NAME/KEY: MOD_RES
<222> LOCATION: (233)..(233)
<223> OTHER INFORMATION: Xaa = variable or unknown amino acid
<220> FEATURE:
<221> NAME/KEY: MOD_RES
<222> LOCATION: (237)..(237)
<223> OTHER INFORMATION: Xaa = variable or unknown amino acid
<220> FEATURE:
<221> NAME/KEY: MOD_RES
<222> LOCATION: (242)..(242)
<223> OTHER INFORMATION: Xaa = variable or unknown amino acid
<220> FEATURE:
<221> NAME/KEY: MOD_RES
<222> LOCATION: (254)..(254)
<223> OTHER INFORMATION: Xaa = variable or unknown amino acid
```

<400> SEQUENCE: 73

```
Gly Ala Gly Lys Arg Ala Arg Ala Arg Ala Ser Ala Val Thr Ala
1               5                   10                  15

Val Ala Gly His Ala Pro Pro Thr Arg Glu Thr Gln Gln Ala Lys Lys
            20                  25                  30

His Glu Ala Ala Ser Ala Asn Lys Ala Glu Xaa Leu Xaa Xaa Tyr Ser
        35                  40                  45

Pro Pro Ala Glu Gly Asn Cys Gly Trp His Cys Ile Ser Ala Ile Ala
50                  55                  60

Asn Arg Met Val Asn Ser Lys Phe Glu Thr Xaa Leu Pro Glu Arg Val
65                  70                  75                  80

Arg Xaa Pro Xaa Asp Trp Ala Thr Asp Glu Asp Leu Val Asn Xaa Ile
            85                  90                  95

Gln Ile Leu Arg Leu Pro Ala Ala Leu Asp Arg Asn Gly Ala Cys Xaa
            100                 105                 110

Ser Ala Lys Tyr Xaa Leu Lys Leu Glu Gly Glu His Trp Thr Val Xaa
            115                 120                 125

Val Xaa Pro Gly Met Ser Pro Ser Leu Leu Pro Leu Glu Cys Val Gln
130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Xaa Val Met
                165                 170                 175

His Leu Pro Ser Ser Ala Ile Pro Ala Ala Leu Ala Glu Xaa Ser Gly
            180                 185                 190

Asp Xaa Asp Arg Xaa Xaa Ser Pro Xaa Xaa Thr Val Trp Thr Val Ser
            195                 200                 205

Gln Phe Tyr Ala Arg His Ser Gly Xaa His Pro Asp Gln Xaa Xaa
210                 215                 220

Leu Xaa Lys Ile Ile Ser Leu Cys Xaa Val Ile Glu Xaa Cys Cys Cys
225                 230                 235                 240

Ser Xaa Asn Lys Thr Asn Arg Val Thr Pro Glu Glu Val Xaa Ala Lys
            245                 250                 255

Ile Asp Gln Tyr Leu Phe Gly Ala Ala Ser Leu Glu Glu Cys Leu Ala
            260                 265                 270

Arg Leu Glu Lys Ala Arg Pro Pro Ser Val Leu Asp Thr Ser Phe Asp
            275                 280                 285

Trp Asp Val Val Leu Pro Gly Val Gly Ala Ala Gln Ala Ala Lys
290                 295                 300

Leu Pro Leu Thr Asn Gln Arg His Ala Leu Ala Thr Val Val Thr Gln
305                 310                 315                 320

Arg Ser Leu Pro Lys Phe Gln Pro Arg Lys Ala Glu Ser Val Lys Ser
            325                 330                 335

Leu Pro Glu Ser Arg Pro Leu Pro Ala Pro Arg Lys Lys Ile Gly Ser
            340                 345                 350

Arg Cys Gly Ser Pro Ile Ser Leu Gly Gly Asn Leu Pro Asp Ser Arg
            355                 360                 365

Glu Asp Leu Ala Gly Gly Ser Phe Asp Phe Pro Thr Leu Pro Glu Leu
            370                 375                 380

Val Ala Ser Ser Glu Pro Val Pro Val Pro Ala Pro Arg Arg Val
385                 390                 395                 400

Val Ser Arg Leu Val Ser Ser Pro Ile Val Ser Thr Pro Val Pro Ala
```

-continued

```
                405                 410                 415
Pro Arg Arg Gly Leu Arg Gln Val Glu Gly Met Asn Leu Ala Ala Val
                420                 425                 430

Thr Leu Ala Cys Gln Asp Glu Pro Leu Asp Leu Ser Ala Ser Ser Gln
                435                 440                 445

Thr Glu Tyr Glu Ala Ser Pro Leu Ala Leu Pro Leu Ser Glu Asp Val
            450                 455                 460

Leu Ala Val Glu Arg Arg Glu Val Glu Val Leu Ser Gly Ile Ser
465                 470                 475                 480

Gly Met Pro Asp Asp Ile Arg Leu Ala Pro Val Ser Ser Ser Ser
                485                 490                 495

Leu Ser Ser Ile Glu Ile Thr Arg Pro Lys Tyr Ser Ala Gln Ala Ile
                500                 505                 510

Ile Asn Ser Gly Gly Pro Cys Cys Gly His Leu Gln Glu Val Lys Glu
                515                 520                 525

Lys Tyr Leu Asn Val Met Arg Glu Ala Cys Asp Ala Thr Lys Leu Asp
            530                 535                 540

Asp Pro Ala Thr Gln Glu Trp Leu Ser Arg Met Trp Asp Arg Val Asp
545                 550                 555                 560

Met Leu Thr Trp Arg Asn Thr Ser Ile Phe Gln Ala Pro Phe Thr Leu
                565                 570                 575

Ala Asp Lys Phe Lys Thr Leu Pro Lys Met Ile Leu Glu Thr Pro Pro
                580                 585                 590

Pro Tyr Pro Cys Gly Phe Val Met Met Pro Arg Thr Pro Ala Pro Ser
            595                 600                 605

Val Gly Ala Glu Ser Asp Leu Thr Val Gly Ser Val Ala Thr Glu Asp
            610                 615                 620

Val Pro Arg Ile Leu Gly Asn Val Gln Gly Val Gly Thr Thr Asp
625                 630                 635                 640

Gln Gly Pro Leu Ala Pro Phe Ala Asp Glu Leu Ala Asp Gln Leu
                645                 650                 655

Ala Arg Glu Pro Arg Thr Gln Thr Pro Pro Ala Ser Thr Gly Gly Ala
                660                 665                 670

Gly Leu Val Ser Asp Ser Gly Arg Ser Pro Glu Leu Thr Asp Leu Pro
            675                 680                 685

Leu Ser Asn Gly Thr Asp Ala Gly Gly Gly Pro Leu His Thr Val
            690                 695                 700

Lys Lys Lys Ala Glu Arg Cys Phe Asp Gln Leu Ser Arg Arg Val Phe
705                 710                 715                 720

Asp Ile Val Ser His Leu Pro Val Phe Phe Ser Arg Leu Phe Lys Pro
                725                 730                 735

Asp Ser His Tyr Ser Ser Gly Asp Trp Ser Phe Ala Ala Phe Thr Leu
            740                 745                 750

Leu Cys Leu Phe Leu Cys Tyr Ser Tyr Pro Ala Phe Gly Val Ala Pro
            755                 760                 765

Leu Leu Gly Val Phe Ser Gly Ser Ser Arg Arg Val Arg Met Gly Val
            770                 775                 780

Phe Gly Cys Trp Leu Ala Phe Ala Val Gly Leu Phe Lys Pro Ala Pro
785                 790                 795                 800

Asp Pro Val Gly Ala Ala Cys Glu Phe Asp Ser Pro Glu Cys Arg Asp
                805                 810                 815

Ile Leu His Ser Phe Glu Leu Leu Gln Pro Trp Asp Pro Val Arg Ser
            820                 825                 830
```

-continued

Leu Val Val Gly Pro Val Gly Leu Gly Leu Ala Ile Ile Gly Arg Leu
        835                 840                 845

Leu Gly Gly Ala Arg Tyr Val Trp Leu Leu Leu Leu Arg Leu Gly Ile
    850                 855                 860

Val Ser Asp Cys Ile Leu Ala Gly Ala Tyr Val Leu Ser Gln Gly Arg
865                 870                 875                 880

Cys Lys Lys Cys Trp Gly Ser Cys Ile Arg Thr Ala Pro Ser Glu Val
                885                 890                 895

Ala Phe Asn Val Phe Pro Phe Thr Arg Ala Thr Arg Ser Ser Leu Val
            900                 905                 910

Asp Leu Cys Asp Arg Phe Cys Ala Pro Lys Gly Met Asp Pro Ile Phe
        915                 920                 925

Leu Ala Thr Gly Trp Arg Gly Cys Trp Ser Gly Gln Ser Pro Ile Glu
    930                 935                 940

Gln Pro Thr Glu Lys Pro Ile Ala Phe Ala Gln Leu Asp Glu Lys Lys
945                 950                 955                 960

Ile Thr Ala Arg Thr Val Ala Gln Pro Tyr Asp Pro Asn Gln Ala
                965                 970                 975

Val Lys Cys Leu Arg Val Leu Gln Ala Gly Ala Met Val Ala Glu
            980                 985                 990

Ala Val Pro Lys Val Val Lys Val Ser Ala Val Pro Phe Arg Ala Pro
        995                 1000                1005

Phe Phe Pro Ala Gly Val Lys Val Asp Pro Glu Cys Arg Val Val
    1010                1015                1020

Val Asp Pro Asp Thr Phe Thr Thr Ala Leu Arg Ser Gly Tyr Ser
    1025                1030                1035

Thr Thr Asn Leu Ile Leu Gly Met Gly Asp Phe Ala Gln Leu Asn
    1040                1045                1050

Gly Leu Lys Ile Arg Gln Ile Ser Lys Pro Ser Gly Gly
    1055                1060                1065

<210> SEQ ID NO 74
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 74

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr

-continued

```
                115                 120                 125
Val Thr Pro Gly Met Ser Pro Ser Leu Leu Pro Leu Glu Cys Val Gln
130                 135                 140

Gly Cys Cys Gly His Lys Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
                180                 185                 190

Asp Ser Asp Arg Ser Ala Ser Pro Val Thr Thr Val Trp Thr Val Ser
                195                 200                 205

Gln Phe Phe Ala Arg His Ser Gly Gly Asn His Pro Asp Gln Val Arg
                210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
                260                 265                 270

Arg Leu Glu Lys Ala Arg Pro Pro Arg Val Ile Asp Thr Ser Phe Asp
                275                 280                 285

Trp Asp Val Val Leu Pro Gly Val Glu Ala Ala Thr Gln Thr Ile Lys
                290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
                340                 345                 350

Leu Thr Ala Val Leu Ser Lys Leu Glu Lys Val Arg Glu Glu Tyr
                355                 360                 365

Gly Leu Met Pro Thr Glu Pro Gly Pro Arg Pro Thr Leu Pro Arg Gly
370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
                420                 425                 430

Pro Pro Pro Lys Val Gln Pro Arg Lys Thr Lys Pro Val Lys Ser Leu
                435                 440                 445

Pro Glu Arg Lys Pro Val Pro Ala Arg Arg Lys Val Gly Ser Asp
                450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Glu Pro
                485                 490                 495

Ala Thr Pro Ser Ser Glu Leu Val Ile Val Ser Ser Pro Gln Cys Ile
                500                 505                 510

Phe Arg Pro Ala Thr Pro Leu Ser Glu Pro Ala Pro Ile Pro Ala Pro
                515                 520                 525

Arg Gly Thr Val Ser Arg Pro Val Thr Pro Leu Ser Glu Pro Ile Pro
                530                 535                 540
```

```
Val Pro Ala Pro Arg Arg Lys Phe Gln Gln Val Lys Arg Leu Ser Ser
545                 550                 555                 560

Ala Ala Ala Ile Pro Pro Tyr Gln Asp Glu Pro Leu Asp Leu Ser Ala
                565                 570                 575

Ser Ser Gln Thr Glu Tyr Glu Ala Ser Pro Pro Ala Pro Pro Gln Ser
            580                 585                 590

Gly Gly Val Leu Gly Val Glu Gly His Glu Ala Glu Glu Thr Leu Ser
            595                 600                 605

Glu Ile Ser Asp Met Ser Gly Asn Ile Lys Pro Ala Ser Val Ser Ser
        610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Pro Cys Ser Gly His Leu Gln Glu
                645                 650                 655

Val Lys Glu Thr Cys Leu Ser Val Met Arg Glu Ala Cys Asp Ala Thr
                660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Tyr Gln Ala Ile
        690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
            755                 760                 765

Met Ala Asn Gln Gly Pro Leu Ala Phe Ser Glu Asp Lys Pro Val Asp
    770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Ala Gly Ser Phe Thr
                805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
    850                 855                 860

Phe Tyr Pro Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Gly Ser Ser Arg Arg Val Arg
            900                 905                 910

Met Gly Val Phe Gly Cys Trp Leu Ala Phe Ala Val Gly Leu Phe Lys
            915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960
```

Val Arg Ser Leu Val Val Gly Pro Val Gly Leu Gly Leu Ala Ile Leu
            965                 970                 975

Gly Arg Leu Leu Gly Gly Ala Arg Cys Ile Trp His Phe Leu Leu Arg
        980                 985                 990

Leu Gly Ile Val Ala Asp Cys Ile Leu Ala Gly Ala Tyr Val Leu Ser
    995                 1000                1005

Gln Gly Arg Cys Lys Lys Cys Trp Gly Ser Cys Ile Arg Thr Ala
1010                1015                1020

Pro Asn Glu Val Ala Phe Asn Val Phe Pro Phe Thr Arg Ala Thr
1025                1030                1035

Arg Ser Ser Leu Ile Asp Leu Cys Asp Arg Phe Cys Ala Pro Lys
1040                1045                1050

Gly Met Asp Pro Ile Phe Leu Ala Thr Gly Trp Arg Gly Cys Trp
1055                1060                1065

Ala Gly Arg Ser Pro Ile Glu Gln Pro Ser Glu Lys Pro Ile Ala
1070                1075                1080

Phe Ala Gln Leu Asp Glu Lys Lys Ile Thr Ala Arg Thr Val Val
1085                1090                1095

Ala Gln Pro Tyr Asp Pro Asn Gln Ala Val Lys Cys Leu Arg Val
1100                1105                1110

Leu Gln Ser Gly Gly Ala Met Val Ala Lys Ala Val Pro Lys Val
1115                1120                1125

Val Lys Val Ser Ala Val Pro Phe Arg Ala Pro Phe Phe Pro Thr
1130                1135                1140

Gly Val Lys Val Asp Pro Asp Cys Arg Val Val Val Asp Pro Asp
1145                1150                1155

Thr Phe Thr Ala Ala Leu Arg Ser Gly Tyr Ser Thr Thr Asn Leu
1160                1165                1170

Val Leu Gly Val Gly Asp Phe Ala Gln Leu Asn Gly Leu Lys Ile
1175                1180                1185

Arg Gln Ile Ser Lys Pro Ser Gly Gly
1190                1195

<210> SEQ ID NO 75
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 75

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
         115                 120                 125

Val Thr Pro Gly Met Ser Pro Ser Leu Leu Pro Leu Glu Cys Val Gln
    130                 135                 140

Gly Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Leu Pro Gly Val Glu Ala Ala Thr Gln Thr Ile Lys
    290                 295                 300

Leu Pro Gln Val Asn Gln Cys Arg Ala Leu Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
        355                 360                 365

Gly Leu Met Pro Thr Glu Pro Gly Pro Arg Pro Thr Leu Pro Arg Gly
    370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
    450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
        515                 520                 525

```
Arg Gly Thr Val Ser Arg Pro Val Thr Pro Leu Ser Glu Pro Ile Pro
    530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Ala Pro Pro Gln Ser
            580                 585                 590

Gly Gly Val Leu Gly Val Glu Gly His Glu Ala Glu Thr Leu Ser
        595                 600                 605

Glu Ile Ser Asp Met Ser Gly Asn Ile Lys Pro Ala Ser Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
                660                 665                 670

Lys Leu Asp Asp Pro Ala Thr Gln Glu Trp Leu Ser Arg Met Trp Asp
                675                 680                 685

Arg Val Asp Met Leu Thr Trp Arg Asn Thr Ser Val Tyr Gln Ala Ile
    690                 695                 700

Cys Thr Leu Asn Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
                740                 745                 750

Thr Glu Asp Val Pro Arg Ile Leu Glu Lys Ile Glu Asn Val Gly Glu
            755                 760                 765

Met Ala Asn Gln Gly Pro Leu Ala Phe Ser Glu Asp Lys Pro Val Asp
    770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Ala Gly Ser Phe Thr
            805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
            835                 840                 845

Gln Val Phe Asp Leu Val Ser His Leu Pro Val Phe Phe Ser Arg Leu
850                 855                 860

Phe Tyr Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
                900                 905                 910

Met Gly Val Phe Gly Cys Trp Leu Ala Phe Ala Val Gly Leu Phe Lys
            915                 920                 925

Pro Val Ser Asp Pro Val Gly Ala Ala Cys Glu Phe Asp Ser Pro Glu
            930                 935                 940

Cys Arg Asn Ile Leu His Ser Phe Glu Leu Leu Lys Pro Trp Asp Pro
```

```
                945                 950                 955                 960
        Val Arg Ser Leu Val Val Gly Pro Val Gly Leu Gly Leu Ala Ile Leu
                        965                 970                 975
        Gly Arg Leu Leu Gly Gly Ala Arg Cys Ile Trp His Phe Leu Leu Arg
                        980                 985                 990
        Leu Gly Ile Val Ala Asp Cys Ile Leu Ala Gly Ala Tyr Val Leu Ser
                    995                1000                1005
        Gln Gly Arg Cys Lys Lys Cys Trp Gly Ser Cys Ile Arg Thr Ala
                1010                1015                1020
        Pro Asn Glu Val Ala Phe Asn Val Phe Pro Phe Thr Arg Ala Thr
                1025                1030                1035
        Arg Ser Ser Leu Ile Asp Leu Cys Asp Arg Phe Cys Ala Pro Lys
                1040                1045                1050
        Gly Met Asp Pro Ile Phe Leu Ala Thr Gly Trp Arg Gly Cys Trp
                1055                1060                1065
        Ala Gly Arg Ser Pro Ile Glu Gln Pro Ser Glu Lys Pro Ile Ala
                1070                1075                1080
        Phe Ala Gln Leu Asp Glu Lys Lys Ile Thr Ala Arg Thr Val Val
                1085                1090                1095
        Ala Gln Pro Tyr Asp Pro Asn Gln Ala Val Lys Cys Leu Arg Val
                1100                1105                1110
        Leu Gln Ala Gly Gly Ala Met Val Ala Lys Ala Val Pro Lys Val
                1115                1120                1125
        Val Lys Val Ser Ala Val Pro Phe Arg Ala Pro Phe Phe Pro Thr
                1130                1135                1140
        Gly Val Lys Val Asp Pro Asp Cys Arg Val Val Val Asp Pro Asp
                1145                1150                1155
        Thr Phe Thr Ala Ala Leu Arg Ser Gly Tyr Ser Thr Thr Asn Leu
                1160                1165                1170
        Val Leu Gly Val Gly Asp Phe Ala Gln Leu Asn Gly Leu Lys Ile
                1175                1180                1185
        Arg Gln Ile Ser Lys Pro Ser Gly Gly
                1190                1195

<210> SEQ ID NO 76
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 76

Gly Ala Gly Lys Arg Ala Arg Lys Ala Arg Ser Cys Ala Thr Ala Thr
        1               5                  10                  15
        Val Ala Gly Arg Ala Leu Ser Val Arg Glu Thr Arg Gln Ala Lys Glu
                    20                  25                  30
        His Glu Val Ala Gly Ala Asn Lys Ala Glu His Leu Lys His Tyr Ser
                35                  40                  45
        Pro Pro Ala Glu Gly Asn Cys Gly Trp His Cys Ile Ser Ala Ile Ala
            50                  55                  60
        Asn Arg Met Val Asn Ser Lys Phe Glu Thr Thr Leu Pro Glu Arg Val
        65                  70                  75                  80
        Arg Pro Pro Asp Asp Trp Ala Thr Asp Glu Asp Leu Val Asn Ala Ile
                        85                  90                  95
```

```
Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
        115                 120                 125

Val Thr Pro Gly Met Ser Pro Ser Leu Leu Pro Leu Glu Cys Val Gln
    130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
        275                 280                 285

Trp Asp Val Val Leu Pro Gly Val Glu Ala Ala Thr Gln Thr Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
        355                 360                 365

Gly Leu Met Pro Thr Glu Pro Gly Pro Arg Pro Thr Leu Pro Arg Gly
    370                 375                 380

Leu Asp Glu Leu Lys Ala Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
        435                 440                 445

Pro Glu Arg Lys Pro Val Pro Ala Pro Arg Arg Lys Val Gly Ser Asp
    450                 455                 460

Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                485                 490                 495

Ala Thr Pro Ser Ser Glu Leu Val Ile Val Ser Ser Pro Gln Cys Ile
            500                 505                 510

Phe Arg Pro Ala Thr Pro Leu Ser Glu Pro Ala Pro Ile Pro Ala Pro
```

```
            515                 520                 525
Arg Gly Thr Val Ser Arg Pro Val Thr Pro Leu Ser Glu Pro Ile Pro
            530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Pro Ala Pro Pro Gln Ser
            580                 585                 590
Gly Gly Val Leu Gly Val Glu Gly His Glu Ala Glu Glu Thr Leu Ser
            595                 600                 605
Glu Ile Ser Asp Met Ser Gly Asn Ile Lys Pro Ala Ser Val Ser Ser
            610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
                675                 680                 685
Arg Val Asp Met Leu Thr Trp Arg Asn Thr Ser Val Tyr Gln Ala Ile
            690                 695                 700
Cys Thr Leu Asp Gly Arg Leu Lys Phe Leu Pro Lys Met Ile Leu Glu
705                 710                 715                 720
Thr Pro Pro Pro Tyr Pro Cys Glu Phe Val Met Met Pro His Thr Pro
                725                 730                 735
Ala Pro Ser Val Gly Ala Glu Ser Asp Leu Thr Ile Gly Ser Val Ala
                740                 745                 750
Thr Glu Asp Val Pro Arg Ile Leu Glu Lys Ile Glu Asn Val Gly Glu
            755                 760                 765
Met Ala Asn Gln Gly Pro Leu Ala Phe Ser Glu Asp Lys Pro Val Asp
            770                 775                 780
Asp Gln Leu Val Asn Asp Pro Arg Ile Ser Ser Arg Arg Pro Asp Glu
785                 790                 795                 800
Ser Thr Ser Ala Pro Ser Ala Gly Thr Gly Gly Ala Gly Ser Phe Thr
                805                 810                 815
Asp Leu Pro Pro Ser Asp Gly Ala Asp Ala Asp Gly Gly Pro Phe
                820                 825                 830
Arg Thr Val Lys Arg Lys Ala Glu Arg Leu Phe Asp Gln Leu Ser Arg
            835                 840                 845
Gln Val Phe Asp Leu Val Ser His Leu Pro Val Phe Phe Ser Arg Leu
            850                 855                 860
Phe Tyr Pro Gly Gly Gly Tyr Ser Pro Gly Asp Trp Gly Phe Ala Ala
865                 870                 875                 880
Phe Thr Leu Leu Cys Leu Phe Leu Cys Tyr Ser Tyr Pro Ala Phe Gly
                885                 890                 895
Ile Ala Pro Leu Leu Gly Val Phe Ser Gly Ser Ser Arg Arg Val Arg
                900                 905                 910
Met Gly Val Phe Gly Cys Trp Leu Ala Phe Ala Val Gly Leu Phe Lys
            915                 920                 925
Pro Val Ser Asp Pro Val Gly Ala Ala Cys Glu Phe Asp Ser Pro Glu
            930                 935                 940
```

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
            965                 970                 975

Gly Arg Leu Leu Gly Gly Ala Arg Cys Ile Trp His Phe Leu Leu Arg
        980                 985                 990

Leu Gly Ile Val Ala Asp Cys Ile Leu Ala Gly Ala Tyr Val Leu Ser
    995                 1000                1005

Gln Gly Arg Cys Lys Lys Cys Trp Gly Ser Cys Ile Arg Thr Ala
1010            1015                1020

Pro Asn Glu Val Ala Phe Asn Val Phe Pro Phe Thr Arg Ala Thr
1025            1030                1035

Arg Ser Ser Leu Ile Asp Leu Cys Asp Arg Phe Cys Ala Pro Lys
1040            1045                1050

Gly Met Asp Pro Ile Phe Leu Ala Thr Gly Trp Arg Gly Cys Trp
1055            1060                1065

Ala Gly Arg Ser Pro Ile Glu Gln Pro Ser Glu Lys Pro Ile Ala
1070            1075                1080

Phe Ala Gln Leu Asp Glu Lys Lys Ile Thr Ala Arg Thr Val Val
1085            1090                1095

Ala Gln Pro Tyr Asp Pro Asn Gln Ala Val Lys Cys Leu Arg Val
1100            1105                1110

Leu Gln Ala Gly Gly Ala Met Val Ala Lys Ala Val Pro Lys Val
1115            1120                1125

Val Lys Val Ser Ala Val Pro Phe Arg Ala Pro Phe Phe Pro Thr
1130            1135                1140

Gly Val Lys Val Asp Pro Asp Cys Arg Val Val Val Asp Pro Asp
1145            1150                1155

Thr Phe Thr Ala Ala Leu Arg Ser Gly Tyr Ser Thr Thr Asn Leu
1160            1165                1170

Val Leu Gly Val Gly Asp Phe Ala Gln Leu Asn Gly Leu Lys Ile
1175            1180                1185

Arg Gln Ile Ser Lys Pro Ser Gly Gly
1190            1195

<210> SEQ ID NO 77
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 77

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asn Lys Ala Glu His Leu Lys His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Pro Asp Asp Trp Ala Thr Asp Glu Asp Leu Val Asn Ala Ile

-continued

```
            85                  90                  95
Gln Ile Leu Arg Leu Pro Ala Ala Leu Asp Arg Asn Gly Ala Cys Thr
            100                 105                 110
Ser Ala Lys Tyr Val Leu Lys Leu Glu Gly Glu His Trp Thr Val Thr
            115                 120                 125
Val Thr Pro Gly Met Ser Pro Ser Leu Leu Pro Leu Glu Cys Val Gln
130                 135                 140
Gly Cys Cys Gly His Lys Gly Leu Gly Ser Pro Asp Ala Val Glu
145                 150                 155                 160
Val Ser Gly Phe Asp Pro Ala Cys Leu Asp Arg Leu Ala Glu Val Met
                165                 170                 175
His Leu Pro Ser Ser Ala Ile Pro Ala Ala Leu Ala Glu Met Ser Gly
            180                 185                 190
Asp Ser Asp Arg Ser Ala Ser Pro Val Thr Thr Val Trp Thr Val Ser
            195                 200                 205
Gln Phe Phe Ala Arg His Ser Gly Gly Asn His Pro Asp Gln Val Arg
        210                 215                 220
Leu Gly Lys Ile Leu Ser Leu Cys Gln Val Ile Glu Asp Cys Cys Cys
225                 230                 235                 240
Ser Gln Asn Lys Thr Asn Arg Val Thr Pro Glu Glu Val Ala Ala Lys
                245                 250                 255
Ile Asp Leu Tyr Leu Arg Gly Ala Thr Asn Leu Glu Glu Cys Leu Ala
            260                 265                 270
Arg Leu Glu Lys Ala Arg Pro Pro Arg Val Ile Asp Thr Phe Phe Asp
        275                 280                 285
Trp Asp Val Val Leu Pro Gly Val Glu Ala Ala Thr Gln Thr Ile Lys
    290                 295                 300
Leu Pro Gln Val Asn Gln Cys Arg Ala Leu Val Pro Val Thr Gln
305                 310                 315                 320
Lys Ser Leu Asp Asn Asn Ser Val Pro Leu Thr Ala Phe Ser Leu Ala
                325                 330                 335
Asn His Tyr Tyr Arg Ala Gln Gly Asp Glu Val Arg His Arg Glu Arg
            340                 345                 350
Leu Thr Ala Val Leu Ser Asn Leu Glu Lys Val Val Arg Glu Glu Tyr
        355                 360                 365
Gly Leu Met Pro Thr Glu Pro Gly Pro Arg Pro Thr Leu Pro Arg Gly
    370                 375                 380
Leu Asp Glu Leu Lys Asp Gln Met Glu Glu Asp Leu Leu Lys Leu Ala
385                 390                 395                 400
Asn Ala Gln Thr Thr Ser Asp Met Met Ala Trp Ala Val Glu Gln Val
                405                 410                 415
Asp Leu Lys Thr Trp Val Lys Asn Tyr Pro Arg Trp Thr Pro Pro
            420                 425                 430
Pro Pro Pro Lys Val Gln Pro Arg Lys Thr Lys Pro Val Lys Ser Leu
        435                 440                 445
Pro Glu Arg Lys Pro Val Pro Ala Pro Arg Arg Lys Val Gly Ser Asp
    450                 455                 460
Cys Gly Ser Pro Val Ser Leu Gly Gly Asp Val Pro Asn Ser Trp Glu
465                 470                 475                 480
Asp Leu Ala Val Ser Ser Pro Phe Asp Leu Pro Thr Pro Glu Pro
                485                 490                 495
Ala Thr Pro Ser Ser Glu Leu Val Ile Val Ser Ser Pro Gln Cys Ile
            500                 505                 510
```

```
Phe Arg Pro Ala Thr Pro Leu Ser Glu Pro Ala Pro Ile Pro Ala Pro
        515                 520                 525

Arg Gly Thr Val Ser Arg Pro Val Thr Pro Leu Ser Glu Pro Ile Pro
530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Pro Ala Pro Pro Gln Ser
            580                 585                 590

Gly Gly Val Leu Gly Val Glu Gly His Glu Ala Glu Thr Leu Ser
            595                 600                 605

Glu Ile Ser Asp Met Ser Gly Asn Ile Lys Pro Ala Ser Val Ser Ser
        610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Ala Cys Leu Ser Val Met Arg Glu Ala Cys Asp Ala Thr
            660                 665                 670

Lys Leu Asp Asp Pro Ala Thr Gln Glu Trp Leu Ser Arg Met Trp Asp
        675                 680                 685

Arg Val Asp Met Leu Thr Trp Arg Asn Thr Ser Val Tyr Gln Ala Ile
690                 695                 700

Cys Thr Leu Asp Gly Arg Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Ala
            740                 745                 750

Thr Glu Asp Val Pro Arg Ile Leu Glu Lys Ile Glu Asn Val Gly Glu
        755                 760                 765

Met Ala Asn Gln Gly Pro Leu Ala Phe Ser Glu Asp Lys Pro Val Asp
770                 775                 780

Asp Gln Leu Val Asn Asp Pro Arg Ile Ser Ser Arg Arg Pro Asp Glu
785                 790                 795                 800

Ser Thr Ser Ala Pro Ser Ala Gly Thr Gly Ala Gly Phe Phe Thr
                805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
850                 855                 860

Phe Cys Pro Gly Gly Tyr Ser Pro Gly Asp Trp Gly Phe Ala Ala
865                 870                 875                 880

Leu Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
        915                 920                 925
```

```
Pro Val Ser Asp Pro Val Gly Ala Ala Cys Glu Phe Asp Ser Pro Glu
        930                 935                 940
Cys Arg Asn Ile Leu His Ser Phe Glu Leu Leu Lys Pro Trp Asp Pro
945                 950                 955                 960
Val Arg Ser Leu Val Val Gly Pro Val Gly Leu Gly Leu Ala Ile Leu
                965                 970                 975
Gly Arg Leu Leu Gly Gly Ala Arg Cys Ile Trp His Phe Leu Leu Arg
            980                 985                 990
Leu Gly Ile Val Ala Asp Cys Ile  Leu Ala Gly Ala Tyr Val Leu Ser
        995                 1000                1005
Gln Gly Arg Cys Lys Lys Cys Trp Gly Ser Cys Ile Arg Thr Ala
    1010                1015                1020
Pro Asn Glu Val Ala Phe Asn Val Phe Pro Phe Thr Arg Ala Thr
    1025                1030                1035
Arg Ser Ser Leu Ile Asp Leu Cys Asp Arg Phe Cys Ala Pro Lys
    1040                1045                1050
Gly Met Asp Pro Ile Phe Leu Ala Thr Gly Trp Arg Gly Cys Trp
    1055                1060                1065
Ala Gly Arg Ser Pro Ile Glu Gln Pro Ser Glu Lys Pro Ile Ala
    1070                1075                1080
Phe Ala Gln Leu Asp Glu Lys Lys Ile Thr Ala Arg Thr Val Val
    1085                1090                1095
Ala Gln Pro Tyr Asp Pro Asn Gln Ala Val Lys Cys Leu Arg Val
    1100                1105                1110
Leu Gln Ala Gly Gly Ala Met Val Ala Lys Ala Val Pro Lys Val
    1115                1120                1125
Val Lys Val Ser Ala Val Pro Phe Arg Ala Pro Phe Phe Pro Thr
    1130                1135                1140
Gly Val Lys Val Asp Pro Asp Cys Arg Val Val Val Asp Pro Asp
    1145                1150                1155
Thr Phe Thr Ala Ala Leu Arg Ser Gly Tyr Ser Thr Thr Asn Leu
    1160                1165                1170
Val Leu Gly Val Gly Asp Phe Ala Gln Leu Asn Gly Leu Lys Ile
    1175                1180                1185
Arg Gln Ile Ser Lys Pro Ser Gly Gly
    1190                1195

<210> SEQ ID NO 78
<211> LENGTH: 1233
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 78

Gly Ala Gly Lys Arg Ala Arg Lys Ala Arg Ser Ser Ala Thr Ala Thr
1               5                   10                  15
Val Ala Gly Arg Ala Leu Pro Val Arg Glu Thr Arg Gln Val Glu Glu
                20                  25                  30
His Glu Val Ala Gly Ala Asn Lys Ala Glu His Leu Lys His Tyr Ser
            35                  40                  45
Pro Pro Ala Glu Gly Asn Cys Gly Trp His Cys Ile Ser Ala Ile Gly
        50                  55                  60
Asn Arg Met Leu Asn Ser Lys Phe Glu Thr Thr Leu Pro Glu Arg Val
65                  70                  75                  80
```

```
Arg Pro Pro Asp Asp Trp Ala Thr Asp Glu Asp Leu Val Asn Ala Ile
            85                  90                  95

Gln Ile Leu Arg Leu Pro Ala Ala Leu Asp Arg Asn Gly Ala Cys Ala
        100                 105                 110

Ser Ala Lys Tyr Val Leu Lys Leu Glu Gly Glu His Trp Thr Val Thr
    115                 120                 125

Val Thr Pro Gly Met Ser Pro Ser Leu Leu Pro Leu Glu Cys Val Gln
130                 135                 140

Gly Cys Cys Glu His Lys Gly Gly Leu Gly Ser Pro Asp Ala Val Glu
145                 150                 155                 160

Val Phe Gly Phe Asp Pro Ala Cys Leu Asp Trp Leu Ala Glu Val Met
                165                 170                 175

His Leu Pro Ser Asn Ala Ile Pro Ala Ala Leu Ala Glu Met Ser Gly
            180                 185                 190

Asp Ser Asn Arg Pro Ala Ser Pro Val Thr Thr Val Trp Thr Val Ser
            195                 200                 205

Gln Phe Leu Ala Arg His Asn Gly Gly Asn His Pro Asp Gln Ile Arg
        210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Val Ala Ala Lys
                245                 250                 255

Ile Asp Leu Tyr Leu Arg Gly Ala Thr Asn Leu Glu Glu Cys Leu Ala
                260                 265                 270

Arg Leu Glu Lys Ala Arg Pro Pro Arg Val Met Asp Thr Ser Phe Asp
            275                 280                 285

Trp Asp Val Val Leu Pro Gly Val Glu Ala Ala Thr Gln Thr Thr Glu
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
                340                 345                 350

Leu Thr Ala Val Leu Ser Lys Leu Glu Gly Val Arg Glu Glu Tyr
                355                 360                 365

Gly Leu Met Pro Thr Gly Pro Gly Pro Arg Pro Thr Leu Pro Arg Gly
    370                 375                 380

Leu Asp Glu Leu Lys Asp Gln Met Glu Val Asp Leu Leu Lys Leu Ala
385                 390                 395                 400

Asn Ala Gln Met Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430

Pro Pro Pro Ile Val Gln Pro Arg Lys Thr Lys Leu Val Lys Ser Leu
            435                 440                 445

Pro Glu Ser Lys Pro Val Pro Ala Pro Arg Arg Lys Val Arg Ser Asp
    450                 455                 460

Cys Asp Cys Pro Thr Leu Ser Gly Asn Asn Leu Pro Asp Ser Trp Glu
465                 470                 475                 480

Asp Leu Ala Val Gly Cys Pro Ser Asp Leu Pro Thr Ser Pro Glu Pro
                485                 490                 495
```

-continued

```
Val Thr Pro Leu Ser Glu Pro Ala Ser Val Ser Ala Pro Arg Arg Ser
            500                 505                 510
Phe Arg Pro Val Lys Pro Leu Ser Glu Pro Val Pro Val Pro Ala Pro
        515                 520                 525
Arg Lys Thr Val Ser Arg Pro Ala Thr Pro Leu Ser Glu Pro Ile Pro
    530                 535                 540
Val Pro Ala Pro Arg Arg Lys Phe Gln Gln Val Glu Lys Val Asn Pro
545                 550                 555                 560
Ala Ala Ala Thr Leu Gly Cys Gln Asp Glu Phe Pro Asp Leu Ser Ala
                565                 570                 575
Ser Ser His Thr Glu Tyr Glu Ala Ser Pro Leu Val Leu Pro Gln Asn
            580                 585                 590
Gly Asp Val Leu Glu Val Glu Arg Glu Ala Glu Glu Ile Leu Ser
        595                 600                 605
Gly Ile Ser Asp Ile Leu Asp Ala Ile Lys Pro Ala Ser Ala Ser Ser
    610                 615                 620
Ser Ser Ser Leu Ser Ser Val Ala Ile Thr Arg Pro Lys Tyr Ser Ala
625                 630                 635                 640
Gln Ala Ile Ile Asp Ser Gly Gly Pro Tyr Ser Gly His Leu Gln Glu
                645                 650                 655
Val Lys Glu Thr Cys Leu Ser Ile Met Ser Glu Ala Cys Asp Val Thr
            660                 665                 670
Lys Leu Asp Asp Pro Ala Thr Gln Glu Trp Leu Ser Arg Met Trp Asp
        675                 680                 685
Arg Val Asp Met Leu Thr Trp Arg Asn Thr Ser Val His Gln Ala Ser
    690                 695                 700
Arg Thr Leu Asp Asp Asp Phe Lys Phe Leu Pro Lys Met Ile Leu Glu
705                 710                 715                 720
Thr Pro Pro Pro Tyr Pro Cys Gly Phe Val Met Met Pro Arg Thr Pro
                725                 730                 735
Ala Pro Ser Val Gly Ala Glu Ser Asp Leu Thr Ile Gly Ser Val Ala
            740                 745                 750
Thr Glu Asp Val Pro Arg Ile Phe Gly Lys Val Asn Asp Val Cys Lys
        755                 760                 765
Met Ile Asp Gln Arg Pro Leu Val Leu Phe Glu Asn Glu Leu Ala Asp
    770                 775                 780
Asp Gln Pro Ala Arg Asp Pro Arg Thr Ser Gln Arg Phe Asp Gly
785                 790                 795                 800
Ser Thr Pro Ala Pro Pro Ala Gly Thr Asp Gly Thr Gly Leu Ala Ser
                805                 810                 815
Gly Pro Gly Val Arg Glu Val Asp Ser Cys Glu Ala Ser Ser Thr Glu
            820                 825                 830
Lys Ile Glu Gln Pro Phe Val Leu Asn Gly Gly Ala Ser Thr Gln Ala
        835                 840                 845
Ser Thr Phe Thr Asn Leu Pro Pro Gly Gly Ile Asp Ala Gly Gly
    850                 855                 860
Ser Gly Pro Leu Gln Thr Val Arg Lys Lys Ala Glu Arg Phe Phe Asp
865                 870                 875                 880
Leu Leu Ser Arg Gln Val Phe Asn Leu Val Ser His Leu Pro Val Phe
                885                 890                 895
Phe Ser Arg Leu Phe Lys Pro Gly Gly Asp Tyr Ser Pro Gly Asp Trp
            900                 905                 910
Gly Phe Ala Ala Phe Thr Leu Leu Cys Leu Phe Leu Cys Tyr Ser Tyr
```

```
                        915                 920                 925

Pro Ala Phe Gly Ala Val Pro Leu Leu Gly Val Phe Ser Gly Ser Ser
            930                 935                 940

Arg Arg Val Arg Met Gly Phe Phe Gly Cys Trp Leu Ala Phe Ala Val
945                 950                 955                 960

Ser Leu Phe Lys Pro Val Ser Asp Pro Val Gly Ala Ala Cys Glu Phe
                965                 970                 975

Asp Ser Pro Glu Cys Arg Asn Ile Leu His Ser Phe Glu Leu Leu Lys
            980                 985                 990

Pro Trp Asp Pro Val Arg Gly Leu Val Val Gly Pro Val Gly Leu Ser
            995                 1000                1005

Leu Ala Ile Phe Gly Arg Leu Leu Gly Gly Ala Arg His Ile Trp
        1010                1015                1020

His Phe Leu Leu Arg Phe Gly Ile Val Ala Asp Cys Ile Leu Ala
        1025                1030                1035

Gly Ala Tyr Val Leu Ser Gln Gly Arg Cys Lys Lys Cys Trp Gly
        1040                1045                1050

Ser Cys Ile Arg Thr Ala Pro Asn Glu Val Ala Phe Asn Val Phe
        1055                1060                1065

Pro Phe Thr Arg Ala Thr Arg Ser Ser Leu Ile Asp Leu Cys Asn
        1070                1075                1080

Arg Phe Cys Ala Pro Lys Gly Met Asp Pro Ile Phe Phe Ala Thr
        1085                1090                1095

Gly Trp Arg Gly Cys Trp Thr Gly Arg Ser Pro Ile Glu Gln Pro
        1100                1105                1110

Ser Glu Lys Pro Ile Ala Phe Ala Gln Leu Asp Glu Lys Lys Ile
        1115                1120                1125

Thr Ala Arg Thr Val Val Ala Gln Pro Tyr Asp Pro Asn Gln Ala
        1130                1135                1140

Val Lys Cys Leu Arg Val Leu Gln Ala Gly Gly Val Met Val Ala
        1145                1150                1155

Glu Ala Val Pro Lys Val Val Lys Val Ser Ala Val Pro Phe Arg
        1160                1165                1170

Ala Pro Phe Phe Pro Thr Gly Val Lys Val Asp Pro Glu Cys Arg
        1175                1180                1185

Ile Val Val Asp Pro Asp Thr Phe Thr Ala Ala Leu Arg Ser Gly
        1190                1195                1200

Tyr Ser Thr Thr Asn Leu Val Leu Gly Val Gly Asp Phe Ala Gln
        1205                1210                1215

Leu Asn Gly Leu Lys Ile Arg Gln Ile Ser Lys Pro Ser Gly Gly
        1220                1225                1230

<210> SEQ ID NO 79
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 79

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30
```

-continued

```
His Glu Val Ala Gly Ala Asn Lys Ala Glu His Leu Lys His Tyr Ser
     35                  40                  45
Pro Pro Ala Glu Gly Asn Cys Gly Trp His Cys Ile Ser Ala Ile Ala
 50                  55                  60
Asn Arg Met Val Asn Ser Lys Phe Glu Thr Thr Leu Pro Glu Arg Val
 65                  70                  75                  80
Arg Pro Pro Asp Asp Trp Ala Thr Asp Glu Asp Leu Val Asn Ala Ile
                 85                  90                  95
Gln Ile Leu Arg Leu Pro Ala Ala Leu Asp Arg Asn Gly Ala Cys Thr
                100                 105                 110
Ser Ala Lys Tyr Val Leu Lys Leu Glu Gly Glu His Trp Thr Val Thr
            115                 120                 125
Val Thr Pro Gly Met Ser Pro Ser Leu Leu Pro Leu Glu Cys Val Gln
130                 135                 140
Gly Cys Cys Gly His Lys Gly Gly Leu Gly Ser Pro Asp Ala Val Glu
145                 150                 155                 160
Val Ser Gly Phe Asp Pro Ala Cys Leu Asp Arg Leu Ala Glu Val Met
                165                 170                 175
His Leu Pro Ser Ser Ala Ile Pro Ala Ala Leu Ala Glu Met Ser Gly
            180                 185                 190
Asp Ser Asp Arg Ser Ala Ser Pro Val Thr Thr Val Trp Thr Val Ser
        195                 200                 205
Gln Phe Phe Ala Arg His Ser Gly Gly Asn His Pro Asp Gln Val Arg
    210                 215                 220
Leu Gly Lys Ile Ile Ser Leu Cys Gln Val Ile Glu Asp Cys Cys Cys
225                 230                 235                 240
Ser Gln Asn Lys Thr Asn Arg Val Thr Pro Glu Glu Val Ala Ala Lys
                245                 250                 255
Phe Asp Leu Tyr Leu Arg Gly Ala Thr Asn Leu Glu Glu Cys Leu Ala
                260                 265                 270
Arg Leu Glu Lys Ala Arg Pro Pro Arg Val Ile Asp Thr Phe Phe Asp
            275                 280                 285
Trp Asp Val Val Leu Pro Gly Val Glu Ala Ala Thr Gln Thr Ile Lys
290                 295                 300
Leu Pro Gln Val Asn Gln Cys Arg Ala Leu Val Pro Val Val Thr Gln
305                 310                 315                 320
Lys Ser Leu Asp Asn Asn Ser Val Pro Leu Thr Ala Phe Ser Leu Ala
                325                 330                 335
Asn Tyr Tyr Tyr Arg Ala Gln Gly Asp Glu Val Arg His Arg Glu Arg
                340                 345                 350
Leu Thr Ala Val Leu Ser Lys Leu Glu Lys Val Val Arg Glu Glu Tyr
            355                 360                 365
Gly Leu Met Pro Thr Lys Pro Gly Pro Arg Pro Thr Leu Pro Arg Gly
370                 375                 380
Leu Asp Glu Leu Lys Asp Gln Met Glu Glu Asp Leu Leu Lys Leu Ala
385                 390                 395                 400
Asn Ala Gln Thr Thr Ser Asp Met Met Ala Trp Ala Ala Glu Gln Val
                405                 410                 415
Asp Leu Lys Thr Trp Val Lys Asn Tyr Pro Arg Trp Thr Pro Pro Pro
                420                 425                 430
Pro Ser Pro Lys Val Gln Leu Arg Lys Thr Lys Pro Val Lys Ser Leu
            435                 440                 445
Pro Lys Arg Lys Pro Val Pro Ala Pro Arg Arg Lys Val Gly Ser Asp
```

```
            450                 455                 460
Cys Gly Ser Pro Val Ser Leu Gly Gly Asp Val Pro Asn Ser Trp Glu
465                 470                 475                 480

Asp Leu Ala Val Ser Ser Pro Phe Asp Leu Pro Thr Pro Pro Glu Pro
                    485                 490                 495

Ala Ile Pro Ser Ser Glu Leu Val Ile Val Ser Ser Pro Gln Cys Ile
                500                 505                 510

Phe Arg Pro Ala Thr Pro Leu Ser Glu Pro Ala Pro Ile Pro Ala Pro
            515                 520                 525

Arg Gly Thr Val Ser Arg Pro Val Thr Pro Leu Ser Glu Pro Ile Pro
        530                 535                 540

Val Pro Ala Pro Arg Arg Lys Phe Gln Gln Val Lys Arg Leu Ser Ser
545                 550                 555                 560

Ala Ala Ala Ile Pro Pro Tyr Gln Asn Glu Pro Leu Asp Leu Ser Ala
                565                 570                 575

Ser Ser Gln Thr Glu Tyr Glu Ala Ser Pro Pro Ala Pro Pro Gln Ser
                580                 585                 590

Gly Gly Val Leu Gly Val Glu Gly His Glu Ala Glu Thr Leu Ser
        595                 600                 605

Glu Ile Ser Asp Met Ser Gly Asn Ile Lys Pro Ala Ser Val Ser Ser
        610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Glu
                645                 650                 655

Val Lys Glu Thr Cys Leu Ser Val Met Arg Glu Ala Cys Asp Ala Thr
                660                 665                 670

Lys Leu Asp Asp Pro Ala Thr Gln Glu Trp Leu Ser Arg Met Trp Asp
            675                 680                 685

Arg Val Asp Met Leu Thr Trp Arg Asn Thr Ser Val Tyr Gln Val Ile
        690                 695                 700

Cys Thr Leu Asp Gly Met Leu Lys Phe Leu Pro Lys Met Ile Leu Glu
705                 710                 715                 720

Thr Pro Pro Pro Tyr Pro Cys Glu Phe Val Met Met Pro His Thr Pro
                725                 730                 735

Ala Pro Ser Val Gly Ala Glu Ser Asp Leu Thr Ile Gly Ser Val Thr
                740                 745                 750

Thr Glu Asp Val Pro Arg Ile Leu Glu Lys Ile Gly Asn Val Gly Glu
            755                 760                 765

Met Ala Asn Gln Gly Pro Leu Ala Phe Ser Glu Asp Lys Pro Val Asp
770                 775                 780

Asp Gln Leu Val Asn Asp Pro Arg Ile Ser Arg Arg Pro Asp Glu
785                 790                 795                 800

Ser Thr Ser Ala Pro Ser Ala Gly Thr Gly Ala Gly Ser Phe Thr
                805                 810                 815

Asp Leu Pro Pro Ser Asp Gly Ala Asp Ala Asp Gly Gly Pro Phe
            820                 825                 830

Arg Thr Val Lys Arg Lys Ala Glu Arg Leu Phe Asp Gln Leu Ser Arg
        835                 840                 845

Gln Val Phe Asp Leu Val Ser His Leu Pro Val Phe Phe Ser Arg Leu
        850                 855                 860

Phe Tyr Pro Gly Gly Gly Tyr Ser Pro Gly Asp Trp Gly Phe Ala Ala
865                 870                 875                 880
```

```
Phe Thr Leu Leu Cys Leu Phe Leu Cys Tyr Ser Tyr Pro Ala Phe Gly
            885                 890                 895

Ile Ala Pro Leu Leu Gly Val Phe Gly Ser Ser Arg Arg Val Arg
        900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
            965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
            995                1000                1005

Gln Gly Arg Cys Lys Lys Cys Trp Gly Ser Cys Ile Arg Thr Ala
        1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Glu Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asn Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 80
<211> LENGTH: 1196
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 80

Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Arg Glu
```

```
                20                  25                  30
His Glu Val Ala Gly Ala Asn Lys Ala Glu His Leu Lys His Tyr Ser
            35                  40                  45

Pro Pro Ala Glu Gly Asn Cys Gly Trp His Cys Ile Ser Ala Ile Ala
 50                  55                  60

Asn Arg Met Val Asn Ser Lys Phe Glu Thr Thr Leu Pro Glu Arg Val
 65                  70                  75                  80

Arg Pro Pro Asp Asp Trp Ala Thr Asp Glu Asp Leu Val Asn Ala Ile
            85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
            115                 120                 125

Val Thr Pro Gly Met Ser Pro Ser Leu Leu Pro Leu Glu Cys Val Gln
            130                 135                 140

Gly Cys Cys Gly His Lys Gly Leu Gly Ser Pro Asp Ala Val Glu
145                 150                 155                 160

Val Ser Gly Phe Asp Pro Ala Cys Leu Asp Arg Leu Ala Glu Val Met
            165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
            210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
            245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Phe Phe Asp
            275                 280                 285

Trp Asp Val Leu Pro Gly Val Glu Ala Ala Thr Gln Thr Ile Lys
            290                 295                 300

Leu Pro Gln Val Asn Gln Cys Arg Ala Leu Val Pro Val Thr Gln
305                 310                 315                 320

Lys Ser Leu Asp Asn Asn Ser Val Pro Leu Thr Ala Phe Ser Leu Ala
            325                 330                 335

Asn Tyr Tyr Arg Ala Gln Gly Asp Glu Val Arg His Arg Glu Arg
            340                 345                 350

Leu Thr Ala Val Leu Ser Asn Leu Glu Lys Val Val Arg Glu Glu Tyr
            355                 360                 365

Gly Leu Met Pro Thr Glu Pro Gly Pro Arg Pro Thr Leu Pro Arg Gly
            370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
            405                 410                 415

Asp Leu Lys Thr Trp Val Lys Asn Tyr Pro Arg Trp Thr Pro Pro Pro
            420                 425                 430

Pro Pro Pro Lys Val Gln Pro Arg Lys Thr Lys Pro Val Lys Ser Leu
            435                 440                 445
```

-continued

```
Pro Glu Arg Lys Pro Val Pro Ala Pro Arg Arg Lys Val Gly Ser Asp
    450                 455                 460
Cys Gly Ser Pro Val Ser Leu Gly Gly Asp Val Pro Asn Ser Trp Glu
465                 470                 475                 480
Asp Leu Ala Val Ser Ser Pro Phe Asp Leu Pro Thr Pro Pro Glu Leu
                    485                 490                 495
Ala Thr Pro Ser Ser Glu Leu Val Ile Val Ser Ser Pro Gln Cys Ile
                500                 505                 510
Phe Arg Pro Ala Thr Pro Leu Ser Glu Pro Ala Pro Ile Pro Ala Pro
            515                 520                 525
Arg Gly Thr Val Ser Arg Pro Val Thr Pro Leu Ser Glu Pro Ile Pro
        530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Pro Ala Pro Pro Gln Ser
                580                 585                 590
Gly Gly Val Leu Gly Val Glu Gly His Glu Ala Glu Glu Thr Leu Ser
            595                 600                 605
Glu Ile Ser Asp Met Ser Gly Asn Ile Lys Pro Ala Ser Val Ser Ser
        610                 615                 620
Ser Ser Ser Leu Ser Ser Val Arg Ile Thr Arg Pro Lys Tyr Ser Ala
625                 630                 635                 640
Gln Ala Ile Ile Asp Ser Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
        675                 680                 685
Arg Val Asp Met Leu Thr Cys Asn Thr Ser Val Tyr Gln Ala Ile Cys
        690                 695                 700
Thr Leu Asp Gly Arg Leu Lys Phe Leu Pro Lys Leu Ile Leu Glu Thr
705                 710                 715                 720
Pro Pro Pro Tyr Pro Cys Glu Phe Val Met Met Pro His Thr Pro Ala
                725                 730                 735
Pro Ser Val Gly Ala Glu Ser Asp Leu Thr Ile Gly Ser Val Ala Thr
                740                 745                 750
Glu Asp Val Pro Arg Ile Leu Glu Lys Thr Glu Asn Val Gly Glu Met
            755                 760                 765
Ala Asn Gln Gly Pro Leu Ala Phe Ser Glu Asp Lys Pro Val Asp Asp
770                 775                 780
Gln Leu Val Asn Asp Pro Arg Ile Ser Ser Arg Arg Pro Asp Glu Ser
785                 790                 795                 800
Thr Ser Ala Pro Ser Ala Gly Thr Gly Gly Ala Gly Ser Phe Thr Asp
                805                 810                 815
Leu Pro Pro Ser Asp Gly Ala Asp Ala Asp Gly Gly Pro Phe Arg
                820                 825                 830
Thr Val Lys Arg Lys Ala Glu Arg Leu Phe Asp Gln Leu Ser Arg Gln
            835                 840                 845
Val Phe Asp Leu Val Ser His Leu Pro Val Phe Phe Ser Arg Leu Phe
        850                 855                 860
```

```
Tyr Pro Gly Gly Gly Tyr Ser Pro Gly Asp Trp Gly Phe Ala Ala Phe
865                 870                 875                 880

Thr Leu Leu Cys Leu Phe Leu Cys Tyr Ser Tyr Pro Ala Phe Gly Ile
            885                 890                 895

Ala Pro Leu Leu Gly Val Phe Ser Gly Ser Ser Arg Arg Val Arg Met
        900                 905                 910

Gly Val Phe Gly Cys Trp Leu Ala Phe Ala Val Gly Leu Phe Lys Pro
    915                 920                 925

Val Ser Asp Pro Val Gly Ala Ala Cys Glu Phe Asp Ser Pro Glu Cys
930                 935                 940

Arg Asn Ile Leu His Ser Phe Glu Leu Leu Lys Pro Trp Asp Pro Val
945                 950                 955                 960

Arg Ser Leu Val Val Gly Pro Val Gly Leu Gly Leu Ala Ile Leu Gly
            965                 970                 975

Arg Leu Leu Gly Gly Ala Arg Cys Ile Trp His Phe Leu Leu Arg Leu
            980                 985                 990

Gly Ile Val Ala Asp Cys Ile Leu Ala Gly Ala Tyr Val Leu Ser Gln
        995                1000                1005

Gly Arg Cys Lys Lys Cys Trp Gly Ser Cys Ile Arg Thr Ala Pro
    1010                1015                1020

Asn Glu Val Ala Phe Asn Val Phe Pro Phe Thr Arg Ala Thr Arg
    1025                1030                1035

Ser Ser Leu Ile Asp Leu Cys Asp Arg Phe Cys Ala Pro Lys Gly
    1040                1045                1050

Met Asp Pro Ile Phe Leu Ala Thr Gly Trp Arg Gly Cys Trp Ala
    1055                1060                1065

Gly Arg Ser Pro Ile Glu Gln Pro Ser Glu Lys Pro Ile Ala Phe
    1070                1075                1080

Ala Gln Leu Asp Glu Lys Lys Ile Thr Ala Arg Thr Val Val Ala
    1085                1090                1095

Gln Pro Tyr Asp Pro Asn Gln Ala Val Lys Cys Leu Arg Val Leu
    1100                1105                1110

Gln Ala Gly Gly Ala Met Val Ala Lys Ala Val Pro Lys Val Val
    1115                1120                1125

Lys Val Ser Ala Val Pro Phe Arg Ala Pro Phe Phe Pro Thr Gly
    1130                1135                1140

Val Lys Val Asp Pro Asp Cys Arg Val Val Asp Pro Asp Thr
    1145                1150                1155

Phe Thr Ala Ala Leu Arg Ser Gly Tyr Pro Thr Thr Asn Leu Val
    1160                1165                1170

Leu Gly Val Gly Asp Phe Ala Gln Leu Asn Gly Leu Lys Ile Arg
    1175                1180                1185

Gln Ile Ser Lys Pro Ser Gly Gly
    1190                1195

<210> SEQ ID NO 81
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 81

Gly Ala Gly Lys Arg Ala Arg Lys Ala Arg Ser Cys Ala Thr Ala Thr
1               5                   10                  15
```

```
Val Ala Gly Arg Ala Leu Ser Val Cys Glu Thr Arg Gln Ala Lys Glu
             20                  25                  30

His Glu Val Ala Gly Thr Asn Lys Ala Glu His Leu Lys His Tyr Ser
         35                  40                  45

Pro Pro Ala Glu Gly Asn Cys Gly Trp His Cys Ile Ser Ala Ile Ala
 50                  55                  60

Asn Arg Met Val Asn Ser Ile Phe Glu Thr Thr Leu Pro Glu Arg Val
65                   70                  75                  80

Arg Pro Pro Asp Asp Trp Ala Thr Asp Glu Asp Leu Val Asn Ala Ile
                 85                  90                  95

Gln Ile Leu Arg Leu Pro Ala Ala Leu Asp Arg Asn Gly Ala Cys Thr
             100                 105                 110

Ser Ala Lys Tyr Val Leu Lys Leu Glu Gly Glu His Trp Thr Val Thr
         115                 120                 125

Val Thr Pro Gly Met Ser Pro Ser Leu Leu Pro Leu Glu Cys Val Gln
130                 135                 140

Gly Cys Cys Gly His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
        195                 200                 205

Gln Phe Phe Ala Arg His Ser Gly Gly Asn His Pro Asp Gln Val Arg
    210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Ser Phe Asp
        275                 280                 285

Trp Asp Val Val Leu Pro Gly Val Glu Ala Ala Thr Gln Met Ile Lys
    290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Lys Val Val Arg Glu Glu Tyr
        355                 360                 365

Gly Leu Val Pro Thr Glu Pro Gly Pro Gln Pro Thr Leu Pro Arg Gly
    370                 375                 380

Leu Asp Glu Leu Lys Asp Gln Met Glu Glu Asp Leu Leu Lys Leu Ala
385                 390                 395                 400

Asn Ala Gln Thr Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
            420                 425                 430
```

```
Pro Pro Pro Lys Val Gln Pro Arg Lys Thr Lys Pro Val Lys Ser Leu
        435                 440                 445
Pro Glu Arg Lys Pro Val Pro Ala Pro Arg Arg Lys Val Gly Ser Asp
    450                 455                 460
Cys Gly Gly Pro Val Ser Leu Gly Gly Asp Val Pro Asn Ser Trp Glu
465                 470                 475                 480
Asp Leu Ala Val Ser Ser Pro Phe Asp Leu Pro Thr Pro Pro Glu Pro
            485                 490                 495
Ala Thr Pro Ser Ser Glu Leu Val Ile Val Ser Ser Pro Gln Cys Ile
            500                 505                 510
Phe Arg Pro Ala Thr Pro Leu Ser Glu Pro Ala Pro Ile Pro Ala Pro
        515                 520                 525
Arg Gly Thr Val Ser Arg Pro Val Thr Pro Leu Ser Glu Pro Ile Pro
    530                 535                 540
Val Pro Ala Pro Arg Arg Lys Phe Gln Gln Val Lys Arg Leu Ser Ser
545                 550                 555                 560
Ala Ala Ala Ile Pro Pro Tyr Gln Asn Glu Pro Leu Asp Leu Ser Ala
                565                 570                 575
Ser Ser Gln Thr Glu Tyr Glu Ala Ser Pro Pro Ala Pro Pro Gln Ser
            580                 585                 590
Gly Gly Val Leu Gly Val Glu Gly His Glu Ala Glu Thr Leu Ser
        595                 600                 605
Glu Ile Ser Asp Met Ser Gly Asn Ile Lys Pro Ala Ser Val Ser Ser
    610                 615                 620
Ser Ser Ser Leu Ser Ser Val Arg Val Thr Arg Pro Lys Tyr Ser Ala
625                 630                 635                 640
Gln Ala Ile Ile Asp Ser Gly Gly Pro Cys Ser Gly His Leu Gln Glu
                645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
        675                 680                 685
Arg Val Asp Met Leu Thr Trp Arg Asn Thr Ser Ala Tyr Gln Ala Ile
    690                 695                 700
Cys Thr Leu Asp Gly Arg Leu Lys Phe Leu Pro Lys Met Ile Leu Glu
705                 710                 715                 720
Thr Pro Pro Pro Tyr Pro Cys Glu Phe Val Met Met Pro His Thr Pro
                725                 730                 735
Ala Pro Ser Val Gly Ala Glu Ser Asp Leu Thr Ile Gly Ser Val Ala
            740                 745                 750
Thr Glu Asp Val Pro Arg Ile Leu Glu Lys Met Glu Asn Val Gly Glu
        755                 760                 765
Met Ala Asn Gln Gly Pro Leu Ala Phe Ser Glu Asp Lys Pro Val Asp
    770                 775                 780
Asp Gln Leu Val Asn Asp Pro Arg Ile Ser Ser Arg Arg Pro Asp Glu
785                 790                 795                 800
Ser Thr Ser Ala Pro Ser Ala Gly Thr Gly Gly Ser Gly Ser Phe Thr
                805                 810                 815
Asp Leu Pro Pro Ser Asp Gly Ala Asp Ala Asp Gly Gly Gly Pro Phe
            820                 825                 830
Arg Thr Ala Lys Arg Lys Ala Glu Arg Leu Phe Asp Gln Leu Ser Arg
        835                 840                 845
Gln Val Phe Asp Leu Val Ser His Leu Pro Val Phe Phe Ser Arg Leu
```

```
            850                 855                 860
Phe His Pro Gly Gly Gly Tyr Ser Pro Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
    930                 935                 940

Cys Arg Asn Ile Leu His Ser Phe Glu Leu Leu Lys Pro Trp Asp Pro
945                 950                 955                 960

Val Arg Gly Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
        995                1000                1005

Gln Gly Arg Cys Lys Lys Cys Trp Gly Ser Cys Ile Arg Thr Ala
   1010                1015                1020

Pro Asn Glu Val Ala Phe Asn Val Phe Pro Phe Thr Arg Ala Thr
   1025                1030                1035

Arg Ser Ser Leu Ile Asp Leu Cys Asp Arg Leu Cys Ala Pro Lys
   1040                1045                1050

Gly Met Asp Pro Ile Ser Leu Ala Thr Gly Trp Arg Gly Cys Trp
   1055                1060                1065

Ala Gly Arg Ser Pro Ile Glu Gln Pro Ser Glu Lys Pro Ile Ala
   1070                1075                1080

Phe Ala Gln Leu Asp Glu Lys Lys Ile Thr Ala Arg Thr Val Ala
   1085                1090                1095

Ala Gln Pro Tyr Asp Pro Asn Gln Ala Val Lys Cys Leu Arg Val
   1100                1105                1110

Leu Gln Ala Gly Gly Ala Met Val Ala Glu Ala Val Pro Lys Val
   1115                1120                1125

Val Lys Val Ser Ala Val Pro Phe Arg Ala Pro Phe Phe Pro Thr
   1130                1135                1140

Gly Val Lys Val Asp Pro Asp Cys Arg Val Val Val Asp Pro Asp
   1145                1150                1155

Thr Phe Thr Ala Ala Leu Arg Ser Gly Tyr Ser Thr Thr Asn Leu
   1160                1165                1170

Val Leu Gly Val Gly Asp Phe Ala Gln Leu Asn Gly Leu Lys Ile
   1175                1180                1185

Arg Gln Ile Ser Lys Pro Ser Gly Gly
   1190                1195

<210> SEQ ID NO 82
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 82
```

```
Gly Ala Gly Lys Arg Ala Arg Lys Ala Arg Ser Cys Ala Thr Ala Thr
1               5                   10                  15

Val Ala Gly Arg Ala Leu Ser Val Arg Glu Thr Arg Gln Ala Lys Glu
            20                  25                  30

His Glu Val Ala Gly Ala Asp Lys Ala Glu His Leu Lys His Tyr Ser
                35                  40                  45

Pro Pro Ala Glu Gly Asn Cys Gly Trp His Cys Ile Ser Ala Ile Ala
50                  55                  60

Asn Arg Met Val Asn Ser Ile Phe Glu Thr Thr Leu Pro Glu Arg Val
65                  70                  75                  80

Arg Pro Pro Asp Asp Trp Ala Thr Asp Asp Leu Ala Asn Ala Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Lys Leu Glu Gly Glu His Trp Thr Val Thr
            115                 120                 125

Val Thr Pro Gly Met Ser Pro Ser Leu Leu Pro Leu Glu Cys Val Gln
            130                 135                 140

Gly Cys Cys Glu His Lys Gly Gly Leu Gly Ser Pro Asp Ala Ile Glu
145                 150                 155                 160

Val Ser Gly Phe Asp Pro Ala Cys Leu Asp Trp Leu Ala Glu Val Met
            165                 170                 175

His Leu Pro Ser Ser Ala Ile Pro Ala Ala Leu Ala Glu Met Ser Gly
            180                 185                 190

Asp Ser Asp Arg Ser Ala Ser Pro Val Thr Thr Val Trp Thr Val Ser
            195                 200                 205

Gln Phe Phe Ala Arg His Ser Gly Gly Asn His Pro Asp Gln Val Arg
            210                 215                 220

Leu Gly Lys Ile Ile Ser Leu Cys Gln Val Ile Glu Asp Cys Cys Cys
225                 230                 235                 240

Ser Gln Asn Lys Thr Asn Arg Val Thr Pro Glu Glu Val Ala Ala Lys
                245                 250                 255

Ile Asp Leu Tyr Leu Arg Gly Ala Thr Asn Leu Glu Glu Cys Leu Ala
            260                 265                 270

Arg Leu Glu Lys Ala Arg Pro Pro Arg Val Ile Asp Thr Ser Phe Asp
            275                 280                 285

Trp Asp Val Val Leu Pro Gly Val Glu Ala Ala Thr Gln Thr Asn Lys
            290                 295                 300

Leu Pro Gln Val Asn Gln Cys Arg Ala Leu Val Pro Val Val Thr Gln
305                 310                 315                 320

Lys Ser Leu Asp Asn Asn Ser Val Pro Leu Thr Ala Phe Ser Leu Ala
                325                 330                 335

Asn Tyr Tyr Tyr Arg Ala Gln Gly Asp Glu Val Arg His Arg Glu Arg
            340                 345                 350

Leu Thr Ala Val Leu Ser Lys Leu Glu Glu Val Arg Glu Glu Tyr
            355                 360                 365

Gly Leu Met Pro Thr Glu Pro Gly Pro Arg Pro Thr Leu Pro Arg Gly
            370                 375                 380

Leu Asp Glu Leu Lys Asp Gln Met Glu Glu Asp Leu Leu Arg Leu Ala
385                 390                 395                 400

Asn Ala Gln Ala Thr Ser Asp Met Met Ala Trp Ala Val Glu Gln Val
                405                 410                 415

Asp Leu Lys Thr Trp Val Lys Asn Tyr Pro Arg Trp Thr Pro Pro Pro
```

```
            420                 425                 430
Pro Pro Pro Lys Val Gln Pro Arg Lys Thr Lys Pro Val Lys Ser Leu
            435                 440                 445
Pro Glu Arg Lys Pro Val Pro Ala Pro Arg Arg Lys Val Gly Pro Asp
            450                 455                 460
Cys Gly Ser Pro Val Ser Leu Gly Gly Asp Val Pro Asn Ser Trp Glu
465                 470                 475                 480
Asp Leu Ala Val Ser Ser Pro Leu Asp Leu Pro Thr Pro Pro Glu Pro
                    485                 490                 495
Ala Thr Leu Ser Ser Glu Leu Val Ile Val Ser Ser Pro Gln Cys Ile
            500                 505                 510
Phe Arg Pro Ala Thr Pro Leu Ser Glu Pro Ala Pro Ile Pro Ala Pro
            515                 520                 525
Arg Gly Thr Val Ser Arg Pro Val Thr Pro Leu Ser Glu Pro Ile Pro
            530                 535                 540
Val Pro Ala Pro Arg Arg Lys Phe Gln Gln Val Lys Arg Leu Ser Ser
545                 550                 555                 560
Ala Ala Ala Val Pro Leu His Gln Asn Glu Pro Leu Asp Leu Ser Ala
                    565                 570                 575
Ser Ser Gln Thr Glu Tyr Glu Ala Ser Pro Ser Ala Pro Pro Gln Ser
            580                 585                 590
Gly Gly Val Leu Gly Val Glu Gly His Glu Ala Glu Glu Thr Leu Ser
            595                 600                 605
Glu Ile Ser Asp Met Ser Gly Asn Ile Lys Pro Ala Ser Val Ser Ser
            610                 615                 620
Ser Ser Ser Leu Ser Ser Val Glu Ile Thr Arg Pro Lys Tyr Ser Ala
625                 630                 635                 640
Gln Ala Ile Ile Asp Ser Gly Gly Pro Cys Ser Gly His Leu Gln Gly
                    645                 650                 655
Val Lys Glu Thr Cys Leu Ser Val Met Arg Glu Ala Cys Asp Ala Thr
            660                 665                 670
Lys Leu Asp Asp Pro Ala Thr Gln Glu Trp Leu Ser Arg Met Trp Asp
            675                 680                 685
Arg Val Asp Met Leu Thr Trp Arg Asn Thr Ser Val Cys Gln Ala Ile
            690                 695                 700
Arg Thr Leu Asp Gly Arg Leu Lys Phe Leu Pro Lys Met Ile Leu Glu
705                 710                 715                 720
Thr Pro Pro Pro Tyr Pro Cys Glu Phe Val Met Met Pro His Thr Pro
                    725                 730                 735
Ala Pro Ser Val Gly Ala Glu Ser Asp Leu Thr Ile Gly Ser Val Ala
            740                 745                 750
Thr Glu Asp Val Pro Arg Ile Leu Glu Lys Ile Glu Asn Val Gly Glu
            755                 760                 765
Met Ala Asn Gln Glu Pro Ser Ala Phe Ser Glu Asp Lys Pro Val Asp
            770                 775                 780
Asp Gln Leu Val Asn Asp Pro Arg Ile Ser Ser Arg Arg Pro Asp Glu
785                 790                 795                 800
Ser Thr Ala Ala Pro Ser Ala Gly Thr Gly Gly Ala Gly Ser Phe Thr
                    805                 810                 815
Asp Leu Pro Ser Ser Asp Gly Ala Asp Ala Asp Gly Gly Pro Phe
            820                 825                 830
Arg Thr Ala Lys Arg Lys Ala Glu Arg Leu Phe Asp Gln Leu Ser Arg
            835                 840                 845
```

Gln Val Phe Asp Leu Val Ser His Leu Pro Phe Phe Ser Arg Leu
    850                 855                 860

Phe His Pro Gly Gly Gly Tyr Ser Thr Gly Asp Trp Gly Phe Ala Ala
865                 870                 875                 880

Phe Thr Leu Leu Cys Leu Phe Leu Cys Tyr Ser Tyr Pro Ala Phe Gly
                885                 890                 895

Ile Ala Pro Leu Leu Gly Val Phe Ser Gly Thr Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Ala Ala Cys Glu Phe Asp Ser Pro Glu
    930                 935                 940

Cys Arg Asn Ile Leu Leu Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Cys Ile Trp His Phe Leu Leu Arg
            980                 985                 990

Leu Gly Ile Val Ala Asp Cys Ile Leu Ala Gly Ala Tyr Val Leu Ser
        995                 1000                1005

Gln Gly Arg Cys Lys Lys Cys Trp Gly Ser Cys Ile Arg Thr Ala
    1010                1015                1020

Pro Asn Glu Val Ala Phe Asn Val Phe Pro Phe Thr Arg Ala Thr
    1025                1030                1035

Arg Ser Ser Leu Ile Asp Leu Cys Asp Arg Phe Cys Ala Pro Lys
    1040                1045                1050

Gly Met Asp Pro Ile Phe Leu Ala Thr Gly Trp Arg Gly Cys Trp
    1055                1060                1065

Ala Gly Arg Ser Pro Ile Glu Gln Pro Ser Glu Lys Pro Ile Ala
    1070                1075                1080

Phe Ala Gln Leu Asp Glu Lys Lys Ile Thr Ala Arg Thr Val Val
    1085                1090                1095

Ala Gln Pro Tyr Asp Pro Asn Gln Ala Val Lys Cys Leu Arg Val
    1100                1105                1110

Leu Gln Ala Gly Gly Ala Met Val Ala Glu Ala Val Pro Lys Val
    1115                1120                1125

Val Lys Val Ser Ala Val Pro Phe Arg Ala Pro Phe Phe Pro Thr
    1130                1135                1140

Gly Val Lys Val Asp Pro Asp Cys Arg Val Val Val Asp Pro Asp
    1145                1150                1155

Thr Phe Thr Ala Ala Leu Arg Ser Gly Tyr Ser Thr Thr Asn Leu
    1160                1165                1170

Val Leu Gly Val Gly Asp Phe Ala Gln Leu Asn Gly Leu Lys Ile
    1175                1180                1185

Arg Gln Ile Ser Lys Pro Ser Gly Gly
    1190                1195

<210> SEQ ID NO 83
<211> LENGTH: 1197
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 83

```
Gly Ala Gly Lys Arg Ala Arg Lys Ala Arg Ser Gly Ala Thr Thr Met
1               5                   10                  15

Val Ala His Arg Ala Leu Ser Ala Arg Glu Thr Arg Gln Ala Lys Lys
            20                  25                  30

His Glu Gly Ala Asp Ala Asn Lys Ala Glu His Leu Glu His Tyr Ser
        35                  40                  45

Pro Pro Ala Glu Gly Asn Cys Gly Trp His Cys Ile Ser Ala Ile Ala
    50                  55                  60

Asn Arg Met Val Asn Ser Asn Phe Glu Thr Thr Leu Pro Glu Arg Ala
65                  70                  75                  80

Arg Pro Leu Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Thr
            100                 105                 110

Ser Ala Lys Tyr Val Leu Arg Leu Glu Gly Glu His Trp Thr Val Ser
        115                 120                 125

Val Thr Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Ala Cys Leu Asp Arg Leu Ala Glu Val Met
                165                 170                 175

His Leu Pro Ser Ser Ala Ile Pro Ala Ala Leu Ala Glu Met Pro Val
            180                 185                 190

Asp Ser Asn Arg Pro Ala Ser Pro Val Thr Thr Ala Trp Thr Val Ser
        195                 200                 205

Gln Phe Tyr Ala Arg His Arg Gly Gly Asn His Arg Asp Gln Val Cys
    210                 215                 220

Leu Gly Lys Ile Ile Ser Leu Cys Gln Val Ile Glu Asp Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ile
            260                 265                 270

Lys Leu Glu Arg Val Ser Pro Pro Ser Ala Ala Asp Thr Ser Phe Asp
        275                 280                 285

Trp Asn Val Val Leu Pro Gly Val Glu Ala Ala Asn Gln Thr Thr Lys
    290                 295                 300

Gln Leu His Val Asn Gln Cys Arg Ala Leu Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Leu Glu Glu Tyr
        355                 360                 365

Gly Leu Met Ser Thr Gly Leu Gly Pro Arg Pro Val Leu Pro Ser Gly
    370                 375                 380

Leu Asp Glu Leu Lys Asp Gln Met Glu Glu Asp Leu Leu Lys Leu Ala
385                 390                 395                 400

Asn Ala Gln Ala Thr Ser Glu Met Met Ala Trp Ala Ala Glu Gln Val
                405                 410                 415
```

```
Asp Leu Lys Ala Trp Val Lys Ser Tyr Pro Arg Trp Thr Pro Pro Pro
            420                 425                 430

Pro Pro Pro Arg Val Gln Pro Arg Lys Thr Lys Pro Val Lys Ser Leu
        435                 440                 445

Pro Glu Asn Lys Pro Val Pro Ala Pro Arg Arg Lys Val Gly Ser Asp
    450                 455                 460

Cys Gly Ser Pro Ile Leu Met Gly Asp Asn Val Pro Asn Gly Trp Glu
465                 470                 475                 480

Asp Phe Ala Val Gly Gly Pro Leu Asp Phe Pro Thr Pro Ser Glu Pro
                485                 490                 495

Met Thr Pro Leu Ser Glu Pro Val Leu Met Pro Ala Ser Gln His Ile
            500                 505                 510

Pro Arg Pro Val Thr Pro Leu Ser Gly Pro Ala Pro Val Pro Ala Pro
        515                 520                 525

Arg Arg Thr Val Ser Arg Pro Met Thr Pro Leu Ser Glu Pro Ile Phe
    530                 535                 540

Val Ser Ala Pro Arg His Lys Phe Gln Gln Val Glu Glu Ala Asn Pro
545                 550                 555                 560

Ala Ala Thr Thr Leu Thr Tyr Gln Asp Glu Pro Leu Asp Leu Ser Ala
                565                 570                 575

Phe Ser Gln Thr Glu Cys Glu Ala Ser Pro Leu Ala Pro Leu Gln Asn
            580                 585                 590

Met Gly Ile Leu Glu Ala Gly Gly Gln Glu Ala Glu Glu Val Leu Ser
        595                 600                 605

Gly Ile Ser Asp Ile Leu Asn Asp Ile Asn Pro Ala Pro Val Ser Ser
    610                 615                 620

Ser Ser Ser Leu Ser Ser Val Arg Ile Thr Arg Pro Lys Tyr Ser Ala
625                 630                 635                 640

Gln Ala Ile Ile Asp Ser Gly Gly Pro Cys Ser Gly His Leu Gln Arg
                645                 650                 655

Glu Lys Glu Ala Cys Leu Ser Ile Met Arg Glu Ala Cys Asp Ala Ala
            660                 665                 670

Lys Leu Ser Asp Pro Ala Thr Gln Glu Trp Leu Ser Arg Met Trp Asp
        675                 680                 685

Arg Val Asp Met Leu Thr Trp Arg Asn Thr Ser Ala Tyr Gln Ala Leu
    690                 695                 700

His Thr Leu Asp Gly Arg Ser Gly Phe Leu Pro Lys Met Ile Leu Glu
705                 710                 715                 720

Thr Pro Pro Pro His Pro Cys Gly Phe Val Met Leu Pro His Thr Pro
                725                 730                 735

Ala Pro Ser Val Ser Ala Lys Ser Asp Leu Thr Ile Gly Ser Val Ala
            740                 745                 750

Thr Glu Asp Val Pro Arg Ile Leu Gly Lys Ile Glu Asn Thr Gly Glu
        755                 760                 765

Met Leu Asn Gln Gly Pro Leu Ala Pro Phe Glu Glu Glu Pro Val Cys
    770                 775                 780

Asp Gln Pro Ala Lys Asp Ser Arg Ile Ser Ser Arg Gly Ser Gly Glu
785                 790                 795                 800

Ser Thr Thr Ala Pro Ser Ala Asp Thr Gly Ala Gly Leu Phe Thr
                805                 810                 815

Asp Leu Leu Pro Ser Asp Gly Met Asp Ala Asp Gly Gly Gly Pro Leu
            820                 825                 830
```

```
Arg Thr Val Lys Lys Thr Glu Lys Leu Phe Asp Gln Leu Ser Arg
            835                 840                 845

Gln Val Phe Asn Leu Val Ser His Leu Pro Val Phe Ser His Leu
        850                 855                 860

Phe Lys Ser Asp Ser Gly Tyr Ser Ser Gly Asp Trp Ser Phe Ala Ala
865                 870                 875                 880

Phe Thr Leu Phe Cys Leu Phe Leu Cys Tyr Ser Tyr Pro Phe Phe Gly
                885                 890                 895

Phe Ala Pro Leu Leu Gly Val Phe Gly Ser Ser Arg Arg Val Arg
        900                 905                 910

Met Gly Val Phe Gly Cys Trp Leu Ala Phe Ala Val Gly Leu Phe Lys
        915                 920                 925

Pro Val Ser Asp Pro Val Gly Thr Ala Cys Glu Phe Asp Ser Pro Glu
        930                 935                 940

Cys Arg Asn Val Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Tyr Ile Trp His Phe Leu Leu Arg
        980                 985                 990

Leu Gly Ile Val Ala Asp Cys Ile Leu Ala Gly Ala Tyr Val Leu Ser
        995                 1000                1005

Gln Gly Arg Cys Lys Lys Cys Trp Gly Ser Cys Val Arg Thr Ala
        1010                1015                1020

Pro Asn Glu Ile Ala Phe Asn Val Phe Pro Phe Thr Arg Ala Thr
        1025                1030                1035

Arg Ser Ser Leu Ile Asp Leu Cys Asp Arg Phe Cys Ala Pro Lys
        1040                1045                1050

Cys Met Asp Pro Ile Phe Leu Ala Thr Gly Trp Arg Gly Cys Trp
        1055                1060                1065

Thr Gly Arg Ser Pro Ile Glu Gln Pro Ser Glu Lys Pro Ile Ala
        1070                1075                1080

Phe Ala Gln Leu Asp Glu Lys Lys Ile Thr Ala Arg Thr Val Val
        1085                1090                1095

Ala Gln Pro Tyr Asp Pro Asn Gln Ala Val Lys Cys Leu Arg Val
        1100                1105                1110

Leu Gln Ala Gly Gly Ala Met Val Ala Glu Ala Val Pro Lys Val
        1115                1120                1125

Val Lys Val Ser Ala Ile Pro Phe Arg Ala Pro Phe Phe Pro Thr
        1130                1135                1140

Gly Val Lys Val Asp Pro Glu Cys Arg Ile Val Val Asp Pro Asp
        1145                1150                1155

Thr Phe Thr Thr Ala Leu Arg Ser Gly Tyr Ser Thr Thr Asn Leu
        1160                1165                1170

Val Leu Gly Val Gly Asp Phe Ala Gln Leu Asn Gly Leu Lys Ile
        1175                1180                1185

Arg Gln Ile Ser Lys Pro Ser Gly Gly
        1190                1195

<210> SEQ ID NO 84
<211> LENGTH: 1186
<212> TYPE: PRT
<213> ORGANISM: Artificial Sequence
<220> FEATURE:
<223> OTHER INFORMATION: Porcine reproductive and respiratory syndrome
``` virus; Nsp2

<400> SEQUENCE: 84

```
Gly Ala Gly Lys Arg Ala Arg Lys Ala Arg Ser Gly Ala Thr Thr Thr
1               5                   10                  15

Val Ala His Arg Ala Ser Ser Ala Arg Glu Thr Arg Gln Ala Lys Lys
            20                  25                  30

His Glu Gly Val Asp Ala Asn Asn Ala Ala His Leu Glu His Tyr Ser
        35                  40                  45

Pro Pro Ala Glu Gly Asn Cys Gly Trp His Cys Ile Ser Ala Ile Val
    50                  55                  60

Asn Arg Met Val Asn Ser Asn Phe Glu Thr Thr Leu Pro Glu Arg Val
65                  70                  75                  80

Arg Pro Ser Asp Asp Trp Ala Thr Asp Glu Asp Phe Val Asn Thr Ile
                85                  90                  95

Gln Ile Leu Arg Leu Pro Ala Ala Leu Asp Arg Asn Gly Ala Cys Lys
            100                 105                 110

Ser Ala Lys Tyr Val Leu Lys Leu Glu Gly Glu His Trp Thr Val Ser
        115                 120                 125

Val Ala Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Thr Cys Leu Asp Arg Leu Ala Glu Val Met
                165                 170                 175

His Leu Pro Ser Ser Val Ile Pro Ala Ala Leu Ala Glu Met Ser Asn
            180                 185                 190

Asn Ser Asp Arg Pro Ala Ser Leu Val Asn Thr Ala Trp Thr Val Ser
        195                 200                 205

Gln Phe Tyr Ala Arg His Thr Gly Gly Asn His Arg Asp Gln Val Arg
    210                 215                 220

Leu Gly Lys Ile Ile Ser Leu Cys Gln Val Ile Glu Glu Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ile
            260                 265                 270

Lys Leu Glu Arg Val Ser Pro Pro Ser Ala Ala Asp Thr Ser Phe Asp
        275                 280                 285

Trp Asn Val Val Leu Pro Gly Val Glu Ala Ala Gly Pro Thr Thr Glu
    290                 295                 300

Gln Pro His Ala Asn Gln Cys Cys Ala Pro Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Glu Val Val Leu Glu Glu Tyr
        355                 360                 365

Gly Leu Met Pro Thr Gly Leu Gly Pro Arg Pro Val Leu Pro Ser Gly
    370                 375                 380

Leu Asp Glu Leu Lys Asp Gln Met Glu Glu Asp Leu Leu Lys Leu Ala
385                 390                 395                 400
```

-continued

```
Asn Ala Gln Ala Thr Ser Glu Met Met Ala Leu Ala Glu Gln Val
                405                 410                 415

Asp Leu Lys Ala Trp Val Lys Ser Tyr Pro Arg Trp Ile Pro Pro
            420                 425                 430

Pro Pro Pro Lys Val Gln Pro Arg Arg Met Lys Pro Val Lys Ser Leu
        435                 440                 445

Pro Glu Asn Lys Pro Val Pro Ala Pro Arg Arg Lys Val Arg Ser Asp
    450                 455                 460

Pro Gly Lys Ser Ile Leu Ala Val Gly Gly Pro Leu Asn Phe Ser Thr
465                 470                 475                 480

Pro Ser Glu Leu Val Thr Pro Leu Gly Glu Pro Val Leu Met Pro Ala
            485                 490                 495

Ser Gln His Val Ser Arg Pro Val Thr Pro Leu Ser Glu Pro Ala Pro
        500                 505                 510

Val Pro Ala Pro Arg Arg Ile Val Ser Arg Pro Met Thr Pro Leu Ser
    515                 520                 525

Glu Pro Thr Phe Val Phe Ala Pro Trp Arg Lys Ser Gln Gln Val Glu
    530                 535                 540

Glu Ala Asn Pro Ala Ala Ala Thr Leu Thr Cys Gln Asp Glu Pro Leu
545                 550                 555                 560

Asp Leu Ser Ala Ser Ser Gln Thr Glu Tyr Glu Ala Tyr Pro Leu Ala
            565                 570                 575

Pro Leu Glu Asn Ile Gly Val Leu Glu Ala Gly Gly Gln Glu Ala Glu
        580                 585                 590

Glu Val Leu Ser Gly Ile Ser Asp Ile Leu Asp Asn Thr Asn Pro Ala
    595                 600                 605

Pro Val Ser Ser Ser Ser Ser Leu Ser Ser Val Lys Ile Thr Arg Pro
    610                 615                 620

Lys Tyr Ser Ala Gln Ala Ile Ile Asp Ser Gly Gly Pro Cys Ser Gly
625                 630                 635                 640

His Leu Gln Lys Glu Lys Glu Ala Cys Leu Arg Ile Met Arg Glu Ala
            645                 650                 655

Cys Asp Ala Ala Arg Leu Gly Asp Pro Ala Thr Gln Glu Trp Leu Ser
        660                 665                 670

His Met Trp Asp Arg Val Asp Val Leu Thr Trp Arg Asn Thr Ser Val
    675                 680                 685

Tyr Gln Ala Phe Arg Thr Leu Asp Gly Arg Phe Gly Phe Leu Pro Lys
    690                 695                 700

Met Ile Leu Glu Thr Pro Pro Tyr Pro Cys Gly Phe Val Met Leu
705                 710                 715                 720

Pro His Thr Pro Thr Pro Ser Val Ser Ala Glu Ser Asp Leu Thr Ile
            725                 730                 735

Gly Ser Val Ala Thr Glu Asp Val Pro Arg Ile Leu Gly Lys Thr Glu
        740                 745                 750

Asn Thr Gly Asn Val Leu Asn Gln Lys Pro Leu Ala Leu Phe Glu Glu
    755                 760                 765

Glu Pro Val Cys Asp Gln Pro Ala Lys Asp Ser Arg Thr Leu Ser Arg
    770                 775                 780

Glu Ser Gly Asp Ser Thr Ala Pro Pro Val Gly Thr Gly Gly Ala
785                 790                 795                 800

Gly Leu Pro Thr Asp Leu Pro Pro Leu Asp Gly Val Asp Ala Asp Gly
            805                 810                 815

Gly Gly Leu Leu Arg Thr Ala Lys Gly Lys Ala Glu Arg Phe Phe Asp
```

```
                  820                 825                 830
Gln Leu Ser Arg Gln Val Phe Asn Ile Val Ser His Leu Pro Val Phe
            835                 840                 845
Phe Ser His Leu Phe Lys Ser Asp Ser Gly Tyr Ser Pro Gly Asp Trp
850                 855                 860
Gly Phe Ala Ala Phe Thr Leu Phe Cys Leu Phe Leu Cys Tyr Ser Tyr
865                 870                 875                 880
Pro Phe Phe Gly Phe Ala Pro Leu Leu Gly Val Phe Ser Gly Ser Ser
                885                 890                 895
Arg Arg Val Arg Met Gly Val Phe Gly Cys Trp Leu Ala Phe Ala Val
            900                 905                 910
Gly Leu Phe Lys Pro Val Ser Asp Pro Val Gly Ala Ala Cys Glu Phe
            915                 920                 925
Asp Ser Pro Glu Cys Arg Asn Ile Leu His Ser Phe Glu Leu Leu Lys
            930                 935                 940
Pro Trp Asp Pro Val Arg Ser Leu Val Val Gly Gly Pro Val Gly Leu
945                 950                 955                 960
Gly Leu Ala Ile Leu Gly Arg Leu Leu Gly Gly Ala Arg Tyr Ile Trp
                965                 970                 975
His Phe Leu Leu Arg Leu Gly Ile Val Ala Asp Cys Ile Leu Ala Gly
            980                 985                 990
Ala Tyr Val Leu Ser Gln Gly Arg Cys Lys Lys Cys Trp Gly Ser Cys
            995                 1000                1005
Ile Arg Thr Ala Pro Asn Glu Ile Ala Phe Asn Val Phe Pro Phe
    1010                1015                1020
Thr Arg Ala Thr Arg Ser Ser Leu Ile Asp Leu Cys Asp Arg Phe
    1025                1030                1035
Cys Ala Pro Lys Gly Met Asp Pro Ile Phe Leu Ala Thr Gly Trp
    1040                1045                1050
Arg Gly Cys Trp Thr Gly Gln Ser Pro Ile Glu Gln Pro Ser Glu
    1055                1060                1065
Lys Pro Ile Ala Phe Ala Gln Leu Asp Glu Lys Arg Ile Thr Ala
    1070                1075                1080
Arg Thr Val Val Ser Gln Pro Tyr Asp Pro Asn Gln Ala Val Lys
    1085                1090                1095
Cys Leu Arg Val Leu Gln Ala Gly Gly Ala Met Val Ala Glu Ala
    1100                1105                1110
Val Pro Lys Val Val Lys Val Ser Ala Ile Pro Phe Arg Ala Pro
    1115                1120                1125
Phe Phe Pro Thr Gly Val Lys Val Asp Pro Glu Cys Arg Ile Val
    1130                1135                1140
Val Asp Pro Asp Thr Phe Thr Thr Ala Leu Arg Ser Gly Tyr Ser
    1145                1150                1155
Thr Thr Asn Leu Val Leu Gly Val Gly Asp Phe Ala Gln Leu Asn
    1160                1165                1170
Gly Leu Lys Ile Arg Gln Ile Ser Lys Pro Ser Gly Gly
    1175                1180                1185

<210> SEQ ID NO 85
<211> LENGTH: 1191
<212> TYPE: PRT
<213> ORGANISM: Artificial Sequence
<220> FEATURE:
<223> OTHER INFORMATION: Porcine reproductive and respiratory syndrome
      virus; Nsp2
```

<400> SEQUENCE: 85

```
Gly Ala Gly Lys Arg Ala Arg Arg Ala Arg Ser Gly Ala Thr Ala Thr
1               5                   10                  15

Val Ala His Cys Ala Leu Pro Ala Arg Glu Ala Gln Gln Ala Lys Lys
            20                  25                  30

Leu Glu Val Ala Ser Ala Asn Arg Ala Glu His Leu Lys Tyr Tyr Ser
        35                  40                  45

Pro Pro Ala Asp Gly Asn Cys Gly Trp His Cys Ile Ser Ala Ile Thr
    50                  55                  60

Asn Arg Met Val Asn Ser Lys Phe Glu Thr Thr Leu Pro Glu Arg Val
65                  70                  75                  80

Arg Pro Ser Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Ala
            100                 105                 110

Gly Ala Lys Tyr Val Leu Lys Leu Glu Gly Glu His Trp Thr Val Ser
        115                 120                 125

Val Thr Pro Gly Met Thr Pro Ser Leu Leu Pro Leu Glu Cys Val Gln
    130                 135                 140

Gly Cys Cys Glu His Lys Ser Gly Leu Gly Phe Pro Asp Val Val Glu
145                 150                 155                 160

Val Ser Gly Phe Asp Pro Ala Cys Leu Asp Arg Leu Ala Glu Ile Met
                165                 170                 175

His Leu Pro Ser Ser Val Ile Pro Ala Ala Leu Ala Glu Met Ser Asp
            180                 185                 190

Asp Phe Asn Arg Leu Ala Ser Pro Ala Ala Thr Val Trp Thr Val Ser
        195                 200                 205

Gln Phe Phe Ala Arg His Arg Gly Gly Glu His Pro Asp Gln Val Cys
    210                 215                 220

Leu Gly Lys Ile Ile Asn Leu Cys Gln Val Ile Glu Glu Cys Cys Cys
225                 230                 235                 240

Ser Arg Asn Lys Ala Asn Arg Ala Thr Pro Glu Glu Val Ala Ala Lys
                245                 250                 255

Val Asp Gln Tyr Leu Arg Gly Ala Ala Ser Leu Gly Glu Cys Leu Ala
            260                 265                 270

Lys Leu Glu Arg Ala Arg Pro Pro Ser Ala Met Asp Thr Ser Phe Asp
        275                 280                 285

Trp Asn Val Val Leu Pro Gly Val Glu Thr Ala Asp Gln Thr Thr Lys
    290                 295                 300

Gln Leu His Val Asn Gln Cys Arg Ala Leu Val Pro Val Val Thr Gln
305                 310                 315                 320

Glu Pro Leu Asp Arg Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Arg Glu Glu Tyr
        355                 360                 365

Gly Leu Thr Pro Thr Gly Pro Gly Pro Arg Pro Ala Leu Pro Asn Gly
    370                 375                 380

Leu Asp Glu Leu Lys Asp Gln Met Glu Glu Asp Leu Leu Lys Leu Val
385                 390                 395                 400

Asn Ala Gln Ala Thr Ser Glu Met Met Ala Trp Ala Ala Glu Gln Val
```

```
            405                 410                 415
Asp Leu Lys Ala Trp Val Lys Asn Tyr Pro Arg Trp Thr Pro Pro
        420                 425                 430

Pro Pro Pro Arg Val Gln Pro Arg Lys Thr Lys Ser Val Lys Ser Leu
            435                 440                 445

Leu Glu Asn Lys Pro Val Pro Ala Pro Arg Arg Lys Val Arg Ser Asp
        450                 455                 460

Tyr Gly Ser Pro Ile Leu Met Gly Asp Asn Val Pro Asn Gly Trp Glu
465                 470                 475                 480

Asp Ser Thr Val Gly Gly Pro Leu Asp Leu Ser Ala Pro Ser Glu Pro
            485                 490                 495

Met Thr Pro Leu Ser Glu Pro Val Leu Ile Ser Arg Pro Val Thr Ser
        500                 505                 510

Leu Ser Val Pro Ala Pro Val Pro Ala Pro Arg Arg Ala Val Ser Arg
            515                 520                 525

Pro Met Thr Pro Ser Ser Glu Pro Ile Phe Val Ser Ala Leu Arg His
        530                 535                 540

Lys Phe Gln Gln Val Glu Lys Ala Asn Leu Ala Ala Ala Ala Pro Met
545                 550                 555                 560

Tyr Gln Asp Glu Pro Leu Asp Leu Ser Ala Ser Ser Gln Thr Glu Tyr
            565                 570                 575

Gly Ala Ser Pro Leu Thr Pro Pro Gln Asn Val Gly Ile Leu Glu Val
        580                 585                 590

Arg Gly Gln Glu Ala Glu Glu Val Leu Ser Glu Ile Ser Asp Ile Leu
            595                 600                 605

Asn Asp Thr Asn Pro Ala Pro Val Ser Ser Ser Ser Leu Ser Ser
        610                 615                 620

Val Arg Ile Thr Arg Pro Lys Tyr Ser Ala Gln Ala Ile Ile Asp Leu
625                 630                 635                 640

Gly Gly Pro Cys Ser Gly His Leu Gln Arg Glu Lys Glu Ala Cys Leu
            645                 650                 655

Arg Ile Met Arg Glu Ala Cys Asp Ala Ala Lys Leu Ser Asp Pro Ala
        660                 665                 670

Thr Gln Glu Trp Leu Ser Arg Met Trp Asp Arg Val Asp Met Leu Thr
            675                 680                 685

Trp Arg Asn Thr Ser Ala Tyr Gln Ala Phe Arg Thr Leu Asp Gly Arg
        690                 695                 700

Phe Gly Phe Leu Pro Lys Met Ile Leu Glu Thr Pro Pro Tyr Pro
705                 710                 715                 720

Cys Gly Phe Val Met Leu Pro His Thr Pro Ala Pro Ser Val Ser Ala
            725                 730                 735

Glu Ser Asp Leu Thr Ile Gly Ser Val Ala Thr Glu Asp Ile Pro Arg
        740                 745                 750

Ile Leu Gly Lys Ile Glu Asn Thr Gly Glu Met Ile Asn Gln Gly Pro
            755                 760                 765

Leu Ala Ser Ser Glu Glu Glu Pro Val Tyr Asn Gln Pro Ala Lys Asp
        770                 775                 780

Ser Arg Ile Ser Ser Arg Gly Ser Asp Glu Ser Thr Ala Ala Pro Ser
785                 790                 795                 800

Ala Gly Thr Gly Gly Ala Gly Leu Pro Thr Asp Leu Pro Pro Ser Asp
            805                 810                 815

Gly Val Asp Ala Asp Gly Gly Pro Leu Gln Thr Val Arg Lys Lys
        820                 825                 830
```

Ala Glu Arg Leu Phe Asp Gln Leu Ser Arg Gln Val Phe Asn Leu Val
    835                 840                 845

Ser His Leu Pro Val Phe Ser His Leu Phe Lys Ser Asp Ser Gly
    850                 855                 860

Tyr Ser Pro Gly Asp Trp Gly Phe Ala Ala Phe Thr Leu Phe Cys Leu
865                 870                 875                 880

Phe Leu Cys Tyr Ser Tyr Pro Phe Phe Gly Phe Val Pro Leu Leu Gly
                885                 890                 895

Val Phe Ser Gly Ser Ser Arg Arg Val Arg Met Gly Val Phe Gly Cys
            900                 905                 910

Trp Leu Ala Phe Ala Val Gly Leu Phe Lys Pro Val Ser Asp Pro Val
            915                 920                 925

Gly Thr Ala Cys Glu Phe Asp Ser Pro Glu Cys Arg Asn Val Leu His
            930                 935                 940

Ser Phe Glu Leu Leu Lys Pro Trp Asp Pro Val Arg Ser Leu Val Val
945                 950                 955                 960

Gly Pro Val Gly Leu Gly Leu Ala Ile Leu Gly Arg Leu Leu Gly Gly
                965                 970                 975

Ala Arg Tyr Ile Trp His Phe Leu Leu Arg Leu Gly Ile Val Ala Asp
            980                 985                 990

Cys Ile Leu Ala Gly Ala Tyr Val Leu Ser Gln Gly Arg Cys Lys Lys
            995                 1000                1005

Cys Trp Gly Ser Cys Ile Arg Thr Ala Pro Asn Glu Ile Ala Phe
    1010                1015                1020

Asn Val Phe Pro Phe Thr Arg Ala Thr Arg Ser Ser Leu Ile Asp
    1025                1030                1035

Leu Cys Asp Arg Phe Cys Ala Pro Lys Gly Met Asp Pro Ile Phe
    1040                1045                1050

Leu Ala Thr Gly Trp Arg Gly Cys Trp Thr Gly Arg Ser Pro Ile
    1055                1060                1065

Glu Gln Pro Ser Glu Lys Pro Ile Ala Phe Ala Gln Leu Asp Glu
    1070                1075                1080

Lys Arg Ile Thr Ala Arg Thr Val Val Ala Gln Pro Tyr Asp Pro
    1085                1090                1095

Asn Gln Ala Val Lys Cys Leu Arg Val Leu Gln Ala Gly Gly Ala
    1100                1105                1110

Met Val Ala Glu Ala Val Pro Lys Val Val Lys Val Ser Ala Ile
    1115                1120                1125

Pro Phe Arg Ala Pro Phe Phe Pro Thr Gly Val Lys Val Asp Pro
    1130                1135                1140

Glu Cys Arg Ile Val Val Asp Pro Asp Thr Phe Thr Thr Ala Leu
    1145                1150                1155

Arg Ser Gly Tyr Ser Thr Thr Asn Leu Val Leu Gly Val Gly Asp
    1160                1165                1170

Phe Ala Gln Leu Asn Gly Leu Lys Ile Arg Gln Ile Ser Lys Pro
    1175                1180                1185

Ser Gly Gly
    1190

<210> SEQ ID NO 86
<211> LENGTH: 1197
<212> TYPE: PRT
<213> ORGANISM: Artificial Sequence
<220> FEATURE:

<223> OTHER INFORMATION: Porcine reproductive and respiratory syndrome
      virus; Nsp2

<400> SEQUENCE: 86

```
Gly Ala Gly Lys Arg Ala Arg Lys Ala Arg Ser Gly Met Thr Thr Thr
1               5                   10                  15

Val Ala His Arg Ala Leu Pro Ala Arg Glu Ile Gln Gln Ala Lys Lys
            20                  25                  30

His Glu Asp Ala Gly Ala Asp Lys Ala Val His Leu Arg His Tyr Ser
        35                  40                  45

Pro Pro Ala Asp Gly Asn Cys Gly Trp His Cys Ile Ser Ala Ile Ala
    50                  55                  60

Asn Arg Met Val Asn Ser Lys Phe Glu Thr Thr Leu Pro Glu Arg Val
65                  70                  75                  80

Arg Pro Ser Asp Asp Trp Ala Thr Asp Glu Asp Leu Val Asn Thr Ile
                85                  90                  95

Gln Ile Leu Lys Leu Pro Ala Ala Leu Asp Arg Asn Gly Ala Cys Val
            100                 105                 110

Gly Ala Lys Tyr Val Leu Lys Leu Glu Gly Glu His Trp Thr Val Ser
        115                 120                 125

Val Thr Leu Gly Met Ser Pro Ser Leu Leu Pro Leu Glu Cys Val Gln
    130                 135                 140

Gly Cys Cys Glu His Lys Ser Gly Leu Gly Pro Pro Asp Ala Val Glu
145                 150                 155                 160

Val Phe Gly Phe Asp Pro Ala Cys Leu Asp Arg Leu Ala Glu Val Met
                165                 170                 175

His Leu Pro Ser Ser Val Ile Pro Ala Ala Leu Ala Glu Met Ser Gly
            180                 185                 190

Asp Pro Asn Cys Pro Ala Ser Pro Val Thr Thr Val Trp Thr Val Ser
        195                 200                 205

Gln Phe Phe Ala Arg His Arg Gly Gly Glu His Pro Asp Gln Val Arg
    210                 215                 220

Leu Gly Lys Ile Ile Ser Leu Cys Gln Val Val Glu Glu Cys Cys Cys
225                 230                 235                 240

His Gln Asn Lys Thr Asn Arg Ala Thr Pro Glu Val Ala Ala Arg
                245                 250                 255

Ile Asp Gln Tyr Leu His Gly Ala Thr Ser Leu Glu Glu Cys Leu Ile
            260                 265                 270

Arg Leu Glu Arg Val Cys Pro Pro Ser Ala Ala Asp Thr Phe Phe Asp
        275                 280                 285

Trp Asn Val Val Leu Pro Gly Val Gly Ala Ser Thr Gln Thr Thr Lys
    290                 295                 300

Gln Leu His Val Asn Gln Cys Arg Ala Leu Val Pro Val Val Thr Gln
305                 310                 315                 320

Glu Pro Leu Asp Lys Asp Ser Val Pro Leu Thr Ala Phe Ser Leu Ser
                325                 330                 335

Asn Cys Tyr Tyr Pro Ala Gln Gly Asp Glu Val Arg His Arg Glu Arg
            340                 345                 350

Leu Asn Ser Val Leu Ser Lys Leu Glu Gly Val Val Arg Glu Glu Tyr
        355                 360                 365

Gly Leu Thr Pro Thr Glu Pro Gly Pro Arg Pro Ala Leu Pro Asn Gly
    370                 375                 380

Leu Val Glu Leu Lys Asp Gln Met Glu Glu Asp Leu Leu Lys Leu Val
385                 390                 395                 400
```

```
Asn Ala Gln Ala Thr Ser Glu Met Met Ala Trp Ala Ala Glu Gln Val
                405                 410                 415
Asp Leu Lys Ala Trp Val Lys Asn Tyr Pro Arg Trp Thr Pro Pro Pro
                420                 425                 430
Pro Pro Pro Arg Val Gln Pro Arg Lys Thr Lys Ser Val Lys Ser Leu
                435                 440                 445
Pro Gly Asn Lys Pro Val Pro Ala Pro Arg Arg Lys Val Arg Ser Asp
            450                 455                 460
Cys Gly Ser Pro Ile Leu Met Gly Asp Asn Val Pro Asp Gly Arg Glu
465                 470                 475                 480
Asp Leu Thr Val Gly Gly Pro Leu Asp Leu Ser Thr Pro Ser Glu Pro
                485                 490                 495
Met Thr Pro Leu Ser Glu Pro Ala Leu Met Pro Ala Leu Gln Tyr Ile
                500                 505                 510
Ser Arg Pro Val Thr Ser Leu Ser Val Leu Ala Pro Val Pro Ala Pro
                515                 520                 525
Arg Arg Thr Val Ser Arg Pro Val Thr Pro Leu Ser Glu Pro Ile Phe
            530                 535                 540
Val Ser Ala Pro Arg His Lys Phe Gln Gln Val Glu Glu Ala Asn Leu
545                 550                 555                 560
Ala Ala Thr Thr Leu Thr His Gln Asp Glu Pro Leu Asp Leu Ser Ala
                565                 570                 575
Ser Ser Gln Thr Glu Tyr Glu Ala Ser Pro Leu Thr Pro Leu Gln Asn
                580                 585                 590
Met Gly Ile Leu Glu Val Gly Gly Gln Glu Ala Glu Glu Val Leu Ser
                595                 600                 605
Glu Ile Ser Asp Thr Leu Asn Asp Ile Asn Pro Ala Pro Val Ser Ser
            610                 615                 620
Ser Ser Ser Leu Ser Ser Val Lys Ile Thr Arg Pro Lys His Ser Ala
625                 630                 635                 640
Gln Ala Ile Ile Asp Ser Gly Gly Pro Cys Ser Gly His Leu Arg Arg
                645                 650                 655
Glu Lys Glu Ala Cys Leu Ser Ile Met Arg Glu Ala Cys Asp Ala Ala
                660                 665                 670
Lys Leu Ser Asp Pro Ala Thr Gln Glu Trp Leu Ser Arg Met Trp Asp
            675                 680                 685
Arg Val Asp Met Leu Thr Trp Arg Asn Thr Ser Ala Tyr Gln Ala Phe
            690                 695                 700
Arg Ile Leu Asp Gly Arg Phe Glu Phe Leu Pro Lys Met Ile Leu Glu
705                 710                 715                 720
Thr Pro Pro Pro Tyr Pro Cys Gly Phe Val Met Leu Pro His Thr Pro
                725                 730                 735
Ala Pro Ser Val Gly Ala Glu Ser Asp Leu Thr Ile Gly Ser Val Ala
                740                 745                 750
Thr Glu Asp Val Pro Arg Ile Leu Gly Lys Ile Glu Asn Ala Gly Glu
                755                 760                 765
Met Pro Asn Gln Gly Leu Leu Thr Ser Phe Gly Glu Glu Pro Val Cys
                770                 775                 780
Asp Gln Pro Val Lys Asp Ser Trp Met Ser Ser Arg Gly Phe Asp Glu
785                 790                 795                 800
Ser Thr Thr Ala Pro Ser Ala Gly Thr Gly Gly Ala Asp Leu Pro Thr
                805                 810                 815
```

Asp Leu Pro Pro Ser Asp Gly Leu Asp Ala Asp Glu Trp Gly Pro Leu
                820                 825                 830

Arg Thr Val Arg Lys Lys Ala Glu Arg Leu Phe Asp Gln Leu Ser Arg
            835                 840                 845

Gln Val Phe Asn Leu Val Ser His Leu Pro Val Phe Phe Ser His Leu
        850                 855                 860

Phe Lys Ser Asp Ser Gly Tyr Ser Pro Gly Asp Trp Gly Phe Ala Ala
865                 870                 875                 880

Phe Thr Leu Phe Cys Leu Phe Leu Cys Tyr Ser Tyr Pro Phe Phe Gly
                885                 890                 895

Phe Val Pro Leu Leu Gly Val Phe Ser Gly Ser Ser Arg Arg Val Arg
            900                 905                 910

Met Gly Val Phe Gly Cys Trp Leu Ala Phe Ala Val Gly Leu Phe Lys
        915                 920                 925

Pro Val Ser Asp Pro Val Gly Thr Ala Cys Glu Phe Asp Ser Pro Glu
930                 935                 940

Cys Arg Asn Val Leu His Ser Phe Glu Leu Leu Lys Pro Trp Asp Pro
945                 950                 955                 960

Val Arg Ser Leu Val Val Gly Pro Val Gly Leu Gly Leu Ala Ile Leu
                965                 970                 975

Gly Arg Leu Leu Gly Gly Ala Arg Tyr Ile Trp His Phe Leu Leu Arg
            980                 985                 990

Leu Gly Ile Val Ala Asp Cys Ile Leu Ala Gly Ala Tyr Val Leu Ser
        995                 1000                1005

Gln Gly Arg Cys Lys Lys Cys Trp Gly Ser Cys Val Arg Thr Ala
        1010                1015                1020

Pro Asn Glu Ile Ala Phe Asn Val Phe Pro Phe Thr Arg Ala Thr
        1025                1030                1035

Arg Ser Ser Leu Ile Asp Leu Cys Asp Arg Phe Cys Ala Pro Lys
        1040                1045                1050

Gly Met Asp Pro Ile Phe Leu Ala Thr Gly Trp Arg Gly Cys Trp
        1055                1060                1065

Thr Gly Arg Ser Pro Ile Glu Gln Pro Ser Glu Lys Pro Ile Ala
        1070                1075                1080

Phe Ala Gln Leu Asp Glu Lys Arg Ile Thr Ala Arg Thr Val Gly
        1085                1090                1095

Ala Gln Pro Tyr Asp Pro Asn Gln Ala Val Lys Cys Leu Arg Val
        1100                1105                1110

Leu Gln Ala Gly Gly Ala Ile Val Ala Glu Ala Val Pro Lys Val
        1115                1120                1125

Val Lys Val Ser Ala Ile Pro Phe Arg Ala Pro Phe Phe Pro Thr
        1130                1135                1140

Gly Val Lys Val Asp Pro Glu Cys Arg Ile Val Val Asp Pro Asp
        1145                1150                1155

Thr Phe Thr Thr Ala Leu Arg Ser Gly Tyr Ser Thr Thr Asn Leu
        1160                1165                1170

Val Leu Gly Val Gly Asp Phe Ala Gln Leu Asn Gly Leu Lys Ile
        1175                1180                1185

Arg Gln Ile Ser Lys Pro Ser Gly Gly
        1190                1195

<210> SEQ ID NO 87
<211> LENGTH: 1194
<212> TYPE: PRT

-continued

<213> ORGANISM: Artificial Sequence
<220> FEATURE:
<223> OTHER INFORMATION: Porcine reproductive and respiratory syndrome
      virus; Nsp2

<400> SEQUENCE: 87

```
Gly Ala Gly Lys Arg Ala Arg Lys Ala Arg Ser Gly Ala Thr Thr Met
1               5                   10                  15

Val Ala His Arg Ala Ser Ser Ala His Glu Thr Arg Gln Ala Thr Lys
            20                  25                  30

His Glu Gly Ala Gly Ala Asn Lys Ala Glu His Leu Lys Leu Tyr Ser
        35                  40                  45

Pro Pro Ala Glu Gly Asn Cys Gly Trp His Cys Ile Ser Ala Ile Val
    50                  55                  60

Asn Arg Met Val Asn Ser Asn Phe Glu Thr Thr Leu Pro Glu Arg Val
65                  70                  75                  80

Arg Pro Pro Asp Asp Trp Ala Thr Asp Glu Asp Leu Val Asn Thr Ile
                85                  90                  95

Gln Ile Leu Arg Leu Pro Ala Ala Leu Asp Arg Asn Gly Ala Cys Gly
            100                 105                 110

Gly Ala Lys Tyr Val Leu Lys Leu Glu Gly Glu His Trp Thr Val Ser
        115                 120                 125

Val Asn Pro Gly Met Ser Pro Ser Leu Leu Pro Leu Glu Cys Val Gln
    130                 135                 140

Gly Cys Cys Glu His Lys Gly Gly Leu Gly Ser Pro Asp Ala Val Glu
145                 150                 155                 160

Val Ser Gly Phe Asp Pro Ala Cys Leu Asp Arg Leu Leu Gln Val Met
                165                 170                 175

His Leu Pro Ser Ser Thr Ile Pro Ala Ala Leu Ala Glu Leu Ser Asp
            180                 185                 190

Asp Ser Asn Arg Pro Val Ser Pro Ala Ala Thr Trp Thr Val Ser
        195                 200                 205

Gln Ser Tyr Ala Arg His Arg Gly Gly Asn His His Asp Gln Val Cys
    210                 215                 220

Leu Gly Lys Ile Ile Ser Leu Cys Gln Val Ile Glu Asp Cys Cys Cys
225                 230                 235                 240

His Gln Asn Lys Thr Asn Arg Ala Thr Pro Glu Glu Val Ala Ala Lys
                245                 250                 255

Ile Asp Gln Tyr Leu Arg Gly Ala Thr Ser Leu Glu Glu Cys Leu Ala
            260                 265                 270

Lys Leu Glu Arg Val Ser Pro Pro Gly Ala Ala Asp Thr Ser Phe Asp
        275                 280                 285

Trp Asn Val Val Leu Pro Gly Val Glu Ala Ala His Gln Thr Thr Glu
    290                 295                 300

Gln Leu His Val Asn Pro Cys Arg Thr Leu Val Pro Pro Val Thr Glu
305                 310                 315                 320

Pro Leu Gly Lys Asp Ser Val Pro Leu Thr Ala Phe Ser Leu Ser Asn
                325                 330                 335

Cys Tyr Tyr Pro Ala Gln Gly Asn Glu Val Arg His Arg Glu Arg Leu
            340                 345                 350

Asn Ser Val Leu Ser Lys Leu Glu Glu Val Val Leu Glu Glu Tyr Gly
        355                 360                 365

Leu Met Ser Thr Gly Leu Gly Pro Arg Pro Val Leu Pro Ser Gly Leu
    370                 375                 380
```

```
Asp Glu Leu Lys Asp Gln Met Glu Glu Asp Leu Lys Leu Ala Asn
385                 390                 395                 400

Thr Gln Ala Thr Ser Glu Met Met Ala Trp Ala Ala Glu Gln Val Asp
            405                 410                 415

Leu Lys Ala Trp Val Lys Ser Tyr Pro Arg Trp Thr Pro Pro Pro
            420                 425                 430

Pro Pro Arg Val Gln Pro Arg Lys Thr Lys Ser Val Lys Ser Leu Pro
            435                 440                 445

Glu Asp Lys Pro Val Pro Ala Pro Arg Arg Lys Val Arg Ser Gly Cys
    450                 455                 460

Gly Ser Pro Val Leu Met Gly Asp Asn Val Pro Asn Gly Ser Glu Asp
465                 470                 475                 480

Leu Thr Val Gly Gly Pro Leu Asn Phe Pro Thr Pro Ser Glu Pro Met
            485                 490                 495

Thr Pro Met Ser Glu Pro Val Leu Thr Pro Ala Leu Gln Arg Val Pro
            500                 505                 510

Lys Leu Met Thr Pro Leu Asp Gly Ser Ala Pro Val Pro Ala Pro Arg
            515                 520                 525

Arg Thr Val Ser Arg Pro Met Thr Pro Leu Ser Glu Pro Ile Phe Leu
    530                 535                 540

Ser Ala Pro Arg His Lys Phe Gln Gln Val Glu Glu Ala Asn Pro Ala
545                 550                 555                 560

Thr Thr Thr Leu Thr His Gln Asn Glu Pro Leu Asp Leu Ser Ala Ser
            565                 570                 575

Ser Gln Thr Glu Tyr Glu Ala Ser Pro Leu Ala Ser Ser Gln Asn Met
            580                 585                 590

Ser Ile Leu Glu Ala Gly Gly Gln Glu Ala Glu Glu Val Leu Ser Glu
            595                 600                 605

Ile Ser Asp Ile Leu Asn Asp Thr Ser Pro Ala Pro Val Ser Ser Ser
    610                 615                 620

Ser Ser Leu Ser Ser Val Lys Ile Thr Arg Pro Lys Tyr Ser Ala Gln
625                 630                 635                 640

Ala Ile Ile Asp Ser Gly Gly Pro Cys Ser Gly His Leu Gln Lys Glu
            645                 650                 655

Lys Glu Ala Cys Leu Ser Ile Met Arg Glu Ala Cys Asp Ala Ser Lys
            660                 665                 670

Leu Ser Asp Pro Ala Gln Glu Trp Leu Ser Arg Met Trp Asp Arg Val
    675                 680                 685

Asp Met Leu Thr Trp Arg Asn Thr Ser Ala Tyr Gln Ala Phe Arg Thr
690                 695                 700

Leu Asn Gly Arg Phe Glu Phe Leu Pro Lys Met Ile Leu Glu Thr Pro
705                 710                 715                 720

Pro Pro His Pro Cys Gly Phe Val Met Leu Pro His Thr Pro Ala Pro
            725                 730                 735

Ser Val Ser Ala Glu Ser Asp Leu Thr Ile Gly Ser Val Ala Thr Glu
            740                 745                 750

Asp Val Pro Arg Ile Leu Gly Lys Ile Gly Asp Thr Gly Glu Leu Leu
            755                 760                 765

Asn Gln Gly Pro Ser Ala Pro Phe Lys Gly Gly Pro Val Cys Asp Gln
            770                 775                 780

Pro Ala Lys Asn Ser Arg Met Ser Pro Arg Glu Ser Asp Glu Ser Ile
785                 790                 795                 800

Ile Ala Pro Pro Ala Asp Thr Gly Gly Ala Gly Ser Phe Thr Asp Leu
```

```
            805                 810                 815
Pro Ser Ser Asp Ser Val Asp Ala Asn Gly Gly Pro Leu Arg Thr Val
                820                 825                 830

Lys Thr Lys Ala Gly Arg Leu Leu Asp Gln Leu Ser Cys Gln Val Phe
                835                 840                 845

Ser Leu Val Ser His Leu Pro Val Phe Phe Ser His Leu Phe Lys Ser
    850                 855                 860

Asp Ser Gly Tyr Ser Pro Gly Asp Trp Gly Phe Ala Ala Phe Thr Leu
865                 870                 875                 880

Phe Cys Leu Phe Leu Cys Tyr Ser Tyr Pro Phe Phe Gly Phe Ala Pro
                885                 890                 895

Leu Leu Gly Val Phe Gly Ser Ser Arg Arg Val Arg Met Gly Val
                900                 905                 910

Phe Gly Cys Trp Leu Ala Phe Ala Val Gly Leu Phe Lys Pro Val Ser
                915                 920                 925

Asp Pro Val Gly Thr Ala Cys Glu Phe Asp Ser Pro Glu Cys Arg Asn
    930                 935                 940

Val Leu His Ser Phe Glu Leu Leu Lys Pro Trp Asp Pro Val Arg Ser
945                 950                 955                 960

Leu Val Val Gly Pro Val Gly Leu Gly Leu Ala Ile Leu Gly Arg Leu
                965                 970                 975

Leu Gly Gly Ala Arg Tyr Val Trp His Phe Leu Leu Arg Phe Gly Ile
                980                 985                 990

Val Ala Asp Cys Ile Leu Ala Gly Ala Tyr Val Leu Ser Gln Gly Arg
            995                 1000                1005

Cys Lys Lys Cys Trp Gly Ser Cys Val Arg Thr Ala Pro Asn Glu
    1010                1015                1020

Ile Ala Phe Asn Val Phe Pro Phe Thr Arg Ala Thr Arg Ser Ser
    1025                1030                1035

Leu Ile Asp Leu Cys Asp Arg Phe Cys Ala Pro Lys Gly Met Asp
    1040                1045                1050

Pro Ile Phe Leu Ala Thr Val Trp Arg Gly Cys Trp Thr Gly Arg
    1055                1060                1065

Ser Pro Ile Glu Gln Pro Ser Glu Lys Pro Ile Ala Phe Ala Gln
    1070                1075                1080

Leu Asp Glu Lys Arg Ile Thr Ala Arg Thr Val Val Ala Gln Pro
    1085                1090                1095

Tyr Asp Pro Asn Gln Ala Val Lys Cys Leu Arg Val Leu Gln Ala
    1100                1105                1110

Gly Gly Ala Met Val Ala Glu Ala Val Pro Lys Val Val Lys Val
    1115                1120                1125

Ser Ala Ile Pro Phe Arg Ala Pro Phe Phe Pro Ala Gly Val Lys
    1130                1135                1140

Val Asp Pro Glu Cys Arg Ile Val Val Asp Pro Asp Thr Phe Thr
    1145                1150                1155

Thr Ala Leu Arg Ser Gly Tyr Ser Thr Thr Asn Leu Val Leu Gly
    1160                1165                1170

Met Gly Asp Phe Ala Gln Leu Asn Gly Leu Lys Ile Arg Gln Ile
    1175                1180                1185

Ser Lys Pro Ser Gly Gly
    1190

<210> SEQ ID NO 88
```

<211> LENGTH: 1061
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 88

```
Ala Ala Gly Lys Arg Ala Arg Ala Lys Arg Ala Thr Lys Ser Gly Lys
1               5                   10                  15

Asp Ser Ala Leu Ala Pro Lys Ile Ala Pro Val Pro Thr Cys Gly
            20                  25                  30

Ile Thr Thr Tyr Ser Pro Pro Thr Asp Gly Ser Cys Gly Trp His Val
        35                  40                  45

Leu Ala Ala Ile Val Asn Arg Met Ile Asn Gly Asp Phe Thr Ser Pro
    50                  55                  60

Le

```
                 370                 375                 380
Thr Pro Asp Asn Pro Gly Ser Asp Ala Ser Ala Leu Pro Ile Ala Val
385                 390                 395                 400

Arg Gly Phe Val Pro Thr Gly Pro Ile Leu Arg His Val Glu His Cys
                405                 410                 415

Gly Thr Glu Ser Gly Asp Ser Ser Pro Leu Asp Leu Ser Phe Ala
                420                 425                 430

Gln Thr Leu Asp Gln Pro Leu Asp Leu Ser Leu Ala Ala Trp Pro Val
                435                 440                 445

Lys Ala Thr Ala Ser Asp Pro Gly Trp Val Arg Gly Arg Cys Glu Pro
                450                 455                 460

Val Phe Leu Lys Pro Arg Lys Ala Phe Ser Asp Gly Asp Ser Ala Leu
465                 470                 475                 480

Gln Phe Gly Glu Leu Ser Glu Ser Ser Val Ile Glu Phe Asp Gln
                485                 490                 495

Thr Lys Asp Thr Leu Val Ala Asp Ala Pro Val Asp Leu Thr Thr Ser
                500                 505                 510

Asn Glu Ala Leu Ser Ala Val Asp Pro Ser Glu Phe Val Glu Leu Arg
                515                 520                 525

Arg Pro Arg His Ser Ala Gln Ala Leu Ile Asp Arg Gly Gly Pro Leu
                530                 535                 540

Ala Asp Val His Ala Lys Ile Lys Asn Arg Val Tyr Glu Gln Cys Leu
545                 550                 555                 560

Gln Ala Cys Glu Pro Gly Ser Arg Ala Thr Pro Ala Thr Arg Glu Trp
                565                 570                 575

Leu Asp Lys Met Trp Asp Arg Val Asp Met Lys Thr Trp Arg Cys Thr
                580                 585                 590

Ser Gln Phe Gln Ala Gly Arg Ile Leu Ala Ser Leu Lys Phe Leu Pro
                595                 600                 605

Asp Met Ile Gln Asp Thr Pro Pro Val Pro Arg Lys Asn Arg Ala
610                 615                 620

Ser Asp Asn Ala Gly Leu Lys Gln Leu Val Ala Arg Trp Asp Lys Lys
625                 630                 635                 640

Leu Ser Val Thr Pro Pro Lys Ser Ala Gly Leu Val Leu Asp Gln
                645                 650                 655

Thr Val Pro Pro Thr Asp Ile Gln Gln Glu Asp Ala Thr Pro Ser
                660                 665                 670

Asp Gly Leu Ser His Ala Ser Asp Phe Ser Ser Arg Val Ser Thr Ser
                675                 680                 685

Trp Ser Trp Lys Gly Leu Met Leu Ser Gly Thr Arg Leu Ala Gly Ser
690                 695                 700

Ala Gly Gln Arg Leu Met Thr Trp Val Phe Glu Val Tyr Ser His Leu
705                 710                 715                 720

Pro Ala Phe Ile Leu Thr Leu Phe Ser Pro Arg Gly Ser Met Ala Pro
                725                 730                 735

Gly Asp Trp Leu Phe Ala Gly Val Val Leu Ala Leu Leu Leu Cys
                740                 745                 750

Arg Ser Tyr Pro Ile Leu Gly Cys Leu Pro Leu Gly Val Phe Ser
                755                 760                 765

Gly Ser Leu Arg Arg Val Arg Leu Gly Val Phe Gly Ser Trp Met Ala
                770                 775                 780

Phe Ala Val Phe Leu Phe Ser Thr Pro Ser Asn Pro Val Gly Ser Ser
785                 790                 795                 800
```

```
Cys Asp His Asp Ser Pro Glu Cys His Ala Glu Leu Glu Leu Glu
                805                 810                 815
Gln Arg Gln Leu Trp Glu Pro Val Arg Gly Leu Val Val Gly Pro Ser
            820                 825                 830
Gly Leu Leu Cys Val Ile Leu Gly Lys Leu Leu Gly Gly Ser Arg His
                835                 840                 845
Leu Trp His Val Ile Leu Arg Leu Cys Met Leu Thr Asp Leu Ala Leu
            850                 855                 860
Ser Leu Val Thr Val Val Ser Gln Gly Arg Cys His Lys Cys Trp Gly
865                 870                 875                 880
Lys Cys Ile Arg Thr Ala Pro Ala Glu Val Ala Leu Asn Val Phe Pro
                885                 890                 895
Phe Ser Arg Ala Thr Arg Asn Ser Leu Thr Ser Leu Cys Asp Arg Phe
                900                 905                 910
Gln Thr Pro Lys Gly Val Asp Pro Val His Leu Ala Thr Gly Trp Arg
            915                 920                 925
Gly Cys Trp Arg Gly Glu Ser Pro Ile His Gln Pro His Gln Lys Pro
            930                 935                 940
Ile Ala Tyr Ala Asn Leu Asp Glu Lys Lys Ile Ser Ala Gln Thr Val
945                 950                 955                 960
Val Ala Val Pro Tyr Asp Pro Ser Gln Ala Ile Lys Cys Leu Lys Val
                965                 970                 975
Leu Gln Ala Gly Gly Ala Ile Val Asp Gln Pro Thr Pro Glu Val Val
            980                 985                 990
Arg Val Ser Glu Ile Pro Phe Ser Ala Pro Phe Phe Pro Lys Val Pro
            995                 1000                1005
Val Asn Pro Asp Cys Arg Ile Val Val Asp Ser Asp Thr Phe Val
    1010                1015                1020
Ala Ala Val Arg Cys Gly Tyr Ser Thr Ala Gln Leu Val Leu Gly
    1025                1030                1035
Arg Gly Asn Phe Ala Lys Leu Asn Gln Thr Pro Leu Arg Asp Ser
    1040                1045                1050
Ala Ser Thr Lys Thr Thr Gly Gly
    1055                1060

<210> SEQ ID NO 89
<211> LENGTH: 1060
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 89

Ala Ala Gly Lys Arg Ala Arg Ala Lys Arg Thr Ala Lys Gly Gly Lys
1               5                   10                  15
Asp Ser Val Pro Ala Leu Lys Val Ala Leu Pro Val Pro Ala Cys Gly
            20                  25                  30
Ile Thr Thr Tyr Ser Pro Pro Thr Asp Gly Ser Cys Gly Trp His Val
        35                  40                  45
Leu Ala Ala Ile Met Asn Arg Met Met Asn Asp Asp Phe Thr Ser Pro
    50                  55                  60
Leu Thr Gln Tyr Asn Arg Pro Glu Asp Asp Trp Ala Ser Asp Tyr Asp
65                  70                  75                  80
Leu Ala Gln Ala Ile Gln Cys Leu Gln Leu Pro Ala Thr Val Val Arg
```

```
                       85                  90                  95
Asn Arg Ala Cys Pro Asn Ala Lys Tyr Leu Ile Lys Leu Asn Gly Val
                100                 105                 110

His Trp Glu Val Glu Val Arg Ser Gly Met Ala Pro Arg Ser Leu Ser
            115                 120                 125

Glu Cys Val Val Gly Val Cys Ser Glu Gly Cys Val Ala Pro Pro Tyr
        130                 135                 140

Pro Ala Asp Gly Leu Pro Lys Arg Ala Leu Glu Ala Leu Ala Ser Ala
145                 150                 155                 160

Tyr Arg Leu Pro Ser Asp Cys Val Cys Ser Gly Ile Ala Asp Phe Leu
                165                 170                 175

Ala Asn Pro Pro Pro Gln Glu Phe Trp Thr Leu Asp Lys Met Leu Thr
            180                 185                 190

Ser Pro Ser Pro Glu Arg Ser Gly Phe Ser Ser Leu Tyr Asn Leu Leu
        195                 200                 205

Leu Glu Val Val Pro Gln Lys Cys Gly Val Thr Glu Gly Ala Phe Thr
    210                 215                 220

Tyr Ala Val Glu Arg Met Leu Met Asp Cys Pro Ser Ser Glu Gln Ala
225                 230                 235                 240

Met Ala Leu Leu Ala Lys Ile Lys Val Pro Ser Ser Lys Ala Pro Ser
                245                 250                 255

Val Ser Leu Asp Glu Cys Phe Pro Ala Asp Val Pro Ala Asp Phe Glu
            260                 265                 270

Pro Thr Ser Gln Lys Arg Pro Gln Ser Ser Gly Ala Ala Val Ala Leu
        275                 280                 285

Cys Ser Ser Asp Ala Glu Gly Phe Glu Glu Ala Ala Pro Glu Gly Val
    290                 295                 300

Gln Glu Arg Gly His Lys Ala Val His Ser Ala Leu Phe Ala Lys Gly
305                 310                 315                 320

Pro Asn Asn Glu Gln Val Gln Val Val Ala Gly Glu Gln Gln Lys Leu
                325                 330                 335

Gly Gly Cys Gly Leu Ala Ile Gly Asn Ala Gln Ser Pro Leu Asn Ser
            340                 345                 350

Met Lys Glu Asn Met Arg Ser Arg Glu Asp Glu Pro Leu Asp Leu
        355                 360                 365

Ser Gln Pro Ala Pro Val Ala Ala Thr Thr Leu Glu Arg Glu Gln Thr
    370                 375                 380

Pro Asp Asn Pro Gly Ser Asp Ala Gly Ala Leu Pro Ala Thr Val Arg
385                 390                 395                 400

Glu Ser Val Pro Thr Gly Pro Met Leu Arg His Val Glu His Cys Gly
                405                 410                 415

Thr Glu Ser Gly Asp Ser Ser Pro Leu Asp Leu Ser Tyr Ala Gln
            420                 425                 430

Thr Leu Asp Gln Pro Leu Asp Leu Ser Leu Ala Val Trp Pro Val Lys
        435                 440                 445

Ala Thr Ala Ser Asp Pro Gly Trp Val His Gly Arg Arg Glu Pro Val
    450                 455                 460

Phe Val Lys Pro Arg Lys Ala Phe Ser Asp Ser Asp Ser Ala Phe Gln
465                 470                 475                 480

Phe Gly Lys Leu Ser Glu Ser Gly Ser Val Ile Glu Phe Asp Arg Thr
                485                 490                 495

Lys Asp Ala Pro Val Val Asp Ala Pro Val Gly Ser Thr Thr Ser Asn
            500                 505                 510
```

-continued

```
Glu Ala Leu Ser Ile Ala Asp Pro Phe Glu Phe Ala Glu Leu Lys Arg
                515                 520                 525

Pro Arg Phe Ser Ala Gln Ala Leu Ile Asp Arg Gly Gly Pro Leu Ala
            530                 535                 540

Asp Val His Ala Lys Ile Lys Asn Arg Val Tyr Glu Arg Cys Leu Gln
545                 550                 555                 560

Ala Cys Glu Pro Gly Ser Arg Ala Thr Pro Ala Thr Lys Glu Trp Leu
                565                 570                 575

Asp Lys Met Trp Asp Arg Val Asp Met Lys Thr Trp Cys Cys Thr Ser
            580                 585                 590

Gln Phe Gln Ala Gly Arg Ile Leu Ala Ser Leu Lys Phe Leu Pro Asp
        595                 600                 605

Met Ile Gln Asp Thr Pro Pro Val Pro Arg Lys Asn Arg Ala Ser
    610                 615                 620

Asp Asn Ala Asp Leu Lys Gln Leu Val Ala Gln Trp Asp Arg Lys Leu
625                 630                 635                 640

Ser Met Thr Pro Pro Gln Lys Pro Val Glu Pro Val Leu Asp Gln Thr
                645                 650                 655

Val Ser Pro Pro Thr Asp Thr Gln Gln Glu Asp Val Thr Pro Ser Asp
            660                 665                 670

Gly Pro Pro His Ala Pro Asp Phe Pro Ser Arg Val Ser Thr Gly Gly
        675                 680                 685

Ser Trp Lys Asp Leu Met Cys Ser Gly Thr Arg Leu Ala Gly Ser Ile
    690                 695                 700

Ser Gln Arg Leu Met Thr Trp Val Phe Glu Val Phe Ser His Leu Pro
705                 710                 715                 720

Ala Phe Met Leu Thr Leu Phe Ser Pro Arg Gly Ser Met Ala Pro Gly
                725                 730                 735

Asp Trp Leu Phe Ala Gly Val Val Leu Leu Ala Leu Leu Cys His
            740                 745                 750

Ser Tyr Pro Ile Leu Gly Cys Leu Pro Leu Leu Gly Val Phe Ser Gly
        755                 760                 765

Ser Leu Arg Arg Val Arg Leu Gly Val Phe Gly Ser Trp Met Ala Phe
    770                 775                 780

Ala Val Phe Leu Phe Ser Thr Pro Ser Asn Pro Val Gly Ser Ser Cys
785                 790                 795                 800

Asp His Asp Ser Pro Glu Cys His Ala Glu Leu Leu Ala Leu Glu Gln
                805                 810                 815

Arg Gln Leu Trp Glu Pro Val Arg Gly Leu Val Val Gly Pro Ser Gly
            820                 825                 830

Leu Leu Cys Val Ile Leu Gly Lys Leu Leu Gly Gly Ser Arg Tyr Leu
        835                 840                 845

Trp His Ile Leu Leu Arg Leu Cys Met Leu Thr Asp Leu Ala Leu Ser
    850                 855                 860

Leu Val Tyr Val Val Ser Gln Gly Arg Cys His Lys Cys Trp Gly Lys
865                 870                 875                 880

Cys Ile Arg Thr Ala Pro Thr Glu Val Ala Leu Asn Val Phe Pro Phe
                885                 890                 895

Thr Arg Ala Thr Arg Ser Ser Leu Val Ser Leu Cys Asp Arg Phe Gln
            900                 905                 910

Thr Pro Lys Gly Val Asp Pro Val His Leu Ala Thr Gly Trp Arg Gly
        915                 920                 925
```

```
Cys Trp Arg Gly Gly Ser Pro Val His Gln Pro His Gln Lys Pro Ile
930                 935                 940

Ala Tyr Ala Asn Leu Asp Glu Lys Lys Ile Ser Ala Gln Thr Val Val
945                 950                 955                 960

Ala Val Pro Tyr Asp Pro Ser Gln Ala Ile Lys Cys Leu Lys Val Leu
            965                 970                 975

Gln Ala Gly Gly Ala Ile Val Asp Gln Pro Thr Pro Glu Val Val Arg
        980                 985                 990

Val Ser Glu Ile Pro Phe Ser Ala Pro Phe Phe Pro Lys Val Pro Val
    995                 1000                1005

Asn Pro Asp Cys Arg Val Val Val Asp Ser Asp Thr Phe Val Ala
    1010                1015                1020

Ala Val Arg Cys Gly Tyr Ser Thr Ala Gln Leu Val Leu Gly Gln
    1025                1030                1035

Gly Asn Phe Ala Lys Leu Asn Gln Thr Pro Pro Arg Asn Ser Thr
    1040                1045                1050

Ser Thr Lys Thr Thr Gly Gly
    1055                1060

<210> SEQ ID NO 90
<211> LENGTH: 1094
<212> TYPE: PRT
<213> ORGANISM: Artificial Sequence
<220> FEATURE:
<223> OTHER INFORMATION: Porcine reproductive and respiratory syndrome
      virus; Nsp2

<400> SEQUENCE: 90

Ala Ala Gly Lys Arg Ala Arg Ala Lys Arg Ala Ala Lys Ser Glu Lys
1               5                   10                  15

Asp Ser Ala Pro Thr Pro Lys Val Ala Leu Pro Val Pro Thr Cys Gly
            20                  25                  30

Ile Thr Thr Tyr Ser Pro Pro Thr Asp Gly Ser Cys Gly Trp His Val
        35                  40                  45

Leu Ala Ala Ile Met Asn Arg Met Ile Asn Gly Asp Phe Thr Ser Pro
    50                  55                  60

Leu Thr Gln Tyr Asn Arg Pro Glu Asp Asp Trp Ala Ser Asp Tyr Asp
65                  70                  75                  80

Leu Val Gln Ala Ile Gln Cys Leu Arg Leu Pro Ala Thr Val Val Arg
                85                  90                  95

Asn Arg Ala Cys Pro Asn Ala Lys Tyr Leu Ile Lys Leu Asn Gly Val
            100                 105                 110

His Trp Glu Val Glu Val Arg Ser Gly Met Ala Pro Arg Ser Leu Ser
        115                 120                 125

Arg Glu Cys Val Val Gly Val Cys Ser Glu Gly Cys Val Ala Pro Pro
    130                 135                 140

Tyr Pro Ala Asp Gly Leu Pro Lys Arg Ala Leu Glu Ala Leu Ala Ser
145                 150                 155                 160

Ala Tyr Arg Leu Pro Ser Asp Cys Val Ser Ser Gly Ile Ala Asp Phe
                165                 170                 175

Leu Ala Asn Pro Pro Pro Gln Glu Phe Trp Thr Leu Asp Lys Met Leu
            180                 185                 190

Thr Ser Pro Ser Pro Glu Arg Ser Gly Phe Ser Ser Leu Tyr Lys Leu
        195                 200                 205

Leu Leu Glu Val Val Pro Gln Lys Cys Gly Ala Thr Glu Gly Ala Phe
    210                 215                 220
```

-continued

```
Ile Tyr Ala Val Glu Arg Met Leu Lys Asp Cys Pro Ser Ser Lys Gln
225                 230                 235                 240

Ala Met Ala Leu Leu Ala Lys Ile Lys Val Pro Ser Ser Lys Gln Ala
            245                 250                 255

Met Ala Leu Leu Ala Lys Ile Lys Val Pro Ser Ser Lys Ala Pro Ser
        260                 265                 270

Val Ser Leu Asp Glu Cys Phe Pro Thr Asp Val Leu Ala Asp Phe Glu
    275                 280                 285

Pro Ala Ser Gln Glu Arg Pro Gln Ser Ser Gly Ala Ala Val Val Leu
290                 295                 300

Cys Ser Pro Asp Ala Lys Glu Phe Glu Ala Ala Pro Glu Glu Val
305                 310                 315                 320

Gln Glu Ser Gly His Lys Ala Val His Ser Ala Leu Leu Ala Glu Gly
                325                 330                 335

Pro Asn Asn Glu Gln Val Gln Val Val Ala Gly Glu Gln Leu Lys Leu
            340                 345                 350

Gly Gly Cys Gly Leu Ala Val Gly Asn Ala His Glu Gly Ala Leu Val
        355                 360                 365

Ser Ala Gly Leu Ile Asn Leu Val Gly Gly Asn Leu Ser Pro Ser Asp
370                 375                 380

Pro Met Lys Glu Asn Met Leu Asn Ser Arg Glu Asp Glu Pro Leu Asp
385                 390                 395                 400

Leu Ser Gln Pro Ala Pro Ala Ser Thr Thr Thr Leu Val Arg Glu Gln
                405                 410                 415

Thr Pro Asp Asn Pro Gly Ser Asp Ala Gly Ala Leu Pro Val Thr Val
            420                 425                 430

Arg Glu Phe Val Pro Thr Gly Pro Ile Leu Cys His Val Glu His Cys
        435                 440                 445

Gly Thr Glu Ser Gly Asp Ser Ser Pro Leu Asp Leu Ser Asp Ala
450                 455                 460

Gln Thr Leu Asp Gln Pro Leu Asn Leu Ser Leu Ala Ala Trp Pro Val
465                 470                 475                 480

Arg Ala Thr Ala Ser Asp Pro Gly Trp Val His Gly Arg Arg Glu Pro
                485                 490                 495

Val Phe Val Lys Pro Arg Asn Ala Phe Ser Asp Gly Asp Ser Ala Leu
            500                 505                 510

Gln Phe Gly Glu Leu Ser Glu Ser Ser Val Ile Glu Phe Asp Arg
        515                 520                 525

Thr Lys Asp Ala Pro Val Val Asp Ala Pro Val Asp Leu Thr Thr Ser
530                 535                 540

Asn Glu Ala Leu Ser Val Val Asp Pro Phe Glu Phe Ala Glu Leu Lys
545                 550                 555                 560

Arg Pro Arg Phe Ser Ala Gln Ala Leu Ile Asp Arg Gly Gly Pro Leu
                565                 570                 575

Ala Asp Val His Ala Lys Ile Lys Asn Arg Val Tyr Glu Gln Cys Leu
            580                 585                 590

Gln Ala Cys Glu Pro Gly Ser Arg Ala Thr Pro Ala Thr Arg Glu Trp
        595                 600                 605

Leu Asp Lys Met Trp Asp Arg Val Asp Met Lys Thr Trp Arg Cys Thr
610                 615                 620

Ser Gln Phe Gln Ala Gly Arg Ile Leu Ala Ser Leu Lys Phe Leu Pro
625                 630                 635                 640
```

```
Asp Met Ile Gln Asp Thr Pro Pro Val Pro Arg Lys Asn Arg Ala
                645                 650                 655

Ser Asp Asn Ala Gly Leu Lys Gln Leu Val Ala Gln Trp Asp Arg Lys
            660                 665                 670

Leu Ser Val Thr Pro Pro Lys Pro Val Gly Pro Val Leu Asp Gln
        675                 680                 685

Ile Val Pro Pro Thr Asp Ile Gln Gln Glu Asp Val Thr Pro Ser
    690                 695                 700

Asp Gly Pro Pro His Ala Pro Asp Phe Pro Ser Arg Val Ser Thr Gly
705                 710                 715                 720

Gly Ser Trp Lys Gly Leu Met Leu Ser Gly Thr Arg Leu Ala Gly Ser
            725                 730                 735

Ile Ser Gln Arg Leu Met Thr Trp Val Phe Glu Val Phe Ser His Leu
        740                 745                 750

Pro Ala Phe Met Leu Thr Leu Phe Ser Pro Arg Gly Ser Met Ala Pro
        755                 760                 765

Gly Asp Trp Leu Phe Ala Gly Val Val Leu Ala Leu Leu Leu Cys
770                 775                 780

Arg Ser Tyr Pro Ile Leu Gly Cys Leu Pro Leu Leu Gly Val Phe Ser
785                 790                 795                 800

Gly Ser Leu Arg Arg Val Arg Leu Gly Val Phe Gly Ser Trp Met Ala
            805                 810                 815

Phe Ala Ala Phe Leu Phe Ser Thr Pro Ser Asn Pro Val Gly Ser Ser
                820                 825                 830

Cys Asp His Asp Ser Pro Glu Cys His Ala Glu Leu Leu Ala Leu Glu
                835                 840                 845

Gln Arg Gln Leu Trp Glu Pro Val Arg Gly Leu Val Val Gly Pro Ser
850                 855                 860

Gly Leu Leu Cys Val Ile Leu Gly Lys Leu Leu Gly Gly Ser Arg Tyr
865                 870                 875                 880

Leu Trp His Val Leu Leu Arg Leu Cys Met Leu Ala Asp Leu Ala Leu
                885                 890                 895

Ser Leu Val Tyr Val Val Ser Gln Gly Arg Cys His Lys Cys Trp Gly
            900                 905                 910

Lys Cys Ile Arg Thr Ala Pro Ala Glu Val Ala Leu Asn Val Phe Pro
        915                 920                 925

Phe Ser Arg Ala Thr Arg Val Ser Leu Val Ser Leu Cys Asp Arg Phe
        930                 935                 940

Gln Thr Pro Lys Gly Val Asp Pro Val His Leu Ala Thr Gly Trp Arg
945                 950                 955                 960

Gly Cys Trp Arg Gly Glu Ser Pro Ile His Gln Pro His Gln Lys Pro
            965                 970                 975

Ile Ala Tyr Ala Asn Leu Asp Glu Lys Lys Met Ser Ala Gln Thr Val
                980                 985                 990

Val Ala Val Pro Tyr Asp Pro Ser  Gln Ala Ile Lys Cys  Leu Lys Val
            995                 1000                1005

Leu Gln  Ala Gly Gly Ala Ile  Val Asp Gln Pro Thr  Pro Glu Val
    1010                1015                1020

Val Arg  Val Ser Glu Ile Pro  Phe Ser Ala Pro Phe  Phe Pro Lys
    1025                1030                1035

Val Pro  Val Asn Pro Asp Cys  Arg Val Val Val Asp  Ser Asp Thr
    1040                1045                1050

Phe Val  Ala Ala Ala Val Arg  Cys Gly Tyr Ser Thr  Ala Gln Leu
```

-continued

```
    1055                1060                1065

Val Leu  Gly Arg Gly Asn Phe  Ala Lys Leu Asn Gln  Thr Pro Pro
    1070                1075                1080

Arg Asn  Ser Ile Ser Thr Lys  Thr Thr Gly Gly
    1085                1090
```

PRRS VIRUSES, INFECTIOUS CLONES, MUTANTS THEREOF, AND METHOD OF USE

CONTINUING APPLICATION DATA

This application is a continuation of U.S. application Ser. No. 11/922,798, filed Jun. 23, 2006, which issued as U.S. Pat. No. 8,110,390 on Feb. 7, 2012 and was a U.S. National Stage application of International Application No. PCT/US2006/024355, filed Jun. 23, 2006, now International Publication No. WO 2007/002321, which claims the benefit of U.S. Provisional Application Ser. No. 60/694,021, filed Jun. 24, 2005, all of which are incorporated by reference herein in their entirety.

BACKGROUND

Porcine reproductive and respiratory syndrome virus (PRRSV) is the causative agent of a disease characterized by respiratory disorders in young pigs and reproductive failure in sows (Benfield et al., *J. Vet. Diagn. Invest.*, 4:127-133 (1992); Collins et al., *J. Vet. Diagn. Invest.*, 4:117-126 (1992); Wensvoort et al., *Vet. Q.*, 13:121-130 (1991)) and is now endemic in most countries. The syndrome was first recognized as a "mystery swine disease" in the United States in 1987 and was discovered in Europe in 1990. The two prototype viral strains (Lelystad and VR-2332) differ in nucleotide sequence by approximately 40% and represent two distinct genotypes, referred to as European (EU or Type 1, Lelystad; Meulenberg et al., *Virology*, 192:62-72 (1993)) and North American (NA or Type 2, VR-2332; Nelsen et al., *J. Virol.*, 73:270-80 (1999)) strains (Fang et al., *Virus Res.*, 100:229-235 (2004); Mardassi et al., *J. Gen. Virol.*, 75:681-5 (1994); Meng et al., *Arch. Virol.*, 140:745-55 (1995); Ropp et al., *J. Virol.*, 78:3684-3703 (2004)). The disease has also been referred to as Wabash syndrome, mystery pig disease, porcine reproductive and respiratory syndrome, swine plague, porcine epidemic abortion and respiratory syndrome, blue abortion disease, blue ear disease, abortus blau, and seuchenhafter spatabort der schweine. The disease is characterized by reproductive failure in pregnant sows and respiratory problems in pigs of all ages. The disease has a significant negative impact on the swine industry.

PRRSV is an enveloped, positive-sense RNA virus belonging to the family Arteriviridae in the order Nidovirales (Cavanagh, *Arch. Virol.*, 142:629:633 (1997)). The PRRSV genome varies from 15.1-15.5 kb long (Meulenberg et al., *Virology*, 192:62-72 (1993); Nelsen et al., *J. Virol.*, 73:270-80 (1999)). The first 75% of the genome encodes the replicase polyprotein essential for virus replication and is comprised of two large open reading frames (ORFs) (1a and 1b) that are processed cotranslationally into smaller proteins by virally encoded proteases (Snijder et al., *J. Gen. Virol.*, 79:961-79 (1998)). The structural proteins are encoded by seven downstream ORFs and are translated from a 3'-coterminal nested set of subgenomic mRNAs (sgmRNA) (Meulenberg et al., *Virology*, 192:62-72 (1993); Pattnaik et al., *Cell*, 69:1011-1020 (1992)). In strain VR-2332, the coding region of the genome (15,411 bases) is flanked by 5' and 3' nontranslated regions of 189 and 151 nucleotides, respectively.

PRRSV strain VR-2332 has been well characterized in terms of its complete genome sequence (Pattnaik et al., *Cell*, 69:1011-1020 (1992)), the ability of PRRSV to constitutively produce defective subgenomic RNA species termed heteroclites (latin: uncommon forms) (Yuan et al., *Virology*, 275: 158-169 (2000); Yuan et al., *Virus Research*, 105:75-87 (2004)), and its growth properties in vitro as well as in vivo (Murtaugh et al., *Vet. Inununol. Innnunopathol.*, 102:105-349 (2004)). In addition, an infectious clone of this 15.4 kb NA PRRSV genome has been produced and examined for its ability to cause disease in swine (pVR-HN; Nielsen et al., *J. Virol.*, 77:3702-3711 (2003)).

PRRSV continues to cause significant economic losses throughout the world. Vaccines are available, but they are based on one PRRSV strain, and there is evidence that PRRSV strains vary at the antigenic and genetic levels. In addition, since the virus was identified in Europe and in the United States, new disease phenotypes have continued to emerge.

SUMMARY OF THE INVENTION

Prior reports had suggested that deletions and/or mutations of any strain of PRRS virus was often extremely detrimental to viral growth. Specifically, individual laboratories had made mutations in the 3' end of the virus, and the resultant virus was either unstable and quickly reverted back to wild-type sequence, or grew very poorly or not at all (Lee et al., *Virol.*, 331:47-62 (2005); Choi et al., *J. Virol.*, 80:723-736 (2006); Lee et al., *Virolog.*, 346:238-250 (2005)). Thus, in comparison of nucleotide sequences of European (Type 1 genotype) and VR-2332 (Type 2 genotype), where to make mutations in VR-2332 NSP2 that were not extremely detrimental was not known. However, alignment of the full genome sequences of new Type 2 PRRS viruses with VR-2332 began to provide insight as to where viable mutants could be made. Further deletion mutagenesis showed that the region between nsp2 amino acids 324-813 was not necessary for growth in vitro.

The present invention provides an isolated infectious polynucleotide having a nucleotide sequence with at least 88% identity to SEQ ID NO:1 and a deletion of at least 39 consecutive nucleotides selected from nucleotide 2062 to nucleotide 3864 of SEQ ID NO:1. Also provided is an isolated infectious polynucleotide having a nucleotide sequence with at least 88% identity to SEQ ID NO:14 and a deletion of at least 39 consecutive nucleotides selected from nucleotide 2061 to nucleotide 3545 of SEQ ID NO:14. The isolated polynucleotide may be present in a vector, in an isolated virus particle, present in a cell, or a combination thereof. When present in a vector an RNA polymerase promoter may be operably linked to the polynucleotide. The isolated polynucleotide may by an RNA. The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention also provides an isolated polynucleotide having a nucleotide sequence with at least 88% identity to SEQ ID NO:1 and at least one deletion of at least 39 consecutive nucleotides selected from nucleotide 2062 to nucleotide 3864 of SEQ ID NO:1, and wherein the polynucleotide replicates and produces infectious virus particles when introduced into a cell. Also provided is an isolated polynucleotide having a nucleotide sequence with at least 88% identity to SEQ ID NO:14 and at least one deletion of at least 39 consecutive nucleotides selected from nucleotide 2061 to nucleotide 3545 of SEQ ID NO:14, wherein the polynucleotide replicates and produces infectious virus particles when introduced into a cell. The isolated polynucleotide may be present in a vector, in an isolated virus particle, present in a cell, or a combination thereof. When present in a vector an RNA polymerase promoter may be operably linked to the polynucleotide. The isolated polynucleotide may be an RNA.

The isolated polynucleotide may include 2 or more deletions, and each deletion may be independently at least 37 consecutive nucleotides. The isolated polynucleotide may further include an exogenous polynucleotide present in the deletion, and the exogenous polynucleotide may encode a polypeptide, such as a detectable marker.

The present invention further provides an infectious clone having a polynucleotide with a nucleotide sequence having at least 88% identity to SEQ ID NO:1 and at least one deletion of at least 39 consecutive nucleotides selected from nucleotide 2062 to nucleotide 3864 of SEQ ID NO:1. Also provided is an infectious clone having a polynucleotide with a nucleotide sequence having at least 88% identity to SEQ ID NO:14 and at least one deletion of at least 39 consecutive nucleotides selected from nucleotide 2061 to nucleotide 3545 of SEQ ID NO:14. The infectious clone may be present in a cell. An RNA polymerase promoter may be operably linked to the polynucleotide. The infectious clone may include 2 or more deletions, and wherein each deletion is independently at least 37 consecutive nucleotides. The isolated polynucleotide may further include an exogenous polynucleotide present in the deletion, and the exogenous polynucleotide may encode a polypeptide, such as a detectable marker.

Also provided by the present invention is an isolated infectious polynucleotide comprising a nucleotide sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13, and an nsp2 polypeptide encoded by an infectious polynucleotide comprising a nucleotide sequence SEQ ID NO:7, SEQ ID NO:8, SEQ ID NO:9, SEQ ID NO:10, SEQ ID NO:11, SEQ ID NO:12, or SEQ ID NO:13.

The terms "comprises" and variations thereof do not have a limiting meaning where these terms appear in the description and claims. Unless otherwise specified, "a," "an," "the," and "at least one" are used interchangeably and mean one or more than one.

BRIEF DESCRIPTION OF THE FIGURES

FIG. 1. A. Nucleotide sequence (SEQ ID NO:1) of infectious polynucleotide VR-V7 (also referred to herein as V6G7475A). B. Nucleotide sequence (SEQ ID NO:2) of infectious polynucleotide VR-V5. C. Nucleotide sequence (SEQ ID NO:3) of infectious polynucleotide VR-V5G7475A. D. Nucleotide sequence (SEQ ID NO:4) of infectious polynucleotide VR-V6. E. Nucleotide sequence (SEQ ID NO:5) of infectious polynucleotide MN184A. F. Nucleotide sequence (SEQ ID NO:6) of infectious polynucleotide MN184B. G. Nucleotide sequence (SEQ ID NO:7) of infectious polynucleotide Nsp2 Δ324-434. H. Nucleotide sequence (SEQ ID NO:8) of infectious polynucleotide Nsp2 Δ324-523. I. Nucleotide sequence (SEQ ID NO:9) of infectious polynucleotide Nsp2 Δ543-632. J. Nucleotide sequence (SEQ ID NO:10) of infectious polynucleotide Nsp2 Δ633-726. K. Nucleotide sequence (SEQ ID NO:11) of infectious polynucleotide Nsp2 Δ543-726. L. Nucleotide sequence (SEQ ID NO:12) of infectious polynucleotide Nsp2 Δ727-813. M. Nucleotide sequence (SEQ ID NO:13) of infectious polynucleotide Nsp2 Δ324-726.

FIG. 5. A. Plaque assays on P3 progeny (first lineage) of all infectious clones as well as wt strain VR-2332 revealed different plaque sizes. B. Progeny of V5-1 P3 after growth in swine (Sw612) produced plaques similar to wt strain VR-2332.

FIG. 7. A. P3 progeny of wt strain VR-2332 (♦), Sw612 (▲), pVR-HN (□), pVR-V5 (×), pVR-V5G7475A (*), pVR-V6 (●), pVR-V6G7475A (○) were simultaneously examined for one step growth kinetics as outlined in Example 1. wt strain VR-2332 and Sw612 viruses replicated to approximately 10-fold higher titers at all time points. pVR-V6G7475A, with no amino acid changes from native virus or vaccine, produced virus that replicated to a higher titer at all time points than all other infectious clone progeny. B. The final titer for each virus preparation is listed in the companion table.

FIG. 9. A. Diagrammatic representation of the PRRSV genome. Putative nonstructural protein cleavages are depicted above ORF1a and 1b, represented by downward arrows. Signature motifs are identified below ORF1a and 1b, indicating their placement in the PRRSV genome [papain-like cysteine protease α and β (PL1); cysteine protease (PL2); serine/3C protease (3CL); polymerase (RdRp); helicase (Hel); *Xenopus laevis* homolog poly(U)-specific endoribonuclease (N); Ziebuhr et al., 2000; Ivanov et al., 2004; Gorbalenya et al., 2006]. B. Schematic diagram of the comparison of ORF1 protein (replicase) of MN184A and MN184B and putative processing. The degeneracy seen in nsp2 is included in the comparison. C. Schematic diagram of the comparison of ORF2-7 proteins of MN184A and MN184B.

FIG. 11. Nsp1β amino acid sequence alignment of divergent PRRSV. The figure derivation and color scheme was described in the FIG. 10 legend. The two completely conserved putative catalytic residues are identified by stars and the boxed amino acids identify MN184 sequence conservation with Type 1 isolates and EAV. The proposed cleavage site is identified by the downward arrow (↓). The following sequences were used for comparison: VR-2332 (SEQ ID NO: 61), Ingelvac MLV (SEQ ID NO: 60), PL97-1 (SEQ ID NO: 62), PA-8 (SEQ ID NO: 65), SP (SEQ ID NO: 66), HN1 (SEQ ID NO: 63), 16244B (SEQ ID NO: 64), HB-1 (SEQ ID NO: 71), HB-2 (SEQ ID NO: 70), CH-1a (SEQ ID NO: 68), P129 (SEQ ID NO: 69), JA142 (SEQ ID NO: 67), EuroPRRSV (SEQ ID NO: 56), Lelystad (SEQ ID NO: 57), MN184A (SEQ ID NO:58), MN184B (SEQ ID NO:59).

FIG. 12. Nsp2 amino acid sequence alignment of divergent PRRSV. The completely conserved putative cysteine protease catalytic residues (Cys and His) are identified by stars and the boxed amino acids signify protease sequence conservation within PRRSV and EAV. The proposed cleavage sites are identified by filled arrows (↓); additional possible cleavage sites are indicated by a hashed arrow; signal peptide, solid grey box; transmembrane regions, shown in hashed black boxes; potential N-glycosylation sites, indicated by an asterisk (*). The figure derivation and color scheme were described in the FIG. 10 legend. Nsp2 amino acid sequences from the following GenBank full-length sequences were used for comparison: VR-2332 (SEQ ID NO: 74), Ingelvac MLV (SEQ ID NO: 75), 01NP1.2 (DQ056373) (SEQ ID NO: 76), PL97-1 (SEQ ID NO: 77), PA-8 (SEQ ID NO: 79), SP (SEQ ID NO: 78), BJ-4 (SEQ ID NO: 80), HN1 (SEQ ID NO: 81), 16244B (SEQ ID NO: 82), HB-1 (SEQ ID NO: 87), HB-2 (SEQ ID NO: 84), CH-1a (SEQ ID NO: 83), P129 (SEQ ID NO: 85), JA142 (SEQ ID NO: 86), SDPRRS-01-08 (AY375474) (SEQ ID NO: 88), EuroPRRSV (SEQ ID NO: 89), Lelystad (SEQ ID NO:90), MN184A (SEQ ID NO:72), MN184B (SEQ ID NO:73).

DETAILED DESCRIPTION OF ILLUSTRATIVE EMBODIMENTS

Figure 2:
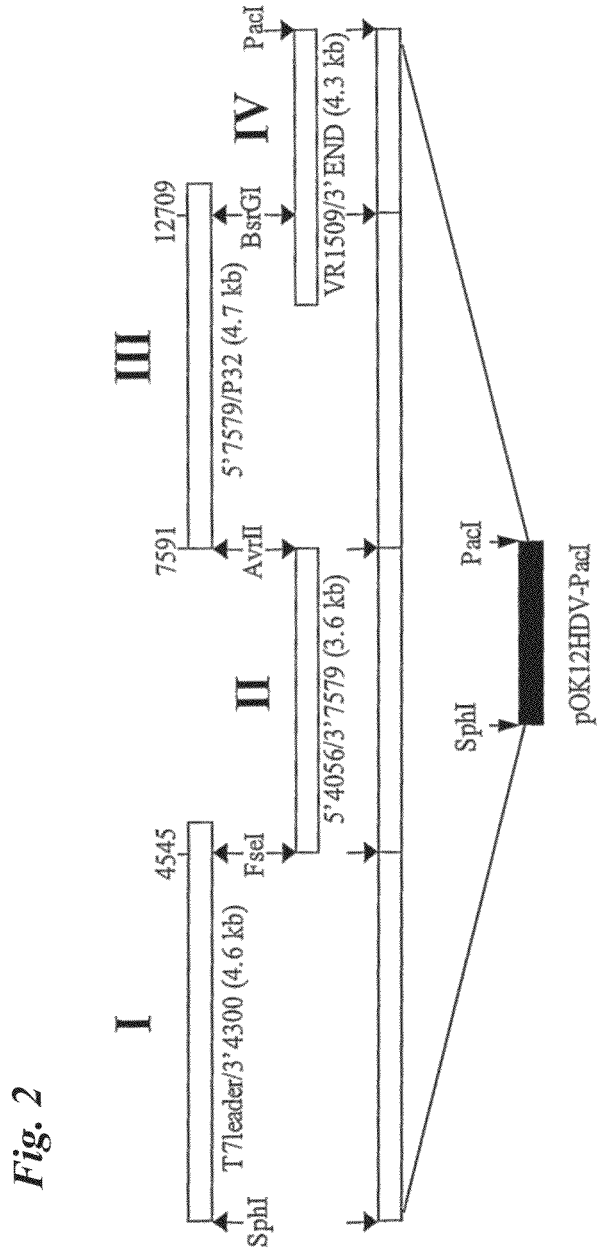
FIG. 2. Assembly of full-length clones of PRRSV strain VR-2332. The 15.4 genome was amplified in four sections (I-IV) that incorporated unique restriction enzyme cleavage sites present in viral cDNA (FseI, AvrII, BsrGI) or added to the PRRSV sequence at the 5' and 3' ends by insertion mutagenesis (SphI, PacI respectively). A T7 polymerase promoter and 2 nontemplated G residues and a T residue preceded the viral sequence. The pOK12 vector (24) was modified to include a PacI site and a hepatitis delta ribozyme downstream of a poly adensine tail of 50 nucleotides.

The present invention includes infectious clones of the Porcine reproductive and respiratory syndrome virus (PRRSV) VR-2332. As used herein, the term "infectious clone" is a polynucleotide having two components; a vector sequence that replicates in a prokaryotic host cell, and a second polynucleotide referred to herein as an infectious polynucleotide. When transcribed in vitro to yield an RNA polynucleotide and introduced into a permissive cell, the infectious polynucleotide replicates (as an RNA) and produces infectious virus particles. Thus, an infectious polynucleotide can be present in a vector as a DNA, as an RNA in a virus particle, or as an isolated DNA or RNA. The term "polynucleotide" refers to a polymeric form of nucleotides of any length, either ribonucleotides or deoxynucleotides, and includes both double- and single-stranded DNA and RNA. Unless otherwise noted, a polynucleotide includes the complement thereof. The nucleotide sequence of the complement of a polynucleotide can be easily determined by a person of skill in the art. A polynucleotide may include nucleotide sequences having different functions, including for instance coding sequences, and non-coding sequences such as regulatory sequences and/or untranslated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

If naturally occurring, a polynucleotide is preferably isolated, more preferably, purified. An "isolated" compound, such as a polynucleotide, polypeptide, or virus particle, is one that is separate and discrete from its natural environment. A "purified" compound is one that is at least 60% free, preferably 75% free, and most preferably 90% free from other components with which they are naturally associated. Compounds such as polynucleotides and polypeptides that are produced outside the organism in which they naturally occur, e.g., through chemical or recombinant means, are considered to be isolated and purified by definition, since they were never present in a natural environment.

An example of an infectious polynucleotide of the present invention includes the infectious polynucleotide VR-V7 (SEQ ID NO:1). VR-V7 is also referred to herein as V6G7475A. Other examples of infectious polynucleotides of the present invention include VR-V5 (SEQ ID NO:2), VR-V5G7475A (SEQ ID NO:3), and VR-V6 (SEQ ID NO:4). It should be noted that while SEQ ID NOs:1, 2, 3, 4, 5, 6 and other virus nucleotide sequences are disclosed herein as a DNA sequence, the present invention contemplates the corresponding RNA sequence, and RNA and DNA complements thereof, as well.

Other infectious polynucleotides of the present invention have a polynucleotide sequence having structural similarity to a reference polynucleotide. Reference polynucleotides include SEQ ID NO:1, SEQ ID NO:2, SEQ ID NO:3, SEQ ID NO:4, SEQ ID NO:5, SEQ ID NO:6, the European prototype strain of PRRS virus, Lelystad (Genbank accession number M96262; SEQ ID NO:14), and the North American prototype strain of PRRS virus, VR-2332 (Genbank accession number U87392; SEQ ID NO:15). The similarity is referred to as "percent identity" and is determined by aligning the residues of the two polynucleotides (i.e., the nucleotide sequence of a candidate infectious polynucleotide and the nucleotide sequence of the reference polynucleotide) to optimize the number of identical nucleotides along the lengths of their sequences; gaps in either or both sequences are permitted in making the alignment in order to optimize the number of shared nucleotides, although the nucleotides in each sequence must nonetheless remain in their proper order. In some aspects of the present invention the gap (also referred to as a deletion) is present in the candidate infectious polynucleotide sequence. A candidate infectious polynucleotide is the polynucleotide that has the nucleotide sequence being compared to the reference polynucleotide. A candidate infectious polynucleotide can be isolated from an animal, such as a pig infected with PRRSV, isolated from a cultured cell line, or can be produced using recombinant techniques, or chemically or enzymatically synthesized. Two nucleotide sequences can be compared using any of the commercially available computer algorithms routinely used to produce alignments of nucleotide sequences. Preferably, two nucleotide sequences are compared using the GAP program of the GCG Wisconsin Package (Accelrys, Inc.) version 10.3 (2001). The GAP program uses the algorithm of Needleman et al. (*J. Mol. Biol.*, 48:443-453 (1970)) to find the alignment of two complete sequences that maximizes the number of matches and minimizes the number of gaps. Preferably, the default values for all GAP search parameters are used, including scoring matrix=NewsgapDNA.cmp, gap weight=50, length weight=3, average match=10, average mismatch=0. In the comparison of two nucleotide sequences using the GAP search algorithm, structural similarity is referred to as "percent identity." Preferably, a polynucleotide has structural similarity with a reference polynucleotide of at least 88%, at least 89%, at least 90%, at least 91%, at least 92%, at least 93%, at least 94%, at least 95%, at least 96%, at least 97%, at least 98%, or at least 99% identity when the structural similarity is determined using the GAP program.

Whether a polynucleotide is an infectious polynucleotide can be determined by inserting into a vector a candidate infectious polynucleotide, transcribing the candidate infectious polynucleotide in vitro, transfecting a permissive cell with the resulting RNA molecules, and detecting progeny viral RNA, progeny viral nucleocapsid protein, detecting infectious virus particles, or a combination thereof. The vector preferably has the characteristics of being low copy number and remains stable after insertion of large (e.g., 15 kb) inserts. An example of a suitable vector is pOK and pOK12 (GenBank Accession AF223639, Vieira et al., *Gene*, 100:189-194 (1991)), and other vectors having these characteristics are known and available. In the vector the candidate infectious polynucleotide is immediately downstream of a promoter. Useful promoters are those that can be induced to yield high levels of transcription, such as a T7 RNA polymerase promoter, for example TAATACGACTCACTATA (SEQ ID N0:16), or the RNA polymerase promoters SP6 and T3. Transcription of the candidate infectious polynucleotide typically includes restriction endonuclease digestion of the vector to make it linear, and producing RNA transcripts by use of routine and well known in vitro transcription methods. Kits for in vitro transcription are commercially available (for instance, mMessage mMachine, available from Ambion, Austin, Tex.).

After in vitro transcription the RNA is purified using routine methods and then used to transfect a permissive cell. Examples of permissive cells include, for instance, BHK-21 (which allows one round of virus particle production), CL-2621, MA-104 (ATCC CRL-2378), MARC-145 (Kim et al., *Arch. Virol.*, 133:477-483 (1993)), cell lines cloned from these cell lines, or primary porcine alveolar macrophages. Methods for efficiently transfecting cells include the use of 1,2-dimyristyloxypropyl-3-dimethyl-hydroxy ethyl ammonium bromide and cholesterol (DMRIE-C), and other commercially available products, preferably, DMRIE-C. Methods for efficiently transfecting primary porcine alveolar macrophages are known to the art (Groot Bramel-Verheige et al., *Virol.*, 278:380-389 (2000)). Generally, 2 to 3 micrograms of RNA can be used for transfection, but lower and higher amounts may be used. After a suitable period of time, the presence of progeny viral RNA can be detected by, for instance, reverse transcriptase-polymerase chain reaction (RT-PCR). Likewise, progeny viral nucleocapsid protein can be detected by, for instance, nucleocapsid specific antibody. Further, whether the virus particles produced by cells transfected with a candidate infectious polynucleotide will infect another cell can be detected by exposing uninfected permissive cells to supernatant from infected cells. Optionally, cytopathic effect (CPE) may be observed. A candidate infectious polynucleotide is considered to be an infectious polynucleotide when it produces progeny viral RNA, progeny viral proteins (nucleocapsid, membrane, GP5, and others), and infects other permissive cells.

In some aspects of the present invention an infectious polynucleotide includes a deletion of nucleotides encoding nonstructural protein 2 (nsp2), one of several (12 predicted) polypeptides present in the polyprotein encoded by ORF1. In a PRRS virus, and infectious polynucleotides thereof, the nucleotides encoding the first amino acid of nsp2 can be determined by identifying the cleavage site of papain-like protease 1 beta, predicted to be after the ORF1 amino acid glycine at position 383 in VR-2332.

With respect to identifying the nucleotides encoding the last amino acid of nsp2, the exact nsp2 C-terminal cleavage site of the ORF1a-encoded polyprotein has not been empirically determined, thus the nucleotides corresponding to the 3' end of the coding region are unknown. However, two predictions of the C-terminal cleavage site have been proposed, one Gly|Gly (where the vertical line between the two glycine residues indicates the cleavage location) at amino acid 980 in VR-2332, and the other at amino acid 1197 in VR-2332. In alignment of all available PRRSV sequences, there are several completely conserved Gly|Gly doublets within this protein that may also be the nsp2 C terminal cleavage site of the polyprotein (amino acids 646, 980, 1116, 1196, 1197, in VR-2332. The locations of the Gly|Gly doublets in the other viruses and infectious polynucleotides can be identified by comparison to the sequences of nsp2 and the Gly|Gly doublets disclosed in FIG. 12. Present studies suggest that there may be at least 3 cleavage sites in nsp2, corresponding to amino acid 980, 116, 1196 or 1197.

The nsp2 polypeptide includes a highly conserved chymotrypsin-like cysteine protease domain (identified as CP in FIG. 3 and PL2 in FIG. 9) present at the N-terminus, and 3-4 predicted transmembrane domains near the C terminus of nsp2 (where the number of transmembrane domains varies depending on the location of the C-terminal cleavage site). Typically, deletion of the nucleotides encoding the amino acids of the PL2 domain or all of the predicted transmembrane domains results in a polynucleotide that can replicate in permissive cells but will not produce infectious virus particles. Thus, an infectious clone of the present invention does not typically include deletion of the entire PL2 domain or all of the predicted transmembrane domains.

The nucleotides encoding the chymotrypsin-like cysteine protease domain are nucleotides 1474 to 1776 of VR-V7 (SEQ ID NO:1), nucleotides 1474 to 1776 of VR2332 (Genbank accession number U87392), and nucleotides 1482 to 1784 of Lelystad (Genbank accession number M96262). The location of a chymotrypsin-like cysteine protease domain in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the chymotrypsin-like cysteine protease domain. Alternatively, the amino acid sequences of nsp2 polypeptides of other PRRS viruses can be identified by aligning the amino acid sequence of the nsp2 polypeptide encoded by a PRRS virus with the amino acid sequence of nsp2 polypeptides produced by other arteriviruses, such as equine arteritis virus (EAV) and lactate dehydrogenase-elevating virus (LDV).

The nucleotides encoding the predicted transmembrane domains of VR-V7 (SEQ ID NO:1), VR-2332 (Genbank accession number U87392), and Lelystad (Genbank accession number M96262) are shown in Table 1.

TABLE 1

Nsp2 nucleotides encoding predicted transmembrane domains.

|  | VR-V7 | VR-2332 | Lelystad |
|---|---|---|---|
| Transmembrane domain I | 881 to 901 | 881 to 901 | 761 to 781 |
| Transmembrane domain II | 913 to 934 | 913 to 934 | 793 to 814 |
| Transmembrane domain III | 963 to 980 | 963 to 980 | 843 to 860 |
| Transmembrane domain IV | 985 to 1003 | 985 to 1003 | 865 to 883 |

The location of the transmembrane domains in the nucleotide sequence of other PRRS viruses can be identified by aligning the amino acid sequence of the nsp2 polypeptide encoded by a PRRS virus with the amino acid sequence alignment disclosed in FIG. 12, and determining which nucleotides encode those amino acids that line up with the transmembrane domains. Alternatively, the location of the transmembrane domains can be identified with a computer algorithm, such as the PredictProtein algorithm as described by Rost et al. (*Nucleic Acids Res.*, 32 (Web Server issue): W321-326 (2004), or the TMHMM algorithm as described by Krogh et al. (*J. Mol. Biol.*, 305:567-580 (2001)) and available through the World Wide Web.

The deletion present in infectious polynucleotides of the present invention is typically between the nucleotides encoding the chymotrypsin-like cysteine protease domain and the nucleotides encoding the transmembrane domains, and does not result in a frameshift in the reading frame of ORF1. As discussed above, the deletion typically does not include all the nucleotides encoding the chymotrypsin-like cysteine protease domain, all the nucleotides encoding the transmembrane domains, or the combination thereof. In some aspects, for instance when the infectious polynucleotide has structural similarity with SEQ ID NO:1, the 5' boundary of a deletion is at nucleotide 2305, nucleotide 2205, nucleotide 2105, or nucleotide 2062, and the 3' boundary of a deletion is at nucleotide 3774, nucleotide 3804, nucleotide 3834, or nucleotide 3864. In other aspects, for instance when the infectious polynucleotide has structural similarity with SEQ ID NO:14, the 5' boundary of a deletion is at nucleotide 2304, nucleotide 2204, nucleotide 2104, or nucleotide 2061, and the 3' boundary of a deletion is at nucleotide 3455, nucleotide 3495, nucleotide 3525, or nucleotide 3545. The deletion can be at least 39 nucleotides, 48 nucleotides, or 57 nucleotides. In some aspects, the deletion can be at least 267 nucleotides, at least 276 nucleotides, or at least 285 nucleotides. In some aspects the deletion is no greater than 489 nucleotides, no greater than 459, no greater than 429, or no greater than 402 nucleotides. An infectious polynucleotide may have more than one deletion in the nsp2 region.

Examples of infectious polynucleotides derived from VR-V7 and containing a deletion are disclosed in Table 2.

TABLE 2

Infectious polynucleotides derived from VR-V7 (SEQ ID NO: 1).

| Polynucleotide* | deleted nucleotides of SEQ ID NO: 1 | amino acids of ORF1 deleted | viral titlers (PFU/ml) | Summary of phenotype** |
|---|---|---|---|---|
| Nsp2 Δ180-323 | 1876-2304 | 563-705 | – | nonviable |
| Nsp2 Δ 242-323 | 2056-2304 | 623-705 | – | nonviable |
| Nsp2 Δ 324-434 | 2305-2637 | 706-816 | + (~$10^5$) | small plaque size |
| Nsp2 Δ 324-523 | 2305-2904 | 706-905 | + (~$10^5$-$10^6$) | intermediate |
| Nsp2 Δ 543-632 | 2962-3231 | 925-1014 | + (~$10^5$) | small plaque size |
| Nsp2 Δ 633-726 | 3232-3513 | 1015-1108 | + (~$10^5$) | small plaque size |
| Nsp2 Δ 543-726 | 2962-3513 | 925-1108 | + (~$10^5$) | small plaque size |
| Nsp2 Δ 727-813 | 3514-3774 | 1109-1195 | + (~$10^5$) | small plaque size |
| Nsp2 Δ 324-726 | 2305-3513 | 706-1108 | + (~$10^{1-2}$) | ND |
| Nsp2 Δ 324-813 | 2305-3774 | 706-1195 | – | nonviable |
| Nsp2 Δ 727-845 | 3514-3870 | 1109-1227 | – | nonviable |
| Nsp2 Δ 324-845 | 2305-3870 | 706-1227 | – | nonviable |

*the deletion refers to the amino acids of nsp2 that are deleted, e.g., in the virus Nsp2 Δ180-323, amino acids 180-323 of nsp2 are deleted.
**plaque size is relative to plaques produced by wildtype VR-2332.

An infectious polynucleotide containing a deletion can include an exogenous polynucleotide inserted in place of the deletion. An "exogenous" polynucleotide refers to a foreign nucleotide sequence, i.e., a nucleotide sequence that is not normally present in a PRRS virus or an infectious clone thereof. The exogenous polynucleotide can, and preferably does encode a polypeptide. Suitable exogenous polynucleotides include those encoding a detectable marker, e.g., a molecule that is easily detected by various methods. Examples include fluorescent polypeptides (e.g., green, yellow, blue, or red fluorescent proteins), luciferase, chloramphenicol acetyl transferase, and other molecules (such as c-myc, flag, 6× his, HisGln (HQ) metal-binding peptide, and V5 epitope) detectable by their fluorescence, enzymatic activity or immunological properties, and are typically useful when detected in a cell, for instance, a cultured cell, or a tissue sample that has been removed from an animal. Other exogenous polynucleotides that can be used are those encoding polypeptides expressed by other entities, such as cells and pathogens. Expression of an exogenous polynucleotide results in an infectious polynucleotide that expresses foreign antigens. Examples of exogenous nucleotide sequences include those encoding proteins expressed by pathogens, preferably porcine pathogens, such as porcine circovirus type 2, *Mycoplasma hyopneumoniae* (e.g., the P46 and P65 proteins of *M. hyopneumoniae*), *Lawsonia intracellularis* (e.g., the outer membrane proteins of *L. intracellularis*), the ORF5 of different strains of PRRSV, and *Streptococcus suis* (e.g., the 38-kDa protein of *S. suis*). The nsp2 polypeptide has B-cell epitopes and is expected to be immunogenic. Inclusion of foreign epitopes in an nsp2 polypeptide is expected to result in an immune response to the foreign epitopes. Additional examples of exogenous polynucleotides include those encoding biological response modifiers, such as, for example, IFN-α, IFN-γ, IL-12, IL-2, TNF-α, and IL-6.

The exogenous polynucleotide is inserted into the deletion region such that it is in frame with the open reading frame encoding nsp1α and nsp1β, and more than one exogenous polynucleotide can be inserted in tandem, for instance, nucleotide sequences encoding three c-myc epitopes can be present. The total size of the infectious polynucleotide containing an exogenous polynucleotide inserted in the place of the deletion is typically no greater than 16,000 bases, no greater than 15,800 bases, no greater than 15,600 bases, no greater than 15,400 bases, or no greater than 15,200 bases (including the poly A tail). An insertion can be present in an infectious polynucleotide having the Nsp2 Δ324-434, Nsp2 Δ324-523, Nsp2 Δ543-632, Nsp2 Δ633-726, Nsp2 Δ543-726, Nsp2 Δ727-813, or Nsp2 Δ324-726 deletion, preferably, the Nsp2 Δ324-434, Nsp2 Δ543-632, Nsp2 Δ633-726, Nsp2 Δ543-726, Nsp2 Δ727-813, or Nsp2 Δ324-726 deletion. Preferred examples of infectious clones containing an exogenous polynucleotide in the location of a deletion include an infectious polynucleotide having the Nsp2 Δ324-434 deletion containing a coding region encoding a 238 amino acid green fluorescent protein, an infectious polynucleotide having the Nsp2 Δ543-632 deletion containing a coding region encoding a 238 amino acid green fluorescent protein, an infectious polynucleotide having the Nsp2 Δ324-434 deletion containing a coding region encoding a 10 amino acid c-myc epitope (EQKLISEEDL, SEQ ID NO:17), an infectious polynucleotide having the Nsp2 Δ324-434 deletion containing a coding region encoding a 10 amino acid c-myc epitope, and an infectious polynucleotide having the Nsp2 Δ324-726 or Nsp2 Δ543-726 deletions each containing a coding region encoding tandem repeat of the 10 amino acid c-myc epitope.

An infectious polynucleotide is typically present in a vector, and the combination of infectious polynucleotide and vector is referred to as an infectious clone, which is made through reverse genetics. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard recombinant DNA techniques known in the art (see, e.g., Sambrook et al., *Molecular Cloning: A Laboratory Manual*, Cold Spring Harbor Laboratory Press (1989)). A vector can provide for further cloning (amplification of the polynucleotide), i.e., a cloning vector, or for expression of the polypeptide encoded by the coding region, i.e., an expression vector, or the combination thereof. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Preferably, a vector suitable for use as part of an infectious clone is both a cloning vector and an expression vector. Useful vectors have a low copy number in a host cell. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative organisms, for example, *E. coli* or *S. typhimurium*. Examplary host cells useful for making, manipulating, and maintaining an infectious clone are DH-5α, DH-1 (ATCC 33849), and AG-1, preferably, DH-1 or AG-1.

A vector includes regulatory sequences operably linked to the infectious polynucleotide. The term "operably linked" refers to a juxtaposition of components such that they are in a relationship permitting them to function in their intended manner. A regulatory sequence is "operably linked" to an infectious polynucleotide of the present invention when it is joined in such a way that expression of the coding region is achieved under conditions compatible with the regulatory sequence. Typically, a promoter is one that provides for high specificity binding of an RNA polymerase, and such promoters include T7, SP6, and T3. Typically the promoter is situated immediately upstream of the first nucleotide of the infectious polynucleotide. Preferably, a GGT is inserted between the promoter and the first nucleotide of the infectious polynucleotide. Optionally and preferably the vector also contains a hepatitis delta virus ribozyme downstream of the poly A region.

The vector optionally, and preferably, includes one or more selection marker sequences, which typically encode a molecule that inactivates or otherwise detects or is detected by a compound in the growth medium. For example, the inclusion of a selection marker sequence can render the transformed cell resistant to an antibiotic, or it can confer compound-specific metabolism on the transformed cell. Examples of a selection marker sequence are sequences that confer resistance to kanamycin, ampicillin, chloramphenicol, tetracycline, and neomycin.

When producing a deletion of nucleotides encoding an nsp2 polypeptide in an infectious clone, standard recombinant DNA techniques known in the art can be used (see, e.g., Sambrook et al., *Molecular Cloning: A Laboratory Manual*, Cold Spring Harbor Laboratory Press (1989)). As the skilled person will recognize, it is standard practice during construction of an infectious clone (and when construction deletions in an infectious clone) to verify by nucleotide sequence analysis the presence of expected nucleotide sequences, such as deletions or other alterations and the absence of other mutations. Likewise, when a candidate infectious polynucleotide is tested to determine if it is infectious, it is standard practice to verify by nucleotide sequence analysis the absence of contaminating wild-type virus.

The present invention also includes isolated infectious polynucleotides disclosed at SEQ ID NO:5 and SEQ ID NO:6, and infectious polynucleotides having structural similarity to SEQ ID NO:5 or SEQ ID NO:6. Methods for determining structural similarity are described herein. Preferably, an infectious polynucleotide of this aspect of the present invention has structural similarity to SEQ ID NO:5 or SEQ ID NO:6 of at least 88%, at least 89%, at least 90%, at least 91%, at least 92%, at least 93%, at least 94%, at least 95%, at least 96%, at least 97%, at least 98%, or at least 99%. A polynucleotide having structural similarity to SEQ ID NO:5 or SEQ ID NO:6 is considered to be an infectious polynucleotide if, when present in a virus particle and exposed to permissive cells, the polynucleotide replicates in the permissive cells and produces infectious virus particles.

The present invention also includes isolated virus particles. As used herein, the terms "virus particle" and "viral particle" are used interchangeably and refer to a polynucleotide of the present invention surrounded by an envelope. A virus particle of the present invention can, when added to a permissive cultured cell, replicate to result in the production of more viral particles.

A virus particle can be grown by passage in vivo or in cell culture. Passage in vivo includes inoculating a pig (Faaberg et al., U.S. Pat. No. 7,041,443). Passage in cell culture includes exposing cultured cells to the virus particle and incubating the cells under conditions suitable for the virus to reproduce and produce more virus particles. Preferably, the cultured cells are not an immortalized or transformed cell line (i.e., the cells are not able to divide indefinitely). Preferably, primary porcine alveolar macrophages are used for passage in cell culture (Faaberg et al., U.S. Pat. No. 7,041,443).

A virus of the present invention can be inactivated, i.e., rendered incapable of reproducing in vivo and/or in cell culture. Methods of inactivation are known to the art and include, for instance, treatment of a virus particle of the invention with a standard chemical inactivating agent such as an aldehyde reagent including formalin, acetaldehyde and the like; reactive acidic alcohols including cresol, phenol and the like; acids such as benzoic acid, benzene sulfonic acid and the like; lactones such as beta propiolactone and caprolactone; and activated lactams, carbodiimides and carbonyl diheteroaromatic compounds such as carbonyl diimidazole. Irradiation such as with ultraviolet and gamma irradiation can also be used to inactivate the virus.

Also included in the present invention are attenuated virus particles (i.e., viruses having reduced ability to cause the symptoms of mystery swine disease in pigs), and methods of making an attenuated virus particle. Methods of producing an attenuated virus are known to the art. Typically, a virus of the present invention is passaged, i.e., used to infect a cell in culture, allowed to reproduce, and then harvested. This process is repeated until the virulence of the virus in pigs is decreased. For instance, the virus can be passaged 10 times in cell culture, and then the virulence of the virus measured. If virulence has not decreased, the virus that was not injected into the animal is passaged an additional 10 times in cell culture. This process is repeated until virulence is decreased. In general, virulence is measured by inoculation of pigs with virus, and evaluating the presence of clinical symptoms and/or $LD_{50}$ (see, for instance, Halbur et al., *J. Vet. Diagn. Invest.*, 8:11-20 (1996), Halbur et al., *Vet. Pathol.*, 32:200-204 (1995), and Park et al., *Am. J. Vet. Res.*, 57:320-323 (1996)). Preferably, virulence is decreased so the attenuated virus does not cause the death of animals, and preferably does not cause clinical symptoms of the disease.

Typically, a cell culture useful for producing an attenuated virus of the present invention includes cells of non-porcine mammal origin. Examples of non-porcine mammal cell cultures include, for instance, the cell line MA-104 (ATCC CRL-2378), the cell line MARC-145 (Kim et al., *Arch. Viral.*, 133:477-483 (1993)), and the cell line CL-2621 (Baustita et al., *J. Vet. Diagn. Invest.*, 5:163-165 (1993)). Preferably, a mixed cell culture is used for producing an attenuated virus particle of the present invention. In a mixed cell culture there are at least two types of cells present. Preferably, a mixed cell culture includes an immortalized or transformed cell line and a primary cell culture. A mixed cell culture is particularly useful when a virus reproduces slowly, or not at all, in an immortalized or transformed cell line. Preferred examples of an immortalized or transformed cell line for use in a mixed cell culture include, for example, the cell line MARC-145 (Kim et al., *Arch. Viral.*, 133:477-483 (1993)), and the cell line MA-104 (ATCC CRL-2378). Preferably, primary cell cultures for use in a mixed cell culture are porcine in origin. A preferred example of a primary cell culture for use in a mixed cell culture is primary porcine alveolar macrophages.

The present invention further includes the polypeptides encoded by the nsp2 coding regions present in the polynucleotides disclosed in Table 2, including those that are viable. Also included in the present invention are antibodies, including monoclonal and polyclonal antibodies, that specifically bind a polypeptide encoded by the nsp2 coding regions present in the polynucleotides disclosed in Table 2. The term "antibody," unless specified to the contrary, includes fragments of whole antibodies which retain their binding activity for a target antigen. Such fragments include Fv, F(ab') and F(ab')$_2$ fragments, as well as single chain antibodies (scFv). As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets. As used herein, the term "polypeptide:antibody complex" refers to the complex that results when an antibody specifically binds to a polypeptide, or a subunit or analog thereof. In some aspects, an antibody of the present invention include those that do not specifically bind to a full length nsp2 polypeptide encoded by VR-2332 (e.g., Genbank accession number U87392, ORF1 amino acids 384-1363 (also see Allende et al., *J. Gen. Virol.*, 80:307-315 (1999) or ORF1 amino acids 384-1580 (also see Ziebuhr et al., *J. Gen. Virol.*, 81:853-879 (2000)). Such antibodies can be identified using routine methods known in the art.

Antibodies of the present invention can be prepared using the intact polypeptide. Optionally, an nsp2 polypeptide described herein can be covalently bound or conjugated to a carrier polypeptide to improve the immunological properties of the polypeptide. Useful carrier polypeptides are known in the art.

The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. Briefly, spleen cells from an animal immunized with a desired antigen are immortalized, commonly by fusion with a myeloma cell (see, for example, *Antibodies: A Laboratory Manual*, Harlow et al., eds., Cold Spring Harbor Laboratory Press: Cold Spring Harbor, N.Y., (1988)). Monoclonal antibodies can be isolated and purified from hybridoma cultures by techniques well known in the art.

In some embodiments, the antibody can be recombinantly produced, for example, by phage display or by combinatorial methods. Phage display and combinatorial methods can be used to isolate recombinant antibodies that bind to a polypeptide described herein, or a biologically active subunit or analog thereof (see, for example, Ladner et al., U.S. Pat. No. 5,223,409). Such methods can be used to generate human monoclonal antibodies.

The present invention also provides compositions including an infectious polynucleotide, PRRS polynucleotide, virus particle, or antibody of the present invention. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmacy. In general, a composition can be formulated to be compatible with its intended route of administration. Examples of routes of administration include perfusion and parenteral, e.g., intravenous, intradermal, subcutaneous, oral (e.g., inhalation), transdermal (topical), and transmucosal. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile solutions can be prepared by incorporating the active compound (i.e., an infectious polynucleotide or PRRS virus of the present invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. These compositions may also be formed into a powder or suspended in an aqueous solution such that these powders and/or solutions can be added to animal feed or to the animals' drinking water. These compositions can be suitably sweetened or flavored by various known agents to promote the uptake of the vaccine orally by the pig.

The active compounds can also be administered by any method suitable for administration of polynucleotide agents, e.g., using gene guns, bio injectors, and skin patches as well as needle-free methods such as the micro-particle DNA vaccine technology disclosed by Johnston et al. (U.S. Pat. No. 6,194,389). Additionally, intranasal delivery is possible, as described in, for instance, Hainajima et al., *Clin. Immunol. Immunopathol.,* 88:205-210 (1998). Liposomes and microencapsulation can also be used.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

Toxicity and therapeutic efficacy of such active compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred.

The data obtained from cell culture assays and animal studies can be used in formulating a range of dosage for use in the field. The dosage of such compounds lies preferably within a range of circulating concentrations that include the $ED_{50}$ with little or no toxicity. The dosage may vary within this range depending upon the dosage form employed and the route of administration used.

The compositions can be administered one or more times per day to one or more times per week, including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polypeptide can include a single treatment or, preferably, can include a series of treatments.

The present invention includes methods for using the compositions described herein. In one aspect the invention includes methods for treating one or more symptoms of mystery swine disease in an animal that may be caused by infection by a PRRS virus. The method includes administering an effective amount of a composition of the present invention to an animal having or at risk of having mystery swine disease, or symptoms of mystery swine disease.

Treatment of mystery swine disease, or symptoms of mystery swine disease, can be prophylactic or, alternatively, can be initiated after the development of disease or symptoms thereof. As used herein, the term "symptom" refers to objective evidence in a subject of mystery swine disease. Symptoms associated with mystery swine disease and the evaluations of such symptoms are routine and known in the art. Examples of symptoms include abortion, anorexia, fever, lethargy, pneumonia, red/blue discoloration of ears, labored breathing (dyspnea), and increased respiratory rate (tachypnea). Treatment that is prophylactic, for instance, initiated before a subject manifests symptoms of a condition caused by a PRRS virus, is referred to herein as treatment of a subject that is "at risk" of developing the disease or symptoms thereof. Typically, an animal "at risk" is an animal present in an area where animals having the disease or symptoms thereof have been diagnosed and/or is likely to be exposed to a PRRS virus. Accordingly, administration of a composition can be performed before, during, or after the occurrence of the conditions described herein. Treatment initiated after the development of a condition may result in decreasing the severity of the symptoms of one of the conditions, or completely removing the symptoms.

In some aspects, the methods typically include administering to an animal a composition including an effective amount of a virus particle of the present invention. An "effective amount" is an amount effective to prevent the manifestation of symptoms of mystery swine disease, decrease the severity of the symptoms of the disease, and/or completely remove the symptoms. Typically, the effective amount is an amount that results in a humoral and/or cellular immune response that protects the animal during future exposure to a PRRS virus. The virus particle used in the composition may contain an infectious polynucleotide that has a deletion as described herein. Optionally, the infectious polynucleotide also includes an exogenous polynucleotide present at the location of the deletion. An advantage of using a virus particle having a deletion (or an exogenous polynucleotide present in the location of the deletion) is it can be easily distinguished from other PRRS viruses, including wild type PRRS viruses present in the field. The virus particle can be identified by isolation of the virus from an animal followed, for instance, by sequencing, restriction enzyme digestion, or PCR-based amplification of specific nucleotides. Such a "marked" virus particle is often referred to in the art as a marker vaccine.

In other aspects of the present invention the infectious clones and/or infectious polynucleotides described herein can be used to investigate viable gene insertions, to investigate alternative expressed RNA or proteins other than full length virus, to investigate viral recombination, and to investigate immunogenic properties of full-length nsp2 as relative to truncated nsp2.

EXAMPLES

Example 1

Full-length cDNA clones of North American porcine reproductive and respiratory syndrome virus (PRRSV) prototype VR-2332 strain were developed, with each progressive version possessing less nucleotide changes than prior versions when compared to wt strain VR-2332. Progeny virus of each infectious clone was recovered and analyzed for nucleotide sequence verification, in vitro growth rate and plaque size. Progeny from one infectious clone confirmed robust in vivo replication, seen by the appearance of a-PRRSV antibodies at the same rate as wt virus. Northern blot analysis of the in vivo progeny also revealed that defective subgenomic RNA species, termed heteroclites (uncommon forms), were present along with full-length genomes. Concurrent northern blot analysis of a passage series of infected MA-104 cell cultures revealed that recombinant virus only gradually gained a profile of both full-length and heteroclite RNA similar to the RNA species seen in in vivo infection.

Materials and Methods

Cells and viral strains. MA-104 cells or its descendent MARC-145 cells (ATCC CRL-11171), an African green monkey kidney epithelial cell line which supports PRRSV replication (Meng et al., *J. Vet. Diagn. Invest.*, 8:374-81 (1996)), were maintained in Eagle's minimal essential medium (EMEM) (JRH Biosciences 56416), supplemented with 1 mg/ml NaHCO$_3$ and 10% fetal bovine serum (FBS), at 37° C. with 5% CO$_2$. The cultured cells were transfected with RNA or infected with virus when monolayer growth had reached 70-80% confluency. PRRSV North American prototype strains VR-2332 and Ingelvac® MLV have been described previously (Yuan et al., *Virus Res.*, 79:189-200 (2001)). Strain VR-2332 grows to equivalent titers on both cell lines.

Viral RNA purification. Viral RNA (vRNA) was purified as described. (Chen et al., *J. Gen. Virol.*, 75:925-930 (1994); Yuan et al., *Virus Res.*, 79:189-200 (2001)). Briefly, supernatant from MARC-145 cells infected with VR-2332 was harvested on day 4 post-infection (p.i.). After removal of cellular debris by centrifugation at 12,000 rpm, the supernatants were layered onto a 2 ml 0.5 M sucrose cushion and centrifuged at 76,000×g for 4 hours. The pelleted virions were resuspended in 0.5 ml LES (0.1 M LiCl/5 mM EDTA/1.0% SDS) and further digested by addition of 100 µg proteinase K at 56° C. to remove all protein. After 10 minutes of incubation, vRNA was extracted several times with acid phenol and phenol/chloroform and then precipitated in 70% v/v ethanol. Pelleted vRNA was immediately resuspended into 50 µl H$_2$O or RNase-free TE buffer (10 mM Tris-HCl, 1 mM EDTA, pH 8.0) and stored at −80° C.

Construction of full-length viral cDNA. cDNA synthesis was performed with Enhanced Avian HS RT-PCR Kit (Sigma, HSRT-100). Eight PCR primers (Table 3) were used to amplify four overlapping cDNA fragments covering the complete VR-2332 genome (FIG. 2). The cycling conditions were 94° C. for 2 minutes, then 35 cycles of 94° C. for 15 seconds, 68° C. for 4-5 seconds, followed by 68° C. for 5 minutes. Each PCR fragment was purified with the QIAEX II Gel Extraction Kit (Qiagen) and cloned into pCR®2.1-TOPO® vector with TOPO TA Cloning® Kit (Invitrogen K450001). Plasmids representing each fragment were submitted for nucleotide sequence analysis. The fragments with the minimum nucleotide mutations compared to parental VR-2332 sequence (GenBank submission number U87392) were used to assemble the full-length cDNA, as shown in FIG. 2. In each overlap region, a unique restriction enzyme site was utilized to join flanking fragments. Four digested fragments, representing full-length genomic sequence, were precisely assembled stepwise into a modified low copy plasmid vector (pOK12HDV-PacI). The vector was modified to include the HDV ribozyme by inserting a 244 by SmaI to SacII fragment containing the HDV antigenome ribozyme and a T7 RNA polymerase terminator sequence from Transcription vector 2.0 (Johnson et al., J. Virol., 71:3323-3327 (1997); Pattnaik et al., Cell, 69:1011-1020 (1992)) into the corresponding sites in pOK12 (Vieira et al., Gene, 100:189-194 (1991)). The NcoI restriction enzyme site in this 244 bp fragment was replaced with a unique PacI site by oligonucleotide mutation with primer sets 5'pOK12HDV-2157/3'pOK12HDV-257 and 5'pOK12HDV-257/polyA-modified (Table 3), followed by fusion PCR. In the full-length cDNA clones, viral genomic sequence was preceded by the T7 RNA polymerase promoter, 1 or 2 G residues and a T residue, and followed by a polyadenylic acid tail of 50 nucleotides. Assembled clones were propagated in the DH5α strain of *Eschericia coli* and then submitted for full-genome nucleotide sequence confirmation.

TABLE 3

Oligonucleotide primers used in this study. Forward primers are indicated with a slash (/) after the designator, reverse primers are preceded by a slash. Inserted restriction enzyme sites are shown in underlined italics.

| Primer | Genome Position* | Sequence |
|---|---|---|
| *Cloning:* | | |
| T7Leader-VR long/ | 1-31 | 5'-ACAT*GCATGC*TTAATACGACTCACTATAGTATGACGTATAGGTGTTGGCTCTATGCCTTGG (SEQ ID NO: 18) |
| /3'-4300 | 4617-4635 | 5'-CTGGGCGACCACAGTCCTA (SEQ ID NO: 19) |
| 5'-4056-AscII | 4055-4080 | 5'-CTTCTC*GGCGCGCC*CGAATGGGAGT (SEQ ID NO: 20) |
| /3'-7579 | 7578-7603 | 5'-TCATCATA*CCTAGG*GCCTGCTCCACG (SEQ ID NO: 21) |
| 5'-7579/ | 7578-7603 | 5'-CGTGGAGCAGGC*CCTAGG*TATGATGA (SEQ ID NO: 22) |
| /P32 | 13293-13310 | 5'-TGCAGGCGAACGCCTGAG (SEQ ID NO: 23) |
| VR1509/ | 11938-11958 | 5'-GTGAGGACTGGGAGGATTACA (SEQ ID NO: 24) |
| /3'end-FL | 15405-15411 | 5'-GTCT*TTAATTAA*CTAG(T)$_{30}$AATTTCG (SEQ ID NO: 25) |
| *Mutagenesis:* | | |
| 5'-pOK12HDV-2S7/(SpbI, PacI) | pOK12HDV-PacI 257-282 | 5'-GAT*GCATGC*CATT*AATTAA*GGGTCGGC (SEQ ID NO: 26) |
| 13'-pOK12HDV-257(SpbI, PacI) | pOK12 HDV-PacI 257-282 | 5'-GCCGACCC*TTAATTAA*TG*GCATGC*ATC (SEQ ID NO: 27) |
| T7leader-VR-2G/ | 1-5 | 5'-ACATGCATGCTTAATACGACTCACTATAGGTATGAC (SEQ ID NO: 28) |
| 7475G2A/ | 7453-7477 | 5'-5Phos/CTGTGTGGACATGTCACCATTGAAA (SEQ ID NO: 29) |
| 13860C2T/ | 13843-13867 | 5'-5Phos/GTGTATCGTGCCGTTCTGTTTTGCT (SEQ ID NO: 30) |
| 14979A2G/ | 14958-14982 | 5'-5Phos/CAGATGCTGGGTAAGATCATCGCTC (SEQ ID NO: 31) |
| *Northern Blot Analyses:* | | |
| /3'-UTR | 15298-15336 | 5'-GCACAATGTCAATCAGTGCCATTCACCACACATTCTTCC (SEQ ID NO: 32) |
| /1a-p222 | 221-261 | 5'-TAGACTTGGCCCTCCGCCATAAACACCCTGGCATTGGGGGT (SEQ ID NO: 33) |

*Genome position is based on GenBank Submission U87392

Modification and sequence analysis of full-length cDNA clones. QuikChange® Multi Site-Directed Mutagenesis Kit (Stratagene) was used to modify all zcDNA clones from pVR-V4 to pVR-V6G7475A. The complete genomic cDNA plasmid inserts were then submitted to the University of Minnesota Advanced Genetic Analysis Center (AGAC) for nucleotide sequence analysis with appropriate sequencing primers (Table 3). Sequence differences between pVR-V4 through pVR-V6G7475A, as well as to those of parental VR-2332, its corresponding attenuated vaccine strain, Inglevac® MLV, and pVR-HN, the first infectious clone of VR-2332, are listed in Table 4 (Nelsen et al., *J. Virol.*, 73:270-80 (1999); Yuan et al., *Virus Res.*, 79:189-200 (2001); Nielsen et al., *J. Virol.*, 77:3702-3711 (2003)).

TABLE 4

Nucleotide differences between PRRSV strains and VR-2332 infectious clones.
Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Inglevac® MLV, and boxes that are shaded black indicate swine unique nucleotides.
Regions that were not sequenced are indicated by a slash.

| Base* | Region | VR-2332 | V4 | V5 | V5-1-P3 | V5-2-P3 | V5-Swine 612 | V5G7 475A | V5G7 475A-P3 | V6 | V6G 7475 A | V6G7 475A-P3 | VR-HN | MLV |
|---|---|---|---|---|---|---|---|---|---|---|---|---|---|---|
| −4 | 5'UTR | | | | | T | | | | | | | | |
| −3 | | | G | G | | T | | G | | | G | G | G | |
| −2 | | | G | G | | T | | G | | | G | G | T/Ø | G |
| −1 | | | T | T | | T | | T | T/Ø | | T | T | T | T | T |
| 48 | | A | A | A | A | A | A | A | A | A | A | A (G/A) | A | A |
| 102 | | A | A | A | A | A | G | A | A | A | A | A | A | A |
| 258 | NSP1a | C | C | C | C | C | C | C | C | C | C | C | A | C |
| 309 | | A | G | G | G | G | G | G | G | G | G | G | A | A |
| 415 | | T | T | T | — | Y (C/T) | T | T | — | T | T | — | T | T |
| 642 | | T | C | C | — | C | C | C | — | C | C | — | T | T |
| 784 | NSP1b | G | G | G | — | G | G | G | — | G | G | — | G | A |
| 827 | | C | C | C | — | C | T | C | — | C | C | — | C | C |
| 1074 | | C | C | C | — | C | C | C | — | C | C | — | T | C |
| 1107 | | A | G | G | — | G | G | G | — | G | G | — | A | A |
| 1122 | | A | A | A | — | R (G/A) | A | A | — | A | A | — | A | A |
| 1181 | | C | C | C | — | C | C | C | — | C | C | — | C | T |
| 1294 | | A | A | A | — | R (G/A) | A | A | — | A | A | — | A | A |
| 1379 | NSP2 | C | C | C | — | C | T | C | — | C | C | — | C | C |
| 1595 | | C | A | C | — | C | C | C | — | C | C | — | C | C |
| 2192 | | C | C | C | — | C | C | C | — | C | C | — | C | T |
| 3040 | | G | G | G | — | G | G | G | — | G | G | — | G | A |
| 3457 | | G | G | G | — | G | G | G | — | G | G | — | G | A |
| 3657 | | C | C | C | — | Y (C/T) | C | C | — | C | C | — | C | C |
| 4407 | NSP3 | T | C | C | — | C | C | C | — | C | C | — | T | T |
| 4593 | | A | G | G | — | G | G | G | — | G | G | — | A | A |
| 4681 | | T | G | G | — | G | G | G | — | G | G | — | G | G |
| 4865 | | T | T | T | — | Y (C/T) | T | T | — | T | T | — | T | T |
| 4866 | | A | G | G | — | G | G | G | — | G | G | — | A | A |
| 5097 | | G | A | A | — | A | A | A | — | A | A | — | A | A |
| 5247 | | T | C | C | — | C | C | C | — | C | C | — | T | T |
| 5519 | | C | C | C | — | C | C | C | — | C | C | — | T | C |
| 5610 | | T | T | T | — | T | T | T | — | T | T | — | A | T |
| 6345 | NSP5 | A | A | A | — | A | A | A | — | A | A | — | A | T |
| 6674 | | C | T | T | — | T | T | T | — | T | T | — | C | T |
| 6853 | NSP7 | G | G | G | — | G | G | — | G | G | — | A | | |
| 6966 | | T | T | T | T | T | T | T | T | T | T | T | C | T |
| 7183 | | A | A | A | A | A | A | A | A | A | R (G/A) | A | A | |
| 7188 | | C | C | C | C | C | C | C | Y (C/T) | C | C | Y (C/T) | C | C |
| 7189 | | C | C | C | C | C | C | C | C | C | C | Y (C/T) | C | C |

TABLE 4-continued

Nucleotide differences between PRRSV strains and VR-2332 infectious clones.
Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Ingelvac ® MLV, and boxes that are shaded black indicate swine unique nucleotides.
Regions that were not sequenced are indicated by a slash.

| Base* | Region | VR-2332 | V4 | V5 | V5-1-P3 | V5-2-P3 | V5-Swine 612 | V5G7 475A | V5G7 475A-P3 | V6 | V6G 7475 A | V6G7 475A-P3 | VR-HN | MLV |
|---|---|---|---|---|---|---|---|---|---|---|---|---|---|---|
| 7213 | | C | C | C | C | C | C | C | M (A/C) | C | C | M (A/C) | C | C |
| 7329 | | G | A | A | A | A | A | A | A | A | A | A | G | G |
| 7475 | | A | G | G | G | G | A | A | A | G | A | A | A | A |
| 7554 | | T | C | C | C | C | C | C | C | C | C | C | C | T |
| 9220 | NSP9 | T | C | T | — | T | T | T | — | T | T | — | T | T |
| 9649 | NSP10 | G | A | G | — | G | G | G | — | G | G | — | G | G |
| 9918 | | T | T | T | — | T | T | T | — | T | T | — | T | G |
| 9958 | | G | A | G | — | G | A | G | — | G | G | — | A | A |
| 10040 | | A | G | A | — | A | A | A | — | A | A | — | A | A |
| 10533 | | T | T | T | — | T | T | T | — | T | T | — | T | G |
| 10643 | | T | T | T | — | T | T | T | — | T | T | — | C | T |
| 10697 | | T | C | T | — | T | T | T | — | T | T | — | C | C |
| 10739 | | C | T | C | — | C | C | C | — | C | C | — | C | C |
| 10781 | | G | A | G | — | G | G | G | — | G | G | — | A | A |
| 10803 | | T | C | T | — | T | T | T | — | T | T | — | C | C |
| 10895 | | C | C | C | — | C | C | C | — | C | C | — | C | T |
| 11055 | NSP11 | T | A | T | — | T | T | T | — | T | T | — | A | A |
| 11081 | | G | A | G | — | G | G | G | — | G | G | — | A | A |
| 11221 | | G | A | G | — | G | A | G | — | G | G | — | A | A |
| 11229 | | G | G | G | — | G | G | G | — | G | G | — | G | T |
| 11259 | | C | G | C | — | C | C | C | — | C | C | — | C | C |
| 11327 | | C | T | C | — | C | C | C | — | C | C | — | C | C |
| 11329 | | G | C | C | — | C | C | C | — | C | C | — | C | C |
| 11501 | | A | G | A | — | A | A | A | — | A | A | — | A | A |
| 11666 | NSP12 | C | T | C | — | C | C | C | — | C | C | — | T | T |
| 11744 | | G | C | G | — | G | G | G | — | G | G | — | C | C |
| 11760 | | G | G | G | — | R (A/G) | G | G | — | G | G | — | G | G |
| 11882 | ORF2a/b | A | G | A | — | A | A | A | — | A | A | — | A | A |
| 12076 | | A | G | A | — | A | A | A | — | A | A | — | A | A |
| 12102 | | G | G | G | — | G | G | G | — | G | G | — | G | T |
| 12153 | | A | G | A | — | A | A | A | — | A | A | — | A | A |
| 12432 | | A | G | A | — | A | A | A | — | A | A | — | A | A |
| 12501 | | T | A | T | — | T | T | T | — | T | T | — | T | T |
| 12600 | | G | G | G | — | G | G | G | — | G | G | — | G | T |
| 12943 | ORF3 | G | G | G | — | G | G | G | — | G | G | — | G | A |
| 12950 | | C | C | C | — | C | C | C | — | C | C | — | C | T |
| 12973 | | T | G | T | — | T | T | T | — | T | T | — | T | T |
| 13011 | | G | G | G | — | G | G | G | — | G | G | — | A | A |
| 13787 | No ORF | T | T | T | — | T | T | T | — | T | T | — | C | T |
| 13825 | ORF5 | G | G | G | — | G | G | G | — | G | G | — | G | A |
| 13860 | | T | T | C | — | C | C | C | — | T | T | — | T | T |
| 14238 | | A | A | A | — | A | A | A | — | A | A | — | A | C |
| 14336 | | T | T | C | — | C | Y (T/C) | C | — | C | C | — | T | T |
| 14404 | ORF6 | T | T | C | — | C | C | C | — | C | C | — | T | T |
| 14420 | | C | C | C | — | C | C | C | — | C | C | — | C | G |
| 14686 | | A | A | A | — | A | G | A | — | A | A | — | A | A |
| 14735 | | C | G | G | — | G | G | G | — | G | G | — | G | G |

TABLE 4-continued

Nucleotide differences between PRRSV strains and VR-2332 infectious clones.
Only positions where nucleotide differences were noted are shown. Nucleotides that are represented in strain VR-2332 are shown in unshaded boxes. Light shaded boxes represent nucleotide differences that are unique to the infectious clone, medium shaded boxes highlight those nucleotides that are also seen in Ingelvac ® MLV, and boxes that are shaded black indicate swine unique nucleotides.
Regions that were not sequenced are indicated by a slash.

| Base* | Region | VR-2332 | V4 | V5 | V5-1-P3 | V5-2-P3 | V5-Swine 612 | V5G7 475A | V5G7 475A-P3 | V6 | V6G 7475A | V6G7 475A-P3 | VR-HN | MLV |
|---|---|---|---|---|---|---|---|---|---|---|---|---|---|---|
| 14737 | | G | C | C | — | C | C | C | — | C | C | — | C | C |
| 14979 | ORF7 | G | A | A | — | A | A | A | — | G | G | — | G | G |
| 15281 | 3'UTR | A | G | A | — | A | A | A | — | A | A | — | A | A |
| 15334 | | T | C | T | — | T | T | T | — | T | T | — | T | T |
| 15339 | | C | C | C | — | Y (T/C) | C | C | — | C | C | — | C | C |
| 15411 | | T | T | T | — | K (T/G) | Y (T/C) | T | — | T | T | — | T | T |

*The negative bases refer to those nucleotides present in the RNA after transcription and derived from the RNA polymerase promoter immediately upstream of the infectious polynucleotide. These promoter-derived nucleotides are typically no longer present in an infectious polynucleotide after it has been passaged 9 times.

In vitro transcription. The full-length cDNA clone was linearized by cleavage with PacI, which cuts downstream of the poly(A) tail. Capped [m$^7$G(5')ppp(5')G cap analog] RNA transcripts were produced using the mMESSAGE MACHINE™ Kit (Ambion) and an optimized 2:1 ratio of methylated cap analogue to GTP. Approximately 50 to 60 μg of RNA was generated from 2 μg of DNA template in a 20-μl of reaction mixture. Increasing the ratio of cap analogue to GTP substantially reduced the RNA yield. The RNA was subsequently purified by acid phenol-chloroform followed by isopropanol precipitation and resuspended in nuclease-free TE buffer (pH 8.0). RNA was evaluated for quality by size comparison with wild-type VR-2332 viral RNA on a 1% glyoxal denaturing agarose gel, and quantified by spectrophotometry at $OD_{260}$.

MARC-145 cell transfection. A modified transfection procedure was generated based on the approached described by Nielsen (Nielsen et al., (J. Virol., 77:3702-3711 (2003)). For transfection, MARC-145 cells were seeded onto six-well plates ($2-3 \times 10^5$ cells/well) in 3 ml of complete medium [EMEM supplemented with 10% fetal bovine serum (FBS)] and then incubated at 37° C., 5% $CO_2$ for 20-24 hours until approximately 80% confluent (Collins et al., J. Vet. Diagn. Invest., 4:117-126 (1992)). 4 μg of in vitro transcribed RNA diluted in 500 μl Opti-MEM® I Reduced Serum Medium (Invitrogen) and 2 μl of 1,2-dimyristyloxypropyl-3-dimethylhydroxy ethyl ammonium bromide and cholesterol (DMRIE-C; Invitrogen) diluted in 1 ml Opti-MEM® medium were combined and vortexed briefly. The MARC-145 cells were washed once with 2 ml Opti-MEM® medium and then immediately overlayed with the lipid:RNA complex solution. DMRIE-C without RNA (2 μl) was used as a negative control and DMRIE-C with 10-100 ng strain (wild type) wt VR-2332 purified viral RNA was used as a positive control. After 4 hours of exposure to the lipid:RNA complexes, the monolayers were washed and fresh complete medium (EMEM with 10% FBS) was added. Supernatants from transfected cells were monitored daily for appearance of cytopathic effect (CPE) and passaged onto fresh MARC-145 at 72-96 hours posttransfection.

Detection of progeny viral RNA. To detect progeny viral RNA, cell culture supernatant from transfected and infected MARC-145 cells were harvested. RNA was isolated with QiaAmp viral RNA Kit (Qiagen). RT-PCR was performed with select primer pairs, specific to the VR-2332 strain nucleotides that were indicative of infectious clone mutated residues (Table 3). Confirmation of infectious clone progeny was obtained by nucleotide sequence verification of clone specific nucleotides present in the RT-PCR products.

Detection of progeny viral nucleocapsid protein. Indirect immunofluorescence assays (IFA) were used to detect viral protein expression in in vitro transcript RNA transfected, or progeny virus infected, MARC-145 cells prepared on coverslips. Infected cells were fixed in 3.7% paraformaldehyde with phosphate buffered saline (PBS), pH 7.5, at room temperature for 10 minutes. The fixed cells were washed with PBS, incubated at 37° C. for 45 minutes in PRRSV nucleocapsid protein specific monoclonal antibody SDOW17 (Magar et al., Can. J. Vet Res., 59:232-234 (1995)) and further incubated with goat anti-mouse immunoglobulin G (IgG) conjugated with fluorescein isothiocyanate at 37° C. for another 45 minutes (1:100 dilution) (Sigma). The coverslips were washed with PBS, mounted to a slide using gel mount oil, and observed under a fluorescence microscope.

Viral plaque assay. MARC-145 cell monolayers on six-well plates were infected with cell supernatant (in 10-fold dilutions) from transfected or infected MARC-145 cells by incubation at room temperature for 1 hour. Infected monolayers were subsequently washed once with fresh EMEM/ 10% FBS, overlaid immediately with sterile 1% SeaPlaque Agarose (BioWhittaker Molecular Applications, Rockland, Me.) in 1×MEM (Sigma M4144)/10% FBS/2% (w/v) NaHCO$_3$/1× glutamine/1× nonessential amino acids/10 mM HEPES/2% (v/v) gentamycin, and incubated at 37° C./5% CO$_2$, inverted, for 5 days. After careful removal of the agarose, cells were stained with 5% crystal violet in 20% ethanol for 10-30 minutes for visualization of plaque size.

Viral growth curve. MARC-145 monolayers in T-75 flasks were inoculated with either parental or recombinant PRRSV diluted in serum-free EMEM at a multiplicity of infection (MOI) of 0.001. After 1 hour attachment at room temperature with gentle mixing, the inocula were removed and the monolayers washed three times with serum-free EMEM. After washing, 4 ml complete medium was added and the flasks were subsequently incubated for up to 5 days at 37° C., 5% CO$_2$. Aliquots (0.5 ml) were harvested immediately after the addition of medium (0 hour time point) and at 24, 48, 72, 96 and 120 hours and stored at −80° C. Serial dilutions of the samples were used to infect fresh MARC-145 cells and the cells then processed as described above. After removal of the agarose, plaques were visualized and counted. Growth curve results were expressed as PFU/ml.

In vivo inoculation of progeny virus. Ten 4-week-old pigs of mixed breed and sex from a PRRSV-seronegative herd were divided into three groups, each consisting of two animals. The first group received $10^{3.5}$ 50% tissue culture infectious dose (TCID$_{50}$) of cloned virus (pVR-V5, third passage on MARC-145 cells) per ml, the second group received $10^{5.4}$ TCID$_{50}$ per ml of the parental virus strain VR-2332 (fourth passage on MARC-145 cells), and the third group was mock inoculated with EMEM. All of the animals received 2 ml of inoculum by intramuscular injection. The animals were kept in separate rooms throughout the experiment and observed daily for clinical signs. All pigs were euthanized on day 28 postinfection. To recover virus, individual serum samples were diluted 5-fold with incomplete EMEM and placed on fresh MARC-145 monolayers for 1 to 2 hours at room temperature with gentle agitation. The inocula were then removed and complete EMEM was added. Infected cells were incubated at 37° C., 5% CO$_2$ and observed daily. Once CPE was evident, infected cell supernatants were frozen at −80° C. until further characterized.

Northern Blot Analysis. pVR-V6G7475A transcripts were transfected into MA104 cells and then passaged onto fresh cells for several passages. For subsequent northern blot analysis, supernatants from passage 1 (P1), P3, P6, P8 and P10 were diluted 1:50 and then used to infect cells (1 ml/T75 flask) on the same day. At the same time, infected swine serum was diluted 10-fold and then used (1 ml) to infect a separate T75 flask. Cytopathic effect was seen on day 3 p.i. for all flasks. Intracellular RNA was extracted using a RNeasy Midi kit (Qiagen) and electrophoresced (15 µg/sample) on a glyoxal denaturing gel as described previously (Nelsen et al., *J. Viral.*, 73:270-80 (1999)). pVR-V6G7475A transcript RNA (100 ng) was run as a control. After RNA transfer to 0.45 micron MagnaGraph Nylon Transfer Membrane (Osmonics), the membrane was probed with labeled oligonucleotide/1a-p222, end labeled with $\gamma$-$^{32}$P-ATP (Amersham) using polynucleotide kinase (Promega) as described previously (Nelsen et al., *J Viral.*, 73:270-80 (1999)).

Nucleic acid sequence analysis of progeny virus. 5'- and 3'-rapid amplification of cDNA ends (RACE) was performed with SMART™ RACE cDNA Amplification Kit (BD Bioscience) or 5' or 3'-Full Race Core Set (TaKaRa Bio Inc) on viral RNA isolated with the QIAmp® Viral RNA Mini Kit (Qiagen). The remaining nucleotide sequence was determined from RT-PCR products of primer pairs developed to cover the entire genome of strain VR-2332 (Table 3), as described previously (Yuan et al., *Virus Res.*, 79:189-200 (2001)). The products were submitted for nucleic acid sequence determination at the Advanced Genetic Analysis Center at the University of Minnesota. Complete viral sequence with at least three fold coverage was initially assembled with the SeqMan suite of the Lasergene® sequence analysis software (DNASTAR, Inc.), and further analyzed using GCG Wisconsin Package Version 10.3 software (Accelrys Inc.). Strain VR-2332 (GenBank Accession U87392) strain Ingelvac® MLV (GenBank Accession AF066183) and cDNA clone pVR-HN (GenBank Accession AY150564; Nielsen et al., *J. Viral.*, 77:3702-3711 (2003)) were used in all nucleotide comparisons to recombinant virus strains.

Results

Modification of pOK12 Vector. pOK12 (GenBank Accession AF223639; Vieira et al., *Gene*, 100:189-194 (1991)), a low copy cloning vector, was modified by digestion with SmaI (enzyme site at 273 bp in pOK12) and SalI (site at 307 bp) and inserting the 244 bp SmaI-SalI fragment of Vector 2.0 (7) containing the hepatitis delta virus (HDV) ribozyme. The vector (pOK12HDV) was then further modified by mutagenesis of an existing KpnI site (p0K12HDV site at 273 bp) to insert a PacI restriction enzyme site through the use of the primer pair 5'-p0K12HDV-257SphIPacI/3'-p0K12HDV-257SphIPacI. The HDV ribozyme was added to provide for effective cleavage precisely at the 3'end of the polyA tract. Studies revealed that the modification was not necessary to obtaining infectious progeny virus.

Construction of full-length cDNA clones. The cloning strategy is depicted in FIG. 2. Four overlapping genome fragments were amplified from purified VR-2332 viral RNA by RT-PCR using the primer pairs indicated (FIG. 2, Table 3). Each fragment was individually cloned into the pCR®2.1-TOPO® vector to generate intermediate clone pCR-SphI-FseI (segment I), pCR-FseI-AvrII (segment II), pCRAvrII-BsrGI (segment III), and pCR-BsrGI-PacI (segment IV). The cDNA clones were then digested with two unique restriction enzymes, as indicated by the clone name. Four fragments were gel-purified and stepwise ligated to vector pOK12HDV-PacI to generate a full-length cDNA clone of PRRSV (pVR-V4). In the full-length cDNA clone, viral genomic sequence was driven by T7 RNA polymerase promoter and followed by polyadenylic acid tail of 50 nucleotides. RNA transcripts of clone pVR-V4 did not display typical PRRSV infectivity when transfected into permissive cells, although viral RNA could be detected over several passages. When compared to strain VR-2332, a total of 45 nucleotide mutations (Table 4) leading to 21 amino acid changes were detected (Table 5), although several mutations were the same as previously identified in Ingelvac® MLV (Yuan et al., *Virus Res.*, 61:87-98 (1999)).

TABLE 5

Amino acid differences between PRRSV strains and VR-2332 infectious clones.
Only positions where nucleotide differences were noted are shown with corresponding amino acid position within the identified genomic region. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac ® MLV, and boxes that are shaded black indicate swine unique nucleotides. Amino acids separated by slashes indicate ORF2a/ORF2b amino acid numbers. Regions that were not sequenced are indicated by a slash.

| NT Position | AA Position | Region | VR-2332 | V4 | V5 | V5-1-P3 | V5-2-P3 | V5-Sw612 | V5G7 475A | V6 | V6G7 475A | VR-HN | MLV |
|---|---|---|---|---|---|---|---|---|---|---|---|---|---|
| 258 | 23 | NSPIα | V | | | | | | | | | Silent | |
| 309 | 40 | | Q | Silent | Silent | Silent | Silent | Silent | Silent | Silent | Silent | | |
| 642 | 151 | | P | Silent | Silent | — | Silent | Silent | Silent | Silent | Silent | | |
| 784 | 199 | NSPIβ | V | | | — | | | | | | | |
| 827 | 213 | | A | | | — | | V | | | | | |

TABLE 5-continued

Amino acid differences between PRRSV strains and VR-2332 infectious clones.
Only positions where nucleotide differences were noted are shown with corresponding amino acid position within the identified genomic region. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac ® MLV, and boxes that are shaded black indicate swine unique nucleotides.
Amino acids separated by slashes indicate ORF2a/ORF2b amino acid numbers. Regions that were not sequenced are indicated by a slash.

| NT Position | AA Position | Region | VR-2332 | V4 | V5 | V5-1-P3 | V5-2-P3 | V5-Sw612 | V5G7 475A | V6 | V6G7 475A | VR-HN | MLV |
|---|---|---|---|---|---|---|---|---|---|---|---|---|---|
| 1074 | 295 | | Y | | | — | | | | | | Silent | |
| 1107 | 306 | | L | Silent | Silent | — | Silent | Silent | Silent | Silent | Silent | | |
| 1181 | 331 | | S | | | — | | | | | | | |
| 1379 | 397 | NSP2 | A | | | — | | V | | | | | |
| 1595 | 469 | | A | D | | — | | | | | | | |
| 2192 | 668 | | S | | | — | | | | | | | T |
| 3040 | 951 | | D | | | — | | | | | | | N |
| 3457 | 1090 | | D | | | — | | | | | | | N |
| 4407 | 1406 | NSP3 | P | Silent | Silent | — | Silent | Silent | Silent | Silent | Silent | | |
| 4593 | 1468 | | Q | Silent | Silent | — | en | Silent | Silent | Silent | Silent | | |
| 4681 | 1498 | | S | A | A | — | A | A | A | A | A | A | A |
| 4866 | 1559 | | V | Silent | Silent | — | Silent | Silent | Silent | Silent | Silent | | |
| 5097 | 1636 | | R | Silent | Silent | — | Silent | Silent | Silent | Silent | Silent | Silent | Silent |
| 5247 | 1686 | | V | Silent | Silent | — | Silent | Silent | Silent | Silent | Silent | | |
| 5519 | 1777 | | T | | | — | | | | | | I | |
| 5610 | 1807 | | L | | | — | | | | | | Silent | |
| 6345 | 2052 | NSP5 | P | | | — | | | | | | | Silent |
| 6674 | 2162 | | P | T | T | — | T | T | T | T | T | | T |
| 6853 | 2222 | NSP7 | D | | | — | | | | | | N | |
| 6966 | 2259 | | D | | | — | | | | | | Silent | |
| 7329 | 2380 | | K | Silent | Silent | Silent | Silent | Silent | Silent | Silent | Silent | | |
| 7475 | 2429 | | E | G | G | G | G | | | G | | | |
| 7554 | 2455 | | V | Silent | Silent | Silent | Silent | Silent | Silent | Silent | Silent | Silent | |
| 9220 | 3011 | NSP9 | L | P | | — | | | | | | | |
| 9649 | 3154 | NSP10 | G | E | | — | | | | | | | |
| 9918 | 3244 | | L | | | — | | | | | | | Silent |
| 9958 | 3257 | | G | E | | — | | G/E | | | | E | E |
| 10040 | 3284 | | V | Silent | | — | | | | | | | |
| 10533 | 3449 | | Y | | | — | | | | | | | H |
| 10643 | 3485 | | V | | | — | | | | | | Silent | |
| 10697 | 3503 | | A | Silent | | — | | | | | | Silent | Silent |
| 10739 | 3517 | | H | Silent | | — | | | | | | | |
| 10781 | 3531 | | T | Silent | | — | | | | | | Silent | Silent |
| 10803 | 3539 | | C | R | | — | | | | | | Silent | R |
| 10895 | 3569 | | D | | | — | | | | | | | Silent |
| 11055 | 3623 | NSP11 | S | T | | — | | | | | | T | T |
| 11081 | 3631 | | P | Silent | | — | | | | | | Silent | Silent |
| 11221 | 3678 | | G | E | | — | | E | | | | E | E |
| 11229 | 3681 | | V | | | — | | | | | | | L |
| 11259 | 3691 | | R | G | | — | | | | | | | |
| 11327 | 3738 | | H | Silent | | — | | | | | | | |
| 11329 | 3739 | | G | A | A | — | A | A | A | A | A | A | A |
| 11501 | 3771 | | E | Silent | | — | | | | | | | |
| 11666 | 3826 | NSP12 | P | Silent | | — | | | | | | Silent | Silent |
| 11744 | 3852 | | W | C | | — | | | | | | | |
| 11882 | 3898 | | K | Silent | | — | | | | | | | |
| 12076 | 2 | ORF2a/b | K | E | | — | | | | | | | |
| 12102 | 10/9 | | L/D | | | — | | | | | | | E/Y |
| 12153 | 27 | | P/I | P/V | | — | | | | | | | |

TABLE 5-continued

Amino acid differences between PRRSV strains and VR-2332 infectious clones.
Only positions where nucleotide differences were noted are shown with corresponding amino acid position within the identified genomic region. Amino acids that are represented in strain VR-2332 are shown in unshaded boxes and infectious clone amino acid identities with VR-2332 are represented by blank boxes. Text in each individual box represent silent or amino acid changes due to nucleotide differences shown in Table 2. Light shaded boxes represent nucleotide differences that are unique to the infectious clone, medium shaded boxes highlight those nucleotides that are also seen in Ingelvac ® MLV, and boxes that are shaded black indicate swine unique nucleotides.
Amino acids separated by slashes indicate ORF2a/ORF2b amino acid numbers. Regions that were not sequenced are indicated by a slash.

| NT Position | AA Position | Region | VR-2332 | V4 | V5 | V5-1-P3 | V5-2-P3 | V5-Sw612 | V5G7 475A | V6 | V6G7 475A | VR-HN | MLV |
|---|---|---|---|---|---|---|---|---|---|---|---|---|---|
| 12432 | 120 | | E | Silent | | — | | | | | | | |
| 12501 | 143 | | D | E | | — | | | | | | | |
| 12600 | 176 | | G | | | — | | | | | | | Silent |
| 12943 | 83 | ORF3 | G | | | — | | | | | | | E |
| 12950 | 85 | | D | | | — | | | | | | | Silent |
| 12973 | 93 | | M | R | | — | | | | | | | |
| 13011 | 106 | | G | | | — | | | | | | S | S |
| 13825 | 13 | ORF5 | R | | | — | | | | | | | Q |
| 13860 | 25 | | F | | L | — | L | L | L | | | | |
| 14238 | 151 | | R | | | — | | | | | | | G |
| 14336 | 183 | | G | | Silent | — | Silent | Silent | Silent | Silent | Silent | | |
| 14404 | 10 | ORF6 | H | | Silent | — | Silent | Silent | Silent | Silent | Silent | | |
| 14420 | 16 | | Q | | | — | | | | | | | E |
| 14686 | 104 | | L | | | — | | | | | | | |
| 14735 | 121 | | R | G | G | — | G | G | G | G | G | G | G |
| 14737 | 121 | | R | G | G | — | G | G | G | G | G | G | G |
| 14979 | 31 | ORF7 | A | T | T | — | T | T | T | | | | |

Because many mutations in pVR-V4 occurred in the critical region encoding putative helicase, polymerase and other Nidovirus motifs (FIG. 3, Table 4), additional clones of genomic segment III (pCR-AvrII-BsrGI) were generated and sequenced in their entirety. After replacing segment III of pVR-V4 with the most sequence accurate fragment obtained, we again determined the nucleotide sequence of the entire genomic full-length clone (pVR-V5). Except for the replaced region and for four spontaneous mutations (nucleotides 1595, 13860, 14336, and 14404), these two genomic clones were identical (Table 4). Sequence analysis of pVR-V5 showed that this clone harbored a total of 23 mutations compared to strain VR-2332. Of these 23 changes, only 8 nucleotide mutations coded for a change in amino acid and five of the amino acid residue mutations were identical to Ingelvac® MLV and thus not predicted to adversely effect in vitro replication (Table 4).

Clone pVR-V6 was derived from site-directed mutagenesis of genome segment IV to repair nucleotides 13860 and 14979 using primers 13860C2T/ and 14979A2G/, respectively. Mutation of these two nucleotides would correct amino acid residue 25 of GP5 (L→F) and residue 31 of the nucleocapsid protein (T→A). Sequence analysis of clone pVR-V6 confirmed that the nucleotides had been corrected back to wild-type (wt) VR-2332 nucleotides and had not resulted in any other nucleotide changes elsewhere in the genome when compared to pVR-V5 (Tables 4 and 5). Finally, site-directed mutagenesis on genome segment III using oligomer 7475G2A was completed on both pVR-V5 and pVR-V6 in order to correct an alteration from wt VR-2332 at nt 7475. The change of G→A at nt 7475 resulted in a glycine (G) at ORF1 amino acid 2429 in the two recombinant clones to the glutamic acid (E) seen in the parental VR-2332 viral strain. The final two clones, pVR-V5G7475A and pVR-V6G7475A were again sequenced in their entirety and found to have only (nt 7475) altered from the original recombinant plasmids pVR-V5 and pVR-V6, respectively (Table 5). pVR-V6G7475A thus contains 11 nucleotide and no amino acid changes from strain VR-2332, besides those also seen in Ingelvac® MLV.

Figure 3:
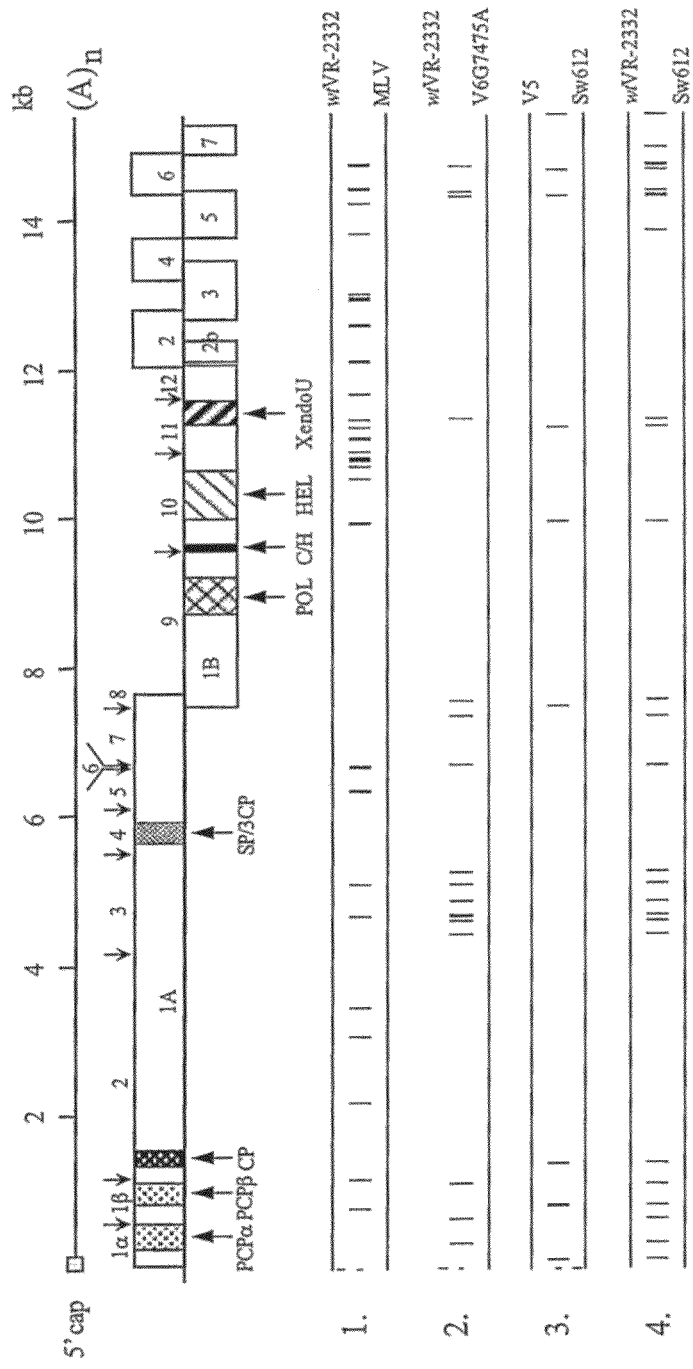
FIG. 3. Schematic of nucleotide changes of infectious clones or swine progeny. Diagram of the PRRSV genome organization is presented under which are full genome comparisons. Putative nonstructural protein cleavages are depicted above ORF1a and 1b, represented by downward arrows. Signature motifs are identified below ORF1a and 1b, with upward arrows indicating their placement in the PRRSV genome [papain-like cysteine protease α and β (PCPα, PCPβ); cysteine protease (CP); serine/3C protease (SP/3CP); polymerase (POL); cysteine/histidine rich (C/H); helicase (Hel); *Xenopus laevis* homolog poly(U)-specific endoribonuclease (XendoU); Ivanov et al., *Proc. Natl. Acad. Sci. USA*, 101:12694-12699 (2004); Ziebuhr et al., *J. Gen. Virol*, 81:853-879 (2000)]. Nucleotide differences are represented by vertical bars. 1. wt strain VR-2332 (U87392) compared to VR-2332 derived vaccine (Ingelvac® MLV or RespPRRS, AF066183). 2. wt strain VR-2332 compared to pVR-V6G7475A. 3. pVR-V5 compared to in vivo passaged V5-1-P3 (Sw612). 4. wt strain VR-2332 compared to Sw612. Detailed nucleotide changes are listed in Tables 4 and 5.

As can be seen schematically in FIG. 3 for the final construct (pVR-V6G7475A), and detailed in Tables 4 and 5, all full-length clones still possess nucleotide changes scattered throughout the genome, primarily in the poorly defined regions of ORF1. However, the large cluster of ORF1b nucleotide changes that presumably prevented pVR-V4 from completing viral replication were repaired in later versions of the full-length genome clones. Only one nucleotide mutation (nt 11329 coding for G3739A mutation) remained in ORF1b of pVR-V5 and later clones, and this mutation does not prevent Ingelvac® MLV from infecting and replicating efficiently in cultured cells. Tables 4 and 5 also display the residue information for the previously published infectious clone, pVR-HN (Nielsen et al., J. Virol., 77:3702-3711 (2003)), shown to replicate in animals. There is a substantial increase in the number of residues in pVR-HN (15 nucleotides) that directly display the sequence of Ingelvac® MLV over the final construct, pVR-V6G7475A (7 nucleotides).

Characterization of recombinant virus. Full-length RNA transcripts of each cDNA clone were produced. MARC-145 cell transfection with the cDNA transcripts or wt VR-2332 viral RNA (vRNA) resulted in CPE, characterized by cell clumping followed by lysis, at 48 to 72 hours post transfection. CPE caused by the recombinant transcripts were delayed and somewhat distinct compared to that induced by wt VR2332 vRNA in which CPE presents as vigorous aggregation, detachment, and disruption. At 96 hours posttransfection, most of the cells transfected with VR-2332 vRNA had undergone lysis and detached from the plate, whereas less severe CPE was apparent in cells transfected with the cloned in vitro derived RNA transcripts.

Virus (P0) was harvested from the transfected cells and an aliquot (10 μl diluted to 1 ml in culture medium) was used to infect MARC-145 cells for progeny virus amplification. After CPE was detected, virus (P1) was again harvested and an aliquot used for reinfection of MARC-145 cells. Recombinant virus in the cell supernatant (P2) was utilized for purification of viral RNA, which was then used to obtain RT-PCR fragments with primer pairs 5'-6800/3'-ORF1b (nt 6796-7614) and P51/05P4 (nt 13757-14341). The PCR fragments obtained were submitted for nucleotide sequence analysis to confirm that the infectivity seen was due to transfected full-length RNA transcripts of the infectious construct and not a result of contamination due to wt virus. Nucleotide mutations at residues 7329, 7475, 7554, and 13860 nucleotide differences were seen in progeny virus from pVR-V5, and 7329, 7554, and 13860 were detected in virus from pVR-V5G7475A. Similarly, mutations at residues 7329, 7475, and 7554 were detected in pVR-V6 progeny and mutations at 7329 and 7554 were detected in virus resulting from pVR-V6G7475A (Tables 4 and 5). Corresponding mutations were not seen in P2 virus from wt vRNA transfections.

Immunofluorescence analysis of recombinant viruses. Direct immunofluorescence assays were used to detect the expression of PRRSV nucleocapsid protein in infected MARC-145 cells. All cells infected by recombinant virus transcripts (P2 and on) as well as vRNA were positive by this method. Massive nucleolar accumulation of the nucleocapsid protein was readily apparent, as previously reported by Rowland et al. (*Virus Res.*, 64:1-12 (1999)).

Figure 4:
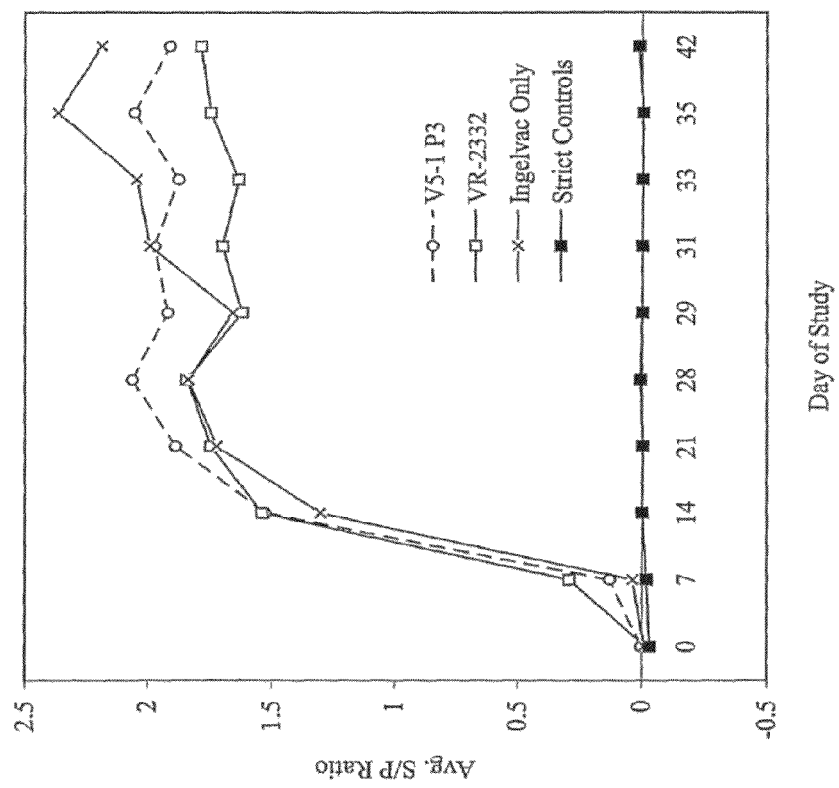
FIG. 4. Seroconversion of swine after PRRSV infection. Growing swine were infected with native wt strain VR-2332 (□), Ingelvac® MLV (×), V5-1 P3 (○) or remained uninfected (■). At days indicated, serum samples were taken and tested by IDEXX Elisa for indication of seroconversion by anti-PRRSV antibodies to the nucleocapsid protein.

In vivo infection with pVR-V5 derived recombinant virus. Recombinant viruses recovered from P3 of MARC-145 cells transfected with RNA transcripts of cDNA clone pVR-V5 were inoculated into young swine in parallel with wt VR-2332, vaccine virus Ingelvac® MLV and saline (negative control). Blood samples were collected on 0, 3, 5, 7, 14, 21 and 28 days p.i. and analyzed for seroconversion by Herd-Chek PRRS 2XR ELISA (IDEXX) and for virus recovery. At day 28, all infected animals had seroconverted with approximately the same kinetics, revealing that pVR-V5 recombinant viruses replicated well in vivo (FIG. 4). Clinical signs were absent from all animals during the course of the experiment, but this was not unexpected as wt strain VR-2332 often does not produce overt disease in young swine and results in enlarged lymph nodes only transiently, typically at day 14 p.i.

A serum sample from one animal infected with progeny of pVR-V5 (Sw612), taken at 14 days p.i., was used to infect fresh MARC-145 monolayers for recovery of in vivo pas-saged recombinant virus. As described previously, the virus derived from in vitro transfection of clone pVR-V5 RNA transcripts caused only minimal CPE (evidenced by aggregation of infected cells) while virus recovered from day 14 serum of the test animal caused typical CPE (cell aggregation, detachment, and disruption) at 96 hours postinfection. This suggested that a shift in viral genotype or phenotype had occurred while pVR-V5 replicated in vivo.

In order to elucidate the reason for the apparent change in phenotype, full-genome sequence analysis was completed on virus recovered from one pig (Sw612) and then passaged once in MARC-145 cells to amplify the Sw612 progeny (FIG. 3, Tables 4 and 5). When compared to the virus used to infect swine, pVR-V5, 17 infectious cDNA clone-specific nucleotide changes were retained in Sw612, some of which are also seen in Ingelvac® MLV (7/17 nucleotides). The two non-viral G residues followed by a T residue present at the 5' end of the original pVR-V5 clone transcript were not seen in the virus derived from in vivo infection. Degeneracy was seen at nucleotide positions 9958 (R), 14336 (Y) and 15411 (Y). The wt VR2332-like nucleotide (G) at position 9958 showed degeneracy with an Ingelvac® MLV-like nucleotide (A). This change results in a mutation of a glycine residue to a glutamic acid residue, respectively (Table 2). At position 14336, degeneracy was detected as an infectious clone-specific base (C) and a wt VR-2332-specific base (T), which reflected a silent mutation. Another mutation (nt 7475) occurred in which a G residue had reverted to the wt residue A. However, there were another 5 nucleotide differences (nt 102, 827, 1379, 14686 and 15411) not seen in any of the other viruses in this study. Nucleotide 102 is located in the leader sequence, thought not be translated. However, if the leader sequence were translated, the encoded ORF (VR-2332 nucleotides 1-100) would be extended by one amino acid residue (W). The mutations at residues 827 and 1379 led to mutations in ORF1a, in both cases resulting in an amino acid change of wt VR-2332 encoded alanine for a Sw612 valine The guanine residue at nt 7475 of pVRV5 had mutated to wt adenine. This resulted in a G3294A non-conservative amino acid mutation, which lies in ORF1a predicted protease cleavage product NSP7 and this genomic region has no defined function to date. Nucleotide 14686, located in ORF6, showed a change from a wt VR-2332 guanine to an alanine in Sw612, which still encodes the amino acid glycine. The other unique nucleotide change occurred at the very 3' end of the viral sequence (nt 15411), before the start of the polyA tail. In this case, a previously conserved thymine residue revealed degeneracy with a cytosine residue. These genetic changes, although informative, did not immediately reveal the cause(s) of the change in growth phenotype observed. However, it did reveal the errant nature of PRRSV replication in vivo and suggests that a moderately different viral genomic sequence from wt VR-2332 was able to replicate efficiently (FIG. 3).

Figures 5A, 5B:
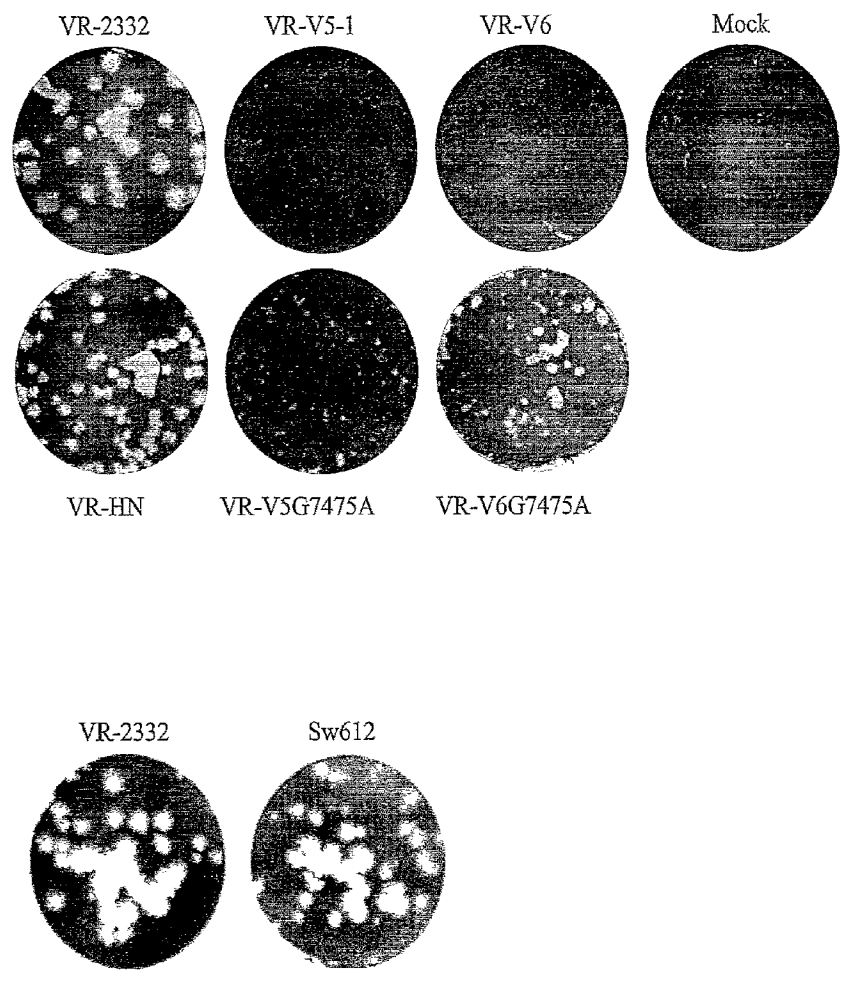

Comparison of viral plaque size. Plaque size determinations of the recombinant viruses as well as wt VR-2332 were completed in parallel on MARC-145 cells at 120 hours p.i. (FIG. 5A). Strain VR-2332 formed plaques that averaged 3 mm in size, while passage 3 progeny of pVR-HN cDNA clone formed slightly smaller plaques (2.5 mm average). In contrast, only pinpoint plaques were obtained from recombinant viruses derived from pVR-V5 and pVR-V6, and these were only readily apparent through microscopic examination (FIG. 5A). Recombinant virus recovered from clones pVRV5G7475A and pVR-V6G7475A formed, on average, 1.5 mm and 2 mm plaques respectively. However, in another assay, the plaques produced by the viral progeny (Sw612) recovered from in vivo infection of VR-FLV5 derived recombinant virus were much larger, approximately equal in both size and number as those derived from wt VR2332 (FIG. 5B).

Figures 6A, 6B:
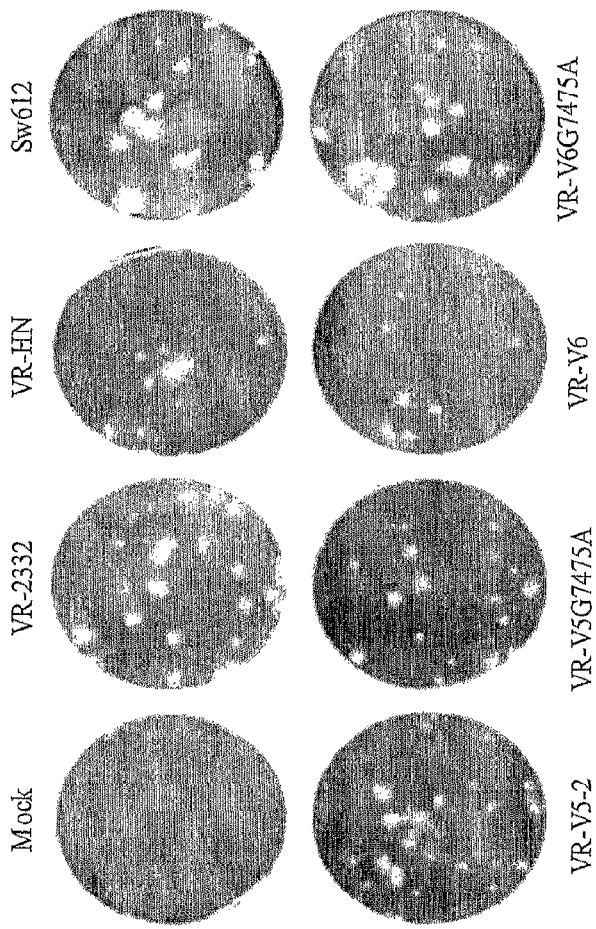
FIG. 6. A. Plaque assays on P3 progeny (second lineage) of all infectious clones as well as wt strain VR-2332 displayed plaque sizes that were different from first lineage virus preparations. B. Titers of P4 virus indicate infectious clone progeny were not replicating as wt strain VR-2332 or Sw612 virus in spite of having similar plaque size.

Only minimal volumes of the cell supernatants containing each recombinant virus remained. Therefore, in order to fully examine the role of nucleotide change in determining plaque size, we transfected fresh RNA transcripts produced from pVR-V5, pVR-V6, pVR-V5G7475A and pVR-V6G7475A into MARC-145 cells (termed second lineage). Passage 3 progeny viruses of each infectious clone at 5 days post-infection were again analyzed for plaque size in comparison to wt VR-2332, VR-HN and Sw612 viruses. In contrast to the previous plaque assay, all plaque sizes appeared similar, with the recombinant viruses obtained from pVR-V5, pVR-V6, pVR-V5G7475A only slightly smaller than the in vivo derived wt VR-2332, Sw612 and pVR-V6G7475A viruses (FIG. 6A). The recombinant viruses, however, were not yet directly mimicking authentic viral infection as shown by the approximately 10-fold lower titers when compared to wt VR-2332 or to pVR-V5 recombinant virus that had been passaged through swine (Sw612) (FIG. 6B).

Nucleotide Sequence Analysis of First and Second Lineage Virus Preparations. Limited nucleotide sequence analysis (due to virus stock limitation) of passage 3 pVRV5-derived virus inoculated into swine (V5-1-P3) and complete nucleotide sequence analysis of passage 3 pVR-V5-derived virus obtained above (V5-2-P3) were completed in order to reveal the genetic reason for the plaque size discrepancies. Such analyses revealed that the two independently prepared V5 viruses differed in sequence at the 5' end (Table 4). The virus that had produced pinpoint plaques (V5-1-P3) had no extraneous 5'-end nucleotides, as shown in the nucleotide sequence of wt strain VR-2332, while that producing larger plaques (V5-2-P3) possessed 4 non-templated thymidine residues at the 5' terminus (Table 4). The remaining V5-1-P3 viral nucleotide sequence we could obtain exactly matched that of V5-2-P3 virus, as well as that of the parental clone. However, complete sequence analysis of V5-2-P3 virus revealed that the virus displayed nucleotide degeneracy at several genomic sites. Similar findings were obtained when analyzing limited regions of second lineage viruses VR-FLV5G7475A-P3 and VR-FLV6G7475A-P3. These last two infectious clone progeny displayed different 5'-termini as well as exhibiting degeneracy in sequence.

Viral Growth Curves. Simultaneous one-step viral growth curve determinations were completed using MARC-145 cells and passage 3 viruses (second lineage) (FIG. 7A-B). The recombinant viruses recovered from pVR-V5, pVR-V5G7475A, pVR-V6, and pVR-V6G7475A and pVR-HN displayed similar one-step viral growth rates, but their peaks of replication were all significantly lower than wt strain VR-2332 and Sw612, the in vivo progeny of pVR-V5. Also, the replication rates of the recombinant virus preparations derived from pVR-V5, pVR-V6 and pVR-HN were somewhat decreased as compared to the virus derived from pVR-V5G7475A and pVR-V6G7475A. The last two infectious clones code for as little as 13 and 11 nucleotide differences, respectively, resulting in 2 and zero amino acid changes, from wt VR-2332 sequence besides the changes seen in Ingelvac® MLV. These data then reveal that viruses with as little as 11 nucleotide changes from wt VR-2332 and its attenuated offspring Ingelvac® MLV are somehow impaired in replication. Correspondingly, the resultant titers of wt VR-2332 and Sw612 viruses were approximately 6-15 fold higher than that of the recombinant viruses that had not been passaged in swine (FIG. 7A-B).

Figure 8:
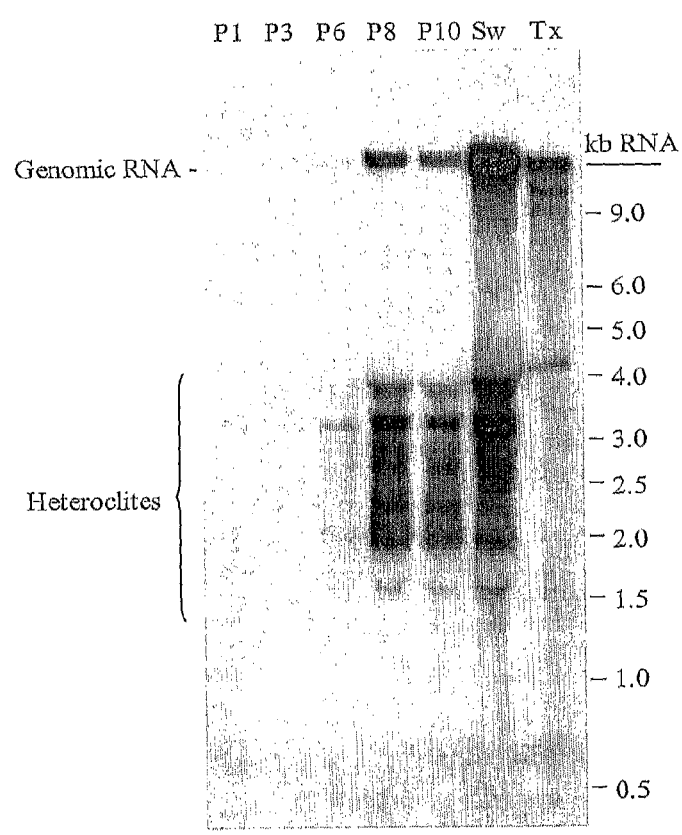
FIG. 8. Northern blot analysis of different progeny passages of pVR-V6G7475A as well as Sw612 and the initial in vitro transcript reveals heteroclites are produced as early as P1 and, along with genomic RNA, are more abundant with passage. However, transcript RNA (Tx) does not contain readily detectable heteroclite species.

Northern analyses of vRNA. PRRSV defective sgRNA species, identified previously as heteroclite subgenomic RNAs (latin: uncommon forms), have been shown to be a constituent of PRRSV infection and cannot be separated from full-length viral genomes by standard methods such as cultured cell passage at low multiplicities of infection or sucrose gradient centrifugation (Yuan et al., *Virology,* 275:158-169; 30 (2000); Yuan et al., *Virus Res.,* 105:75-87 (2004)). To explore whether or not PRRSV heteroclites are produced during in vitro transcription of full-length cDNA genome clones or appear after subsequent transfection/infection, northern blot analysis was completed. The full-length RNA transcript and passages 1, 3, 6, 8 and 10 of the virus produced from transfected MA-104 cells were used to inoculate flesh T-75 flasks of MA-104 cells with 10 µl supernatant diluted 1:100, as well as Sw612 serum diluted 1:10 (2 ml total/flask). After 4 days, intracellular PRRSV RNA was harvested and 15 µg of each preparation was separated by electrophoresis through a denaturing agarose gel and transferred to a nylon membrane. After RNA crosslinking, the membrane was hybridized with a $^{32}$P-radiolabeled probe complementary to the 5' end of ORF1a that selects for full-length VR-2332 genomes as well as heteroclites (/1a-222; 29). As shown in FIG. 8, the RNA transcript is mostly a single band, migrating as full-length vRNA, while PRRSV RNA species from passage 1 and later migrate as both full-length and subgenomic-sized species previously identified as heteroclites. In addition, the strength of hybridization increases over passage. Since the virus was harvested from an equal volume of infected cell supernatant at the same time point, this observation suggests that the vRNA becomes more efficient at replication over time. Lastly, when comparing virus generated from Sw612 with the cell culture generated virus, the RNA banding pattern is indistinguishable, strongly suggesting that the defective RNA species are readily formed and replicated in vitro as well as in vivo and thus are a natural part of PRRSV infection.

Discussion

In theory, an infectious cDNA clone of a virus should be identical to the parental sequence in order to generate a reverse genetic system that mimics wild-type infection. Considerable effort was exerted to reproduce a fully faithful PRRSV strain VR-2332 genome, yet due to unpredictable spontaneous mutations at several sites, we have not yet been successful at deriving an infectious clone that has no differences from the wt strain VR-2332 sequenced in our laboratory. High fidelity DNA polymerases, used in this study, are available to decrease artificial mutations, but such mutation cannot be avoided during reverse transcription (Malet et al., *J. Virol. Methods,* 109:161-70 (2003)). In addition, the fact that PRRSV exhibits astonishing viral evolution and strain variation (Chang et al., *J. Virol.,* 76:4750-6 (2002); Murtaugh et al., *Adv. Exp. Med. Biol.,* 440:787-94 (1998); Yoon et al., *Adv. Exp. Med. Biol.,* 494:25-30 (2001)) recombines readily at high frequency to result in intergenic recombinants between strains (Yuan et al., *Virus Res.,* 61:87-98 (1999)), undergoes intragenic recombination to form PRRSV subgenomic RNAs and heteroclites (Nelsen et al., *J. Virol.,* 73:270-80 (1999); Yuan et al., *Virology,* 275:158-169 (2000); Yuan et al., *Virus Research,* 105:75-87 (2004)) and often displays nucleotide degeneracy at unpredictable nucleotide sites in field isolates serve to make this initial goal time-consuming and of negligible gain. An infectious DNA construct possessing as little as 11 nucleotide mutations, as compared to strain VR-2332, outside of domains known to be involved in viral replication (5' and 3' ends, ORF1b) was thought sufficient for wt virus production and the downstream goals of infectious clone use for pathogenesis queries and structure:function studies. pVR-HN is more similar to Ingelvac® MLV in the region of the virus encoding the helicase motif (NSP 10). Further pathogenic comparison of these two infectious clones may shed light on the differences between the parental strain, VR-2332, and its vaccine strain offspring, Ingelvac® MLV.

Valuable information can be derived from the construction and evaluation of the infectious clones for PRRSV strain VR-2332. First of all, PRRSV strain VR-2332 cannot tolerate all mutations for survival. Particular nucleotide or amino acid mutations may help or hinder viral replication, and the challenge is to ascertain which are lethal to survival. In clone pVR-V4, which did not produce infectious virions, there were total of forty-two nucleotide differences from wt parental strain VR-2332. In these forty-two nucleotide changes, several nucleotides result in silent mutations (20 residues) or exist in other known PRRSV strains (9 amino acid residue mutations directly mimic Ingelvac® MLV) allowed prediction that these changes may be non-lethal for virus replication. Eleven nucleotide changes leading to 12 amino acid changes and two 3'UTR nucleotide mutations, each not seen in Ingelvac® MLV, were thus predicted to be lethal to PRRSV strain VR-2332. In pVR-V5 and later constructs, 19 changes were corrected, including several silent mutations and 9 aberrant amino acid changes not seen in the genome of Ingelvac® MLV and 8 other changes seen in the vaccine strain. This lead to the first evidence that the constructs were infectious, although in pVR-V5 two amino acid mutations were still present, one of which was altered through site directed mutagenesis to produce pVR-6. The remaining amino acid change was repaired in pVR-V5G7475A and pVR-V6G7475A, although these clones still harbor silent mutations that are not found in strain VR-2332 and the derived vaccine strain.

Several unique observations were obtained from this study. First of all, each lineage of produced virus may result in a unique 5' terminal sequence that was not detected in wt strain VR-2332. We also cannot yet correlate plaque size with nucleotide sequence. Secondly, we saw unique nucleotide changes after replication in swine, which may reflect the inherent nature of the PRRSV polymerase. All nucleotide changes were transitional in nature and did not exhibit a bias (5 A/G and 4 C/T). Although the G A reversion at nucleotide 7475 was seen after in vivo passage, we could not correlate this site with the subsequent increased plaque size because other non-templated changes had occurred. In addition, full-genome sequence analyses of passage 3 of a VS-derived virus that produced larger plaques (V5-2-P3) revealed a different 5'terminal sequence from the pinpoint plaque-producing VS virus used to infect swine (V5-1-P3). However, we can conclude that the mutations were not lethal to virus replication because this virus, after passage in swine, produced wt-sized plaques on MARC-145 cells ad grew at almost the same rate as the parental virus (FIGS. 5A, 6 and 7).

Of considerable interest is the fact that sequence analysis of the third in vitro passage of V5, V5G7475A and V6G7475A seemed to suggest that the PRRSV replicase complex allows frequent transitions, and infrequent transversions, to occur while undergoing viral replication. This may reflect a viral replicase that has evolved so that it may generate new genetic forms of a PRRSV genome and then assess their competence amid other variants, resulting in an optimally "fit" virus. These observations have also been noted during PRRSV sequential passage in vivo (Chang et al., J. Virol., 76:4750-63 (2002)). Present sequencing efforts are to examine the full-length genomes of later passages, when a more robust replication is detected. Finally, it is now clear that PRRSV strain VR-2332 replicase readily synthesizes heteroclites at the same time it is producing full-length vRNA. This prototype strain, isolated and characterized in 1992, may be unique in the gradual acquisition of replication fitness, as other investigators producing infectious clones of more recent strain have not observed the same effect (Truong et al., Virology, 325:308-319 (2004)). The role of heteroclite formation and the concomitant appearance of vigorous viral replication suggest that there is an advantageous role for heteroclites in PRRSV evolution.

Example 2

Many virulent isolates of a seemingly novel PRRSV were recently identified in the State of Minnesota, USA. ORF5 nucleotide sequence analysis and comparison to the University of Minnesota Veterinary Diagnostic Laboratory PRRSV database (>5000 isolates) revealed that the isolates were of Type 2 lineage, but were significantly different than previous isolates. Furthermore, they were most closely related to those isolates previously seen in Canada in the early 1990s (Mardassi et al., J. Gen. Virol., 75:681-685 (1994)) and in the State of Minnesota in 1998. Restriction fragment length polymorphism (RFLP) analysis of ORF5 also demonstrated that they belonged to the same group of viruses as these early cases, known as 1-8-4 isolates (Wesley et al., J. Vet. Diagn. Invest., 10:140-144 (1998)) and were thus named MN184 isolates. Because of the striking dissimilarity with all but one previously isolated MN PRRSV isolate, two of these new isolates were amplified just one time on porcine alveolar macrophages (PAM), the host cell, and full-length genome analyses was completed on the viruses, designated as MN184A and MN184B. These two isolates were collected at different times from two separate farms.

Materials and Methods

To sequence the MN184 isolates, viral RNA (vRNA) was extracted from PRRSV infected cell supernatant with QIAmp® Viral RNA Mini Kit (Qiagen, Valencia, Calif.)) and RT-PCR was performed (Qiagen® OneStep RT-PCR Kit). Primers (available on request) were designed based on the published sequences of different strains of PRRSV deposited in GenBank as well as newly generated MN184 sequence. The 5' nucleotide sequence of the two PRRSV isolates was derived using the 5'-Full RACE Core Kit (TaKaRa Bio, Madison, Wis.). 3'-RACE was performed with SMART™ RACE cDNA Amplification Kit (Clontech, Mountain View, Calif.). RT-PCR products were gel purified (QIAquick®, Qiagen), cloned into the pGEM-T Vector (Promega, Madison, Wis.) and 3 to 5 clones for each RT-PCR product were chosen for sequencing. The nucleotide sequence determination was completed in both directions with the PCR specific primers or the vector encoded SP6 and T7 promoter primers. The products were submitted to the Advanced Genetic Analysis Center at the University of Minnesota for sequence determination with an ABI 377 automated DNA fragment analyzer. A quality sequence representing at least three-fold genome coverage was obtained. Sequence data was assembled and analyzed by using the GeneTool sequence analysis program (BioTools Inc., Edmonton, Alberta Calif.) and Lasergene (DNASTAR, Madison, Wis.).

Multiple sequence alignments were generated with CLUSTALX (Thompson et al., Nucleic Acids Res., 24:4876-4882 (1997)) or Wisconsin Package Version 10.3 (Accelrys Inc., San Diego, Calif.). Full-length PRRSV sequences were aligned using ClustalX (version 1.83.1; IUB DNA weight matrix, gap penalty 15.00, gap length penalty 6.66). The resulting alignment was further analyzed using the Wisconsin Package Version 10.3 Distances Program (Jukes-Cantor distance method, partial matches due to degenerate symbols considered). For FIG. 10, sequences were aligned with the Pileup program of the Wisconsin Package (Blosum62 Scoring Matrix, Gap Weight=8, Length Weight=2, Weighted Ends). The alignment was scored for redundancy and colored for percent identity using Jalview (Clamp et al., Bioinformatics, 12:426-427 (2004)) and then transferred to Adobe Photoshop® CS, version 8.0, for grayscale transformation. For FIG. 11, sequences were aligned with the Pileup program of the Wisconsin Package (Blosum62 Scoring Matrix, Gap Weight=8, Length Weight=2, Weighted Ends). For FIG. 12, a signal peptide was predicted using the SignalP server (Bendtsen et al., J. Mol. Biol., 340:783-795 (2004)). Transmembrane regions were derived by PHDhtm (Rost et al., Protein Sci., 5:1704-1718 (1996)) and potential N-glycosylation sites were identified by PROSITE (Bairoch et al., Nucleic Acids Res., 25:217-221 (1997)) using the PredictProtein server (Rost et al., Nucleic Acids Res., 32:W321-W326 (2003)).

Sequences were aligned with the Pileup program of the Wisconsin Package (Blosum62 Scoring Matrix, Gap Weight=8, Length Weight=2, Weighted Ends).

Results

Genomic alignment demonstrated that these two PRRSV were quite distinct (>14.5% nucleotide dissimilarity) from other North American Type 2 full-length sequenced genomes, yet comparison with Type 1 (European) full-length sequences confirmed that the isolates were solely of Type 2 genotype origin as they were only approximately 59% similar at the nucleotide level to both EuroPRRSV and Lelystad strains. Strikingly, these Type 2 MN184 isolates represented the shortest PRRSV genomes detected to date (15019 nucleotides, not including the poly A tail). In addition, no specific area was discerned that suggested that these isolates were derived from viral recombination between Type 1 and Type 2 strains.

Full-length sequence analysis revealed that the two MN184 isolates were actually genetically distinct. They shared 98.0% nucleotide similarity or 2% difference. This percentage of dissimilarity was unexpected due to their sudden simultaneous appearance in Minnesota, with no clear recent related isolate seen in our PRRSV database at that time. Table 6 presents the detailed nucleotide and amino acid comparison between the two isolates and FIG. 9 depicts the amino acid differences seen between these two strains. Both of these isolates possessed nucleotide degeneracy in several regions of the genome, predominantly in the predicted nsp2 region of ORF1 (Table 6). The fact that nucleotide degeneracy was seen in these isolates suggested that PRRSV can be made up of several individual species, often referred to as a swarm of related but distinct viral sequences, within infected animals.

accounting for the difference in Type 2 viral genome length, these two isolates were compared to the sequence of the prototype Type 2 strain VR-2332. The differences between the two isolates could again be discerned, with isolate MN184B possessing slightly increased similarity to strain VR-2332 than isolate MN184A. The nucleotide and amino acid comparisons to VR-2332 showed individual MN184 isolate regions varied from 81.5-94.7% and 78.4-100%, respectively, but the regions corresponding to ORF5 (86.4-86.7% and 87.0-87.5%, respectively) predicted nsp113 (83.8-84.0% and 84.8-85.4%, respectively, and nsp2 (81.5-85.5% and 78.4-79.5%, respectively) were the most variable. Most interesting was that only the predicted nsp2 genomic region showed a difference in nucleotide length and that both MN184 isolates possessed the same nsp2 deletion, detailed below. The comparison also revealed that the 5' and 3' UTR's were the most conserved regions of the genome (94.7% and 94.0%, respectively), indicating sequence conservation in important regions for viral replication and transcription.

ORF5 encodes a heterogeneous PRRSV structural protein (GP5) and is often used for PRRSV diagnostic identification (Kapur et al., *J. Gen. Virol.*, 77:1271-1276 (1996)). GP5 is a predicted three transmembrane protein with an endodomain and ectodomain. The 30 amino acid ectodomain is composed of a short highly conserved domain usually containing at least two N-glycosylation sites bounded by two hypervariable regions. The highly conserved domain of this 30 amino acid region has been shown to code for the viral attachment epitope in Type 2 strains (Plagemann, *Virology*, 290:11-20 (2001); Ostrowski et al., *J. Virol.*, 76:4241-4250 (2002); Plagemann et al., *Arch. Virol.*, 147:2327-2347 (2002)). GP5 of the same set of full-length genomes, as well as the original RFLP184 isolates identified in Canada (IAF-93-653, IAF-

TABLE 6

Detailed analysis of individual PRRSV genomic regions and translated proteins, and number of degenerate bases detected in each region. Degeneracy is defined as more than one nucleotide detected for a particular base on separate trace files of three or more trace files.

| Region | Bases | Nucleotide length | % Nucleotide Similarity | % Nucleotide Identity | Number of Degenerate Bases (184A/184B) | Amino Acid Length | % Amino Acid Similarity | % Amino Acid Identity |
|---|---|---|---|---|---|---|---|---|
| 5' UTR | 1-190 | 190 | 99.5 | 98.9 | 1/0 | — | — | — |
| ORF1A | 191-7309 | 7119 | 98.5 | 96.7 | 16/109 | 2372 | 96.8 | 96.5 |
| NSP1a | 191-688 | 498 | 98.8 | 98.5 | 1/0 | 166 | 97.6 | 97.6 |
| NSP1b | 689-1339 | 651 | 98.3 | 97.5 | 2/3 | 217 | 97.2 | 95.9 |
| NSP2 | 1340-3886 | 2547 | 98.0 | 94.6 | 10/76 | 849 | 94.2 | 94.2 |
| NSP3 | 3887-5224 | 1338 | 98.7 | 98.7 | 0/0 | 446 | 99.3 | 98.9 |
| NSP4 | 5225-5836 | 612 | 98.5 | 96.4 | 0/13 | 204 | 97.1 | 97.1 |
| NSP5 | 5837-6346 | 510 | 99.2 | 95.3 | 3/17 | 170 | 97.1 | 97.1 |
| NSP6 | 6347-6394 | 48 | 100.0 | 100.0 | 0/0 | 16 | 100 | 100 |
| NSP7 | 6395-7171 | 777 | 99.3 | 99.3 | 0/0 | 259 | 99.6 | 99.2 |
| NSP8 | 7172-7309 | 138 | 99.3 | 99.3 | 0/0 | 46 | 97.6 | 97.6 |
| ORF1B | 7306-11679 | 4374 | 99.2 | 98.9 | 5/4 | 1457 | 99.5 | 99.2 |
| NSP9 | 7288-9225 | 1938 | 98.9 | 98.8 | 1/1 | 646 | 99.4 | 98.9 |
| NSP10 | 9226-10548 | 1323 | 99.3 | 98.9 | 3/3 | 441 | 99.8 | 99.3 |
| NSP11 | 10549-11217 | 669 | 99.3 | 99.3 | 0/0 | 223 | 99.5 | 99.5 |
| NSP12 | 11218-11679 | 462 | 99.6 | 99.4 | 1/0 | 153 | 99.3 | 99.3 |
| ORF2a/GP2 | 11681-12451 | 771 | 99.0 | 98.3 | 1/0 | 222 | 98.0 | 97.3 |
| ORF2b/E | 11686-11907 | 222 | 99.6 | 99.6 | 0/0 | 73 | 100 | 100 |
| ORF3/GP3 | 12304-13068 | 765 | 98.6 | 98.6 | 0/0 | 254 | 97.6 | 97.6 |
| ORF4/GP4 | 12849-13385 | 537 | 98.5 | 98.5 | 0/0 | 178 | 98.9 | 98.9 |
| ORF5/GP5 | 13396-13998 | 603 | 97.8 | 97.7 | 1/0 | 200 | 96.5 | 96.5 |
| ORF6/M | 13983-14507 | 525 | 99.6 | 97.4 | 0/0 | 174 | 100 | 100 |
| ORF7/N | 14497-14868 | 372 | 98.9 | 98.9 | 0/0 | 123 | 97.6 | 97.6 |
| 3' UTR | 14869-15019 | 151 | 100 | 98.0 | 1/1 | — | — | — |

Figure 10:
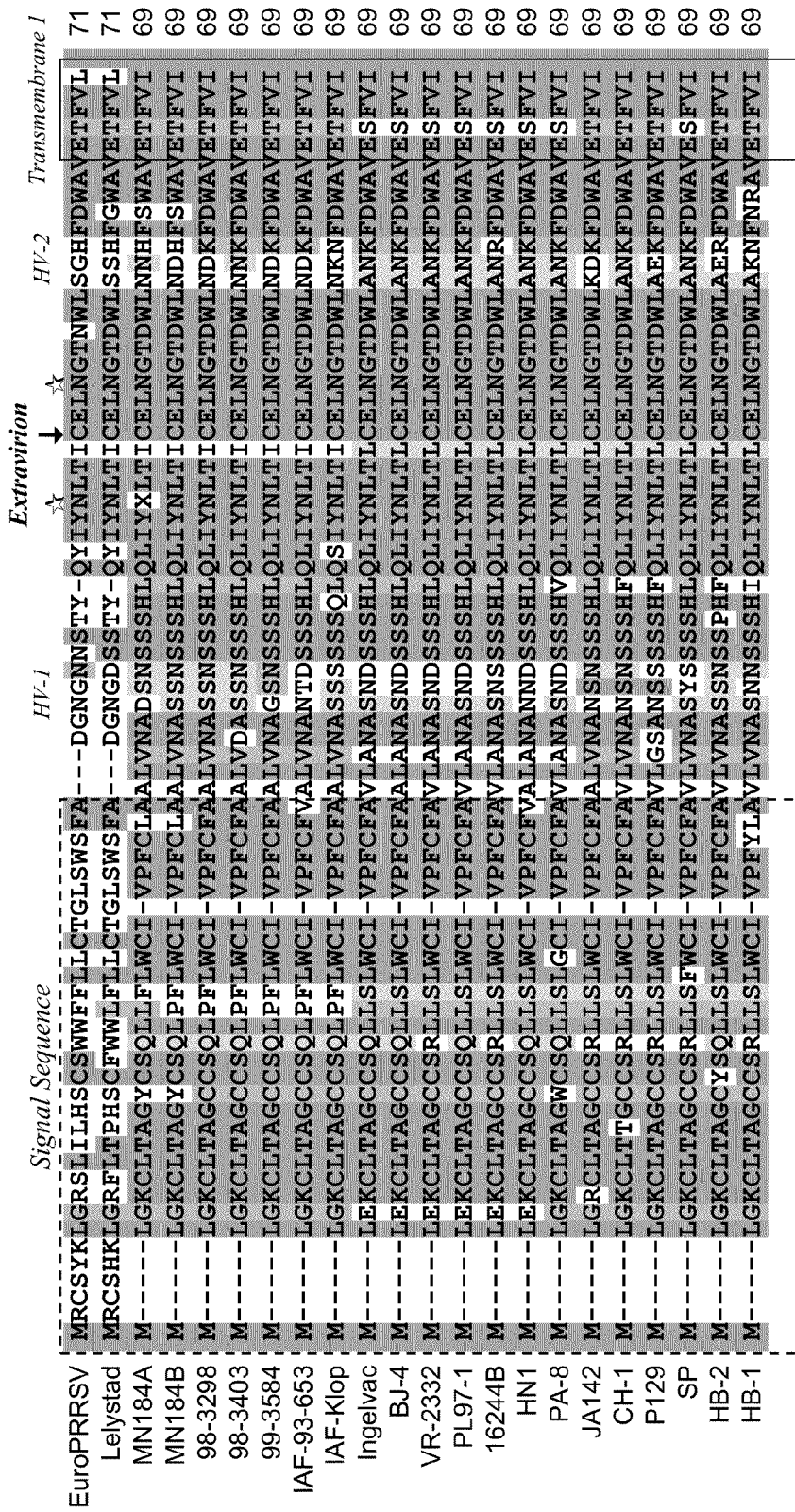
FIG. 10. ORF5 amino acid sequence alignment of divergent PRRSV. Dark grey boxes indicate high amino acid conservation (>80%; between 16 and 19 residues are identical), medium grey (>60%; between 12 and 15 residues are identical), lighter grey (>40%; between 8 and 11 residues are identical) and unshaded (<40%; less than 8 residues are identical) boxes identify less conserved residues. The dashed region indicates the putative signal sequence, the boxed regions identify the proposed transmembrane regions, the hypervariable regions are indicated (HV-1 and HV-2), and the proposed orientation of the protein in the virion is identified in bold italics. The conserved cysteine residue that is proposed to interact with the M protein is identified by the downward arrow (↓). The two conserved putative N-glycosylation sites are identified by stars and hypervariable region 1 contains strain/isolate specific N-glycosylation sites (NxS/T). ORF5 amino acid sequences from the following GenBank full-length sequences were used for comparison: VR-2332 (U87392) (SEQ ID NO: 45), Ingelvac MLV (AF066183) (SEQ ID NO: 43), PL97-1 (A Y58524) (SEQ ID NO: 46), PA-8 (AF176348) (SEQ ID NO: 49), SP (AF184212) (SEQ ID NO: 53), BJ-4 (AF331831) (SEQ ID NO: 44), HN1 (AY457635) (SEQ ID NO: 48), 16244B (AF046869) (SEQ ID NO: 47), HB-1 (AY150312) (SEQ ID NO: 55), HB-2 (AY262352) (SEQ ID NO: 54), CH-1a (AY032626) (SEQ ID NO: 51), P129 (AF494042) (SEQ ID NO: 52), JA142 (AY424271) (SEQ ID NO: 50), EuroPRRSV (AY366525) (SEQ ID NO: 34), Lelystad (M96262) (SEQ ID NO: 35), IAF-93-653 (U64931) (SEQ ID NO: 41), IAF-Klop (AY184209) (SEQ ID NO: 42), 98-3298 (DQ306877) (SEQ ID NO: 38), 98-3403 (DQ306878) (SEQ ID NO: 39), 99-3584 (DQ306879) (SEQ ID NO: 40), MN184A (SEQ ID NO:36), MN184B (SEQ ID NO:37).

In order to more closely pinpoint the individual regions of these MN184 isolates that showed the most dissimilarity from other PRRSV strains and to assign the region(s) Klop) and in 1998-1999 in Minnesota (98-3298, 98-3403, 99-3584) were aligned (FIG. 10). The alignment of PRRSV GP5 revealed amino acid identities ranging from 82.5% to 87.7% between the new MN184 isolates and other non-RFLP184 Type 2 strains. Interestingly, the amino acid differences between the new MN184 isolates and the older RFLP184 isolates were quite large (5.7%-12.2%) and thus we detected no clear origin of the new RFLP 184 virus. The limited alignment shows that most of the amino acid differences observed were found in the hypervariable regions (FIG. 10). The two conserved N-glycosylation sites were maintained in the MN184 isolates, except for detected nucleotide degeneracy coding for amino acid 44 in isolate MN184B.

Nsp1β encodes a papain-like cysteine protease (den Boon et al., *J Virol.*, 69:4500-4505 (1995)). An amino acid alignment of the MN184 isolates with a non-redundant set of available Type 2 nsp1β (3 sequences as well as Type 1 strains EuroPRRSV and Lelystad was completed (FIG. 11). The nsp1β protein possesses a number of completely conserved amino acids, and the proposed catalytic residues were maintained in all sequenced genomes (den Boon et al., *J. Virol.*, 69:4500-4505 (1995)). The alignment, ordered by amino acid similarity, indicates that the MN184 isolates are more similar to Type 1 strains than the other sequenced full-length Type 2 sequences. In particular, five amino acids (boxed in FIG. 11) directly mimic the Type 1 strains However, the amino acids that were conserved in the other non-redundant Type 2 sequences were also mostly conserved in the MN184 isolates, but scattered amino acids and the amino acid similarity (84.8-85.4%) revealed a more divergent Type 2 protein than had been evidenced to date. Thus, the alignment further defines maintained residues of nsp1l3 that may be critical to the replication cycle of PRRSV.

An amino acid alignment of non-redundant sequences of nsp2, ordered by pairwise identity, is shown in FIG. 12. A highly conserved chymotrypsin-like cysteine protease (PL2) domain is present at the N-terminus, previously predicted by alignment with equine arteritis virus (EAV) nsp2 (Snijder et al., *J. Gen. Virol.*, 79:961979 (1998); Ziebuhr et al., *J Gen. Virol.*, 81:853-879 (2000)). There are 3-4 predicted transmembrane domains near the C terminus of this protein (McGuffin et al., *Bioinforinatics*, 16:404-405 (2000)), but the exact C terminal cleavage site has not been empirically determined. Two predictions of the C-terminal cleavage site have been proposed, one G|G at VR-2332 nsp2 amino acid 980 (Allende et al., *J. Gen. Virol.*, 80:307-315 (1999)) and the other at amino acid 1197 (Ziebuhr et al., *J. Gen. Virol.*, 81:853-879 (2000)), but there are several completely conserved G|G doublets within this protein (VR-23332 nsp2 amino acids 646, 980, 1116, 1196, 1197; downward arrows in FIG. 12). Prior work had also shown that the predicted nsp2 protein is proline rich and contains multiple potential B-cell epitopes (Oleksiewicz et al., *J. Virol.*, 75:3277-3290 (2001); Fang et al., *Virus Res.*, 100:229-235 (2004); Ropp et al., *J. Virol.*, 78:3684-3703 (2004)). The large middle region of PRRSV nsp2 (VR-2332 nsp2 amino acids 148-880) has no assigned function but is highly variable in length. Furthermore, the length difference between sequenced Type 1 and Type 2 strains of PRRSV has been mapped to this variable middle region of nsp2 (FIG. 12). Until now, sequenced Type 1 genomes have been shown to be 313-364 bases shorter than most Type 2 PRRSV (Meulenberg et al., *Virology*, 192:62-72 (1993); Fang et al., *Virus Res.*, 100:229-235 (2004), Ropp et al., *J. Virol.*, 78:3684-3703 (2004)). However, the multiple sequence alignment established that the MN184 genome contains the shortest predicted nsp2 to date (2547 bp), 393 bp shorter than prototype Type 2 strain VR-2332. Furthermore, it contained three discontinuous deletions in the translated protein with deletion sizes consisting of 111, 1 and 19 amino acids, respectively, corresponding to the amino acid positions in PRRSV strain VR-2332 nsp2 of 324-434, 486 and 505-523, respectively (FIG. 12). The three deletions resulted in the loss of several proline residues and predicted B-cell epitopes. Besides these deletions, significant alterations in nsp2 amino acid sequence from other Type 2 strains were also seen, sometimes corresponding to the Type 1 amino acid seen at the same relative position (FIG. 12). Comparison of the nsp2 predicted protein of the two PRRSV genotypes demonstrated that the amino acid identity within Type 2 viruses ranged from 66% to 99% and from 88-90% within Type 1 viruses, but differed greatly between genotypes (<45% similarity). In particular, the MN184 isolates displayed 66-80% amino acid identity to all Type 2 nsp2 predicted proteins and only 43-45% identity to Type 1 strains. When surveying the multiple sequence alignment in FIG. 12, we also noted that all instances of insertion or deletion in both genotypes occurred in this hypervariable middle region. To this point, Shen et al. (*Arch. Virol.*, 145:871-883 (2000)) first reported that PRRSV North American Type 2 strain SP has a unique insertion of 36 aa relative to the position between aa 813 and 814 of PRRSV VR-2332 nsp2. Another investigator found a unique 12 aa deletion at position 466-477 in PRRSV isolate HB-2(sh)/2002 nsp2 (Gao et al., *Arch. Virol.*, 149:1341-1351 (2004)). A 17 aa deletion occurred in newly identified European-like PRRSV isolates when compared to strain LV (Fang et al., *Virus Res.*, 100; 229-235 (2004); Ropp et al., *J Virol.*, 78:3684-3703 (2004)). The instances of mutation did not consistently occur along the same stretch of amino acids, although the deletions seen between the MN184 isolates and other Type 2 viruses encompass most of the largest deletion detected between Type 1 and other Type 2 PRRSV. All of these data suggested that the nsp2 ORF contains a conserved protease motif and predicted transmembrane spanning regions that may be necessary for replication of PRRSV, but is highly susceptible to mutation in the large middle section.

The sudden appearance of field isolates of PRRSV in Minnesota reflecting the 184 RFLP pattern is still a mystery, but the consequences of this event are even now being realized. The Minnesota Veterinary Diagnostic Laboratory now performs routine sequencing on similar 184 RFLP isolates from approximately one fourth of the total number of ORF5 sequence requests. In addition, the 184 RFLP pattern has now been detected not only in Minnesota, but in Iowa, Wisconsin, South Dakota, Kansas, Missouri, Illinois, Nebraska, Kentucky, Oklahoma and Wyoming as well. We chose to derive the full-length sequences from two isolates because of the need to understand if this could be more than a single virus type and the fact that the swine herd diagnosed with isolate MN184A presented with a milder case of PRRS than the herd infected with isolate MN184B, as reported by the attending pathologist. The strains have not been inoculated into naive animals to verify the case presentations, but it is interesting to note that isolate MN184B had many more nucleotide degeneracies detected when analyzing the genome and this might reflect the severity of the disease reported.

This genome analysis increased our understanding of the immense nucleotide and amino acid sequence variation that exists in the field. Factors driving this variation may be related to the way swine are now managed, the interstate and international transport of swine and boar semen, the intermixing of different PRRSV isolates within herds and the nature of the virus itself. Full genome sequence generation also allows us to monitor where on the genome variation is tolerated and which regions are more conserved. As a result of this study, as well as a previous publication (Ropp et al., *J. Virol.*, 78:3684-3703 (2004)), a picture is emerging that indicates nsp2, nsp1β and ORF5 are extraordinarily versatile proteins.

This study has also provided clear evidence that nsp2 size can no longer be used to differentiate between the two PRRSV genotypes. The novel finding that nsp2 evolved to display a Type 2 genome with three discontinuous deletions, leading to the shortest genome to date (15,019 kb), suggests that PRRSV may be evolving to eliminate dispensable genomic regions and make the genome more compact. Finally, although the significance of genetic variations in PRRSV can only be surmised at present, the evolutionary change seen in ORF5, nsp1β and nsp2 should reasonably be related to the biological fitness of PRRSV during selection pressure.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. An isolated polynucleotide comprising a sequence having at least 88% identity to SEQ ID NO:1 and a deletion of at least 57 consecutive nucleotides in a region corresponding to nucleotide 2062 to nucleotide 3864 of SEQ ID No:1, wherein the polynucleotide further comprises an exogenous polynucleotide present in the deletion.

2. The isolated polynucleotide of claim 1, wherein the exogenous polynucleotide encodes a detectable marker.

3. An isolated polynucleotide comprising a nucleotide sequence having at least 88% identity to SEQ ID NO: 1 and at least one deletion of at least 57 consecutive nucleotides in a region corresponding to nucleotide 2062 to nucleotide 3864 of SEQ ID NO:1, wherein the polynucleotide replicates and produces infectious virus particles when introduced into a cell, and further wherein the polynucleotide further comprises an exogenous polynucleotide present in the deletion.

4. The isolated polynucleotide of claim 3, wherein the exogenous polynucleotide encodes a detectable marker.

5. The isolated polynucleotide of claim 1, wherein the polynucleotide is present in a vector.

6. The isolated polynucleotide of claim 1, wherein the polynucleotide comprises 2 or more deletions, and wherein each deletion is independently at least 57 consecutive nucleotides.

7. The isolated polynucleotide of claim 1, wherein the polynucleotide is present in an isolated virus particle.

8. The isolated polynucleotide of claim 1, wherein the polynucleotide is an RNA polynucleotide.

9. The isolated polynucleotide of claim 1, wherein the polynucleotide is present in a cell.

10. The isolated polynucleotide of claim 1, wherein an RNA polymerase promoter is operably linked to the polynucleotide.

11. The isolated polynucleotide of claim 3, wherein the polynucleotide is present in a vector.

12. The isolated polynucleotide of claim 3, wherein the polynucleotide comprises 2 or more deletions, and wherein each deletion is independently at least 57 consecutive nucleotides.

13. The isolated polynucleotide of claim 3, wherein the polynucleotide is present in an isolated virus particle.

14. The isolated polynucleotide of claim 3, wherein the polynucleotide is an RNA polynucleotide.

15. The isolated polynucleotide of claim 3, wherein the polynucleotide is present in a cell.

16. The isolated polynucleotide of claim 3, wherein an RNA polymerase promoter is operably linked to the polynucleotide.

* * * * *